US012673989B2

(12) United States Patent
Nichols et al.

(10) Patent No.: US 12,673,989 B2
(45) Date of Patent: Jul. 7, 2026

(54) pH-DEPENDENT ANTIGEN-BINDING CONSTRUCTS SPECIFIC TO FOLR1

(71) Applicant: Mythic Therapeutics, Inc., Waltham, MA (US)

(72) Inventors: Alexander J. Nichols, Lincoln, MA (US); Brian P. Fiske, Cambridge, MA (US); Nimish Gera, Waltham, MA (US)

(73) Assignee: Mythic Therapeutics, Inc., Waltham, MA (US)

( * ) Notice: Subject to any disclaimer, the term of this patent is extended or adjusted under 35 U.S.C. 154(b) by 1203 days.

(21) Appl. No.: 17/616,745

(22) PCT Filed: Jun. 5, 2020

(86) PCT No.: PCT/US2020/036435
§ 371 (c)(1),
(2) Date: Dec. 6, 2021

(87) PCT Pub. No.: WO2020/247827
PCT Pub. Date: Dec. 10, 2020

(65) Prior Publication Data
US 2022/0298260 A1      Sep. 22, 2022

Related U.S. Application Data

(60) Provisional application No. 62/897,965, filed on Sep. 9, 2019, provisional application No. 62/858,310, filed on Jun. 6, 2019.

(51) Int. Cl.
| | |
|---|---|
| *C07K 16/28* | (2006.01) |
| *A61K 47/68* | (2017.01) |
| *A61P 35/00* | (2006.01) |
| *C07K 16/30* | (2006.01) |

(52) U.S. Cl.
CPC ........ *C07K 16/28* (2013.01); *A61K 47/68031* (2023.08); *A61K 47/68035* (2023.08); *A61P 35/00* (2018.01); *C07K 16/30* (2013.01); *C07K 2317/31* (2013.01); *C07K 2317/565* (2013.01); *C07K 2317/77* (2013.01); *C07K 2317/92* (2013.01); *C07K 2317/94* (2013.01)

(58) Field of Classification Search
CPC .... C07K 16/28; C07K 16/30; C07K 2317/31; C07K 2317/565; C07K 2317/77; C07K 2317/92; C07K 2317/94; C07K 2317/90; A61K 47/68031; A61K 47/68035; A61K 47/6849; A61K 2039/505; A61P 35/00
See application file for complete search history.

(56) References Cited

U.S. PATENT DOCUMENTS

| | | | |
|---|---|---|---|
| 7,612,181 | B2 | 11/2009 | Wu et al. |
| 8,088,376 | B2 | 1/2012 | Chamberlain et al. |
| 8,258,268 | B2 | 9/2012 | Wu et al. |
| 8,394,925 | B2 | 3/2013 | Chamberlain et al. |
| 8,557,966 | B2 * | 10/2013 | Ab ..................... A61K 31/5365 |
| | | | 530/391.1 |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,822,645 | B2 | 9/2014 | Ghayur et al. |
| 9,890,377 | B2 | 2/2018 | Igawa et al. |
| 10,336,818 | B2 | 7/2019 | Chamberlain et al. |
| 2013/0243775 | A1 | 9/2013 | Papadopoulos et al. |
| 2017/0007715 | A1 | 1/2017 | Andreev et al. |
| 2017/0191055 | A1 | 7/2017 | Short et al. |
| 2018/0208658 | A1 | 7/2018 | Liu et al. |
| 2019/0024078 | A1 | 1/2019 | Short et al. |
| 2019/0083641 | A1 | 3/2019 | Stafford et al. |

FOREIGN PATENT DOCUMENTS

| | | | | |
|---|---|---|---|---|
| CN | 102844332 | 12/2012 | | |
| CN | 102918057 | 2/2013 | | |
| CN | 103747802 | 4/2014 | | |
| CN | 104302664 | 1/2015 | | |
| EP | 2552955 | 2/2013 | | |
| KR | 10-2018-0025865 | 3/2018 | | |
| WO | WO 2011/111007 | 9/2011 | | |
| WO | WO 2011/122011 | 10/2011 | | |
| WO | WO 2012/135675 | 10/2012 | | |
| WO | WO 2013/138400 | 9/2013 | | |
| WO | WO-2013138400 A1 * | 9/2013 | ......... | A61K 39/3955 |
| WO | WO-2015031815 A2 * | 3/2015 | ......... | A61K 47/6803 |
| WO | WO 2017/040344 A2 | 3/2017 | | |
| WO | WO 2017/134197 | 8/2017 | | |
| WO | WO 2018/044619 | 3/2018 | | |
| WO | WO 2018/136455 | 7/2018 | | |

OTHER PUBLICATIONS

Rudikoff et al., PNAS, 79:1979-1983, March (Year: 1982).*
Chiu ML et al. Antibody Structure and Function: The Basis for Engineering Therapeutics. Antibodies 2019 8, 55, 1-80 (Year: 2019).*
Almagro JC & Fransson J, Humanization of antibodies. Frontiers in Bioscience 2008; 13:1619-33 (Year: 2008).*
Ewert, S., et al., 2004. Stability improvement of antibodies for extracellular and intracellular applications: CDR grafting to stable frameworks and structure-based framework engineering. Methods, 34(2), pp. 184-199 (Year: 2004).*
Bonvin et al., "De novo isolation of antibodies with pH-dependent binding properties," Mabs, 2015, 7(2):294-302.

(Continued)

*Primary Examiner* — Gregory S Emch
*Assistant Examiner* — Kathleen Cunningchen
(74) *Attorney, Agent, or Firm* — Fish & Richardson P.C.

(57) ABSTRACT

Provided herein are antigen-binding protein constructs capable of specifically binding FOLR1 or an epitope of FOLR1 presented on the surface of a target mammalian cell, wherein said antigen binding is pH-dependent. Provided are also uses of said antigen-binding protein constructs.

21 Claims, 251 Drawing Sheets

Specification includes a Sequence Listing.

(56)        References Cited

OTHER PUBLICATIONS

Borrok et al., "pH-dependent Binding Engineering Reveals an FcRn Affinity Threshold That Governs IgG Recycling," The Journal of Biological Chemistry, Feb. 13, 2015, 290(7):4282-4290.

Igawa et al., "pH-dependent antigen-binding antibodies as a novel therapeutic modality," Biochimica et Biophysica Acta (BBA)—Proteins and Proteomics, Nov. 2014, 1844(11):1943-1950.

Abdiche et al., "Exploring blocking assays using Octet, ProteOn, and Biacore biosensors", Anal Biochem. 386(2):172-180, Mar. 2009.

Abrahams et al., "Preclinical Activity and Safety of STRO-002, a Novel ADC Targeting Folate Receptor Alpha for Ovarian Cancer", Poster, Presented at 12th Biennial Ovarian Cancer Research Symposium, Seattle, WA, Sep. 13-15, 2018; Gynecologic Oncol. 149(Supp. 1):50, Jun. 2018.

Altwerger et al., "In Vitro and In Vivo Activity of IMGN853, an Antibody-Drug Conjugate Targeting Folate Receptor Alpha Linked to DM4, in Biologically Aggressive Endometrial Cancers", Mol Cancer Ther. 17(5):1003-1011, May 2018.

BroadInstitute.Org [online], "Cancer Cell Line Encyclopedia", available on or before Jul. 2016, retrieved on Mar. 29, 2022, retrieved from URL <https://portals.broadinstitute.org/ccle>, 6 pages.

Carter et al., "Antibody-Drug Conjugates for Cancer Therapy", Cancer J. 14(3):154-169, May 2008.

Catcott et al., "Microscale screening of antibody libraries as maytansinoid antibody-drug conjugates", mAbs 8(3):513-523, 2016.

Chandna, "Single-Cell Gel Electrophoresis Assay Monitors Precise Kinetics of DNA Fragmentation Induced During Programmed Cell Death", Cytometry 61A:127-133, 2004.

Chari, "Targeted Cancer Therapy: Conferring Specificity to Cytotoxic Drugs", Acc. Chem. Res. 41(1):98-107, Jan. 2008.

Cheung et al., "Targeting folate receptor alpha for cancer treatment", Oncotarget 7(32):52553-52574, Aug. 2016.

Cromie et al., "Nanobodies and their use in GPCR drug discovery", Curr. Top. Med. Chem. 15(24):2543-2557, 2015.

De Genst et al., "Antibody repertoire development in camelids", Dev. Comp.Immunol. 30(1-2):187-198, 2006.

De Meyer et al., "Nanobody-based products as research and diagnostic tools", Trends Biotechnol. 32(5):263-270, May 2014.

DiGiammarino et al., "Design and generation of DVD-Ig™ molecules for dual-specific targeting", Methods Mol. Biol. 899:145-156, 2012.

Ebel et al., "Preclinical evaluation of MORAb-003, a humanized monoclonal antibody antagonizing folate receptor-alpha", Cancer Immun. 7, 8 pages, Mar. 2007.

Fischer et al., "The assay design used for measurement of therapeutic antibody concentrations can affect pharmacokinetic parameters", mAbs 4(5):623-631, 2012.

Garber, "Bispecific antibodies rise again", Nat. Rev. Drug Discov. 13:799-801, Nov. 2014.

Gera et al., "Design of pH Sensitive Binding Proteins from the Hyperthermophilic Sso7d Scaffold", PLoS One 7(11):e48928, 14 pages, Nov. 2012.

Gupta et al., "Preclinical pharmacokinetics of MHAA4549A, a human monoclonal antibody to influenza A virus, and the prediction of its efficacious clinical dose for the treatment of patients hospitalized with influenza A", mAbs, 8(5):991-997, 2016.

Huang et al., "Assessment of Histone H2AX Phosphory lation Induced by DNA Topoisomerase I and II Inhibitors Topotecan and Mitoxantrone and by the DNA Cross-Linking Agent Cisplatin", Cytometry Part A 58A:99-110, 2004.

International Preliminary Report on Patentability in Appln. No. PCT/US2020/036435, dated Dec. 16, 2021, 15 pages.

International Search Report and Written Opinion in International Appln. No. PCT/US2020/036435, dated Nov. 4, 2020, 28 pages.

Invitation to Pay Additional Fees in International Appln. No. PCT/US2020/036435, dated Sep. 10, 2020, 21 pages.

Jakob et al., "Structure reveals function of the dual variable domain immunoglobulin (DVD-IgTM) molecule", mAbs, 5(3):358-363, 2013.

Jamur et al., "Permeabilization of cell membranes", Methods Mol Biol., 588:63-66, 2010.

Kijanka et al., "Nanobody-based cancer therapy of solid tumors", Nanomedicine 10:161-174, 2015.

Kontermann et al., "Bispecific antibodies," Drug Discover Today, Jul. 2015, 20(7), 10 pages.

Kovaleva et al., "Shark variable new antigen receptor biologics—a novel technology platform for therapeutic drug development", Expert. Opin. Biol. Ther. 14(10):1527-1539, 2014.

Krah et al., "Single-domain antibodies for biomedical applications", Immunopharmacol. Immunotoxicol. 38:21-28, 2016.

Labrijn et al., "Controlled Fab-arm exchange for the generation of stable bispecific IgG1", Nature Protcols 9(10):2450-2463, 2014.

Lefranc, "The IMGT unique numbering for Immunoglobulins, T cell receptors and Ig-like domains", Immunologist, Jul. 1999, 7(4):132-136.

Li et al., "A Biparatopic HER2-Targeting Antibody-Drug Conjugate Induces Tumor Regression in Primary Models Refractory to or Ineligible for HER2-Targeted Therapy", Cancer Cell 29:117-29, Jan. 2016.

Lu et al., "Linkers Having a Crucial Role in Antibody-Drug Conjugates", Int. J. Mol. Sci. 17(4):561, 22 pages, Apr. 2016.

Mahmutefendic et al., "Segregation of open Major Histocompatibility Class I conformers at the plasma membrane and during endosomal trafficking reveals conformation-based sorting in the endosomal system", Int. J. Biochem. Cell Bio. 43(4):504-515, Apr. 2011.

McCombs et al., "Antibody drug conjugates: design and selection of linker, payload and conjugation chemistry", AAPS J. 17(2):339-351, Mar. 2015.

Mendoza et al., "Inhibition of Ligand-mediated HER2 Activation in Androgen-independent Prostate Cancer", Cancer Res. 62:5485-5488, Oct. 2002.

Mujic-Delic et al., "GPCR-targeting nanobodies: attractive research tools, diagnostics, and therapeutics", Trends Pharmacol. Sci. 35(5):247-255, May 2014.

Muyldermans et al., "Recognition of antigens by single-domain antibody fragments: the superfluous luxury of paired domains", Trends Biochem. Sci. 26(4):230-235, Apr. 2001.

Muyldermans, "Nanobodies: Natural Single-Domain Antibodies", Annu. Rev. Biochem. 82:775-797, Jun. 2013.

Muyldermans, "Single domain camel antibodies: current status", Rev. Mol. Biotechnol. 74:277-302, 2001.

Oflazoglu et al., "Potent Anticarcinoma Activity of the Humanized Anti-CD70 Antibody h1F6 Conjugated to the Tubulin Inhibitor Auristatin via an Uncleavable Linker", Clin. Cancer Res. 14(19):6171-6180, 2008.

Promega Corporation, "CellTiter-Glo™ Luminescent Cell Viability Assay," Technical Bulletin #TB288, revised Mar. 2015, 15 pages.

Rahbarizadeh et al., "Nanobody; an Old Concept and New Vehicle for Immunotargeting", Immunol. Invest. 40:299-338, 2011.

Sanderson et al., "In vivo Drug-Linker Stability of an Anti-CD30 Dipeptide-Linked Auristatin Immunoconjugate", Clin. Cancer Res. 11(2 Pt1):843-852, Jan. 2005.

Schneider et al., "Quantification of human Alu sequences by real-time PCR—an improved method to measure theapeutic efficacy of anti-metastatic drugs in human xenotransplants", Clin. Exp. Metas. 19:571-582, 2002.

Singh et al., "Measurement and Mathematical Characterization of Cell-Level Pharmacokinetics of Antibody-Drug Conjugates: A Case Study with Trastuzumab-vc-MMAE", Drug Metabolism and Disposition 45(11):1120-1132, 2017.

Sorkin et al., "Quantitative analysis of endocytosis and turnover of epidermal growth factor (EGF) and EGF receptor", Curr. Protoc. Cell Biol. Chapter 15, Unit-15.14, Mar. 2010.

Spiess et al., "Alternative molecular formats and therapeutic applications of bispecific antibodies", Mol. Immunol. 67(2 Pt A):95-106, 2015.

(56) References Cited

OTHER PUBLICATIONS

Tiberghien et al., "Design and Synthesis of Tesirine, a Clinical Antibody-Drug Conjugate Pyrrolobenzodiazepine Dimer Payload", ACS Med Chem Lett 7(11):983-987, Nov. 2016.

Vainshtein et al., "Quantitative Measurement of the Target-Mediated Internalization Kinetics of Biopharmaceuticals", Pharm Res. 32:286-299, 2015.

Van Audenhove et al., "Nanobodies as Versatile Tools to Understand, Diagnose, Visualize and Treat Cancer", EBioMedicine 8:40-48, Jun. 2016.

Van Bockstaele et al., "The development of nanobodies for therapeutic applications", Curr. Opin. Investig. Drugs 10(11):1212-1224, 2009.

Vincke et al., "Introduction to heavy chain antibodies and derived Nanobodies", Methods Mol. Biol. 911:15-26, 2012.

Wesolowski et al., "Single domain antibodies: promising experimental and therapeutic tools in infection and immunity", Med. Microbiol. Immunol. 198(3):157-174, Aug. 2009.

Wiley et al., "The Role of Tyrosine Kinase Activity in Endocytosis, Compartmentation, and Down-regulation of the Epidermal Growth Factor Receptor", J. Biol. Chem. 266(17):11083-11094, 1991.

Wustner, "Steady State Analysis and Experimental Validation of a Model for Hepatic High-Density Lipoprotein Transport", Traffic 7(6):699-715, 2006.

Office Action in Chinese Appln. No. 202080056438.5, mailed on Nov. 2, 2023, 71 pages (with English translation).

* cited by examiner

|         | Heavy | Light | CDRH1 | CDRH2 | CDRH3 | CDRL1 | CDRL2 | CDRL3 |
|---------|-------|-------|-------|-------|-------|-------|-------|-------|
| MYT0596 | 1     | 2     | 3     | 4     | 5     | 6     | 7     | 8     |
| MYT0597 | 13    | 2     |       |       |       |       |       |       |
| MYT0598 | 14    | 2     |       |       |       |       |       |       |
| MYT0599 | 15    | 2     |       |       |       |       |       |       |
| MYT0600 | 16    | 2     |       |       |       |       |       |       |
| MYT0601 | 17    | 2     |       |       |       |       |       |       |
| MYT0602 | 18    | 2     |       |       |       |       |       |       |
| MYT0603 | 19    | 2     |       |       |       |       |       |       |
| MYT0604 | 20    | 2     |       |       |       |       |       |       |
| MYT0605 | 21    | 2     |       |       |       |       |       |       |
| MYT0606 | 22    | 2     |       |       |       |       |       |       |
| MYT0607 | 23    | 2     |       |       |       |       |       |       |
| MYT0608 | 24    | 2     |       |       |       |       |       |       |
| MYT0609 | 25    | 2     |       |       |       |       |       |       |
| MYT0610 | 26    | 2     |       |       |       |       |       |       |
| MYT0611 | 27    | 2     |       |       |       |       |       |       |
| MYT0612 | 28    | 2     |       |       |       |       |       |       |
| MYT0613 | 29    | 2     |       |       |       |       |       |       |
| MYT0614 | 30    | 2     |       |       |       |       |       |       |
| MYT0615 | 31    | 2     |       |       |       |       |       |       |
| MYT0616 | 32    | 2     |       |       |       |       |       |       |
| MYT0617 | 33    | 2     |       |       |       |       |       |       |
| MYT0618 | 34    | 2     |       |       |       |       |       |       |
| MYT0619 | 35    | 2     |       |       |       |       |       |       |
| MYT0620 | 36    | 2     |       |       |       |       |       |       |
| MYT0621 | 37    | 2     |       |       |       |       |       |       |
| MYT0622 | 38    | 2     |       |       |       |       |       |       |
| MYT0623 | 39    | 2     |       |       |       |       |       |       |
| MYT0624 | 40    | 2     |       |       |       |       |       |       |
| MYT0625 | 41    | 2     |       |       |       |       |       |       |
| MYT0626 | 42    | 2     |       |       |       |       |       |       |
| MYT0627 | 43    | 2     |       |       |       |       |       |       |
| MYT0628 | 44    | 2     |       |       |       |       |       |       |
| MYT0629 | 45    | 2     |       |       |       |       |       |       |
| MYT0630 | 46    | 2     |       |       |       |       |       |       |
| MYT0631 | 47    | 2     |       |       |       |       |       |       |
| MYT0632 | 48    | 2     |       |       |       |       |       |       |
| MYT0633 | 49    | 2     |       |       |       |       |       |       |
| MYT0634 | 50    | 2     |       |       |       |       |       |       |
| MYT0635 | 51    | 2     |       |       |       |       |       |       |
| MYT0636 | 52    | 2     |       |       |       |       |       |       |
| MYT0637 | 53    | 2     |       |       |       |       |       |       |

FIGURE 3

MYT1569, FOLR, pH 5.4          MYT1569, FOLR, pH 7.4

MYT1577, FOLR, pH 5.4          MYT1577, FOLR, pH 7.4

| | Heavy | Light | CDRH1 | CDRH2 | CDRH3 | CDRL1 | CDRL2 | CDRL3 |
|---|---|---|---|---|---|---|---|---|
| MYT0596 | 1 | 2 | 3 | 4 | 5 | 6 | 7 | 8 |
| MYT1559 | 1 | 54 | | | | | | |
| MYT1560 | 1 | 55 | | | | | | |
| MYT1561 | 1 | 56 | | | | | | |
| MYT1562 | 1 | 57 | | | | | | |
| MYT1563 | 1 | 58 | | | | | | |
| MYT1564 | 1 | 59 | | | | | | |
| MYT1565 | 1 | 60 | | | | | | |
| MYT1566 | 1 | 61 | | | | | | |
| MYT1567 | 1 | 62 | | | | | | |
| MYT1568 | 1 | 63 | | | | | | |
| MYT1569 | 1 | 64 | | | | | | |
| MYT1570 | 1 | 65 | | | | | | |
| MYT1571 | 1 | 66 | | | | | | |
| MYT1572 | 1 | 67 | | | | | | |
| MYT1573 | 1 | 68 | | | | | | |
| MYT1574 | 1 | 69 | | | | | | |
| MYT1575 | 1 | 70 | | | | | | |
| MYT1576 | 1 | 71 | | | | | | |
| MYT1577 | 1 | 72 | | | | | | |
| MYT1578 | 1 | 73 | | | | | | |
| MYT1579 | 1 | 74 | | | | | | |
| MYT1580 | 1 | 75 | | | | | | |
| MYT1581 | 1 | 76 | | | | | | |
| MYT1582 | 1 | 77 | | | | | | |
| MYT1583 | 1 | 78 | | | | | | |
| MYT1584 | 1 | 79 | | | | | | |
| MYT1585 | 1 | 80 | | | | | | |
| MYT1586 | 1 | 81 | | | | | | |
| MYT1587 | 1 | 82 | | | | | | |
| MYT1588 | 1 | 83 | | | | | | |
| MYT1589 | 1 | 84 | | | | | | |

FIGURE 6

FOLR, PBST pH 5.4            FOLR, PBST pH 7.4

|  | Heavy | Light | CDRH1 | CDRH2 | CDRH3 | CDRL1 | CDRL2 | CDRL3 |
|---|---|---|---|---|---|---|---|---|
| MYT0596 | 1 | 2 | 3 | 4 | 5 | 6 | 7 | 8 |
| MYT1142 | 85 | 2 | | | | | | |
| MYT1143 | 86 | 2 | | | | | | |
| MYT1144 | 87 | 2 | | | | | | |
| MYT1145 | 88 | 2 | | | | | | |
| MYT1146 | 89 | 2 | | | | | | |
| MYT1147 | 90 | 2 | | | | | | |
| MYT1148 | 91 | 2 | | | | | | |
| MYT1149 | 92 | 2 | | | | | | |
| MYT1150 | 93 | 2 | | | | | | |
| MYT1151 | 94 | 2 | | | | | | |
| MYT1152 | 95 | 2 | | | | | | |
| MYT1153 | 96 | 2 | | | | | | |
| MYT1154 | 97 | 2 | | | | | | |
| MYT1155 | 98 | 2 | | | | | | |
| MYT1156 | 99 | 2 | | | | | | |
| MYT1157 | 100 | 2 | | | | | | |
| MYT1158 | 101 | 2 | | | | | | |
| MYT1159 | 102 | 2 | | | | | | |
| MYT1160 | 103 | 2 | | | | | | |
| MYT1161 | 104 | 2 | | | | | | |

FIGURE 9

| | Heavy | Light | CDRH1 | CDRH2 | CDRH3 | CDRL1 | CDRL2 | CDRL3 |
|---|---|---|---|---|---|---|---|---|
| MYT2224 | 105 | 106 | 107 | 108 | 109 | 110 | 111 | 112 |
| MYT2225 | 113 | 106 | | | | | | |
| MYT2226 | 114 | 106 | | | | | | |
| MYT2227 | 115 | 106 | | | | | | |
| MYT2228 | 116 | 106 | | | | | | |
| MYT2229 | 117 | 106 | | | | | | |
| MYT2230 | 118 | 106 | | | | | | |
| MYT2231 | 119 | 106 | | | | | | |
| MYT2232 | 120 | 106 | | | | | | |
| MYT2233 | 121 | 106 | | | | | | |
| MYT2234 | 122 | 106 | | | | | | |
| MYT2235 | 123 | 106 | | | | | | |
| MYT2236 | 124 | 106 | | | | | | |
| MYT2237 | 125 | 106 | | | | | | |
| MYT2238 | 126 | 106 | | | | | | |
| MYT2239 | 127 | 106 | | | | | | |
| MYT2240 | 128 | 106 | | | | | | |
| MYT2241 | 129 | 106 | | | | | | |
| MYT2242 | 130 | 106 | | | | | | |
| MYT2243 | 131 | 106 | | | | | | |
| MYT2244 | 132 | 106 | | | | | | |
| MYT2245 | 133 | 106 | | | | | | |
| MYT2246 | 134 | 106 | | | | | | |
| MYT2247 | 135 | 106 | | | | | | |
| MYT2248 | 136 | 106 | | | | | | |
| MYT2249 | 137 | 106 | | | | | | |
| MYT2250 | 138 | 106 | | | | | | |
| MYT2251 | 139 | 106 | | | | | | |
| MYT2252 | 140 | 106 | | | | | | |
| MYT2253 | 141 | 106 | | | | | | |
| MYT2254 | 142 | 106 | | | | | | |
| MYT2255 | 143 | 106 | | | | | | |
| MYT2256 | 144 | 106 | | | | | | |
| MYT2257 | 145 | 106 | | | | | | |
| MYT2258 | 146 | 106 | | | | | | |
| MYT2259 | 147 | 106 | | | | | | |
| MYT2260 | 148 | 106 | | | | | | |
| MYT2261 | 149 | 106 | | | | | | |
| MYT2262 | 150 | 106 | | | | | | |
| MYT2263 | 151 | 106 | | | | | | |
| MYT2264 | 152 | 106 | | | | | | |
| MYT2265 | 153 | 106 | | | | | | |
| MYT2266 | 154 | 106 | | | | | | |
| MYT2267 | 155 | 106 | | | | | | |
| MYT2268 | 156 | 106 | | | | | | |

FIGURE 12

FOLR-1 (5.4)                    FOLR-1 (7.4)

| | Heavy | Light | CDRH1 | CDRH2 | CDRH3 | CDRL1 | CDRL2 | CDRL3 |
|---|---|---|---|---|---|---|---|---|
| MYT2224 | 105 | 106 | 107 | 108 | 109 | 110 | 111 | 112 |
| MYT4493 | 105 | 157 | | | | | | |
| MYT4494 | 105 | 158 | | | | | | |
| MYT4495 | 105 | 159 | | | | | | |
| MYT4496 | 105 | 160 | | | | | | |
| MYT4497 | 105 | 161 | | | | | | |
| MYT4498 | 105 | 162 | | | | | | |
| MYT4499 | 105 | 163 | | | | | | |
| MYT4500 | 105 | 164 | | | | | | |
| MYT4501 | 105 | 165 | | | | | | |
| MYT4502 | 105 | 166 | | | | | | |
| MYT4503 | 105 | 167 | | | | | | |
| MYT4504 | 105 | 168 | | | | | | |
| MYT4505 | 105 | 169 | | | | | | |
| MYT4506 | 105 | 170 | | | | | | |
| MYT4507 | 105 | 171 | | | | | | |
| MYT4508 | 105 | 172 | | | | | | |
| MYT4509 | 105 | 173 | | | | | | |
| MYT4510 | 105 | 174 | | | | | | |
| MYT4511 | 105 | 175 | | | | | | |
| MYT4512 | 105 | 176 | | | | | | |
| MYT4513 | 105 | 177 | | | | | | |
| MYT4514 | 105 | 178 | | | | | | |
| MYT4515 | 105 | 179 | | | | | | |
| MYT4516 | 105 | 180 | | | | | | |
| MYT4517 | 105 | 181 | | | | | | |
| MYT4518 | 105 | 182 | | | | | | |
| MYT4519 | 105 | 183 | | | | | | |

FIGURE 15

| | Heavy | Light | CDRH1 | CDRH2 | CDRH3 | CDRL1 | CDRL2 | CDRL3 |
|---|---|---|---|---|---|---|---|---|
| MYT2184 | 184 | 185 | 186 | 187 | 188 | 189 | 190 | 191 |
| MYT2185 | 192 | 185 | | | | | | |
| MYT2186 | 193 | 185 | | | | | | |
| MYT2187 | 194 | 185 | | | | | | |
| MYT2188 | 195 | 185 | | | | | | |
| MYT2189 | 196 | 185 | | | | | | |
| MYT2190 | 197 | 185 | | | | | | |
| MYT2191 | 198 | 185 | | | | | | |
| MYT2192 | 199 | 185 | | | | | | |
| MYT2193 | 200 | 185 | | | | | | |
| MYT2194 | 201 | 185 | | | | | | |
| MYT2195 | 202 | 185 | | | | | | |
| MYT2196 | 203 | 185 | | | | | | |
| MYT2197 | 204 | 185 | | | | | | |
| MYT2198 | 205 | 185 | | | | | | |
| MYT2199 | 206 | 185 | | | | | | |
| MYT2200 | 207 | 185 | | | | | | |
| MYT2201 | 208 | 185 | | | | | | |
| MYT2202 | 209 | 185 | | | | | | |
| MYT2203 | 210 | 185 | | | | | | |
| MYT2204 | 211 | 185 | | | | | | |
| MYT2205 | 212 | 185 | | | | | | |
| MYT2206 | 213 | 185 | | | | | | |
| MYT2207 | 214 | 185 | | | | | | |
| MYT2208 | 215 | 185 | | | | | | |
| MYT2209 | 216 | 185 | | | | | | |
| MYT2210 | 217 | 185 | | | | | | |
| MYT2211 | 218 | 185 | | | | | | |
| MYT2212 | 219 | 185 | | | | | | |
| MYT2213 | 220 | 185 | | | | | | |
| MYT2214 | 221 | 185 | | | | | | |
| MYT2215 | 222 | 185 | | | | | | |
| MYT2216 | 223 | 185 | | | | | | |
| MYT2217 | 224 | 185 | | | | | | |
| MYT2218 | 225 | 185 | | | | | | |
| MYT2219 | 226 | 185 | | | | | | |
| MYT2220 | 227 | 185 | | | | | | |
| MYT2221 | 228 | 185 | | | | | | |
| MYT2222 | 229 | 185 | | | | | | |
| MYT2223 | 230 | 185 | | | | | | |

FIGURE 18

| | Heavy | Light | CDRH1 | CDRH2 | CDRH3 | CDRL1 | CDRL2 | CDRL3 |
|---|---|---|---|---|---|---|---|---|
| MYT2184 | 184 | 185 | 186 | 187 | 188 | 189 | 190 | 191 |
| MYT4520 | 184 | 231 | | | | | | |
| MYT4521 | 184 | 232 | | | | | | |
| MYT4522 | 184 | 233 | | | | | | |
| MYT4523 | 184 | 234 | | | | | | |
| MYT4524 | 184 | 235 | | | | | | |
| MYT4525 | 184 | 236 | | | | | | |
| MYT4526 | 184 | 237 | | | | | | |
| MYT4527 | 184 | 238 | | | | | | |
| MYT4528 | 184 | 239 | | | | | | |
| MYT4529 | 184 | 240 | | | | | | |
| MYT4530 | 184 | 241 | | | | | | |
| MYT4531 | 184 | 242 | | | | | | |
| MYT4532 | 184 | 243 | | | | | | |
| MYT4533 | 184 | 244 | | | | | | |
| MYT4534 | 184 | 245 | | | | | | |
| MYT4535 | 184 | 246 | | | | | | |
| MYT4536 | 184 | 247 | | | | | | |
| MYT4537 | 184 | 248 | | | | | | |
| MYT4538 | 184 | 249 | | | | | | |
| MYT4539 | 184 | 250 | | | | | | |
| MYT4540 | 184 | 251 | | | | | | |
| MYT4541 | 184 | 252 | | | | | | |
| MYT4542 | 184 | 253 | | | | | | |
| MYT4543 | 184 | 254 | | | | | | |
| MYT4544 | 184 | 255 | | | | | | |
| MYT4545 | 184 | 256 | | | | | | |
| MYT4546 | 184 | 257 | | | | | | |

FIGURE 21

ANTIGEN-BINDING PROTEIN CONSTRUCTS AND USES THEREOF
Mythic Therapeutics, Inc.
45395-0029US1
REPLACEMENT SHEET

251/251

|  | Tm (°C) 1 | Tm (°C) 2 |
|---|---|---|
| MYT0596 | 69.3 | 77.3 |
| MYT0598 | 67.5 |  |
| MYT0601 | 68.1 |  |
| MYT0603 | 67.9 |  |
| MYT0614 | 68.9 | 77.1 |
| MYT0618 | 69.3 |  |
| MYT0619 | 69.5 | 76.9 |
| MYT1143 | 67.3 |  |
| MYT1145 | 67.3 |  |
| MYT1148 | 71.7 |  |
| MYT1150 | 69.1 | 75.9 |
| MYT1154 | 67.3 |  |

FIGURE 24 pH-DEPENDENT ANTIGEN-BINDING CONSTRUCTS SPECIFIC TO FOLR 1

CROSS-REFERENCE TO RELATED APPLICATION

This application is a National Stage Application under 35 U.S.C. § 371 and claims the benefit of International Patent Application No. PCT/US2020/036435 filed on Jun. 5, 2020, which priority to U.S. Provisional Patent Application Ser. No. 62/858,310 filed on Jun. 6, 2019 and U.S. Provisional Patent Application Ser. No. 62/897,965 filed on Sep. 9, 2019. The contents of each of these applications are incorporated herein by reference in their entireties.

TECHNICAL FIELD

The present disclosure relates to the field of biotechnology, and more specifically, to antigen-binding molecules.

BACKGROUND

Antibody-drug-conjugates have been designed to combat a variety of diseases. One particular advantage of this approach is the ability for antibody-drug conjugates to have cytostatic or cytotoxic effects. Despite years of development, improved antibody-drug conjugates are desired.

SUMMARY

The present invention is based on the concept that antigen-binding protein constructs can be generated that display enhanced efficacy (e.g., one or more of an increase (e.g., a detectable increase) in toxin liberation in a target mammalian cell, an increase (e.g., a detectable increase) in target mammalian cell killing, and an increase (e.g., a detectable increase) in endolysosomal delivery).

Provided herein are pharmaceutical compositions including an effective amount of an antigen-binding protein construct (ABPC) including a first antigen-binding domain that is capable of specifically binding FOLR1 or an epitope of FOLR1 presented on the surface of a target mammalian cell, where (a) the dissociation rate of the first antigen-binding domain at a pH of about 4.0 to about 6.5 is faster than the dissociation rate at a pH of about 7.0 to about 8.0 or (b) the dissociation constant (KD) of the first antigen-binding domain at a pH of about 4.0 to about 6.5 is greater than the KD at a pH of about 7.0 to about 8.0.

In some embodiments of any of the pharmaceutical compositions described herein, the ABPC is degraded in the target mammalian cell following internalization of the ABPC by the target mammalian cell.

In some embodiments of any of the pharmaceutical compositions described herein, the ABPC includes a conjugated toxin, radioisotope, drug, or small molecule.

Also provided herein are pharmaceutical compositions including an effective amount of an antigen-binding protein construct (ABPC) including: a first antigen-binding domain that is capable of specifically binding FOLR1 or an epitope of FOLR1 presented on the surface of a target mammalian cell; and a conjugated toxin, radioisotope, drug, or small molecule, where (a) the dissociation rate of the first antigen-binding domain at a pH of about 4.0 to about 6.5 is faster than the dissociation rate at a pH of about 7.0 to about 8.0 or the dissociation constant (KD) of the first antigen-binding domain at a pH of about 4.0 to about 6.5 is greater than the KD at a pH of about 7.0 to about 8.0 and (b) the composition provides for one or more of an increase in toxin liberation in the target mammalian cell as compared to a composition including the same amount of a control ABPC, an increase in target mammalian cell killing as compared to a composition including the same amount of a control ABPC, and an increase in endolysosomal delivery in the target mammalian cell as compared to a composition including the same amount of a control ABPC.

In some embodiments of any of the pharmaceutical compositions described herein, the first antigen-binding domain includes one of (a) through (c): (a) a heavy chain variable domain of mirvetuximab with one or more amino acids substituted with a histidine, where the heavy chain variable domain of mirvetuximab includes SEQ ID NO: 1, and/or a light chain variable domain of mirvetuximab with one or more amino acids substituted with a histidine, where the light chain variable domain of mirvetuximab includes SEQ ID NO: 2, (b) a heavy chain variable domain of STRO-002 with one or more amino acids substituted with a histidine, where the heavy chain variable domain of STRO-002 includes SEQ ID NO: 105, and/or a light chain variable domain of STRO-002 with one or more amino acids substituted with a histidine, where the light chain variable domain of STRO-002 includes SEQ ID NO: 106, (c) a heavy chain variable domain of farletuzumab with one or more amino acids substituted with a histidine, where the heavy chain variable domain of farletuzumab includes SEQ ID NO: 184; and/or a light chain variable domain of farletuzumab with one or more amino acids substituted with a histidine, where the light chain variable domain of farletuzumab includes SEQ ID NO: 185.

In some embodiments of any of the pharmaceutical compositions described herein, the first FOLR1-binding domain includes one of (a) through (c): (a) a heavy chain variable domain including a CDR1, a CDR2, and a CDR3 of SEQ ID NOs: 3-5, respectively, with collectively a total of one or more amino acid positions in SEQ ID NOs: 3-5 substituted with a histidine; and/or a light chain variable domain including a CDR1, a CDR2, and a CDR3 of SEQ ID NOs: 6-8, respectively, with collectively a total of one or more amino acid positions in SEQ ID NOs: 6-8 substituted with a histidine; (b) a heavy chain variable domain including a CDR1, a CDR2, and a CDR3 of SEQ ID NOs: 107-109 respectively, with collectively a total of one or more amino acid positions in SEQ ID NOs: 107-109 substituted with a histidine; and/or a light chain variable domain including a CDR1, a CDR2, and a CDR3 of SEQ ID NOs: 110-112, respectively, with collectively a total of one or more amino acid positions in SEQ ID NOs: 110-112 substituted with a histidine; (c) a heavy chain variable domain including a CDR1, a CDR2, and a CDR3 of SEQ ID NOs: 186-188, respectively, with collectively a total of one or more amino acid positions in SEQ ID NOs: 186-188 substituted with a histidine; and a light chain variable domain including a CDR1, a CDR2, and a CDR3 of SEQ ID NOs: 189-191, respectively, with collectively a total of one or more amino acid positions in SEQ ID NOs: 189-191 substituted with a histidine.

In some embodiments of any of the pharmaceutical compositions described herein, the first antigen-binding domain includes one of (a) through (c): (a) a heavy chain variable domain that is at least 90% identical to SEQ ID NO: 1, where the heavy chain variable domain includes a histidine at one or more positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107; and/or a light chain variable domain that is at least 90% identical to SEQ ID NO: 2, where the light chain variable domain includes a histidine at one or more positions in SEQ ID NO: 2 selected from the group consisting of: 28, 30, 31, 32, 34, 35, 36, 55, 59, 93, 94, 95, 96, 97, 98, and 100; (b) a heavy chain variable domain that is at least 90% identical to SEQ ID NO: 105, where the heavy chain variable domain includes a histidine at one or more positions in SEQ ID NO: 105 selected from the group consisting of: 29, 33, 34, 50, 51, 52, 53, 55, 56, 57, 101, 102, 103, 108, 109, 110, 111, 112, and 113; and a light chain variable domain that is at least 90% identical to SEQ ID NO: 106, where the light chain variable domain includes a histidine at one or more positions in SEQ ID NO: 106 selected from the group consisting of: 28, 29, 30, 31, 50, 92, 93, 94, 95, and 96; (c) a heavy chain variable domain that is at least 90% identical to SEQ ID NO: 184, where the heavy chain variable domain includes a histidine at one or more positions in SEQ ID NO: 184 selected from the group consisting of: 26, 27, 28, 29, 30, 32, 33, 34, 53, 56, 57, 59, 62, 63, 103, and 105; and/or a light chain variable domain that is at least 90% identical to SEQ ID NO: 185, where the light chain variable domain includes a histidine at one or more positions in SEQ ID NO: 185 selected from the group consisting of 29, 33, 34, 51, 52, 53, 54, 55, 90, 92, 94, 96, 97, 98, 99, and 100.

In some embodiments of any of the pharmaceutical compositions described herein, the first antigen-binding domain includes one of (a) through (c): (a) a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83, and/or a heavy chain variable domain of SEQ ID NO: 1, SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 36, SEQ ID NO: 43, SEQ ID NO: 44, SEQ ID NO: 45, SEQ ID NO: 46, SEQ ID NO: 48, SEQ ID NO: 49, SEQ ID NO: 51, SEQ ID NO: 53, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103, where the first antigen-binding domain does not comprise (i) a light chain variable domain of SEQ ID NO: 2 and heavy chain variable domain of SEQ ID NO: 1; (ii) a light chain variable domain of SEQ ID NO: 2 and heavy chain variable domain that is not one of SEQ ID NOs: 14, 17, 19, 21-24, 26, 28, 30, 31, 33-36, 43-46, 48, 49, 51, 53, and 85-103; (iii) a heavy chain variable domain of SEQ ID NO: 1 and a light chain variable domain that is not one of SEQ ID NOs: 58, 60-62, 64-66, 68, 70, 74, 76-81 and 83; and/or (b) a light chain variable domain of SEQ ID NO: 106, SEQ ID NO: 161, SEQ ID NO: 162, SEQ ID NO: 163, SEQ ID NO: 164, SEQ ID NO: 168, SEQ ID NO: 177, SEQ ID NO: 178, SEQ ID NO: 179, SEQ ID NO: 180, SEQ ID NO: 181, or SEQ ID NO: 182, and/or a heavy chain variable domain of SEQ ID NO: 105, SEQ ID NO: 116, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 128, SEQ ID NO: 129, SEQ ID NO: 130, SEQ ID NO: 144, SEQ ID NO: 145, SEQ ID NO: 146, SEQ ID NO: 151, SEQ ID NO: 152, SEQ ID NO: 153, SEQ ID NO: 154, SEQ ID NO: 155, or SEQ ID NO: 156; where the first antigen-binding domain does not comprise (i) a light chain variable domain of SEQ ID NO: 106 and a heavy chain variable domain of SEQ ID NO: 105; (ii) a light chain variable domain of SEQ ID NO: 106 and a heavy chain variable domain that is not one of SEQ ID NOs: 116, 120-126,128-130, 144-146, and 151-156; (iii) a heavy chain variable domain of SEQ ID NO: 105 and a light chain variable domain that is not one of SEQ ID NOs: 161-164, 168, and 177-182; (c) a light chain variable domain of SEQ ID NO: 185, SEQ ID NO: 233, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 247, SEQ ID NO: 249, SEQ ID NO: 251, SEQ ID NO: 253, SEQ ID NO: 254, SEQ ID NO: 255, SEQ ID NO: 256, or SEQ ID NO: 257, and/or a heavy chain variable domain of SEQ ID NO: 184, SEQ ID NO: 192, SEQ ID NO: 193, SEQ ID NO: 194, SEQ ID NO: 195, SEQ ID NO: 196, SEQ ID NO: 198, SEQ ID NO: 199, SEQ ID NO: 200, SEQ ID NO: 205, SEQ ID NO: 208, SEQ ID NO: 209, SEQ ID NO: 211, SEQ ID NO: 214, SEQ ID NO: 215, SEQ ID NO: 221, SEQ ID NO: 225, or SEQ ID NO: 227, where the first antigen-binding domain does not comprise (i) a light chain variable domain of SEQ ID NO: 185 and a heavy chain variable domain of SEQ ID NO: 184; (ii) a light chain variable domain of SEQ ID NO: 185 and a heavy chain variable domain that is not one of SEQ ID NOs: 192-196, 198-200, 205, 208, 209, 211, 214, 215, 221, 225 and 227; (iii) a heavy chain variable domain of SEQ ID NO: 184 and a light chain variable domain that is not one of SEQ ID NOs: 233, 237-244, 247, 249, 251, and 253-257.

In some embodiments of any of the pharmaceutical compositions described herein, the composition provides for an increase in toxin liberation in the target mammalian cell as compared to a composition including the same amount of a control ABPC; and/or an increase in target mammalian cell killing as compared to a composition including the same amount of a control ABPC.

In some embodiments of any of the pharmaceutical compositions described herein, the composition provides for an increase in endolysosomal delivery in the target mammalian cell as compared to a composition including the same amount of a control ABPC.

In some embodiments of any of the pharmaceutical compositions described herein, the composition: results in a less of a reduction in the level of FOLR1 presented on the surface of the target mammalian cell as compared to a composition including the same amount of a control ABPC; or does not result in a detectable reduction in the level of FOLR1 presented on the surface of the target mammalian cell.

In some embodiments of any of the pharmaceutical compositions described herein, the target mammalian cell is a cancer cell. In some embodiments of any of the pharmaceutical compositions described herein, the ABPC is cytotoxic or cytostatic to the target mammalian cell.

In some embodiments of any of the pharmaceutical compositions described herein, the ABPC is cross-reactive with a non-human primate FOLR1 and human FOLR1 or cross-reactive with a non-human primate FOLR1, a human FOLR1, and one or both of rat FOLR1 and a mouse FOLR1.

In some embodiments of any of the pharmaceutical compositions described herein, the ABPC includes a single polypeptide. In some embodiments of any of the pharmaceutical compositions described herein, the antigen-binding domain is selected from the group consisting of: a VH domain, a VHH domain, a VNAR domain, and a scFv. In some embodiments of any of the pharmaceutical compositions described herein, the ABPC includes two or more polypeptides. In some embodiments of any of the pharmaceutical compositions described herein, the ABPC is an antibody.

In some embodiments of any of the pharmaceutical compositions described herein, the half-life of the ABPC in vivo is decreased as compared to the half-life of a control ABPC in vivo.

In some embodiments of any of the pharmaceutical compositions described herein, the ABPC includes a second antigen-binding domain.

Also provided herein are an antigen-binding protein constructs (ABPCs) including a first antigen-binding domain that is capable of specifically binding FOLR1 or an epitope of FOLR1 presented on the surface of a target mammalian cell, where: (a) the dissociation rate of the first antigen-binding domain at a pH of about 4.0 to about 6.5 is faster than the dissociation rate at a pH of about 7.0 to about 8.0; or (b) the dissociation constant (KD) of the first antigen-binding domain at a pH of about 4.0 to about 6.5 is greater than the KD at a pH of about 7.0 to about 8.0.

In some embodiments of any of the ABCPs described herein, the ABPC is degraded in the target mammalian cell following internalization of the ABPC by the target mammalian cell. In some embodiments of any of the ABCPs described herein, the ABPC includes a conjugated toxin, radioisotope, drug, or small molecule.

Also provided herein are an antigen-binding protein constructs (ABPCs) including: a first antigen-binding domain that is capable of specifically binding FOLR1 or an epitope of FOLR1 presented on the surface of a target mammalian cell; and a conjugated toxin, radioisotope, drug, or small molecule, where: (a) the dissociation rate of the first antigen-binding domain at a pH of about 4.0 to about 6.5 is faster than the dissociation rate at a pH of about 7.0 to about 8.0; or the dissociation constant (KD) of the first antigen-binding domain at a pH of about 4.0 to about 6.5 is greater than the KD at a pH of about 7.0 to about 8.0; and (b) the composition provides for one or more of: an increase in toxin liberation in the target mammalian cell as compared to a composition including the same amount of a control ABPC; an increase in target mammalian cell killing as compared to a composition including the same amount of a control ABPC; and an increase in endolysosomal delivery in the target mammalian cell as compared to a composition including the same amount of a control ABPC.

In some embodiments of any of the ABCPs described herein, the first antigen-binding domain includes one of (a) through (c): (a) a heavy chain variable domain of mirvetuximab with one or more amino acids substituted with a histidine, where the heavy chain variable domain of mirvetuximab includes SEQ ID NO: 1; and/or a light chain variable domain of mirvetuximab with one or more amino acids substituted with a histidine, where the light chain variable domain of mirvetuximab includes SEQ ID NO: 2; (b) a heavy chain variable domain of STRO-002 with one or more amino acids substituted with a histidine, where the heavy chain variable domain of STRO-002 includes SEQ ID NO: 105; and/or a light chain variable domain of STRO-002 with one or more amino acids substituted with a histidine, where the light chain variable domain of STRO-002 includes SEQ ID NO: 106; (c) a heavy chain variable domain of farletuzumab with one or more amino acids substituted with a histidine, where the heavy chain variable domain of farletuzumab includes SEQ ID NO: 184; and/or a light chain variable domain of farletuzumab with one or more amino acids substituted with a histidine, where the light chain variable domain of farletuzumab includes SEQ ID NO: 185.

In some embodiments of any of the ABCPs described herein, the first FOLR1-binding domain includes one of (a) through (c): (a) a heavy chain variable domain including a CDR1, a CDR2, and a CDR3 of SEQ ID NOs: 3-5, respectively, with collectively a total of one or more amino acid positions in SEQ ID NOs: 3-5 substituted with a histidine; and/or a light chain variable domain including a CDR1, a CDR2, and a CDR3 of SEQ ID NOs: 6-8, respectively, with collectively a total of one or more amino acid positions in SEQ ID NOs: 6-8 substituted with a histidine; (b) a heavy chain variable domain including a CDR1, a CDR2, and a CDR3 of SEQ ID NOs: 107-109, respectively, with collectively a total of one or more amino acid positions in SEQ ID NOs: 107-109 substituted with a histidine; and/or a light chain variable domain including a CDR1, a CDR2, and a CDR3 of SEQ ID NOs: 110-112, respectively, with collectively a total of one or more amino acid positions in SEQ ID NOs: 110-112 substituted with a histidine; (c) a heavy chain variable domain including a CDR1, a CDR2, and a CDR3 of SEQ ID NOs: 186-188, respectively, with collectively a total of one or more amino acid positions in SEQ ID NOs: 186-188 substituted with a histidine; and/or a light chain variable domain including a CDR1, a CDR2, and a CDR3 of SEQ ID NOs: 189-191, respectively, with collectively a total of one or more amino acid positions in SEQ ID NOs: 189-191 substituted with a histidine.

In some embodiments of any of the ABCPs described herein, the first antigen-binding domain includes one of (a) through (c): (a) a heavy chain variable domain that is at least 90% identical to SEQ ID NO: 1, where the heavy chain variable domain includes a histidine at one or more positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107; and/or a light chain variable domain that is at least 90% identical to SEQ ID NO: 2, where the light chain variable domain includes a histidine at one or more positions in SEQ ID NO: 2 selected from the group consisting of: 28, 30, 31, 32, 34, 35, 36, 55, 59, 93, 94, 95, 96, 97, 98, and 100; (b) a heavy chain variable domain that is at least 90% identical to SEQ ID NO: 105, where the heavy chain variable domain includes a histidine at one or more positions in SEQ ID NO: 105 selected from the group consisting of: 29, 33, 34, 50, 51, 52, 53, 55, 56, 57, 101, 102, 103, 108, 109, 110, 111, 112, and 113; and/or a light chain variable domain that is at least 90% identical to SEQ ID NO: 106, where the light chain variable domain includes a histidine at one or more positions in SEQ ID NO: 106 selected from the group consisting of: 28, 29, 30, 31, 50, 92, 93, 94, 95, and 96; (c) a heavy chain variable domain that is at least 90% identical to SEQ ID NO: 184, where the heavy chain variable domain includes a histidine at one or more positions in SEQ ID NO: 184 selected from the group consisting of: 26, 27, 28, 29, 30, 32, 33, 34, 53, 56, 57, 59, 62, 63, 103, and 105; and/or a light chain variable domain that is at least 90% identical to SEQ ID NO: 185, where the light chain variable domain includes a histidine at one or more positions in SEQ ID NO: 185 selected from the group consisting of: 29, 33, 34, 51, 52, 53, 54, 55, 90, 92, 94, 96, 97, 98, 99, and 100.

In some embodiments of any of the ABCPs described herein, the first antigen-binding domain includes one of (a) through (c): (a) a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO:

66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83, and/or a heavy chain variable domain of SEQ ID NO: 1, SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 36, SEQ ID NO: 43, SEQ ID NO: 44, SEQ ID NO: 45, SEQ ID NO: 46, SEQ ID NO: 48, SEQ ID NO: 49, SEQ ID NO: 51, SEQ ID NO: 53, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103; where the first antigen-binding domain does not comprise (i) a light chain variable domain of SEQ ID NO: 2 and heavy chain variable domain of SEQ ID NO: 1; (ii) a light chain variable domain of SEQ ID NO: 2 and heavy chain variable domain that is not one of SEQ ID NOs: 14, 17, 19, 21-24, 26, 28, 30, 31, 33-36, 43-46, 48, 49, 51, 53, and 85-103; (iii) a heavy chain variable domain of SEQ ID NO: 1 and a light chain variable domain that is not one of SEQ ID NOs: 58, 60-62, 64-66, 68, 70, 74, 76-81 and 83; and/or (b) a light chain variable domain of SEQ ID NO: 106, SEQ ID NO: 161, SEQ ID NO: 162, SEQ ID NO: 163, SEQ ID NO: 164, SEQ ID NO: 168, SEQ ID NO: 177, SEQ ID NO: 178, SEQ ID NO: 179, SEQ ID NO: 180, SEQ ID NO: 181, or SEQ ID NO: 182, and/or a heavy chain variable domain of SEQ ID NO: 105, SEQ ID NO: 116, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 128, SEQ ID NO: 129, SEQ ID NO: 130, SEQ ID NO: 144, SEQ ID NO: 145, SEQ ID NO: 146, SEQ ID NO: 151, SEQ ID NO: 152, SEQ ID NO: 153, SEQ ID NO: 154, SEQ ID NO: 155, or SEQ ID NO: 156; where the first antigen-binding domain does not comprise (i) a light chain variable domain of SEQ ID NO: 106 and a heavy chain variable domain of SEQ ID NO: 105; (ii) a light chain variable domain of SEQ ID NO: 106 and a heavy chain variable domain that is not one of SEQ ID NOs: 116, 120-126,128-130, 144-146, and 151-156; (iii) a heavy chain variable domain of SEQ ID NO: 105 and a light chain variable domain that is not one of SEQ ID NOs: 161-164, 168, and 177-182; (c) a light chain variable domain of SEQ ID NO: 185, SEQ ID NO: 233, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 247, SEQ ID NO: 249, SEQ ID NO: 251, SEQ ID NO: 253, SEQ ID NO: 254, SEQ ID NO: 255, SEQ ID NO: 256, or SEQ ID NO: 257 and/or a heavy chain variable domain of SEQ ID NO: 184, SEQ ID NO: 192, SEQ ID NO: 193, SEQ ID NO: 194, SEQ ID NO: 195, SEQ ID NO: 196, SEQ ID NO: 198, SEQ ID NO: 199, SEQ ID NO: 200, SEQ ID NO: 205, SEQ ID NO: 208, SEQ ID NO: 209, SEQ ID NO: 211, SEQ ID NO: 214, SEQ ID NO: 215, SEQ ID NO: 221, SEQ ID NO: 225, or SEQ ID NO: 227, where the first antigen-binding domain does not comprise (i) a light chain variable domain of SEQ ID NO: 185 and a heavy chain variable domain of SEQ ID NO: 184; (ii) a light chain variable domain of SEQ ID NO: 185 and a heavy chain variable domain that is not one of SEQ ID NOs: 192-196, 198-200, 205, 208, 209, 211, 214, 215, 221, 225 and 227; (iii) a heavy chain variable domain of SEQ ID NO: 184 and a light chain variable domain that is not one of SEQ ID NOs: 233, 237-244, 247, 249, 251, and 253-257.

In some embodiments of any of the ABCPs described herein, a composition including the ABPC provides for an increase in toxin liberation in the target mammalian cell as compared to a composition including the same amount of a control ABPC; and/or an increase in target mammalian cell killing as compared to a composition including the same amount of a control ABPC.

In some embodiments of any of the ABCPs described herein, a composition including the ABPC provides for an increase in endolysosomal delivery in the target mammalian cell as compared to a composition including the same amount of a control ABPC.

In some embodiments of any of the ABCPs described herein, a composition including the ABPC results in a less of a reduction in the level of FOLR1 presented on the surface of the target mammalian cell as compared to a composition including the same amount of a control ABPC; or does not result in a detectable reduction in the level of FOLR1 presented on the surface of the target mammalian cell.

In some embodiments of any of the ABCPs described herein, the target mammalian cell is a cancer cell. In some embodiments of any of the ABCPs described herein, the ABPC is cytotoxic or cytostatic to the target mammalian cell.

In some embodiments of any of the ABCPs described herein, the ABPC is cross-reactive with a non-human primate FOLR1 and human FOLR1 or cross-reactive with a non-human primate FOLR1, a human FOLR1, and one or both of rat FOLR1 and a mouse FOLR1.

In some embodiments of any of the ABCPs described herein, the ABPC includes a single polypeptide.

In some embodiments of any of the ABCPs described herein, the antigen-binding domain is selected from the group consisting of: a VH domain, a VHH domain, a VNAR domain, and a scFv. In some embodiments of any of the ABCPs described herein, the ABPC includes two or more polypeptides. In some embodiments of any of the ABCPs described herein, the ABPC is an antibody.

In some embodiments of any of the ABCPs described herein, the half-life of the ABPC in vivo is decreased as compared to the half-life of a control ABPC in vivo.

In some embodiments of any of the ABCPs described herein, the ABPC includes a second antigen-binding domain.

Also provided herein are kits including at least one dose of the pharmaceutical composition of any one of the pharmaceutical compositions described herein or any one of the ABPCs described herein.

Also provided herein are methods of treating a cancer characterized by having a population of cancer cells that have FOLR1 or an epitope of FOLR1 presented on their surface, the method including, administering a therapeutically effective amount of any of the pharmaceutical-compositions described herein or any of the ABPCs described herein to a subject identified as having a cancer characterized by having the population of cancer cells.

Also provided herein are methods of reducing the volume of a tumor in a subject, where the tumor is characterized by having a population of cancer cells that have FOLR1 or an epitope of FOLR1 presented on their surface, the method including, administering a therapeutically effective amount of any of the pharmaceutical compositions described herein or any of the ABPCs described herein to a subject identified as having a cancer characterized by having the population of cancer cells.

Also provided herein are methods of inducing cell death in a cancer cell in a subject, where the cancer cell has FOLR1 or an epitope of FOLR1 presented on its surface, where the method includes, administering a therapeutically effective amount of any of the pharmaceutical compositions described herein or any of the ABPCs described herein to a subject identified as having a cancer characterized by having a population of the cancer cells.

Also provided herein are methods of decreasing the risk of developing a metastasis or decreasing the risk of developing an additional metastasis in a subject having a cancer, where the cancer is characterized by having a population of cancer cells that have FOLR1 or an epitope of FOLR1 presented on their surface the method including, administering a therapeutically effective amount of any of the pharmaceutical compositions described herein or any of the ABPCs described herein to a subject identified as having a cancer characterized by having the population of cancer cells.

Provided herein are pharmaceutical compositions including an effective amount of an antigen-binding protein construct (ABPC) including a first antigen-binding domain that is capable of specifically binding FOLR1 or an epitope of FOLR1 presented on the surface of a target mammalian cell, where (a) the dissociation rate of the first antigen-binding domain at a pH of about 4.0 to about 6.5 is faster than the dissociation rate at a pH of about 7.0 to about 8.0 or (b) the dissociation constant (KD) of the first antigen-binding domain at a pH of about 4.0 to about 6.5 is greater than the KD at a pH of about 7.0 to about 8.0.

In some embodiments of any of the pharmaceutical compositions described herein, the ABPC is degraded in the target mammalian cell following internalization of the ABPC by the target mammalian cell.

In some embodiments of any of the pharmaceutical compositions described herein, the ABPC includes a conjugated toxin, radioisotope, drug, or small molecule.

Also provided herein are pharmaceutical compositions including an effective amount of an antigen-binding protein construct (ABPC) including: a first antigen-binding domain that is capable of specifically binding FOLR1 or an epitope of FOLR1 presented on the surface of a target mammalian cell; and a conjugated toxin, radioisotope, drug, or small molecule, where (a) the dissociation rate of the first antigen-binding domain at a pH of about 4.0 to about 6.5 is faster than the dissociation rate at a pH of about 7.0 to about 8.0 or the dissociation constant (KD) of the first antigen-binding domain at a pH of about 4.0 to about 6.5 is greater than the KD at a pH of about 7.0 to about 8.0 and (b) the composition provides for one or more of an increase in toxin liberation in the target mammalian cell as compared to a composition including the same amount of a control ABPC, an increase in target mammalian cell killing as compared to a composition including the same amount of a control ABPC, and an increase in endolysosomal delivery in the target mammalian cell as compared to a composition including the same amount of a control ABPC.

In some embodiments of any of the pharmaceutical compositions described herein, the first antigen-binding domain includes one of (a) through (c): (a) a heavy chain variable domain of mirvetuximab with one or more amino acids substituted with a histidine, where the heavy chain variable domain of mirvetuximab includes SEQ ID NO: 1, and/or a light chain variable domain of mirvetuximab with one or more amino acids substituted with a histidine, where the light chain variable domain of mirvetuximab includes SEQ ID NO: 2, (b) a heavy chain variable domain of STRO-002 with one or more amino acids substituted with a histidine, where the heavy chain variable domain of STRO-002 includes SEQ ID NO: 105, and/or a light chain variable domain of STRO-002 with one or more amino acids substituted with a histidine, where the light chain variable domain of STRO-002 includes SEQ ID NO: 106, (c) a heavy chain variable domain of farletuzumab with one or more amino acids substituted with a histidine, where the heavy chain variable domain of farletuzumab includes SEQ ID NO: 184; and/or a light chain variable domain of farletuzumab with one or more amino acids substituted with a histidine, where the light chain variable domain of farletuzumab includes SEQ ID NO: 185.

In some embodiments of any of the pharmaceutical compositions described herein, the first FOLR1-binding domain includes one of (a) through (c): (a) a heavy chain variable domain including a CDR1, a CDR2, and a CDR3 of SEQ ID NOs: 3-5, respectively, with collectively a total of one or more amino acid positions in SEQ ID NOs: 3-5 substituted with a histidine; and/or a light chain variable domain including a CDR1, a CDR2, and a CDR3 of SEQ ID NOs: 6-8, respectively, with collectively a total of one or more amino acid positions in SEQ ID NOs: 6-8 substituted with a histidine; (b) a heavy chain variable domain including a CDR1, a CDR2, and a CDR3 of SEQ ID NOs: 107-109 respectively, with collectively a total of one or more amino acid positions in SEQ ID NOs: 107-109 substituted with a histidine; and/or a light chain variable domain including a CDR1, a CDR2, and a CDR3 of SEQ ID NOs: 110-112, respectively, with collectively a total of one or more amino acid positions in SEQ ID NOs: 110-112 substituted with a histidine; (c) a heavy chain variable domain including a CDR1, a CDR2, and a CDR3 of SEQ ID NOs: 186-188, respectively, with collectively a total of one or more amino acid positions in SEQ ID NOs: 186-188 substituted with a histidine; and a light chain variable domain including a CDR1, a CDR2, and a CDR3 of SEQ ID NOs: 189-191, respectively, with collectively a total of one or more amino acid positions in SEQ ID NOs: 189-191 substituted with a histidine.

In some embodiments of any of the pharmaceutical compositions described herein, the first antigen-binding domain includes one of (a) through (c): (a) a heavy chain variable domain that is at least 90% identical to SEQ ID NO: 1, where the heavy chain variable domain includes a histidine at one or more positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107; and/or a light chain variable domain that is at least 90% identical to SEQ ID NO: 2, where the light chain variable domain includes a histidine at one or more positions in SEQ ID NO: 2 selected from the group consisting of: 28, 30, 31, 32, 34, 35, 36, 55, 59, 93, 94, 95, 96, 97, 98, and 100; (b) a heavy chain variable domain that is at least 90% identical to SEQ ID NO: 105, where the heavy chain variable domain includes a histidine at one or more positions in SEQ ID NO: 105 selected from the group consisting of: 29, 33, 34, 50, 51, 52, 53, 55, 56, 57, 101, 102, 103, 108, 109, 110, 111, 112, and 113; and a light chain variable domain that is at least 90% identical to SEQ ID NO: 106, where the light chain variable domain includes a histidine at one or more positions in SEQ ID NO: 106 selected from the group consisting of: 28, 29, 30, 31, 50, 92, 93, 94, 95, and 96; (c) a heavy chain variable domain that is at least 90% identical to SEQ ID NO: 184, where the heavy chain variable domain includes a histidine at one or more positions in SEQ ID NO: 184 selected from the group consisting of: 26, 27, 28, 29, 30, 32, 33, 34, 53, 56, 57, 59, 62, 63, 103, and 105; and/or a light chain variable domain that is at least 90% identical to SEQ ID NO: 185, where the light chain variable domain includes a histidine at one or more positions in SEQ ID NO: 185 selected from the group consisting of 29, 33, 34, 51, 52, 53, 54, 55, 90, 92, 94, 96, 97, 98, 99, and 100.

In some embodiments of any of the pharmaceutical compositions described herein, the first antigen-binding domain includes one of (a) through (c): (a) a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83, and/or a heavy chain variable domain of SEQ ID NO: 1, SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 36, SEQ ID NO: 43, SEQ ID NO: 44, SEQ ID NO: 45, SEQ ID NO: 46, SEQ ID NO: 48, SEQ ID NO: 49, SEQ ID NO: 51, SEQ ID NO: 53, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103, where the first antigen-binding domain does not comprise (i) a light chain variable domain of SEQ ID NO: 2 and heavy chain variable domain of SEQ ID NO: 1; (ii) a light chain variable domain of SEQ ID NO: 2 and heavy chain variable domain that is not one of SEQ ID NOs: 14, 17, 19, 21-24, 26, 28, 30, 31, 33-36, 43-46, 48, 49, 51, 53, and 85-103; (iii) a heavy chain variable domain of SEQ ID NO: 1and a light chain variable domain that is not one of SEQ ID NOs: 58, 60-62, 64-66, 68, 70, 74, 76-81 and 83; and/or (b) a light chain variable domain of SEQ ID NO: 106, SEQ ID NO: 161, SEQ ID NO: 162, SEQ ID NO: 163, SEQ ID NO: 164, SEQ ID NO: 168, SEQ ID NO: 177, SEQ ID NO: 178, SEQ ID NO: 179, SEQ ID NO: 180, SEQ ID NO: 181, or SEQ ID NO: 182, and/or a heavy chain variable domain of SEQ ID NO: 105, SEQ ID NO: 116, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 128, SEQ ID NO: 129, SEQ ID NO: 130, SEQ ID NO: 144, SEQ ID NO: 145, SEQ ID NO: 146, SEQ ID NO: 151, SEQ ID NO: 152, SEQ ID NO: 153, SEQ ID NO: 154, SEQ ID NO: 155, or SEQ ID NO: 156; where the first antigen-binding domain does not comprise (i) a light chain variable domain of SEQ ID NO: 106 and a heavy chain variable domain of SEQ ID NO: 105; (ii) a light chain variable domain of SEQ ID NO: 106 and a heavy chain variable domain that is not one of SEQ ID NOs: 105, 116, 120-126, 128-130, 144-146, and 151-156; (iii) a heavy chain variable domain of SEQ ID NO: 105 and a light chain variable domain that is not one of SEQ ID NOs: 161-164, 168, and 177-182; (c) a light chain variable domain of SEQ ID NO: 185, SEQ ID NO: 233, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 247, SEQ ID NO: 249, SEQ ID NO: 251, SEQ ID NO: 253, SEQ ID NO: 254, SEQ ID NO: 255, SEQ ID NO: 256, or SEQ ID NO: 257, and/or a heavy chain variable domain of SEQ ID NO: 184, SEQ ID NO: 192, SEQ ID NO: 193, SEQ ID NO: 194, SEQ ID NO: 195, SEQ ID NO: 196, SEQ ID NO: 198, SEQ ID NO: 199, SEQ ID NO: 200, SEQ ID NO: 205, SEQ ID NO: 208, SEQ ID NO: 209, SEQ ID NO: 211, SEQ ID NO: 214, SEQ ID NO: 215, SEQ ID NO: 221, SEQ ID NO: 225, or SEQ ID NO: 227, where the first antigen-binding domain does not comprise (i) a light chain variable domain of SEQ ID NO: 185 and a heavy chain variable domain of SEQ ID NO: 184; (ii) a light chain variable domain of SEQ ID NO: 185 and a heavy chain variable domain that is not one of SEQ ID NOs: 184, 192-196, 198-200, 205, 208, 209, 211, 214, 215, 221, 225 and 227; (iii) a heavy chain variable domain of SEQ ID NO: 184 and alight chain variable domain that is not one of SEQ ID NOs: 233, 237-244, 247, 249, 251, and 253-257.

In some embodiments of any of the pharmaceutical compositions described herein, the composition provides for an increase in toxin liberation in the target mammalian cell as compared to a composition including the same amount of a control ABPC; and/or an increase in target mammalian cell killing as compared to a composition including the same amount of a control ABPC.

In some embodiments of any of the pharmaceutical compositions described herein, the composition provides for an increase in endolysosomal delivery in the target mammalian cell as compared to a composition including the same amount of a control ABPC.

In-some embodiments of any of the pharmaceutical compositions described herein, the composition results in a less of a reduction in the level of FOLR1 presented on the surface of the target mammalian cell as compared to a composition including the same amount of a control ABPC or does not result in a detectable reduction in the level of FOLR1 presented on the surface of the target mammalian cell.

In some embodiments of any of the pharmaceutical compositions described herein, the target mammalian cell is a cancer cell. In some embodiments of any of the pharmaceutical compositions described herein, the ABPC is cytotoxic or cytostatic to the target mammalian cell.

In some embodiments of any of the pharmaceutical compositions described herein, the ABPC is cross-reactive with a non-human primate FOLR1 and human FOLR1 or cross-reactive with a non-human primate FOLR1, a human FOLR1, and one or both of rat FOLR1 and a mouse FOLR1.

In some embodiments of any of the pharmaceutical compositions described herein, the ABPC includes a single polypeptide. In some embodiments of any of the pharmaceutical compositions described herein, the antigen-binding domain is selected from the group consisting of: a VH domain, a VHH domain, a VNAR domain, and a scFv. In some embodiments of any of the pharmaceutical compositions described herein, the ABPC includes two or more polypeptides. In some embodiments of any of the pharmaceutical compositions described herein, the ABPC is an antibody.

In some embodiments of any of the pharmaceutical compositions described herein, the half-life of the ABPC in vivo is decreased as compared to the half-life of a control ABPC in vivo.

In some embodiments of any of the pharmaceutical compositions described herein, the ABPC includes a second antigen-binding domain.

Also provided herein are antigen-binding protein constructs (ABPCs) including a first antigen-binding domain that is capable of specifically binding FOLR1 or an epitope of FOLR1 presented on the surface of a target mammalian cell, where (a) the dissociation rate of the first antigen-binding domain at a pH of about 4.0 to about 6.5 is faster than the dissociation rate at a pH of about 7.0 to about 8.0; or (b) the dissociation constant (KD) of the first antigen-binding domain at a pH of about 4.0 to about 6.5 is greater than the KD at a pH of about 7.0 to about 8.0.

In some embodiments of any of the ABPCs described herein, the ABPC is degraded in the target mammalian cell following internalization of the ABPC by the target mammalian cell.

In some embodiments of any of the ABPCs described herein, the ABPC includes a conjugated toxin, radioisotope, drug, or small molecule.

Also provided herein are an antigen-binding protein constructs (ABPCs) including a first antigen-binding domain that is capable of specifically binding FOLR1 or an epitope of FOLR1 presented on the surface of a target mammalian cell; and a conjugated toxin, radioisotope, drug, or small molecule, where: (a) the dissociation rate of the first antigen-binding domain at a pH of about 4.0 to about 6.5 is faster than the dissociation rate at a pH of about 7.0 to about 8.0; or the dissociation constant (KD) of the first antigen-binding domain at a pH of about 4.0 to about 6.5 is greater than the KD at a pH of about 7.0 to about 8.0; and (b) the composition provides for one or more of: an increase in toxin liberation in the target mammalian cell as compared to a composition including the same amount of a control ABPC; an increase in target mammalian cell killing as compared to a composition including the same amount of a control ABPC; and an increase in endolysosomal delivery in the target mammalian cell as compared to a composition including the same amount of a control ABPC.

In some embodiments of any of the ABPCs described herein, the first antigen-binding domain includes one of (a) through (c): (a) a heavy chain variable domain of mirvetuximab with one or more amino acids substituted with a histidine, where the heavy chain variable domain of mirvetuximab includes SEQ ID NO: 1; and/or a light chain variable domain of mirvetuximab with one or more amino acids substituted with a histidine, where the light chain variable domain of mirvetuximab includes SEQ ID NO: 2; (b) a heavy chain variable domain of STRO-002 with one or more amino acids substituted with a histidine, where the heavy chain variable domain of STRO-002 includes SEQ ID NO: 105; and/or a light chain variable domain of STRO-002 with one or more amino acids substituted with a histidine, where the light chain variable domain of STRO-002 includes SEQ ID NO: 106; (c) a heavy chain variable domain of farletuzumab with one or more amino acids substituted with a histidine, where the heavy chain variable domain of farletuzumab includes SEQ ID NO: 184; and/or a light chain variable domain of farletuzumab with one or more amino acids substituted with a histidine, where the light chain variable domain of farletuzumab includes SEQ ID NO: 185.

In some embodiments of any of the ABPCs described herein, the first FOLR1-binding domain includes one of (a) through (c): (a) a heavy chain variable domain including a CDR1, a CDR2, and a CDR3 of SEQ ID NOs: 3-5, respectively, with collectively a total of one or more amino acid positions in SEQ ID NOs: 3-5 substituted with a histidine; and/or a light chain variable domain including a CDR1, a CDR2, and a CDR3 of SEQ ID NOs: 6-8, respectively, with collectively a total of one or more amino acid positions in SEQ ID NOs: 6-8 substituted with a histidine; (b) a heavy chain variable domain including a CDR1, a CDR2, and a CDR3 of SEQ ID NOs: 107-109, respectively, with collectively a total of one or more amino acid positions in SEQ ID NOs: 107-109 substituted with a histidine; and/or a light chain variable domain including a CDR1, a CDR2, and a CDR3 of SEQ ID NOs: 110-112, respectively, with collectively a total of one or more amino acid positions in SEQ ID NOs: 110-112 substituted with a histidine; (c) a heavy chain variable domain including a CDR1, a CDR2, and a CDR3 of SEQ ID NOs: 186-188, respectively, with collectively a total of one or more amino acid positions in SEQ ID NOs: 186-188 substituted with a histidine; and/or a light chain variable domain including a CDR1, a CDR2, and a CDR3 of SEQ ID NOs: 189-191, respectively, with collectively a total of one or more amino acid positions in SEQ ID NOs: 189-191 substituted with a histidine.

In some embodiments of any of the ABPCs described herein, the first antigen-binding domain includes one of (a) through (c): (a) a heavy chain variable domain that is at least 90% identical to SEQ ID NO: 1, where the heavy chain variable domain includes a histidine at one or more positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107; and/or a light chain variable domain that is at least 90% identical to SEQ ID NO: 2, where the light chain variable domain includes a histidine at one or more positions in SEQ ID NO: 2 selected from the group consisting of: 28, 30, 31, 32, 34, 35, 36, 55, 59, 93, 94, 95, 96, 97, 98, and 100; (b) a heavy chain variable domain that is at least 90% identical to SEQ ID NO: 105, where the heavy chain variable domain includes a histidine at one or more positions in SEQ ID NO: 105 selected from the group consisting of: 29, 33, 34, 50, 51, 52, 53, 55, 56, 57, 101, 102, 103, 108, 109, 110, 111, 112, and 113; and/or a light chain variable domain that is at least 90% identical to SEQ ID NO: 106, where the light chain variable domain includes a histidine at one or more positions in SEQ ID NO: 106 selected from the group consisting of: 28, 29, 30, 31, 50, 92, 93, 94, 95, and 96; (c) a heavy chain variable domain that is at least 90% identical to SEQ ID NO: 184, where the heavy chain variable domain includes a histidine at one or more positions in SEQ ID NO: 184 selected from the group consisting of: 26, 27, 28, 29, 30, 32, 33, 34, 53, 56, 57, 59, 62, 63, 103, and 105; and/or a light chain variable domain that is at least 90% identical to SEQ ID NO: 185, where the light chain variable domain includes a histidine at one or more positions in SEQ ID NO: 185 selected from the group consisting of: 29, 33, 34, 51, 52, 53, 54, 55, 90, 92, 94, 96, 97, 98, 99, and 100.

In some embodiments of any of the ABPCs described herein, the first antigen-binding domain includes one of (a) through (c): (a) a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83, and/or a heavy chain variable domain of SEQ ID NO: 1, SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 36, SEQ ID NO: 43, SEQ ID NO: 44, SEQ ID NO: 45, SEQ ID NO: 46, SEQ ID NO: 48, SEQ ID NO: 49, SEQ ID NO: 51, SEQ ID NO: 53, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103; where the first antigen-binding domain does not comprise (i) a light chain variable domain of SEQ ID NO: 2 and heavy chain variable domain of SEQ ID NO: 1; (ii) a light chain variable domain of SEQ ID NO: 2 and heavy chain variable domain that is not one of SEQ ID NOs: 14, 17, 19, 21-24, 26, 28, 30, 31, 33-36, 43-46, 48, 49, 51, 53, and 85-103; (iii) a heavy chain variable domain of SEQ ID NO: 1 and a light chain variable domain that is not one of SEQ ID NOs: 58, 60-62, 64-66, 68, 70, 74, 76-81 and 83; and/or (b) a light chain variable domain of SEQ ID NO: 106, SEQ ID NO: 161, SEQ ID NO: 162, SEQ ID NO: 163, SEQ ID NO: 164, SEQ ID NO: 168, SEQ ID NO: 177, SEQ ID NO: 178, SEQ ID NO: 179, SEQ ID NO: 180, SEQ ID NO: 181, or SEQ ID NO: 182, and/ora heavy chain variable domain of SEQ ID NO: 105, SEQ ID NO: 116, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 128, SEQ ID NO: 129, SEQ ID NO: 130, SEQ ID NO: 144, SEQ ID NO: 145, SEQ ID NO: 146, SEQ ID NO: 151, SEQ ID NO: 152, SEQ ID NO: 153, SEQ ID NO: 154, SEQ ID NO: 155, or SEQ ID NO: 156; where the first antigen-binding domain does not comprise (i) a light chain variable domain of SEQ ID NO: 106 and a heavy chain variable domain of SEQ ID NO: 105; (ii) a light chain variable domain of SEQ ID NO: 106 and a heavy chain variable domain that is not one of SEQ ID NOs: 116, 120-126,128-130, 144-146, and 151-156; (iii) a heavy chain variable domain of SEQ ID NO: 105 and a light chain variable domain that is not one of SEQ ID NOs: 161-164, 168, and 177-182; (c) a light chain variable domain of SEQ ID NO: 185, SEQ ID NO: 233, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 247, SEQ ID NO: 249, SEQ ID NO: 251, SEQ ID NO: 253, SEQ ID NO: 254, SEQ ID NO: 255, SEQ ID NO: 256, or SEQ ID NO: 257 and/or a heavy chain variable domain of SEQ ID NO: 184, SEQ ID NO: 192, SEQ ID NO: 193, SEQ ID NO: 194, SEQ ID NO: 195, SEQ ID NO: 196, SEQ ID NO: 198, SEQ ID NO: 199, SEQ ID NO: 200, SEQ ID NO: 205, SEQ ID NO: 208, SEQ ID NO: 209, SEQ ID NO: 211, SEQ ID NO: 214, SEQ ID NO: 215, SEQ ID NO: 221, SEQ ID NO: 225, or SEQ ID NO: 227, where the first antigen-binding domain does not comprise (i) a light chain variable domain of SEQ ID NO: 185 and a heavy chain variable domain of SEQ ID NO: 184; (ii) a light chain variable domain of SEQ ID NO: 185 and a heavy chain variable domain that is not one of SEQ ID NOs: 192-196, 198-200, 205, 208, 209, 211, 214, 215, 221, 225 and 227; (iii) a heavy chain variable domain of SEQ ID NO: 184 and a light chain variable domain that is not one of SEQ ID NOs: 233, 237-244, 247, 249, 251, and 253-257.

In some embodiments of any of the ABPCs described herein, a composition including the ABPC provides for an increase in toxin liberation in the target mammalian cell as compared to a composition including the same amount of a control ABPC; and/or an increase in target mammalian cell killing as compared to a composition including the same amount of a control ABPC.

In some embodiments of any of the ABPCs described herein, a composition including the ABPC provides for an increase in endolysosomal delivery in the target mammalian cell as compared to a composition including the same amount of a control ABPC.

In some embodiments of any of the ABPCs described herein, a composition including the ABPC results in a less of a reduction in the level of FOLR1 presented on the surface of the target mammalian cell as compared to a composition including the same amount of a control ABPC;

or does not result in a detectable reduction in the level of FOLR1 presented on the surface of the target mammalian cell.

In some embodiments of any of the ABPCs described herein, the target mammalian cell is a cancer cell. In some embodiments of any of the ABPCs described herein, the ABPC is cytotoxic or cytostatic to the target mammalian cell.

In some embodiments of any of the ABPCs described herein, the ABPC is cross-reactive with a non-human primate FOLR1 and human FOLR1; or cross-reactive with a non-human primate FOLR1, a human FOLR1, and one or both of rat FOLR1 and a mouse FOLR1.

In some embodiments of any of the ABPCs described herein, the ABPC includes a single polypeptide.

In some embodiments of any of the ABPCs described herein, the antigen-binding domain is selected from the group consisting of: a VH domain, a VHH domain, a VNAR domain, and a scFv. In some embodiments of any of the ABPCs described herein, the ABPC includes two or more polypeptides. In some embodiments of any of the ABPCs described herein, the ABPC is an antibody.

In some embodiments of any of the ABPCs described herein, the half-life of the ABPC in vivo is decreased as compared to the half-life of a control ABPC in vivo.

In some embodiments of any of the ABPCs described herein, the ABPC includes a second antigen-binding domain.

Also provided herein are kits including at least one dose of any of the the pharmaceutical compositions described herein or any one of the ABPCs described herein.

Also provided herein are methods of treating a cancer characterized by having a population of cancer cells that have FOLR1 or an epitope of FOLR1 presented on their surface, the method including administering a therapeutically effective amount of any one of the pharmaceutical compositions described herein or any one of the ABPCs described herein to a subject identified as having a cancer characterized by having the population of cancer cells.

Also provided herein are methods of reducing the volume of a tumor in a subject, where the tumor is characterized by having a population of cancer cells that have FOLR1 or an epitope of FOLR1 presented on their surface, the method including administering a therapeutically effective amount of any of the pharmaceutical compositions described herein or any one of the ABPCs described herein to a subject identified as having a cancer characterized by having the population of cancer cells.

Also provided herein are methods of inducing cell death in a cancer cell in a subject, where the cancer cell has FOLR1 or an epitope of FOLR1 presented on its surface, where the method includes administering a therapeutically effective amount of any one of the pharmaceutical compositions described herein or any one of the ABPCs described herein to a subject identified as having a cancer characterized by having a population of the cancer cells.

Also provided herein are methods of decreasing the risk of developing a metastasis or decreasing the risk of developing an additional metastasis in a subject having a cancer, where the cancer is characterized by having a population of cancer cells that have FOLR1 or an epitope of FOLR1 presented on their surface the method including administering a therapeutically effective amount of any one of the pharmaceutical compositions described herein or any one of the ABPCs described herein to a subject identified as having a cancer characterized by having the population of cancer cells.

As used herein, the term "antigen-binding protein construct" is (i) a single polypeptide that includes at least one antigen-binding domain or (ii) a complex of two or more polypeptides (e.g., the same or different polypeptides) that together form at least one antigen-binding domain. Non-limiting examples and aspects of antigen-binding protein constructs are described herein.

Additional examples and aspects of antigen-binding protein constructs are known in the art.

A "multi-specific antigen-binding protein construct" is an antigen-binding protein construct that includes two or more different antigen-binding domains that collectively specifically bind two or more different epitopes. The two or more different epitopes may be epitopes on the same antigen (e.g., a single polypeptide present on the surface of a cell) or on different antigens (e.g., different proteins present on the surface of the same cell or present on the surface of different cells). In some aspects, the antigen is present on the surface of the cell. In some aspects, a multi-specific antigen-binding protein construct binds two different epitopes (i.e., a "bispecific antigen-binding protein construct"). In some aspects, a multi-specific antigen-binding protein construct binds three different epitopes (i.e., a "trispecific antigen-binding protein construct"). In some aspects, a multi-specific antigen-binding protein construct binds four different epitopes (i.e., a "quadspecific antigen-binding protein construct"). In some aspects, a multi-specific antigen-binding protein construct binds five different epitopes (i.e., a "quintspecific antigen-binding protein construct"). Each binding specificity may be present in any suitable valency. Non-limiting examples of multi-specific antigen-binding protein constructs are described herein.

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art. In some examples, an antigen-binding domain can bind to a single antigen.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins, e.g., human IgG (e.g., human IgG1, human IgG2, human IgG3, human IgG4)), antibody fragments, and multi-specific antibodies. One example of an antigen-binding domain is an antigen-binding domain formed by a VH-VL dimer. Additional examples of an antibody are described herein. Additional examples of an antibody are known in the art.

The phrase "endosomal/lysosomal pathway" refers to a network of endosomes (early endosomes, multi-vesicular bodies, late endosomes, and lysosomes) in the cytoplasm of a mammalian cell, wherein molecules internalized through cell-mediated internalization processes, e.g., pinocytosis, micropinocytosis, receptor-mediated endocytosis, and/or phagocytosis, are sorted.

Once the endosomes in the endosomal/lysosomal pathway are purified or isolated, assays for a target protein (e.g., an antigen-binding protein construct described herein) can be performed using methods known in the art (ELISA, Western blot, immunofluorescence, and immunoprecipitation followed by an assay for protein concentration), and can be used to determine the concentration or relative level of the target protein in the endosomes.

Alternatively, endosomes in the endosomal/lysosomal pathway can be imaged using immunofluorescence microscopy using an detectably-labelled antibody (e.g., a fluorophore-labelled, a dye-labelled, or a GFP-labelled antibody, e.g., CellLight™ Early Endosome-GFP) that specifically binds to a characteristic protein present in the endosomes (e.g., EEA1 for early endosomes) and a fluorophore-labelled antibody that specifically binds to the protein of interest (e.g., an antigen-binding protein construct), and the level of the target protein in the endosomes can be determined by quantitation of the overlap in the fluorescence emissions of the two different antibodies.

The phrase "endolysosomal delivery" refers to rate of accumulation over time or the total accumulation at a specific timepoint of an antigen-binding protein construct (e.g., any of the antigen-binding protein constructs described herein) in the endosomal/lysosomal pathway in a mammalian cell (e.g., any of the exemplary target mammalian cells described herein).

An exemplary method to calculate the increase in endolysosomal delivery of a pH engineered ABPC variant as compared to its corresponding starting ABPC from cellular fluorescence data is to measure the ratio of the variant's mean fluorescence intensity minus the mean fluorescence intensity of a non-binding IgG control, then all divided by the variant's corresponding starting ABPC's mean fluorescence intensity minus the mean fluorescence intensity of the IgG control.

An exemplary assay for measuring endolysosomal delivery of any of the ABPCs described herein include those which involve labeling of an ABPC with a fluorescent dye, followed by incubation of the labeled ABPC with cells and measurement of cellular fluorescence as an indicator of endolysosmal delivery of the ABPC (e.g., as described generally in Wustner, *Traffic* 7(6):699-715, 2006). Alternatively, pH-sensitive dyes which preferentially fluoresce at acidic pH but not neutral pH can be used to label any of the ABPCs described herein, which can then be incubated with cells and the cellular fluorescence measured as an indicator of delivery of the ABPC into acidic endolysosomal compartments.

The term "population" when used before a noun means two or more of the specific noun. For example, the phrase "a population of cancer cells" means "two or more cancer cells." Non-limiting examples of cancer cells are described herein.

The phrase "cytostatic to a cell" refers to a direct or indirect decrease in the proliferation (cell division) of the cell (e.g., a cancer cell) in vivo or in vitro. When an agent is cytostatic to a cell, the agent can, e.g., directly or indirectly result in cell cycle arrest of the cell (e.g., a cancer cell). In some examples, an agent that is cytostatic to a cell can reduce the number of cells in a population of the cells that are in S phase (as compared to the number of cells in a population of the cells that are in S phase prior to contact with the agent). In some examples, an agent that is cytostatic to a cell can reduce the percentage of the cells in S phase by at least 20%, at least 40%, at least 60%, or at least 80% (e.g., as compared to the percentage of cells in a population of the cells that are in S phase prior to contact with the agent).

The phrase "cytotoxic to a cell" refers to the inducement, directly or indirectly, in the death (e.g., necrosis or apoptosis) of the cell (e.g., a mammalian cell, e.g., a cancer cell).

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). Affinity can be measured by common methods known in the art, including those described herein. Affinity can be determined, for example, using surface plasmon resonance (SPR) technology (e.g., BIACORE® (surface plasmon responance systems)) or biolayer interferometry (e.g., FORTEBIO® (biolayer interferometry systems). Additional methods for determining the affinity for an antigen-binding domain and its corresponding antigen or epitope are known in the art.

The term "epitope" means a portion of an antigen that is specifically bound by an antigen-binding domain through a set of physical interactions between: (i) all monomers (e.g. individual amino acid residues, sugar side chains, and post-translationally modified amino acid residues) on the portion of the antigen-binding domain that specifically binds the antigen and (ii) all monomers (e.g. individual amino acid residues, sugar side chains, post-translationally modified amino acid residues) on the portion of the antigen that is specifically bound by the antigen-binding domain. Epitopes can, e.g., consist of surface-accessible amino acid residues, sugar side chains, phosphorylated amino acid residues, methylated amino acid residues, and/or acetylated amino acid residues and may have specific three-dimensional structural characteristics, as well as specific charge characteristics. Conformational and non-conformational epitopes are distinguished in that binding to the former, but not the latter, may be lost in the presence of denaturing solvents. In some embodiments, an epitope is defined by a linear amino acid sequence of at least about 3 to 6 amino acids, or about 10 to 15 amino acids.

In some embodiments, an epitope refers to a portion of a full-length protein or a portion thereof that is defined by a three-dimensional structure (e.g., protein folding). In some embodiments, an epitope is defined by a discontinuous amino acid sequence that is brought together via protein folding. In some embodiments, an epitope is defined by a discontinuous amino acid sequence that is brought together by quaternary structure (e.g., a cleft formed by the interaction of two different polypeptide chains). The amino acid sequences between the residues that define the epitope may not be critical to three-dimensional structure of the epitope. A conformational epitope may be determined and screened using assays that compare binding of antigen-binding protein construct to a denatured version of the antigen, such that a linear epitope is generated. An epitope may include amino acid residues that are directly involved in the binding, and other amino acid residues, which are not directly involved in the binding.

Methods for identifying an epitope to which an antigen-binding domain specifically binds are known in the art, e.g., structure-based analysis (e.g. X-ray crystallography, NMR, and/or electron microscopy) (e.g. on the antigen and/or the antigen-antigen binding domain complex) and/or mutagenesis-based analysis (e.g. alanine scanning mutagenesis, glycine scanning mutagenesis, and homology scanning mutagenesis) wherein mutants are measured in a binding assay with a binding partner, many of which are known in the art.

The term "paratope" means a portion of an antigen-binding domain that specifically binds to an antigen through a set of physical interactions between: (i) all monomers (e.g. individual amino acid residues, sugar side chains, posttranslationally modified amino acid residues) on the portion of the antigen-binding domain that specifically binds the antigen and (ii) all monomers (e.g. individual amino acid residues, sugar side chains, posttranslationally modified amino acid residues) on the portion of the antigen that is specifically bound by the antigen-binding domain.

Paratopes can, e.g. consist of surface-accessible amino acid residues and may have specific three-dimensional structural characteristics, as well as specific charge characteristics. In some embodiments, a paratope refers to a portion of a full-length antigen-binding domain or a portion thereof that is defined by a three-dimensional structure (e.g., protein folding). In some embodiments, a paratope is defined by a discontinuous amino acid sequence that is brought together via protein folding. In some embodiments, an epitope is defined by a discontinuous amino acid sequence that is brought together by quaternary structure (e.g., a cleft formed by the interaction of two different polypeptide chains). The amino acid sequences between the residues that define the paratope may not be critical to three-dimensional structure of the paratope. A paratope may comprise amino acid residues that are directly involved in the binding, and other amino acid residues, which are not directly involved in the binding.

Methods for identifying a paratope to which an antigen-binding domain specifically binds are known in the art, e.g., structure-based analysis (e.g., X-ray crystallography, NMR, and/or electron microscopy) (e.g. on the antigen-binding domain, and/or the antigen binding domain-antigen complex), and/or mutagenesis-based analysis (e.g., alanine scanning mutagenesis, glycine scanning mutagenesis, and homology scanning mutagenesis) wherein mutants are measured in a binding assay with a binding partner, many of which are known in the art.

The phrase "present on the surface of a mammalian cell" means (1) an antigen that physically attached to or at least partially embedded in the plasma membrane of a mammalian cell (e.g., a transmembrane protein, a peripheral membrane protein, a lipid-anchored protein (e.g., a GPI-anchor), an N-myristolyated protein, or a S-palmitoylated protein) or (2) an antigen that is stably bound to its cognate receptor, where the cognate receptor is physically attached to the plasma membrane of a mammalian cell (e.g., a ligand bound to its cognate receptor, where the cognate receptor is physically attached to the plasma membrane). Non-limiting methods for determining the presence of antigen on the surface of a mammalian cell include fluorescence-activated cell sorting (FACS), immunohistochemistry, cell-fractionation assays and Western blotting.

The phrase "control ABPC" or "control antigen-binding protein construct" means (i) an ABPC that is capable of specifically binding to FOLR1 or an epitope of FOLR1 presented on the surface of a mammalian cell (e.g., a target mammalian cell), where one or both of the following is true: (a) the dissociation rate of the first antigen-binding domain at a pH of about 4.0 to about 6.5 (e.g., any of the subranges of this range described herein) is no more than 3-fold (e.g., no more than 2.8-fold, no more than 2.6-fold, no more than 2.5-fold, no more than 2.4-fold, no more than 2.2-fold, no more than 2.0-fold, no more than 1.8-fold, no more than 1.6-fold, no more than 1.5-fold, no more than 1.4-fold, no more than 1.2-fold, no more than 1.0-fold, no more than 0.8-fold, no more than 0.6-fold, no more than 0.5-fold, no more than 0.4-fold, no more than 0.3-fold no more than 0.2-fold, or no more than 0.1-fold) faster than the dissociation rate at a pH of about 7.0 to about 8.0 (e.g., any of the subranges of this range described herein); or (b) the dissociation constant (KD) of the first antigen-binding domain at a pH of about 4.0 to about 6.5 (e.g., any of the subranges of this range described herein) is no more than 3-fold (e.g., no more than 2.8-fold, no more than 2.6-fold, no more than 2.5-fold, no more than 2.4-fold, no more than 2.2-fold, no more than 2.0-fold, no more than 1.8-fold, no more than 1.6-fold, no more than 1.5-fold, no more than 1.4-fold, no more than 1.2-fold, no more than 1.0-fold, no more than 0.8-fold, no more than 0.6-fold, no more than 0.5-fold, no more than 0.4-fold, no more than 0.3-fold no more than 0.2-fold, or no more than 0.1-fold) greater than the KD at a pH of about 7.0 to about 8.0 (e.g., any of the subranges of this range described herein); and/or (ii) mirvetuximab; and/or (iii) STRO-002; and/or (iv) farletuzumab.

The term "extracellular space" means the liquid exterior to the plasma membrane of a mammalian cell. When a mammalian cell is in vitro, the extracellular space can be a liquid culture medium. When a mammalian cell is in vivo, the extracellular space can be, e.g., plasma, serum, blood, interstitial fluid, or lymph.

The term "endolysosomal space" means the fluid encapsulated by the vesicles and organelles that make-up the endosomal/lysosomal pathway in a mammalian cell. The phrase "a reduced level" or "a decreased level" can be a reduction or decrease of at least a 1% (e.g., at least 2%, at least 4%, at least 6%, at least 8%, at least 10%, at least 12%, at least 14%, at least 16%, at least 18%, at least 20%, at least 22%, at least 24%, at least 26%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) reduction as compared to a reference level or value.

The term "cell killing potency" refers to the ability of an agent (e.g., any of the ABPCs described herein) to induce, directly or indirectly, the apoptosis and/or necrosis of a mammalian cell (e.g., a cancer cell), measured as a rate over time or at a relevant timepoint. Methods for determining the cell killing potency of a cell are known in the art (e.g., trypan blue staining, microscopy, fluorescence-assisted cell sorting, and assays to detect markers of apoptosis (e.g., Annexin V)). In non-limiting examples, cell killing potency can be measured, e.g., by cell killing at a single concentration of an agent, by the IC50 of the agent (i.e. the concentration of the agent whereby half the maximal cell killing potency is achieved), or by the ratio of an agent's dissociation constant KD on mammalian cells divided by its IC50. In some non-limiting examples, the IC50s and/or the KD ratios described herein are compared to those of a control ABPC (as defined herein), and, optionally, demonstrate that the ABPCs described herein have a higher cell killing potency as compared to the control ABPC.

The term "toxin liberation" refers to the ability of a mammalian cell (e.g., a non-cancerous mammalian cell or a cancer cell) to internalize (e.g., via pinocytosis and/or receptor-mediated endocytosis) any of the ABPCs described herein (e.g., any of ABPCs or control ABPCs described herein) that are conjugated to a toxin, and subsequently release the toxin conjugated to the ABPC, measured as a rate over time or at a specific timepoint. Toxin liberation can be assessed using a variety of different exemplary assays, e.g., ELISA, immunofluorescence, cell killing assays, cell cycle arrest assays, DNA damage assays, mass spectrometry, HPLC, and/or an isotope-labeled toxin.

The phrase "target cell" or "target mammalian cell" or "mammalian target cell" means a mammalian cell that has at least one FOLR1 present on its surface. In some examples, a mammalian target cell can be a cancer cell. In some embodiments of a target mammalian cell can have a total of about 1 to about 10,000,000, about 1 to about 9,000,000, about 1 to about 8,000,000, about 1 to about 7,000,000, about 1 to about 6,000,000, about 1 to about 5,000,000, about 1 to about 4,000,000, about 1 to about 3,000,000, about 1 to about 2,000,000, about 1 to about 1,000,000, about 1 to about 800,000, about 1 to about 600,000, about 1 to about 400,000, about 1 to about 200,000, about 1 to about 100,000, about 1 to about 80,000, about 1 to about 80,000, about 1 to about 75,000, about 1 to about 70,000, about 1 to about 65,000, about 1 to about 60,000, about 1 to about 55,000, about 1 to about 50,000, about 1 to about 45,000, about 1 to about 40,000, about 1 to about 35,000, about 1 to about 30,000, about 1 to about 25,000, about 1 to about 20,000, about 1 to about 15,000, about 1 to about 10,000, about 1 to about 7,500, about 1 to about 5,000, about 1 to about 4,000, about 1 to about 3,000, about 1 to about 2,000, about 1 to about 1,000, about 1 to about 500, about 1 to about 100, about 1 to about 50, about 1 to about 10, about 10 to about 10,000,000, about 10 to about 9,000,000, about 10 to about 8,000,000, about 10 to about 7,000,000, about 10 to about 6,000,000, about 10 to about 5,000,000, about 10 to about 4,000,000, about 10 to about 3,000,000, about 10 to about 2,000,000, about 10 to about 1,000,000, about 10 to about 800,000, about 10 to about 600,000, about 10 to about 400,000, about 10 to about 200,000, about 10 to about 100,000, about 10 to about 80,000, about 10 to about 80,000, about 10 to about 75,000, about 10 to about 70,000, about 10 to about 65,000, about 10 to about 60,000, about 10 to about 55,000, about 10 to about 50,000, about 10 to about 45,000, about 10 to about 40,000, about 10 to about 35,000, about 10 to about 30,000, about 10 to about 25,000, about 10 to about 20,000, about 10 to about 15,000, about 10 to about 10,000, about 10 to about 7,500, about 10 to about 5,000, about 10 to about 4,000, about 10 to about 3,000, about 10 to about 2,000, about 10 to about 1,000, about 10 to about 500, about 10 to about 100, about 10 to about 50, about 50 to about 10,000,000, about 50 to about 9,000,000, about 50 to about 8,000,000, about 50 to about 7,000,000, about 50 to about 6,000,000, about 50 to about 5,000,000, about 50 to about 4,000,000, about 50 to about 3,000,000, about 50 to about 2,000,000, about 50 to about 1,000,000, about 50 to about 800,000, about 50 to about 600,000, about 50 to about 400,000, about 50 to about 200,000, about 50 to about 100,000, about 50 to about 80,000, about 50 to about 80,000, about 50 to about 75,000, about 50 to about 70,000, about 50 to about 65,000, about 50 to about 60,000, about 50 to about 55,000, about 50 to about 50,000, about 50 to about 45,000, about 50 to about 40,000, about 50 to about 35,000, about 50 to about 30,000, about 50 to about 25,000, about 50 to about 20,000, about 50 to about 15,000, about 50 to about 10,000, about 50 to about 7,500, about 50 to about 5,000, about 50 to about 4,000, about 50 to about 3,000, about 50 to about 2,000, about 50 to about 1,000, about 50 to about 500, about 50 to about 100, about 100 to about 10,000,000, about 100 to about 9,000,000, about 100 to about 8,000,000, about 100 to about 7,000,000, about 100 to about 6,000,000, about 100 to about 5,000,000, about 100 to about 4,000,000, about 100 to about 3,000,000, about 100 to about 2,000,000, about 100 to about 1,000,000, about 100 to about 800,000, about 100 to about 600,000, about 100 to about 400,000, about 100 to about 200,000, about 100 to about 100,000, about 100 to about 80,000, about 100 to about 75,000, about 100 to about 70,000, about 100 to about 65,000, about 100 to about 60,000, about 100 to about 55,000, about 100 to about 50,000, about 100 to about 45,000, about 100 to about 40,000, about 100 to about 35,000, about 100 to about 30,000, about 100 to about 25,000, about 100 to about 20,000, about 100 to about 15,000, about 100 to about 10,000, about 100 to about 7,500, about 100 to about 5,000, about 100 to about 4,000, about 100 to about 3,000, about 100 to about 2,000, about 100 to about 1,000, about 100 to about 500, about 500 to about 10,000,000, about 500 to about 9,000,000, about 500 to about 8,000,000, about 500 to about 7,000,000, about 500 to about 6,000,000, about 500 to about 5,000,000, about 500 to about 4,000,000, about 500 to about 3,000,000, about 500 to about 2,000,000, about 500 to about 1,000,000, about 500 to about 800,000, about 500 to about 600,000, about 500 to about 400,000, about 500 to about 200,000, about 500 to about 100,000, about 500 to about 80,000, about 500 to about 75,000, about 500 to about 70,000, about 500 to about 65,000, about 500 to about 60,000, about 500 to about 55,000, about 500 to about 50,000, about 500 to about 45,000, about 500 to about 40,000, about 500 to about 35,000, about 500 to about 30,000, about 500 to about 25,000, about 500 to about 20,000, about 500 to about 15,000, about 500 to about 10,000, about 500 to about 7,500, about 500 to about 5,000, about 500 to about 4,000, about 500 to about 3,000, about 500 to about 2,000, about 500 to about 1,000, about 1,000 to about 10,000,000, about 1,000 to about 9,000,000, about 1,000 to about 8,000,000, about 1,000 to about 7,000,000, about 1,000 to about 6,000,000, about 1,000 to about 5,000,000, about 1,000 to about 4,000,000, about 1,000 to about 3,000,000, about 1,000 to about 2,000,000, about 1,000 to about 1,000,000, about 1,000 to about 800,000, about 1,000 to about 600,000, about 1,000 to about 400,000, about 1,000 to about 200,000, about 1,000 to about 100,000, about 1,000 to about 80,000, about 1,000 to about 75,000, about 1,000 to about 70,000, about 1,000 to about 65,000, about 1,000 to about 60,000, about 1,000 to about 55,000, about 1,000 to about 50,000, about 1,000 to about 45,000, about 1,000 to about 40,000, about 1,000 to about 35,000, about 1,000 to about 30,000, about 1,000 to about 25,000, about 1,000 to about 20,000, about 1,000 to about 15,000, about 1,000 to about 10,000, about 1,000 to about 7,500, about 1,000 to about 5,000, about 1,000 to about 4,000, about 1,000 to about 3,000, about 1,000 to about 2,000, about 2,000 to about 10,000,000, about 2,000 to about 9,000,000, about 2,000 to about 8,000,000, about 2,000 to about 7,000,000, about 2,000 to about 6,000,000, about 2,000 to about 5,000,000, about 2,000 to about 4,000,000, about 2,000 to about 3,000,000, about 2,000 to about 2,000,000, about 2,000 to about 1,000,000, about 2,000 to about 800,000, about 2,000 to about 600,000, about 2,000 to about 400,000, about 2,000 to about 200,000, about 2,000 to about 100,000, about 2,000 to about 80,000, about 2,000 to about 75,000, about 2,000 to about 70,000, about 2,000 to about 65,000, about 2,000 to about 60,000, about 2,000 to about 55,000, about 2,000 to about 50,000, about 2,000 to about 45,000, about 2,000 to about 40,000, about 2,000 to about 35,000, about 2,000 to about 30,000, about 2,000 to about 25,000, about 2,000 to about 20,000, about 2,000 to about 15,000, about 2,000 to about 10,000, about 2,000 to about 7,500, about 2,000 to about 5,000, about 2,000 to about 4,000, about 2,000 to about 3,000, about 3,000 to about 10,000,000, about 3,000 to about 9,000,000, about 3,000 to about 8,000,000, about 3,000 to about 7,000,000, about 3,000 to about 6,000,000, about 3,000 to about 5,000,000, about 3,000 to about 4,000, 000, about 3,000 to about 3,000,000, about 3,000 to about 2,000,000, about 3,000 to about 1,000,000, about 3,000 to about 800,000, about 3,000 to about 600,000, about 3,000 to about 400,000, about 3,000 to about 200,000, about 3,000 to about 100,000, about 3,000 to about 80,000, about 3,000 to about 75,000, about 3,000 to about 70,000, about 3,000 to about 65,000, about 3,000 to about 60,000, about 3,000 to about 55,000, about 3,000 to about 50,000, about 3,000 to about 45,000, about 3,000 to about 40,000, about 3,000 to about 35,000, about 3,000 to about 30,000, about 3,000 to about 25,000, about 3,000 to about 20,000, about 3,000 to about 15,000, about 3,000 to about 10,000, about 3,000 to about 7,500, about 3,000 to about 5,000, about 3,000 to about 4,000, about 4,000 to about 10,000,000, about 4,000 to about 9,000,000, about 4,000 to about 8,000,000, about 4,000 to about 7,000,000, about 4,000 to about 6,000,000, about 4,000 to about 5,000,000, about 4,000 to about 4,000, 000, about 4,000 to about 3,000,000, about 4,000 to about 2,000,000, about 4,000 to about 1,000,000, about 4,000 to about 800,000, about 4,000 to about 600,000, about 4,000 to about 400,000, about 4,000 to about 200,000, about 4,000 to about 100,000, about 4,000 to about 80,000, about 4,000 to about 75,000, about 4,000 to about 70,000, about 4,000 to about 65,000, about 4,000 to about 60,000, about 4,000 to about 55,000, about 4,000 to about 50,000, about 4,000 to about 45,000, about 4,000 to about 40,000, about 4,000 to about 35,000, about 4,000 to about 30,000, about 4,000 to about 25,000, about 4,000 to about 20,000, about 4,000 to about 15,000, about 4,000 to about 10,000, about 4,000 to about 7,500, about 4,000 to about 5,000, about 5,000 to about 10,000,000, about 5,000 to about 9,000,000, about 5,000 to about 8,000,000, about 5,000 to about 7,000,000, about 5,000 to about 6,000,000, about 5,000 to about 5,000, 000, about 5,000 to about 4,000,000, about 5,000 to about 3,000,000, about 5,000 to about 2,000,000, about 5,000 to about 1,000,000, about 5,000 to about 800,000, about 5,000 to about 600,000, about 5,000 to about 400,000, about 5,000 to about 200,000, about 5,000 to about 100,000, about 5,000 to about 80,000, about 5,000 to about 75,000, about 5,000 to about 70,000, about 5,000 to about 65,000, about 5,000 to about 60,000, about 5,000 to about 55,000, about 5,000 to about 50,000, about 5,000 to about 45,000, about 5,000 to about 40,000, about 5,000 to about 35,000, about 5,000 to about 30,000, about 5,000 to about 25,000, about 5,000 to about 20,000, about 5,000 to about 15,000, about 5,000 to about 10,000, about 5,000 to about 7,500, about 7,500 to about 10,000,000, about 7,500 to about 9,000,000, about 7,500 to about 8,000,000, about 7,500 to about 7,000,000, about 7,500 to about 6,000,000, about 7,500 to about 5,000, 000, about 7,500 to about 4,000,000, about 7,500 to about 3,000,000, about 7,500 to about 2,000,000, about 7,500 to about 1,000,000, about 7,500 to about 800,000, about 7,500 to about 600,000, about 7,500 to about 400,000, about 7,500 to about 200,000, about 7,500 to about 100,000, about 7,500 to about 80,000, about 7,500 to about 75,000, about 7,500 to about 70,000, about 7,500 to about 65,000, about 7,500 to about 60,000, about 7,500 to about 55,000, about 7,500 to about 50,000, about 7,500 to about 45,000, about 7,500 to about 40,000, about 7,500 to about 35,000, about 7,500 to about 30,000, about 7,500 to about 25,000, about 7,500 to about 20,000, about 7,500 to about 15,000, about 7,500 to about 10,000, about 10,000 to about 10,000,000, about 10,000 to about 9,000,000, about 10,000 to about 8,000,000, about 10,000 to about 7,000,000, about 10,000 to about 6,000,000, about 10,000 to about 5,000,000, about 10,000 to about 4,000,000, about 10,000 to about 3,000,000, about 10,000 to about 2,000,000, about 10,000 to about 1,000,000, about 10,000 to about 800,000, about 10,000 to about 600,000, about 10,000 to about 400,000, about 10,000 to about 200,000, about 10,000 to about 100,000, about 10,000 to about 80,000, about 10,000 to about 75,000, about 10,000 to about 70,000, about 10,000 to about 65,000, about 10,000 to about 60,000, about 10,000 to about 55,000, about 10,000 to about 50,000, about 10,000 to about 45,000, about 10,000 to about 40,000, about 10,000 to about 35,000, about 10,000 to about 30,000, about 10,000 to about 25,000, about 10,000 to about 20,000, about 10,000 to about 15,000, about 15,000 to about 10,000,000, about 15,000 to about 9,000,000, about 15,000 to about 8,000,000, about 15,000 to about 7,000,000, about 15,000 to about 6,000,000, about 15,000 to about 5,000,000, about 15,000 to about 4,000,000, about 15,000 to about 3,000,000, about 15,000 to about 2,000,000, about 15,000 to about 1,000,000, about 15,000 to about 800,000, about 15,000 to about 600,000, about 15,000 to about 400,000, about 15,000 to about 200,000, about 15,000 to about 100,000, about 15,000 to about 80,000, about 15,000 to about 75,000, about 15,000 to about 70,000, about 15,000 to about 65,000, about 15,000 to about 60,000, about 15,000 to about 55,000, about 15,000 to about 50,000, about 15,000 to about 45,000, about 15,000 to about 40,000, about 15,000 to about 35,000, about 15,000 to about 30,000, about 15,000 to about 25,000, about 15,000 to about 20,000, about 20,000 to about 10,000,000, about 20,000 to about 9,000,000, about 20,000 to about 8,000,000, about 20,000 to about 7,000,000, about 20,000 to about 6,000,000, about 20,000 to about 5,000,000, about 20,000 to about 4,000,000, about 20,000 to about 3,000,000, about 20,000 to about 2,000,000, about 20,000 to about 1,000,000, about 20,000 to about 800,000, about 20,000 to about 600,000, about 20,000 to about 400,000, about 20,000 to about 200,000, about 20,000 to about 100,000, about 20,000 to about 80,000, about 20,000 to about 75,000, about 20,000 to about 70,000, about 20,000 to about 65,000, about 210,000 to about 60,000, about 20,000 to about 55,000, about 20,000 to about 50,000, about 20,000 to about 45,000, about 20,000 to about 40,000, about 20,000 to about 35,000, about 20,000 to about 30,000, about 20,000 to about 25,000, about 25,000 to about 10,000,000, about 25,000 to about 9,000,000, about 25,000 to about 8,000,000, about 25,000 to about 7,000,000, about 25,000 to about 6,000,000, about 25,000 to about 5,000,000, about 25,000 to about 4,000,000, about 25,000 to about 3,000,000, about 25,000 to about 2,000,000, about 25,000 to about 1,000,000, about 25,000 to about 800,000, about 25,000 to about 600,000, about 25,000 to about 400,000, about 25,000 to about 200,000, about 25,000 to about 100,000, about 25,000 to about 80,000, about 25,000 to about 75,000, about 25,000 to about 70,000, about 25,000 to about 65,000, about 25,000 to about 60,000, about 25,000 to about 55,000, about 25,000 to about 50,000, about 25,000 to about 45,000, about 25,000 to about 40,000, about 25,000 to about 35,000, about 25,000 to about 30,000, about 30,000 to about 10,000,000, about 30,000 to about 9,000,000, about 30,000 to about 8,000,000, about 30,000 to about 7,000,000, about 30,000 to about 6,000,000, about 30,000 to about 5,000,000, about 30,000 to about 4,000,000, about 30,000 to about 3,000,000, about 30,000 to about 2,000,000, about 30,000 to about 1,000,000, about 30,000 to about 800,000, about 30,000 to about 600,000, about 30,000 to about 400,000, about 30,000 to about 200,000, about 30,000 to about 100,000, about 30,000 to about 80,000, about 30,000 to about 75,000, about 30,000 to about 70,000, about 30,000 to about 65,000, about 30,000 to about 60,000, about 30,000 to about 55,000, about 30,000 to about 50,000, about 30,000 to about 45,000, about 30,000 to about 40,000, about 30,000 to about 35,000, about 35,000 to about 10,000,000, about 35,000 to about 9,000,000, about 35,000 to about 8,000,000, about 35,000 to about 7,000,000, about 35,000 to about 6,000,000, about 35,000 to about 5,000,000, about 35,000 to about 4,000,000, about 35,000 to about 3,000,000, about 35,000 to about 2,000,000, about 35,000 to about 1,000,000, about 35,000 to about 800,000, about 35,000 to about 600,000, about 35,000 to about 400,000, about 35,000 to about 200,000, about 35,000 to about 100,000, about 35,000 to about 80,000, about 35,000 to about 75,000, about 35,000 to about 70,000, about 35,000 to about 65,000, about 35,000 to about 60,000, about 35,000 to about 55,000, about 35,000 to about 50,000, about 35,000 to about 45,000, about 35,000 to about 40,000, about 40,000 to about 10,000,000, about 40,000 to about 9,000,000, about 40,000 to about 8,000,000, about 40,000 to about 7,000,000, about 40,000 to about 6,000,000, about 40,000 to about 5,000,000, about 40,000 to about 4,000,000, about 40,000 to about 3,000,000, about 40,000 to about 2,000,000, about 40,000 to about 1,000,000, about 40,000 to about 800,000, about 40,000 to about 600,000, about 40,000 to about 400,000, about 40,000 to about 200,000, about 40,000 to about 100,000, about 40,000 to about 80,000, about 40,000 to about 75,000, about 40,000 to about 70,000, about 40,000 to about 65,000, about 40,000 to about 60,000, about 40,000 to about 55,000, about 40,000 to about 50,000, about 40,000 to about 45,000, about 45,000 to about 10,000,000, about 45,000 to about 9,000,000, about 45,000 to about 8,000,000, about 45,000 to about 7,000,000, about 45,000 to about 6,000,000, about 45,000 to about 5,000,000, about 45,000 to about 4,000,000, about 45,000 to about 3,000,000, about 45,000 to about 2,000,000, about 45,000 to about 1,000,000, about 45,000 to about 800,000, about 45,000 to about 600,000, about 45,000 to about 400,000, about 45,000 to about 200,000, about 45,000 to about 100,000, about 45,000 to about 80,000, about 45,000 to about 75,000, about 45,000 to about 70,000, about 45,000 to about 65,000, about 45,000 to about 60,000, about 45,000 to about 55,000, about 45,000 to about 50,000, about 50,000 to about 10,000,000, about 50,000 to about 9,000,000, about 50,000 to about 8,000,000, about 50,000 to about 7,000,000, about 50,000 to about 6,000,000, about 50,000 to about 5,000,000, about 50,000 to about 4,000,000, about 50,000 to about 3,000,000, about 50,000 to about 2,000,000, about 50,000 to about 1,000,000, about 50,000 to about 800,000, about 50,000 to about 600,000, about 50,000 to about 400,000, about 50,000 to about 200,000, about 50,000 to about 100,000, about 50,000 to about 80,000, about 50,000 to about 75,000, about 50,000 to about 70,000, about 50,000 to about 65,000, about 50,000 to about 60,000, about 50,000 to about 55,000, about 55,000 to about 10,000,000, about 55,000 to about 9,000,000, about 55,000 to about 8,000,000, about 55,000 to about 7,000,000, about 55,000 to about 6,000,000, about 55,000 to about 5,000,000, about 55,000 to about 4,000,000, about 55,000 to about 3,000,000, about 55,000 to about 2,000,000, about 55,000 to about 1,000,000, about 55,000 to about 800,000, about 55,000 to about 600,000, about 55,000 to about 400,000, about 55,000 to about 200,000, about 55,000 to about 100,000, about 55,000 to about 80,000, about 55,000 to about 75,000, about 55,000 to about 70,000, about 55,000 to about 65,000, about 55,000 to about 60,000, about 60,000 to about 10,000,000, about 60,000 to about 9,000,000, about 60,000 to about 8,000,000, about 60,000 to about 7,000,000, about 60,000 to about 6,000,000, about 60,000 to about 5,000,000, about 60,000 to about 4,000,000, about 60,000 to about 3,000,000, about 60,000 to about 2,000,000, about 60,000 to about 1,000,000, about 60,000 to about 800,000, about 60,000 to about 600,000, about 60,000 to about 400,000, about 60,000 to about 200,000, about 60,000 to about 100,000, about 60,000 to about 80,000, about 60,000 to about 75,000, about 60,000 to about 70,000, about 60,000 to about 65,000, about 65,000 to about 10,000,000, about 65,000 to about 9,000,000, about 65,000 to about 8,000,000, about 65,000 to about 7,000,000, about 65,000 to about 6,000,000, about 65,000 to about 5,000,000, about 65,000 to about 4,000,000, about 65,000 to about 3,000,000, about 65,000 to about 2,000,000, about 65,000 to about 1,000,000, about 65,000 to about 800,000, about 65,000 to about 600,000, about 65,000 to about 400,000, about 65,000 to about 200,000, about 65,000 to about 100,000, about 65,000 to about 80,000, about 65,000 to about 75,000, about 65,000 to about 70,000, about 70,000 to about 10,000,000, about 70,000 to about 9,000,000, about 70,000 to about 8,000,000, about 70,000 to about 7,000,000, about 70,000 to about 6,000,000, about 70,000 to about 5,000,000, about 70,000 to about 4,000,000, about 70,000 to about 3,000,000, about 70,000 to about 2,000,000, about 70,000 to about 1,000,000, about 70,000 to about 800,000, about 70,000 to about 600,000, about 70,000 to about 400,000, about 70,000 to about 200,000, about 70,000 to about 100,000, about 70,000 to about 90,000, about 70,000 to about 80,000, about 80,000 to about 10,000,000, about 80,000 to about 9,000,000, about 80,000 to about 8,000,000, about 80,000 to about 7,000,000, about 80,000 to about 6,000,000, about 80,000 to about 5,000,000, about 80,000 to about 4,000,000, about 80,000 to about 3,000,000, about 80,000 to about 2,000,000, about 80,000 to about 1,000,000, about 80,000 to about 800,000, about 80,000 to about 600,000, about 80,000 to about 400,000, about 80,000 to about 200,000, about 80,000 to about 100,000, about 80,000 to about 90,000, about 90,000 to about 10,000,000, about 90,000 to about 9,000,000, about 90,000 to about 8,000,000, about 90,000 to about 7,000,000, about 90,000 to about 6,000,000, about 90,000 to about 5,000,000, about 90,000 to about 4,000,000, about 90,000 to about 3,000,000, about 90,000 to about 2,000,000, about 90,000 to about 1,000,000, about 90,000 to about 800,000, about 90,000 to about 600,000, about 90,000 to about 400,000, about 90,000 to about 200,000, about 90,000 to about 100,000, about 100,000 to about 10,000,000, about 100,000 to about 9,000,000, about 100,000 to about 8,000,000, about 100,000 to about 7,000,000, about 100,000 to about 6,000,000, about 100,000 to about 5,000,000, about 100,000 to about 4,000,000, about 100,000 to about 3,000,000, about 100,000 to about 2,000,000, about 100,000 to about 1,000,000, about 100,000 to about 800,000, about 100,000 to about 600,000, about 100,000 to about 400,000, about 100,000 to about 200,000, about 200,000 to about 10,000,000, about 200,000 to about 9,000,000, about 200,000 to about 8,000,000, about 200,000 to about 7,000,000, about 200,000 to about 6,000,000, about 200,000 to about 5,000,000, about 200,000 to about 4,000,000, about 200,000 to about 3,000,000, about 200,000 to about 2,000,000, about 200,000 to about 1,000,000, about 200,000 to about 800,000, about 200,000 to about 600,000, about 200,000 to about 400,000, about 400,000 to about 10,000,000, about 400,000 to about 9,000,000, about 400,000 to about 8,000,000, about 400,000 to about 7,000,000, about 400,000 to about 6,000,000, about 400,000 to about 5,000,000, about 400,000 to about 4,000,000, about 400,000 to about 3,000,000, about 400,000 to about 2,000,000, about 400,000 to about 1,000,000, about 400,000 to about 800,000, about 400,000 to about 600,000, about 600,000 to about 10,000,000, about 600,000 to about 9,000,000, about 600,000 to about 8,000,000, about 600,000 to about 7,000,000, about 600,000 to about 6,000,000, about 600,000 to about 5,000,000, about 600,000 to about 4,000,000, about 600,000 to about 3,000,000, about 600,000 to about 2,000,000, about 600,000 to about 1,000,000, about 600,000 to about 800,000, about 800,000 to about 10,000,000, about 800,000 to about 9,000,000, about 800,000 to about 8,000,000, about 800,000 to about 7,000,000, about 800,000 to about 6,000,000, about 800,000 to about 5,000,000, about 800,000 to about 4,000,000, about 800,000 to about 3,000,000, about 800,000 to about 2,000,000, about 800,000 to about 1,000,000, about 1,000,000 to about 10,000,000, about 1,000,000 to about 9,000,000, about 1,000,000 to about 8,000,000, about 1,000,000 to about 7,000,000, about 1,000,000 to about 6,000,000, about 1,000,000 to about 5,000,000, about 1,000,000 to about 4,000,000, about 1,000,000 to about 3,000,000, about 1,000,000 to about 2,000,000, about 2,000,000 to about 10,000,000, about 2,000,000 to about 9,000,000, about 2,000,000 to about 8,000,000, about 2,000,000 to about 7,000,000, about 2,000,000 to about 6,000,000, about 2,000,000 to about 5,000,000, about 2,000,000 to about 4,000,000, about 2,000,000 to about 3,000,000, about 3,000,000 to about 10,000,000, about 3,000,000 to about 9,000,000, about 3,000,000 to about 8,000,000, about 3,000,000 to about 7,000,000, about 3,000,000 to about 6,000,000, about 3,000,000 to about 5,000,000, about 3,000,000 to about 4,000,000, about 4,000,000 to about 10,000,000, about 4,000,000 to about 9,000,000, about 4,000,000 to about 8,000,000, about 4,000,000 to about 7,000,000, about 4,000,000 to about 6,000,000, about 4,000,000 to about 5,000,000, about 5,000,000 to about 10,000,000, about 5,000,000 to about 9,000,000, about 5,000,000 to about 8,000,000, about 5,000,000 to about 7,000,000, about 5,000,000 to about 6,000,000, about 6,000,000 to about 10,000,000, about 6,000,000 to about 9,000,000, about 6,000,000 to about 8,000,000, about 6,000,000 to about 7,000,000, about 7,000,000 to about 10,000,000, about 7,000,000 to about 9,000,000, about 7,000,000 to about 8,000,000, about 8,000,000 to about 10,000,000, about 8,000,000 to about 9,000,000, or about 9,000,000 to about 10,000,000 of the FOLR1 on present on the plasma membrane of the target mammalian cell.

The phrase "antigen density" means the number of FOLR1 present on the surface of a target mammalian cell or the average number of FOLR1 on the surface of a population of particular type of target mammalian cells. It can be measured, e.g., using the Quantibright bead kit or radiolabel (e.g., BD Biosciences PE Phycoerythrin Fluorescence Quantitation Kit, catalog #340495).

The phrase "amino acid substituted with a histidine" means the substitution of an amino acid residue that is not histidine in a reference polypeptide sequence with a histidine.

Non-limiting methods for substituting an amino acid residue in a reference polypeptide with a histidine are described herein. Additional methods for substituting an amino acid residue in a reference polypeptide with a histidine are known in the art.

The phrase "amino acid substituted with an alanine" means the substitution of an amino acid residue that is a histidine in a reference polypeptide sequence with an alanine. Non-limiting methods for substituting a histidine in a reference polypeptide with an alanine are described herein. Additional methods for substituting a histidine in a reference polypeptide with an alanine are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 3: Construct identifier to SEQ ID NO correspondence table. Constructs, heavy chain histidine scanning and alanine scanning variants, are listed in the first column of the table, SEQ ID NOs are listed and correspond to constructs on the left and the appropriate heavy chain, light chain, and CDR categories along the top.

FIG. 6: Construct identifier to SEQ ID NO correspondence table. Constructs, light chain histidine scanning and alanine scanning variants, are listed in the first column of the table, SEQ ID NOs are listed and correspond to constructs on the left and the appropriate heavy chain, light chain, and CDR categories along the top.

Arrows show the corresponding size for an IgG on a non-reduced SDS PAGE gel. MYT1142-MYT1161 are MIRVETUXIMAB heavy chain combinations histidine scanning and alanine scanning variants.

Figure 8A:
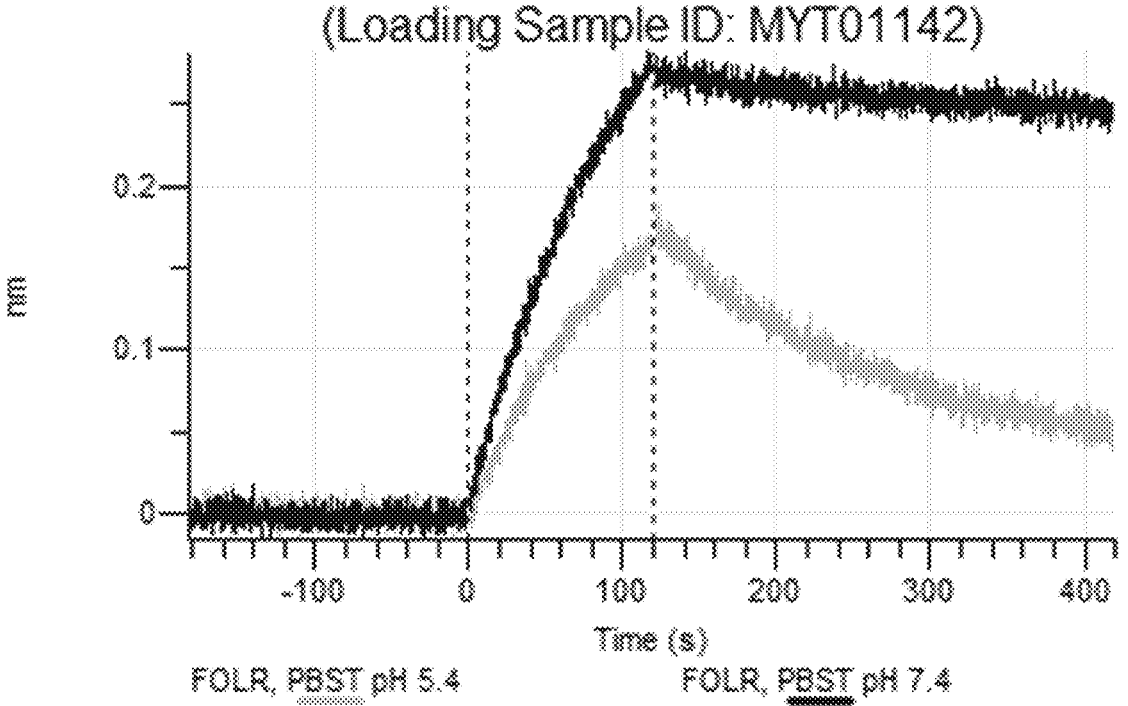
Figure 8B:
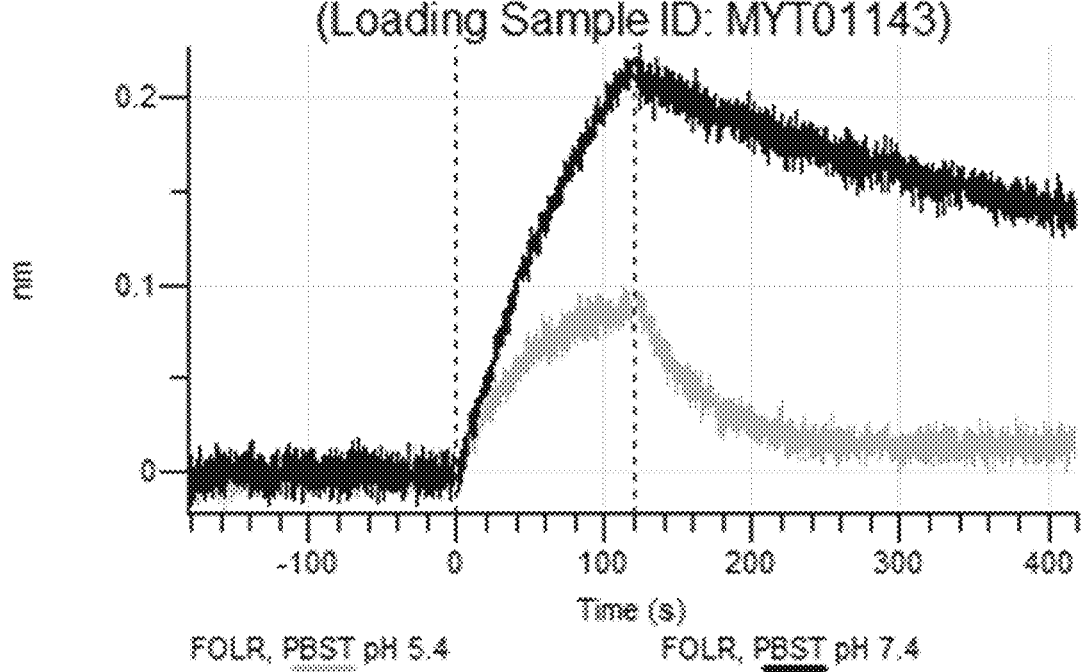
Figure 8C:
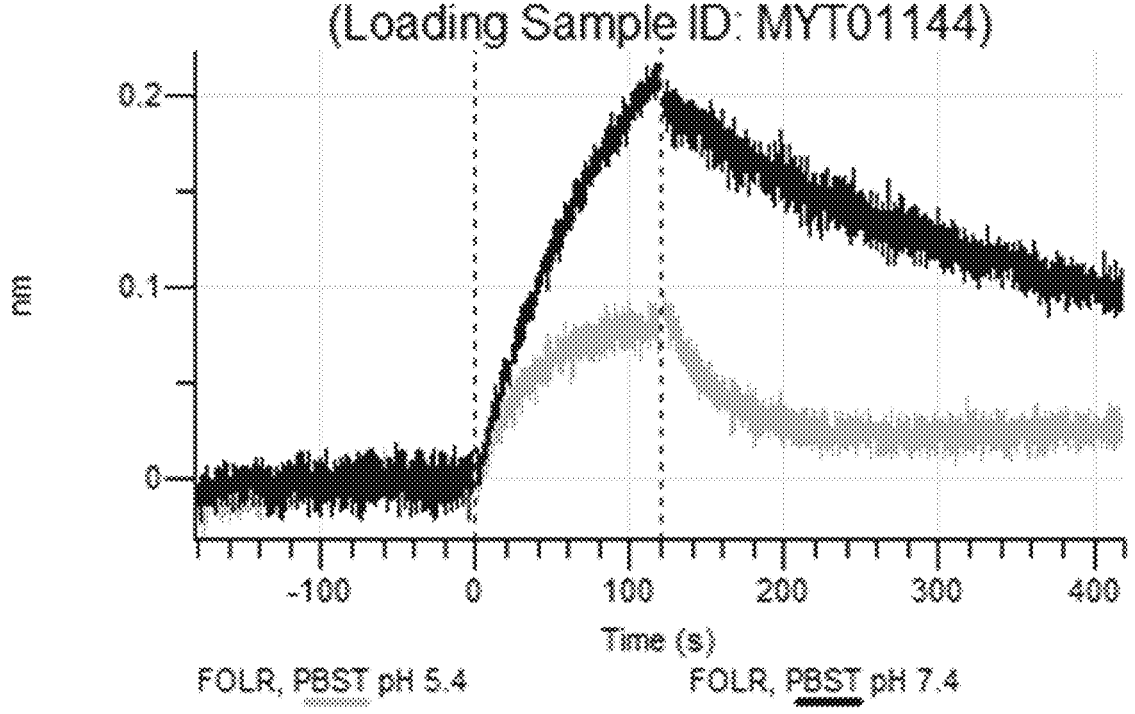
Figure 8D:
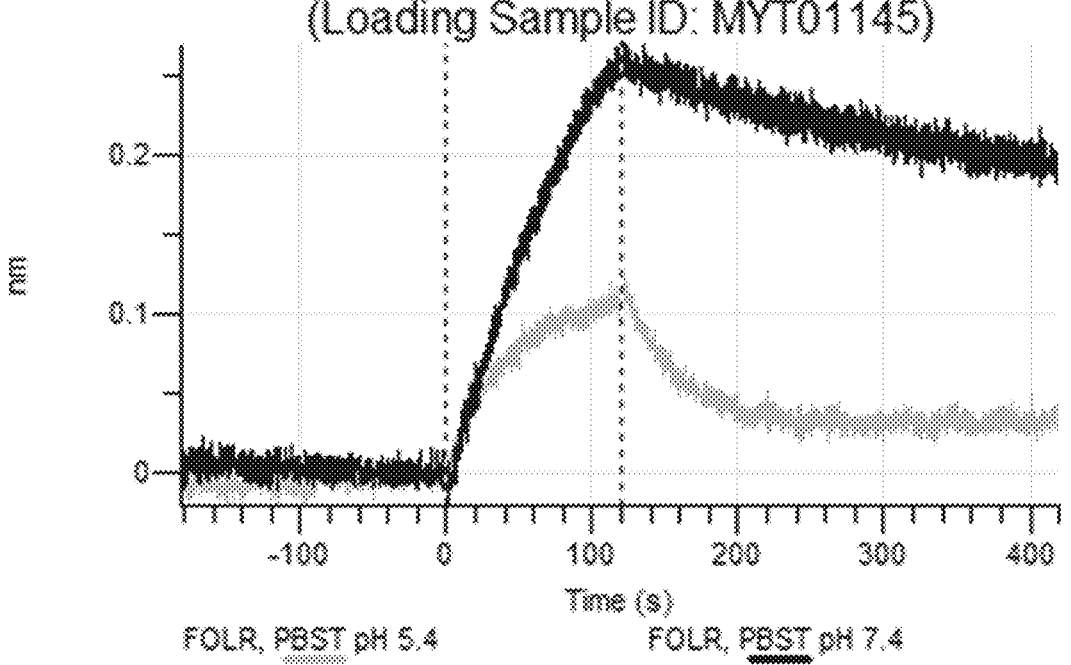
Figure 8E:
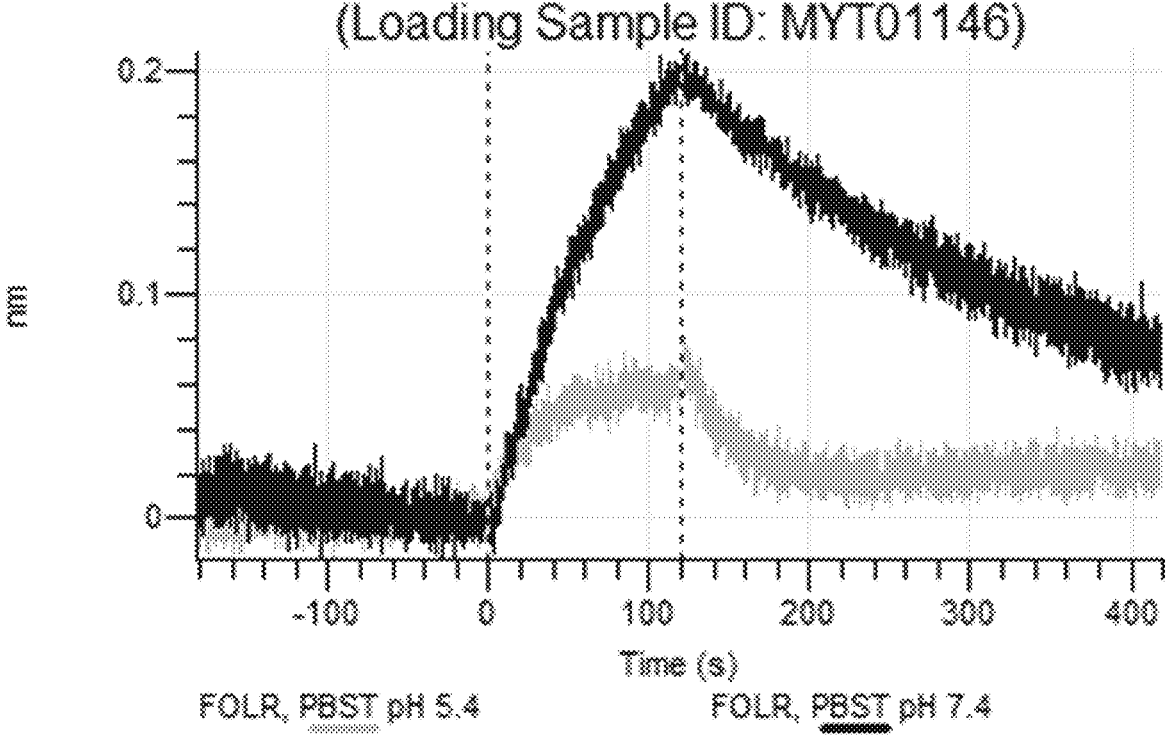
Figure 8F:
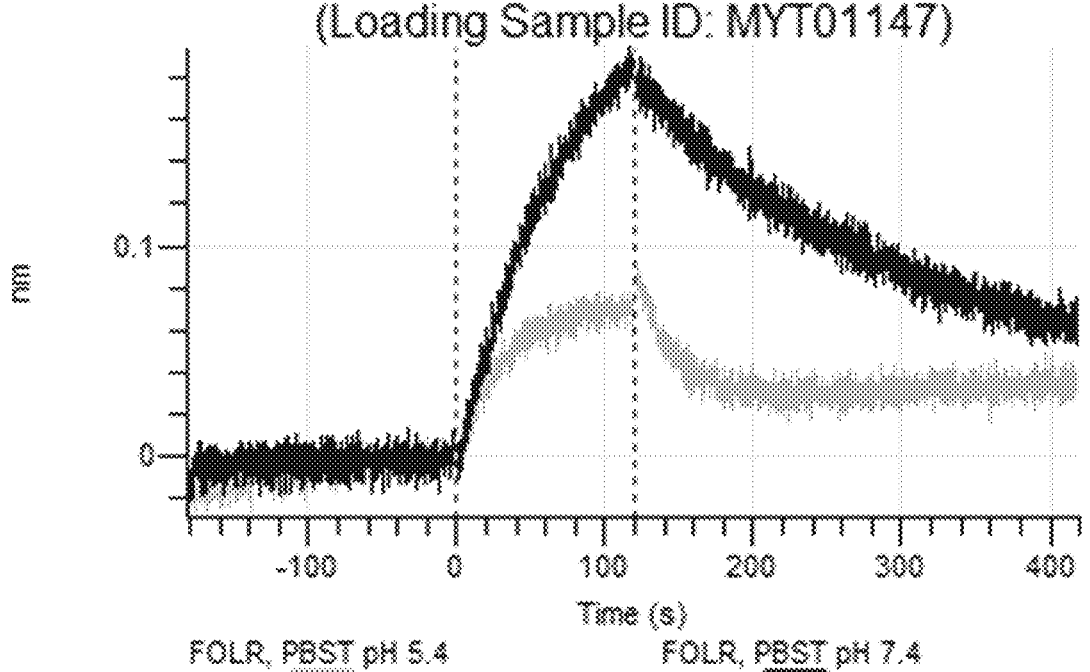
Figure 8G:
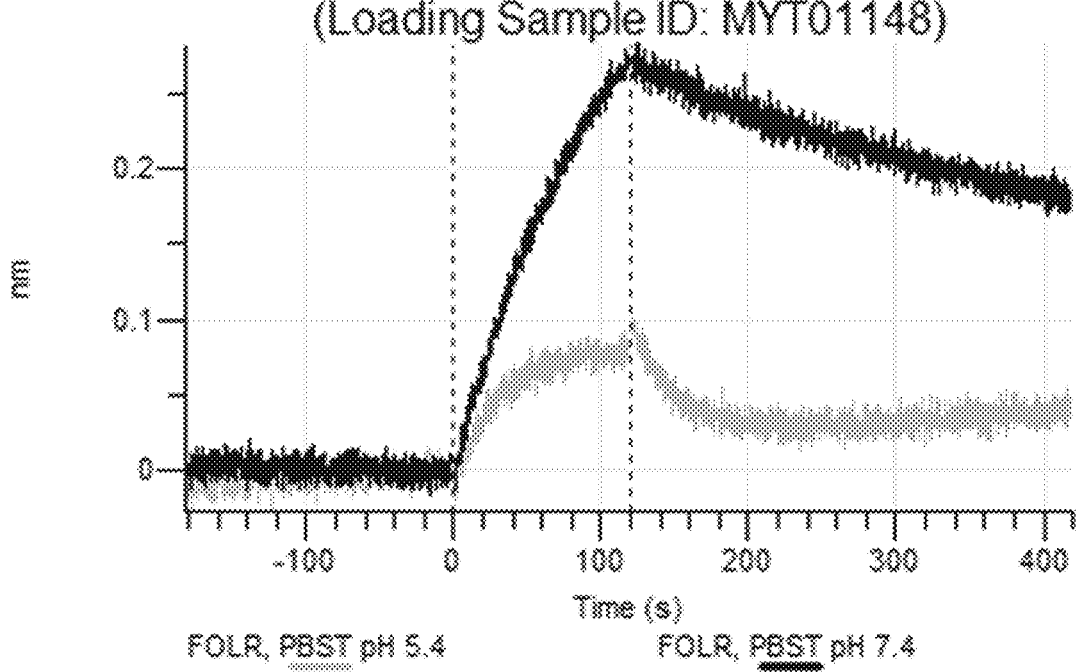
Figure 8H:
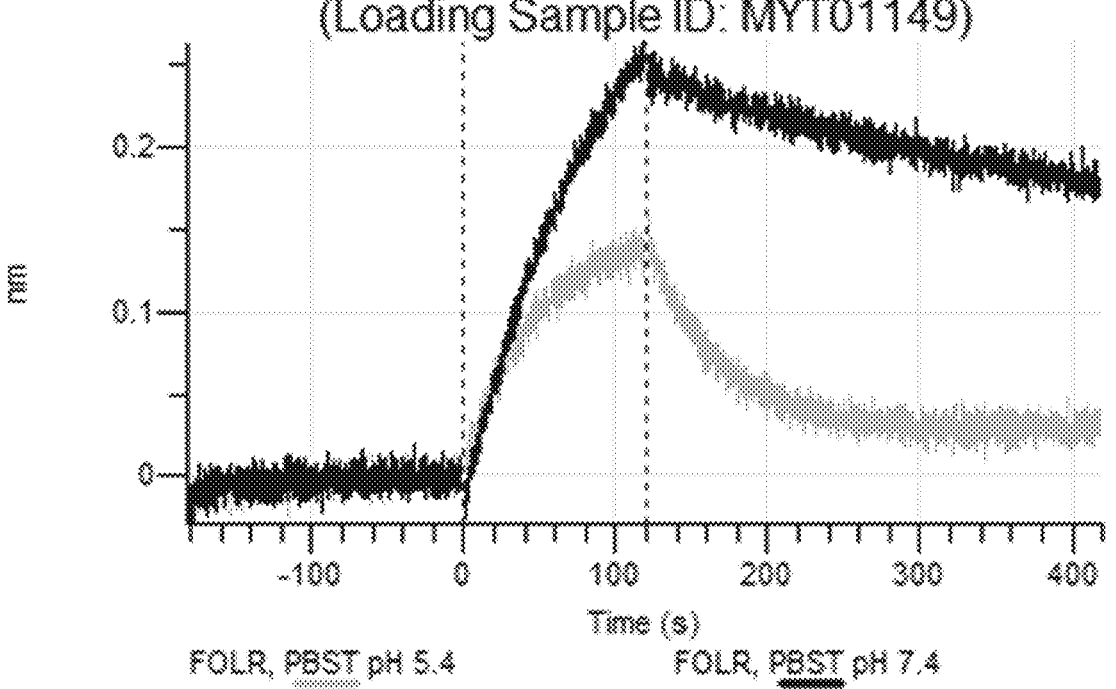
Figure 8I:
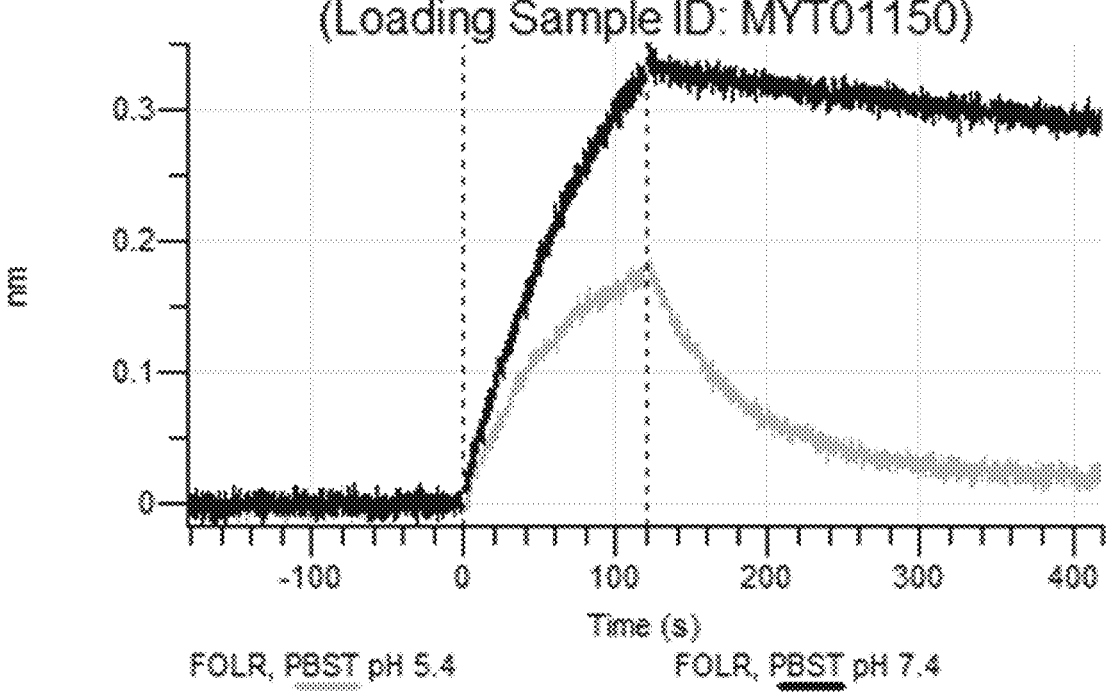
Figure 8J:
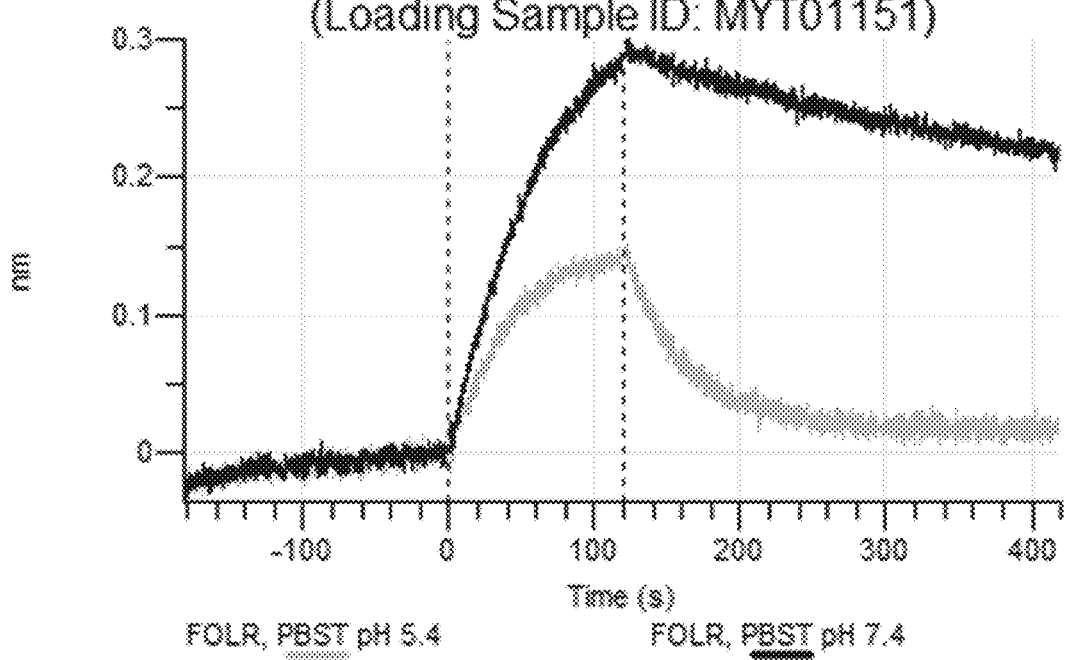
Figure 8K:
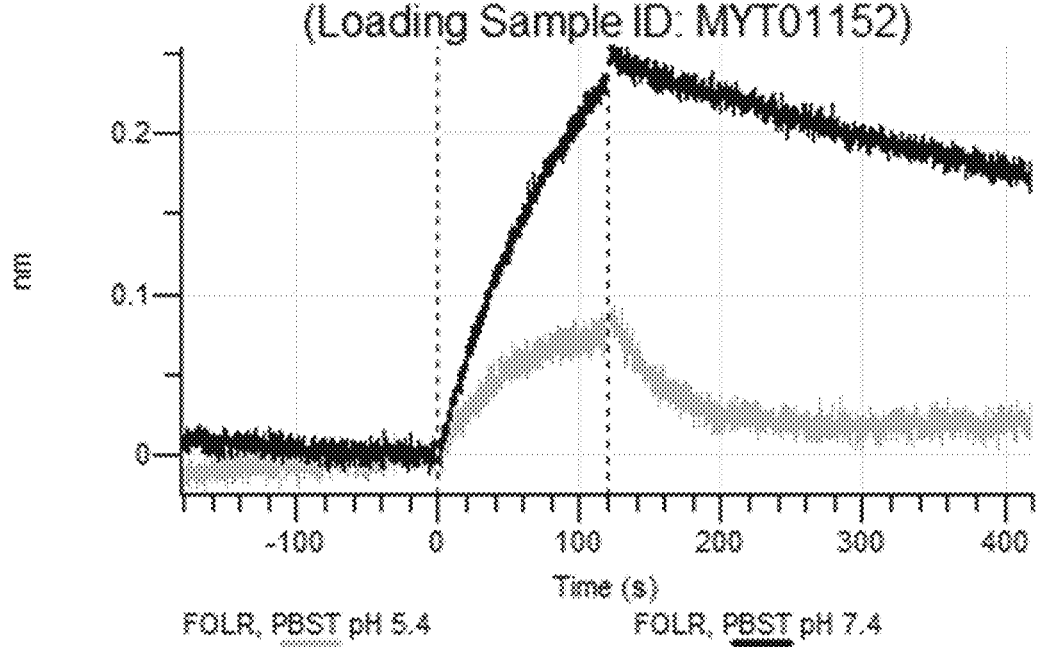
Figure 8I:
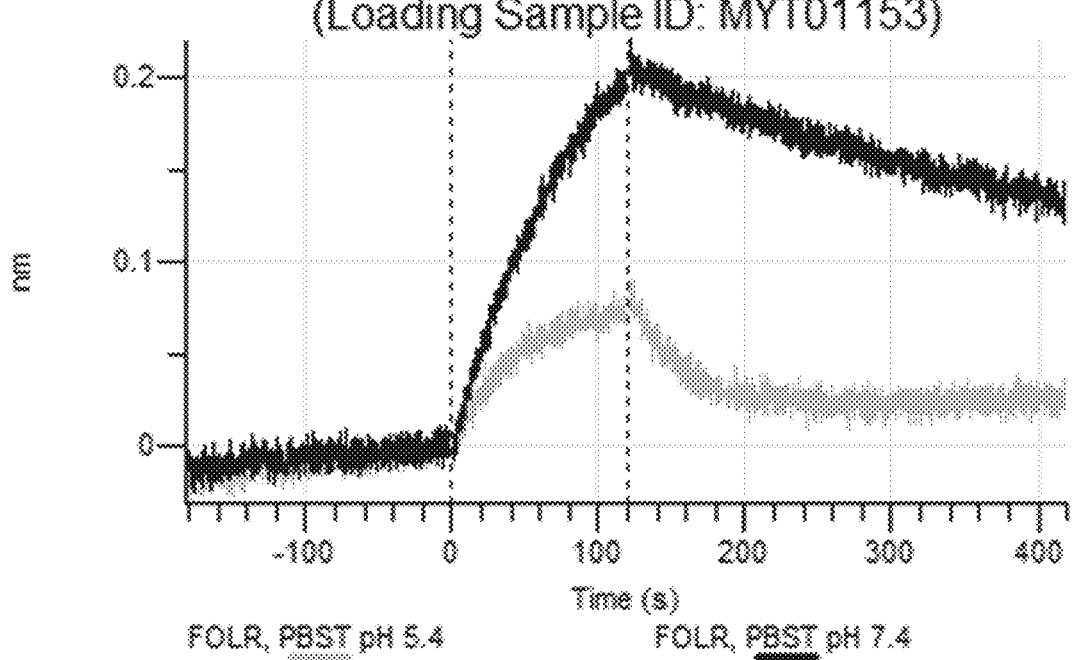
Figure 8M:
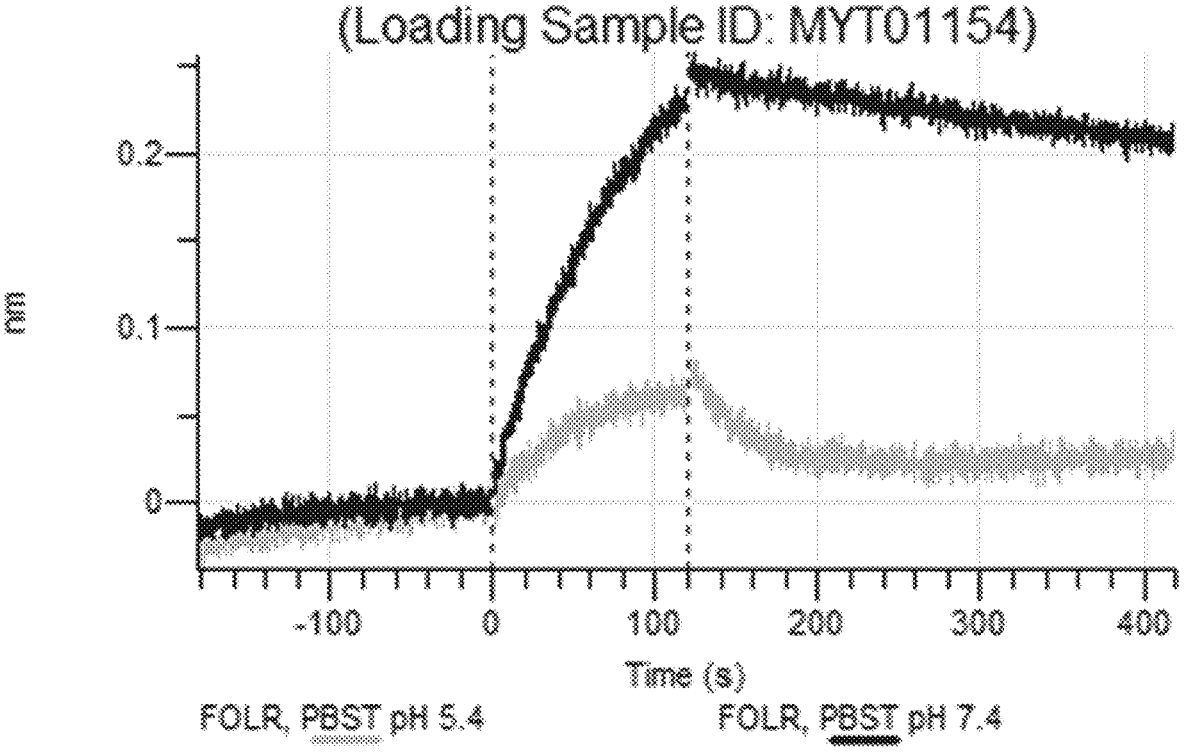
Figure 8N:
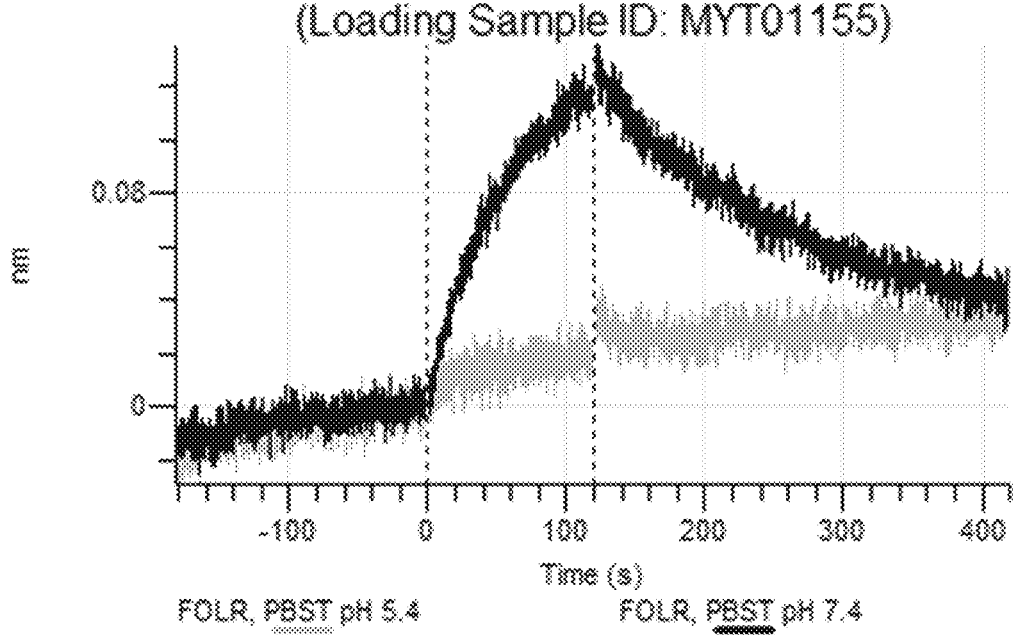
Figure 8O:
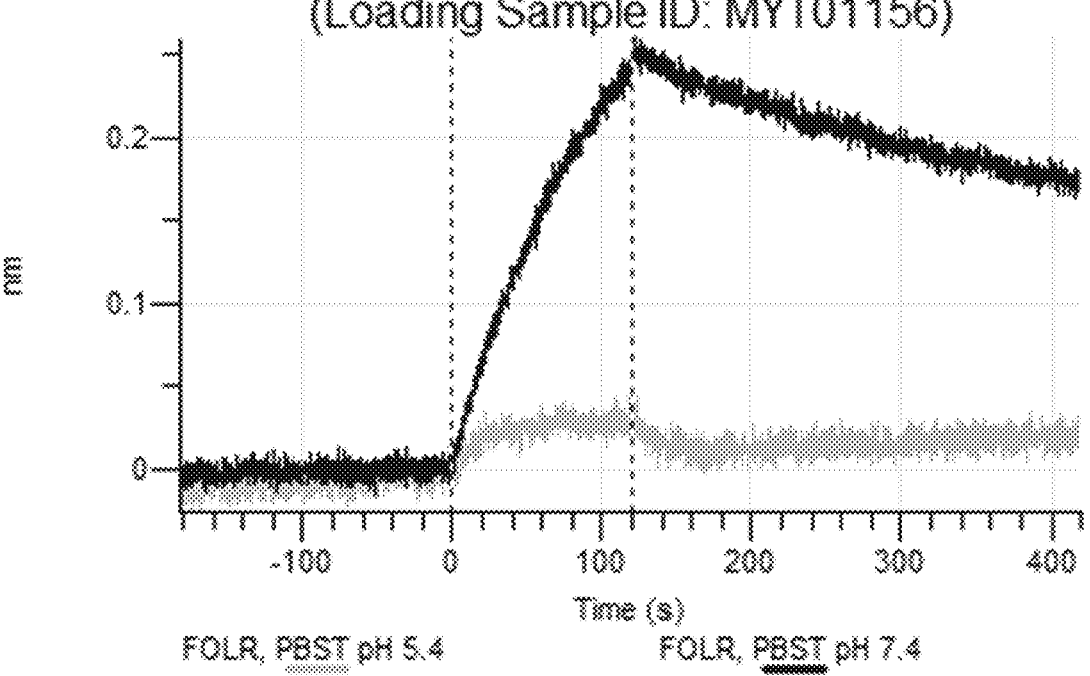
Figure 8P:
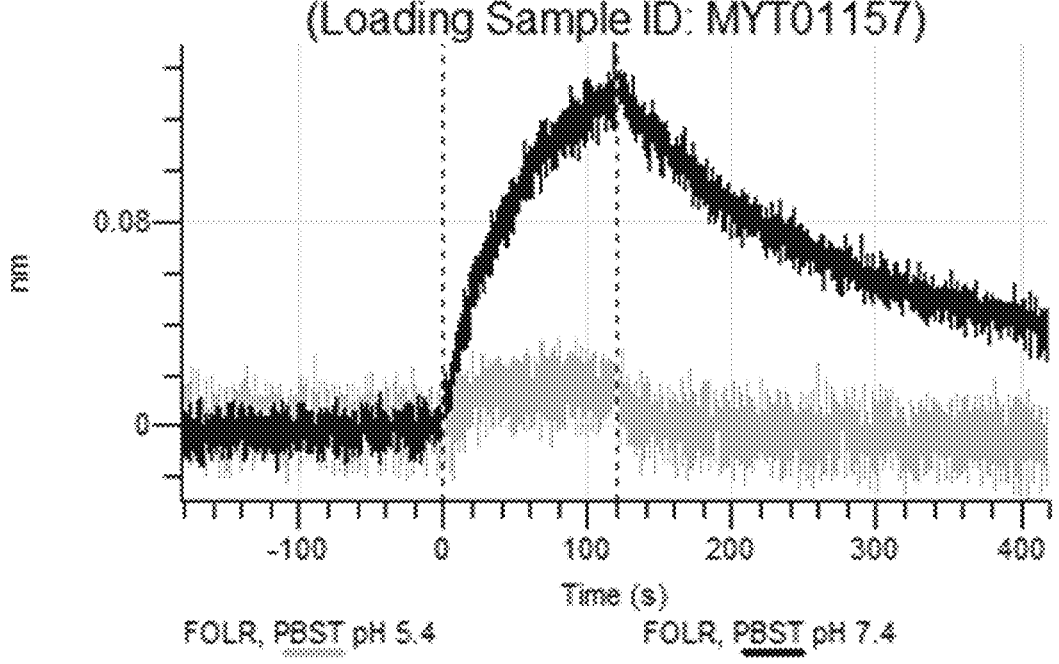
Figure 8Q:
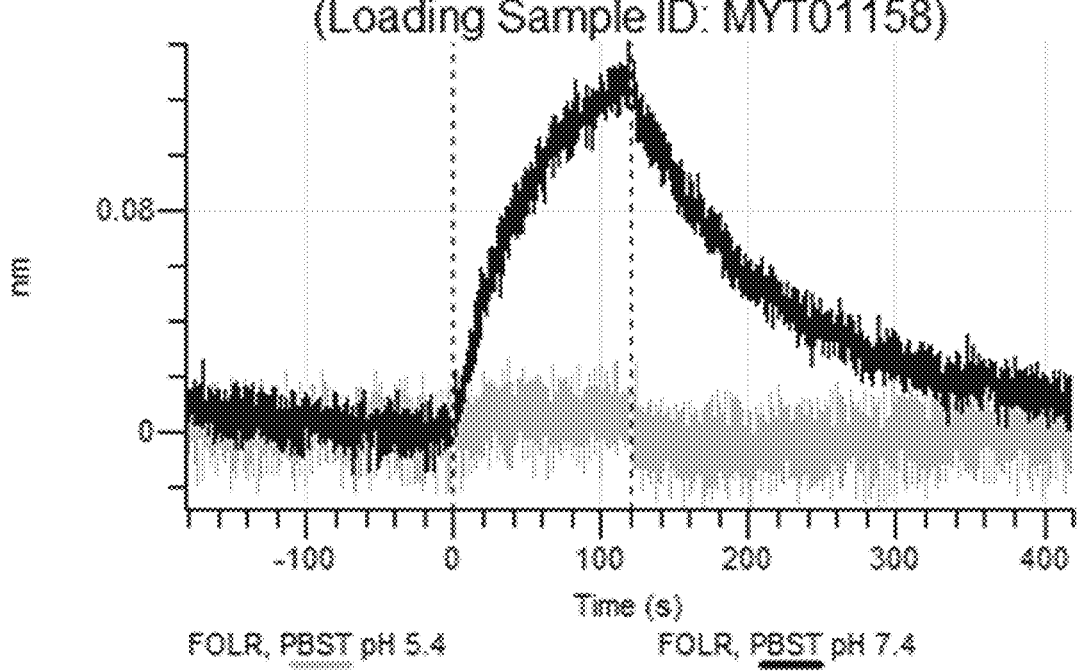
Figure 8R:
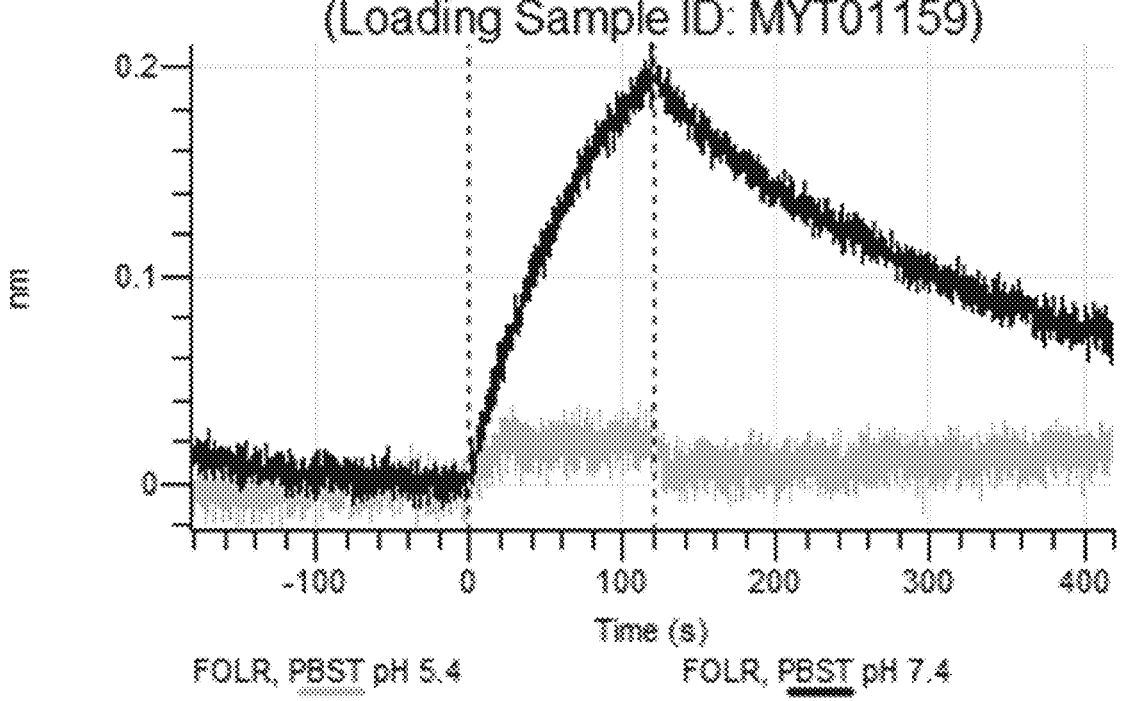
Figure 8S:
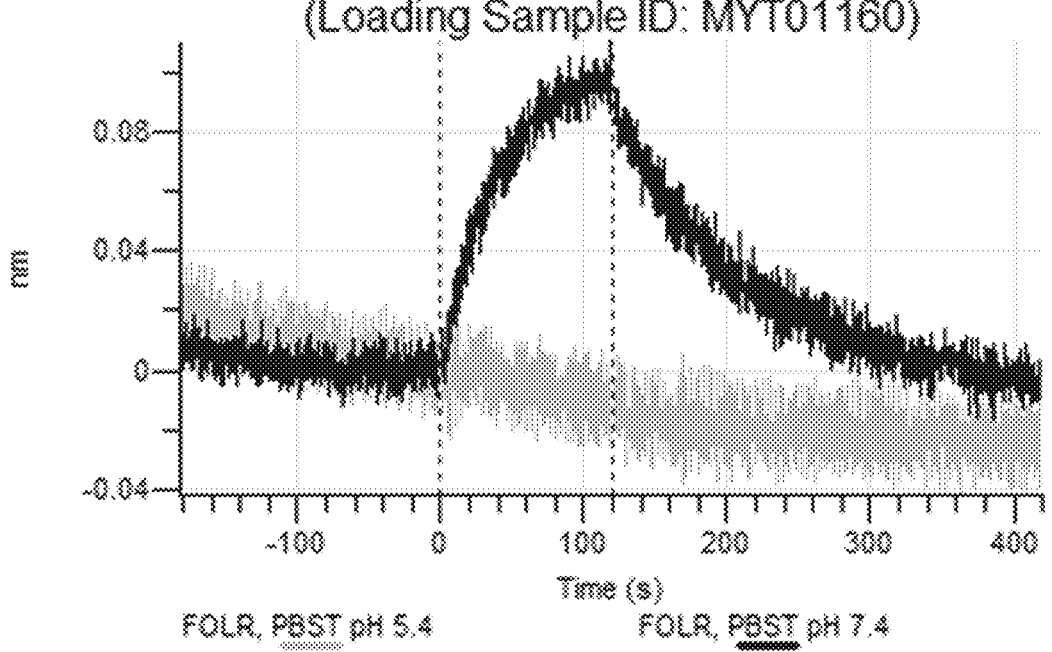
Figure 8T:
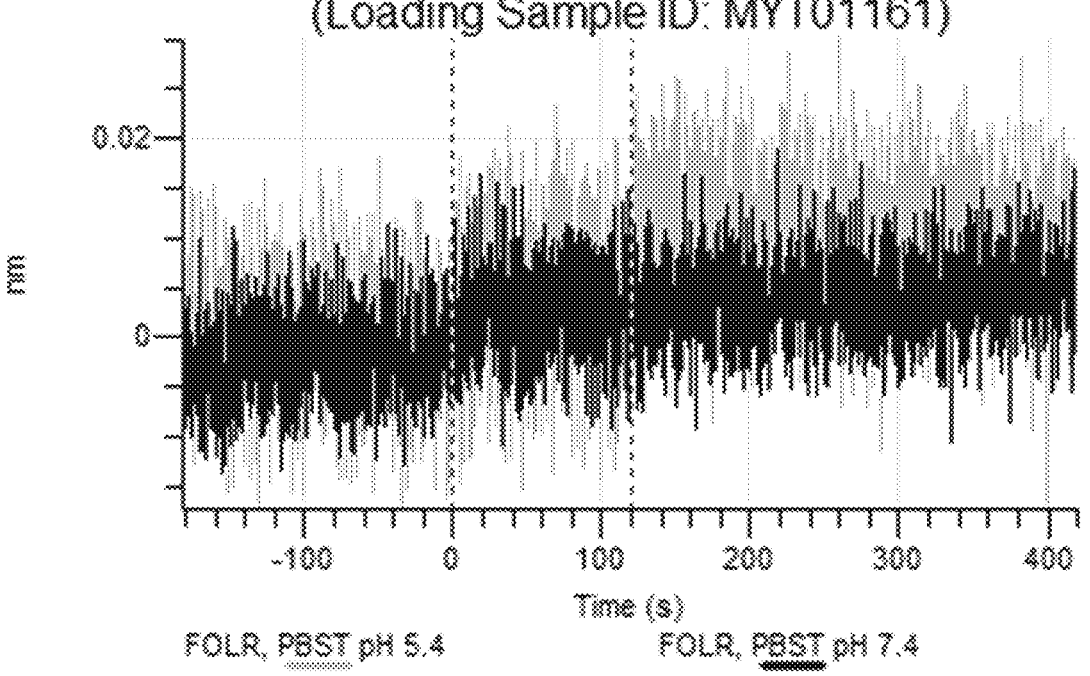

FIGS. 8a to 8t: Binding of histidine scanning and alanine scanning variants of MIRVETUXIMAB to FOLR1 by biolayer interferometry. MYT1142-MYT1161, heavy chain combinations histidine scanning and alanine scanning variants, were captured on anti-human Fc biosensors and associated with FOLR1 at low pH or high pH, as specified in the figures.

FIG. 9: Construct identifier to SEQ ID NO correspondence table. Constructs, heavy chain combinations histidine scanning and alanine scanning variants, are listed in the first column of the table, SEQ ID NOs are listed and correspond to constructs on the left and the appropriate heavy chain, light chain, and CDR categories along the top.

Figure 10:
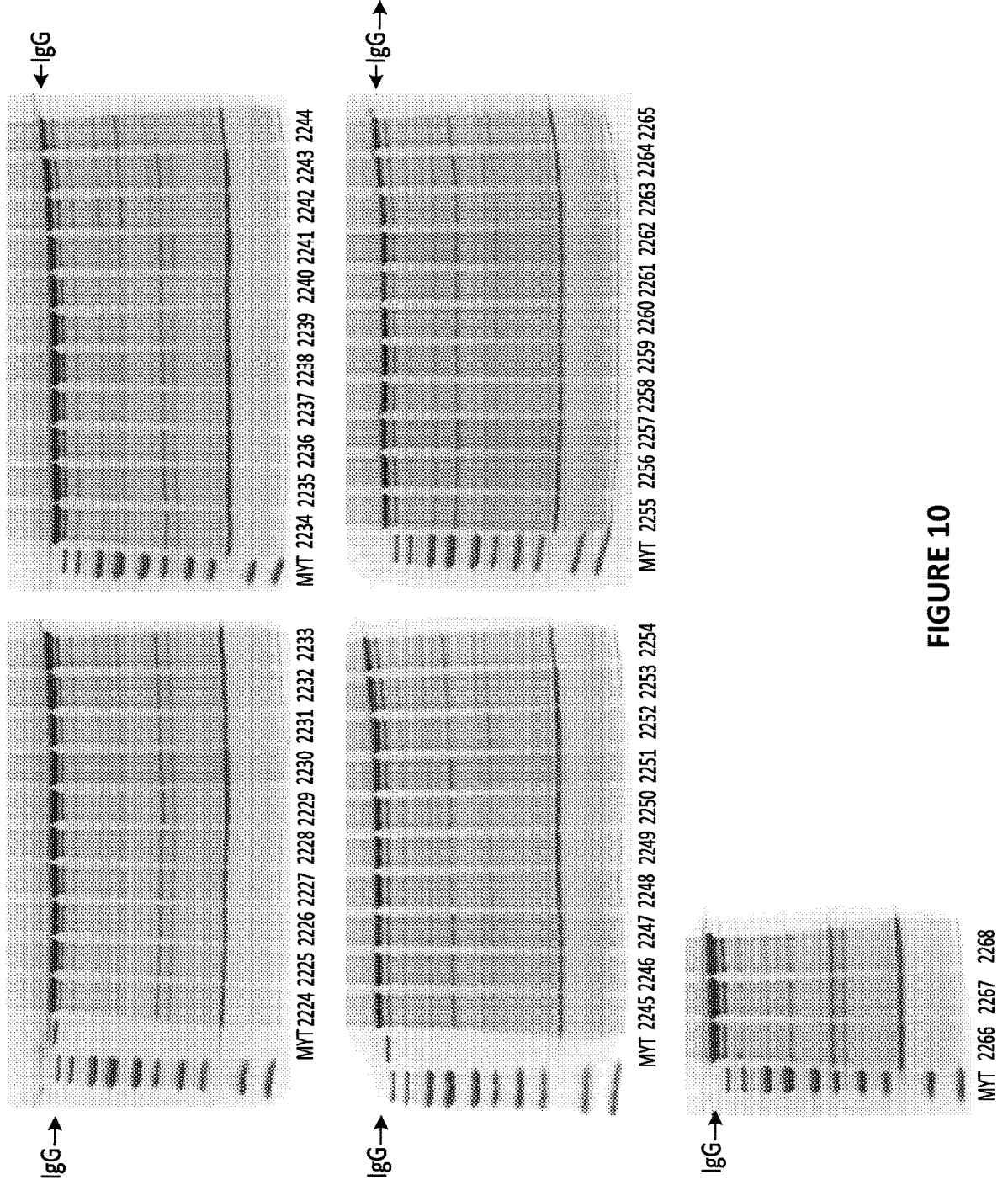

FIG. 10: SDS PAGE for STRO-002 histidine scanning and alanine scanning. Expi293 cell culture supernatants post-harvest were loaded on non-reduced SDS PAGE gels to confirm expression of STRO-002 and histidine scanning and alanine scanning variants. Arrows show the corresponding size for an IgG on a non-reduced SDS PAGE gel. MYT2224 is STRO-002 and the rest of the lanes (MYT2225-MYT2268) are STRO-002 heavy chain histidine scanning and alanine scanning variants.

Figure 11A:
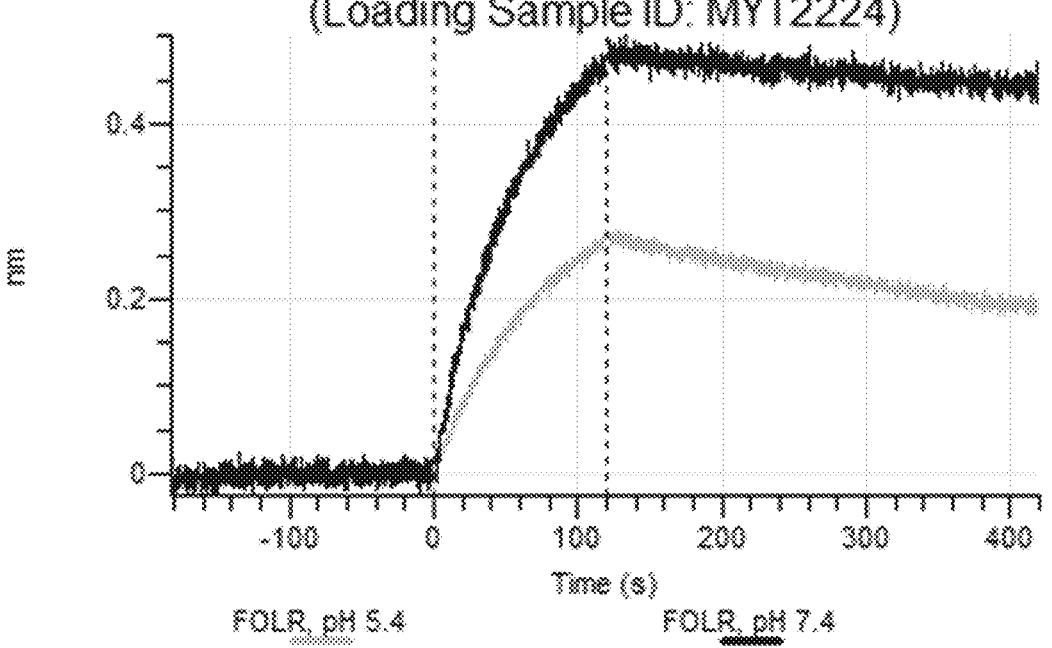
Figure 11B:
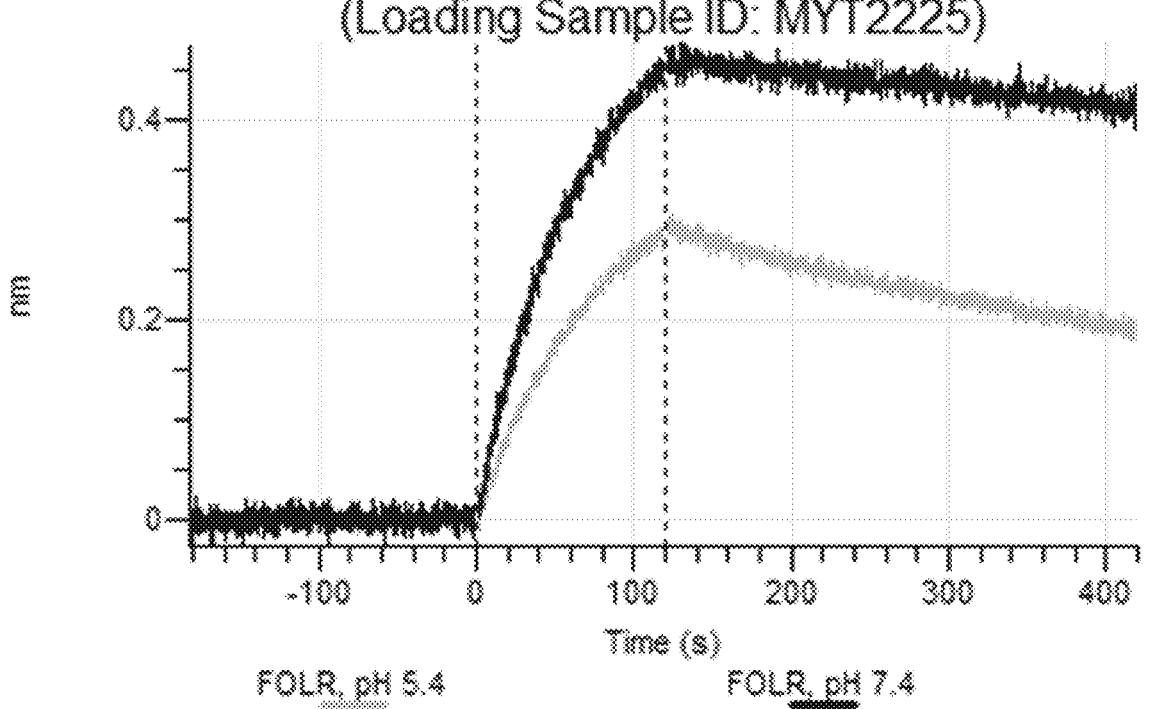
Figure 11C:
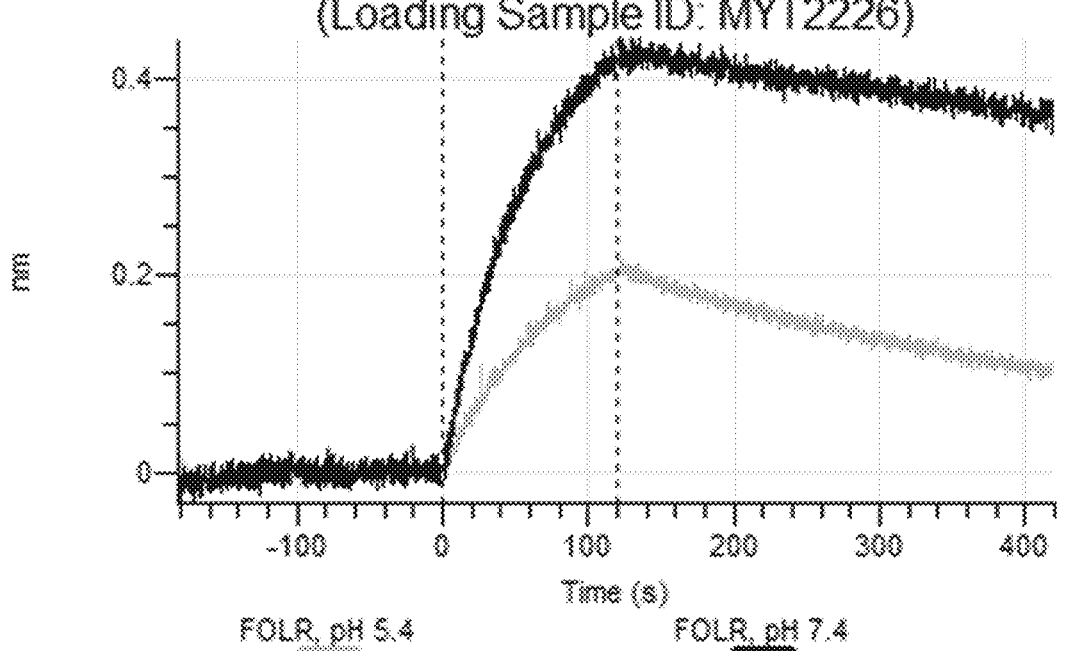
Figure 11D:
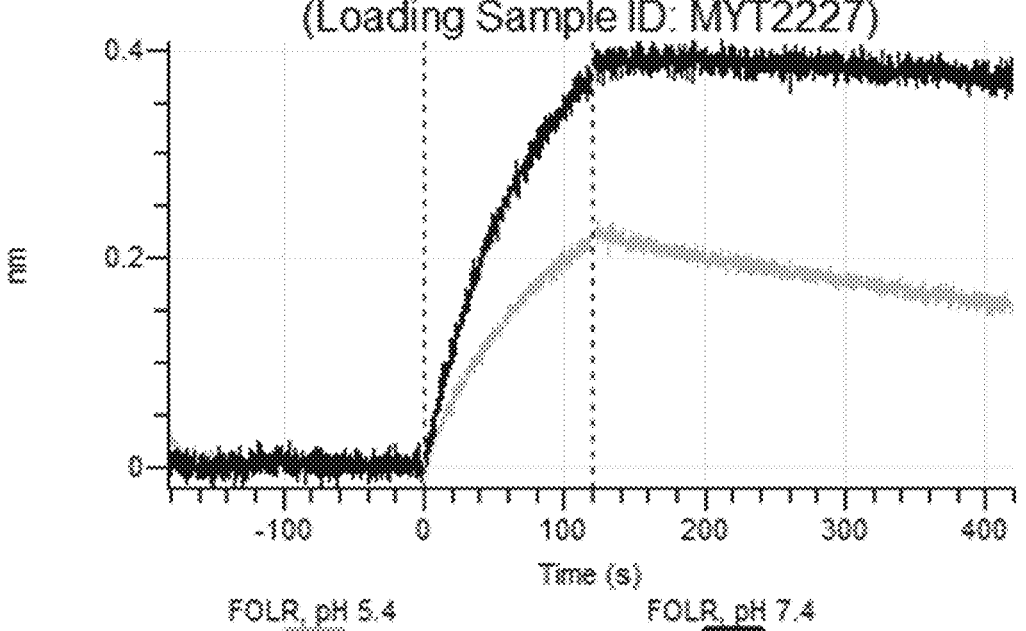
Figure 11E:
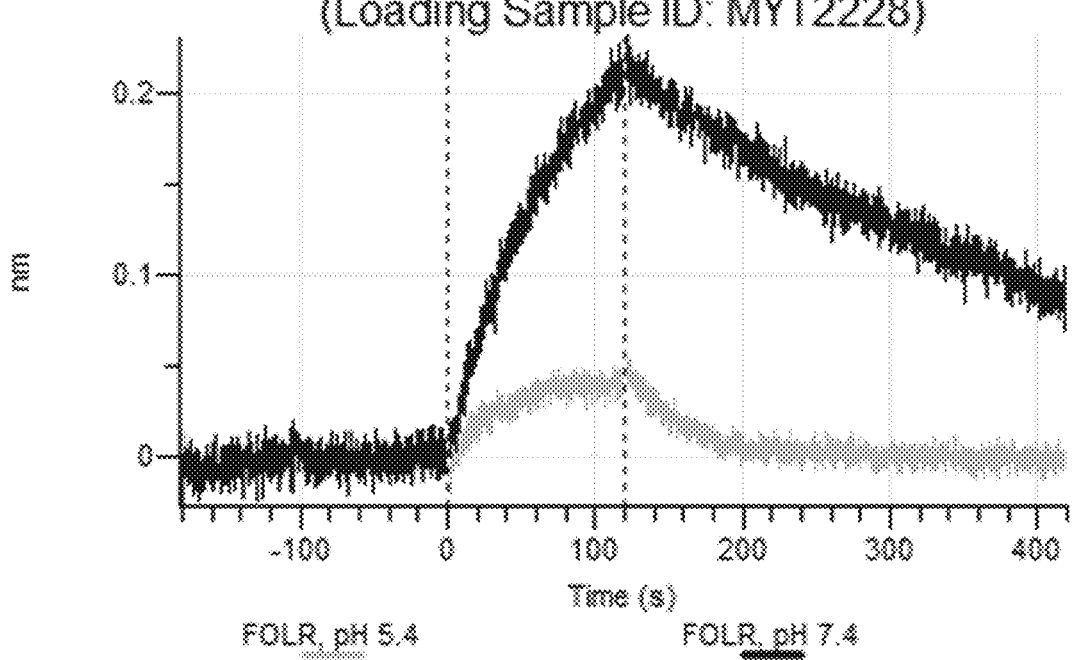
Figure 11F:
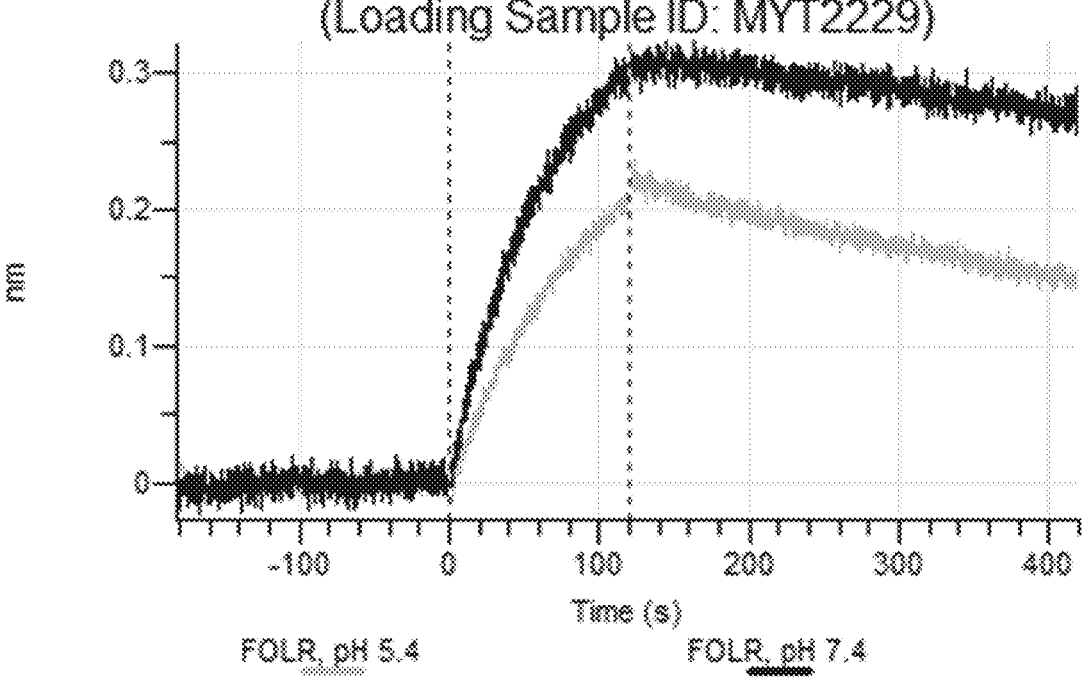
Figure 11G:
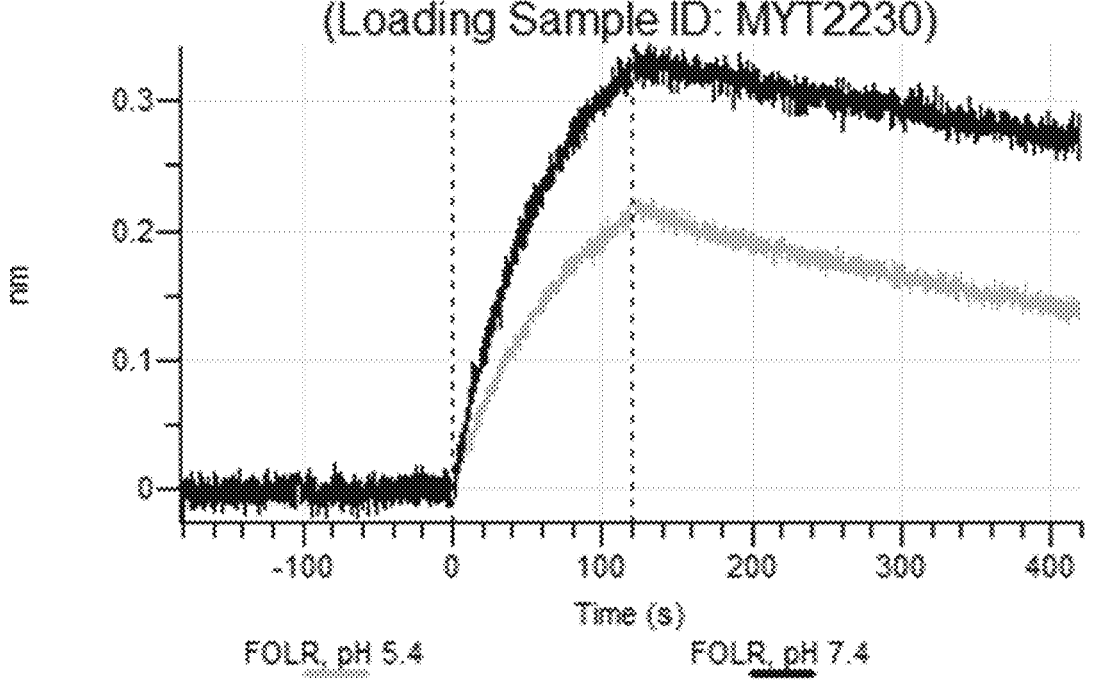
Figure 11H:
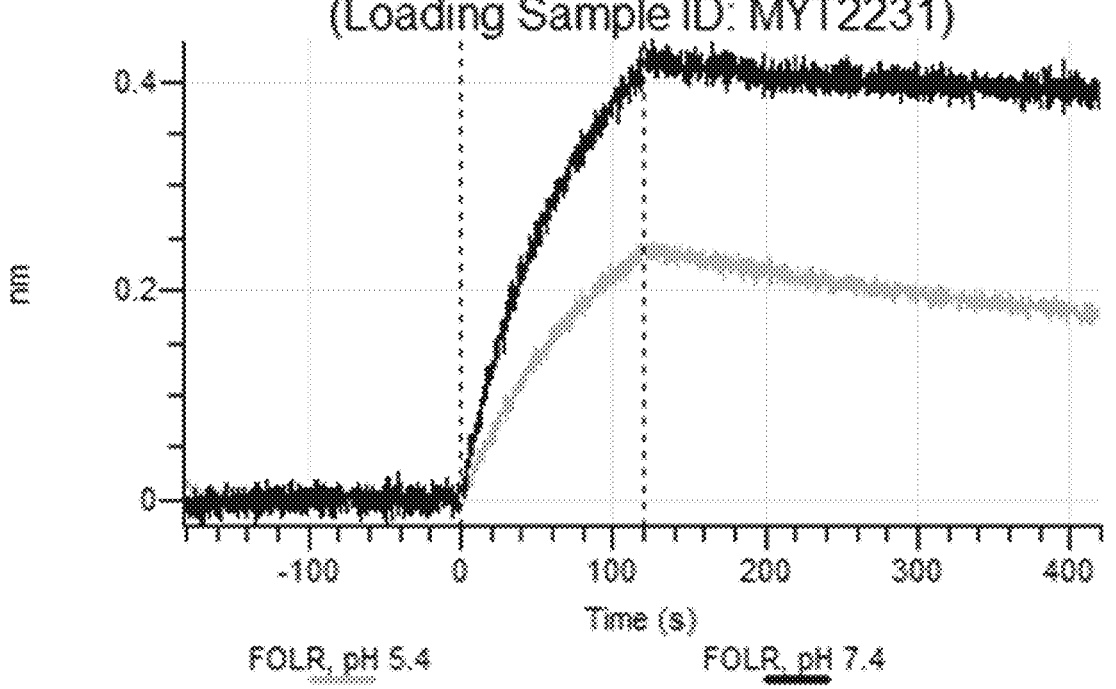
Figure 11I:
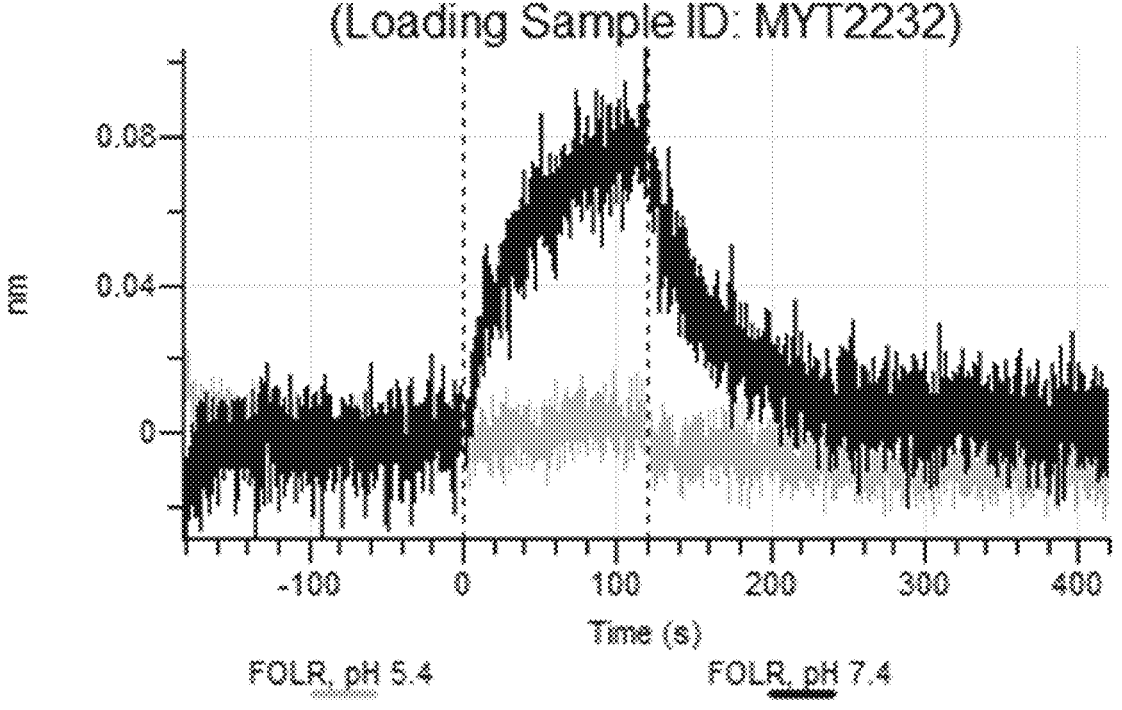
Figure 11J:
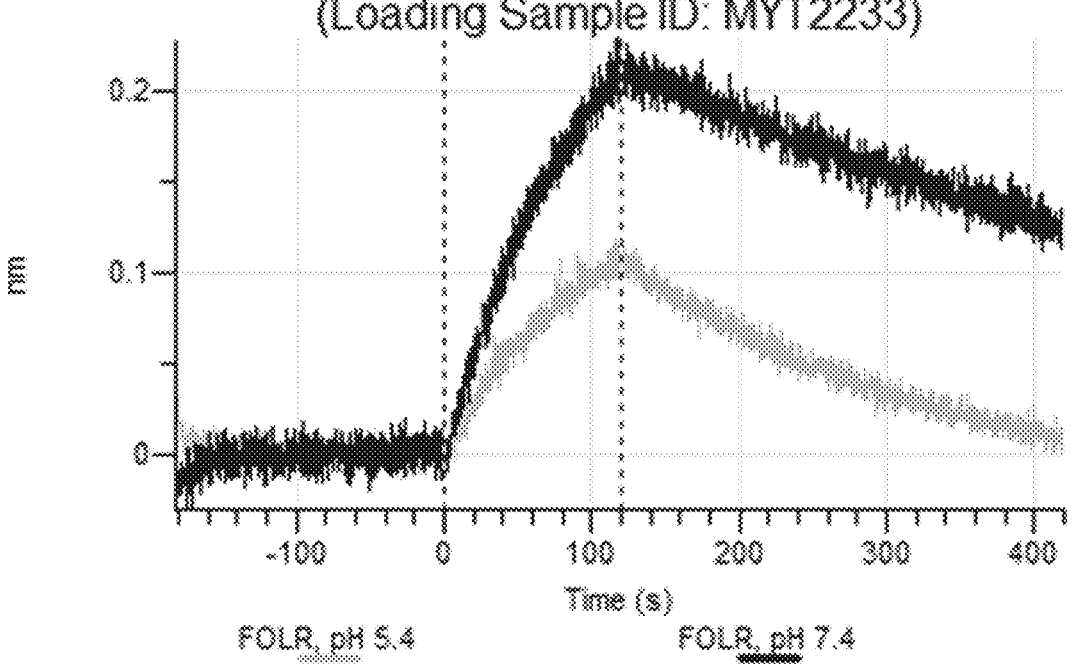
Figure 11K:
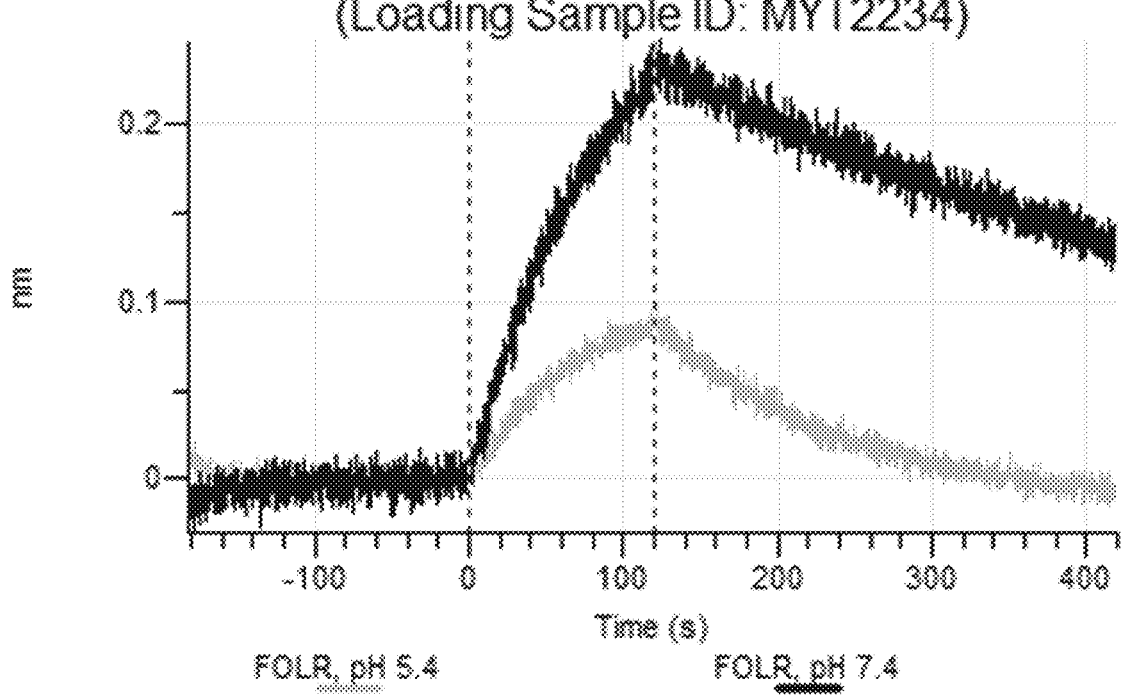
Figure 11I:
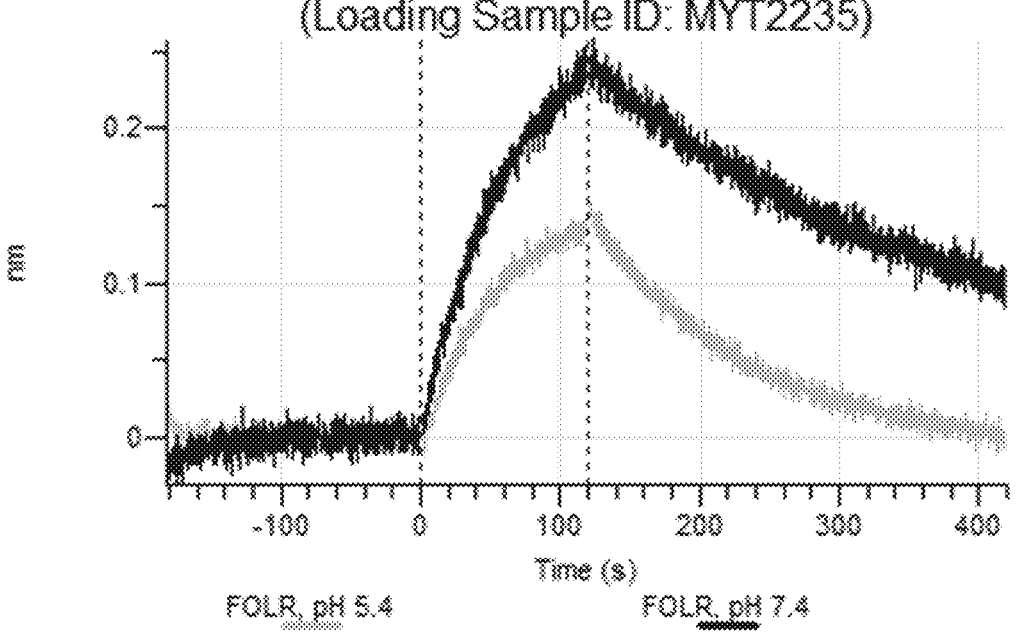
Figure 11M:
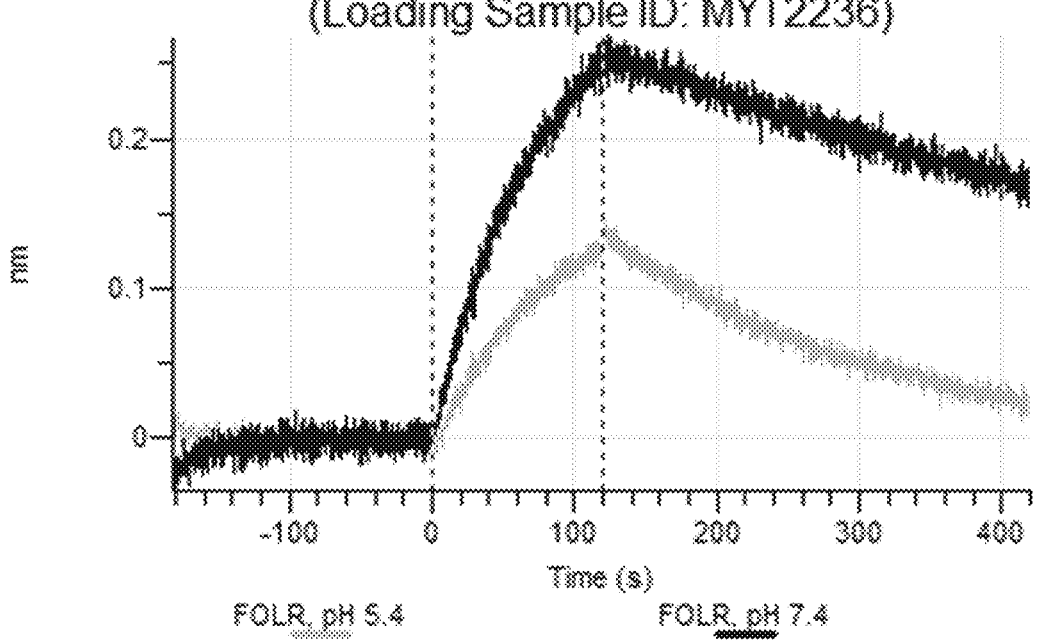
Figure 11N:
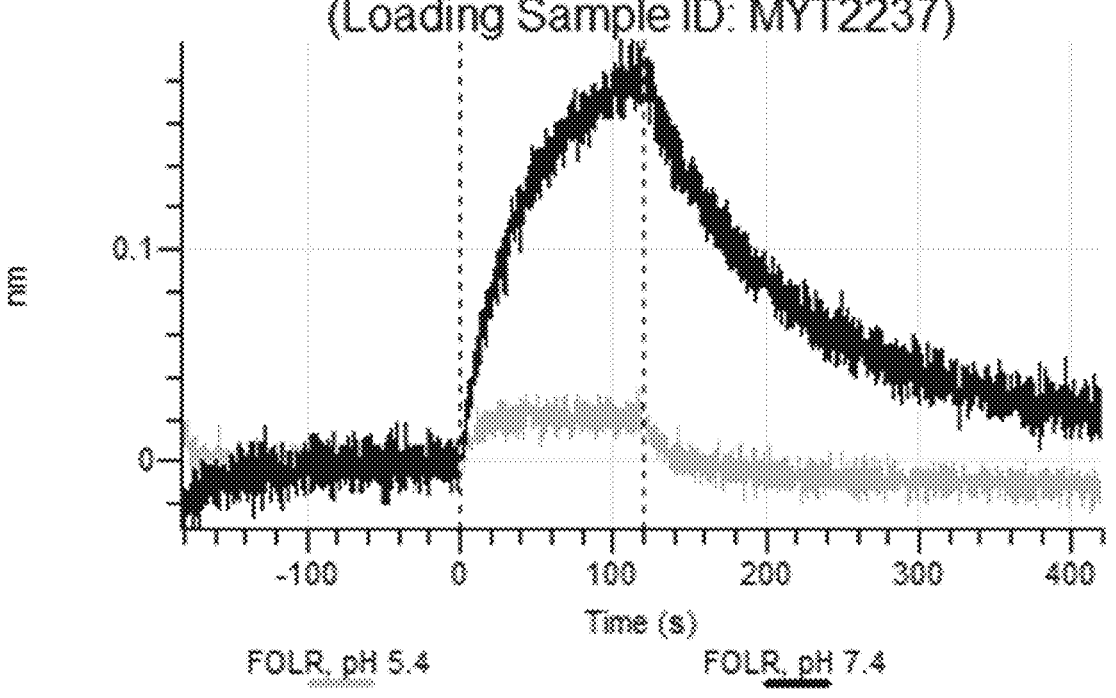
Figure 11O:
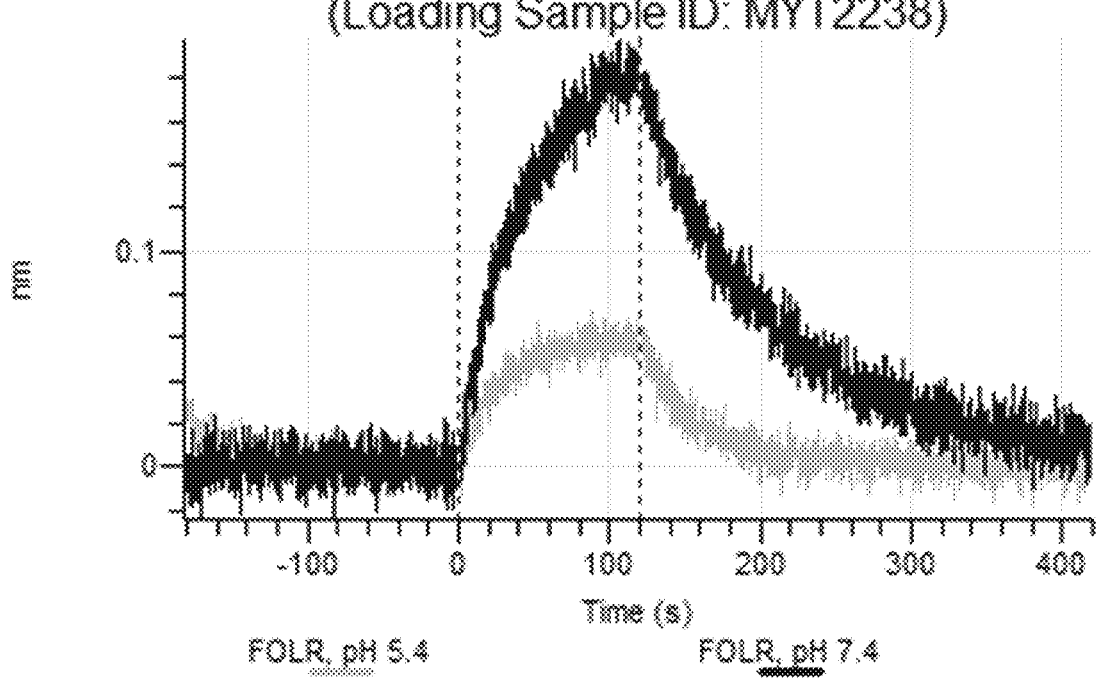
Figure 11P:
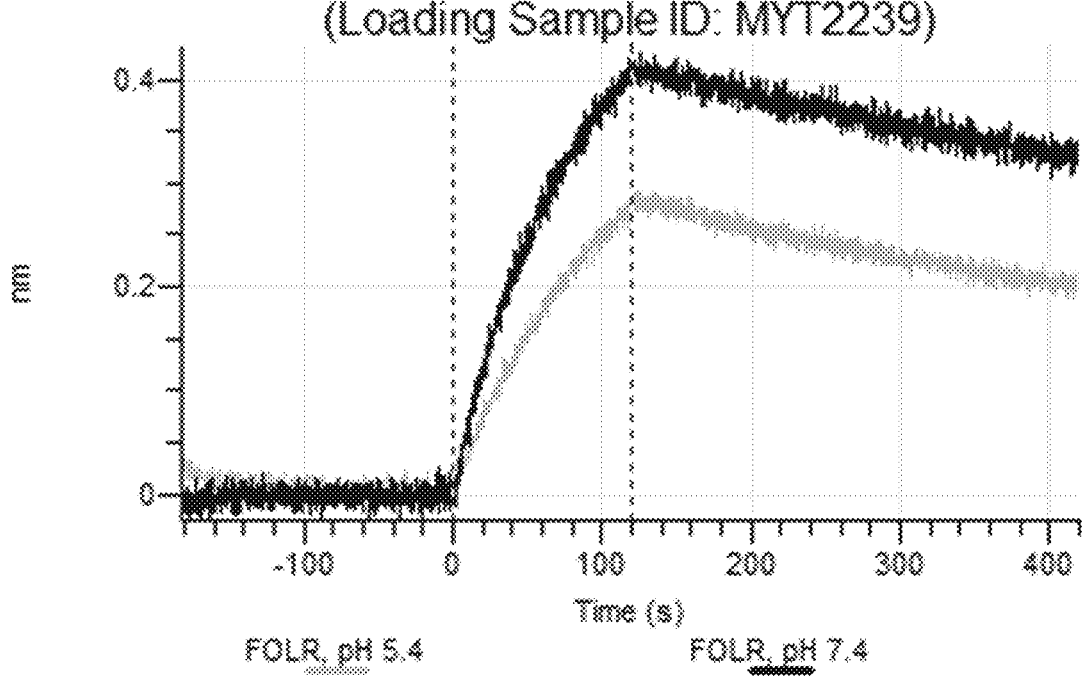
Figure 11Q:
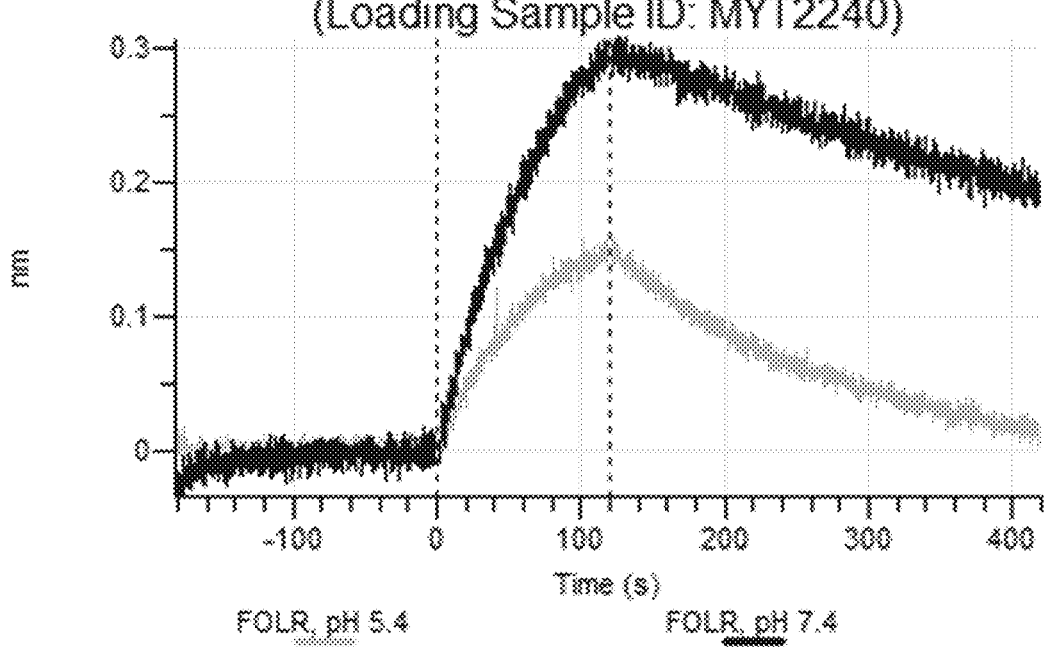
Figure 11R:
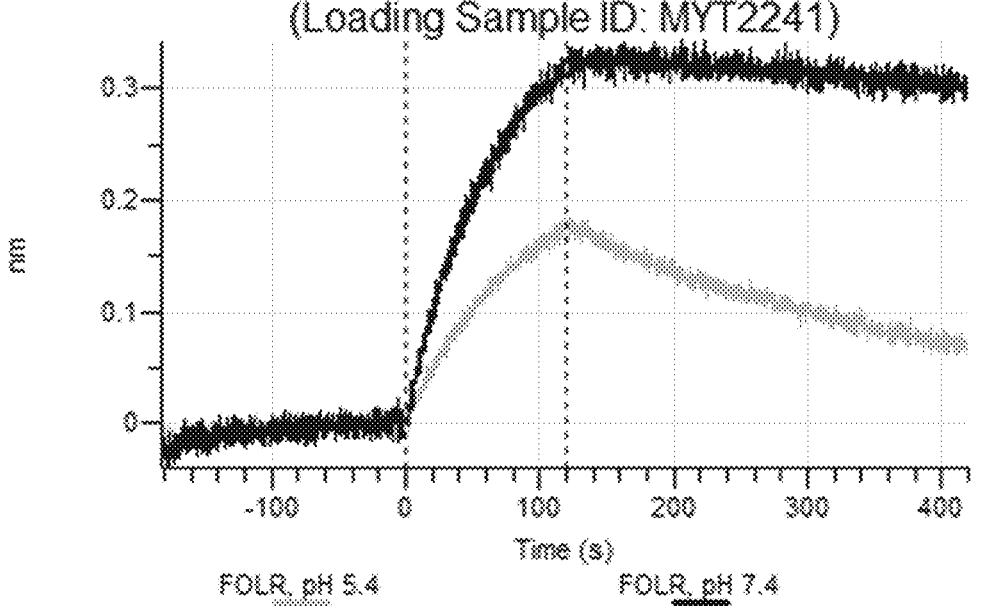
Figure 11S:
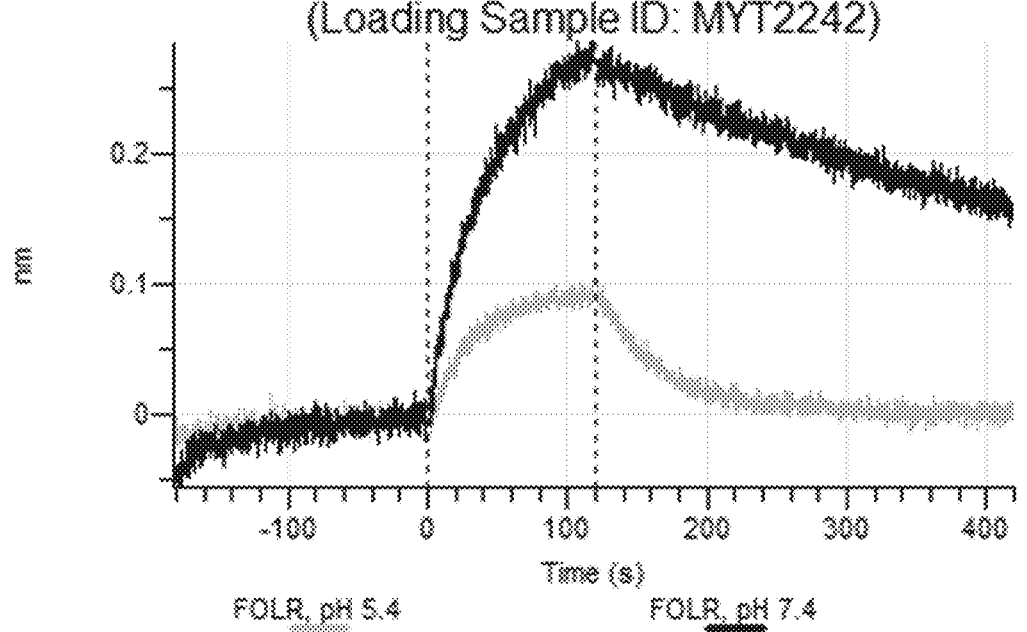
Figure 11T:
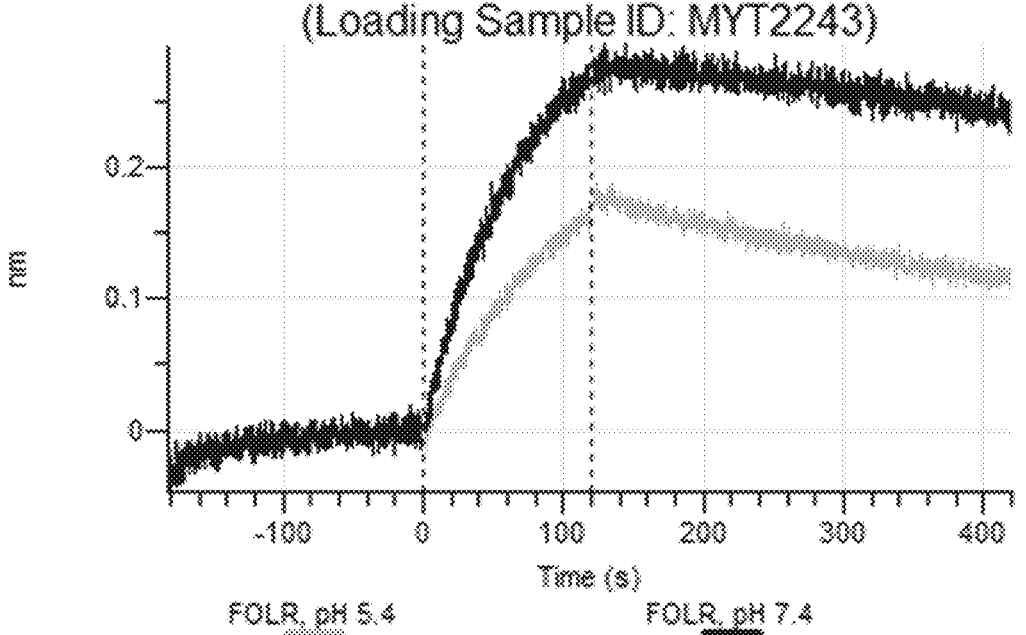
Figure 11U:
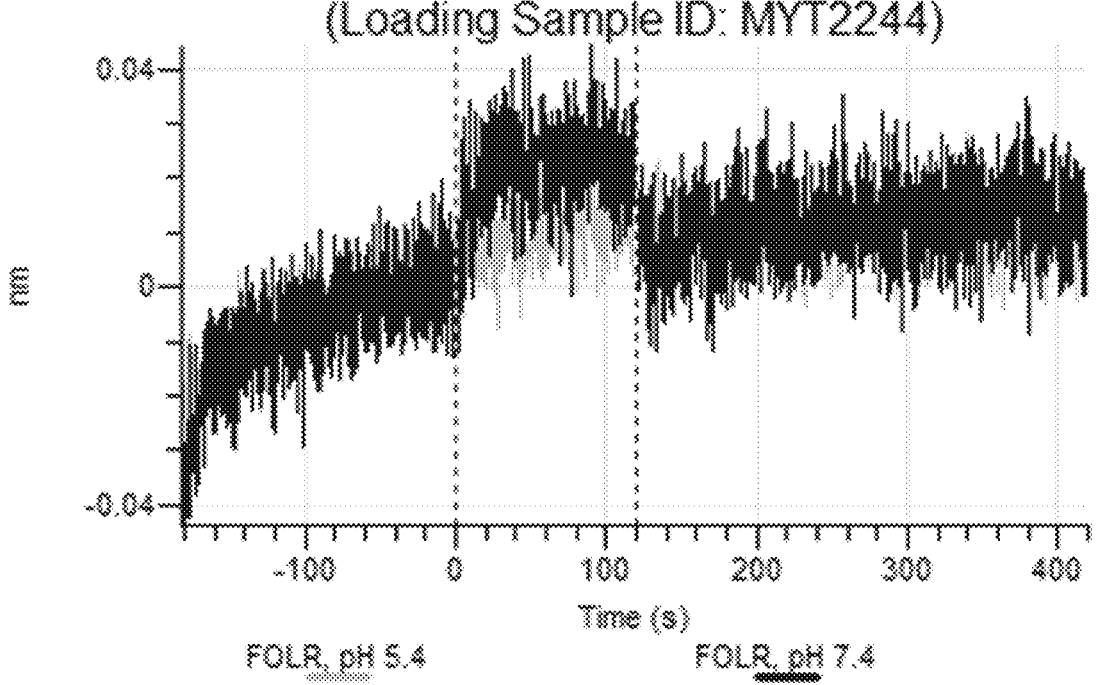
Figure 11V:
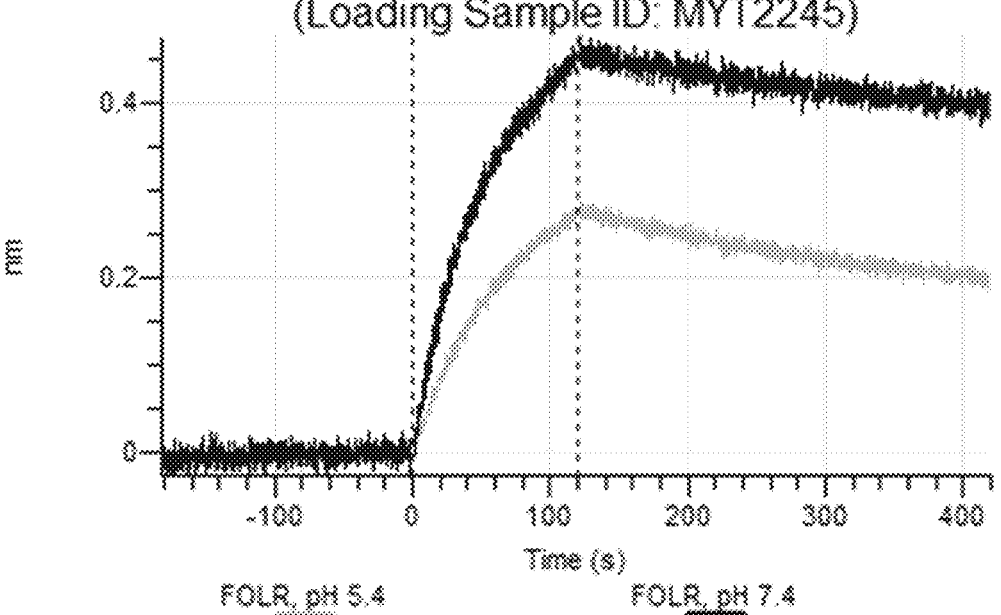
Figure 11W:
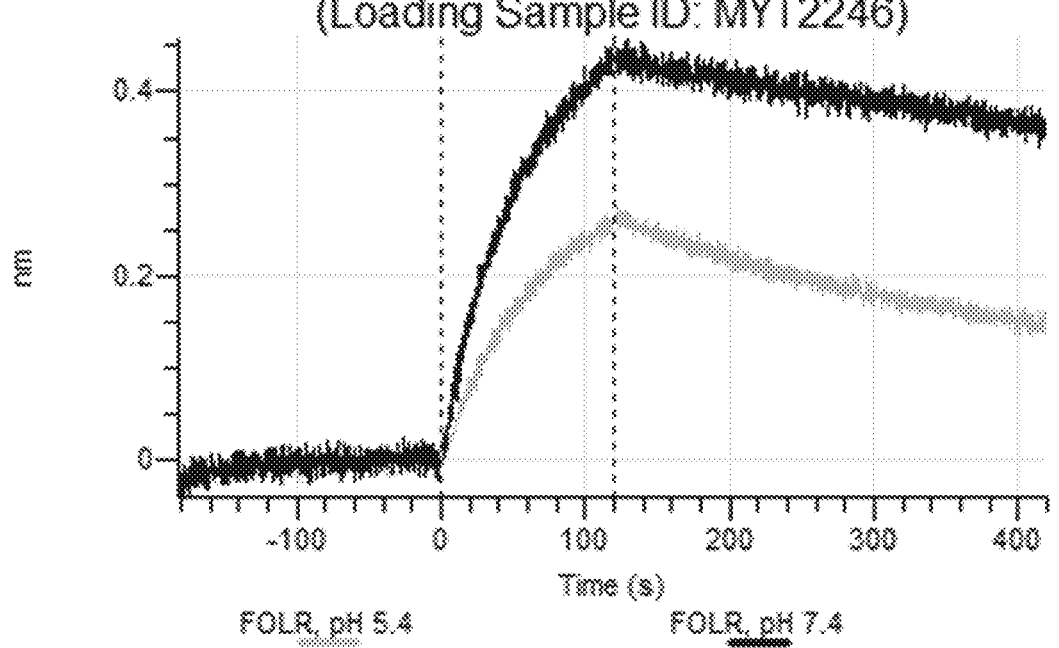
Figure 11X:
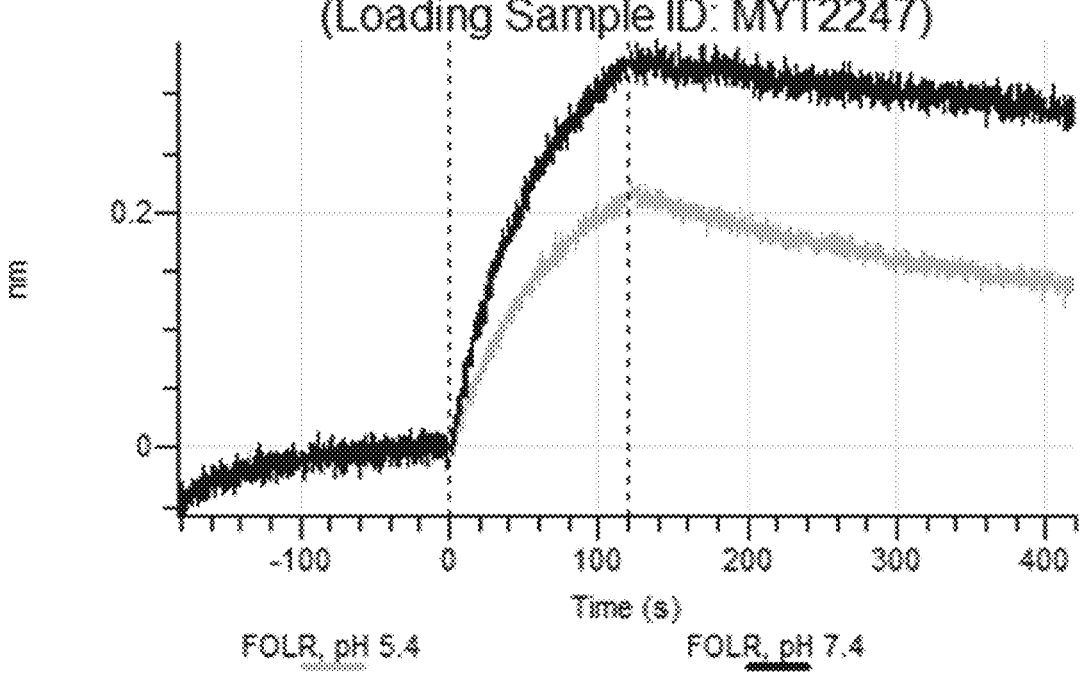
Figure 11Y:
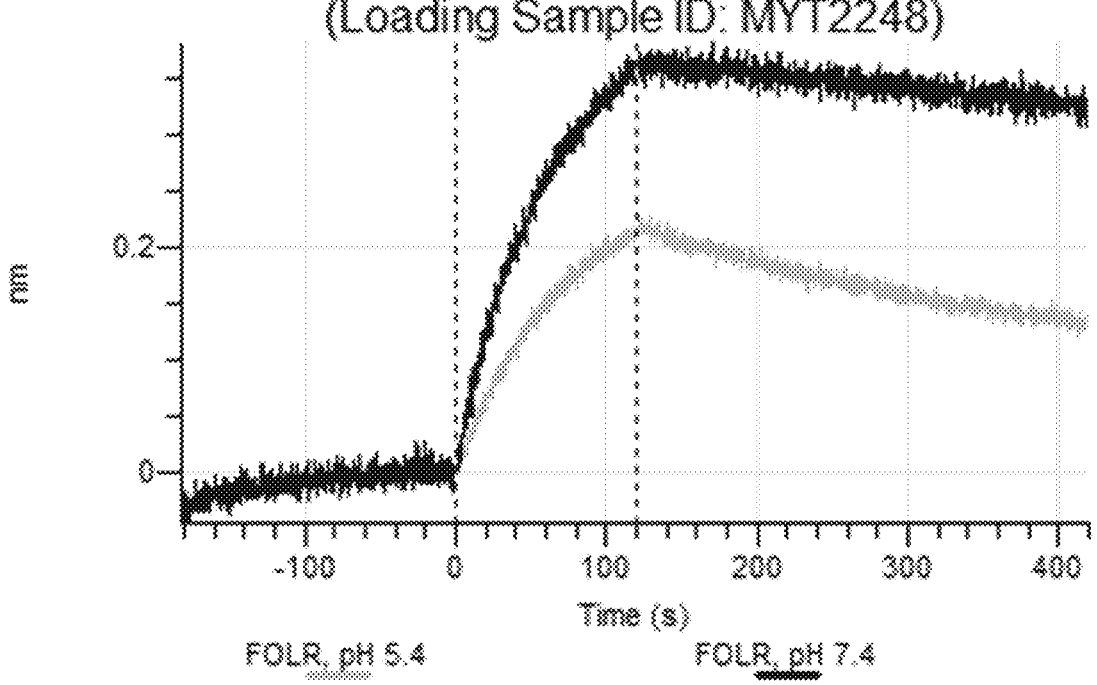
Figure 11Z:
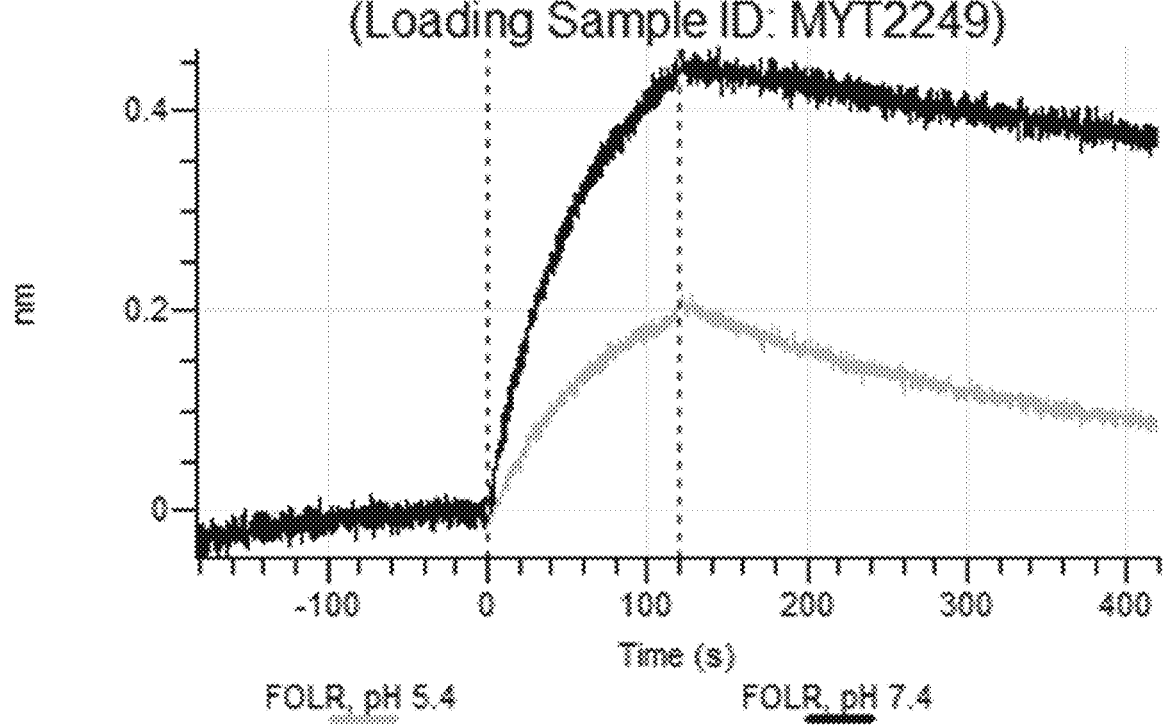
Figure 11A:
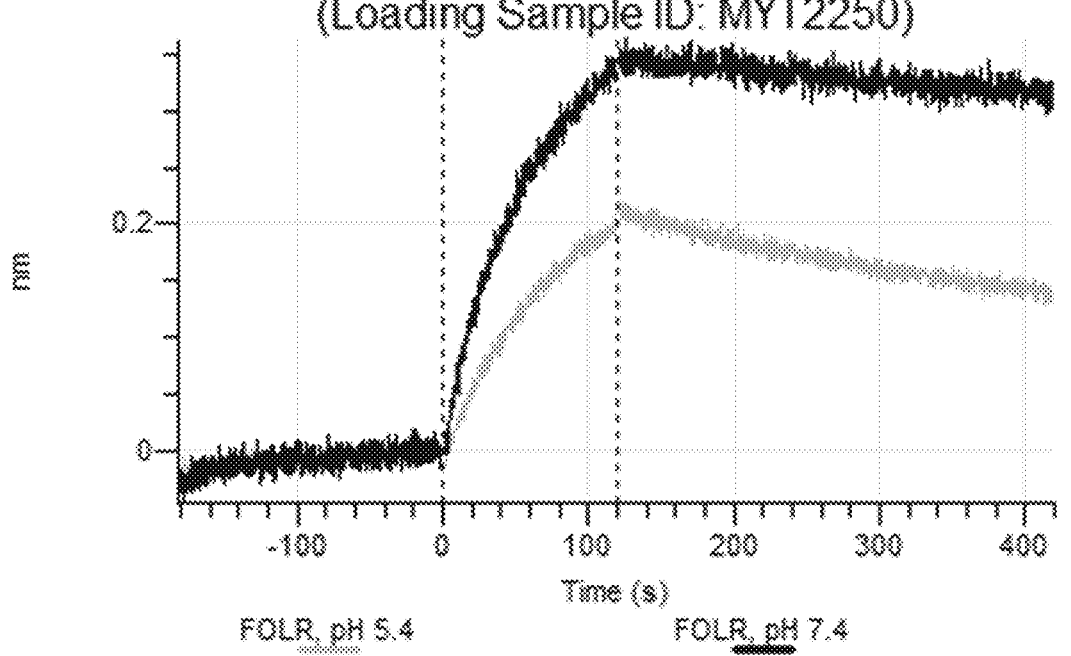
Figure 11A:
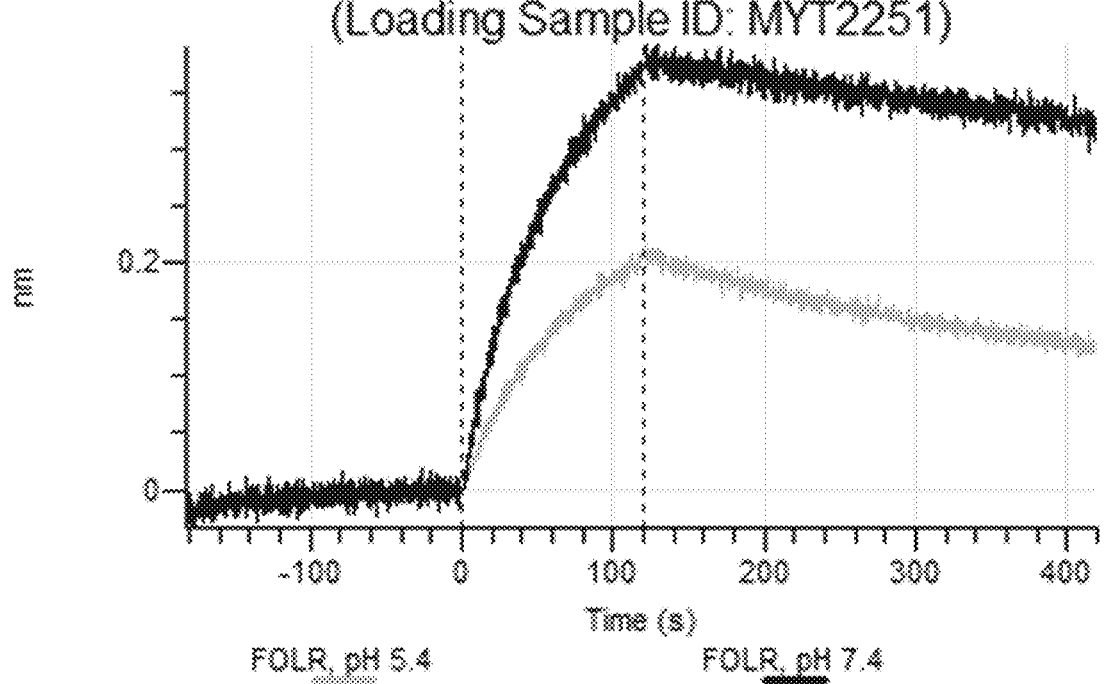
Figure 11A:
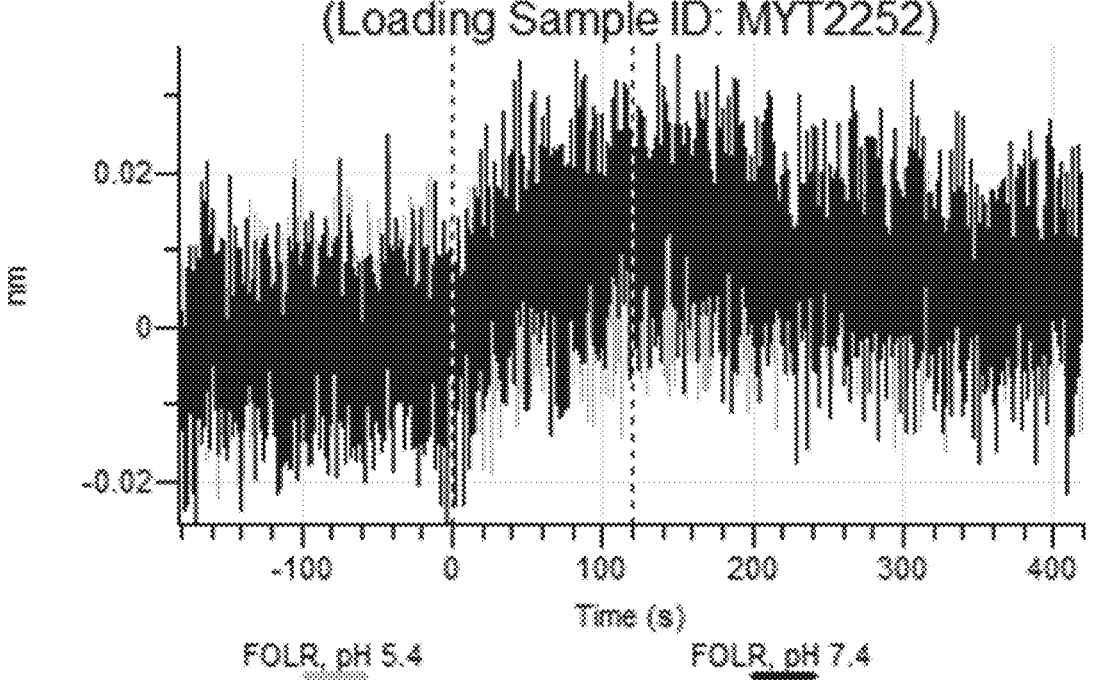
Figure 11A:
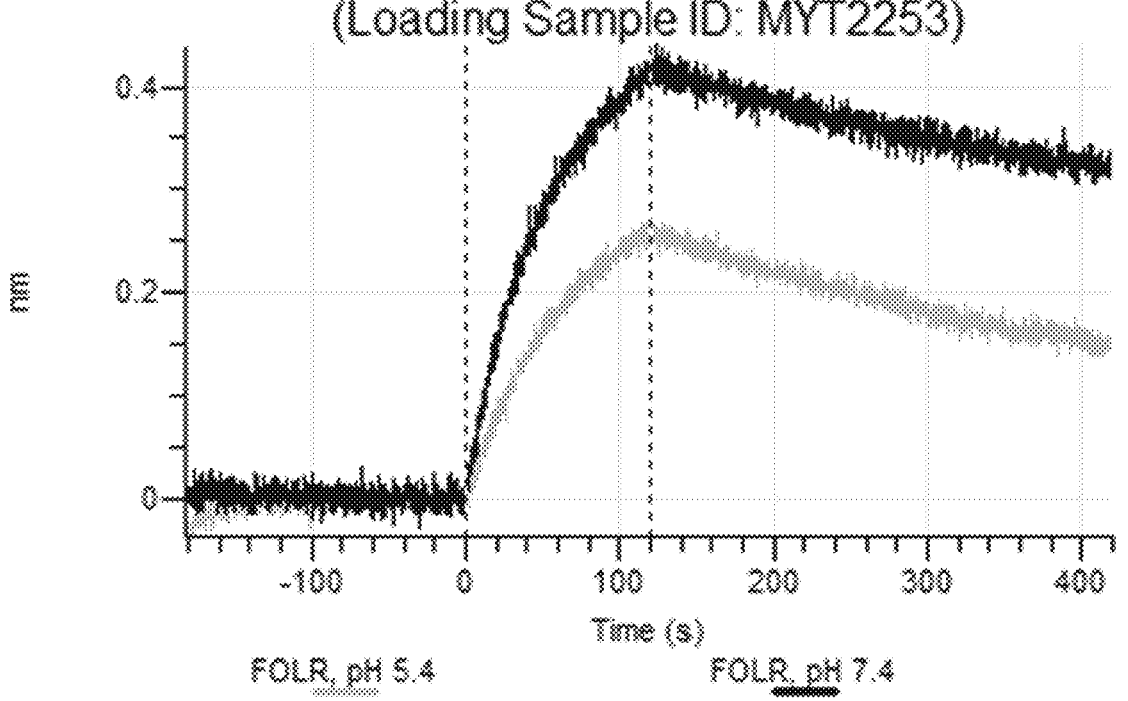
Figure 11A:
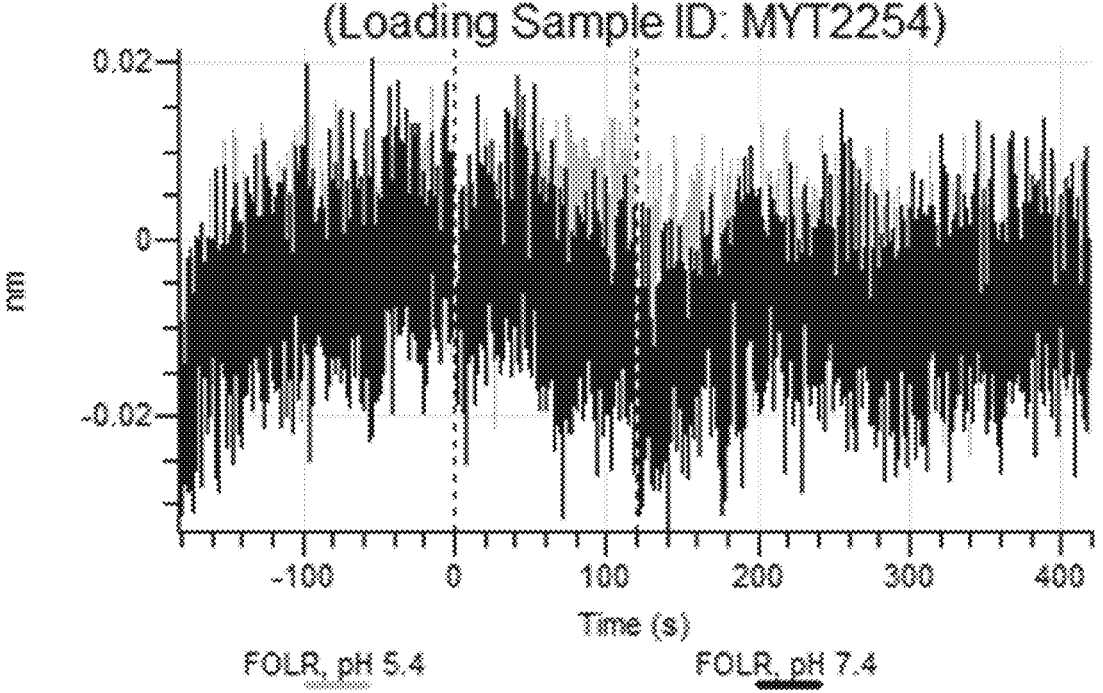
Figure 11A:
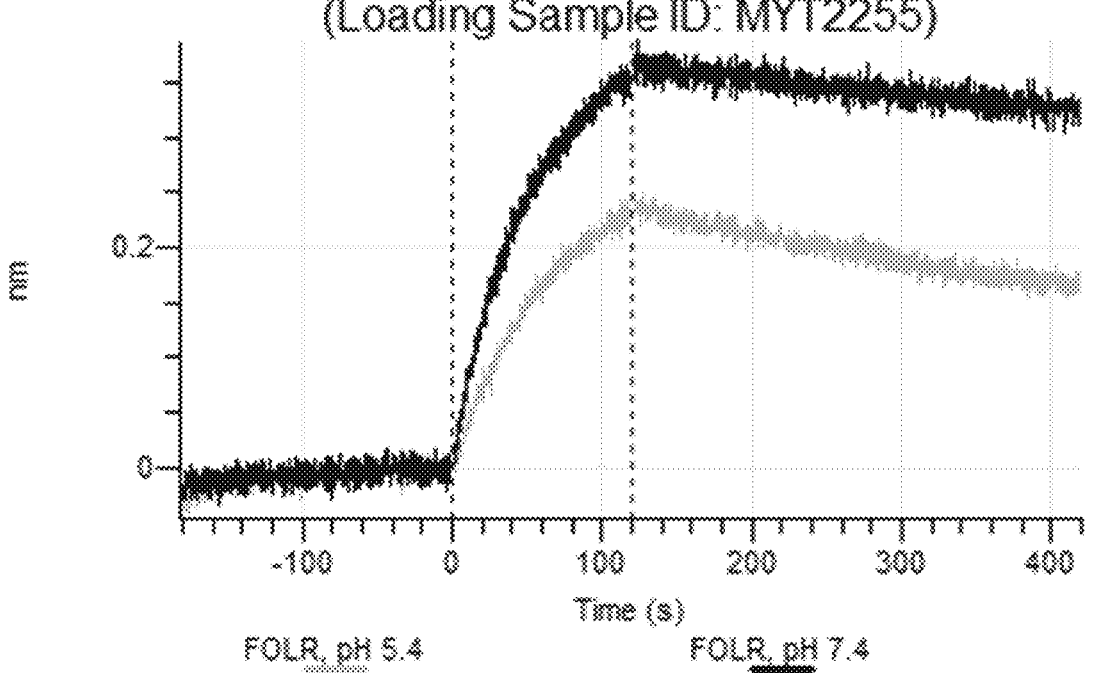
Figure 11A:
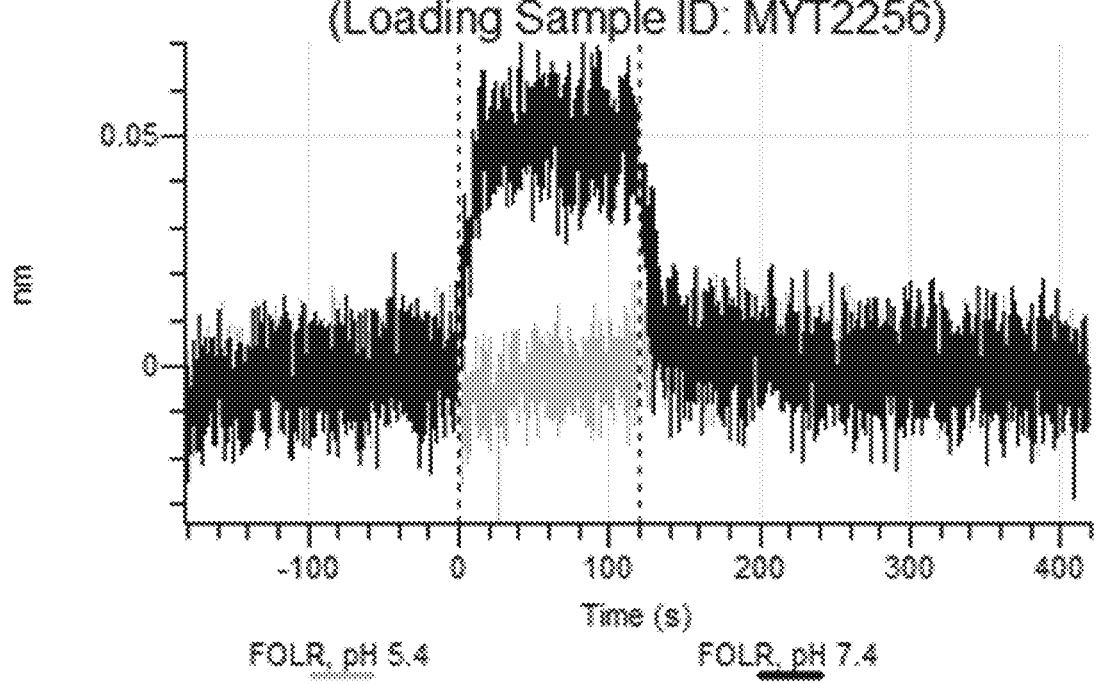
Figure 11A:
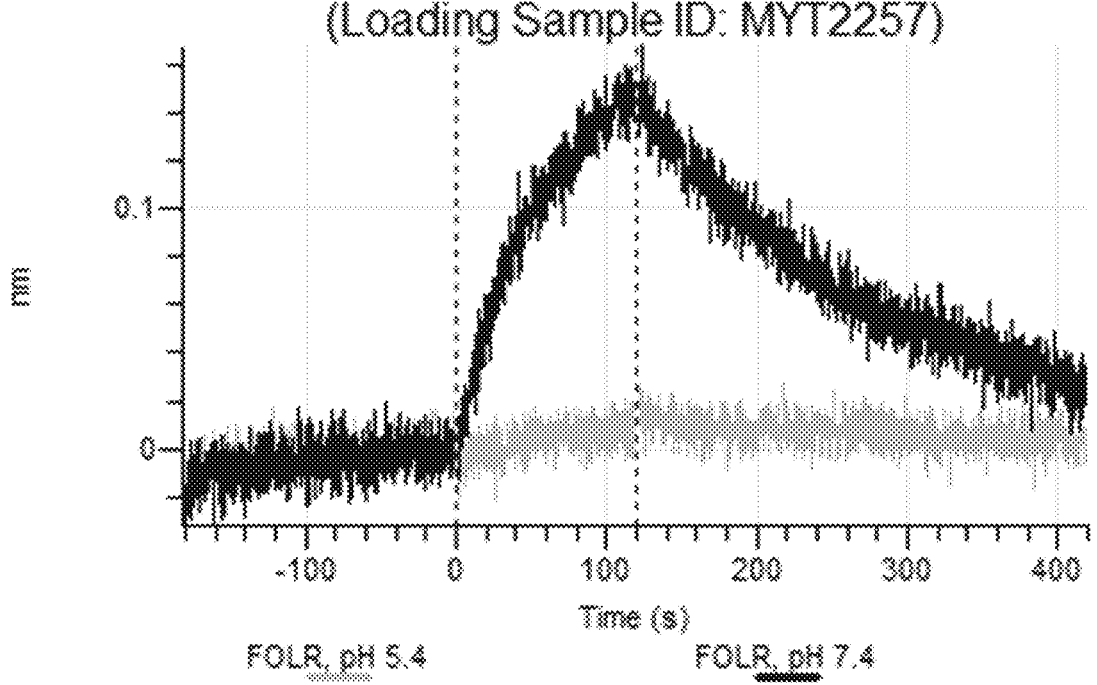
Figure 11A:
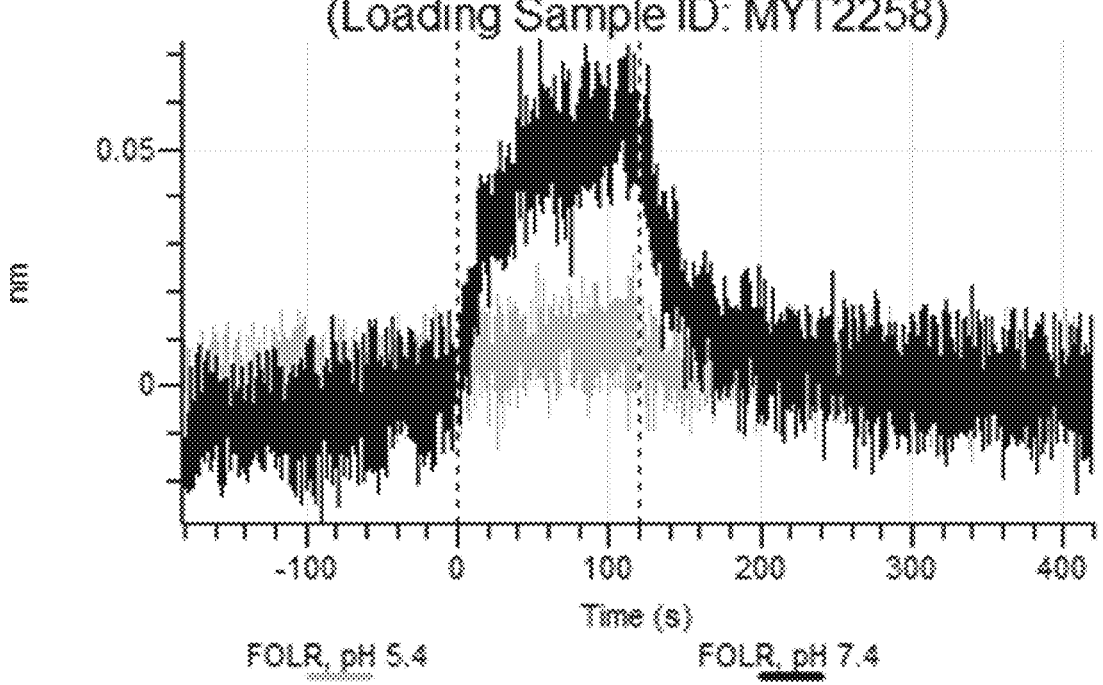
Figure 11A:
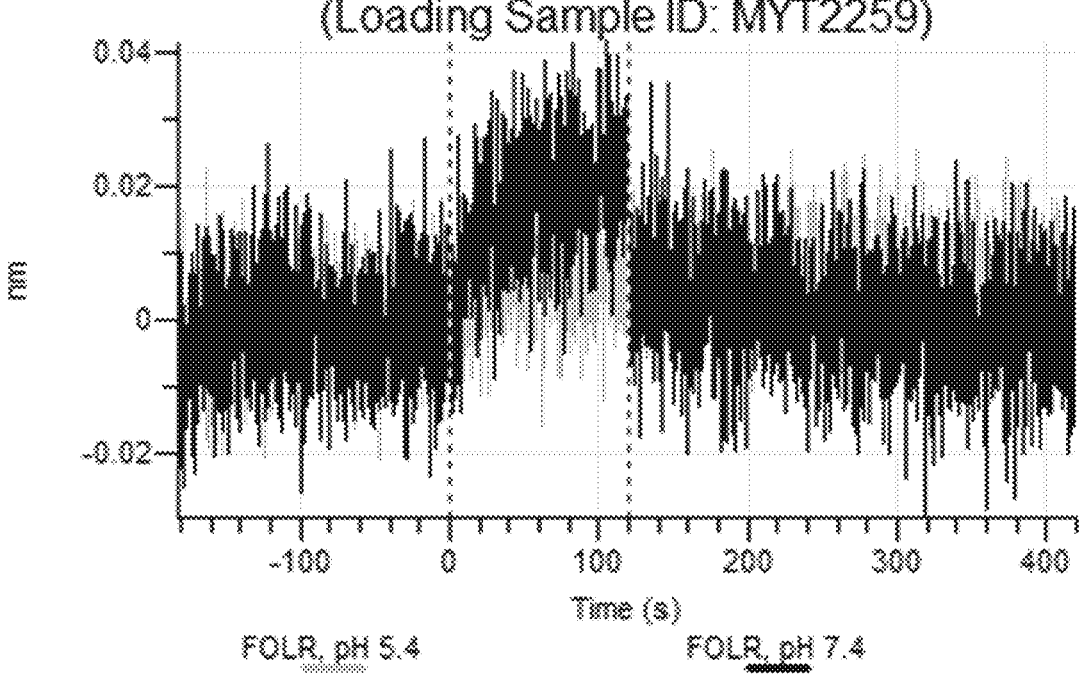
Figure 11A:
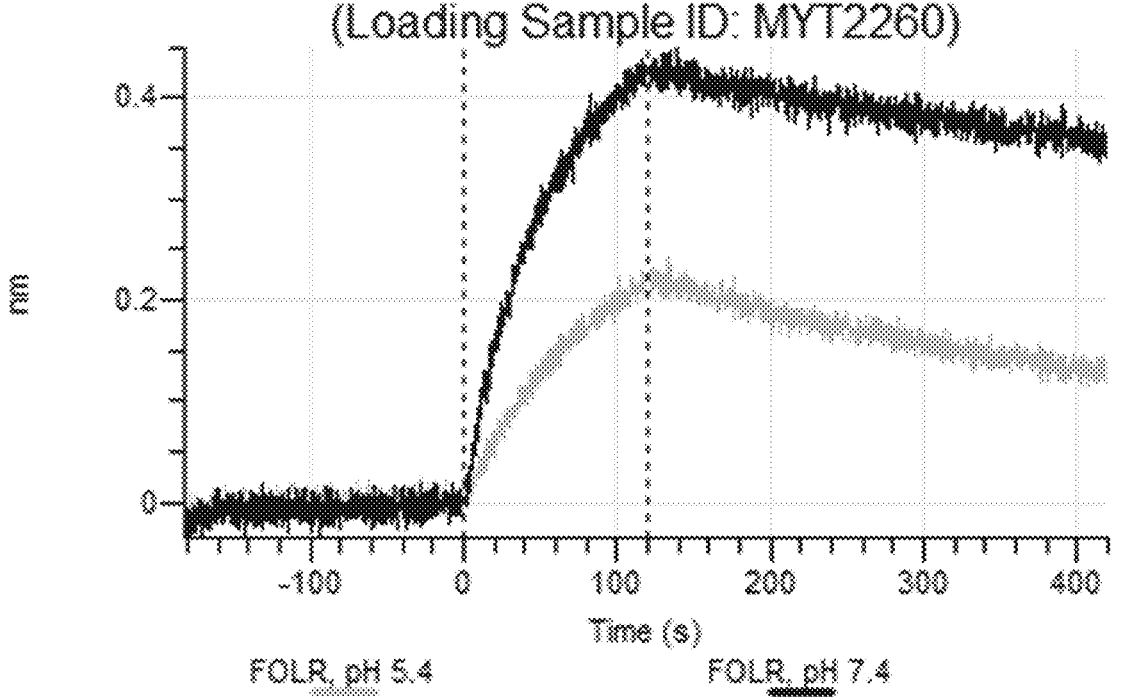
Figure 11A:
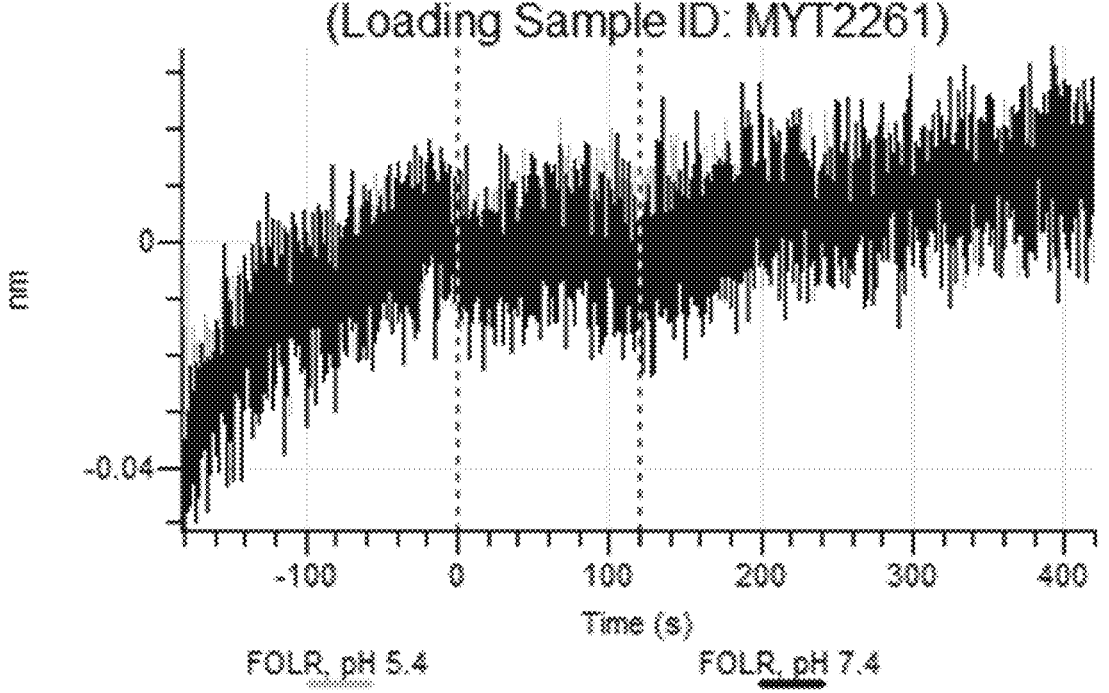
Figure 11A:
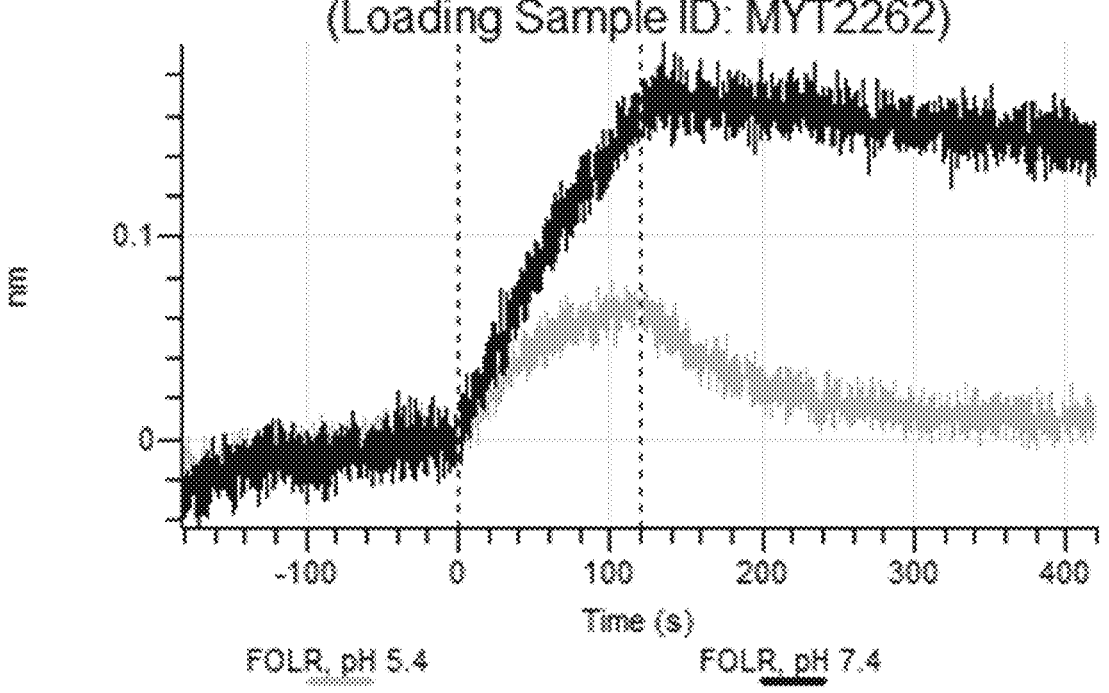
Figure 11A:
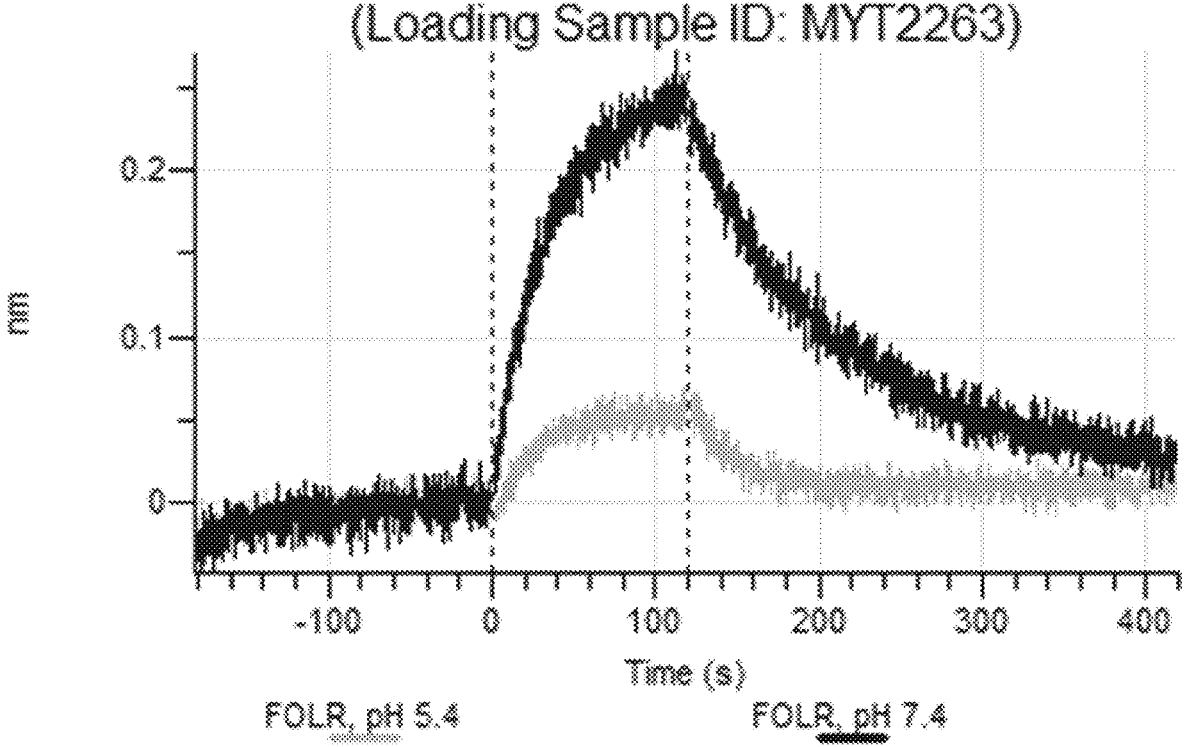
Figure 11A:
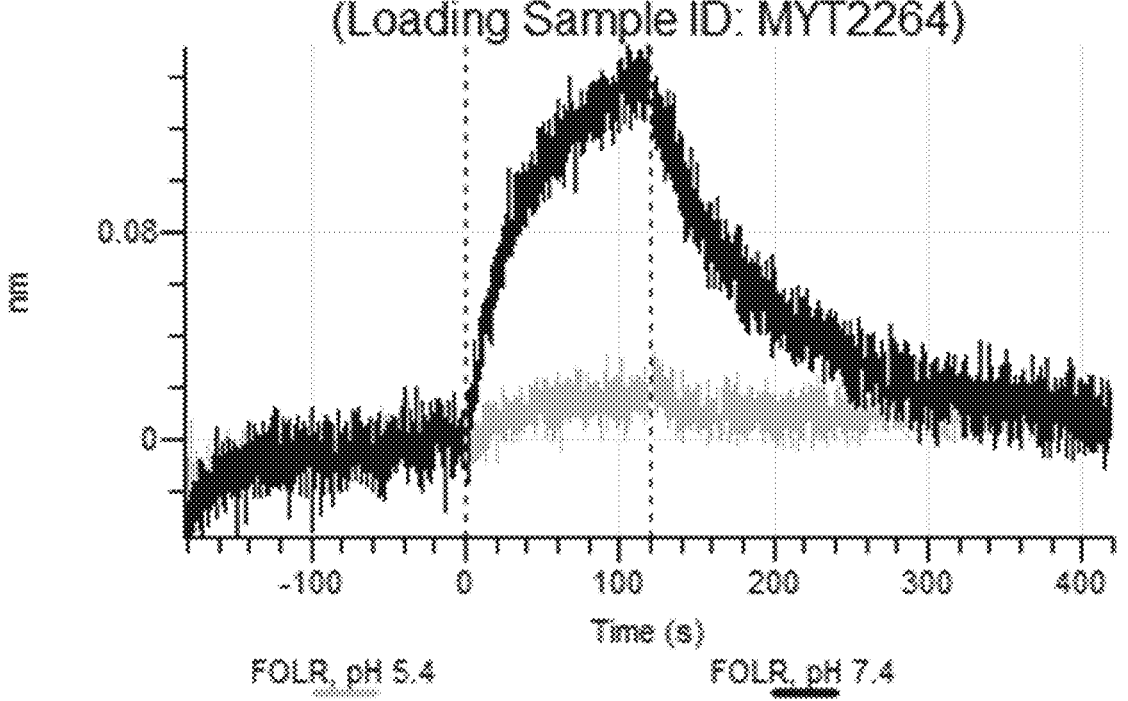
Figure 11A:
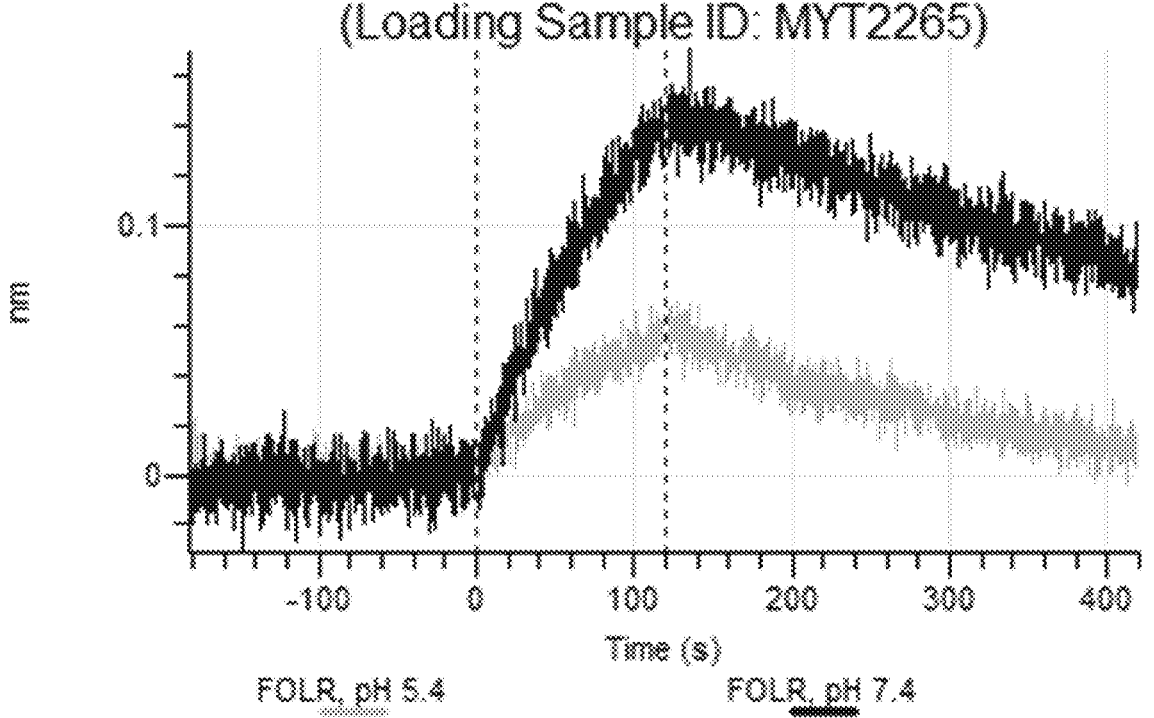
Figure 11A:
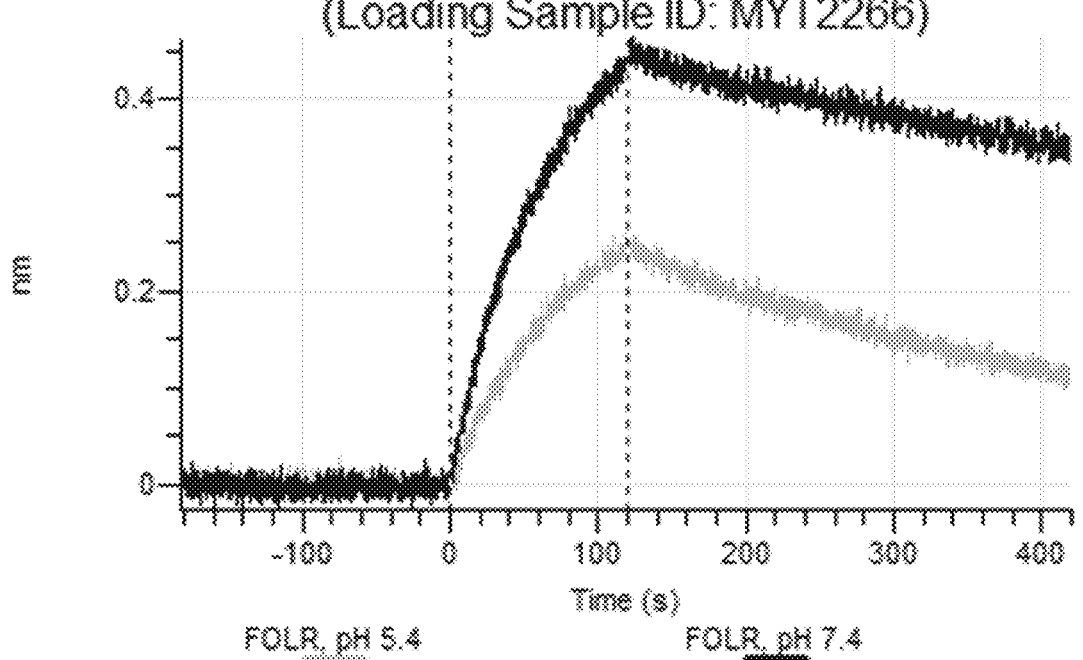
Figure 11A:
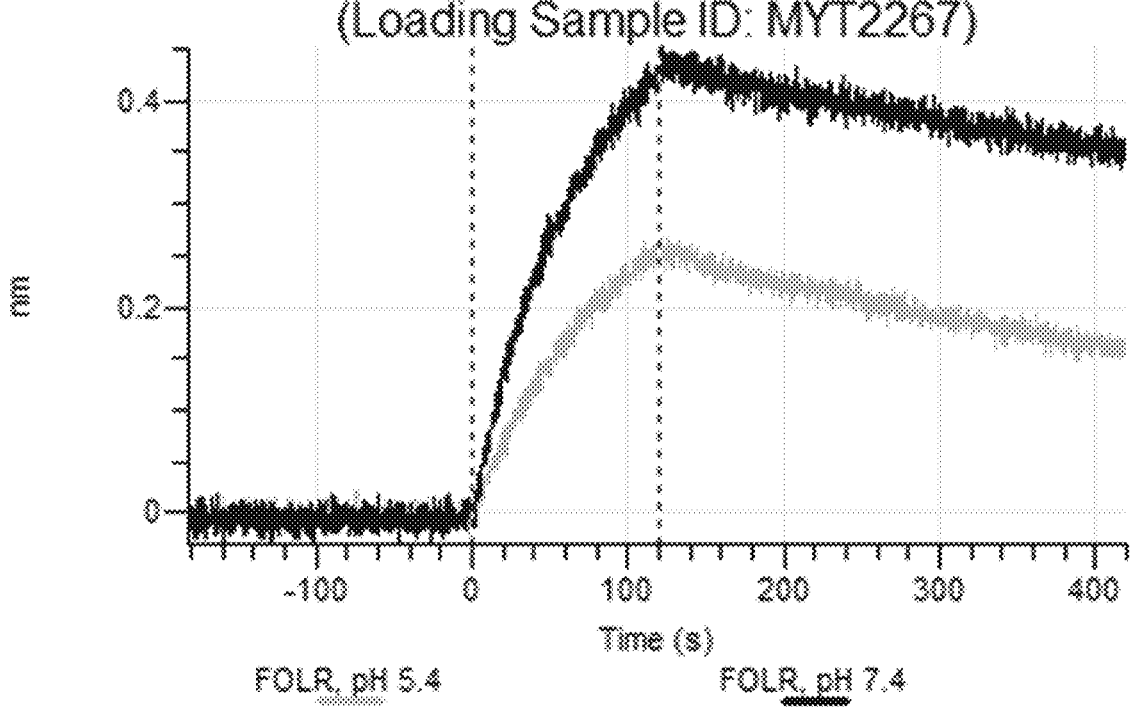
Figure 11A:
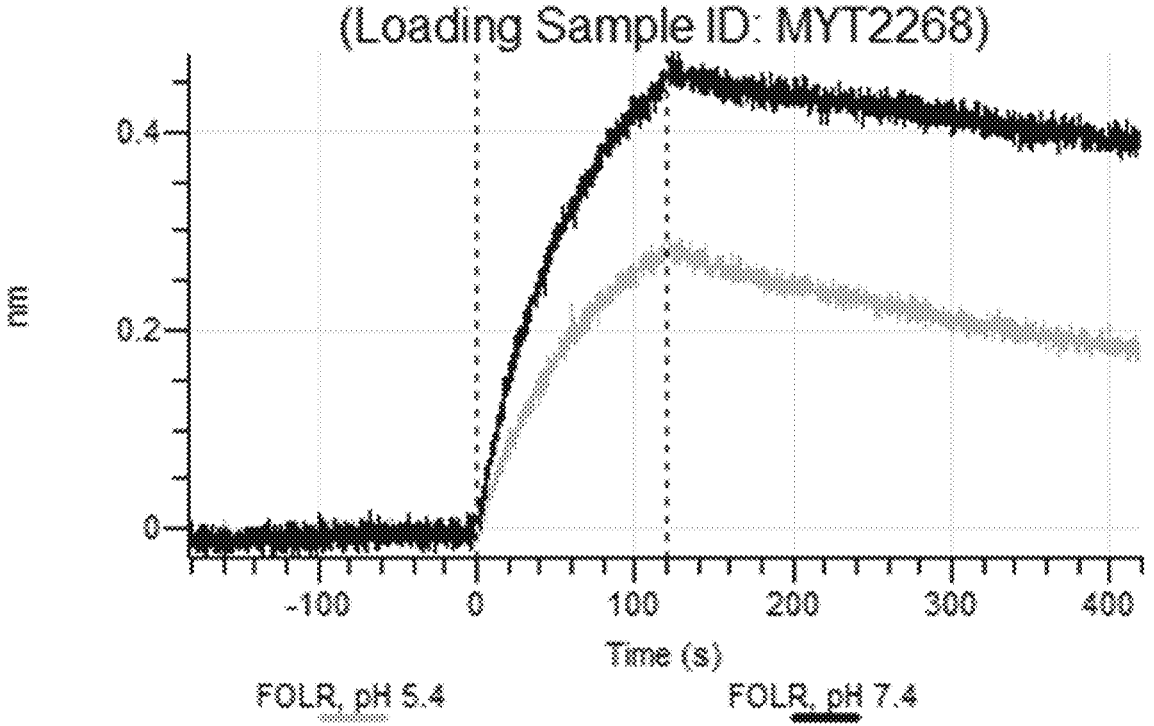

FIGS. 11a to 11as: Binding of STRO-002 starting ABPC and histidine scanning and alanine scanning variants to FOLR1 by biolayer interferometry. MYT2224 (STRO-002) and MYT2225-MYT2268, heavy chain histidine scanning and alanine scanning variants, were captured on anti-human Fc biosensors and associated with FOLR1 at low pH or high pH, as specified in the figures.

FIG. 12: Construct identifier to SEQ ID NO correspondence table. Constructs, heavy chain histidine scanning and alanine scanning variants, are listed in the first column of the table, SEQ ID NOs are listed and correspond to constructs on the left and the appropriate heavy chain, light chain, and CDR categories along the top.

Figure 13:
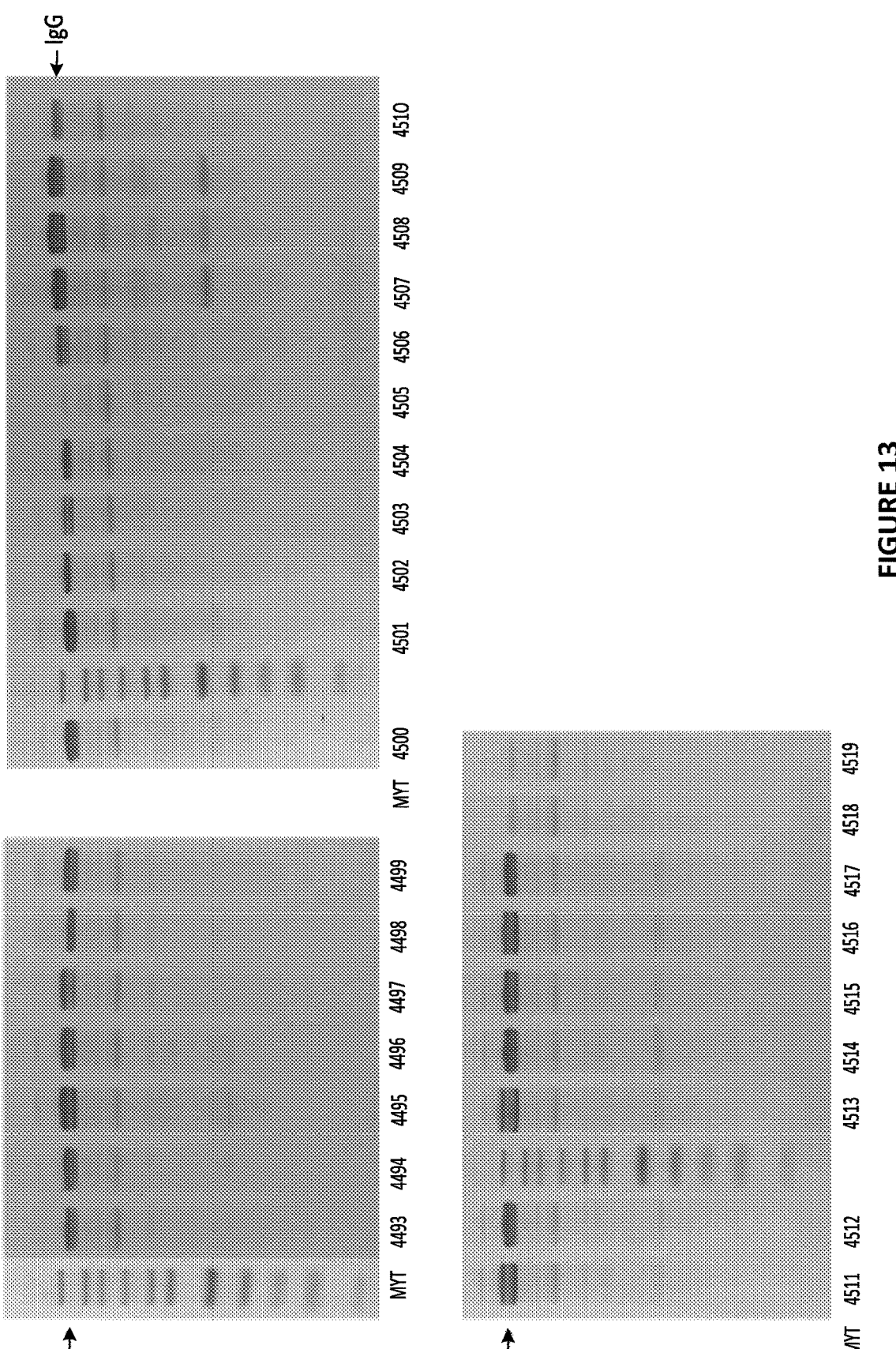

FIG. 13: SDS PAGE for STRO-002 histidine scanning and alanine scanning. Expi293 cell culture supernatants post-harvest were loaded on non-reduced SDS PAGE gels to confirm expression of STRO-002 histidine scanning and alanine scanning variants. Arrows show the corresponding size for an IgG on a non-reduced SDS PAGE gel. MYT4493-MYT4519 are STRO-002 light chain histidine scanning and alanine scanning variants.

Figure 14A:
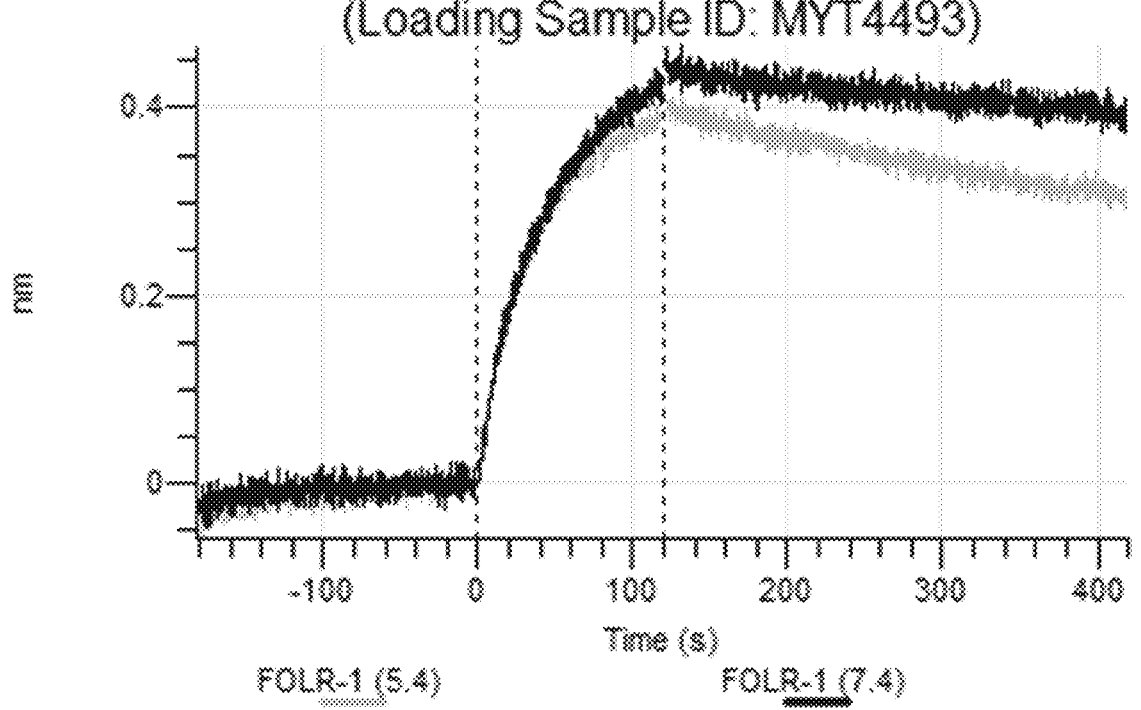
Figure 14B:
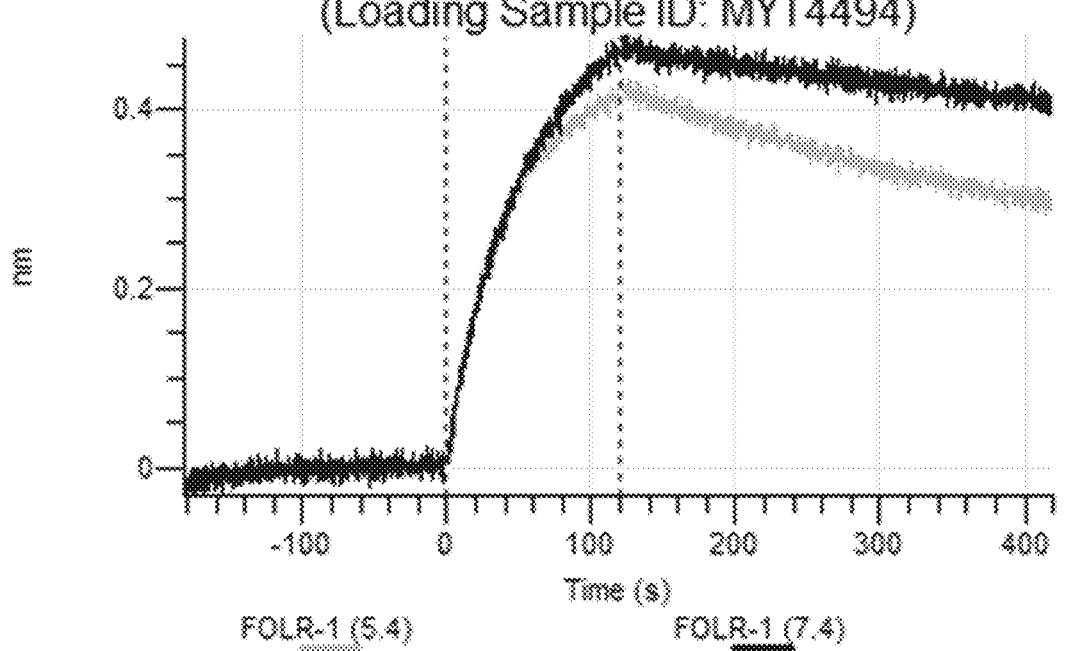
Figure 14C:
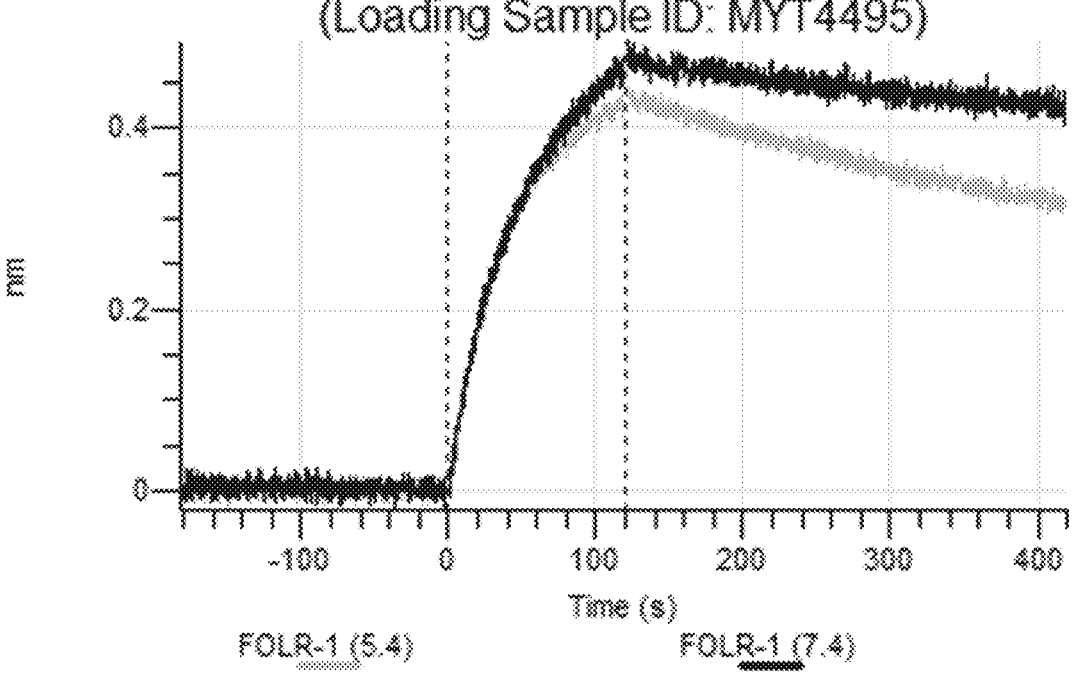
Figure 14D:
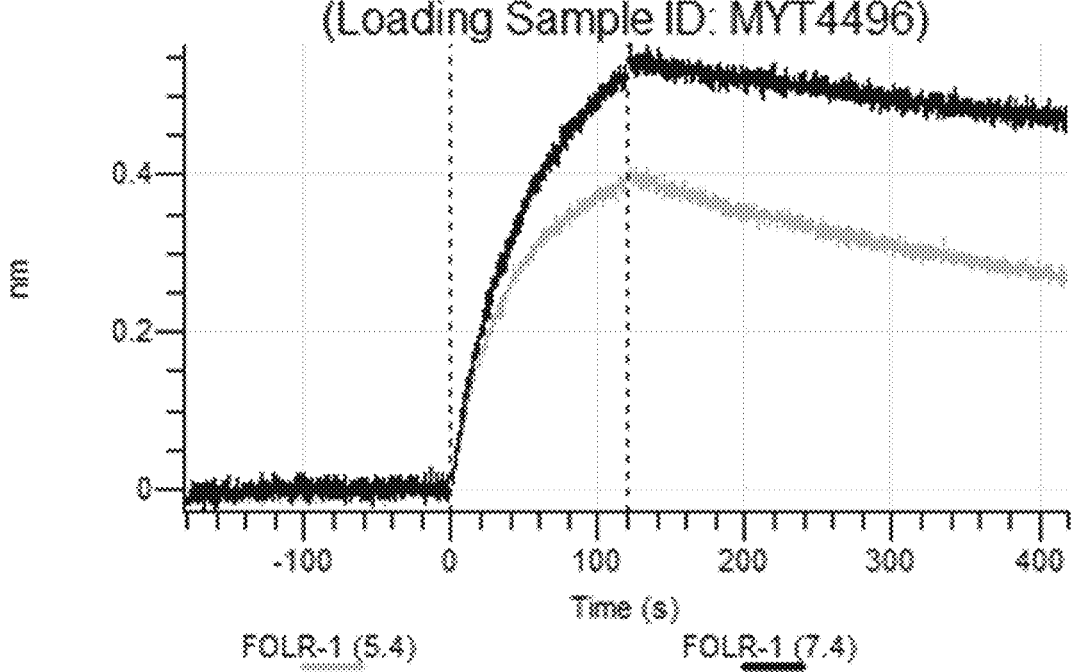
Figure 14E:
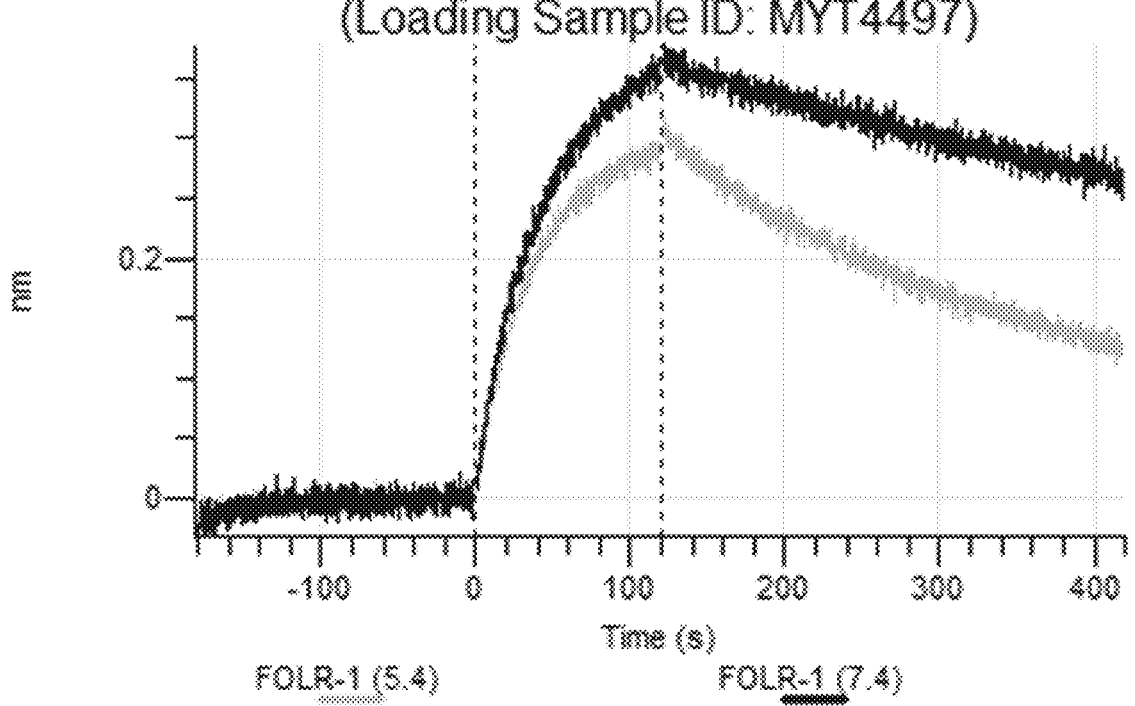
Figure 14F:
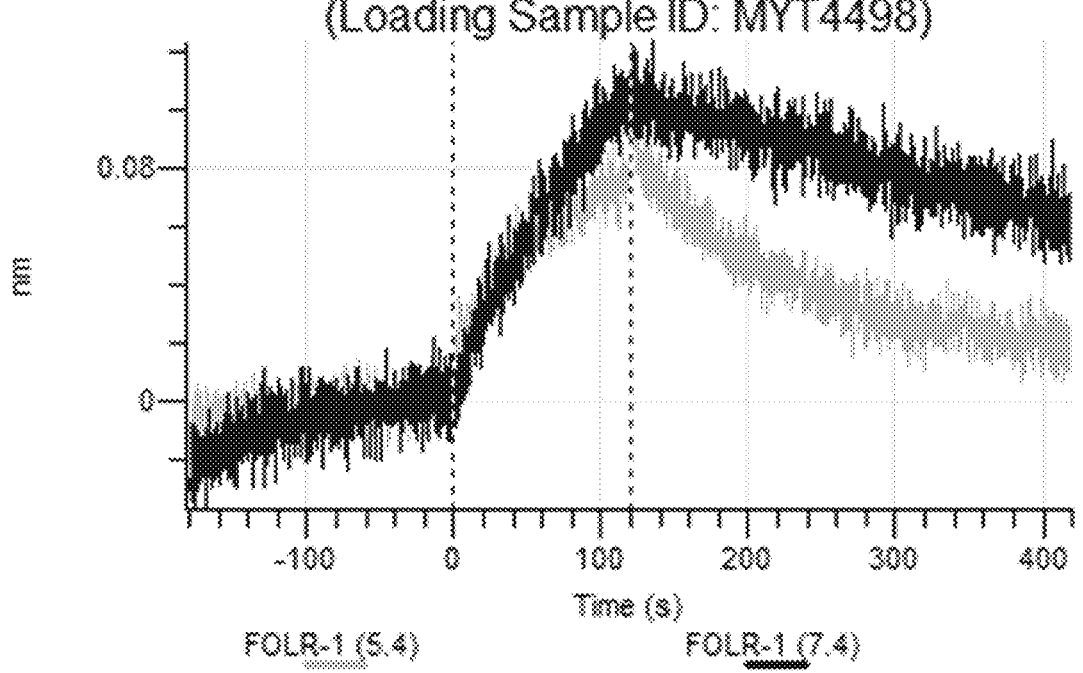
Figure 14G:
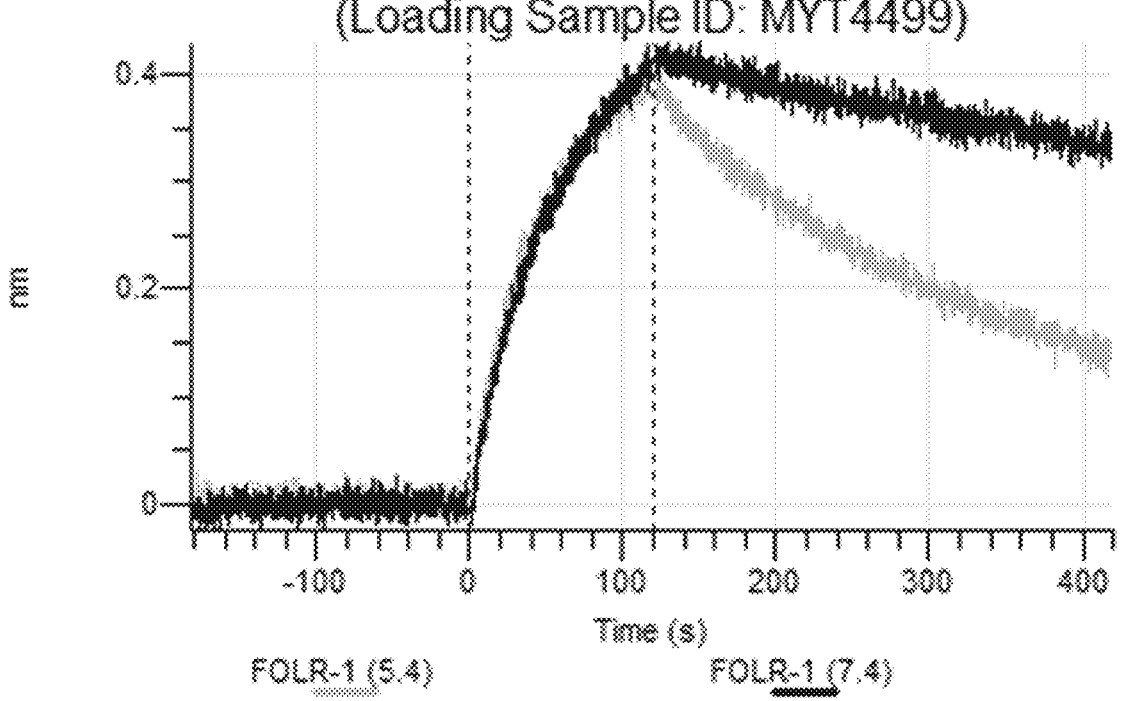
Figure 14H:
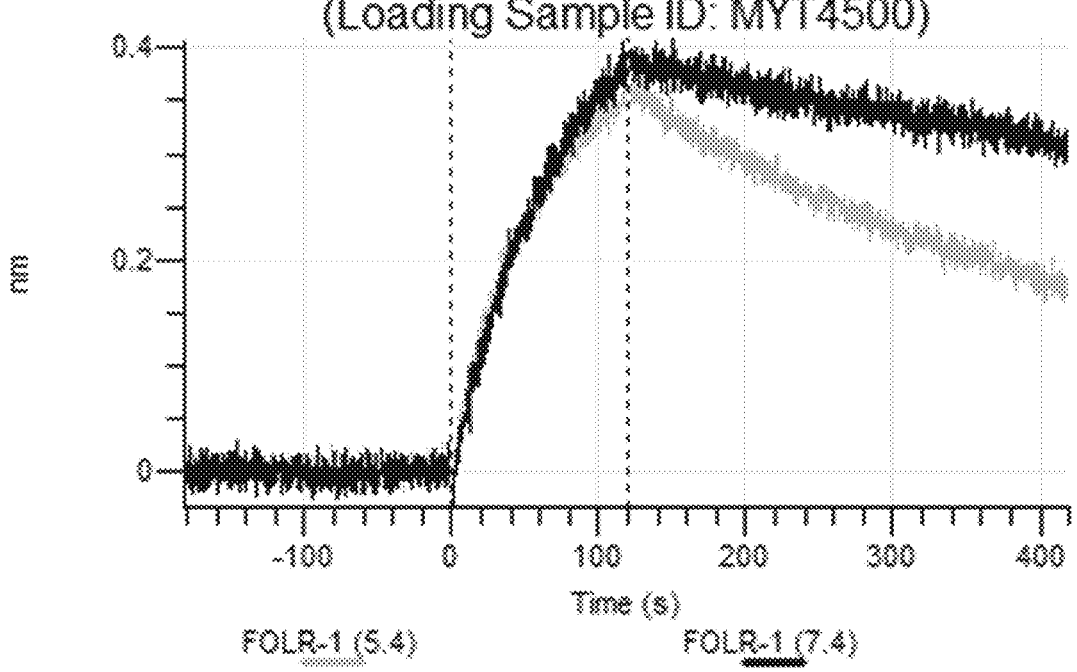
Figure 14I:
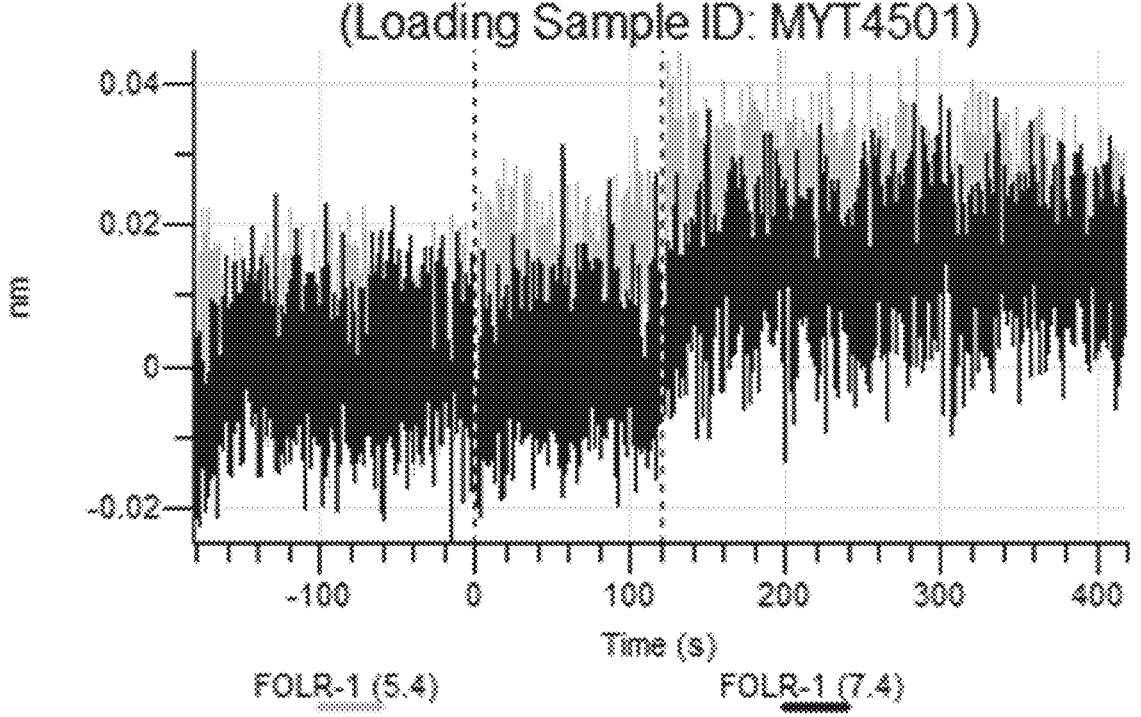
Figure 14J:
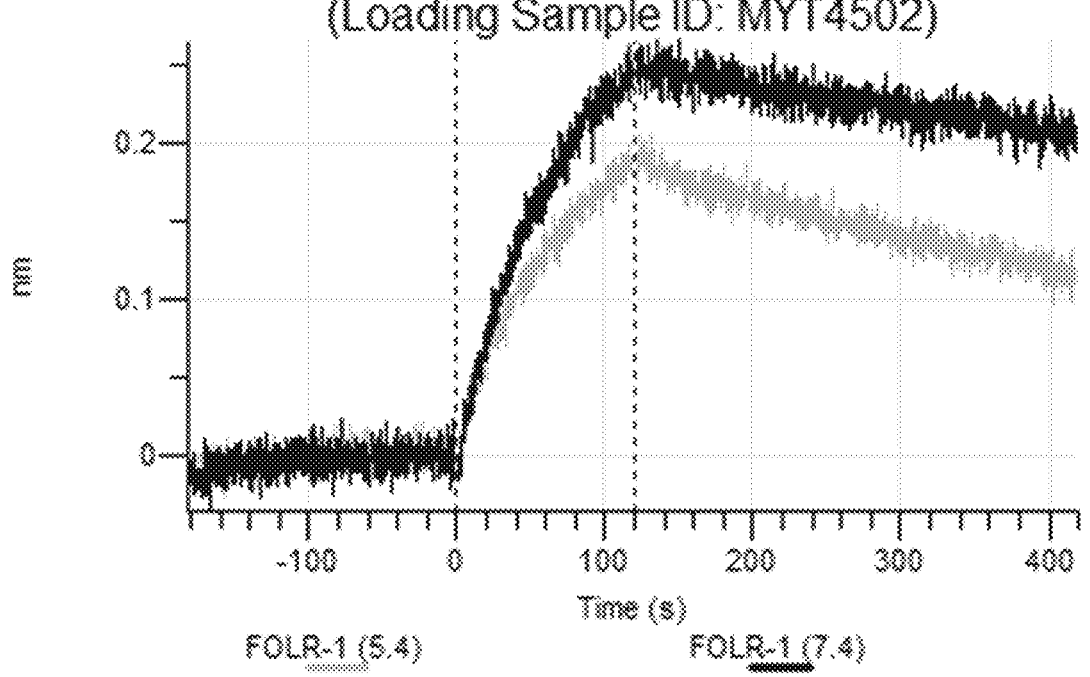
Figure 14K:
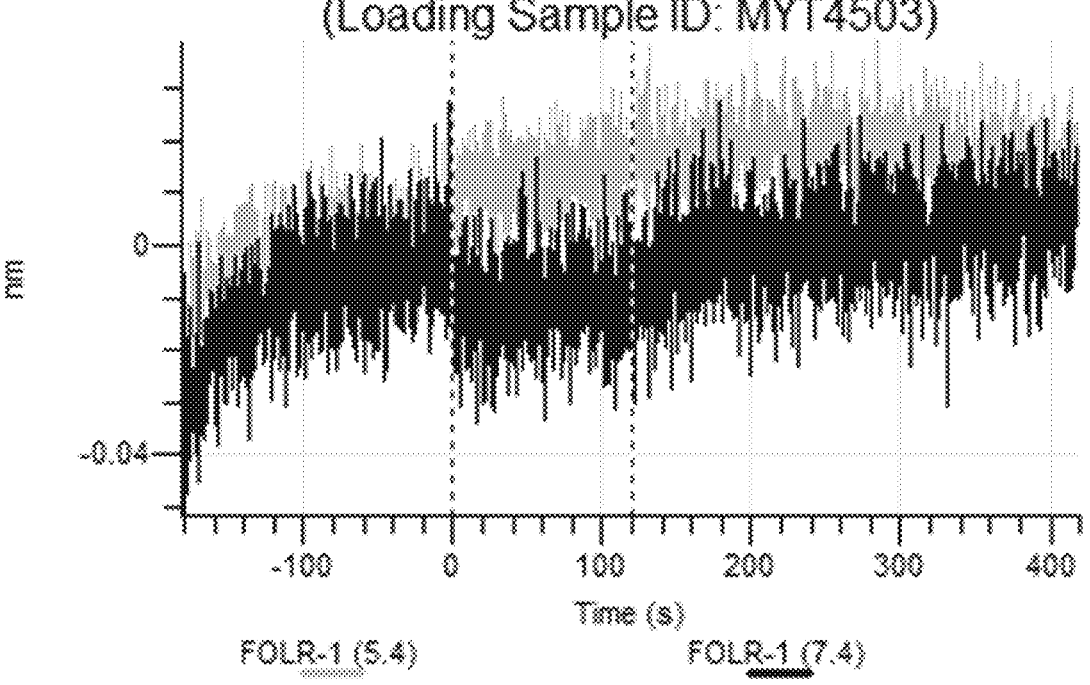
Figure 14I:
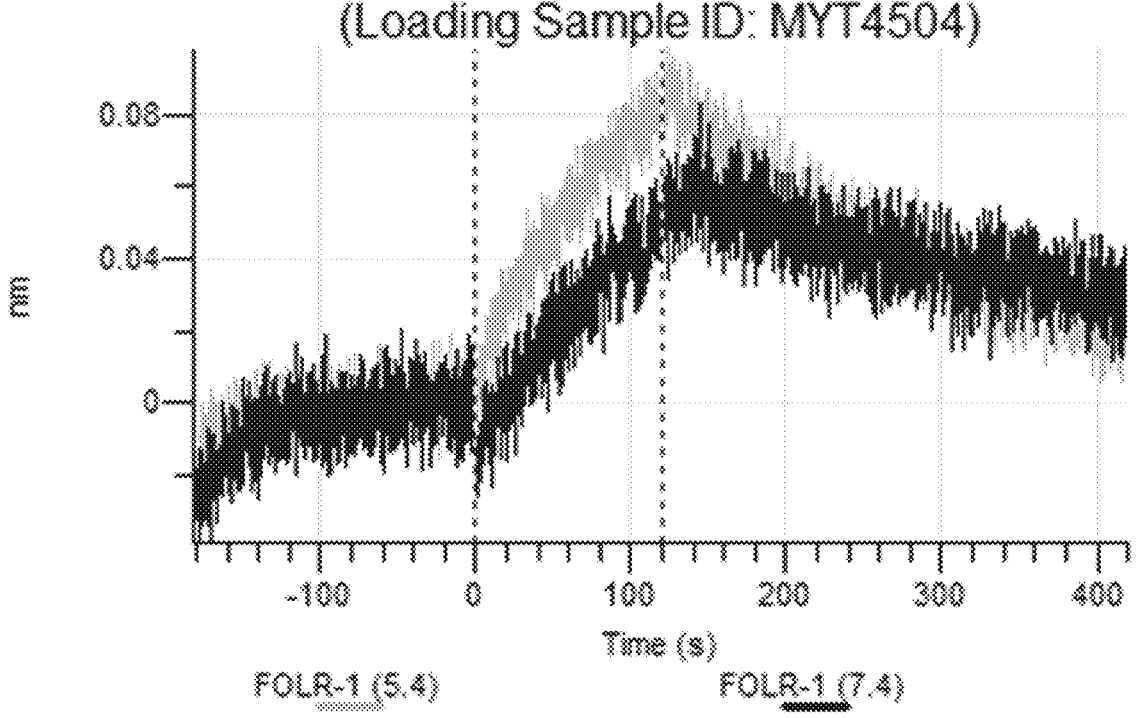
Figure 14M:
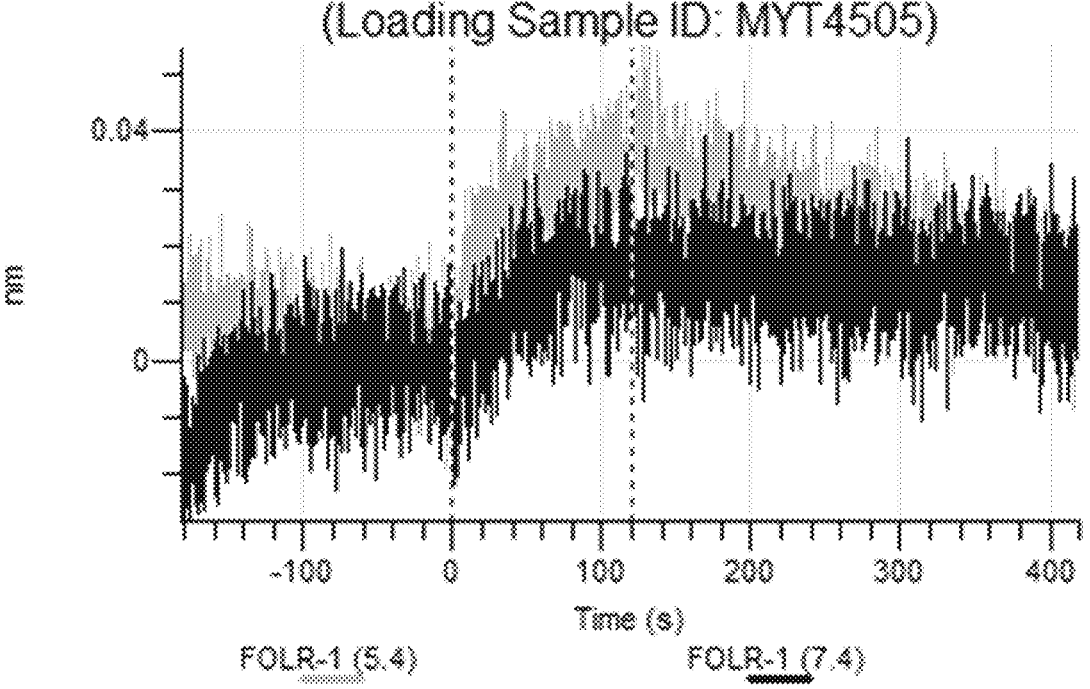
Figure 14N:
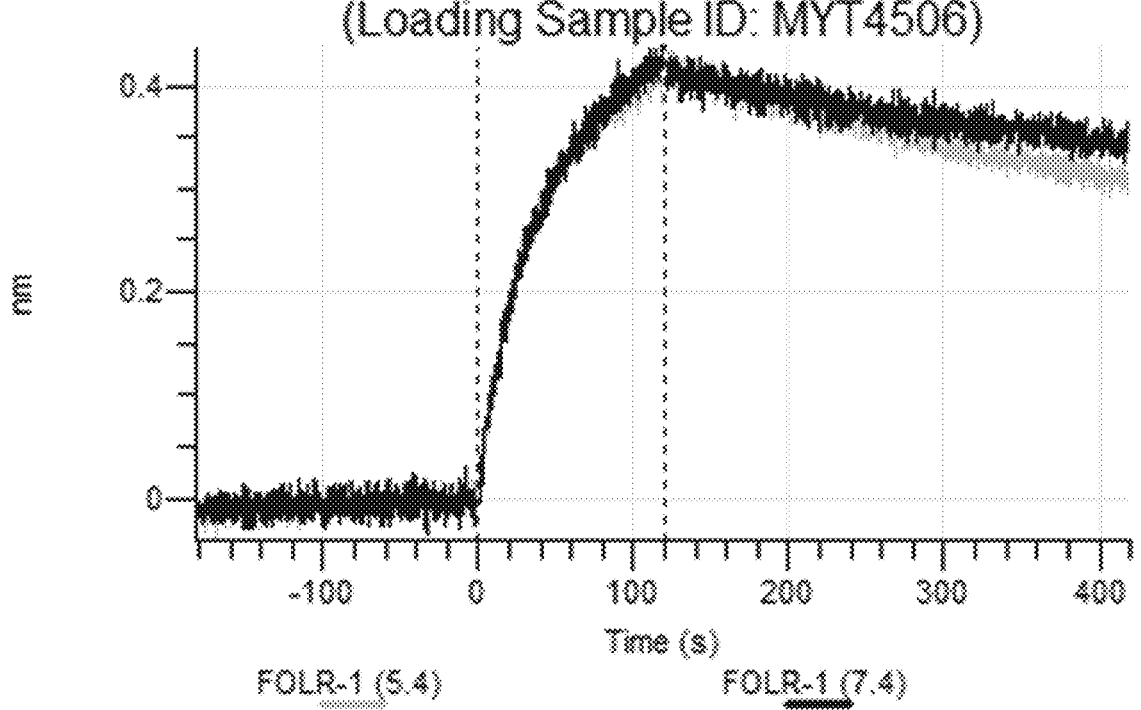
Figure 14O:
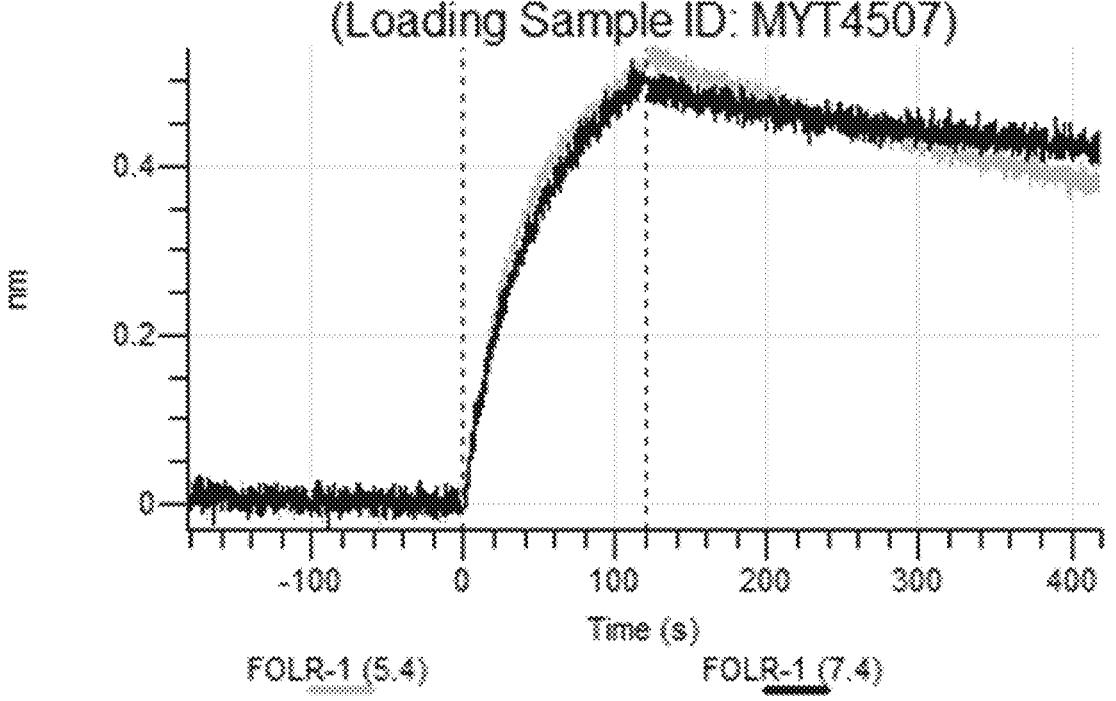
Figure 14P:
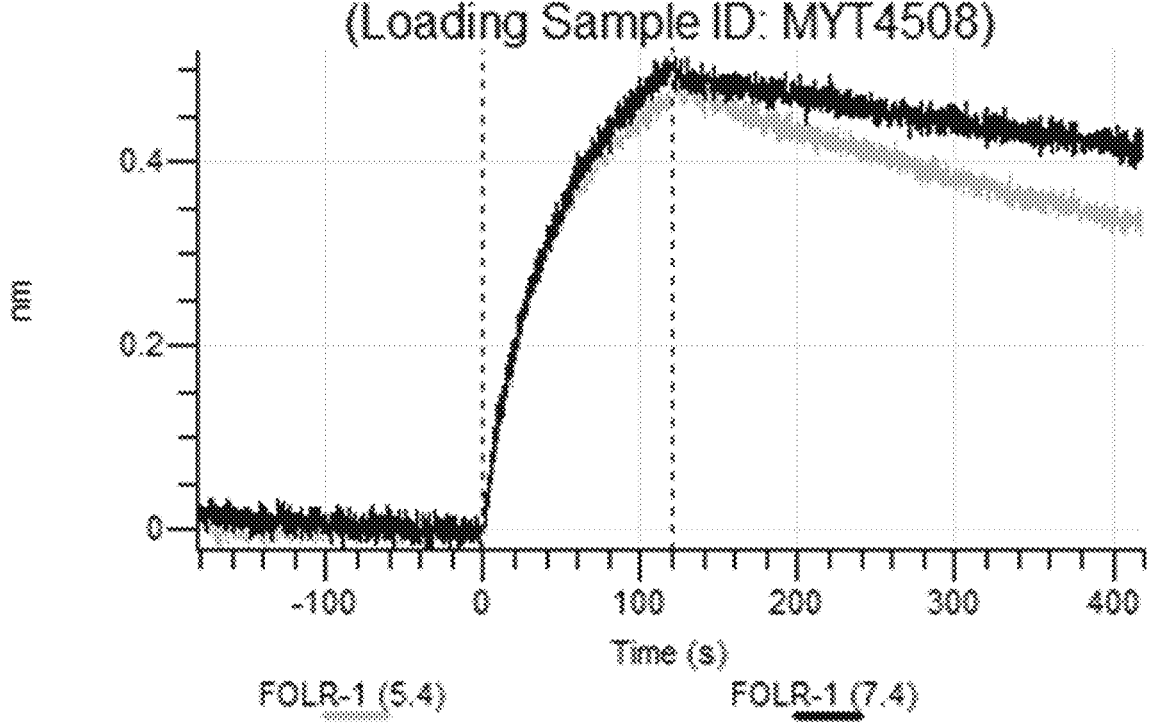
Figure 14Q:
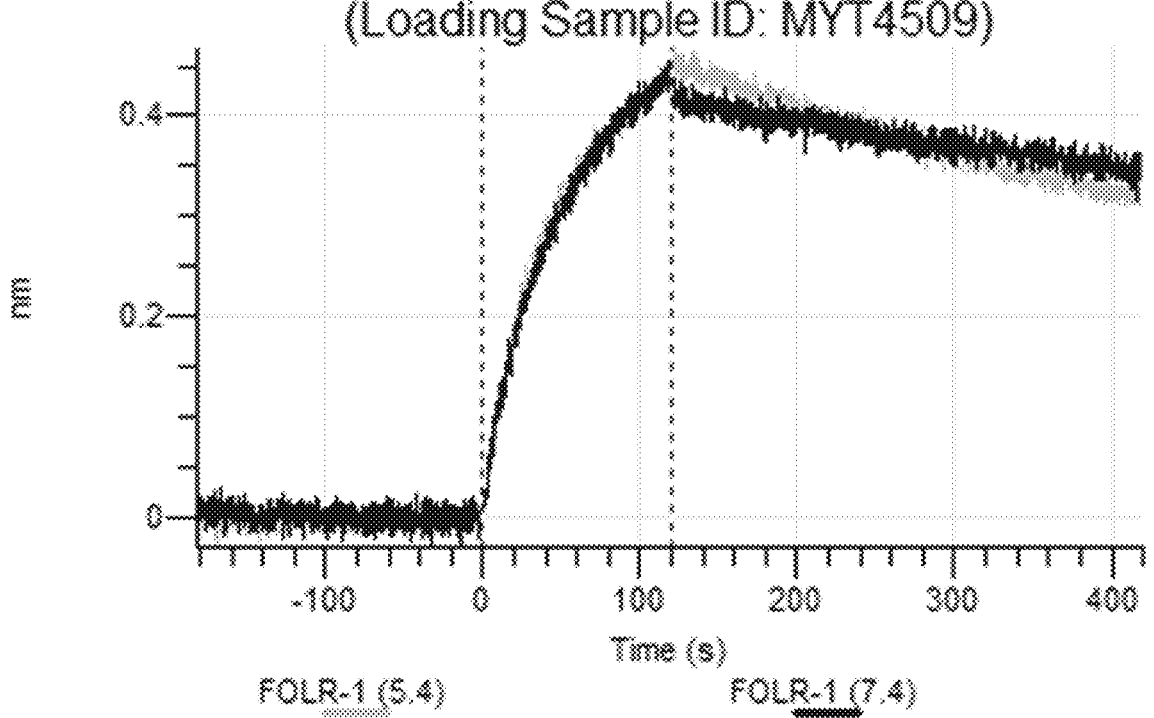
Figure 14R:
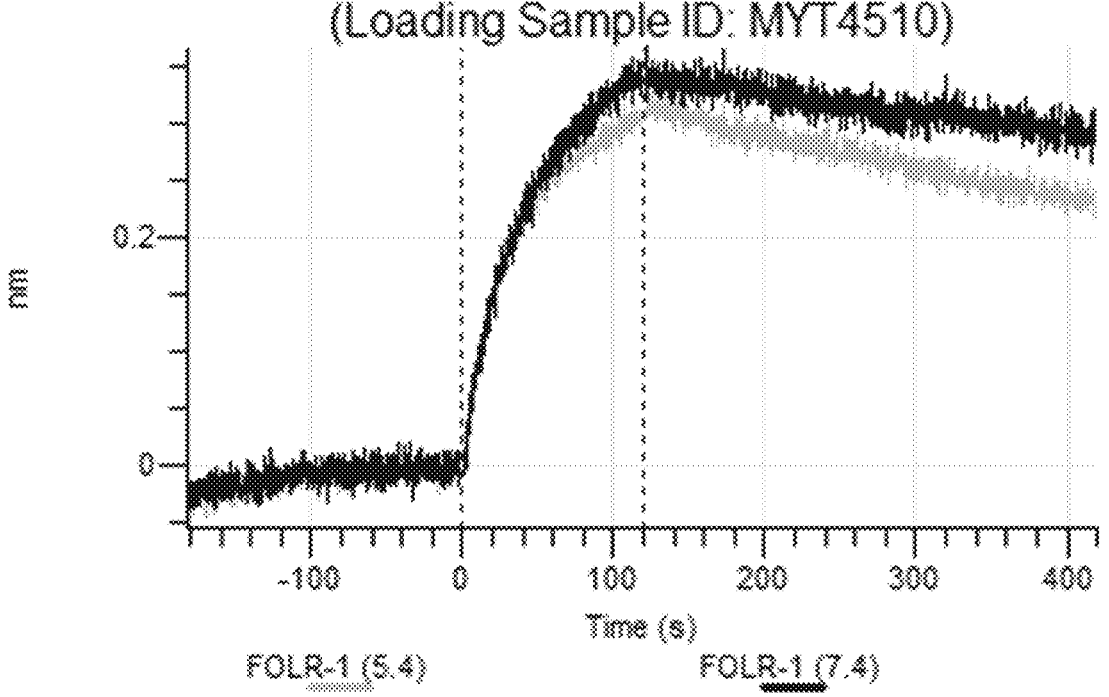
Figure 14S:
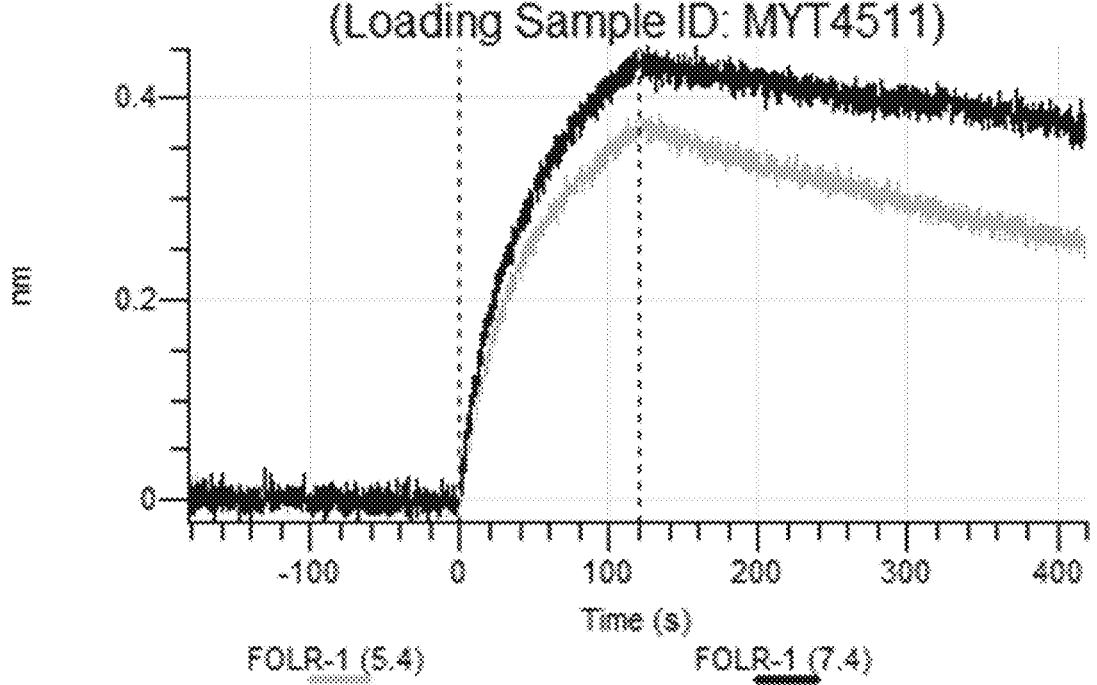
Figure 14T:
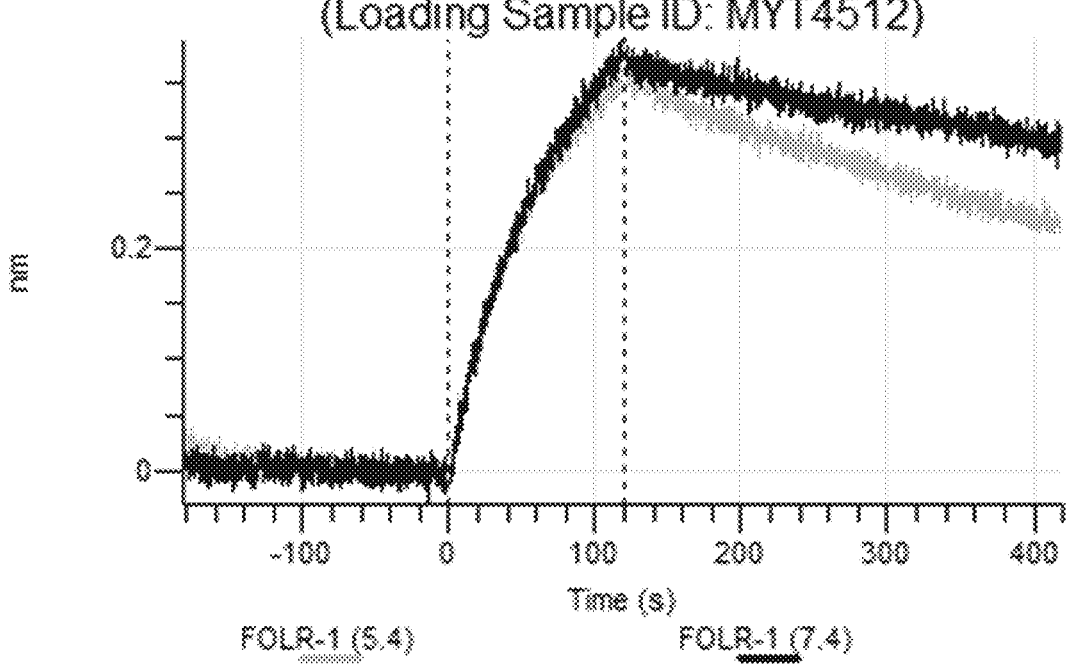
Figure 14U:
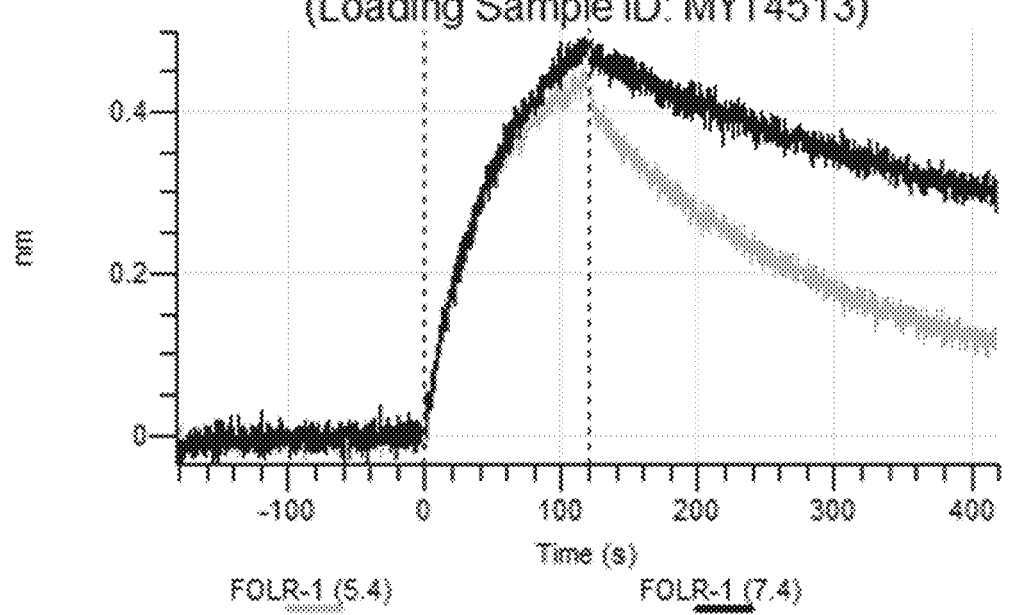
Figure 14V:
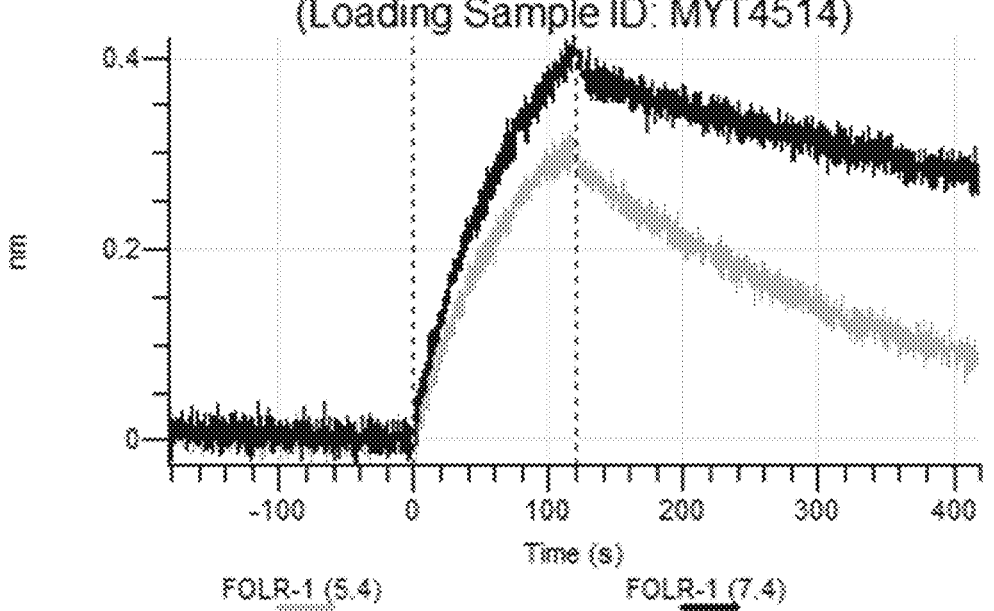
Figure 14W:
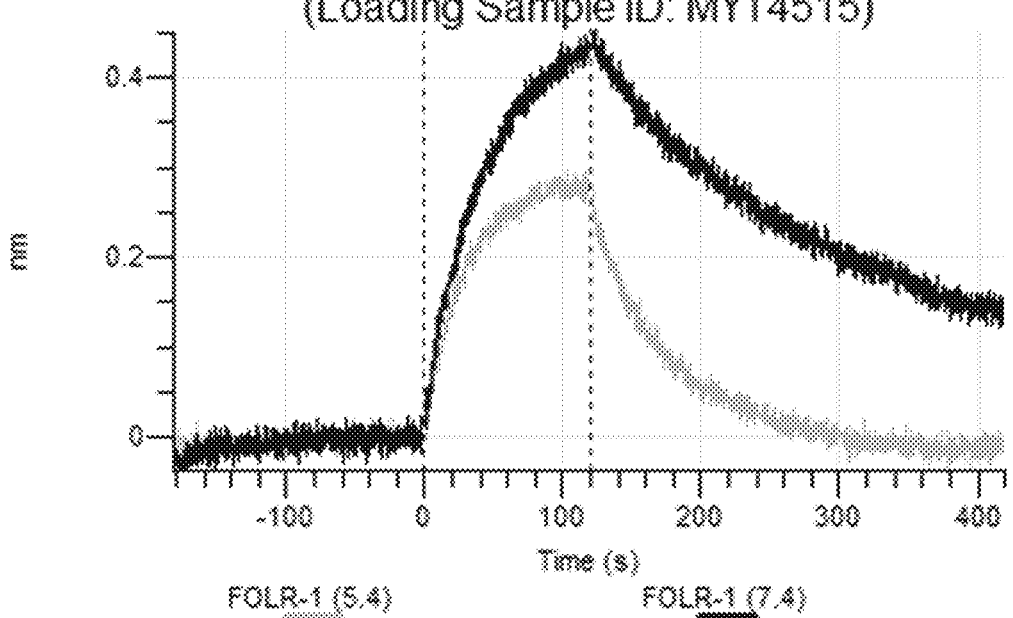
Figure 14X:
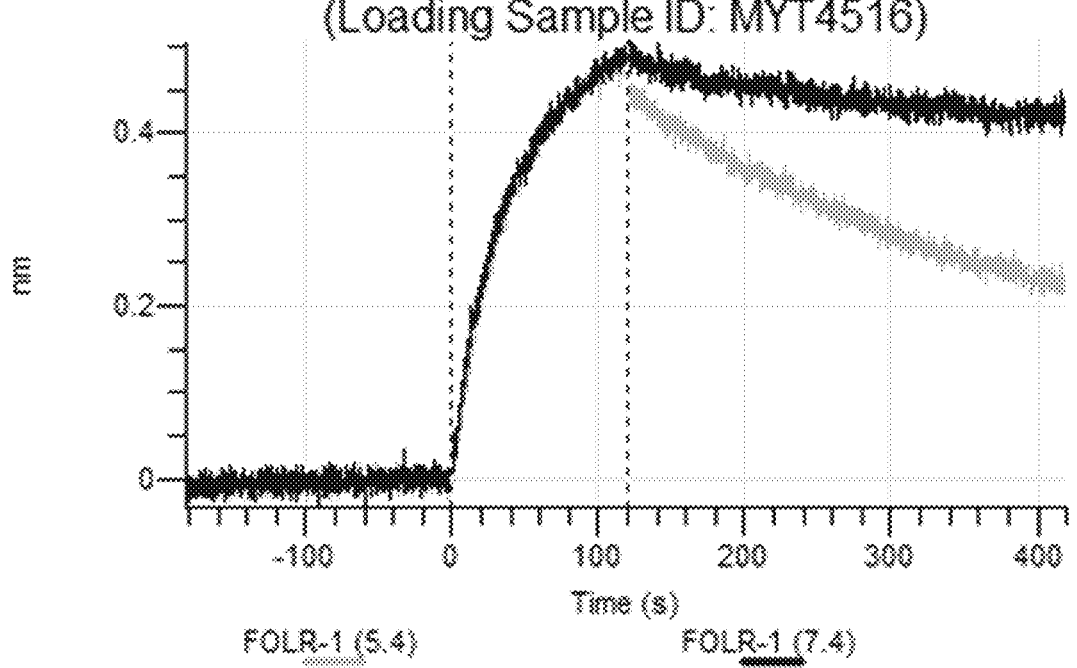
Figure 14Y:
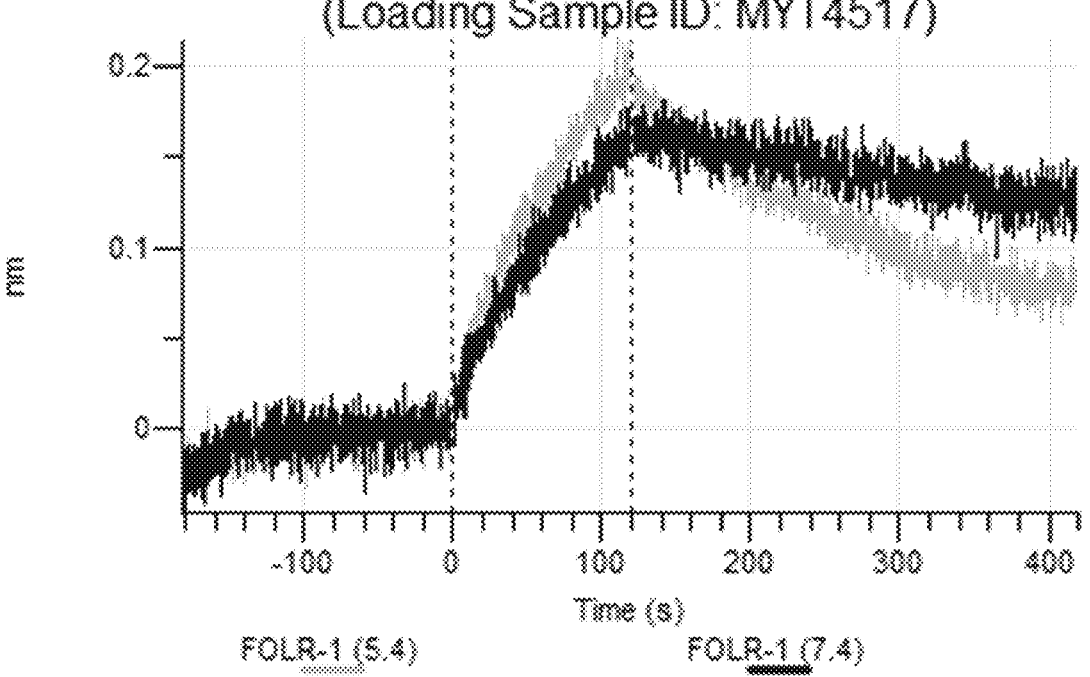
Figure 14Z:
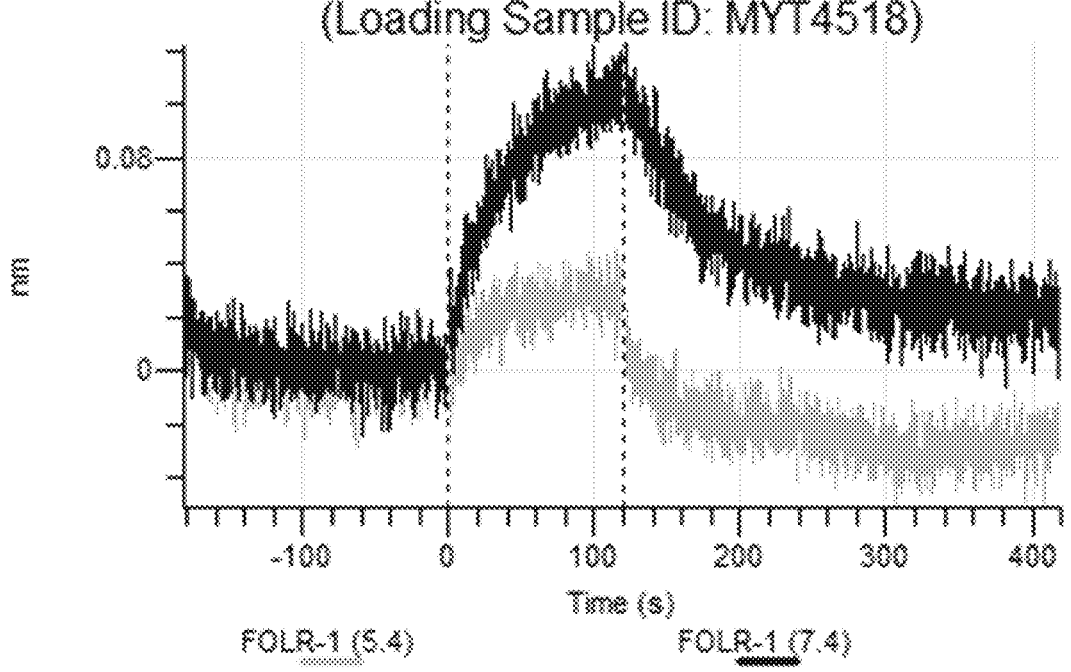
Figure 14A:
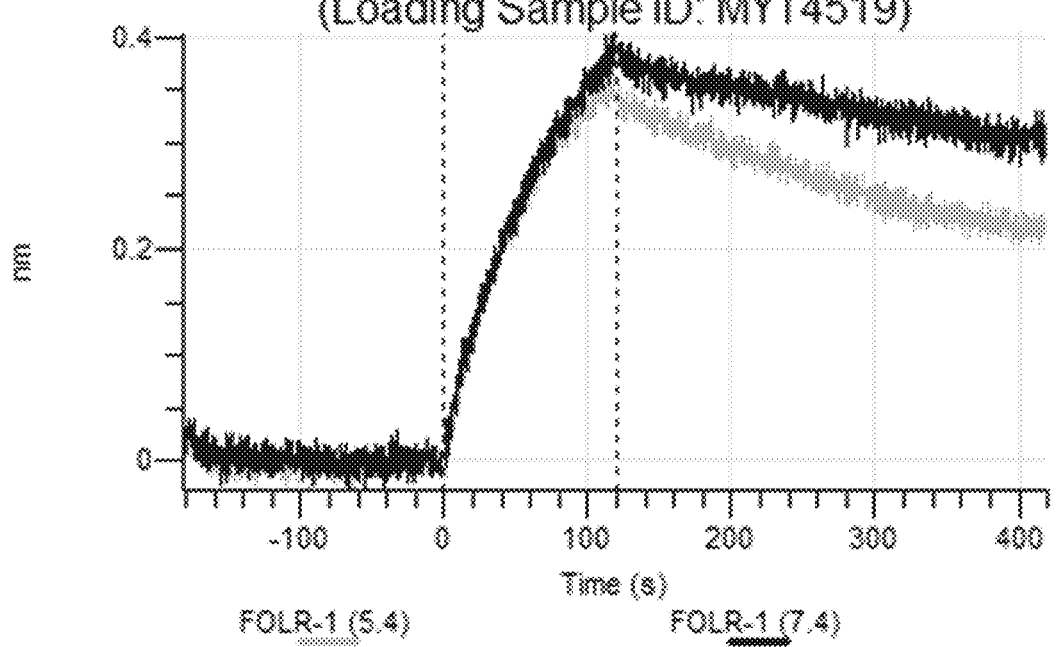

FIGS. 14a to 14aa: Binding of STRO-002 histidine scanning and alanine scanning variants to FOLR1 by biolayer interferometry. MYT4493-MYT4519, light chain histidine scanning and alanine scanning variants, were captured on anti-human Fc biosensors and associated with FOLR1 at low pH or high pH, as specified in the figures.

FIG. 15: Construct identifier to SEQ ID NO correspondence table. Constructs, light chain histidine scanning and alanine scanning variants, are listed in the first column of the table, SEQ ID NOs are listed and correspond to constructs on the left and the appropriate heavy chain, light chain, and CDR categories along the top.

Figure 16:
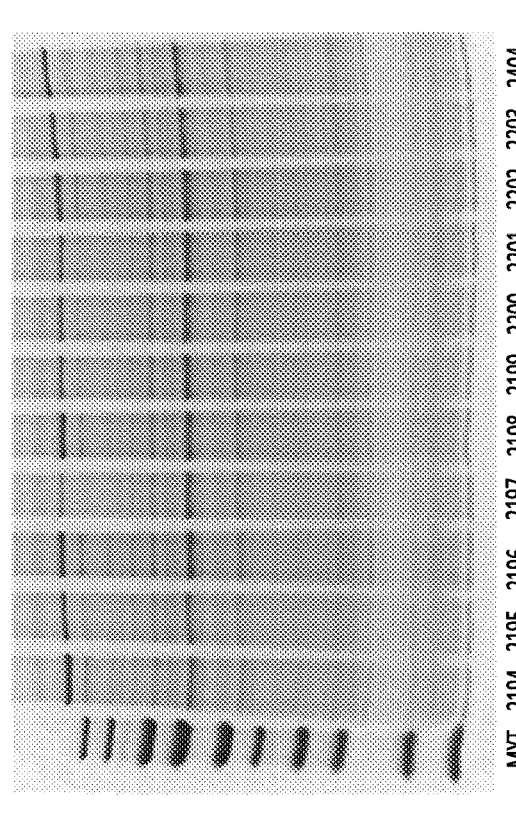
Figure 16:
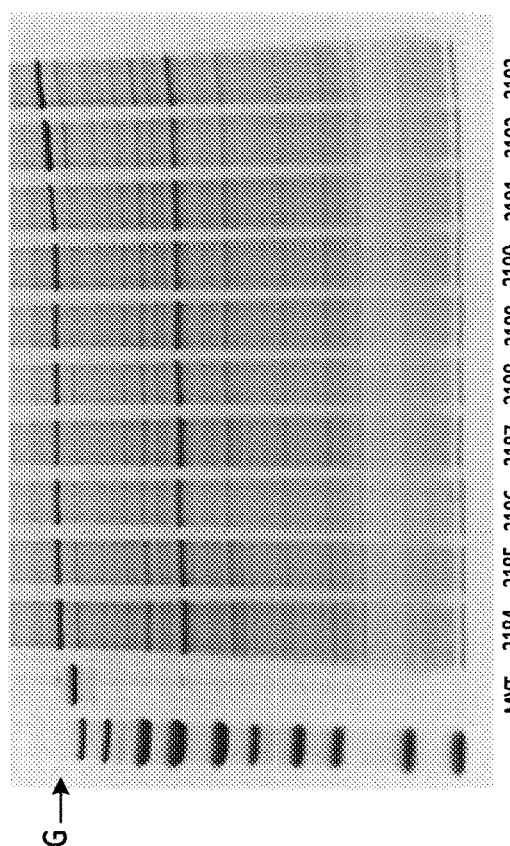
Figure 16:
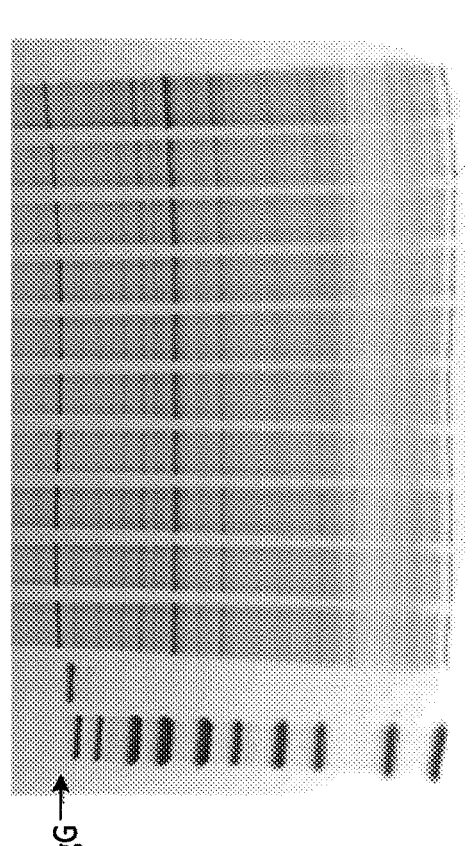

FIG. 16: SDS PAGE for FARLETUZUMAB histidine scanning and alanine scanning. Expi293 cell culture supernatants post-harvest were loaded on non-reduced SDS PAGE gels to confirm expression of FARLETUZUMAB and histidine scanning and alanine scanning variants. Arrows show the corresponding size for an IgG on a non-reduced SDS PAGE gel. MYT2184 is FARLE-TUZUMAB and the rest of the lanes (MYT2185-MYT2223) are FARLETUZUMAB heavy chain histidine scanning and alanine scanning variants.

Figure 17A:
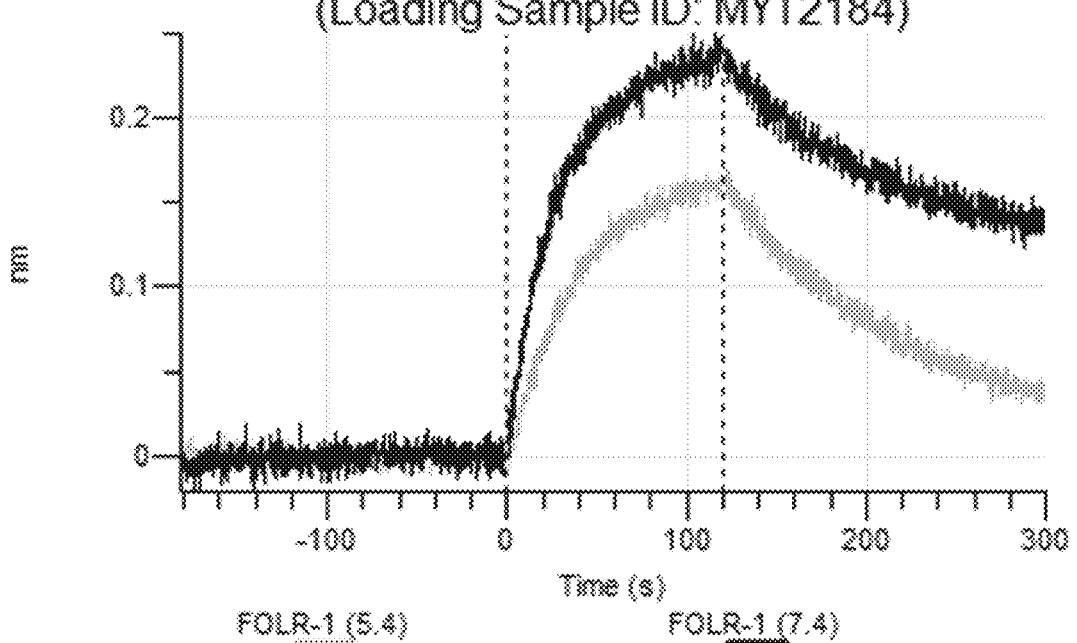
Figure 17B:
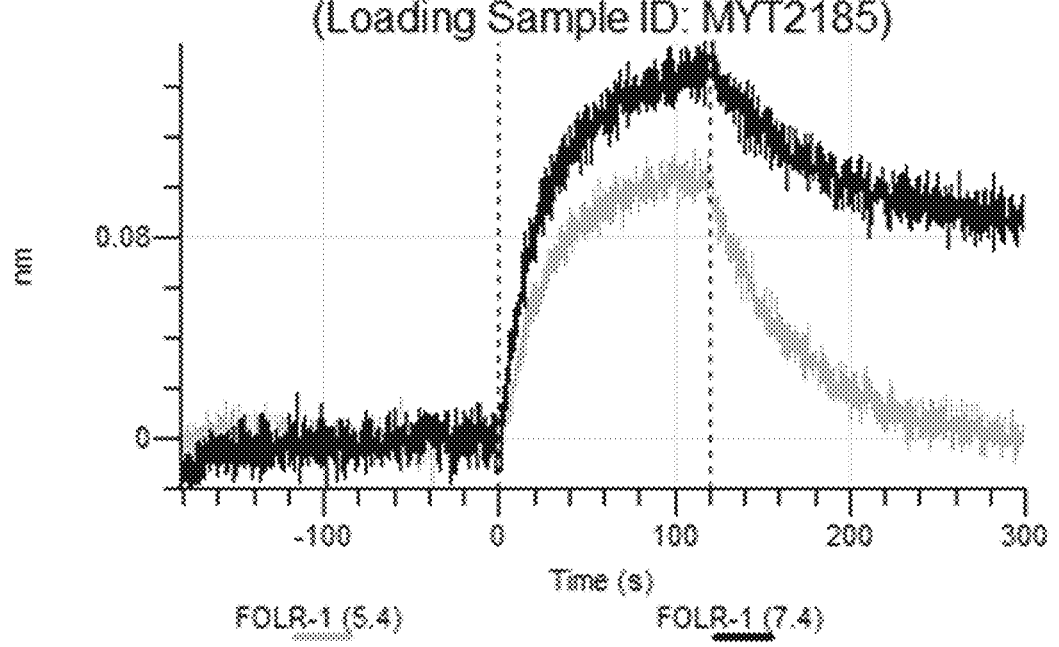
Figure 17C:
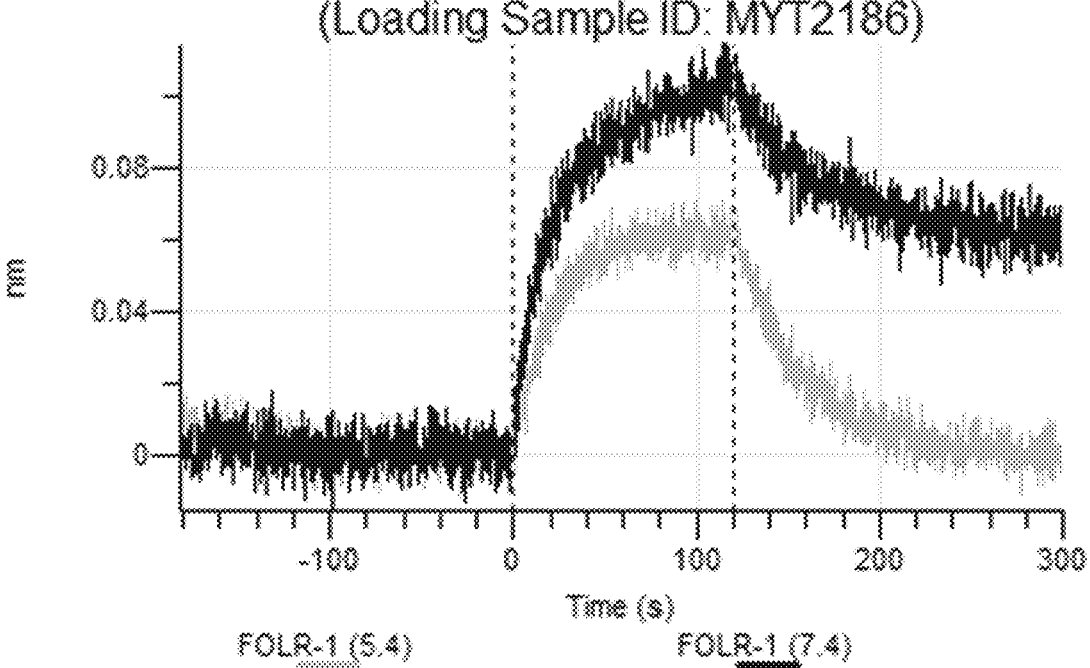
Figure 17D:
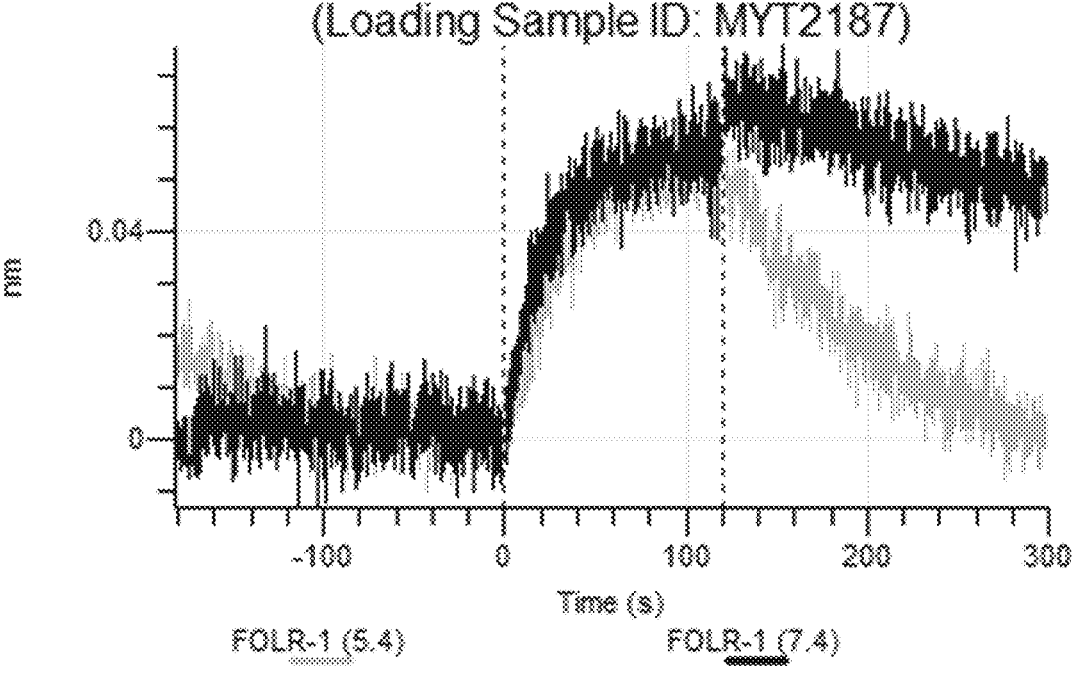
Figure 17E:
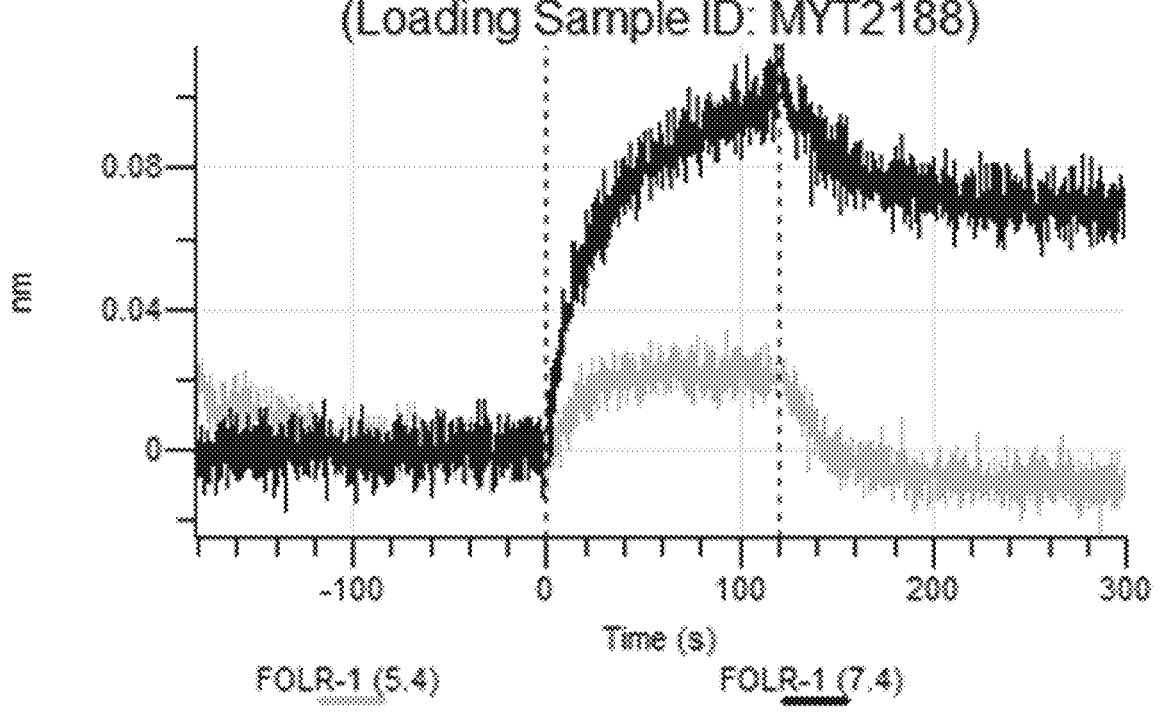
Figure 17F:
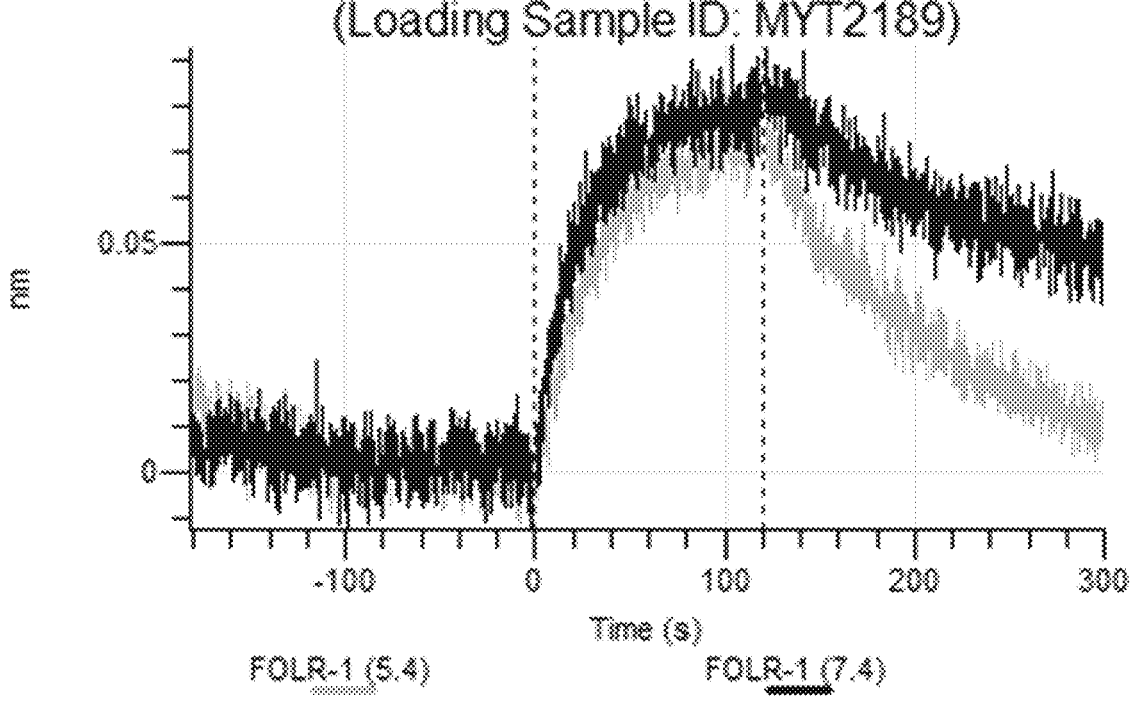
Figure 17G:
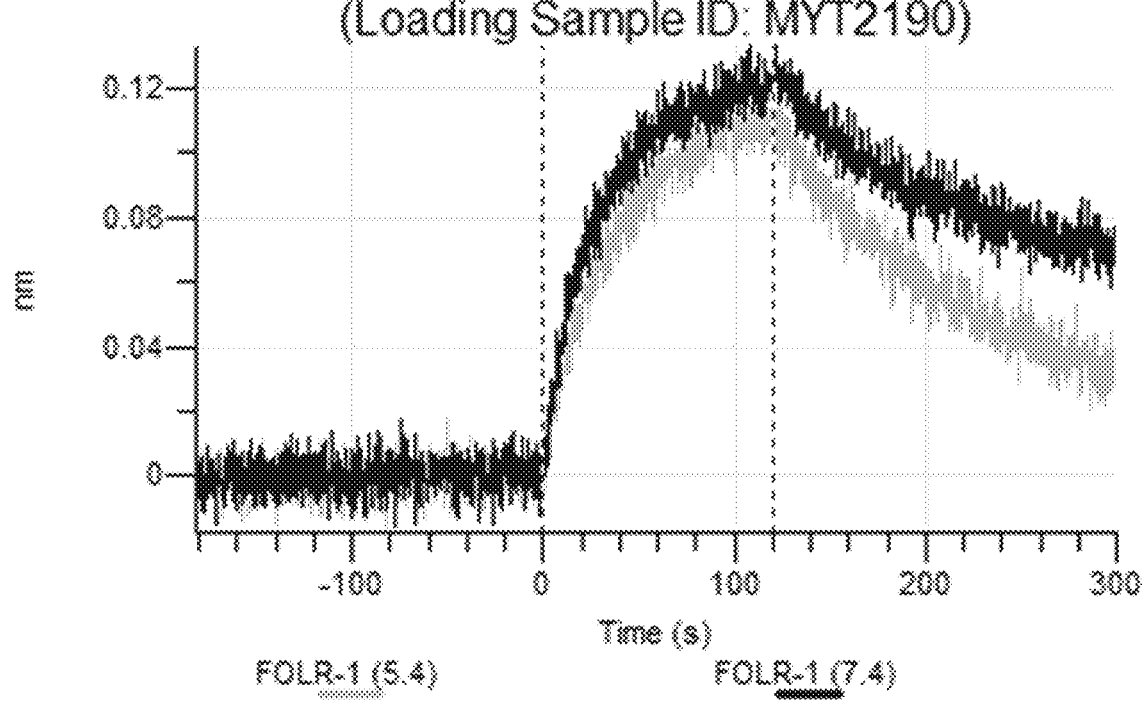
Figure 17H:
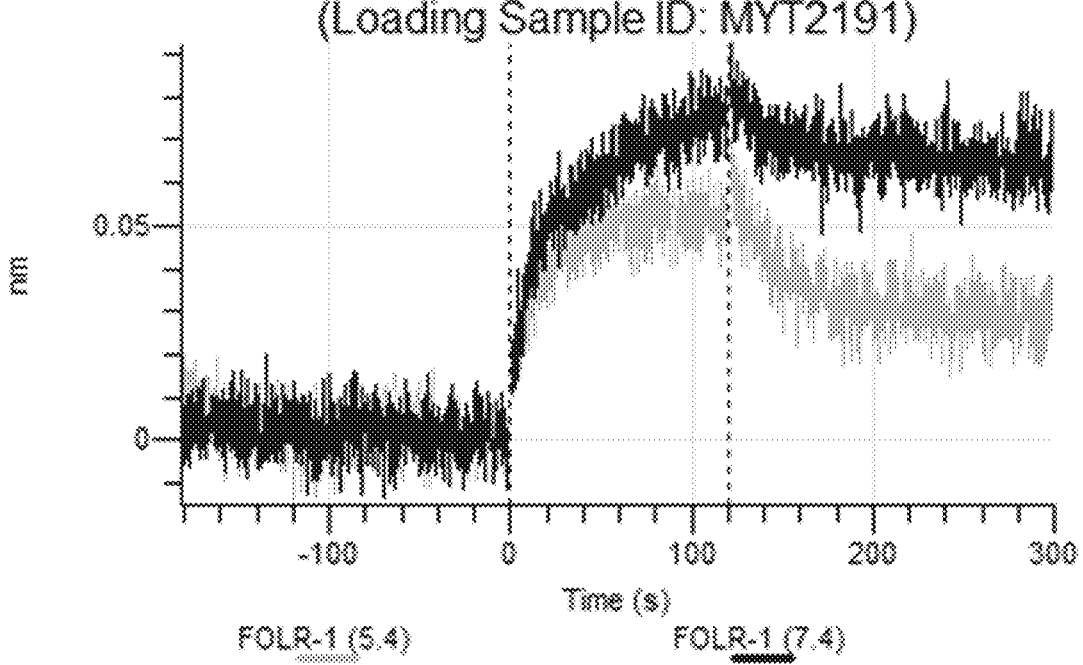
Figure 17I:
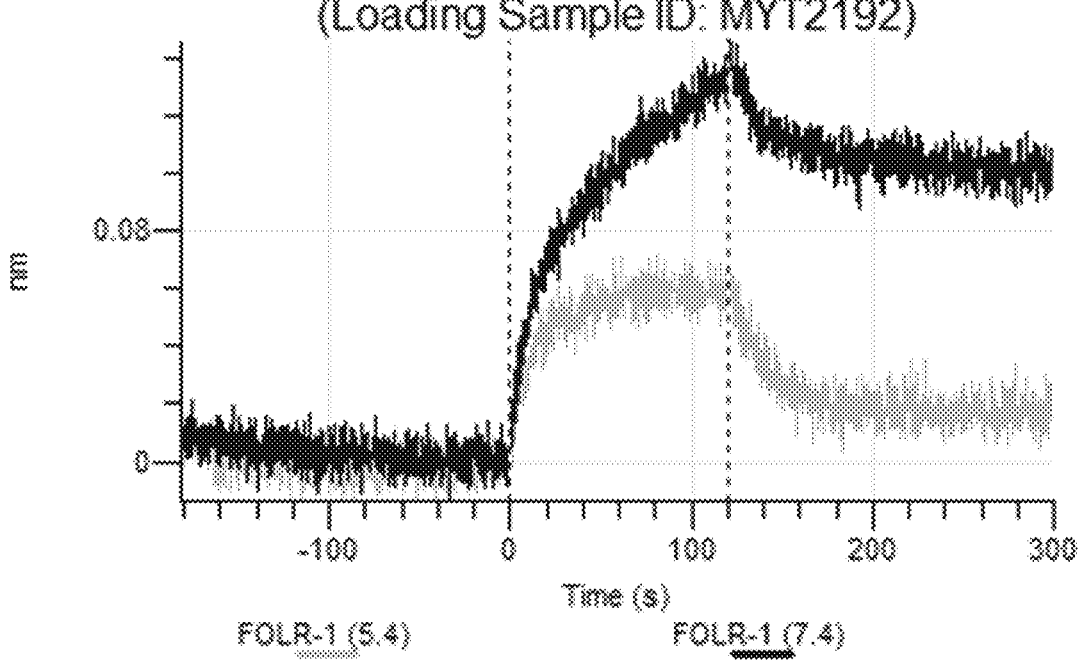
Figure 17J:
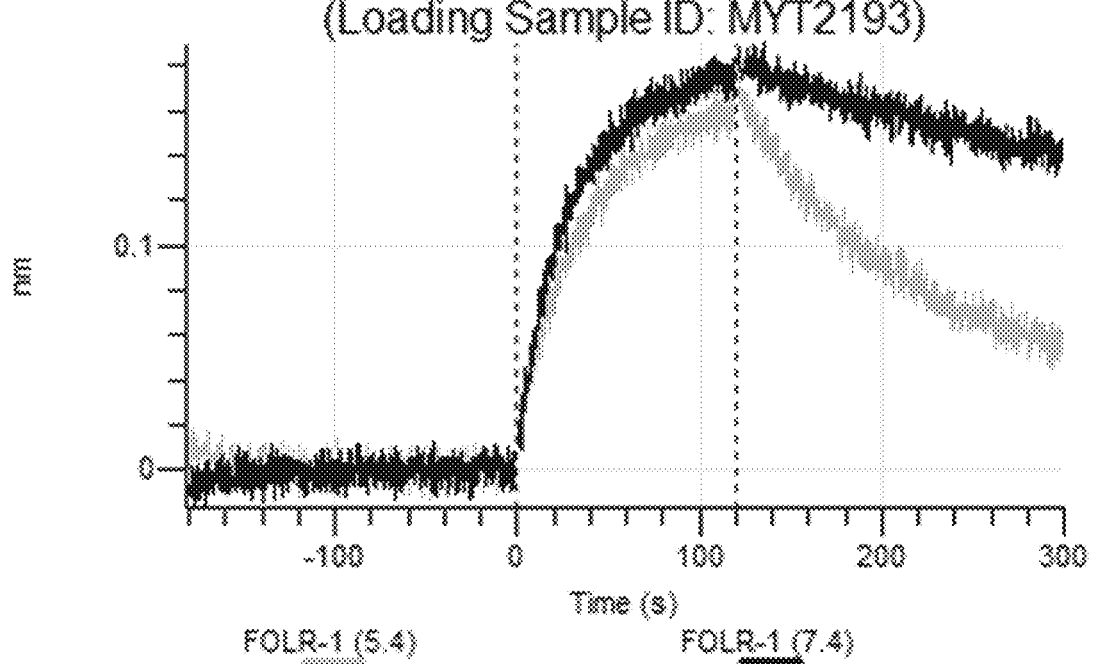
Figure 17K:
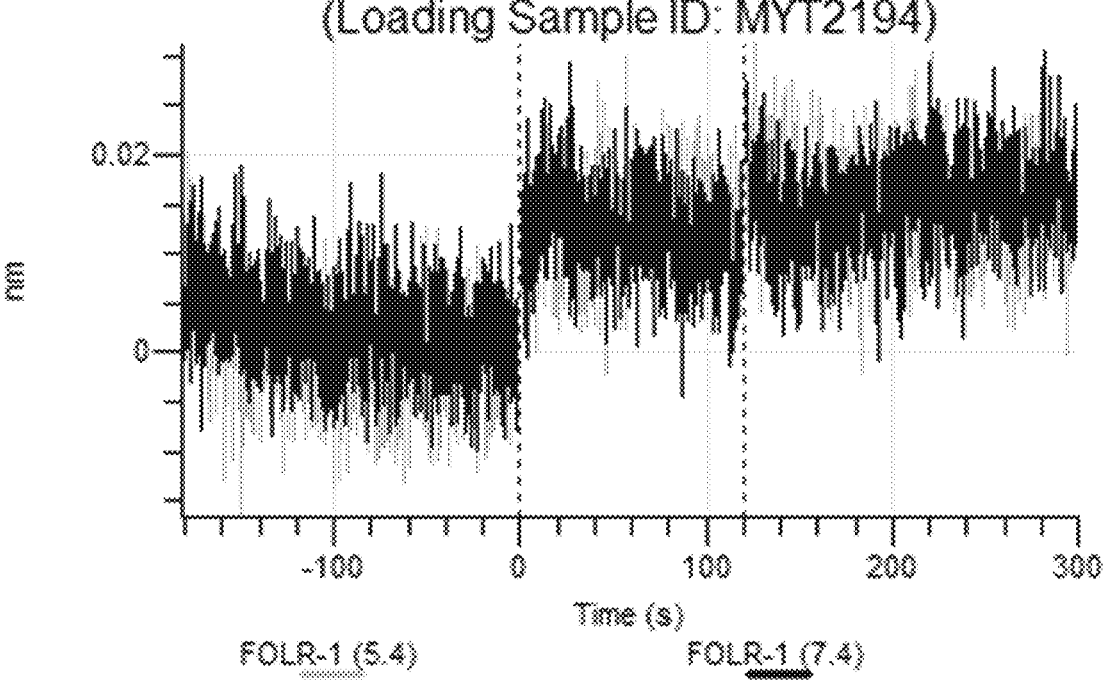
Figure 17I:
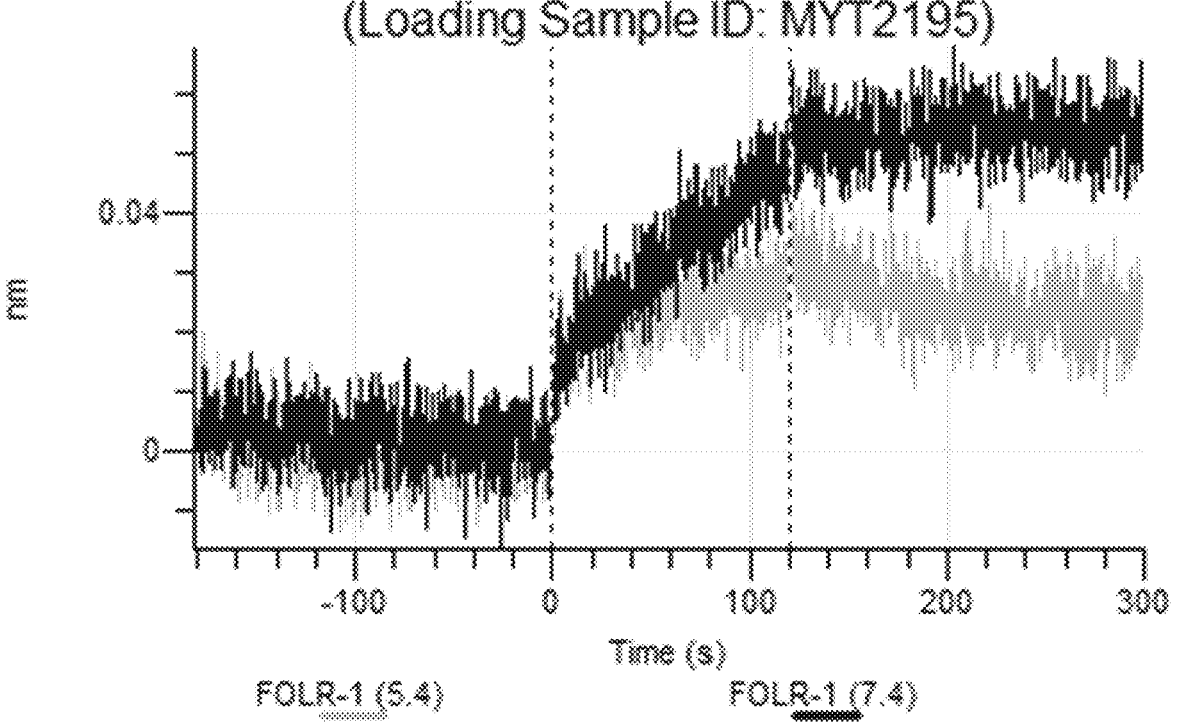
Figure 17M:
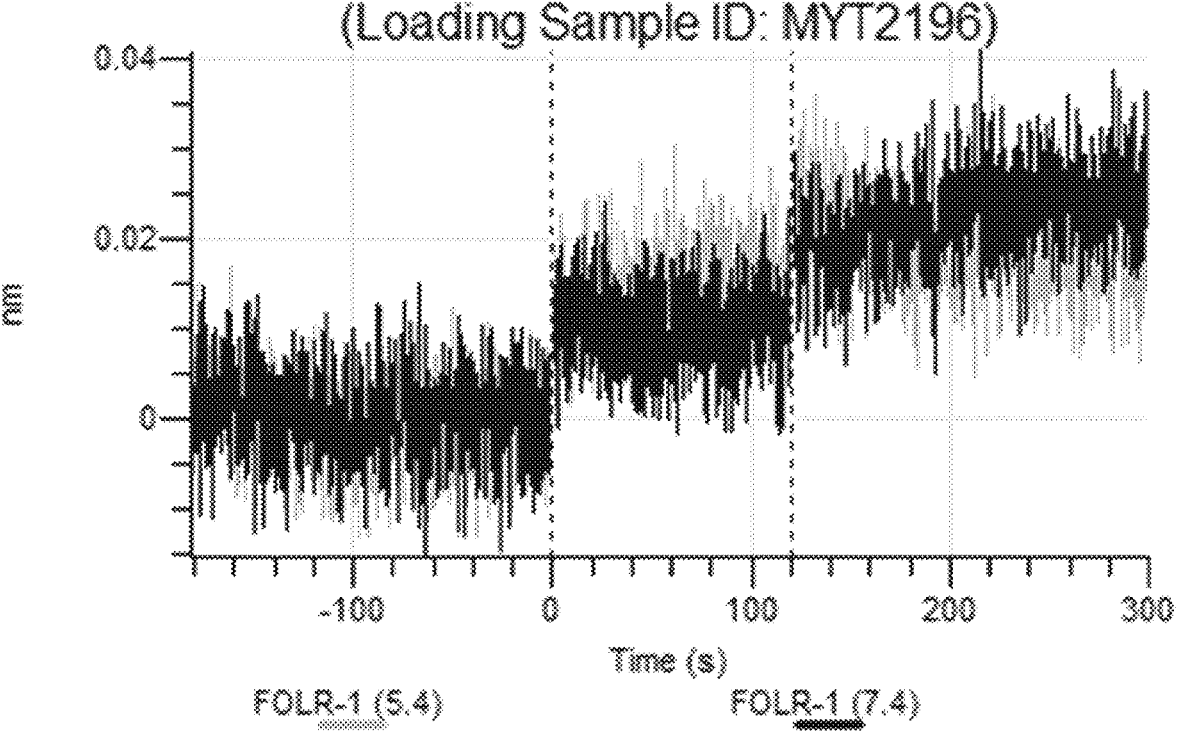
Figure 17N:
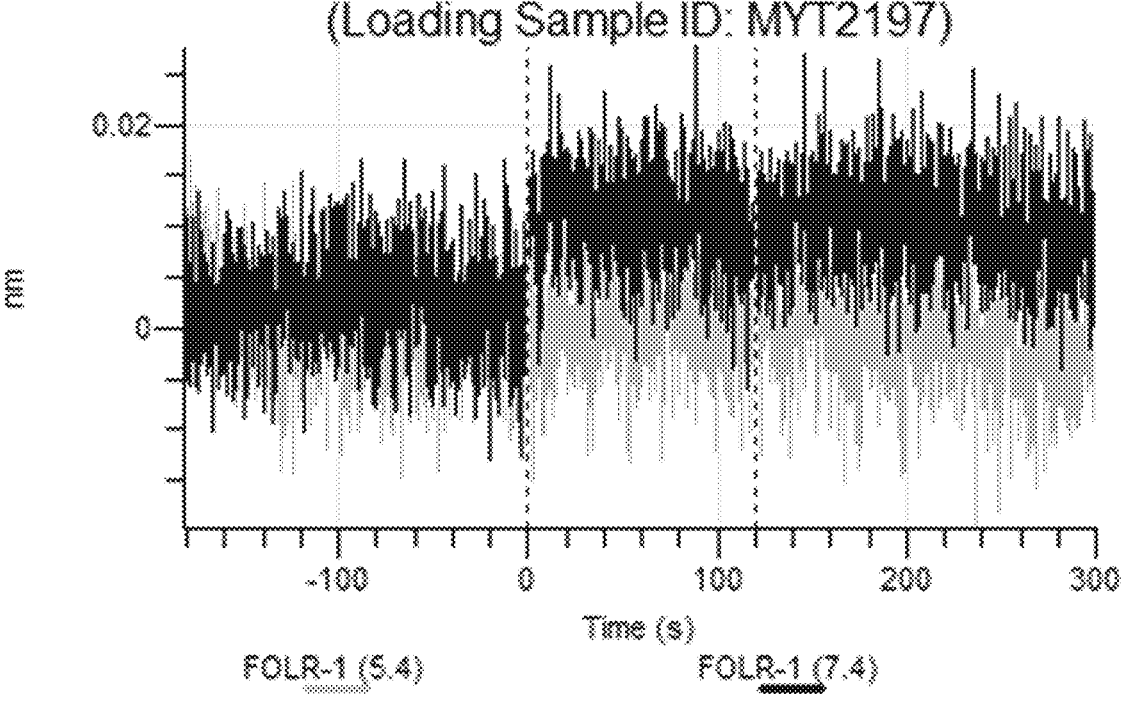
Figure 17O:
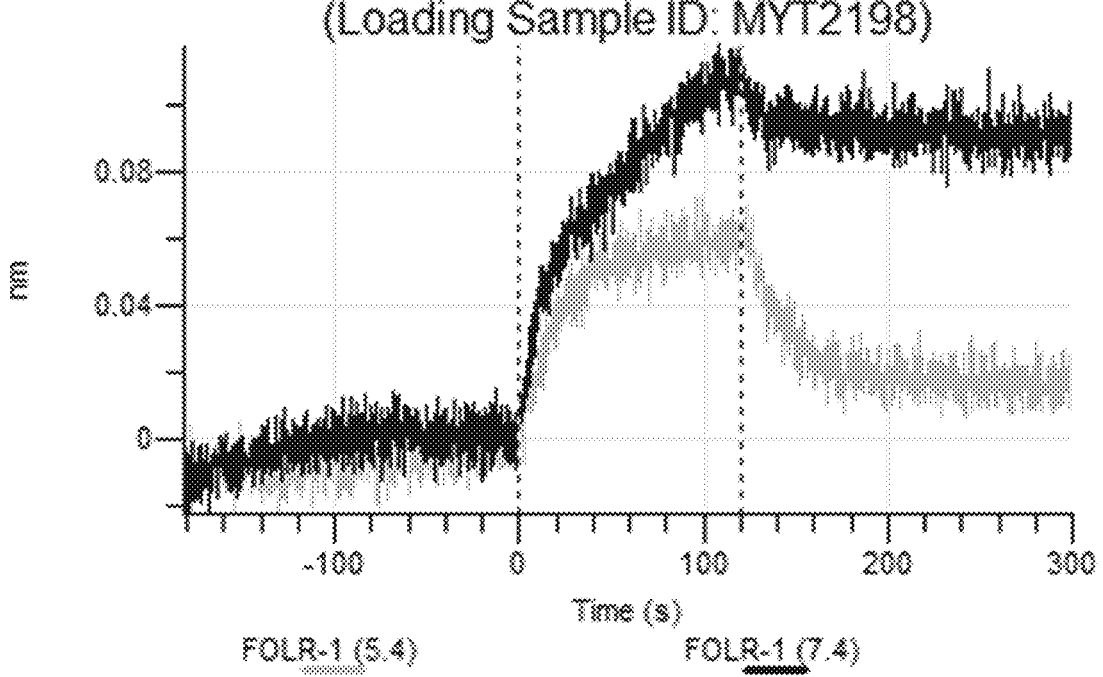
Figure 17P:
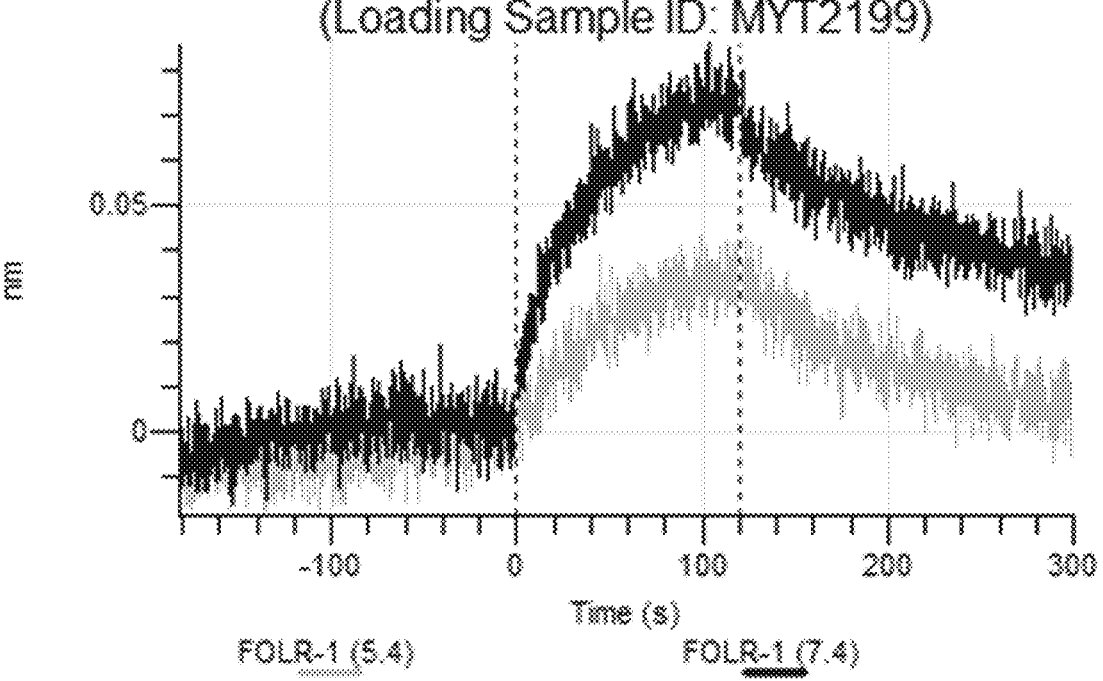
Figure 17Q:
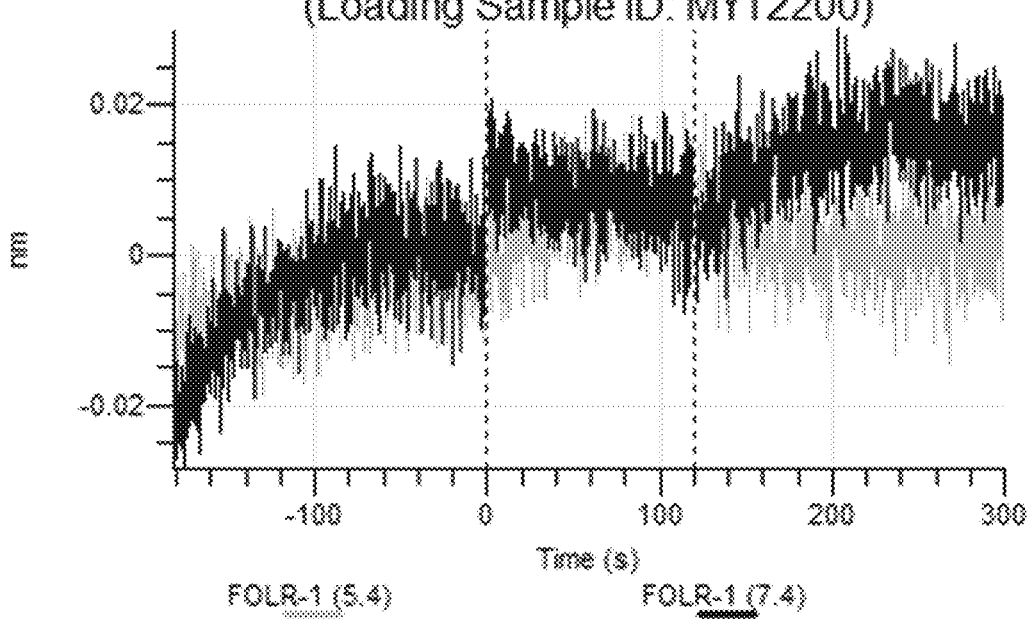
Figure 17R:
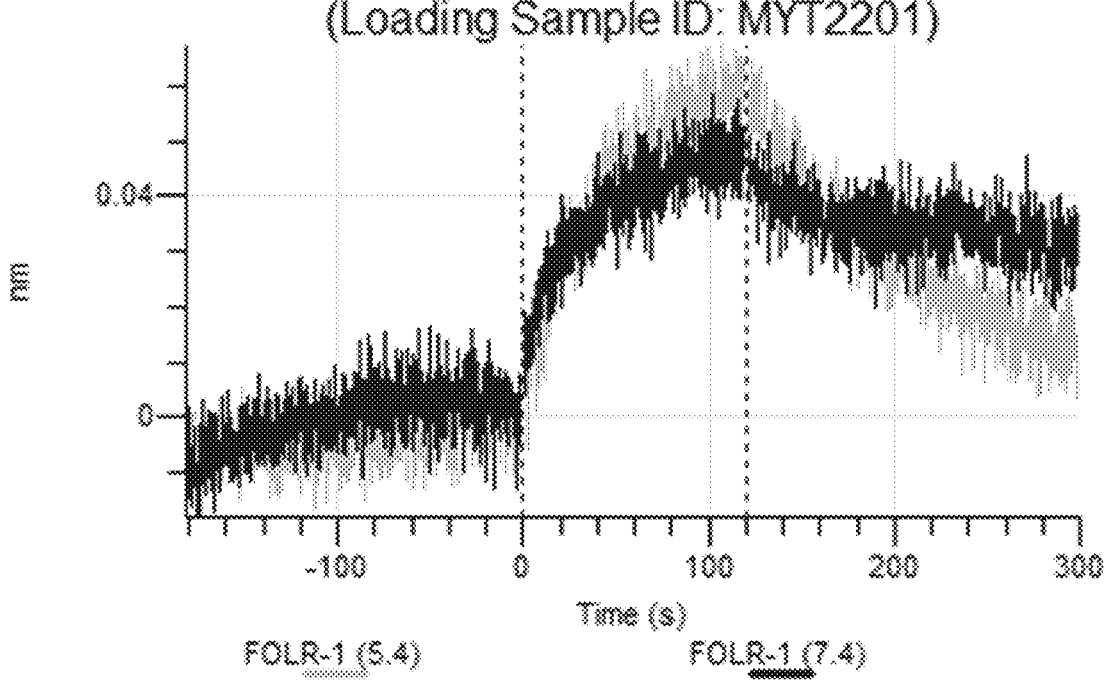
Figure 17S:
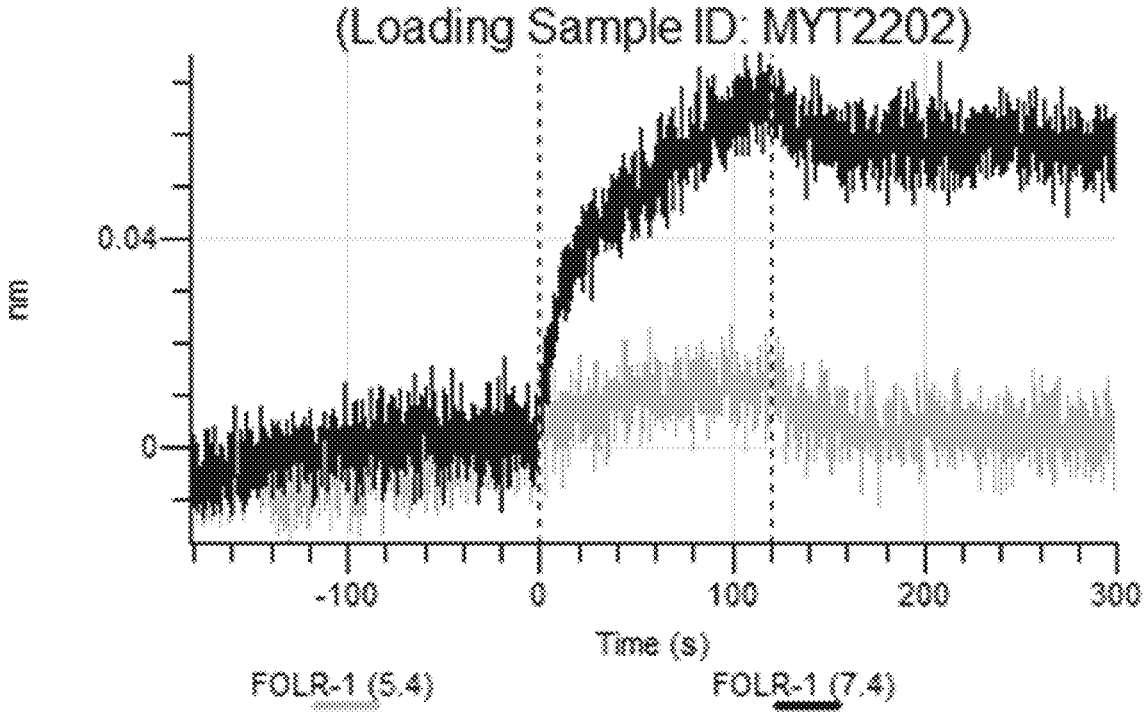
Figure 17T:
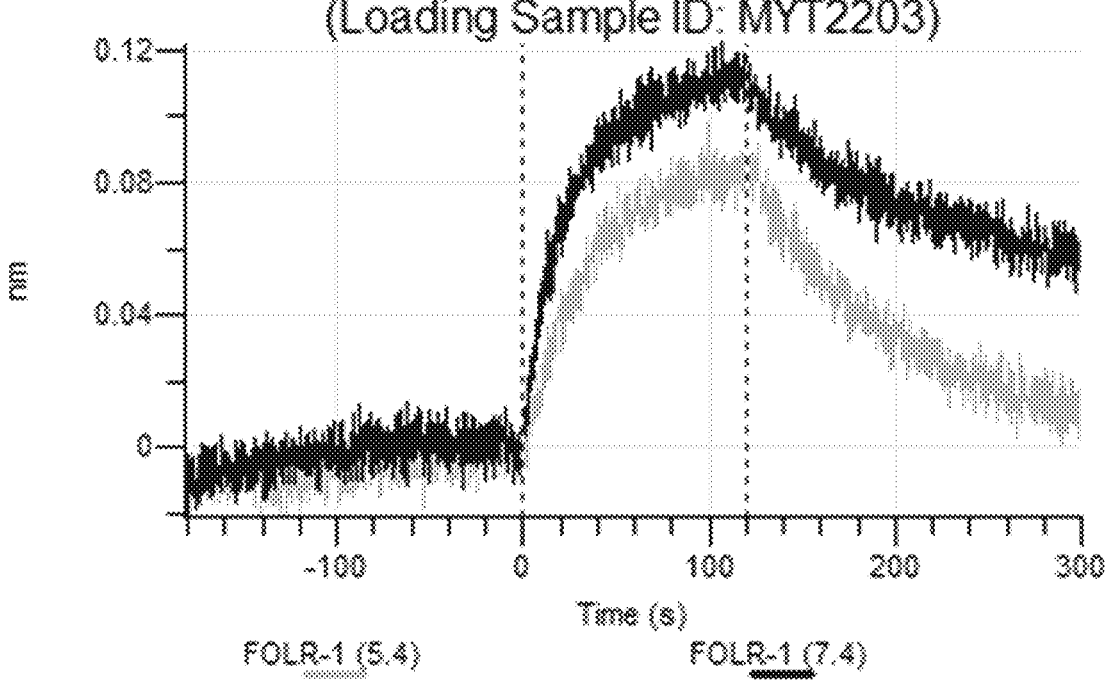
Figure 17U:
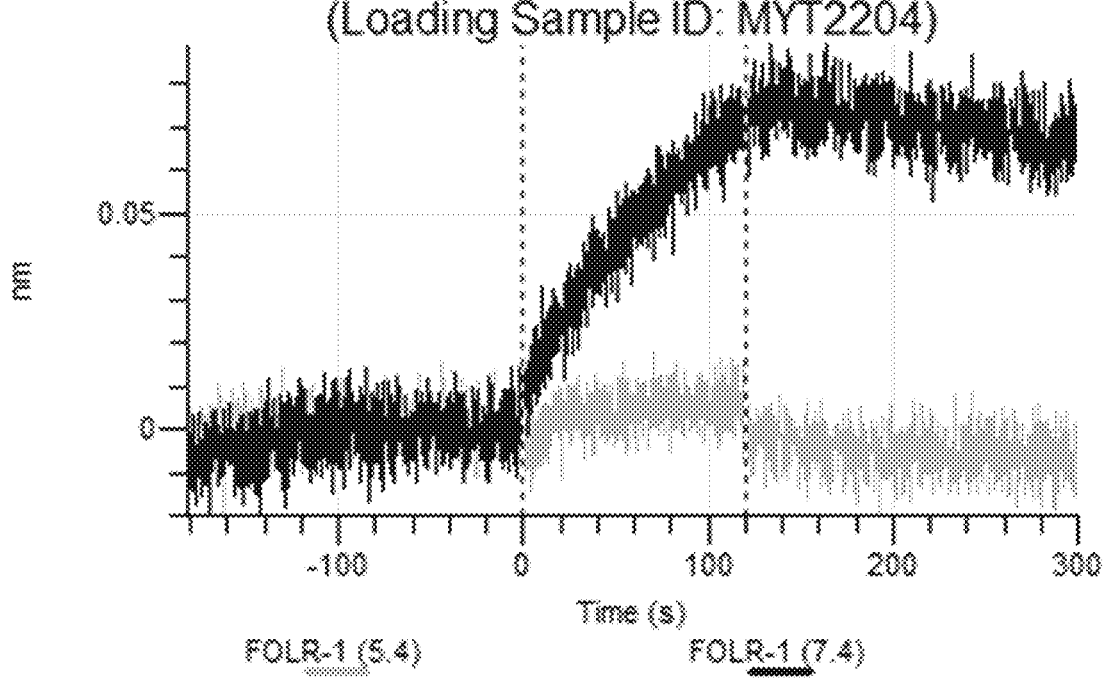
Figure 17V:
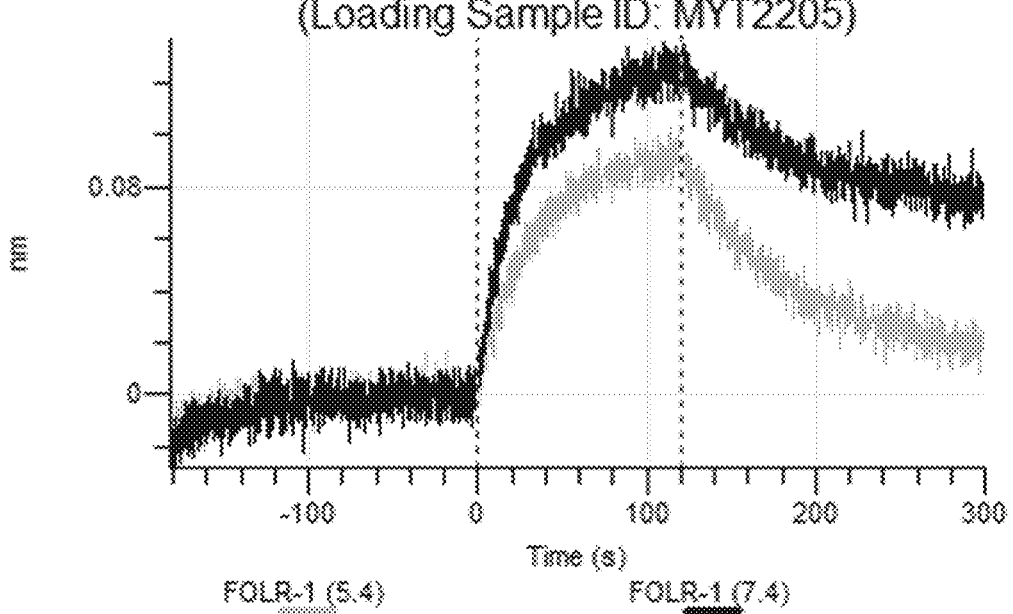
Figure 17W:
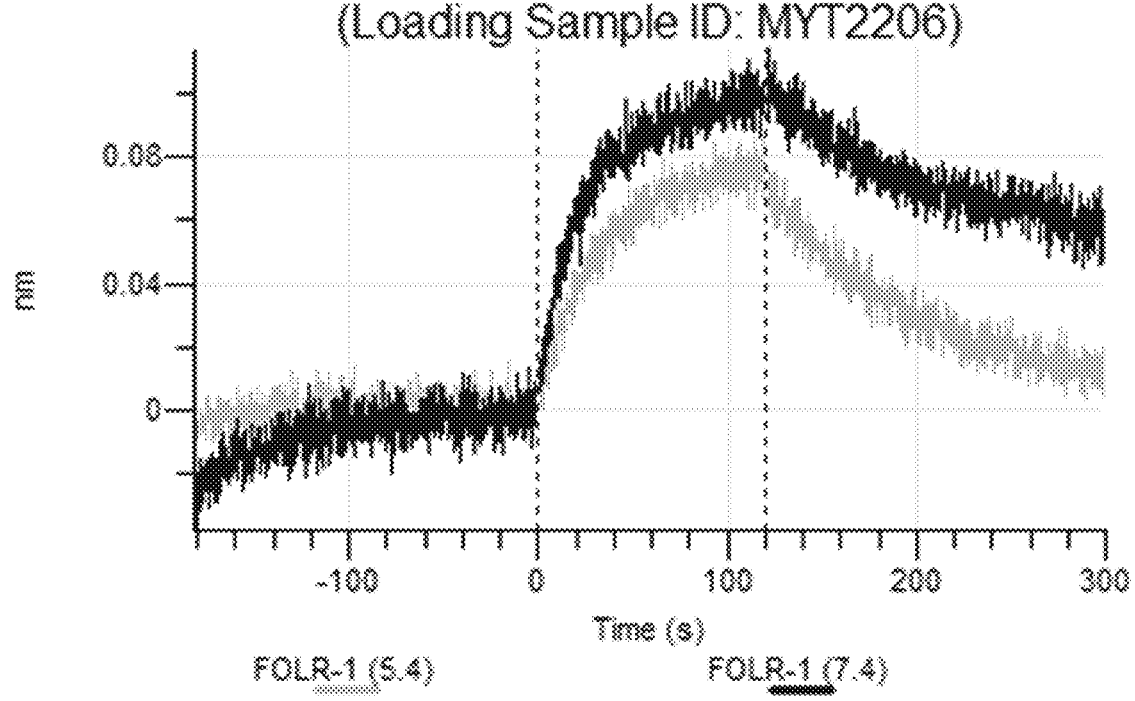
Figure 17X:
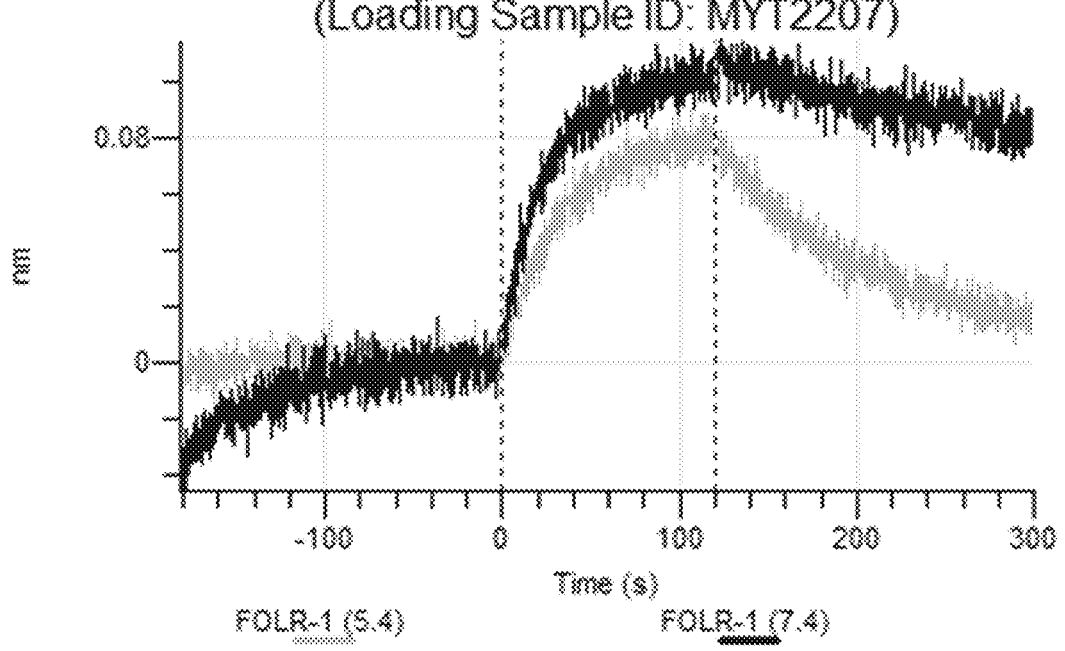
Figure 17Y:
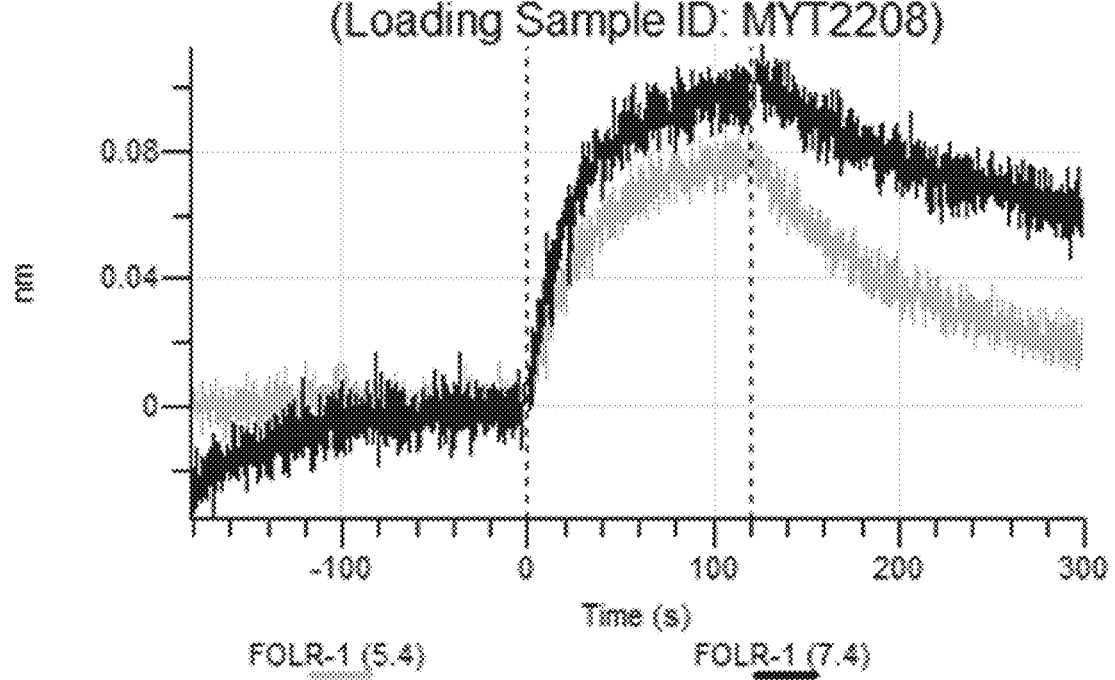
Figure 17Z:
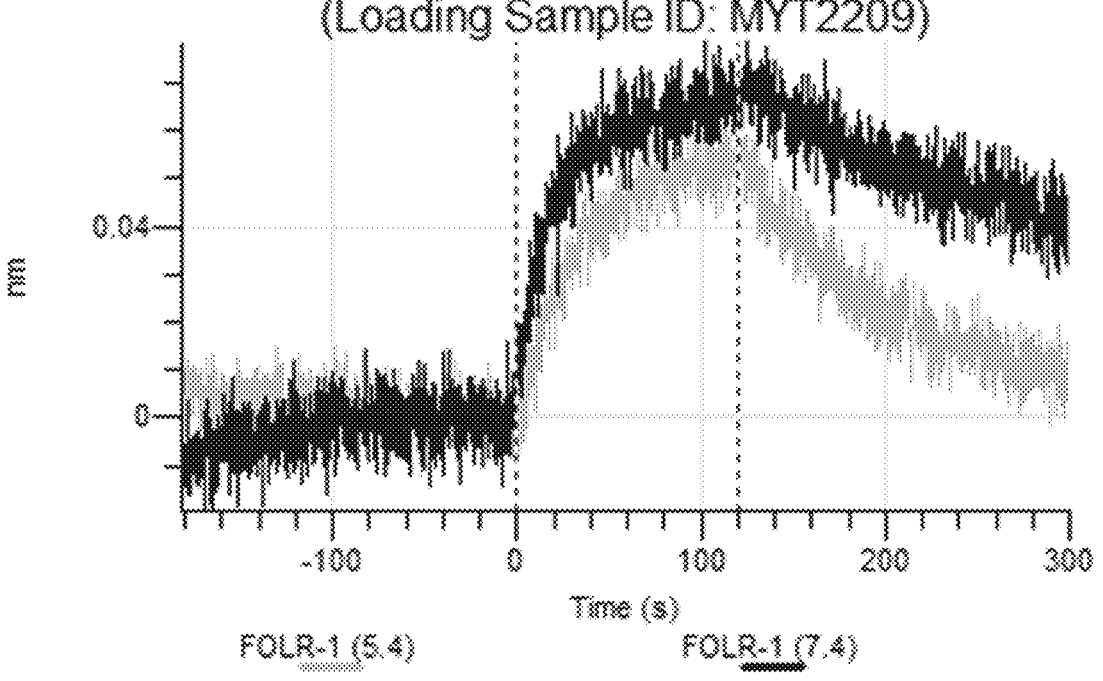
Figure 17A:
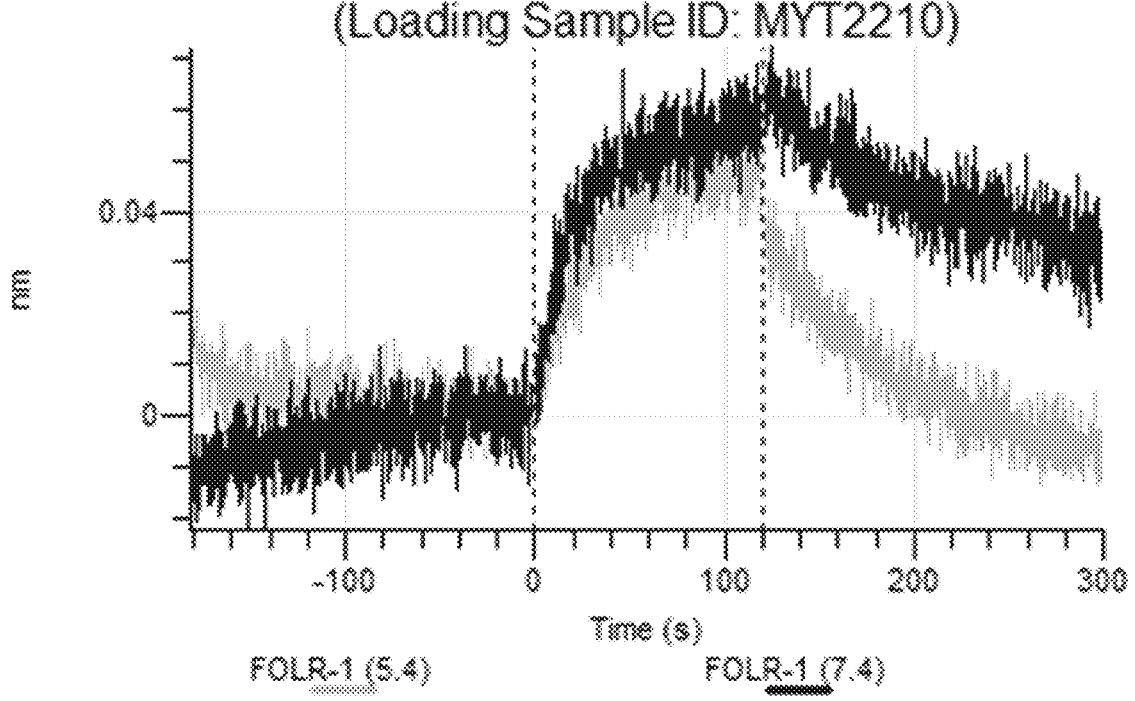
Figure 17A:
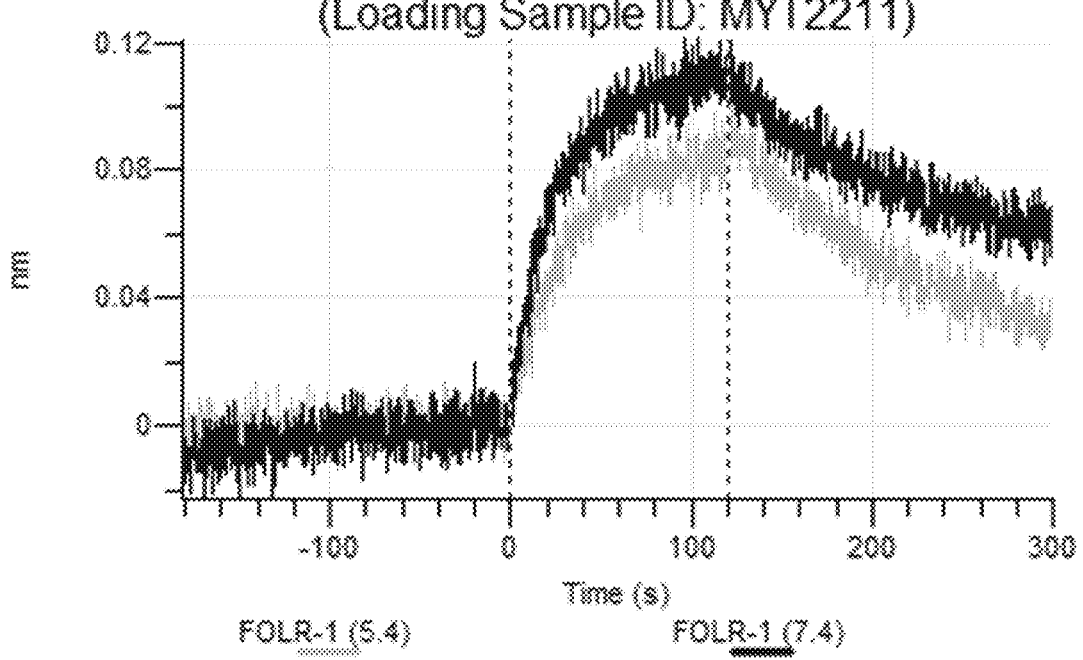
Figure 17A:
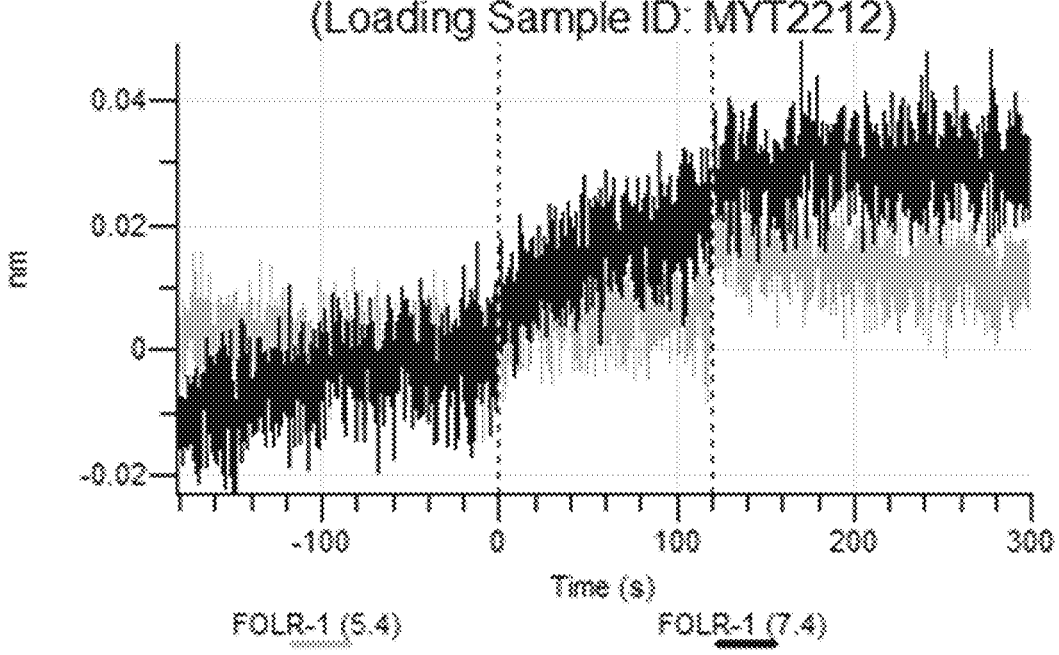
Figure 17A:
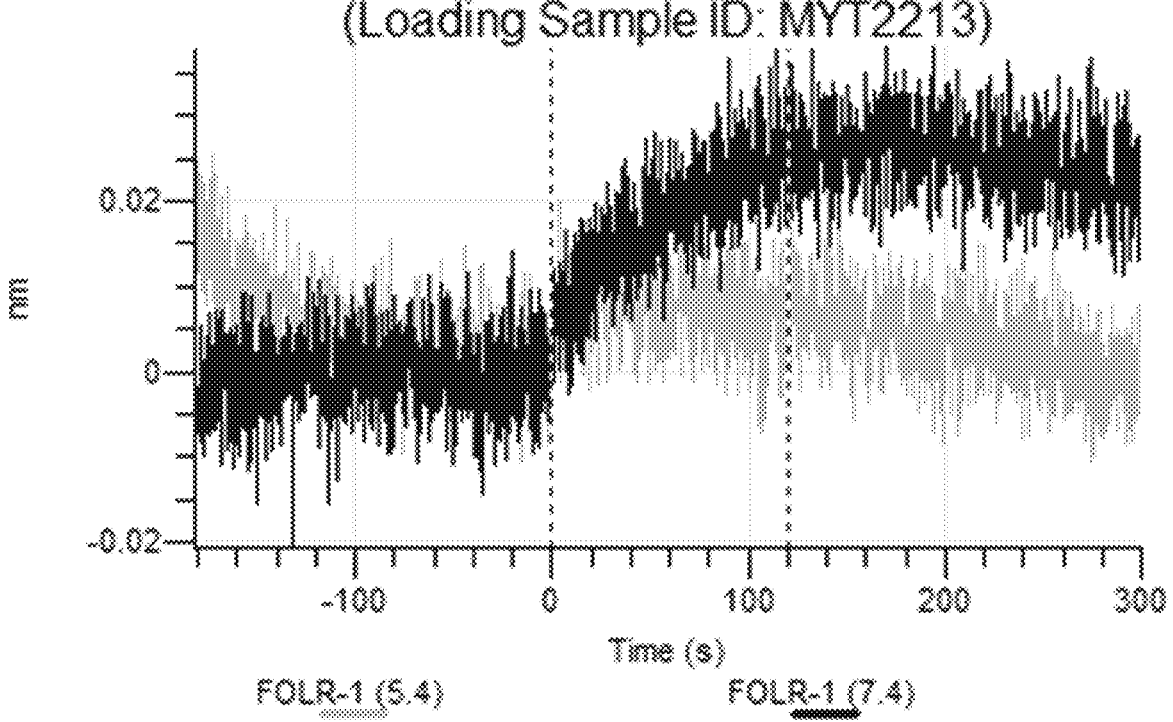
Figure 17A:
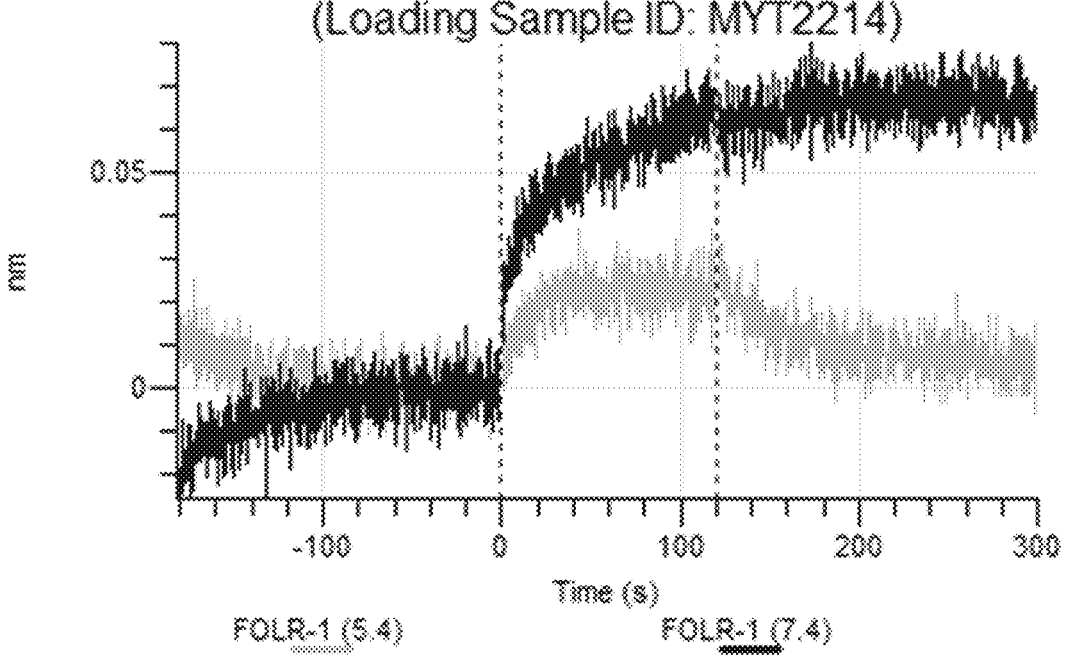
Figure 17A:
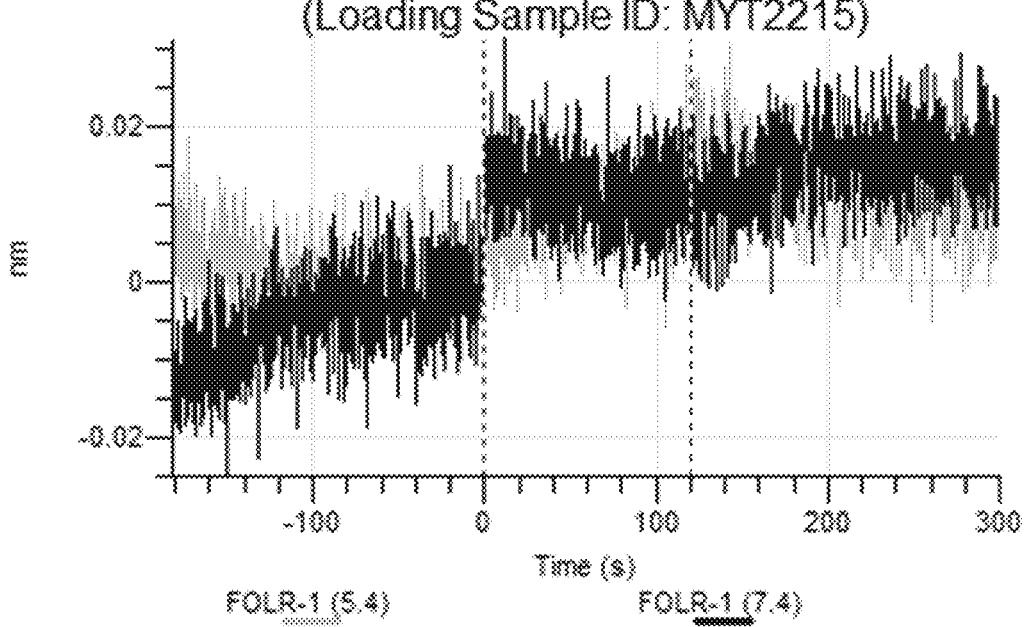
Figure 17A:
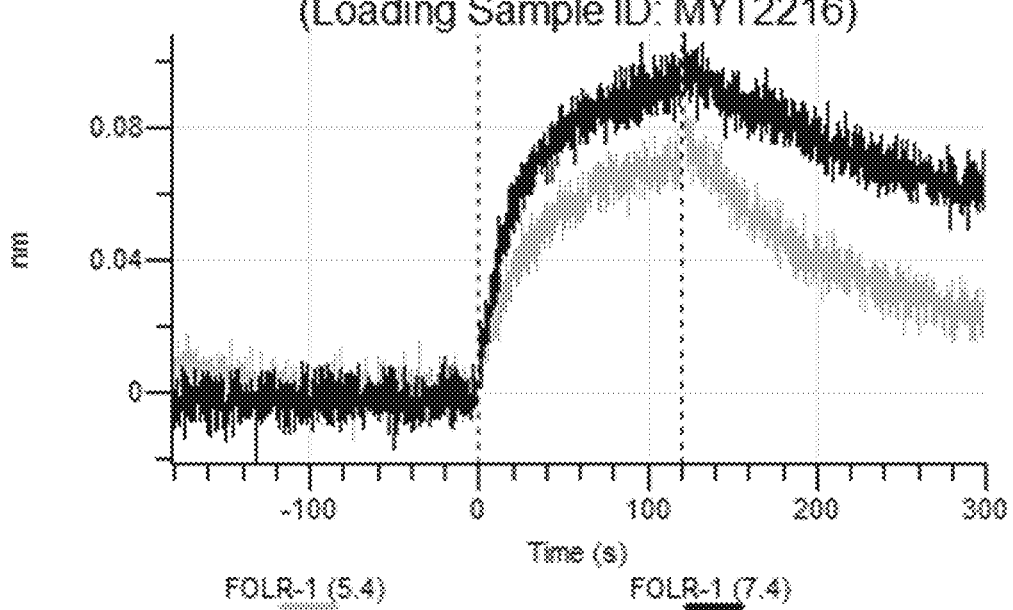
Figure 17A:
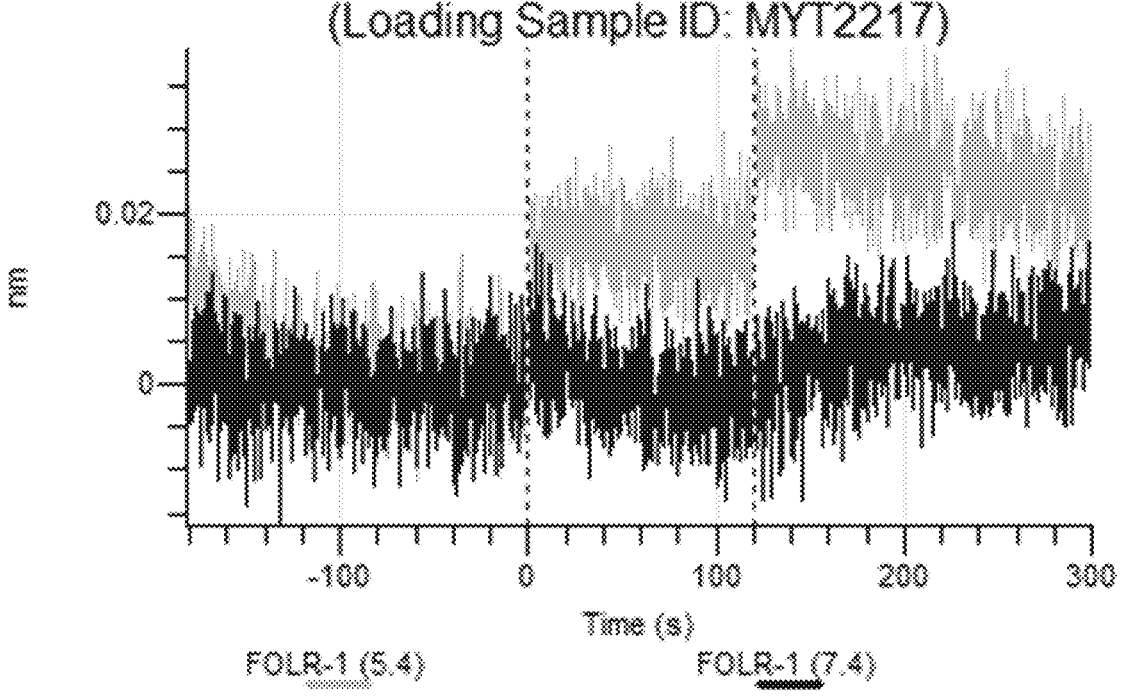
Figure 17A:
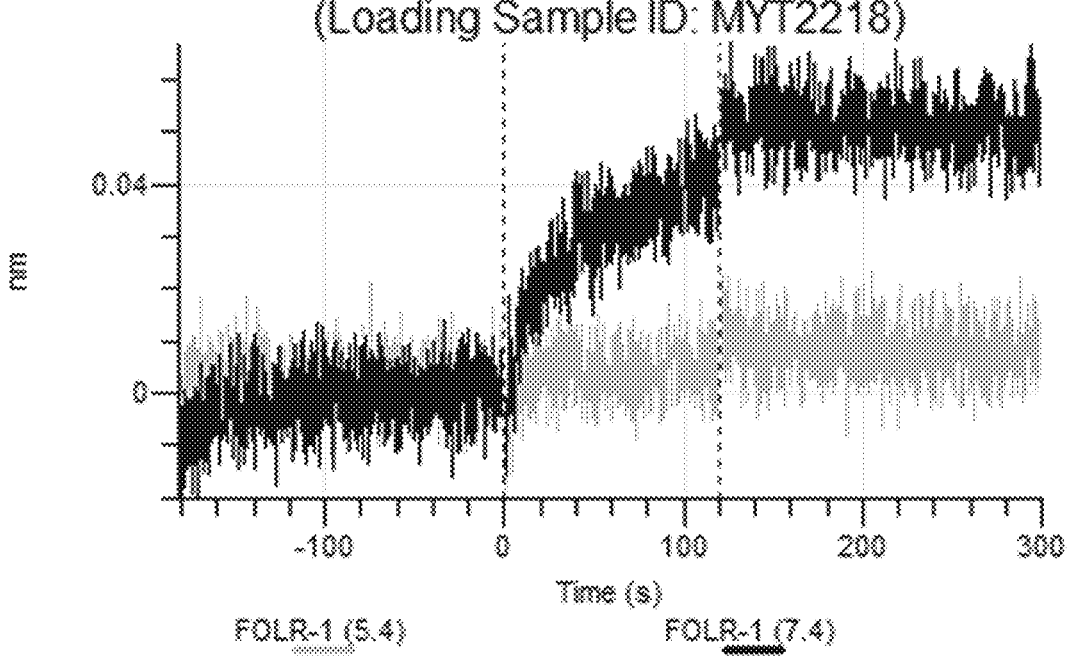
Figure 17A:
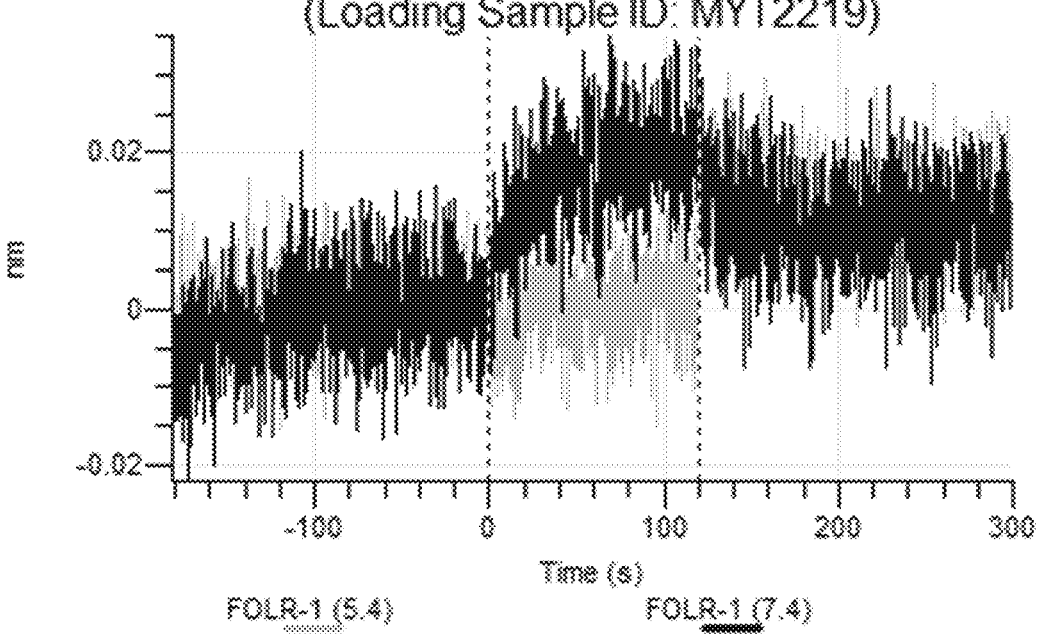
Figure 17A:
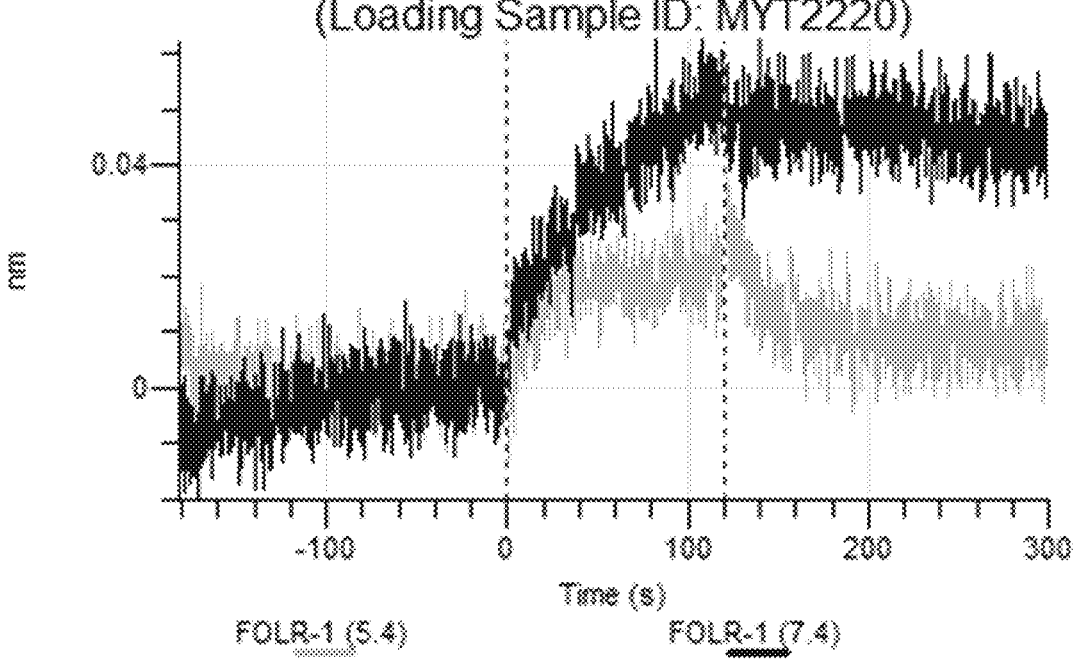
Figure 17A:
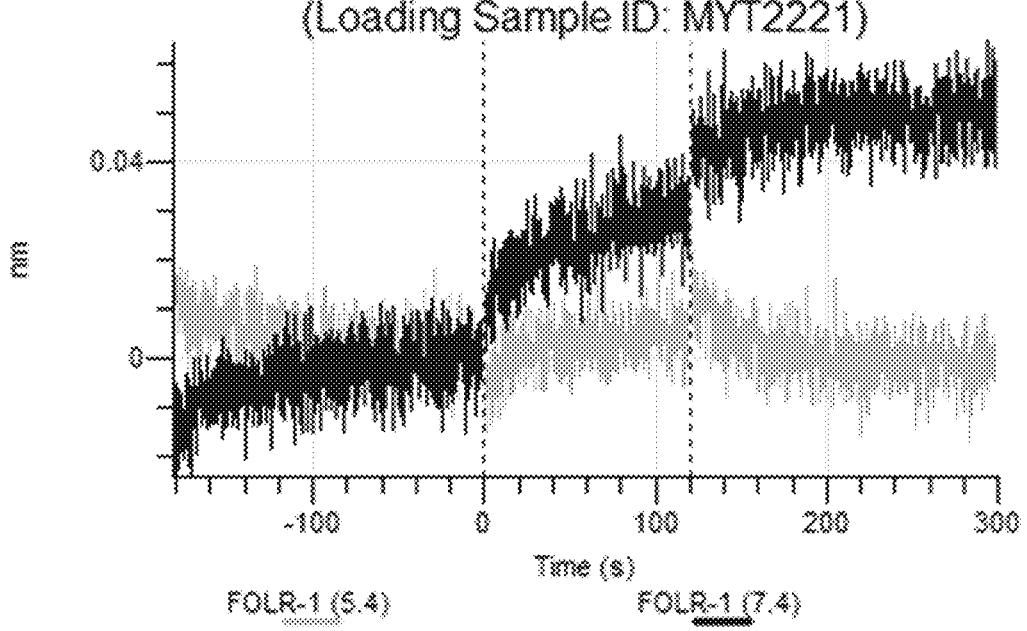
Figure 17A:
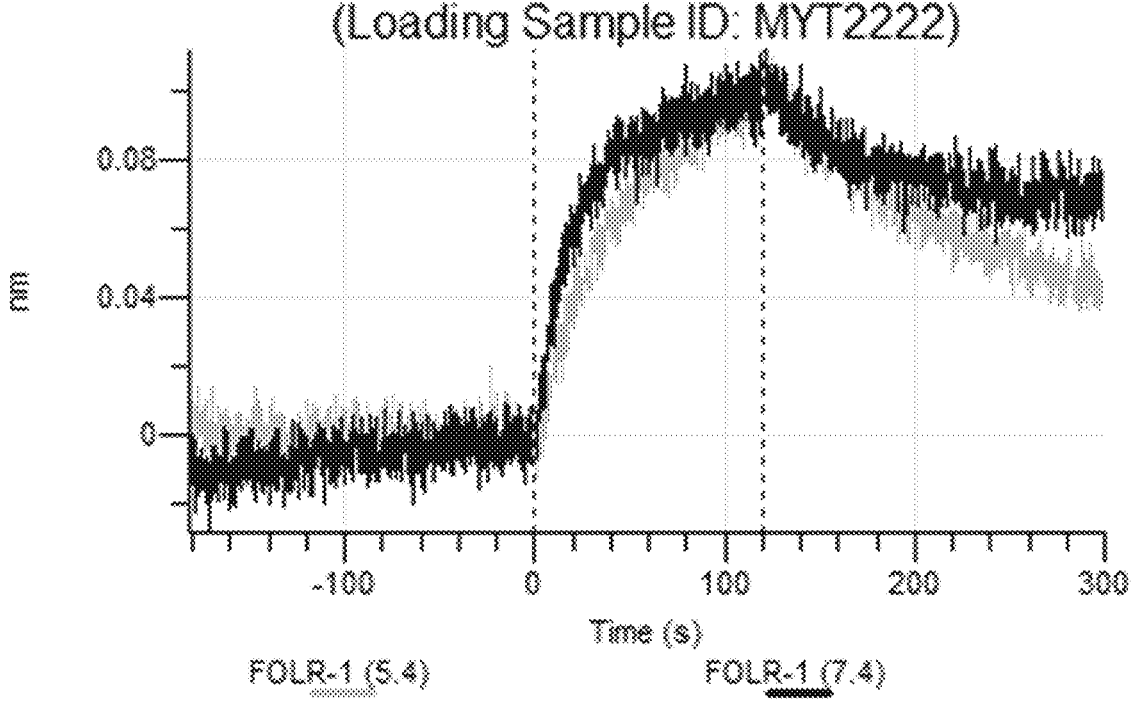
Figure 17A:
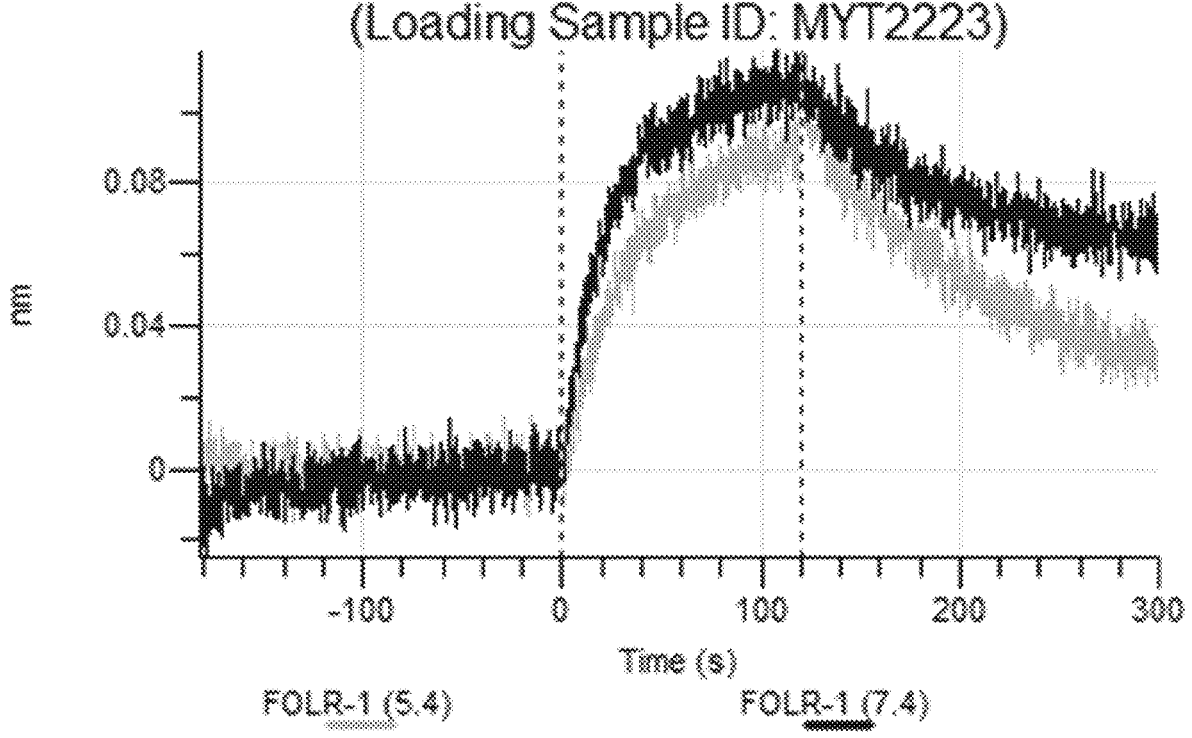

FIGS. 17a to 17an: Binding of FARLETUZUMAB starting ABPC and histidine scanning and alanine scanning variants to FOLR1 by biolayer interferometry. MYT2184 (FARLETUZUMAB) and MYT2185-MYT2223, heavy chain histidine scanning and alanine scanning variants, were captured on anti-human Fc biosensors and associated with FOLR1 at low pH or high pH, as specified in the figures.

FIG. 18: Construct identifier to SEQ ID NO correspondence table. Constructs, heavy chain histidine scanning and alanine scanning variants, are listed in the first column of the table, SEQ ID NOs are listed and correspond to constructs on the left and the appropriate heavy chain, light chain, and CDR categories along the top.

Figure 19:
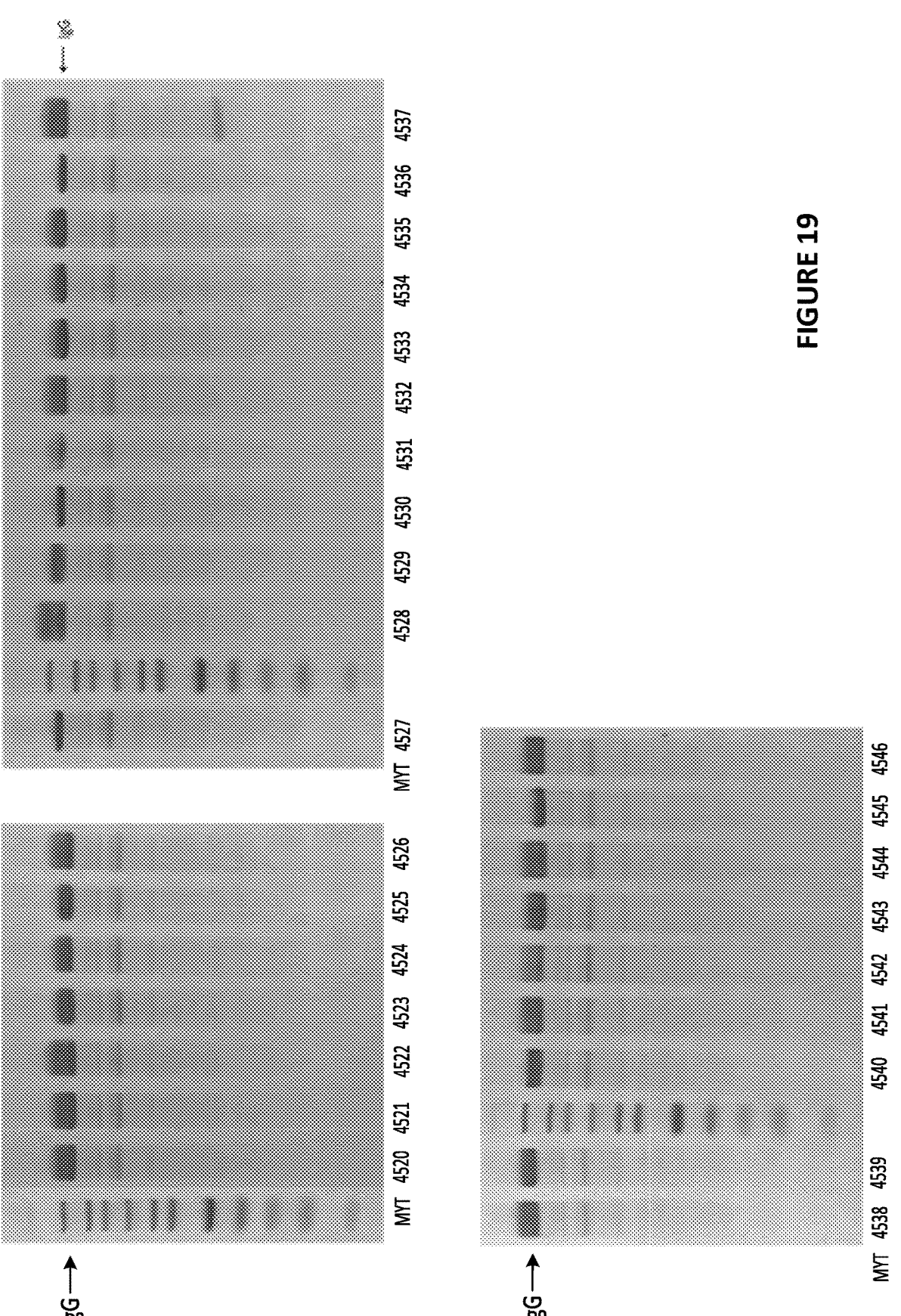

FIG. 19: SDS PAGE for FARLETUZUMAB histidine scanning and alanine scanning. Expi293 cell culture supernatants post-harvest were loaded on non-reduced SDS PAGE gels to confirm expression of FARLETUZUMAB histidine scanning and alanine scanning variants. Arrows show the corresponding size for an IgG on a non-reduced SDS PAGE gel. MYT4520-MYT4546 are FARLETUZUMAB light chain histidine scanning and alanine scanning variants.

Figure 20A:
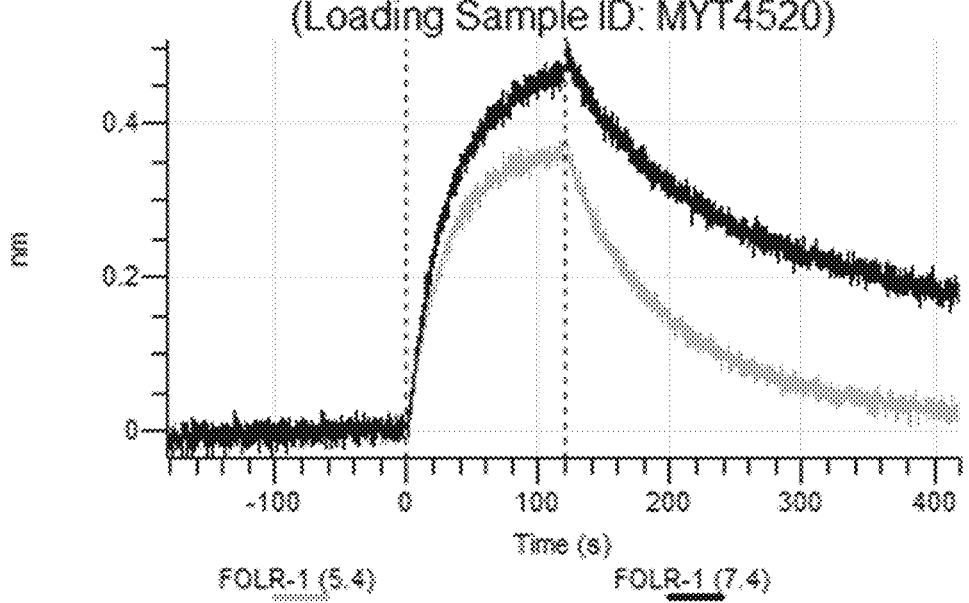
Figure 20B:
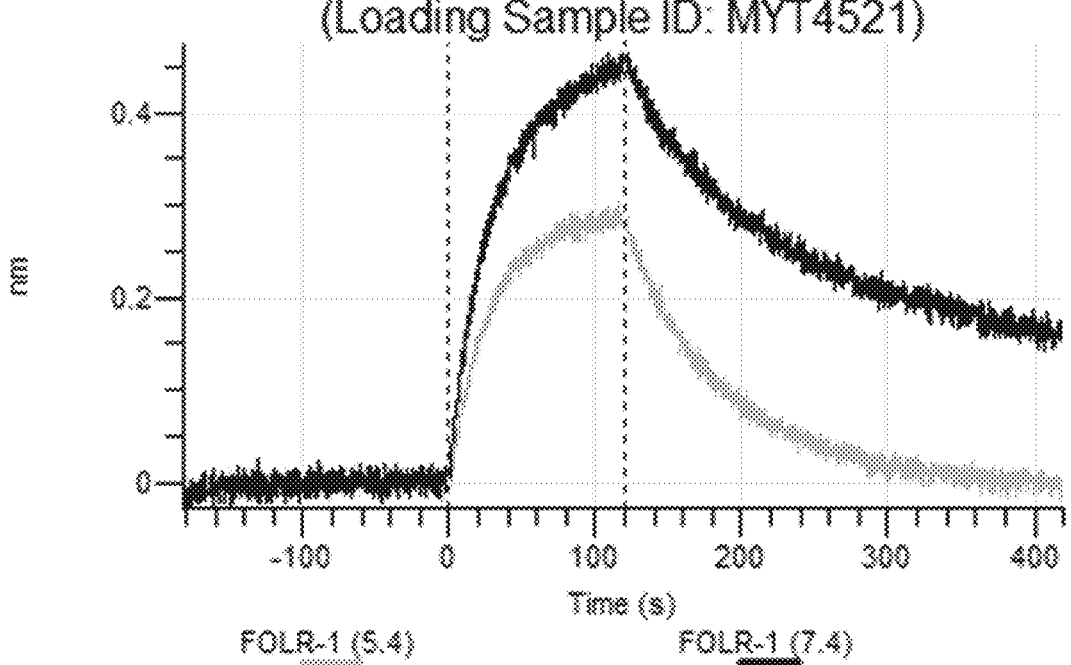
Figure 20C:
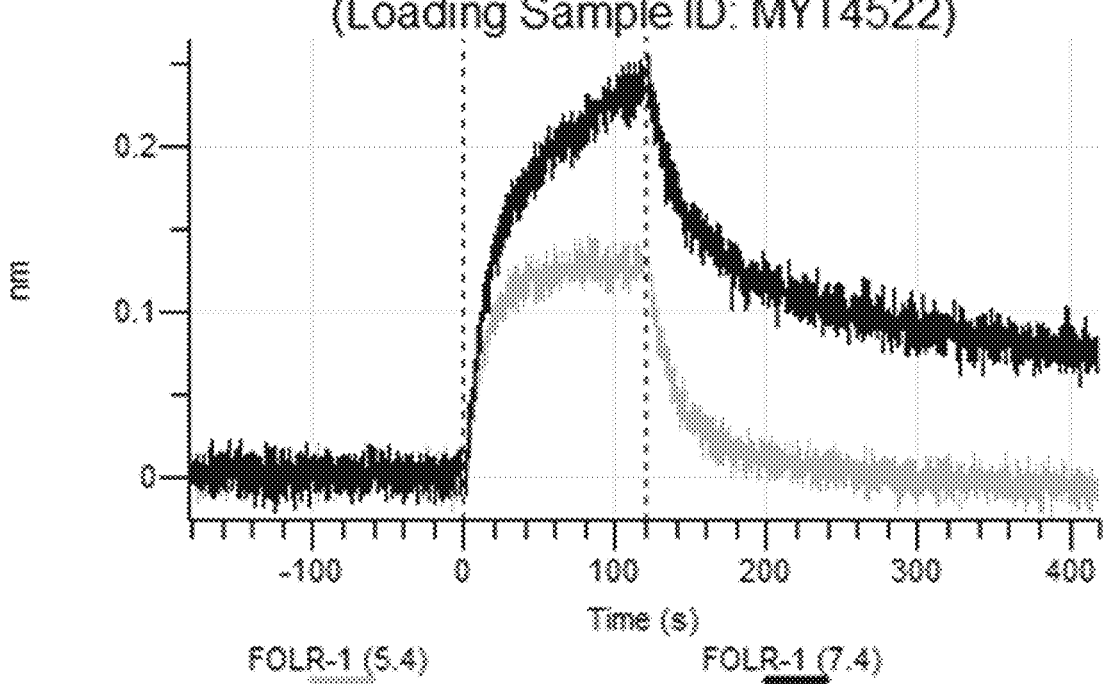
Figure 20D:
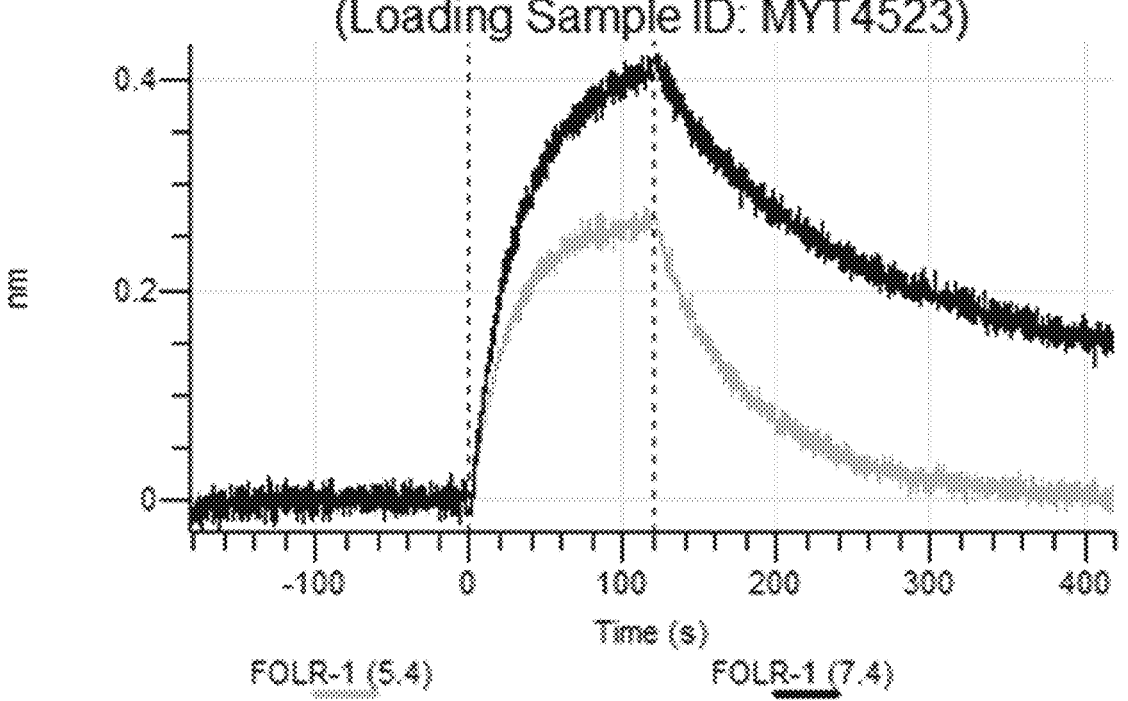
Figure 20E:
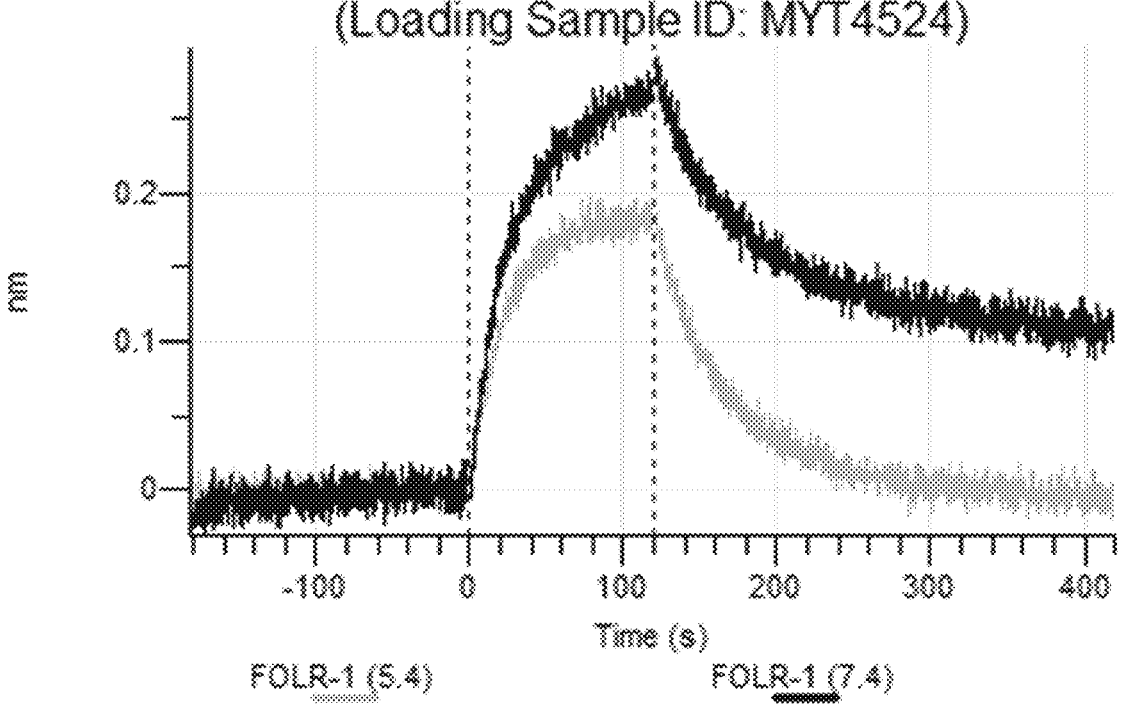
Figure 20F:
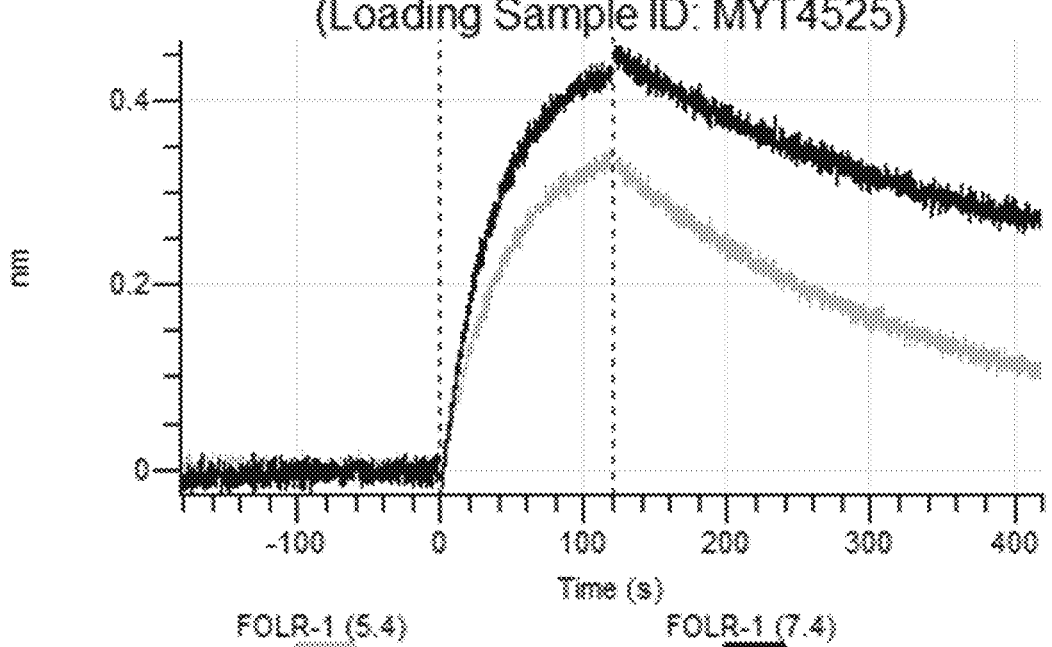
Figure 20G:
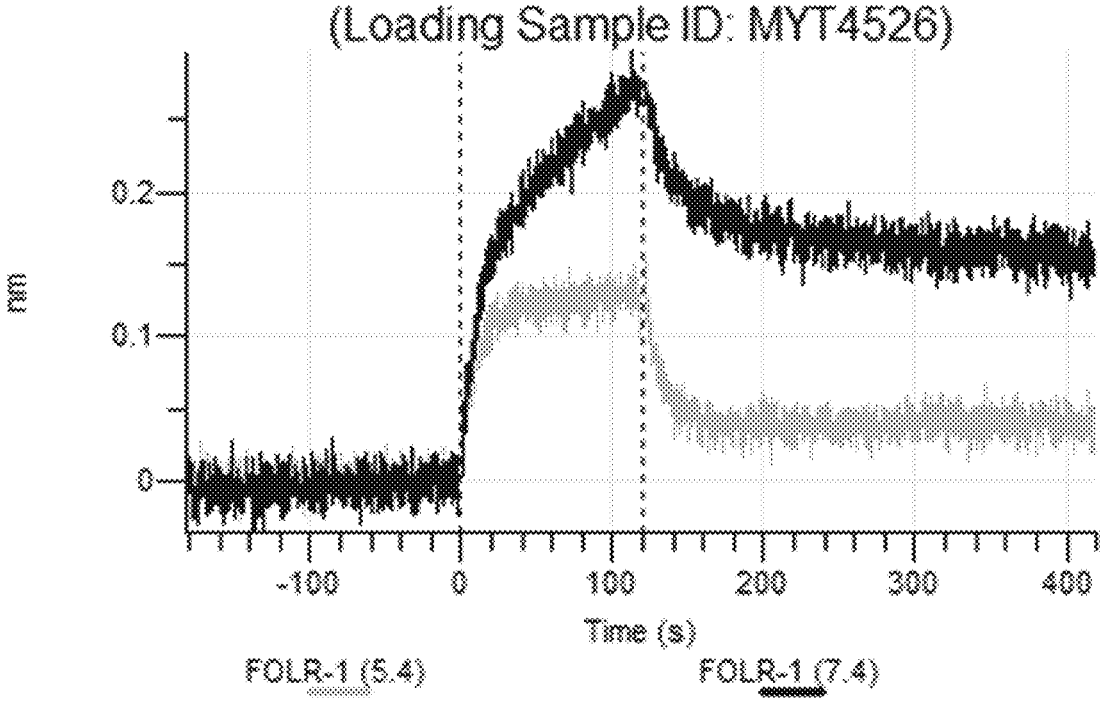
Figure 20H:
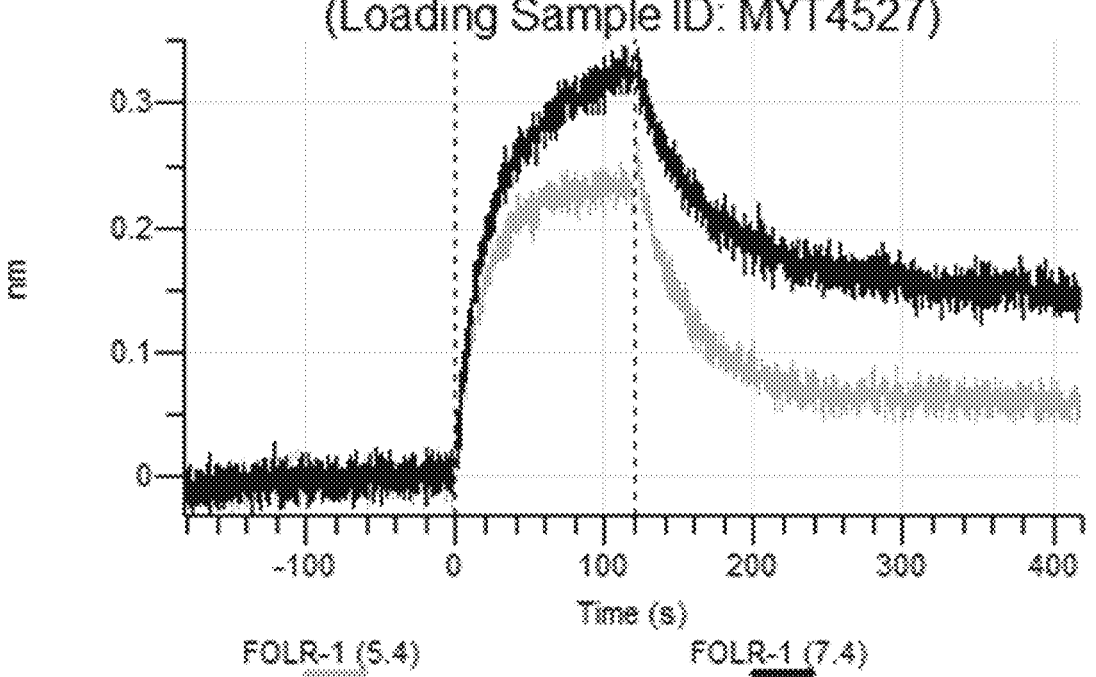
Figure 20I:
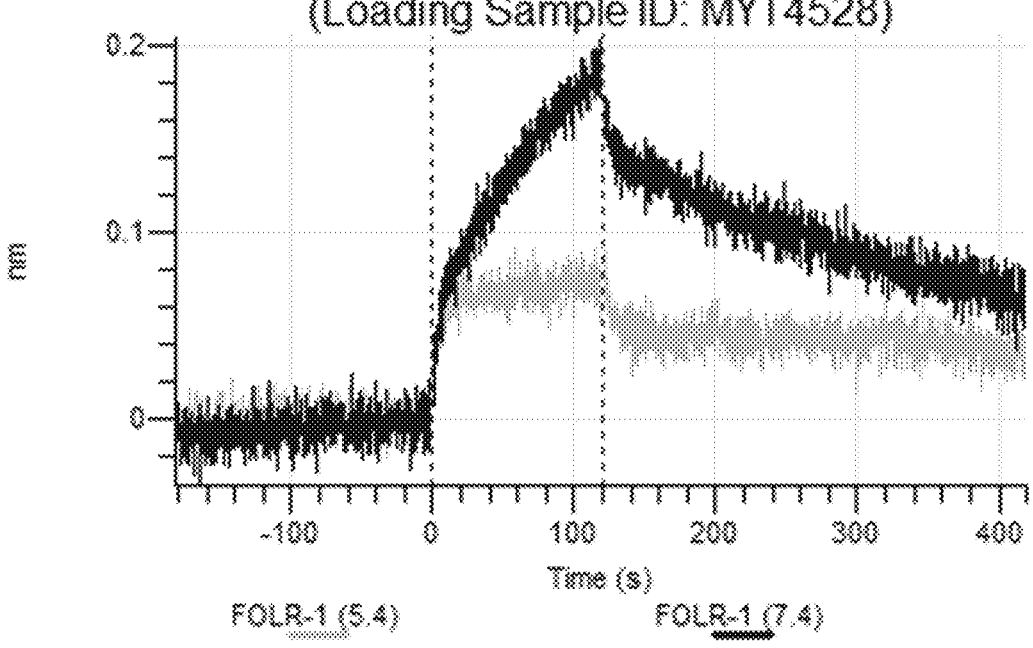
Figure 20J:
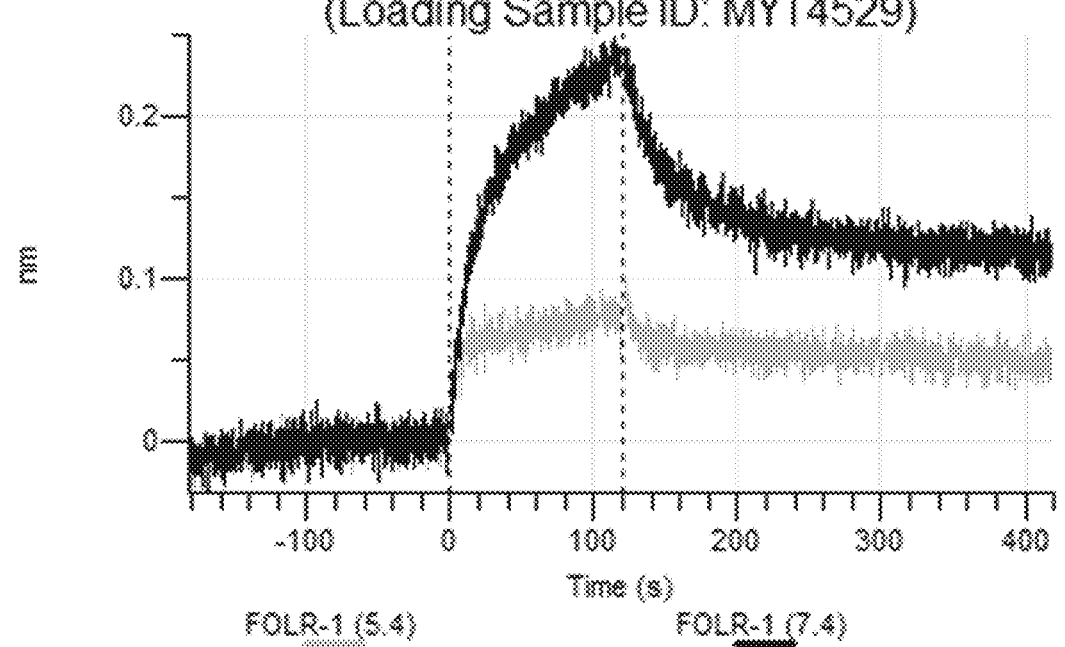
Figure 20K:
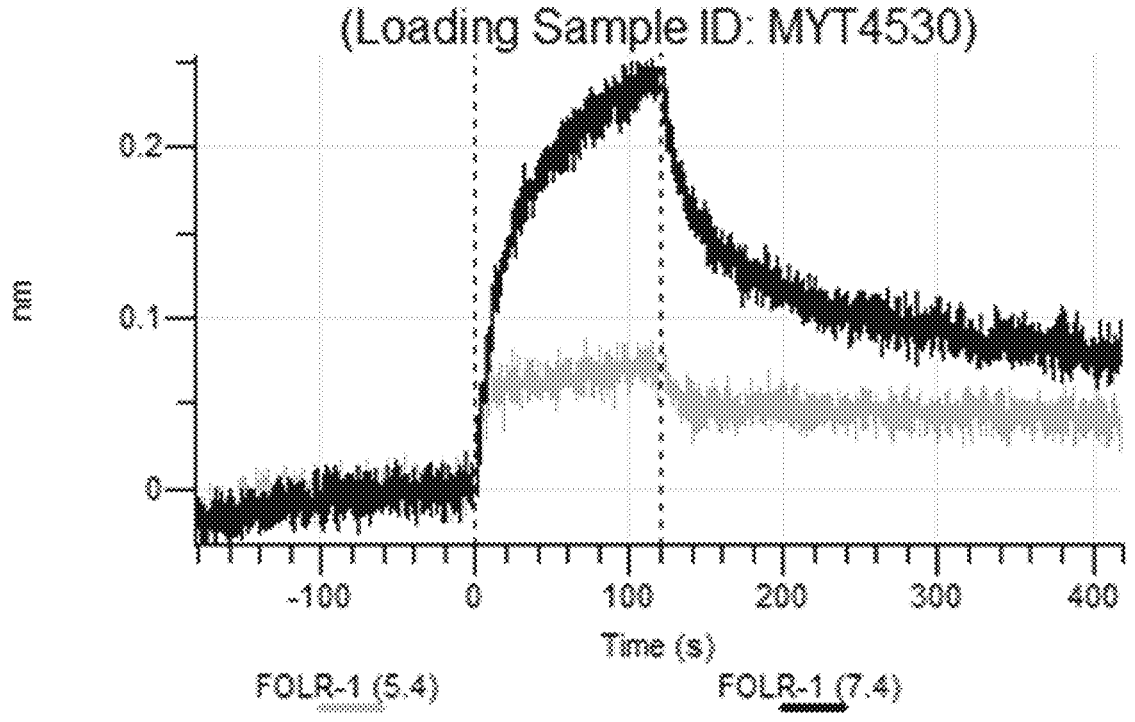
Figure 20I:
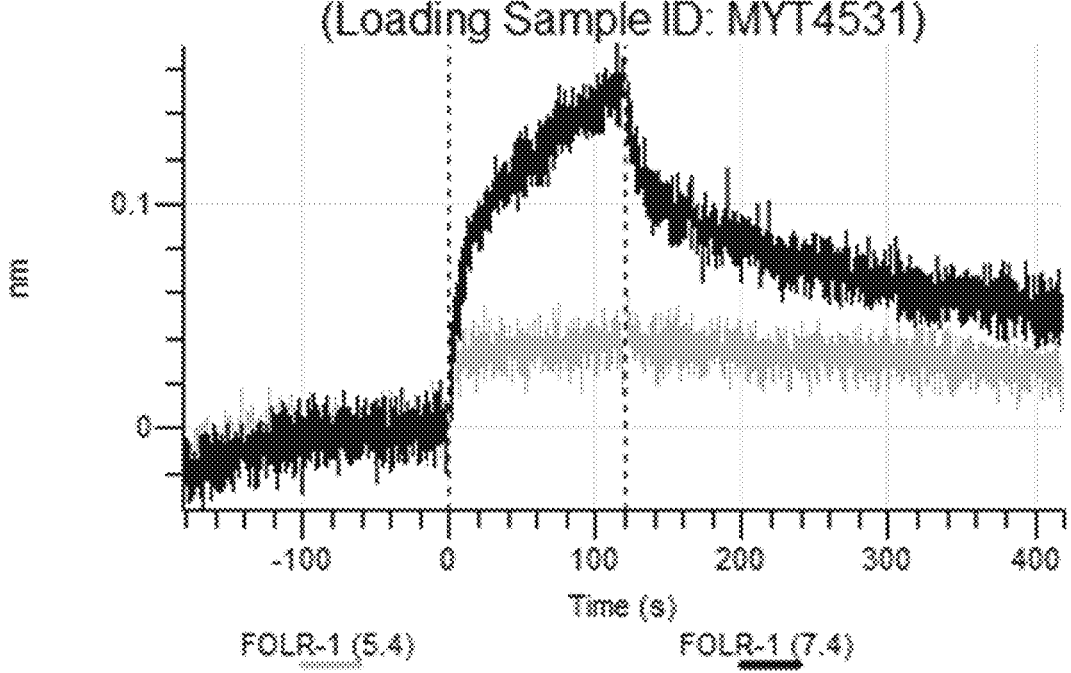
Figure 20M:
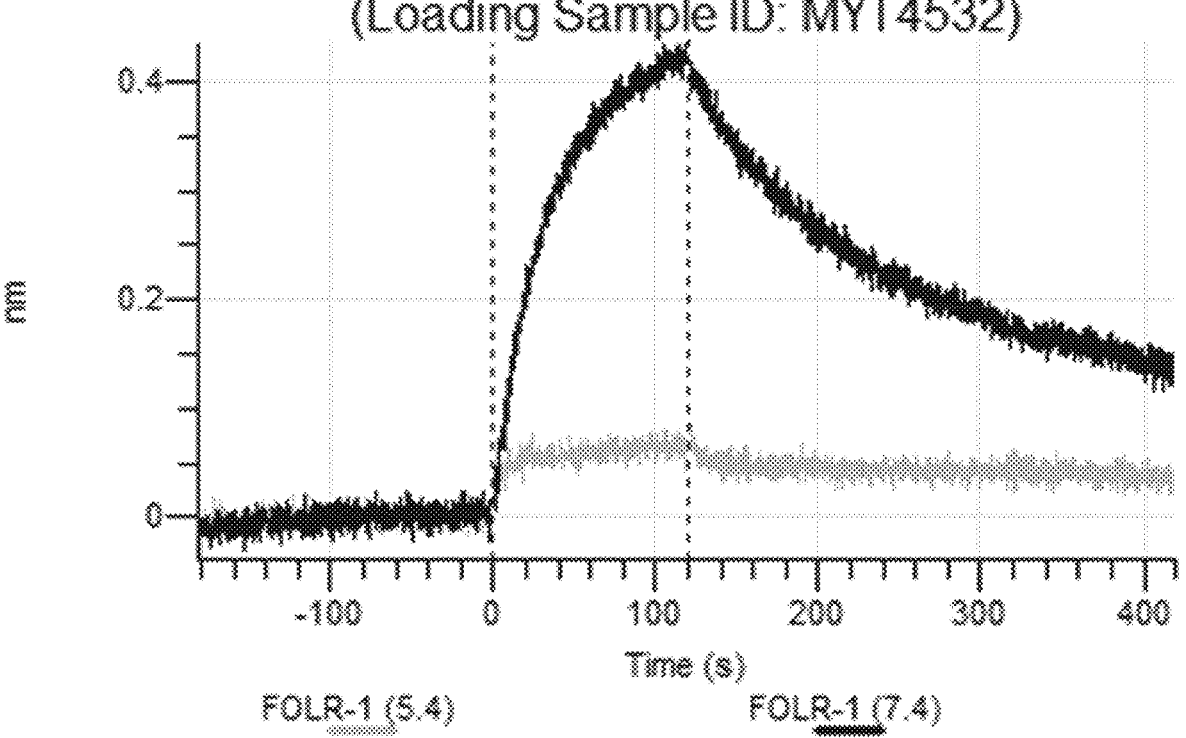
Figure 20N:
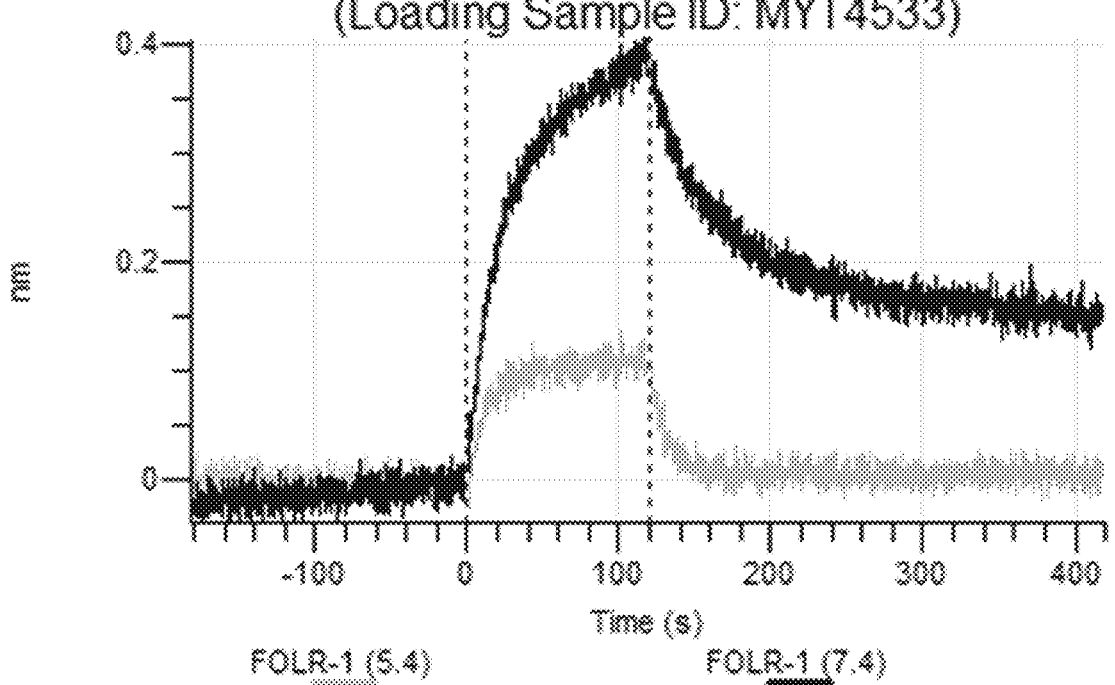
Figure 20O:
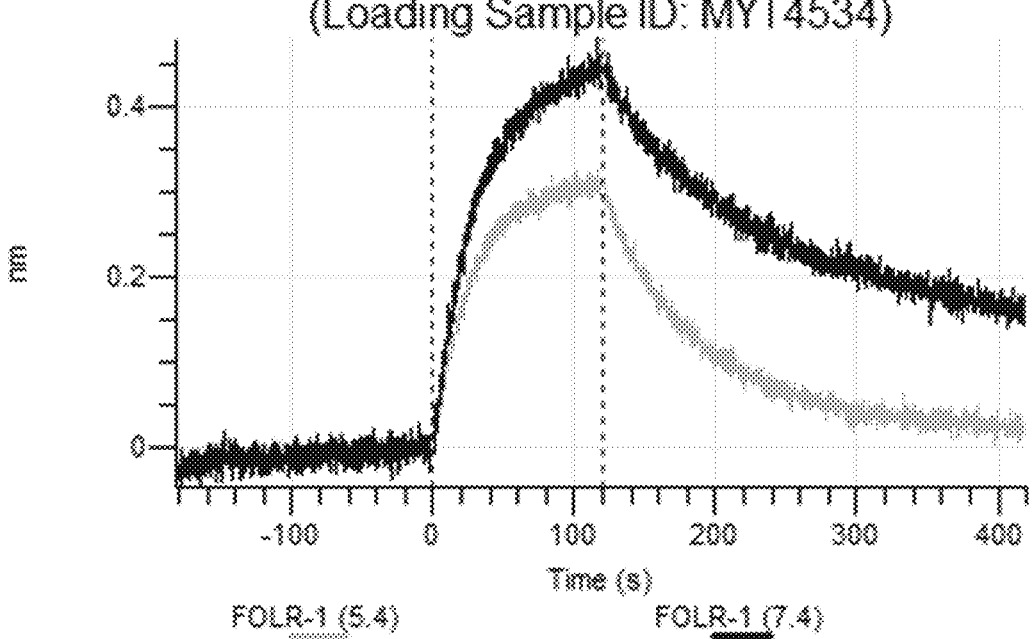
Figure 20P:
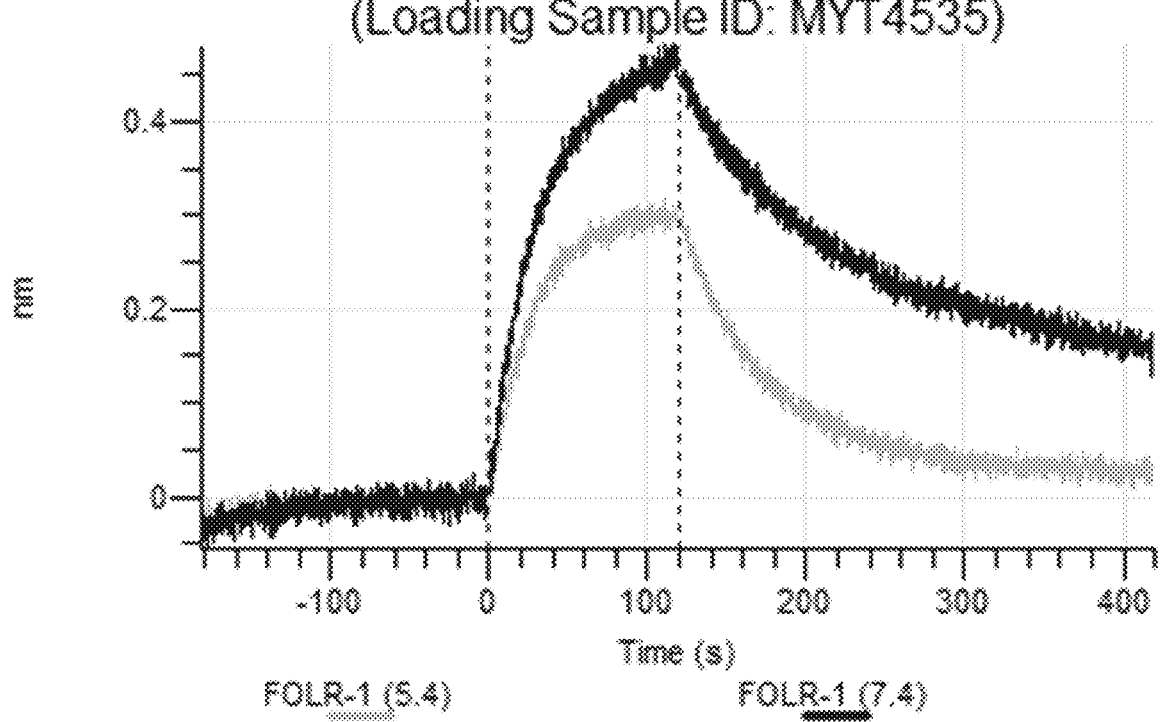
Figure 20Q:
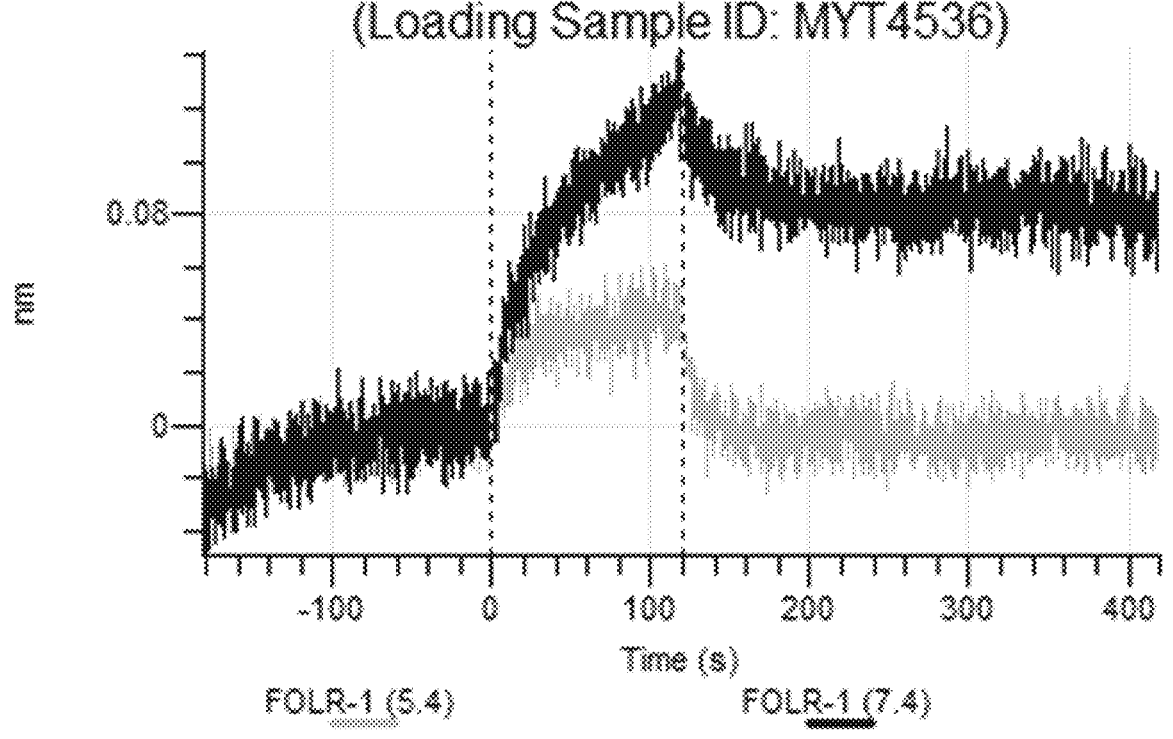
Figure 20R:
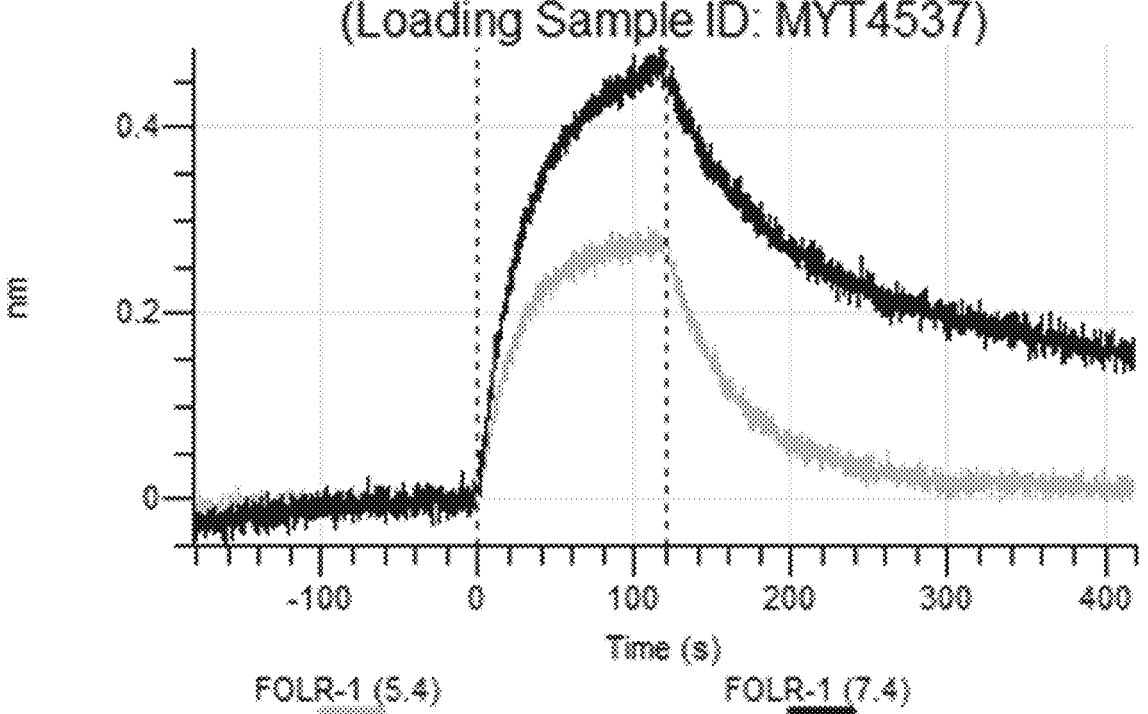
Figure 20S:
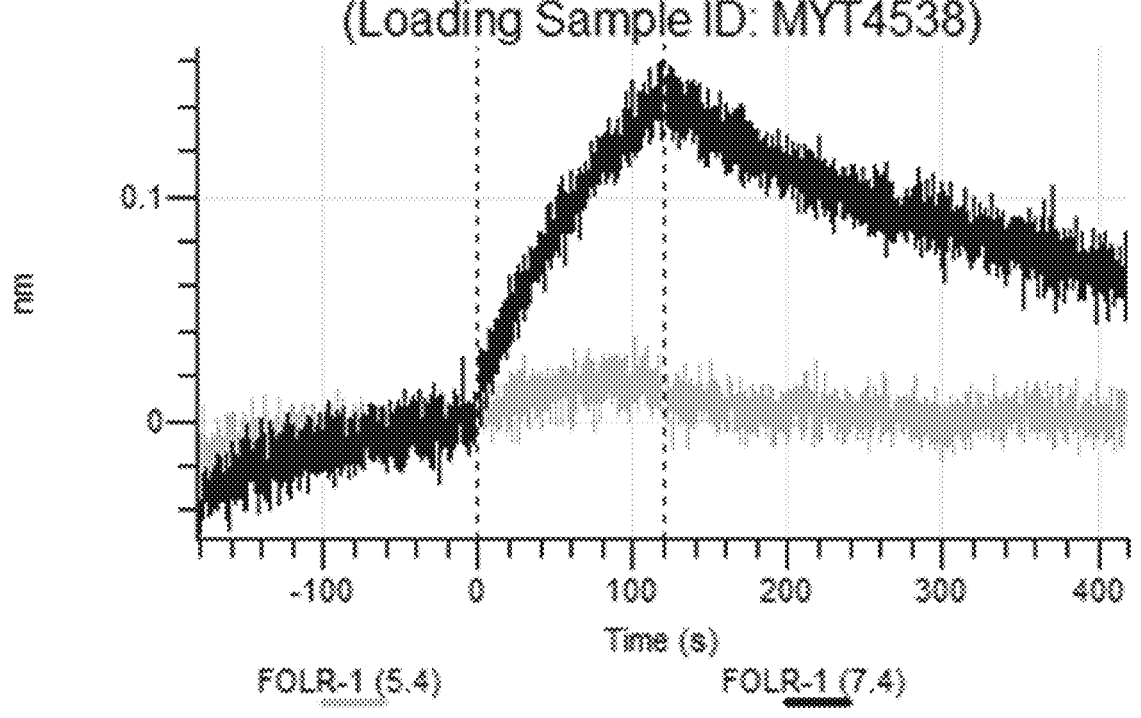
Figure 20T:
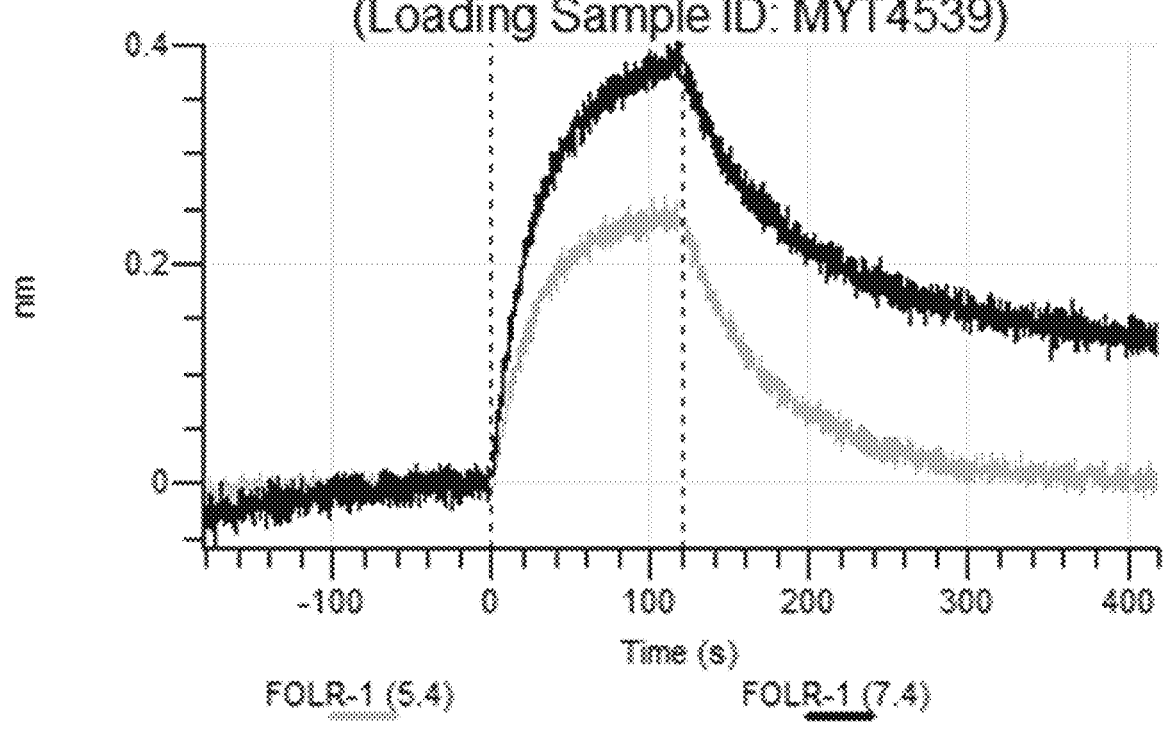
Figure 20U:
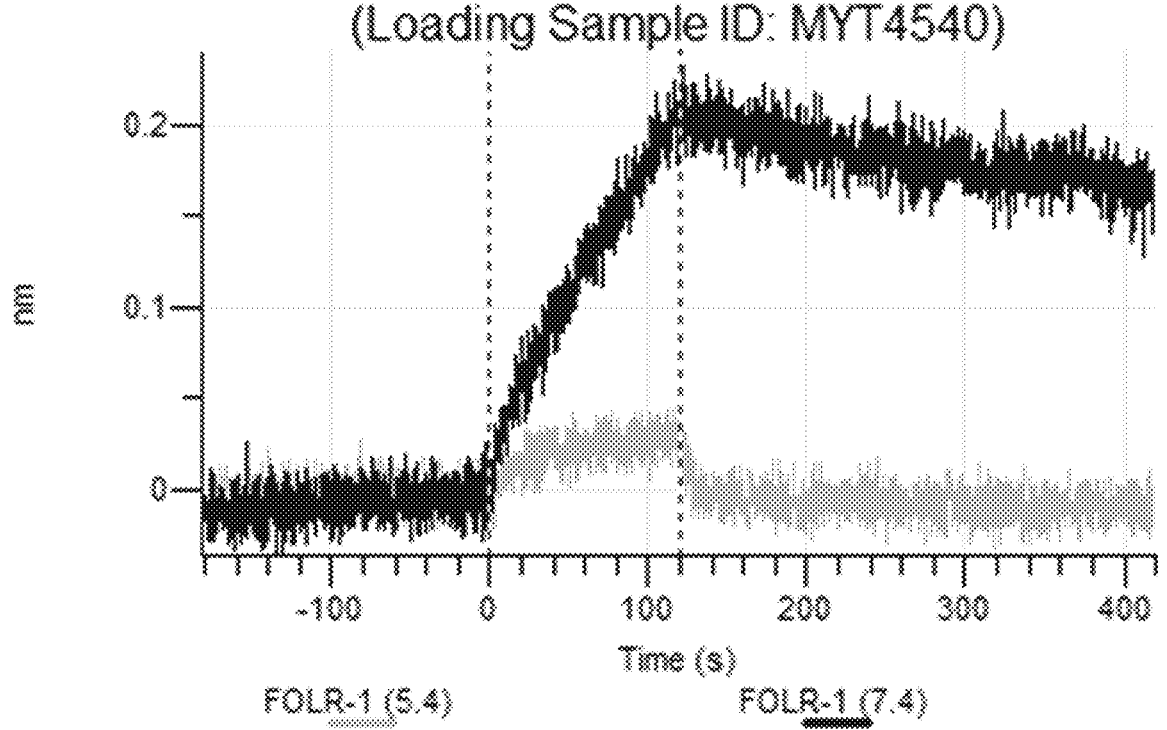
Figure 20V:
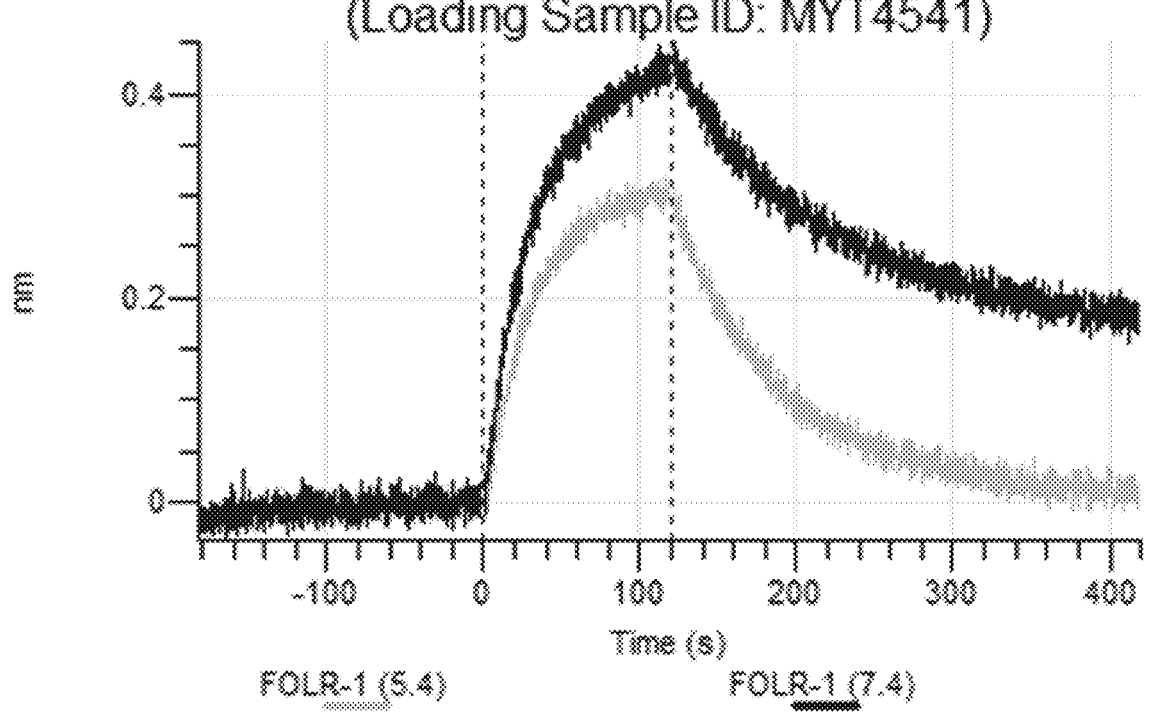
Figure 20W:
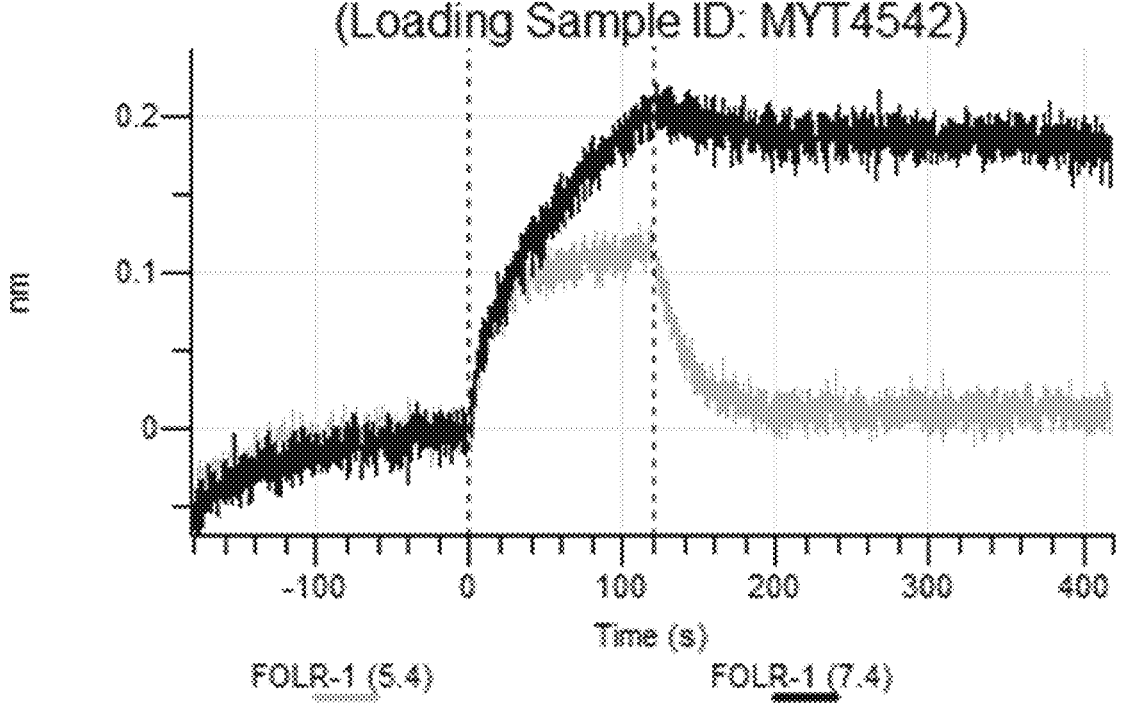
Figure 20X:
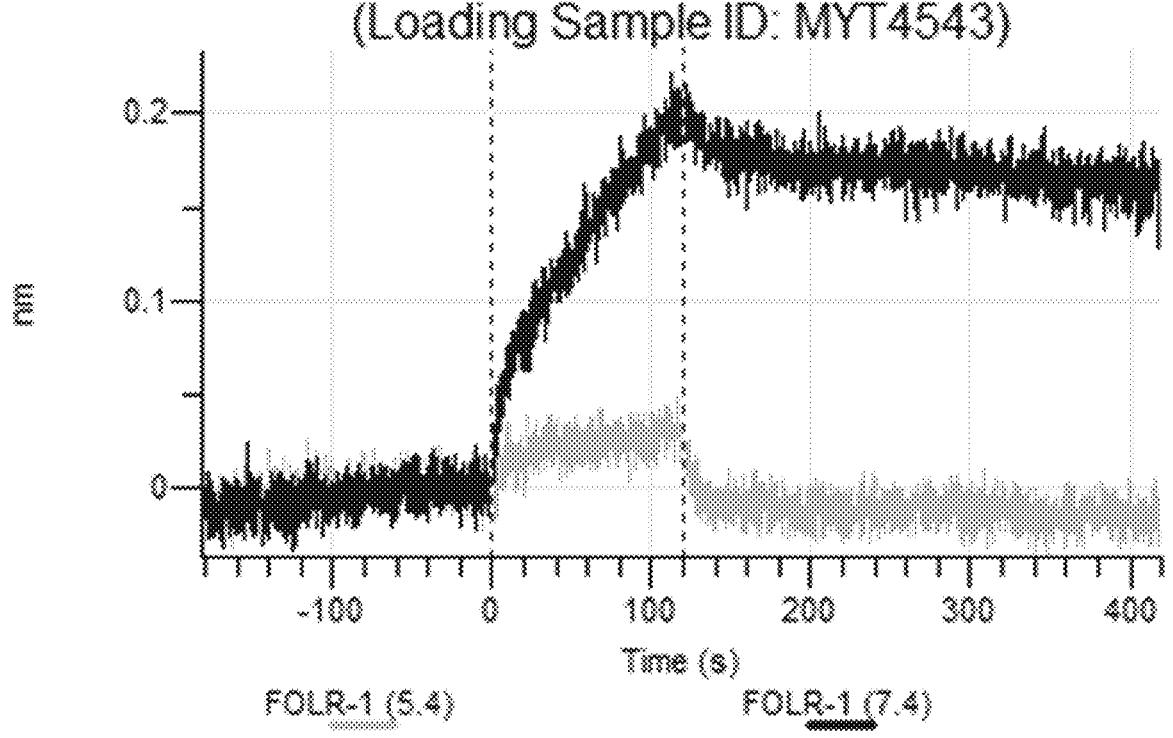
Figure 20Y:
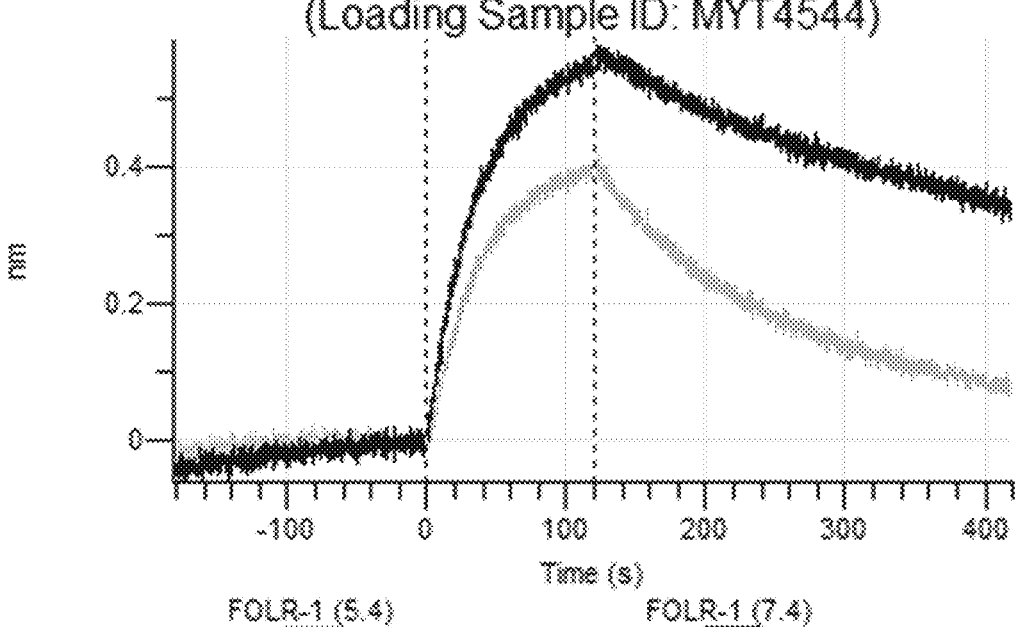
Figure 20Z:
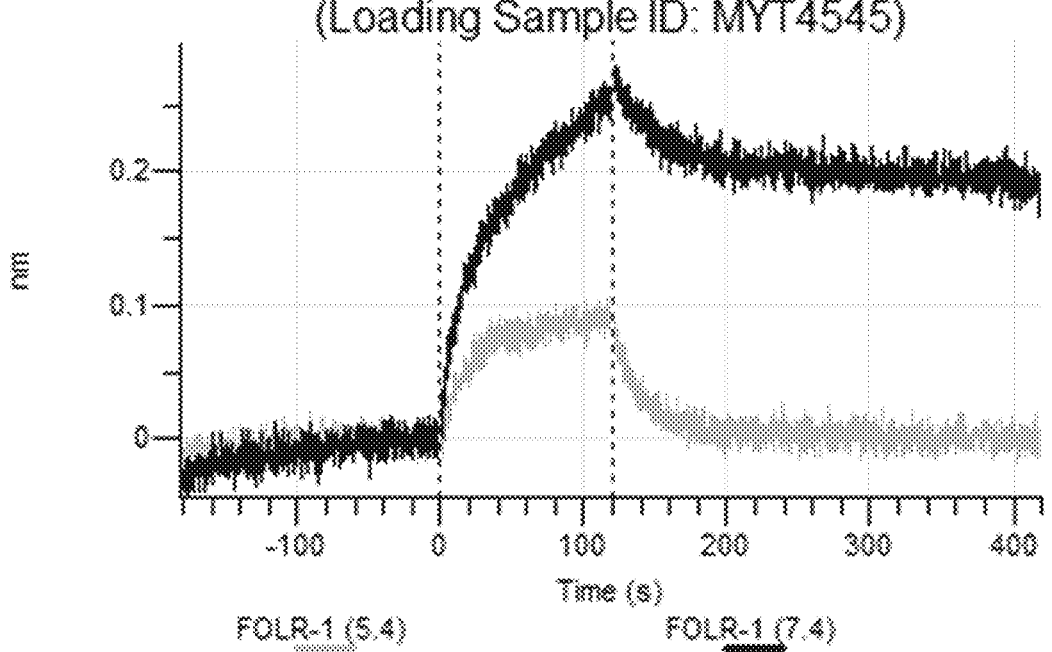
Figure 20A:
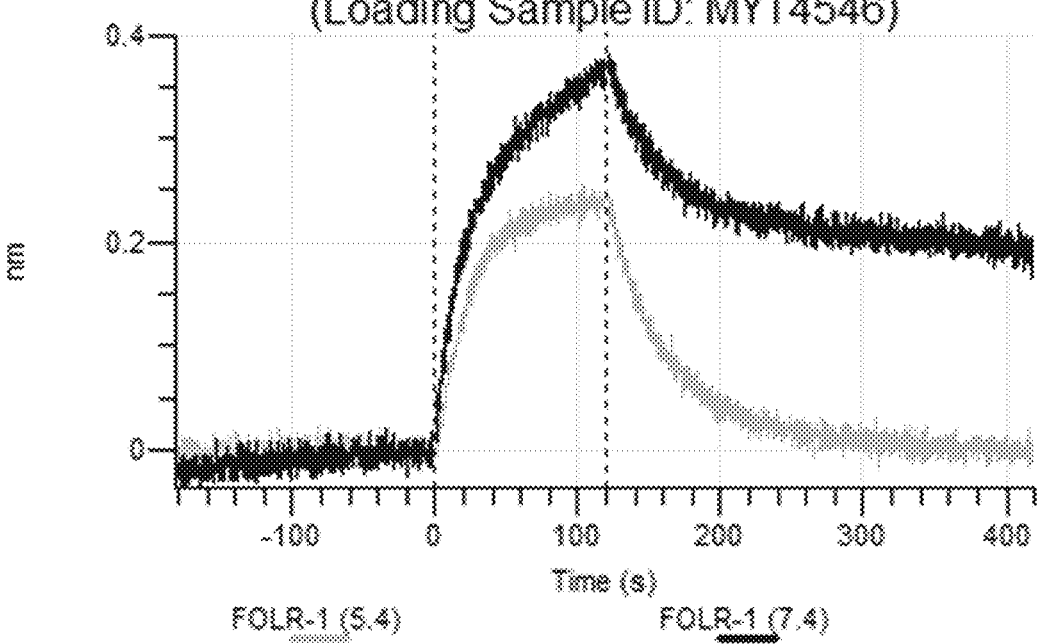

FIGS. 20a to 20aa: Binding of FARLETUZUMAB histidine scanning and alanine scanning variants to FOLR1 by biolayer interferometry. MYT4520-MYT4546, light chain histidine scanning and alanine scanning variants, were captured on anti-human Fc biosensors and associated with FOLR1 at low pH or high pH, as specified in the figures. FIG. 21: Construct identifier to SEQ ID NO correspondence table. Constructs, light chain histidine scanning and alanine scanning variants, are listed in the first column of the table, SEQ ID NOs are listed and correspond to constructs on the left and the appropriate heavy chain, light chain, and CDR categories along the top.

Figure 22:
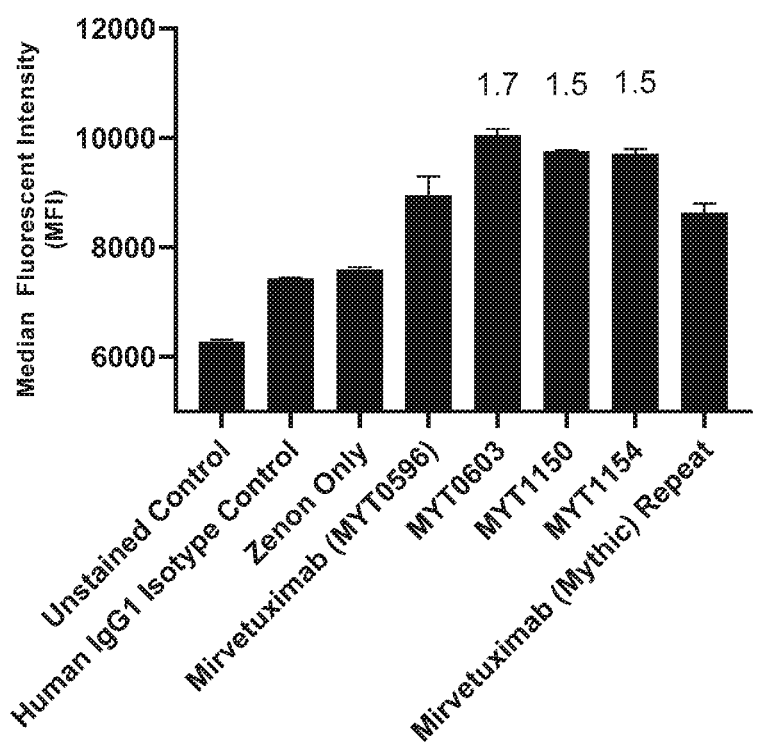

FIG. 22: Internalization of anti-FOLR1 mAbs in NIH: OVCAR-3 cells. Anti-FOLR1 pH engineered antibody variants, corresponding starting ABPC antibodies, control IgG1 isotype control (BP0297, Bioxcell), along with a vehicle control, as specified in FIG. 22 were assayed for internalization and endolysosomal delivery as measured by mean fluorescence intensity on NIH:OVCAR-3 cells at 24 hours. Error bars represent standard deviation. Numbers above the bars represent fold change over wild-type.

FIGS. 23a-23c: Characterization of binding affinity for anti-FOLR1 mAbs. Anti-FOLR1 mA bs were assayed for their binding to NIH:OVCAR-3 cells. FIG. 23a shows mirvetuximab with an IC50 of 0.250 nM, FIG. 23b shows MYT0603 with an IC50 of 0.650 nM, FIG. 23c shows MYT1154 with an IC50 of 0.396 nM.

FIG. 24: Melting temperature of select anti-FOLR1 mAbs. Mirvetuximab (MYT0596) and histidine and alanine scanning variants were assayed for their melting temperature by Differential Scanning Flourimetry (DSF), and the resulting Sypro Orange signal was plotted as its first derivative. Melting temperature (Tm) was calculated as the local maxima of this graph and listed in the table as shown. Constructs are listed in the first column of the table, Tm 1, and if applicable (for example, if the graph had two local maxima), Tm 2, are listed in the second and third columns, respectively.

DETAILED DESCRIPTION

Provided herein are antigen-binding protein constructs (ABPCs) that include: a first antigen-binding domain that is capable of specifically binding FOLR1 or an epitope of FOLR1 presented on the surface of a target mammalian cell, where: (a) the dissociation rate of the first antigen-binding domain at a pH of about 4.0 to about 6.5 is faster than the dissociation rate at a pH of about 7.0 to about 8.0; and/or (b) the dissociation constant (KD) of the first antigen-binding domain at a pH of about 4.0 to about 6.5 is greater than the KD at a pH of about 7.0 to about 8.0. In some examples of these ABPCs, the ABPC is degraded in the target mammalian cell following internalization of the ABPC by the target mammalian cell. Some examples of any of the ABPCs described herein can further include a conjugated toxin, radioisotope, drug, or small molecule (e.g., a fluorophore or dye).

Also provided are antigen-binding protein constructs (ABPCs) that include: a first antigen-binding domain that is capable of specifically binding FOLR1 or an epitope of FOLR1 presented on the surface of a target mammalian cell; and a conjugated toxin, radioisotope, drug, or small molecule, where: (a) the dissociation rate of the first antigen-binding domain at a pH of about 4.0 to about 6.5 is faster than the dissociation rate at a pH of about 7.0 to about 8.0; and/or the dissociation constant (KD) of the first antigen-binding domain at a pH of about 4.0 to about 6.5 is greater than the KD at a pH of about 7.0 to about 8.0; and (b) a composition including the ABPC provides for one or more (e.g., two or three) of: an increase (e.g., a detectable increase) in toxin liberation in the target mammalian cell as compared to a composition comprising the same amount of a control ABPC; an increase (e.g., a detectable increase) in target mammalian cell killing as compared to a composition comprising the same amount of a control ABPC; and an increase (e.g., a detectable increase) in endolysosomal delivery in the target mammalian cell as compared to a composition comprising the same, amount of a control ABPC.

In some examples of any of the ABPCs described herein, the first antigen-binding domain includes a heavy chain variable domain of mirvetuximab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a light chain variable domain of mirvetuximab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a heavy chain variable domain of mirvetuximab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine; and a light chain variable domain of mirvetuximab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the heavy chain variable domain of mirvetuximab comprises SEQ ID NO: 1. In some examples of any of the ABPCs described herein, the light chain variable domain of mirvetuximab comprises SEQ ID NO: 2.

In some examples of any of the ABPCs described herein, the first antigen-binding domain comprises a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) amino acid positions in SEQ ID NOs: 3-5 substituted with a histidine. In some examples of any of the ABPCs described herein, the first antigen-binding domain comprises a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) amino acid positions in SEQ ID NOs: 6-8 substituted with a histidine. In some examples of any of the ABPCs described herein, the first antigen-binding domain includes: a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) amino acid positions in SEQ ID NOs: 3-5 substituted with a histidine; and a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) amino acid positions in SEQ ID NOs: 6-8 substituted with a histidine.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107. In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 28, 30, 31, 32, 34, 35, 36, 55, 59, 93, 94, 95, 96, 97, 98, and 100. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107, and a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 28, 30, 31, 32, 34, 35, 36, 55, 59, 93, 94, 95, 96, 97, 98, and 100.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes an alanine at position 52 in SEQ ID NO: 1.

In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 1, where the heavy chain variable domain includes an alanine at position 52 in SEQ ID NO: 1, and a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 28, 30, 31, 32, 34, 35, 36, 38, 55, 59, 93, 94, 95, 96, 97, 98, and 100.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107, and where the heavy chain variable domain includes an alanine at position 52 in SEQ ID NO: 1. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107, and where the heavy chain variable domain includes an alanine at position 52 in SEQ ID NO: 100, and a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 28, 30, 31, 32, 34, 35, 36, 55, 59, 93, 94, 95, 96, 97, 98, and 100.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1 and where the heavy chain variable domain includes an alanine at position 52 of SEQ ID NO: 1.

TABLE 1

Exemplary Combinations of Amino Acid Positions in
SEQ ID NO: 1 that can be Substituted with Histidine 24 + 27, 24 + 29, 24 + 31, 24 + 32, 24 + 33, 24 + 34, 24 + 50, 24 + 54, 24 + 55, 24 + 57, 24 + 58, 24 + 59, 24 + 60, 24 + 97, 24 + 98, 24 + 99, 24 + 100, 24 + 102, 24 + 103, 24 + 105, 24 + 107, 27 + 29, 27 + 31, 27 + 32, 27 + 33, 27 + 34, 27 + 50, 27 + 54, 27 + 55, 27 + 57, 27 + 58, 27 + 59, 27 + 60, 27 + 97, 27 + 98, 27 + 99, 27 + 100, 27 + 102, 27 + 103, 27 + 105, 27 + 107, 29 + 31, 29 + 32, 29 + 33, 29 + 34, 29 + 50, 29 + 54, 29 + 55, 29 + 57, 29 + 58, 29 + 59, 29 + 60, 29 + 97, 29 + 98, 29 + 99, 29 + 100, 29 + 102, 29 + 103, 29 + 105, 29 + 107, 31 + 32, 31 + 33, 31 + 34, 31 + 50, 31 + 54, 31 + 55, 31 + 57, 31 + 58, 31 + 59, 31 + 60, 31 + 97, 31 + 98, 31 + 99, 31 + 100, 31 + 102, 31 + 103, 31 + 105, 31 + 107, 32 + 33, 32 + 34, 32 + 50, 32 + 54, 32 + 55, 32 + 57, 32 + 58, 32 + 59, 32 + 60, 32 + 97, 32 + 98, 32 + 99, 32 + 100, 32 + 102, 32 + 103, 32 + 105, 32 + 107, 33 + 34, 33 + 50, 33 + 54, 33 + 55, 33 + 57, 33 + 58, 33 + 59, 33 + 60, 33 + 97, 33 + 98, 33 + 99, 33 + 100, 33 + 102, 33 + 103, 33 + 105, 33 + 107, 34 + 50, 34 + 54, 34 + 55, 34 + 57, 34 + 58, 34 + 59, 34 + 60, 34 + 97, 34 + 98, 34 + 99, 34 + 100, 34 + 102, 34 + 103, 34 + 105, 34 + 107, 50 + 54, 50 + 55, 50 + 57, 50 + 58, 50 + 59, 50 + 60, 50 + 97, 50 + 98, 50 + 99, 50 + 100, 50 + 102, 50 + 103, 50 + 105, 50 + 107, 54 + 55, 54 + 57, 54 + 58, 54 + 59, 54 + 60, 54 + 97, 54 + 98, 54 + 99, 54 + 100, 54 + 102, 54 + 103, 54 + 105, 54 + 107, 55 + 57, 55 + 58, 55 + 59, 55 + 60, 55 + 97, 55 + 98, 55 + 99, 55 + 100, 55 + 102, 55 + 103, 55 + 105, 55 + 107, 57 + 58, 57 + 59, 57 + 60, 57 + 97, 57 + 98, 57 + 99, 57 + 100, 57 + 102, 57 + 103, 57 + 105, 57 + 107, 58 + 59, 58 + 60, 58 + 97, 58 + 98, 58 + 99, 58 + 100, 58 + 102, 58 + 103, 58 + 105, 58 + 107, 59 + 60, 59 + 97, 59 + 98, 59 + 99, 59 + 100, 59 + 102, 59 + 103, 59 + 105, 59 + 107, 60 + 97, 60 + 98, 60 + 99, 60 + 100, 60 + 102, 60 + 103, 60 + 105, 60 + 107, 97 + 98, 97 + 99, 97 + 100, 97 + 102, 97 + 103, 97 + 105, 97 + 107, 98 + 99, 98 + 100, 98 + 102, 98 + 103, 98 + 105, 98 + 107, 99 + 100, 99 + 102, 99 + 103, 99 + 105, 99 + 107, 100 + 102, 100 + 103, 100 + 105, 100 + 107, 102 + 103, 102 + 105, 102 + 107, 103 + 105, 103 + 107, 105 + 107, 24 + 27 + 29, 24 + 27 + 31, 24 + 27 + 32, 24 + 27 + 33, 24 + 27 + 34, 24 + 27 + 50, 24 + 27 + 54, 24 + 27 + 55, 24 + 27 + 57, 24 + 27 + 58, 24 + 27 + 59, 24 + 27 + 60, 24 + 27 + 97, 24 + 27 + 98, 24 + 27 + 99, 24 + 27 + 100, 24 + 27 + 102, 24 + 27 + 103, 24 + 27 + 105, 24 + 27 + 107, 24 + 29 + 31, 24 + 29 + 32, 24 + 29 + 33, 24 + 29 + 34, 24 + 29 + 50, 24 + 29 + 54, 24 + 29 + 55, 24 + 29 + 57, 24 + 29 + 58, 24 + 29 + 59, 24 + 29 + 60, 24 + 29 + 97, 24 + 29 + 98, 24 + 29 + 99, 24 + 29 + 100, 24 + 29 + 102, 24 + 29 + 103, 24 + 29 + 105, 24 + 29 + 107, 24 + 31 + 32, 24 + 31 + 33, 24 + 31 + 34, 24 + 31 + 50, 24 + 31 + 54, 24 + 31 + 55, 24 + 31 + 57, 24 + 31 + 58, 24 + 31 + 59, 24 + 31 + 60, 24 + 31 + 97, 24 + 31 + 98, 24 + 31 + 99, 24 + 31 + 100, 24 + 31 + 102, 24 + 31 + 103, 24 + 31 + 105, 24 + 31 + 107, 24 + 32 + 33, 24 + 32 + 34, 24 + 32 + 50, 24 + 32 + 54, 24 + 32 + 55, 24 + 32 + 57, 24 + 32 + 58, 24 + 32 + 59, 24 + 32 + 60, 24 + 32 + 97, 24 + 32 + 98, 24 + 32 + 99, 24 + 32 + 100, 24 + 32 + 102, 24 + 32 + 103, 24 + 32 + 105, 24 + 32 + 107, 24 + 33 + 34, 24 + 33 + 50, 24 + 33 + 54, 24 + 33 + 55, 24 + 33 + 57, 24 + 33 + 58, 24 + 33 + 59, 24 + 33 + 60, 24 + 33 + 97, 24 + 33 + 98, 24 + 33 + 99, 24 + 33 + 100, 24 + 33 + 102, 24 + 33 + 103, 24 + 33 + 105, 24 + 33 + 107, 24 + 34 + 50, 24 + 34 + 54, 24 + 34 + 55, 24 + 34 + 57, 24 + 34 + 58, 24 + 34 + 59, 24 + 34 + 60, 24 + 34 + 97, 24 + 34 + 98, 24 + 34 + 99, 24 + 34 + 100, 24 + 34 + 102, 24 + 34 + 103, 24 + 34 + 105, 24 + 34 + 107, 24 + 50 + 54, 24 + 50 + 55, 24 + 50 + 57, 24 + 50 + 58, 24 + 50 + 59, 24 + 50 + 60, 24 + 50 + 97, 24 + 50 + 98, 24 + 50 + 99, 24 + 50 + 100, 24 + 50 + 102, 24 + 50 + 103, 24 + 50 + 105, 24 + 50 + 107, 24 + 54 + 55, 24 + 54 + 57, 24 + 54 + 58, 24 + 54 + 59, 24 + 54 + 60, 24 + 54 + 97, 24 + 54 + 98, 24 + 54 + 99, 24 + 54 + 100, 24 + 54 + 102, 24 + 54 + 103, 24 + 54 + 105, 24 + 54 + 107, 24 + 55 + 57, 24 + 55 + 58, 24 + 55 + 59, 24 + 55 + 60, 24 + 55 + 97, 24 + 55 + 98, 24 + 55 + 99, 24 + 55 + 100, 24 + 55 + 102, 24 + 55 + 103, 24 + 55 + 105, 24 + 55 + 107, 24 + 57 + 58, 24 + 57 + 59, 24 + 57 + 60, 24 + 57 + 97, 24 + 57 + 98, 24 + 57 + 99, 24 + 57 + 100, 24 + 57 + 102, 24 + 57 + 103, 24 + 57 + 105, 24 + 57 + 107, 24 + 58 + 59, 24 + 58 + 60, 24 + 58 + 97, 24 + 58 + 98, 24 + 58 + 99, 24 + 58 + 100, 24 + 58 + 102, 24 + 58 + 103, 24 + 58 + 105, 24 + 58 + 107, 24 + 59 + 60, 24 + 59 + 97, 24 + 59 + 98, 24 + 59 + 99, 24 + 59 + 100, 24 + 59 + 102, 24 + 59 + 103, 24 + 59 + 105, 24 + 59 + 107, 24 + 60 + 97, 24 + 60 + 98, 24 + 60 + 99, 24 + 60 + 100, 24 + 60 + 102, 24 + 60 + 103, 24 + 60 + 105, 24 + 60 + 107, 24 + 97 + 98, 24 + 97 + 99, 24 + 97 + 100, 24 + 97 + 102, 24 + 97 + 103, 24 + 97 + 105, 24 + 97 + 107, 24 + 98 + 99, 24 + 98 + 100, 24 + 98 + 102, 24 + 98 + 103, 24 + 98 + 105, 24 + 98 + 107, 24 + 99 + 100, 24 + 99 + 102, 24 + 99 + 103, 24 + 99 + 105, 24 + 99 + 107, 24 + 100 + 102, 24 + 100 + 103, 24 + 100 + 105, 24 + 100 + 107, 24 + 102 + 103, 24 + 102 + 105, 24 + 102 + 107, 24 + 103 + 105, 24 + 103 + 107, 24 + 105 + 107, 27 + 29 + 31, 27 + 29 + 32, 27 + 29 + 33, 27 + 29 + 34, 27 + 29 + 50, 27 + 29 + 54, 27 + 29 + 55, 27 + 29 + 57, 27 + 29 + 58, 27 + 29 + 59, 27 + 29 + 60, 27 + 29 + 97, 27 + 29 + 98, 27 + 29 + 99, 27 + 29 + 100, 27 + 29 + 102, 27 + 29 + 103, 27 + 29 + 105, 27 + 29 + 107, 27 + 31 + 32, 27 + 31 + 33, 27 + 31 + 34, 27 + 31 + 50, 27 + 31 + 54, 27 + 31 + 55, 27 + 31 + 57, 27 + 31 + 58, 27 + 31 + 59, 27 + 31 + 60, 27 + 31 + 97, 27 + 31 + 98, 27 + 31 + 99, 27 + 31 + 100, 27 + 31 + 102, 27 + 31 + 103, 27 + 31 + 105, 27 + 31 + 107, 27 + 32 + 33, 27 + 32 + 34, 27 + 32 + 50, 27 + 32 + 54, 27 + 32 + 55, 27 + 32 + 57, 27 + 32 + 58, 27 + 32 + 59, 27 + 32 + 60, 27 + 32 + 97, 27 + 32 + 98, 27 + 32 + 99, 27 + 32 + 100, 27 + 32 + 102, 27 + 32 + 103, 27 + 32 + 105, 27 + 32 + 107, 27 + 33 + 34, 27 + 33 + 50, 27 + 33 + 54, 27 + 33 + 55, 27 + 33 + 57, 27 + 33 + 58, 27 + 33 + 59, 27 + 33 + 60, 27 + 33 + 97, 27 + 33 + 98, 27 + 33 + 99, 27 + 33 + 100, 27 + 33 + 102, 27 + 33 + 103, 27 + 33 + 105, 27 + 33 + 107, 27 + 34 + 50, 27 + 34 + 54, 27 + 34 + 55, 27 + 34 + 57, 27 + 34 + 58, 27 + 34 + 59, 27 + 34 + 60, 27 + 34 + 97, 27 + 34 + 98, 27 + 34 + 99, 27 + 34 + 100, 27 + 34 + 102, 27 + 34 + 103, 27 + 34 + 105, 27 + 34 + 107, 27 + 50 + 54, 27 + 50 + 55, 27 + 50 + 57, 27 + 50 + 58, 27 + 50 + 59, 27 + 50 + 60, 27 + 50 + 97, 27 + 50 + 98, 27 + 50 + 99, 27 + 50 + 100, 27 + 50 + 102, 27 + 50 + 103, 27 + 50 + 105, 27 + 50 + 107, 27 + 54 + 55, 27 + 54 + 57, 27 + 54 + 58, 27 + 54 + 59, 27 + 54 + 60, 27 + 54 + 97, 27 + 54 + 98, 27 + 54 + 99, 27 + 54 + 100, 27 + 54 + 102, 27 + 54 + 103, 27 + 54 + 105, 27 + 54 + 107, 27 + 55 + 57,

TABLE 1-continued

Exemplary Combinations of Amino Acid Positions in
SEQ ID NO: 1 that can be Substituted with Histidine 27 + 55 + 58, 27 + 55 + 59, 27 + 55 + 60, 27 + 55 + 97, 27 + 55 + 98, 27 + 55 + 99, 27 + 55 +
100, 27 + 55 + 102, 27 + 55 + 103, 27 + 55 + 105, 27 + 55 + 107, 27 + 57 + 58, 27 + 57 + 59,
27 + 57 + 60, 27 + 57 + 97, 27 + 57 + 98, 27 + 57 + 99, 27 + 57 + 100, 27 + 57 + 102, 27 +
57 + 103, 27 + 57 + 105, 27 + 57 + 107, 27 + 58 + 59, 27 + 58 + 60, 27 + 58 + 97, 27 + 58 +
98, 27 + 58 + 99, 27 + 58 + 100, 27 + 58 + 102, 27 + 58 + 103, 27 + 58 + 105, 27 + 58 + 107,
27 + 59 + 60, 27 + 59 + 97, 27 + 59 + 98, 27 + 59 + 99, 27 + 59 + 100, 27 + 59 + 102, 27 +
59 + 103, 27 + 59 + 105, 27 + 59 + 107, 27 + 60 + 97, 27 + 60 + 98, 27 + 60 + 99, 27 + 60 +
100, 27 + 60 + 102, 27 + 60 + 103, 27 + 60 + 105, 27 + 60 + 107, 27 + 97 + 98, 27 + 97 + 99,
27 + 97 + 100, 27 + 97 + 102, 27 + 97 + 103, 27 + 97 + 105, 27 + 97 + 107, 27 + 98 + 99, 27 +
98 + 100, 27 + 98 + 102, 27 + 98 + 103, 27 + 98 + 105, 27 + 98 + 107, 27 + 99 + 100, 27 +
99 + 102, 27 + 99 + 103, 27 + 99 + 105, 27 + 99 + 107, 27 + 100 + 102, 27 + 100 + 103, 27 +
100 + 105, 27 + 100 + 107, 27 + 102 + 103, 27 + 102 + 105, 27 + 102 + 107, 27 + 103 + 105,
27 + 103 + 107, 27 + 105 + 107, 29 + 31 + 32, 29 + 31 + 33, 29 + 31 + 34, 29 + 31 + 50, 29 +
31 + 54, 29 + 31 + 55, 29 + 31 + 57, 29 + 31 + 58, 29 + 31 + 59, 29 + 31 + 60, 29 + 31 + 97,
29 + 31 + 98, 29 + 31 + 99, 29 + 31 + 100, 29 + 31 + 102, 29 + 31 + 103, 29 + 31 + 105, 29 +
31 + 107, 29 + 32 + 33, 29 + 32 + 34, 29 + 32 + 50, 29 + 32 + 54, 29 + 32 + 55, 29 + 32 + 57,
29 + 32 + 58, 29 + 32 + 59, 29 + 32 + 60, 29 + 32 + 97, 29 + 32 + 98, 29 + 32 + 99, 29 + 32 +
100, 29 + 32 + 102, 29 + 32 + 103, 29 + 32 + 105, 29 + 32 + 107, 29 + 33 + 34, 29 + 33 + 50,
29 + 33 + 54, 29 + 33 + 55, 29 + 33 + 57, 29 + 33 + 58, 29 + 33 + 59, 29 + 33 + 60, 29 + 33 +
97, 29 + 33 + 98, 29 + 33 + 99, 29 + 33 + 100, 29 + 33 + 102, 29 + 33 + 103, 29 + 33 + 105,
29 + 33 + 107, 29 + 34 + 50, 29 + 34 + 54, 29 + 34 + 55, 29 + 34 + 57, 29 + 34 + 58, 29 + 34 +
59, 29 + 34 + 60, 29 + 34 + 97, 29 + 34 + 98, 29 + 34 + 99, 29 + 34 + 100, 29 + 34 + 102,
29 + 34 + 103, 29 + 34 + 105, 29 + 34 + 107, 29 + 50 + 54, 29 + 50 + 55, 29 + 50 + 57, 29 +
50 + 58, 29 + 50 + 59, 29 + 50 + 60, 29 + 50 + 97, 29 + 50 + 98, 29 + 50 + 99, 29 + 50 + 100,
29 + 50 + 102, 29 + 50 + 103, 29 + 50 + 105, 29 + 50 + 107, 29 + 54 + 55, 29 + 54 + 57, 29 +
54 + 58, 29 + 54 + 59, 29 + 54 + 60, 29 + 54 + 97, 29 + 54 + 98, 29 + 54 + 99, 29 + 54 + 100,
29 + 54 + 102, 29 + 54 + 103, 29 + 54 + 105, 29 + 54 + 107, 29 + 55 + 57, 29 + 55 + 58, 29 +
55 + 59, 29 + 55 + 60, 29 + 55 + 97, 29 + 55 + 98, 29 + 55 + 99, 29 + 55 + 100, 29 + 55 +
102, 29 + 55 + 103, 29 + 55 + 105, 29 + 55 + 107, 29 + 57 + 58, 29 + 57 + 59, 29 + 57 + 60,
29 + 57 + 97, 29 + 57 + 98, 29 + 57 + 99, 29 + 57 + 100, 29 + 57 + 102, 29 + 57 + 103, 29 +
57 + 105, 29 + 57 + 107, 29 + 58 + 59, 29 + 58 + 60, 29 + 58 + 97, 29 + 58 + 98, 29 + 58 +
99, 29 + 58 + 100, 29 + 58 + 102, 29 + 58 + 103, 29 + 58 + 105, 29 + 58 + 107, 29 + 59 + 60,
29 + 59 + 97, 29 + 59 + 98, 29 + 59 + 99, 29 + 59 + 100, 29 + 59 + 102, 29 + 59 + 103, 29 +
59 + 105, 29 + 59 + 107, 29 + 60 + 97, 29 + 60 + 98, 29 + 60 + 99, 29 + 60 + 100, 29 + 60 +
102, 29 + 60 + 103, 29 + 60 + 105, 29 + 60 + 107, 29 + 97 + 98, 29 + 97 + 99, 29 + 97 + 100,
29 + 97 + 102, 29 + 97 + 103, 29 + 97 + 105, 29 + 97 + 107, 29 + 98 + 99, 29 + 98 + 100, 29 +
98 + 102, 29 + 98 + 103, 29 + 98 + 105, 29 + 98 + 107, 29 + 99 + 100, 29 + 99 + 102, 29 +
99 + 103, 29 + 99 + 105, 29 + 99 + 107, 29 + 100 + 102, 29 + 100 + 103, 29 + 100 + 105, 29 +
100 + 107, 29 + 102 + 103, 29 + 102 + 105, 29 + 102 + 107, 29 + 103 + 105, 29 + 103 +
107, 29 + 105 + 107, 31 + 32 + 33, 31 + 32 + 34, 31 + 32 + 50, 31 + 32 + 54, 31 + 32 + 55,
31 + 32 + 57, 31 + 32 + 58, 31 + 32 + 59, 31 + 32 + 60, 31 + 32 + 97, 31 + 32 + 98, 31 + 32 +
99, 31 + 32 + 100, 31 + 32 + 102, 31 + 32 + 103, 31 + 32 + 105, 31 + 32 + 107, 31 + 33 + 34,
31 + 33 + 50, 31 + 33 + 54, 31 + 33 + 55, 31 + 33 + 57, 31 + 33 + 58, 31 + 33 + 59, 31 + 33 +
60, 31 + 33 + 97, 31 + 33 + 98, 31 + 33 + 99, 31 + 33 + 100, 31 + 33 + 102, 31 + 33 + 103,
31 + 33 + 105, 31 + 33 + 107, 31 + 34 + 50, 31 + 34 + 54, 31 + 34 + 55, 31 + 34 + 57, 31 +
34 + 58, 31 + 34 + 59, 31 + 34 + 60, 31 + 34 + 97, 31 + 34 + 98, 31 + 34 + 99, 31 + 34 + 100,
31 + 34 + 102, 31 + 34 + 103, 31 + 34 + 105, 31 + 34 + 107, 31 + 50 + 54, 31 + 50 + 55, 31 +
50 + 57, 31 + 50 + 58, 31 + 50 + 59, 31 + 50 + 60, 31 + 50 + 97, 31 + 50 + 98, 31 + 50 + 99,
31 + 50 + 100, 31 + 50 + 102, 31 + 50 + 103, 31 + 50 + 105, 31 + 50 + 107, 31 + 54 + 55, 31 +
54 + 57, 31 + 54 + 58, 31 + 54 + 59, 31 + 54 + 60, 31 + 54 + 97, 31 + 54 + 98, 31 + 54 +
99, 31 + 54 + 100, 31 + 54 + 102, 31 + 54 + 103, 31 + 54 + 105, 31 + 54 + 107, 31 + 55 + 57,
31 + 55 + 58, 31 + 55 + 59, 31 + 55 + 60, 31 + 55 + 97, 31 + 55 + 98, 31 + 55 + 99, 31 + 55 +
100, 31 + 55 + 102, 31 + 55 + 103, 31 + 55 + 105, 31 + 55 + 107, 31 + 57 + 58, 31 + 57 + 59,
31 + 57 + 60, 31 + 57 + 97, 31 + 57 + 98, 31 + 57 + 99, 31 + 57 + 100, 31 + 57 + 102, 31 +
57 + 103, 31 + 57 + 105, 31 + 57 + 107, 31 + 58 + 59, 31 + 58 + 60, 31 + 58 + 97, 31 + 58 +
98, 31 + 58 + 99, 31 + 58 + 100, 31 + 58 + 102, 31 + 58 + 103, 31 + 58 + 105, 31 + 58 + 107,
31 + 59 + 60, 31 + 59 + 97, 31 + 59 + 98, 31 + 59 + 99, 31 + 59 + 100, 31 + 59 + 102, 31 +
59 + 103, 31 + 59 + 105, 31 + 59 + 107, 31 + 60 + 97, 31 + 60 + 98, 31 + 60 + 99, 31 + 60 +
100, 31 + 60 + 102, 31 + 60 + 103, 31 + 60 + 105, 31 + 60 + 107, 31 + 97 + 98, 31 + 97 + 99,
31 + 97 + 100, 31 + 97 + 102, 31 + 97 + 103, 31 + 97 + 105, 31 + 97 + 107, 31 + 98 + 99, 31 +
98 + 100, 31 + 98 + 102, 31 + 98 + 103, 31 + 98 + 105, 31 + 98 + 107, 31 + 99 + 100, 31 +
99 + 102, 31 + 99 + 103, 31 + 99 + 105, 31 + 99 + 107, 31 + 100 + 102, 31 + 100 + 103, 31 +
100 + 105, 31 + 100 + 107, 31 + 102 + 103, 31 + 102 + 105, 31 + 102 + 107, 31 + 103 + 105,
31 + 103 + 107, 31 + 105 + 107, 32 + 33 + 34, 32 + 33 + 50, 32 + 33 + 54, 32 + 33 + 55, 32 +
33 + 57, 32 + 33 + 58, 32 + 33 + 59, 32 + 33 + 60, 32 + 33 + 97, 32 + 33 + 98, 32 + 33 + 99,
32 + 33 + 100, 32 + 33 + 102, 32 + 33 + 103, 32 + 33 + 105, 32 + 33 + 107, 32 + 34 + 50, 32 +
34 + 54, 32 + 34 + 55, 32 + 34 + 57, 32 + 34 + 58, 32 + 34 + 59, 32 + 34 + 60, 32 + 34 +
97, 32 + 34 + 98, 32 + 34 + 99, 32 + 34 + 100, 32 + 34 + 102, 32 + 34 + 103, 32 + 34 + 105,
32 + 34 + 107, 32 + 50 + 54, 32 + 50 + 55, 32 + 50 + 57, 32 + 50 + 58, 32 + 50 + 59, 32 + 50 +
60, 32 + 50 + 97, 32 + 50 + 98, 32 + 50 + 99, 32 + 50 + 100, 32 + 50 + 102, 32 + 50 + 103,
32 + 50 + 105, 32 + 50 + 107, 32 + 54 + 55, 32 + 54 + 57, 32 + 54 + 58, 32 + 54 + 59, 32 +
54 + 60, 32 + 54 + 97, 32 + 54 + 98, 32 + 54 + 99, 32 + 54 + 100, 32 + 54 + 102, 32 + 54 +
103, 32 + 54 + 105, 32 + 54 + 107, 32 + 55 + 57, 32 + 55 + 58, 32 + 55 + 59, 32 + 55 + 60,
32 + 55 + 97, 32 + 55 + 98, 32 + 55 + 99, 32 + 55 + 100, 32 + 55 + 102, 32 + 55 + 103, 32 +
55 + 105, 32 + 55 + 107, 32 + 57 + 58, 32 + 57 + 59, 32 + 57 + 60, 32 + 57 + 97, 32 + 57 +
98, 32 + 57 + 99, 32 + 57 + 100, 32 + 57 + 102, 32 + 57 + 103, 32 + 57 + 105, 32 + 57 + 107,
32 + 58 + 59, 32 + 58 + 60, 32 + 58 + 97, 32 + 58 + 98, 32 + 58 + 99, 32 + 58 + 100, 32 + 58 +

TABLE 1-continued

Exemplary Combinations of Amino Acid Positions in
SEQ ID NO: 1 that can be Substituted with Histidine 102, 32 + 58 + 103, 32 + 58 + 105, 32 + 58 + 107, 32 + 59 + 60, 32 + 59 + 97, 32 + 59 +
98, 32 + 59 + 99, 32 + 59 + 100, 32 + 59 + 102, 32 + 59 + 103, 32 + 59 + 105, 32 + 59 + 107,
32 + 60 + 97, 32 + 60 + 98, 32 + 60 + 99, 32 + 60 + 100, 32 + 60 + 102, 32 + 60 + 103, 32 +
60 + 105, 32 + 60 + 107, 32 + 97 + 98, 32 + 97 + 99, 32 + 97 + 100, 32 + 97 + 102, 32 + 97 +
103, 32 + 97 + 105, 32 + 97 + 107, 32 + 98 + 99, 32 + 98 + 100, 32 + 98 + 102, 32 + 98 +
103, 32 + 98 + 105, 32 + 98 + 107, 32 + 99 + 100, 32 + 99 + 102, 32 + 99 + 103, 32 + 99 +
105, 32 + 99 + 107, 32 + 100 + 102, 32 + 100 + 103, 32 + 100 + 105, 32 + 100 + 107, 32 +
102 + 103, 32 + 102 + 105, 32 + 102 + 107, 32 + 103 + 105, 32 + 103 + 107, 32 + 105 + 107,
33 + 34 + 50, 33 + 34 + 54, 33 + 34 + 55, 33 + 34 + 57, 33 + 34 + 58, 33 + 34 + 59, 33 + 34 +
60, 33 + 34 + 97, 33 + 34 + 98, 33 + 34 + 99, 33 + 34 + 100, 33 + 34 + 102, 33 + 34 + 103,
33 + 34 + 105, 33 + 34 + 107, 33 + 50 + 54, 33 + 50 + 55, 33 + 50 + 57, 33 + 50 + 58, 33 +
50 + 59, 33 + 50 + 60, 33 + 50 + 97, 33 + 50 + 98, 33 + 50 + 99, 33 + 50 + 100, 33 + 50 +
102, 33 + 50 + 103, 33 + 50 + 105, 33 + 50 + 107, 33 + 54 + 55, 33 + 54 + 57, 33 + 54 + 58,
33 + 54 + 59, 33 + 54 + 60, 33 + 54 + 97, 33 + 54 + 98, 33 + 54 + 99, 33 + 54 + 100, 33 + 54 +
102, 33 + 54 + 103, 33 + 54 + 105, 33 + 54 + 107, 33 + 55 + 57, 33 + 55 + 58, 33 + 55 +
59, 33 + 55 + 60, 33 + 55 + 97, 33 + 55 + 98, 33 + 55 + 99, 33 + 55 + 100, 33 + 55 + 102, 33 +
55 + 103, 33 + 55 + 105, 33 + 55 + 107, 33 + 57 + 58, 33 + 57 + 59, 33 + 57 + 60, 33 + 57 +
97, 33 + 57 + 98, 33 + 57 + 99, 33 + 57 + 100, 33 + 57 + 102, 33 + 57 + 103, 33 + 57 +
105, 33 + 57 + 107, 33 + 58 + 59, 33 + 58 + 60, 33 + 58 + 97, 33 + 58 + 98, 33 + 58 + 99, 33 +
58 + 100, 33 + 58 + 102, 33 + 58 + 103, 33 + 58 + 105, 33 + 58 + 107, 33 + 59 + 60, 33 +
59 + 97, 33 + 59 + 98, 33 + 59 + 99, 33 + 59 + 100, 33 + 59 + 102, 33 + 59 + 103, 33 + 59 +
105, 33 + 59 + 107, 33 + 60 + 97, 33 + 60 + 98, 33 + 60 + 99, 33 + 60 + 100, 33 + 60 + 102,
33 + 60 + 103, 33 + 60 + 105, 33 + 60 + 107, 33 + 97 + 98, 33 + 97 + 99, 33 + 97 + 100, 33 +
97 + 102, 33 + 97 + 103, 33 + 97 + 105, 33 + 97 + 107, 33 + 98 + 99, 33 + 98 + 100, 33 + 98 +
102, 33 + 98 + 103, 33 + 98 + 105, 33 + 98 + 107, 33 + 99 + 100, 33 + 99 + 102, 33 + 99 +
103, 33 + 99 + 105, 33 + 99 + 107, 33 + 100 + 102, 33 + 100 + 103, 33 + 100 + 105, 33 +
100 + 107, 33 + 102 + 103, 33 + 102 + 105, 33 + 102 + 107, 33 + 103 + 105, 33 + 103 + 107,
33 + 105 + 107, 34 + 50 + 54, 34 + 50 + 55, 34 + 50 + 57, 34 + 50 + 58, 34 + 50 + 59, 34 +
50 + 60, 34 + 50 + 97, 34 + 50 + 98, 34 + 50 + 99, 34 + 50 + 100, 34 + 50 + 102, 34 + 50 +
103, 34 + 50 + 105, 34 + 50 + 107, 34 + 54 + 55, 34 + 54 + 57, 34 + 54 + 58, 34 + 54 + 59,
34 + 54 + 60, 34 + 54 + 97, 34 + 54 + 98, 34 + 54 + 99, 34 + 54 + 100, 34 + 54 + 102, 34 +
54 + 103, 34 + 54 + 105, 34 + 54 + 107, 34 + 55 + 57, 34 + 55 + 58, 34 + 55 + 59, 34 + 55 +
60, 34 + 55 + 97, 34 + 55 + 98, 34 + 55 + 99, 34 + 55 + 100, 34 + 55 + 102, 34 + 55 + 103,
34 + 55 + 105, 34 + 55 + 107, 34 + 57 + 58, 34 + 57 + 59, 34 + 57 + 60, 34 + 57 + 97, 34 +
57 + 98, 34 + 57 + 99, 34 + 57 + 100, 34 + 57 + 102, 34 + 57 + 103, 34 + 57 + 105, 34 + 57 +
107, 34 + 58 + 59, 34 + 58 + 60, 34 + 58 + 97, 34 + 58 + 98, 34 + 58 + 99, 34 + 58 + 100, 34 +
58 + 102, 34 + 58 + 103, 34 + 58 + 105, 34 + 58 + 107, 34 + 59 + 60, 34 + 59 + 97, 34 + 59 +
98, 34 + 59 + 99, 34 + 59 + 100, 34 + 59 + 102, 34 + 59 + 103, 34 + 59 + 105, 34 + 59 +
107, 34 + 60 + 97, 34 + 60 + 98, 34 + 60 + 99, 34 + 60 + 100, 34 + 60 + 102, 34 + 60 + 103,
34 + 60 + 105, 34 + 60 + 107, 34 + 97 + 98, 34 + 97 + 99, 34 + 97 + 100, 34 + 97 + 102, 34 +
97 + 103, 34 + 97 + 105, 34 + 97 + 107, 34 + 98 + 99, 34 + 98 + 100, 34 + 98 + 102, 34 + 98 +
103, 34 + 98 + 105, 34 + 98 + 107, 34 + 99 + 100, 34 + 99 + 102, 34 + 99 + 103, 34 + 99 +
105, 34 + 99 + 107, 34 + 100 + 102, 34 + 100 + 103, 34 + 100 + 105, 34 + 100 + 107, 34 +
102 + 103, 34 + 102 + 105, 34 + 102 + 107, 34 + 103 + 105, 34 + 103 + 107, 34 + 105 + 107,
50 + 54 + 55, 50 + 54 + 57, 50 + 54 + 58, 50 + 54 + 59, 50 + 54 + 60, 50 + 54 + 97, 50 + 54 +
98, 50 + 54 + 99, 50 + 54 + 100, 50 + 54 + 102, 50 + 54 + 103, 50 + 54 + 105, 50 + 54 + 107,
50 + 55 + 57, 50 + 55 + 58, 50 + 55 + 59, 50 + 55 + 60, 50 + 55 + 97, 50 + 55 + 98, 50 + 55 +
99, 50 + 55 + 100, 50 + 55 + 102, 50 + 55 + 103, 50 + 55 + 105, 50 + 55 + 107, 50 + 57 + 58,
50 + 57 + 59, 50 + 57 + 60, 50 + 57 + 97, 50 + 57 + 98, 50 + 57 + 99, 50 + 57 + 100, 50 + 57 +
102, 50 + 57 + 103, 50 + 57 + 105, 50 + 57 + 107, 50 + 58 + 59, 50 + 58 + 60, 50 + 58 +
97, 50 + 58 + 98, 50 + 58 + 99, 50 + 58 + 100, 50 + 58 + 102, 50 + 58 + 103, 50 + 58 + 105,
50 + 58 + 107, 50 + 59 + 60, 50 + 59 + 97, 50 + 59 + 98, 50 + 59 + 99, 50 + 59 + 100, 50 +
59 + 102, 50 + 59 + 103, 50 + 59 + 105, 50 + 59 + 107, 50 + 60 + 97, 50 + 60 + 98, 50 + 60 +
99, 50 + 60 + 100, 50 + 60 + 102, 50 + 60 + 103, 50 + 60 + 105, 50 + 60 + 107, 50 + 97 + 98,
50 + 97 + 99, 50 + 97 + 100, 50 + 97 + 102, 50 + 97 + 103, 50 + 97 + 105, 50 + 97 + 107, 50 +
98 + 99, 50 + 98 + 100, 50 + 98 + 102, 50 + 98 + 103, 50 + 98 + 105, 50 + 98 + 107, 50 +
99 + 100, 50 + 99 + 102, 50 + 99 + 103, 50 + 99 + 105, 50 + 99 + 107, 50 + 100 + 102, 50 +
100 + 103, 50 + 100 + 105, 50 + 100 + 107, 50 + 102 + 103, 50 + 102 + 105, 50 + 102 + 107,
50 + 103 + 105, 50 + 103 + 107, 50 + 105 + 107, 54 + 55 + 57, 54 + 55 + 58, 54 + 55 + 59,
54 + 55 + 60, 54 + 55 + 97, 54 + 55 + 98, 54 + 55 + 99, 54 + 55 + 100, 54 + 55 + 102, 54 +
55 + 103, 54 + 55 + 105, 54 + 55 + 107, 54 + 57 + 58, 54 + 57 + 59, 54 + 57 + 60, 54 + 57 +
97, 54 + 57 + 98, 54 + 57 + 99, 54 + 57 + 100, 54 + 57 + 102, 54 + 57 + 103, 54 + 57 + 105,
54 + 57 + 107, 54 + 58 + 59, 54 + 58 + 60, 54 + 58 + 97, 54 + 58 + 98, 54 + 58 + 99, 54 + 58 +
100, 54 + 58 + 102, 54 + 58 + 103, 54 + 58 + 105, 54 + 58 + 107, 54 + 59 + 60, 54 + 59 +
97, 54 + 59 + 98, 54 + 59 + 99, 54 + 59 + 100, 54 + 59 + 102, 54 + 59 + 103, 54 + 59 + 105,
54 + 59 + 107, 54 + 60 + 97, 54 + 60 + 98, 54 + 60 + 99, 54 + 60 + 100, 54 + 60 + 102, 54 +
60 + 103, 54 + 60 + 105, 54 + 60 + 107, 54 + 97 + 98, 54 + 97 + 99, 54 + 97 + 100, 54 + 97 +
102, 54 + 97 + 103, 54 + 97 + 105, 54 + 97 + 107, 54 + 98 + 99, 54 + 98 + 100, 54 + 98 +
102, 54 + 98 + 103, 54 + 98 + 105, 54 + 98 + 107, 54 + 99 + 100, 54 + 99 + 102, 54 + 99 +
103, 54 + 99 + 105, 54 + 99 + 107, 54 + 100 + 102, 54 + 100 + 103, 54 + 100 + 105, 54 +
100 + 107, 54 + 102 + 103, 54 + 102 + 105, 54 + 102 + 107, 54 + 103 + 105, 54 + 103 + 107,
54 + 105 + 107, 55 + 57 + 58, 55 + 57 + 59, 55 + 57 + 60, 55 + 57 + 97, 55 + 57 + 98, 55 +
57 + 99, 55 + 57 + 100, 55 + 57 + 102, 55 + 57 + 103, 55 + 57 + 105, 55 + 57 + 107, 55 + 58 +
59, 55 + 58 + 60, 55 + 58 + 97, 55 + 58 + 98, 55 + 58 + 99, 55 + 58 + 100, 55 + 58 + 102,
55 + 58 + 103, 55 + 58 + 105, 55 + 58 + 107, 55 + 59 + 60, 55 + 59 + 97, 55 + 59 + 98, 55 +
59 + 99, 55 + 59 + 100, 55 + 59 + 102, 55 + 59 + 103, 55 + 59 + 105, 55 + 59 + 107, 55 + 60 +
97, 55 + 60 + 98, 55 + 60 + 99, 55 + 60 + 100, 55 + 60 + 102, 55 + 60 + 103, 55 + 60 +

TABLE 1-continued

Exemplary Combinations of Amino Acid Positions in
SEQ ID NO: 1 that can be Substituted with Histidine 105, 55 + 60 + 107, 55 + 97 + 98, 55 + 97 + 99, 55 + 97 + 100, 55 + 97 + 102, 55 + 97 + 103,
55 + 97 + 105, 55 + 97 + 107, 55 + 98 + 99, 55 + 98 + 100, 55 + 98 + 102, 55 + 98 + 103, 55 +
98 + 105, 55 + 98 + 107, 55 + 99 + 100, 55 + 99 + 102, 55 + 99 + 103, 55 + 99 + 105, 55 +
99 + 107, 55 + 100 + 102, 55 + 100 + 103, 55 + 100 + 105, 55 + 100 + 107, 55 + 102 + 103,
55 + 102 + 105, 55 + 102 + 107, 55 + 103 + 105, 55 + 103 + 107, 55 + 105 + 107, 57 + 58 +
59, 57 + 58 + 60, 57 + 58 + 97, 57 + 58 + 98, 57 + 58 + 99, 57 + 58 + 100, 57 + 58 + 102, 57 +
58 + 103, 57 + 58 + 105, 57 + 58 + 107, 57 + 59 + 60, 57 + 59 + 97, 57 + 59 + 98, 57 + 59 +
99, 57 + 59 + 100, 57 + 59 + 102, 57 + 59 + 103, 57 + 59 + 105, 57 + 59 + 107, 57 + 60 +
97, 57 + 60 + 98, 57 + 60 + 99, 57 + 60 + 100, 57 + 60 + 102, 57 + 60 + 103, 57 + 60 + 105,
57 + 60 + 107, 57 + 97 + 98, 57 + 97 + 99, 57 + 97 + 100, 57 + 97 + 102, 57 + 97 + 103, 57 +
97 + 105, 57 + 97 + 107, 57 + 98 + 99, 57 + 98 + 100, 57 + 98 + 102, 57 + 98 + 103, 57 + 98 +
105, 57 + 98 + 107, 57 + 99 + 100, 57 + 99 + 102, 57 + 99 + 103, 57 + 99 + 105, 57 + 99 +
107, 57 + 100 + 102, 57 + 100 + 103, 57 + 100 + 105, 57 + 100 + 107, 57 + 102 + 103, 57 +
102 + 105, 57 + 102 + 107, 57 + 103 + 105, 57 + 103 + 107, 57 + 105 + 107, 58 + 59 + 60,
58 + 59 + 97, 58 + 59 + 98, 58 + 59 + 99, 58 + 59 + 100, 58 + 59 + 102, 58 + 59 + 103, 58 +
59 + 105, 58 + 59 + 107, 58 + 60 + 97, 58 + 60 + 98, 58 + 60 + 99, 58 + 60 + 100, 58 + 60 +
102, 58 + 60 + 103, 58 + 60 + 105, 58 + 60 + 107, 58 + 97 + 98, 58 + 97 + 99, 58 + 97 + 100,
58 + 97 + 102, 58 + 97 + 103, 58 + 97 + 105, 58 + 97 + 107, 58 + 98 + 99, 58 + 98 + 100, 58 +
98 + 102, 58 + 98 + 103, 58 + 98 + 105, 58 + 98 + 107, 58 + 99 + 100, 58 + 99 + 102, 58 +
99 + 103, 58 + 99 + 105, 58 + 99 + 107, 58 + 100 + 102, 58 + 100 + 103, 58 + 100 + 105, 58 +
100 + 107, 58 + 102 + 103, 58 + 102 + 105, 58 + 102 + 107, 58 + 103 + 105, 58 + 103 +
107, 58 + 105 + 107, 59 + 60 + 97, 59 + 60 + 98, 59 + 60 + 99, 59 + 60 + 100, 59 + 60 + 102,
59 + 60 + 103, 59 + 60 + 105, 59 + 60 + 107, 59 + 97 + 98, 59 + 97 + 99, 59 + 97 + 100, 59 +
97 + 102, 59 + 97 + 103, 59 + 97 + 105, 59 + 97 + 107, 59 + 98 + 99, 59 + 98 + 100, 59 + 98 +
102, 59 + 98 + 103, 59 + 98 + 105, 59 + 98 + 107, 59 + 99 + 100, 59 + 99 + 102, 59 + 99 +
103, 59 + 99 + 105, 59 + 99 + 107, 59 + 100 + 102, 59 + 100 + 103, 59 + 100 + 105, 59 +
100 + 107, 59 + 102 + 103, 59 + 102 + 105, 59 + 102 + 107, 59 + 103 + 105, 59 + 103 + 107,
59 + 105 + 107, 60 + 97 + 98, 60 + 97 + 99, 60 + 97 + 100, 60 + 97 + 102, 60 + 97 + 103, 60 +
97 + 105, 60 + 97 + 107, 60 + 98 + 99, 60 + 98 + 100, 60 + 98 + 102, 60 + 98 + 103, 60 +
98 + 105, 60 + 98 + 107, 60 + 99 + 100, 60 + 99 + 102, 60 + 99 + 103, 60 + 99 + 105, 60 +
99 + 107, 60 + 100 + 102, 60 + 100 + 103, 60 + 100 + 105, 60 + 100 + 107, 60 + 102 + 103,
60 + 102 + 105, 60 + 102 + 107, 60 + 103 + 105, 60 + 103 + 107, 60 + 105 + 107, 97 + 98 +
99, 97 + 98 + 100, 97 + 98 + 102, 97 + 98 + 103, 97 + 98 + 105, 97 + 98 + 107, 97 + 99 +
100, 97 + 99 + 102, 97 + 99 + 103, 97 + 99 + 105, 97 + 99 + 107, 97 + 100 + 102, 97 + 100 +
103, 97 + 100 + 105, 97 + 100 + 107, 97 + 102 + 103, 97 + 102 + 105, 97 + 102 + 107, 97 +
103 + 105, 97 + 103 + 107, 97 + 105 + 107, 98 + 99 + 100, 98 + 99 + 102, 98 + 99 + 103, 98 +
99 + 105, 98 + 99 + 107, 98 + 100 + 102, 98 + 100 + 103, 98 + 100 + 105, 98 + 100 + 107,
98 + 102 + 103, 98 + 102 + 105, 98 + 102 + 107, 98 + 103 + 105, 98 + 103 + 107, 98 + 105 +
107, 99 + 100 + 102, 99 + 100 + 103, 99 + 100 + 105, 99 + 100 + 107, 99 + 102 + 103, 99 +
102 + 105, 99 + 102 + 107, 99 + 103 + 105, 99 + 103 + 107, 99 + 105 + 107, 100 + 102 +
103, 100 + 102 + 105, 100 + 102 + 107, 100 + 103 + 105, 100 + 103 + 107, 100 + 105 + 107,
102 + 103 + 105, 102 + 103 + 107, 102 + 105 + 107, 103 + 105 + 107

In some examples of any of the ABPCs described herein, a light chain variable domain includes a light chain variable domain that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in Table 2.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 2, where the light chain variable domain includes an alanine at position 38 in SEQ ID NO: 2.

In some examples of any of the ABPCs described herein the first antigen-binding domain includes: a light chain variable domain that is at least 90% (e.g., at least 92%, at least 94%, at least 96%, at least 98%, at least 99%, or 100%) identical to SEQ ID NO: 2, where the light chain variable domain includes an alanine at position 38 in SEQ ID NO: 2, and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 24, 27, 29, 31, 32, 33, 34, 50, 54, 55, 57, 58, 59, 60, 97, 98, 99, 100, 102, 103, 105, and 107.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 28, 30, 31, 32, 34, 35, 36, 55, 59, 93, 94, 95, 96, 97, 98, and 100 and where the light chain variable domain includes an alanine at position 38 in SEQ ID NO: 2. In some examples of any of the ABPCs described herein the first antigen-binding domain includes: a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 28, 30, 31, 32, 34, 35, 36, 55, 59, 93, 94, 95, 96, 97, 98, and 100 and where the light chain variable domain includes an alanine at position 38 in SEQ ID NO: 2, and a heavy chain variable domain that is at least 90% (e.g., at least 92%, at least 94%, at least 96%, at least 98%, at least 99%, or 100%) identical 5 to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 10 selected from the group consisting of: 24, 27, 29, 31, 32, 33, 34, 50, 54, 55, 57, 58, 59, 60, 97, 98, 99, 100, 102, 103, 105, and 107.

In some examples of any of the ABPCs described herein, a light chain variable domain includes a light chain variable 15 domain that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in 20 Table 2 and where the light chain variable domain includes an alanine at position 38 of SEQ ID NO: 2.

TABLE 2

Exemplary Combinations of Amino Acid Positions in
SEQ ID NO: 2 that can be Substituted with Histidine 28 + 30, 28 + 31, 28 + 32, 28 + 34, 28 + 35, 28 + 36, 28 + 55, 28 + 59, 28 + 93, 28 + 94, 28 + 95, 28 + 96, 28 + 97, 28 + 98, 28 + 100, 30 + 31, 30 + 32, 30 + 34, 30 + 35, 30 + 36, 30 + 55, 30 + 59, 30 + 93, 30 + 94, 30 + 95, 30 + 96, 30 + 97, 30 + 98, 30 + 100, 31 + 32, 31 + 34, 31 + 35, 31 + 36, 31 + 55, 31 + 59, 31 + 93, 31 + 94, 31 + 95, 31 + 96, 31 + 97, 31 + 98, 31 + 100, 32 + 34, 32 + 35, 32 + 36, 32 + 55, 32 + 59, 32 + 93, 32 + 94, 32 + 95, 32 + 96, 32 + 97, 32 + 98, 32 + 100, 34 + 35, 34 + 36, 34 + 55, 34 + 59, 34 + 93, 34 + 94, 34 + 95, 34 + 96, 34 + 97, 34 + 98, 34 + 100, 35 + 36, 35 + 55, 35 + 59, 35 + 93, 35 + 94, 35 + 95, 35 + 96, 35 + 97, 35 + 98, 35 + 100, 36 + 55, 36 + 59, 36 + 93, 36 + 94, 36 + 95, 36 + 96, 36 + 97, 36 + 98, 36 + 100, 55 + 59, 55 + 93, 55 + 94, 55 + 95, 55 + 96, 55 + 97, 55 + 98, 55 + 100, 59 + 93, 59 + 94, 59 + 95, 59 + 96, 59 + 97, 59 + 98, 59 + 100, 93 + 94, 93 + 95, 93 + 96, 93 + 97, 93 + 98, 93 + 100, 94 + 95, 94 + 96, 94 + 97, 94 + 98, 94 + 100, 95 + 96, 95 + 97, 95 + 98, 95 + 100, 96 + 97, 96 + 98, 96 + 100, 97 + 98, 97 + 100, 98 + 100, 28 + 30 + 31, 28 + 30 + 32, 28 + 30 + 34, 28 + 30 + 35, 28 + 30 + 36, 28 + 30 + 55, 28 + 30 + 59, 28 + 30 + 93, 28 + 30 + 94, 28 + 30 + 95, 28 + 30 + 96, 28 + 30 + 97, 28 + 30 + 98, 28 + 30 + 100, 28 + 31 + 32, 28 + 31 + 34, 28 + 31 + 35, 28 + 31 + 36, 28 + 31 + 55, 28 + 31 + 59, 28 + 31 + 93, 28 + 31 + 94, 28 + 31 + 95, 28 + 31 + 96, 28 + 31 + 97, 28 + 31 + 98, 28 + 31 + 100, 28 + 32 + 34, 28 + 32 + 35, 28 + 32 + 36, 28 + 32 + 55, 28 + 32 + 59, 28 + 32 + 93, 28 + 32 + 94, 28 + 32 + 95, 28 + 32 + 96, 28 + 32 + 97, 28 + 32 + 98, 28 + 32 + 100, 28 + 34 + 35, 28 + 34 + 36, 28 + 34 + 55, 28 + 34 + 59, 28 + 34 + 93, 28 + 34 + 94, 28 + 34 + 95, 28 + 34 + 96, 28 + 34 + 97, 28 + 34 + 98, 28 + 34 + 100, 28 + 35 + 36, 28 + 35 + 55, 28 + 35 + 59, 28 + 35 + 93, 28 + 35 + 94, 28 + 35 + 95, 28 + 35 + 96, 28 + 35 + 97, 28 + 35 + 98, 28 + 35 + 100, 28 + 36 + 55, 28 + 36 + 59, 28 + 36 + 93, 28 + 36 + 94, 28 + 36 + 95, 28 + 36 + 96, 28 + 36 + 97, 28 + 36 + 98, 28 + 36 + 100, 28 + 55 + 59, 28 + 55 + 93, 28 + 55 + 94, 28 + 55 + 95, 28 + 55 + 96, 28 + 55 + 97, 28 + 55 + 98, 28 + 55 + 100, 28 + 59 + 93, 28 + 59 + 94, 28 + 59 + 95, 28 + 59 + 96, 28 + 59 + 97, 28 + 59 + 98, 28 + 59 + 100, 28 + 93 + 94, 28 + 93 + 95, 28 + 93 + 96, 28 + 93 + 97, 28 + 93 + 98, 28 + 93 + 100, 28 + 94 + 95, 28 + 94 + 96, 28 + 94 + 97, 28 + 94 + 98, 28 + 94 + 100, 28 + 95 + 96, 28 + 95 + 97, 28 + 95 + 98, 28 + 95 + 100, 28 + 96 + 97, 28 + 96 + 98, 28 + 96 + 100, 28 + 97 + 98, 28 + 97 + 100, 28 + 98 + 100, 30 + 31 + 32, 30 + 31 + 34, 30 + 31 + 35, 30 + 31 + 36, 30 + 31 + 55, 30 + 31 + 59, 30 + 31 + 93, 30 + 31 + 94, 30 + 31 + 95, 30 + 31 + 96, 30 + 31 + 97, 30 + 31 + 98, 30 + 31 + 100, 30 + 32 + 34, 30 + 32 + 35, 30 + 32 + 36, 30 + 32 + 55, 30 + 32 + 59, 30 + 32 + 93, 30 + 32 + 94, 30 + 32 + 95, 30 + 32 + 96, 30 + 32 + 97, 30 + 32 + 98, 30 + 32 + 100, 30 + 34 + 35, 30 + 34 + 36, 30 + 34 + 55, 30 + 34 + 59, 30 + 34 + 93, 30 + 34 + 94, 30 + 34 + 95, 30 + 34 + 96, 30 + 34 + 97, 30 + 34 + 98, 30 + 34 + 100, 30 + 35 + 36, 30 + 35 + 55, 30 + 35 + 59, 30 + 35 + 93, 30 + 35 + 94, 30 + 35 + 95, 30 + 35 + 96, 30 + 35 + 97, 30 + 35 + 98, 30 + 35 + 100, 30 + 36 + 55, 30 + 36 + 59, 30 + 36 + 93, 30 + 36 + 94, 30 + 36 + 95, 30 + 36 + 96, 30 + 36 + 97, 30 + 36 + 98, 30 + 36 + 100, 30 + 55 + 59, 30 + 55 + 93, 30 + 55 + 94, 30 + 55 + 95, 30 + 55 + 96, 30 + 55 + 97, 30 + 55 + 98, 30 + 55 + 100, 30 + 59 + 93, 30 + 59 + 94, 30 + 59 + 95, 30 + 59 + 96, 30 + 59 + 97, 30 + 59 + 98, 30 + 59 + 100, 30 + 93 + 94, 30 + 93 + 95, 30 + 93 + 96, 30 + 93 + 97, 30 + 93 + 98, 30 + 93 + 100, 30 + 94 + 95, 30 + 94 + 96, 30 + 94 + 97, 30 + 94 + 98, 30 + 94 + 100, 30 + 95 + 96, 30 + 95 + 97, 30 + 95 + 98, 30 + 95 + 100, 30 + 96 + 97, 30 + 96 + 98, 30 + 96 + 100, 30 + 97 + 98, 30 + 97 + 100, 30 + 98 + 100, 31 + 32 + 34, 31 + 32 + 35, 31 + 32 + 36, 31 + 32 + 55, 31 + 32 + 59, 31 + 32 + 93, 31 + 32 + 94, 31 + 32 + 95, 31 + 32 + 96, 31 + 32 + 97, 31 + 32 + 98, 31 + 32 + 100, 31 + 34 + 35, 31 + 34 + 36, 31 + 34 + 55, 31 + 34 + 59, 31 + 34 + 93, 31 + 34 + 94, 31 + 34 + 95, 31 + 34 + 96, 31 + 34 + 97, 31 + 34 + 98, 31 + 34 + 100, 31 + 35 + 36, 31 + 35 + 55, 31 + 35 + 59, 31 + 35 + 93, 31 + 35 + 94, 31 + 35 + 95, 31 + 35 + 96, 31 + 35 + 97, 31 + 35 + 98, 31 + 35 + 100, 31 + 36 + 55, 31 + 36 + 59, 31 + 36 + 93, 31 + 36 + 94, TABLE 2-continued Exemplary Combinations of Amino Acid Positions in
SEQ ID NO: 2 that can be Substituted with Histidine 31 + 36 + 95, 31 + 36 + 96, 31 + 36 + 97, 31 + 36 + 98, 31 + 36 + 100, 31 + 55 + 59, 31 +
55 + 93, 31 + 55 + 94, 31 + 55 + 95, 31 + 55 + 96, 31 + 55 + 97, 31 + 55 + 98, 31 + 55 +
100, 31 + 59 + 93, 31 + 59 + 94, 31 + 59 + 95, 31 + 59 + 96, 31 + 59 + 97, 31 + 59 + 98,
31 + 59 + 100, 31 + 93 + 94, 31 + 93 + 95, 31 + 93 + 96, 31 + 93 + 97, 31 + 93 + 98, 31 +
93 + 100, 31 + 94 + 95, 31 + 94 + 96, 31 + 94 + 97, 31 + 94 + 98, 31 + 94 + 100, 31 + 95 +
96, 31 + 95 + 97, 31 + 95 + 98, 31 + 95 + 100, 31 + 96 + 97, 31 + 96 + 98, 31 + 96 +
100, 31 + 97 + 98, 31 + 97 + 100, 31 + 98 + 100, 32 + 34 + 35, 32 + 34 + 36, 32 + 34 +
55, 32 + 34 + 59, 32 + 34 + 93, 32 + 34 + 94, 32 + 34 + 95, 32 + 34 + 96, 32 + 34 + 97,
32 + 34 + 98, 32 + 34 + 100, 32 + 35 + 36, 32 + 35 + 55, 32 + 35 + 59, 32 + 35 + 93, 32 +
35 + 94, 32 + 35 + 95, 32 + 35 + 96, 32 + 35 + 97, 32 + 35 + 98, 32 + 35 + 100, 32 + 36 +
55, 32 + 36 + 59, 32 + 36 + 93, 32 + 36 + 94, 32 + 36 + 95, 32 + 36 + 96, 32 + 36 + 97,
32 + 36 + 98, 32 + 36 + 100, 32 + 55 + 59, 32 + 55 + 93, 32 + 55 + 94, 32 + 55 + 95, 32 +
55 + 96, 32 + 55 + 97, 32 + 55 + 98, 32 + 55 + 100, 32 + 59 + 93, 32 + 59 + 94, 32 + 59 +
95, 32 + 59 + 96, 32 + 59 + 97, 32 + 59 + 98, 32 + 59 + 100, 32 + 93 + 94, 32 + 93 + 95,
32 + 93 + 96, 32 + 93 + 97, 32 + 93 + 98, 32 + 93 + 100, 32 + 94 + 95, 32 + 94 + 96, 32 +
94 + 97, 32 + 94 + 98, 32 + 94 + 100, 32 + 95 + 96, 32 + 95 + 97, 32 + 95 + 98, 32 + 95 +
100, 32 + 96 + 97, 32 + 96 + 98, 32 + 96 + 100, 32 + 97 + 98, 32 + 97 + 100, 32 + 98 +
100, 34 + 35 + 36, 34 + 35 + 55, 34 + 35 + 59, 34 + 35 + 93, 34 + 35 + 94, 34 + 35 + 95,
34 + 35 + 96, 34 + 35 + 97, 34 + 35 + 98, 34 + 35 + 100, 34 + 36 + 55, 34 + 36 + 59, 34 +
36 + 93, 34 + 36 + 94, 34 + 36 + 95, 34 + 36 + 96, 34 + 36 + 97, 34 + 36 + 98, 34 + 36 +
100, 34 + 55 + 59, 34 + 55 + 93, 34 + 55 + 94, 34 + 55 + 95, 34 + 55 + 96, 34 + 55 + 97,
34 + 55 + 98, 34 + 55 + 100, 34 + 59 + 93, 34 + 59 + 94, 34 + 59 + 95, 34 + 59 + 96, 34 +
59 + 97, 34 + 59 + 98, 34 + 59 + 100, 34 + 93 + 94, 34 + 93 + 95, 34 + 93 + 96, 34 + 93 +
97, 34 + 93 + 98, 34 + 93 + 100, 34 + 94 + 95, 34 + 94 + 96, 34 + 94 + 97, 34 + 94 + 98,
34 + 94 + 100, 34 + 95 + 96, 34 + 95 + 97, 34 + 95 + 98, 34 + 95 + 100, 34 + 96 + 97, 34 +
96 + 98, 34 + 96 + 100, 34 + 97 + 98, 34 + 97 + 100, 34 + 98 + 100, 35 + 36 + 55, 35 +
36 + 59, 35 + 36 + 93, 35 + 36 + 94, 35 + 36 + 95, 35 + 36 + 96, 35 + 36 + 97, 35 + 36 +
98, 35 + 36 + 100, 35 + 55 + 59, 35 + 55 + 93, 35 + 55 + 94, 35 + 55 + 95, 35 + 55 + 96,
35 + 55 + 97, 35 + 55 + 98, 35 + 55 + 100, 35 + 59 + 93, 35 + 59 + 94, 35 + 59 + 95, 35 +
59 + 96, 35 + 59 + 97, 35 + 59 + 98, 35 + 59 + 100, 35 + 93 + 94, 35 + 93 + 95, 35 + 93 +
96, 35 + 93 + 97, 35 + 93 + 98, 35 + 93 + 100, 35 + 94 + 95, 35 + 94 + 96, 35 + 94 + 97,
35 + 94 + 98, 35 + 94 + 100, 35 + 95 + 96, 35 + 95 + 97, 35 + 95 + 98, 35 + 95 + 100, 35 +
96 + 97, 35 + 96 + 98, 35 + 96 + 100, 35 + 97 + 98, 35 + 97 + 100, 35 + 98 + 100, 36 +
55 + 59, 36 + 55 + 93, 36 + 55 + 94, 36 + 55 + 95, 36 + 55 + 96, 36 + 55 + 97, 36 + 55 +
98, 36 + 55 + 100, 36 + 59 + 93, 36 + 59 + 94, 36 + 59 + 95, 36 + 59 + 96, 36 + 59 + 97,
36 + 59 + 98, 36 + 59 + 100, 36 + 93 + 94, 36 + 93 + 95, 36 + 93 + 96, 36 + 93 + 97, 36 +
93 + 98, 36 + 93 + 100, 36 + 94 + 95, 36 + 94 + 96, 36 + 94 + 97, 36 + 94 + 98, 36 + 94 +
100, 36 + 95 + 96, 36 + 95 + 97, 36 + 95 + 98, 36 + 95 + 100, 36 + 96 + 97, 36 + 96 + 98,
36 + 96 + 100, 36 + 97 + 98, 36 + 97 + 100, 36 + 98 + 100, 55 + 59 + 93, 55 + 59 + 94,
55 + 59 + 95, 55 + 59 + 96, 55 + 59 + 97, 55 + 59 + 98, 55 + 59 + 100, 55 + 93 + 94, 55 +
93 + 95, 55 + 93 + 96, 55 + 93 + 97, 55 + 93 + 98, 55 + 93 + 100, 55 + 94 + 95, 55 + 94 +
96, 55 + 94 + 97, 55 + 94 + 98, 55 + 94 + 100, 55 + 95 + 96, 55 + 95 + 97, 55 + 95 + 98,
55 + 95 + 100, 55 + 96 + 97, 55 + 96 + 98, 55 + 96 + 100, 55 + 97 + 98, 55 + 97 + 100,
55 + 98 + 100, 59 + 93 + 94, 59 + 93 + 95, 59 + 93 + 96, 59 + 93 + 97, 59 + 93 + 98, 59 +
93 + 100, 59 + 94 + 95, 59 + 94 + 96, 59 + 94 + 97, 59 + 94 + 98, 59 + 94 + 100, 59 + 95 +
96, 59 + 95 + 97, 59 + 95 + 98, 59 + 95 + 100, 59 + 96 + 97, 59 + 96 + 98, 59 + 96 +
100, 59 + 97 + 98, 59 + 97 + 100, 59 + 98 + 100, 93 + 94 + 95, 93 + 94 + 96, 93 + 94 +
97, 93 + 94 + 98, 93 + 94 + 100, 93 + 95 + 96, 93 + 95 + 97, 93 + 95 + 98, 93 + 95 + 100,
93 + 96 + 97, 93 + 96 + 98, 93 + 96 + 100, 93 + 97 + 98, 93 + 97 + 100, 93 + 98 + 100,
94 + 95 + 96, 94 + 95 + 97, 94 + 95 + 98, 94 + 95 + 100, 94 + 96 + 97, 94 + 96 + 98, 94 +
96 + 100, 94 + 97 + 98, 94 + 97 + 100, 94 + 98 + 100, 95 + 96 + 97, 95 + 96 + 98, 95 +
96 + 100, 95 + 97 + 98, 95 + 97 + 100, 95 + 98 + 100, 96 + 97 + 98, 96 + 97 + 100, 96 +
98 + 100, 97 + 98 + 100, In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1; and a light chain variable domain that that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in Table 2.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1, and where the heavy chain variable domain includes an alanine at position 52 in SEQ ID NO: 1; and a light chain variable domain that that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in Table 2.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in Table 2, and where the light chain variable domain includes an alanine at position 38 in SEQ ID NO: 2; and a heavy chain variable domain that that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 28 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain comprising SEQ ID NO: 2, and a heavy chain variable domain that is at least 90% identical (e.g., at least 92%, at least 94%, at least 96%, at least 98%, at least 99%, or 100%) identical to SEQ ID NO: 1, where the heavy chain variable domain includes a histidine at any of the specific combinations of one or more (e.g., two, three, four, five, six, seven, eight, nine, or ten) amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 30 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 31 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 32 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 34 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 35 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 36 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 55 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 59 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 93 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 94 in SEQ ID NO: 2; and a heavy chain variable domain that is at least 90% (e.g., at least 92%, at least 94%, at least 96%, at least 98%, at least 99%, or 100%)

identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 95 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 96 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 97 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 98 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 100 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain includes a heavy chain variable domain of mirvetuximab with one or more (e.g., one, two, three, four, five, six, seven, eight, nine, ten, eleven, twelve, thirteen, fourteen, fifteen, sixteen, seventeen, nineteen, or twenty) histidine(s) substituted with an alanine. In some examples of any of the ABPCs described herein, the first antigen-binding domain includes a light chain variable domain of mirvetuximab with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a heavy chain variable domain of mirvetuximab with one or more (e.g., one, two, three, four, five, six, seven, eight, nine, ten, eleven, twelve, thirteen, fourteen, fifteen, sixteen, seventeen, eighteen, nineteen, or twenty) histidines substituted with an alanine; and a light chain variable domain of mirvetuximab with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the heavy chain variable domain of mirvetuximab comprises SEQ ID NO: 1. In some examples of any of the ABPCs described herein, the light chain variable domain of mirvetuximab comprises SEQ ID NO: 2.

In some examples of any of the ABPCs described herein, the first antigen-binding domain comprises a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) histidine(s) in SEQ ID NOs: 3-5 substituted with an alanine. In some examples of any of the ABPCs described herein, the first antigen-binding domain comprises a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) histidine(s) in SEQ ID NOs: 6-8 substituted with an alanine. In some examples of any of the ABPCs described herein, the first antigen-binding domain includes: a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) histidine(s) in SEQ ID NOs: 3-5 substituted with an alanine; and a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) histidine(s) in SEQ ID NOs: 6-8 substituted with an alanine.

In some examples of any of the ABPCs described herein, the first antigen-binding domain comprises a heavy chain variable domain of SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain of SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, or SEQ ID NO: 84.

In some examples of any of the ABPCs described herein, the first antigen-binding domain includes a light chain variable domain comprising SEQ ID NO: 2, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 54, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 55, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 56, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 57, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 58, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 59, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 60, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 61, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 62, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 63, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 64, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 65, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 66, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 67, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 68, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 69, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 70, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 71, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 72, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 73, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 74, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 75, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 76, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 77, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 78, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 79, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 80, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 81, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 82, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 83, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 84, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a heavy chain variable domain comprising SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, or SEQ ID NO: 104.

In some examples of any of the ABPCs described herein, the first antigen-binding domain includes a light chain variable domain comprising SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 85, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 86, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 87, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 88, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 89, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 90, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 91, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 92, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 93, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 94, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 95, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 96, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 97, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ-ID NO: 83.

In some examples of any of the ABPCs described herein, the first antigen-binding domain includes a heavy chain variable domain comprising SEQ ID NO: 98, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 99, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising: SEQ ID NO: 100, and a light chain variable domain comprising SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 101, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 102, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 103, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain comprising SEQ ID NO: 104, and a light chain variable domain comprising: SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 74, SEQ ID NO: 76, SEQ ID NO: 77, SEQ ID NO: 78, SEQ ID NO: 79, SEQ ID NO: 80, SEQ ID NO: 81, or SEQ ID NO: 83.

In some examples of any of the ABPCs described herein, the first antigen-binding domain includes a heavy chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a light chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a heavy chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine; and a light chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the heavy chain variable domain of STRO-002 comprises SEQ ID NO: 105. In some examples of any of the ABPCs described herein, the light chain variable domain of STRO-002 comprises SEQ ID NO: 106.

In some examples of any of the ABPCs described herein, the first antigen-binding domain comprises a heavy chain variable domain comprising a CDR1, a CDR2, and a CDR3 of SEQ ID NO: 107, SEQ ID NO: 108, and SEQ ID NO: 109, respectively, with collectively a total of one or more (e.g., one, two, three, four, five, six, seven, eight, nine, or ten) amino acid positions in SEQ ID NOs: 107-109 substituted with a histidine. In some examples of any of the ABPCs described herein, the first antigen-binding domain comprises a light chain variable domain comprising a CDR1, a CDR2, and a CDR3 of SEQ ID NO: 110, SEQ ID NO: 111, and SEQ ID NO: 112, respectively, with collectively a total of one or more (e.g., one, two, three, four, five, six, seven, eight, nine, or ten) amino acid positions in SEQ ID NOs: 110-112 substituted with a histidine. In some examples of any of the ABPCs described herein, the first antigen-binding domain includes: a heavy chain variable domain comprising a CDR1, a CDR2, and a CDR3 of SEQ ID NO: 107, SEQ ID NO: 108, and SEQ ID NO: 109, respectively, with collectively a total of one or more (e.g., one, two, three, four, five, six, seven, eight, nine, or ten) amino acid positions in SEQ ID NOs: 107-109 substituted with a histidine; and a light chain variable domain comprising a CDR1, a CDR2, and a CDR3 of SEQ ID NO: 110, SEQ ID NO: 111, and SEQ ID NO: 112, respectively, with collectively a total of one or more (e.g., one, two, three, four, five, six, seven, eight, nine, or ten) amino acid positions in SEQ ID NOs: 110-112 substituted with a histidine.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 105 selected from the group consisting of: 29, 33, 34, 50, 51, 52, 53, 55, 56, 57, 101, 102, 103, 108, 109, 110, 111, 112, and 113. In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 106, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 106 selected from the group consisting of: 28, 29, 30, 31, 50, 92, 93, 94, 95, and 96. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 105 selected from the group consisting of: 29, 33, 34, 50, 51, 52, 53, 55, 56, 57, 101, 102, 103, 108, 109, 110, 111, 112, and 113, and a light chain variable domain that is at least 90% (e.g., at least 92%, at least 94%, at least 96%, at least 98%, at least 99%, or 100%) identical to SEQ ID NO: 106, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 106 selected from the group consisting of: 28, 29, 30, 31, 50, 92, 93, 94, 95, and 96.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 105, where the heavy chain variable domain includes an alanine at position 35 in SEQ ID NO: 105.

In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 105, where the heavy chain variable domain includes an alanine at position 35 in SEQ ID NO: 105, and a light chain variable domain that is at least 90% (e.g., at least 92%, at least 94%, at least 96%, at least 98%, at least 99%, or 100%) identical to SEQ ID NO: 106, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 106 selected from the group consisting of: 28, 29, 30, 31, 50, 92, 93, 94, 95, and 96.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 105 selected from the group consisting of: 29, 33, 34, 50, 51, 52, 53, 55, 56, 57, 101, 102, 103, 108, 109, 110, 111, 112, and 113, and where the heavy chain variable domain includes an alanine at position 35 in SEQ ID NO: 105. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 105 selected from the group consisting of: 29, 33, 34, 50, 51, 52, 53, 55, 56, 57, 101, 102, 103, 108, 109, 110, 111, 112, and 113, and where the heavy chain variable domain includes an alanine at position 35 in SEQ ID NO: 105, and a light chain variable domain that is at least 90% (e.g., at least 92%, at least 94%, at least 96%, at least 98%, at least 99%, or 100%) identical to SEQ ID NO: 106, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 106 selected from the group consisting of: 28, 29, 30, 31, 50, 92, 93, 94, 95, and 96.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3 and where the heavy chain variable domain includes an alanine at position 35 of SEQ ID NO: 105.

TABLE 3

Exemplary Combinations of Amino Acid Positions in SEQ
ID NO: 105 that can be Substituted with Histidine 29 + 33, 29 + 34, 29 + 50, 29 + 51, 29 + 52, 29 + 53, 29 + 55, 29 + 56, 29 + 57, 29 + 101, 29 + 102, 29 + 103, 29 + 108, 29 + 109, 29 + 110, 29 + 111, 29 + 112, 29 + 113, 33 + 34, 33 + 50, 33 + 51, 33 + 52, 33 + 53, 33 + 55, 33 + 56, 33 + 57, 33 + 101, 33 + 102, 33 + 103, 33 + 108, 33 + 109, 33 + 110, 33 + 111, 33 + 112, 33 + 113, 34 + 50, 34 + 51, 34 + 52, 34 + 53, 34 + 55, 34 + 56, 34 + 57, 34 + 101, 34 + 102, 34 + 103, 34 + 108, 34 + 109, 34 + 110, 34 + 111, 34 + 112, 34 + 113, 50 + 51, 50 + 52, 50 + 53, 50 + 55, 50 + 56, 50 + 57, 50 + 101, 50 + 102, 50 + 103, 50 + 108, 50 + 109, 50 + 110, 50 + 111, 50 + 112, 50 + 113, 51 + 52, 51 + 53, 51 + 55, 51 + 56, 51 + 57, 51 + 101, 51 + 102, 51 + 103, 51 + 108, 51 + 109, 51 + 110, 51 + 111, 51 + 112, 51 + 113, 52 + 53, 52 + 55, 52 + 56, 52 + 57, 52 + 101, 52 + 102, 52 + 103, 52 + 108, 52 + 109, 52 + 110, 52 + 111, 52 + 112, 52 + 113, 53 + 55, 53 + 56, 53 + 57, 53 + 101, 53 + 102, 53 + 103, 53 + 108, 53 + 109, 53 + 110, 53 + 111, 53 + 112, 53 + 113, 55 + 56, 55 + 57, 55 + 101, 55 + 102, 55 + 103, 55 + 108, 55 + 109, 55 + 110, 55 + 111, 55 + 112, 55 + 113, 56 + 57, 56 + 101, 56 + 102, 56 + 103, 56 + 108, 56 + 109, 56 + 110, 56 + 111, 56 + 112, 56 + 113, 57 + 101, 57 + 102, 57 + 103, 57 + 108, 57 + 109, 57 + 110, 57 + 111, 57 + 112, 57 + 113, 101 + 102, 101 + 103, 101 + 108, 101 + 109, 101 + 110, 101 + 111, 101 + 112, 101 + 113, 102 + 103, 102 + 108, 102 + 109, 102 + 110, 102 + 111, 102 + 112, 102 + 113, 103 + 108, 103 + 109, 103 + 110, 103 + 111, 103 + 112, 103 + 113, 108 + 109, 108 + 110, 108 + 111, 108 + 112, 108 + 113, 109 + 110, 109 + 111, 109 + 112, 109 + 113, 110 + 111, 110 + 112, 110 + 113, 111 + 112, 111 + 113, 112 + 113, 29 + 33 + 34, 29 + 33 + 50, 29 + 33 + 51, 29 + 33 + 52, 29 + 33 + 53, 29 + 33 + 55, 29 + 33 + 56, 29 + 33 + 57, 29 + 33 + 101, 29 + 33 + 102, 29 + 33 + 103, 29 + 33 + 108, 29 + 33 + 109, 29 + 33 + 110, 29 + 33 + 111, 29 + 33 + 112, 29 + 33 + 113, 29 + 34 +

TABLE 3-continued

Exemplary Combinations of Amino Acid Positions in SEQ
ID NO: 105 that can be Substituted with Histidine 50, 29 + 34 + 51, 29 + 34 + 52, 29 + 34 + 53, 29 + 34 + 55, 29 + 34 + 56, 29 + 34 + 57,
29 + 34 + 101, 29 + 34 + 102, 29 + 34 + 103, 29 + 34 + 108, 29 + 34 + 109, 29 + 34 +
110, 29 + 34 + 111, 29 + 34 + 112, 29 + 34 + 113, 29 + 50 + 51, 29 + 50 + 52, 29 + 50 +
53, 29 + 50 + 55, 29 + 50 + 56, 29 + 50 + 57, 29 + 50 + 101, 29 + 50 + 102, 29 + 50 +
103, 29 + 50 + 108, 29 + 50 + 109, 29 + 50 + 110, 29 + 50 + 111, 29 + 50 + 112, 29 + 50 +
113, 29 + 51 + 52, 29 + 51 + 53, 29 + 51 + 55, 29 + 51 + 56, 29 + 51 + 57, 29 + 51 +
101, 29 + 51 + 102, 29 + 51 + 103, 29 + 51 + 108, 29 + 51 + 109, 29 + 51 + 110, 29 + 51 +
111, 29 + 51 + 112, 29 + 51 + 113, 29 + 52 + 53, 29 + 52 + 55, 29 + 52 + 56, 29 + 52 +
57, 29 + 52 + 101, 29 + 52 + 102, 29 + 52 + 103, 29 + 52 + 108, 29 + 52 + 109, 29 + 52 +
110, 29 + 52 + 111, 29 + 52 + 112, 29 + 52 + 113, 29 + 53 + 55, 29 + 53 + 56, 29 + 53 +
57, 29 + 53 + 101, 29 + 53 + 102, 29 + 53 + 103, 29 + 53 + 108, 29 + 53 + 109, 29 + 53 +
110, 29 + 53 + 111, 29 + 53 + 112, 29 + 53 + 113, 29 + 55 + 56, 29 + 55 + 57, 29 + 55 +
101, 29 + 55 + 102, 29 + 55 + 103, 29 + 55 + 108, 29 + 55 + 109, 29 + 55 + 110, 29 + 55 +
111, 29 + 55 + 112, 29 + 55 + 113, 29 + 56 + 57, 29 + 56 + 101, 29 + 56 + 102, 29 + 56 +
103, 29 + 56 + 108, 29 + 56 + 109, 29 + 56 + 110, 29 + 56 + 111, 29 + 56 + 112, 29 +
56 + 113, 29 + 57 + 101, 29 + 57 + 102, 29 + 57 + 103, 29 + 57 + 108, 29 + 57 + 109, 29 +
57 + 110, 29 + 57 + 111, 29 + 57 + 112, 29 + 57 + 113, 29 + 101 + 102, 29 + 101 + 103,
29 + 101 + 108, 29 + 101 + 109, 29 + 101 + 110, 29 + 101 + 111, 29 + 101 + 112, 29 +
101 + 113, 29 + 102 + 103, 29 + 102 + 108, 29 + 102 + 109, 29 + 102 + 110, 29 + 102 +
111, 29 + 102 + 112, 29 + 102 + 113, 29 + 103 + 108, 29 + 103 + 109, 29 + 103 + 110, 29 +
103 + 111, 29 + 103 + 112, 29 + 103 + 113, 29 + 108 + 109, 29 + 108 + 110, 29 + 108 +
111, 29 + 108 + 112, 29 + 108 + 113, 29 + 109 + 110, 29 + 109 + 111, 29 + 109 + 112, 29 +
109 + 113, 29 + 110 + 111, 29 + 110 + 112, 29 + 110 + 113, 29 + 111 + 112, 29 + 111 +
113, 29 + 112 + 113, 33 + 34 + 50, 33 + 34 + 51, 33 + 34 + 52, 33 + 34 + 53, 33 + 34 +
55, 33 + 34 + 56, 33 + 34 + 57, 33 + 34 + 101, 33 + 34 + 102, 33 + 34 + 103, 33 + 34 +
108, 33 + 34 + 109, 33 + 34 + 110, 33 + 34 + 111, 33 + 34 + 112, 33 + 34 + 113, 33 + 50 +
51, 33 + 50 + 52, 33 + 50 + 53, 33 + 50 + 55, 33 + 50 + 56, 33 + 50 + 57, 33 + 50 + 101,
33 + 50 + 102, 33 + 50 + 103, 33 + 50 + 108, 33 + 50 + 109, 33 + 50 + 110, 33 + 50 +
111, 33 + 50 + 112, 33 + 50 + 113, 33 + 51 + 52, 33 + 51 + 53, 33 + 51 + 55, 33 + 51 +
56, 33 + 51 + 57, 33 + 51 + 101, 33 + 51 + 102, 33 + 51 + 103, 33 + 51 + 108, 33 + 51 +
109, 33 + 51 + 110, 33 + 51 + 111, 33 + 51 + 112, 33 + 51 + 113, 33 + 52 + 53, 33 + 52 +
55, 33 + 52 + 56, 33 + 52 + 57, 33 + 52 + 101, 33 + 52 + 102, 33 + 52 + 103, 33 + 52 +
108, 33 + 52 + 109, 33 + 52 + 110, 33 + 52 + 111, 33 + 52 + 112, 33 + 52 + 113, 33 + 53 +
55, 33 + 53 + 56, 33 + 53 + 57, 33 + 53 + 101, 33 + 53 + 102, 33 + 53 + 103, 33 + 53 +
108, 33 + 53 + 109, 33 + 53 + 110, 33 + 53 + 111, 33 + 53 + 112, 33 + 53 + 113, 33 + 55 +
56, 33 + 55 + 57, 33 + 55 + 101, 33 + 55 + 102, 33 + 55 + 103, 33 + 55 + 108, 33 + 55 +
109, 33 + 55 + 110, 33 + 55 + 111, 33 + 55 + 112, 33 + 55 + 113, 33 + 56 + 57, 33 + 56 +
101, 33 + 56 + 102, 33 + 56 + 103, 33 + 56 + 108, 33 + 56 + 109, 33 + 56 + 110, 33 + 56 +
111, 33 + 56 + 112, 33 + 56 + 113, 33 + 57 + 101, 33 + 57 + 102, 33 + 57 + 103, 33 +
57 + 108, 33 + 57 + 109, 33 + 57 + 110, 33 + 57 + 111, 33 + 57 + 112, 33 + 57 + 113, 33 +
101 + 102, 33 + 101 + 103, 33 + 101 + 108, 33 + 101 + 109, 33 + 101 + 110, 33 + 101 +
111, 33 + 101 + 112, 33 + 101 + 113, 33 + 102 + 103, 33 + 102 + 108, 33 + 102 + 109, 33 +
102 + 110, 33 + 102 + 111, 33 + 102 + 112, 33 + 102 + 113, 33 + 103 + 108, 33 + 103 +
109, 33 + 103 + 110, 33 + 103 + 111, 33 + 103 + 112, 33 + 103 + 113, 33 + 108 + 109, 33 +
108 + 110, 33 + 108 + 111, 33 + 108 + 112, 33 + 108 + 113, 33 + 109 + 110, 33 + 109 +
111, 33 + 109 + 112, 33 + 109 + 113, 33 + 110 + 111, 33 + 110 + 112, 33 + 110 + 113, 33 +
111 + 112, 33 + 111 + 113, 33 + 112 + 113, 34 + 50 + 51, 34 + 50 + 52, 34 + 50 + 53,
34 + 50 + 55, 34 + 50 + 56, 34 + 50 + 57, 34 + 50 + 101, 34 + 50 + 102, 34 + 50 + 103, 34 +
50 + 108, 34 + 50 + 109, 34 + 50 + 110, 34 + 50 + 111, 34 + 50 + 112, 34 + 50 + 113,
34 + 51 + 52, 34 + 51 + 53, 34 + 51 + 55, 34 + 51 + 56, 34 + 51 + 57, 34 + 51 + 101, 34 +
51 + 102, 34 + 51 + 103, 34 + 51 + 108, 34 + 51 + 109, 34 + 51 + 110, 34 + 51 + 111, 34 +
51 + 112, 34 + 51 + 113, 34 + 52 + 53, 34 + 52 + 55, 34 + 52 + 56, 34 + 52 + 57, 34 +
52 + 101, 34 + 52 + 102, 34 + 52 + 103, 34 + 52 + 108, 34 + 52 + 109, 34 + 52 + 110, 34 +
52 + 111, 34 + 52 + 112, 34 + 52 + 113, 34 + 53 + 55, 34 + 53 + 56, 34 + 53 + 57, 34 +
53 + 101, 34 + 53 + 102, 34 + 53 + 103, 34 + 53 + 108, 34 + 53 + 109, 34 + 53 + 110, 34 +
53 + 111, 34 + 53 + 112, 34 + 53 + 113, 34 + 55 + 56, 34 + 55 + 57, 34 + 55 + 101, 34 +
55 + 102, 34 + 55 + 103, 34 + 55 + 108, 34 + 55 + 109, 34 + 55 + 110, 34 + 55 + 111, 34 +
55 + 112, 34 + 55 + 113, 34 + 56 + 57, 34 + 56 + 101, 34 + 56 + 102, 34 + 56 + 103, 34 +
56 + 108, 34 + 56 + 109, 34 + 56 + 110, 34 + 56 + 111, 34 + 56 + 112, 34 + 56 + 113,
34 + 57 + 101, 34 + 57 + 102, 34 + 57 + 103, 34 + 57 + 108, 34 + 57 + 109, 34 + 57 +
110, 34 + 57 + 111, 34 + 57 + 112, 34 + 57 + 113, 34 + 101 + 102, 34 + 101 + 103, 34 +
101 + 108, 34 + 101 + 109, 34 + 101 + 110, 34 + 101 + 111, 34 + 101 + 112, 34 + 101 +
113, 34 + 102 + 103, 34 + 102 + 108, 34 + 102 + 109, 34 + 102 + 110, 34 + 102 + 111, 34 +
102 + 112, 34 + 102 + 113, 34 + 103 + 108, 34 + 103 + 109, 34 + 103 + 110, 34 + 103 +
111, 34 + 103 + 112, 34 + 103 + 113, 34 + 108 + 109, 34 + 108 + 110, 34 + 108 + 111, 34 +
108 + 112, 34 + 108 + 113, 34 + 109 + 110, 34 + 109 + 111, 34 + 109 + 112, 34 + 109 +
113, 34 + 110 + 111, 34 + 110 + 112, 34 + 110 + 113, 34 + 111 + 112, 34 + 111 + 113, 34 +
112 + 113, 50 + 51 + 52, 50 + 51 + 53, 50 + 51 + 55, 50 + 51 + 56, 50 + 51 + 57, 50 +
51 + 101, 50 + 51 + 102, 50 + 51 + 103, 50 + 51 + 108, 50 + 51 + 109, 50 + 51 + 110, 50 +
51 + 111, 50 + 51 + 112, 50 + 51 + 113, 50 + 52 + 53, 50 + 52 + 55, 50 + 52 + 56, 50 +
52 + 57, 50 + 52 + 101, 50 + 52 + 102, 50 + 52 + 103, 50 + 52 + 108, 50 + 52 + 109, 50 +
52 + 110, 50 + 52 + 111, 50 + 52 + 112, 50 + 52 + 113, 50 + 53 + 55, 50 + 53 + 56, 50 +
53 + 57, 50 + 53 + 101, 50 + 53 + 102, 50 + 53 + 103, 50 + 53 + 108, 50 + 53 + 109, 50 +
53 + 110, 50 + 53 + 111, 50 + 53 + 112, 50 + 53 + 113, 50 + 55 + 56, 50 + 55 + 57, 50 +
55 + 101, 50 + 55 + 102, 50 + 55 + 103, 50 + 55 + 108, 50 + 55 + 109, 50 + 55 + 110, 50 +
55 + 111, 50 + 55 + 112, 50 + 55 + 113, 50 + 56 + 57, 50 + 56 + 101, 50 + 56 + 102, 50 +
56 + 103, 50 + 56 + 108, 50 + 56 + 109, 50 + 56 + 110, 50 + 56 + 111, 50 + 56 + 112, TABLE 3-continued Exemplary Combinations of Amino Acid Positions in SEQ
ID NO: 105 that can be Substituted with Histidine 50 + 56 + 113, 50 + 57 + 101, 50 + 57 + 102, 50 + 57 + 103, 50 + 57 + 108, 50 + 57 +
109, 50 + 57 + 110, 50 + 57 + 111, 50 + 57 + 112, 50 + 57 + 113, 50 + 101 + 102, 50 +
101 + 103, 50 + 101 + 108, 50 + 101 + 109, 50 + 101 + 110, 50 + 101 + 111, 50 + 101 +
112, 50 + 101 + 113, 50 + 102 + 103, 50 + 102 + 108, 50 + 102 + 109, 50 + 102 + 110, 50 +
102 + 111, 50 + 102 + 112, 50 + 102 + 113, 50 + 103 + 108, 50 + 103 + 109, 50 + 103 +
110, 50 + 103 + 111, 50 + 103 + 112, 50 + 103 + 113, 50 + 108 + 109, 50 + 108 + 110, 50 +
108 + 111, 50 + 108 + 112, 50 + 108 + 113, 50 + 109 + 110, 50 + 109 + 111, 50 + 109 +
112, 50 + 109 + 113, 50 + 110 + 111, 50 + 110 + 112, 50 + 110 + 113, 50 + 111 + 112, 50 +
111 + 113, 50 + 112 + 113, 51 + 52 + 53, 51 + 52 + 55, 51 + 52 + 56, 51 + 52 + 57, 51 +
52 + 101, 51 + 52 + 102, 51 + 52 + 103, 51 + 52 + 108, 51 + 52 + 109, 51 + 52 + 110, 51 +
52 + 111, 51 + 52 + 112, 51 + 52 + 113, 51 + 53 + 55, 51 + 53 + 56, 51 + 53 + 57, 51 +
53 + 101, 51 + 53 + 102, 51 + 53 + 103, 51 + 53 + 108, 51 + 53 + 109, 51 + 53 + 110, 51 +
53 + 111, 51 + 53 + 112, 51 + 53 + 113, 51 + 55 + 56, 51 + 55 + 57, 51 + 55 + 101, 51 +
55 + 102, 51 + 55 + 103, 51 + 55 + 108, 51 + 55 + 109, 51 + 55 + 110, 51 + 55 + 111, 51 +
55 + 112, 51 + 55 + 113, 51 + 56 + 57, 51 + 56 + 101, 51 + 56 + 102, 51 + 56 + 103, 51 +
56 + 108, 51 + 56 + 109, 51 + 56 + 110, 51 + 56 + 111, 51 + 56 + 112, 51 + 56 + 113,
51 + 57 + 101, 51 + 57 + 102, 51 + 57 + 103, 51 + 57 + 108, 51 + 57 + 109, 51 + 57 +
110, 51 + 57 + 111, 51 + 57 + 112, 51 + 57 + 113, 51 + 101 + 102, 51 + 101 + 103, 51 +
101 + 108, 51 + 101 + 109, 51 + 101 + 110, 51 + 101 + 111, 51 + 101 + 112, 51 + 101 +
113, 51 + 102 + 103, 51 + 102 + 108, 51 + 102 + 109, 51 + 102 + 110, 51 + 102 + 111, 51 +
102 + 112, 51 + 102 + 113, 51 + 103 + 108, 51 + 103 + 109, 51 + 103 + 110, 51 + 103 +
111, 51 + 103 + 112, 51 + 103 + 113, 51 + 108 + 109, 51 + 108 + 110, 51 + 108 + 111, 51 +
108 + 112, 51 + 108 + 113, 51 + 109 + 110, 51 + 109 + 111, 51 + 109 + 112, 51 + 109 +
113, 51 + 110 + 111, 51 + 110 + 112, 51 + 110 + 113, 51 + 111 + 112, 51 + 111 + 113, 51 +
112 + 113, 52 + 53 + 55, 52 + 53 + 56, 52 + 53 + 57, 52 + 53 + 101, 52 + 53 + 102, 52 +
53 + 103, 52 + 53 + 108, 52 + 53 + 109, 52 + 53 + 110, 52 + 53 + 111, 52 + 53 + 112, 52 +
53 + 113, 52 + 55 + 56, 52 + 55 + 57, 52 + 55 + 101, 52 + 55 + 102, 52 + 55 + 103, 52 +
55 + 108, 52 + 55 + 109, 52 + 55 + 110, 52 + 55 + 111, 52 + 55 + 112, 52 + 55 + 113, 52 +
56 + 57, 52 + 56 + 101, 52 + 56 + 102, 52 + 56 + 103, 52 + 56 + 108, 52 + 56 + 109, 52 +
56 + 110, 52 + 56 + 111, 52 + 56 + 112, 52 + 56 + 113, 52 + 57 + 101, 52 + 57 + 102,
52 + 57 + 103, 52 + 57 + 108, 52 + 57 + 109, 52 + 57 + 110, 52 + 57 + 111, 52 + 57 +
112, 52 + 57 + 113, 52 + 101 + 102, 52 + 101 + 103, 52 + 101 + 108, 52 + 101 + 109, 52 +
101 + 110, 52 + 101 + 111, 52 + 101 + 112, 52 + 101 + 113, 52 + 102 + 103, 52 + 102 +
108, 52 + 102 + 109, 52 + 102 + 110, 52 + 102 + 111, 52 + 102 + 112, 52 + 102 + 113, 52 +
103 + 108, 52 + 103 + 109, 52 + 103 + 110, 52 + 103 + 111, 52 + 103 + 112, 52 + 103 +
113, 52 + 108 + 109, 52 + 108 + 110, 52 + 108 + 111, 52 + 108 + 112, 52 + 108 + 113, 52 +
109 + 110, 52 + 109 + 111, 52 + 109 + 112, 52 + 109 + 113, 52 + 110 + 111, 52 + 110 +
112, 52 + 110 + 113, 52 + 111 + 112, 52 + 111 + 113, 52 + 112 + 113, 53 + 55 + 56, 53 +
55 + 57, 53 + 55 + 101, 53 + 55 + 102, 53 + 55 + 103, 53 + 55 + 108, 53 + 55 + 109, 53 +
55 + 110, 53 + 55 + 111, 53 + 55 + 112, 53 + 55 + 113, 53 + 56 + 57, 53 + 56 + 101, 53 +
56 + 102, 53 + 56 + 103, 53 + 56 + 108, 53 + 56 + 109, 53 + 56 + 110, 53 + 56 + 111, 53 +
56 + 112, 53 + 56 + 113, 53 + 57 + 101, 53 + 57 + 102, 53 + 57 + 103, 53 + 57 + 108,
53 + 57 + 109, 53 + 57 + 110, 53 + 57 + 111, 53 + 57 + 112, 53 + 57 + 113, 53 + 101 +
102, 53 + 101 + 103, 53 + 101 + 108, 53 + 101 + 109, 53 + 101 + 110, 53 + 101 + 111, 53 +
101 + 112, 53 + 101 + 113, 53 + 102 + 103, 53 + 102 + 108, 53 + 102 + 109, 53 + 102 +
110, 53 + 102 + 111, 53 + 102 + 112, 53 + 102 + 113, 53 + 103 + 108, 53 + 103 + 109, 53 +
103 + 110, 53 + 103 + 111, 53 + 103 + 112, 53 + 103 + 113, 53 + 108 + 109, 53 + 108 +
110, 53 + 108 + 111, 53 + 108 + 112, 53 + 108 + 113, 53 + 109 + 110, 53 + 109 + 111, 53 +
109 + 112, 53 + 109 + 113, 53 + 110 + 111, 53 + 110 + 112, 53 + 110 + 113, 53 + 111 +
112, 53 + 111 + 113, 53 + 112 + 113, 55 + 56 + 57, 55 + 56 + 101, 55 + 56 + 102, 55 + 56 +
103, 55 + 56 + 108, 55 + 56 + 109, 55 + 56 + 110, 55 + 56 + 111, 55 + 56 + 112, 55 +
56 + 113, 55 + 57 + 101, 55 + 57 + 102, 55 + 57 + 103, 55 + 57 + 108, 55 + 57 + 109, 55 +
57 + 110, 55 + 57 + 111, 55 + 57 + 112, 55 + 57 + 113, 55 + 101 + 102, 55 + 101 + 103,
55 + 101 + 108, 55 + 101 + 109, 55 + 101 + 110, 55 + 101 + 111, 55 + 101 + 112, 55 +
101 + 113, 55 + 102 + 103, 55 + 102 + 108, 55 + 102 + 109, 55 + 102 + 110, 55 + 102 +
111, 55 + 102 + 112, 55 + 102 + 113, 55 + 103 + 108, 55 + 103 + 109, 55 + 103 + 110, 55 +
103 + 111, 55 + 103 + 112, 55 + 103 + 113, 55 + 108 + 109, 55 + 108 + 110, 55 + 108 +
111, 55 + 108 + 112, 55 + 108 + 113, 55 + 109 + 110, 55 + 109 + 111, 55 + 109 + 112, 55 +
109 + 113, 55 + 110 + 111, 55 + 110 + 112, 55 + 110 + 113, 55 + 111 + 112, 55 + 111 +
113, 55 + 112 + 113, 56 + 57 + 101, 56 + 57 + 102, 56 + 57 + 103, 56 + 57 + 108, 56 + 57 +
109, 56 + 57 + 110, 56 + 57 + 111, 56 + 57 + 112, 56 + 57 + 113, 56 + 101 + 102, 56 +
101 + 103, 56 + 101 + 108, 56 + 101 + 109, 56 + 101 + 110, 56 + 101 + 111, 56 + 101 +
112, 56 + 101 + 113, 56 + 102 + 103, 56 + 102 + 108, 56 + 102 + 109, 56 + 102 + 110, 56 +
102 + 111, 56 + 102 + 112, 56 + 102 + 113, 56 + 103 + 108, 56 + 103 + 109, 56 + 103 +
110, 56 + 103 + 111, 56 + 103 + 112, 56 + 103 + 113, 56 + 108 + 109, 56 + 108 + 110, 56 +
108 + 111, 56 + 108 + 112, 56 + 108 + 113, 56 + 109 + 110, 56 + 109 + 111, 56 + 109 +
112, 56 + 109 + 113, 56 + 110 + 111, 56 + 110 + 112, 56 + 110 + 113, 56 + 111 + 112, 56 +
111 + 113, 56 + 112 + 113, 57 + 101 + 102, 57 + 101 + 103, 57 + 101 + 108, 57 + 101 +
109, 57 + 101 + 110, 57 + 101 + 111, 57 + 101 + 112, 57 + 101 + 113, 57 + 102 + 103, 57 +
102 + 108, 57 + 102 + 109, 57 + 102 + 110, 57 + 102 + 111, 57 + 102 + 112, 57 + 102 +
113, 57 + 103 + 108, 57 + 103 + 109, 57 + 103 + 110, 57 + 103 + 111, 57 + 103 + 112, 57 +
103 + 113, 57 + 108 + 109, 57 + 108 + 110, 57 + 108 + 112, 57 + 108 +
113, 57 + 109 + 110, 57 + 109 + 111, 57 + 109 + 112, 57 + 109 + 113, 57 + 110 + 111, 57 +
110 + 112, 57 + 110 + 113, 57 + 111 + 112, 57 + 111 + 113, 57 + 112 + 113, 101 + 102 +
103, 101 + 102 + 108, 101 + 102 + 109, 101 + 102 + 110, 101 + 102 + 111, 101 + 102 +
112, 101 + 102 + 113, 101 + 103 + 108, 101 + 103 + 109, 101 + 103 + 110, 101 + 103 +
111, 101 + 103 + 112, 101 + 103 + 113, 101 + 108 + 109, 101 + 108 + 110, 101 + 108 +

TABLE 3-continued

Exemplary Combinations of Amino Acid Positions in SEQ
ID NO: 105 that can be Substituted with Histidine 111, 101 + 108 + 112, 101 + 108 + 113, 101 + 109 + 110, 101 + 109 + 111, 101 + 109 +
112, 101 + 109 + 113, 101 + 110 + 111, 101 + 110 + 112, 101 + 110 + 113, 101 + 111 +
112, 101 + 111 + 113, 101 + 112 + 113, 102 + 103 + 108, 102 + 103 + 109, 102 + 103 +
110, 102 + 103 + 111, 102 + 103 + 112, 102 + 103 + 113, 102 + 108 + 109, 102 + 108 +
110, 102 + 108 + 111, 102 + 108 + 112, 102 + 108 + 113, 102 + 109 + 110, 102 + 109 +
111, 102 + 109 + 112, 102 + 109 + 113, 102 + 110 + 111, 102 + 110 + 112, 102 + 110 +
113, 102 + 111 + 112, 102 + 111 + 113, 102 + 112 + 113, 103 + 108 + 109, 103 + 108 +
110, 103 + 108 + 111, 103 + 108 + 112, 103 + 108 + 113, 103 + 109 + 110, 103 + 109 +
111, 103 + 109 + 112, 103 + 109 + 113, 103 + 110 + 111, 103 + 110 + 112, 103 + 110 +
113, 103 + 111 + 112, 103 + 111 + 113, 103 + 112 + 113, 108 + 109 + 110, 108 + 109 +
111, 108 + 109 + 112, 108 + 109 + 113, 108 + 110 + 111, 108 + 110 + 112, 108 + 110 +
113, 108 + 111 + 112, 108 + 111 + 113, 108 + 112 + 113, 109 + 110 + 111, 109 + 110 +
112, 109 + 110 + 113, 109 + 111 + 112, 109 + 111 + 113, 109 + 112 + 113, 110 + 111 +
112, 110 + 111 + 113, 110 + 112 + 113, 111 + 112 + 113

In some examples of any of the ABPCs described herein, a light chain variable domain includes a light chain variable domain that is at least 90% (e.g., at least 92%, at least 94%, at least 96%, at least 98%, at least 99%, or 100%) identical to SEQ ID NO: 106, where the light chain variable domain includes a histidine at any of the specific combinations of one or more amino acid positions in SEQ ID NO: 106 listed in Table 4.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 106, where the light chain variable domain includes an alanine at position 91 in SEQ ID NO: 106.

In some examples of any of the ABPCs described herein the first antigen-binding domain includes: a light chain variable domain that is at least 90% (e.g., at least 92%, at least 94%, at least 96%, at least 98%, at least 99%, or 100%) identical to SEQ ID NO: 106, where the light chain variable domain includes an alanine at position 91 in SEQ ID NO: 2, and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 105 selected from the group consisting of: 29, 33, 34, 50, 51, 52, 53, 55, 56, 57, 101, 102, 103, 108, 109, 110, 111, 112, and 113.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 106, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 106 selected from the group consisting of: 28, 29, 30, 31, 50, 92, 93, 94, 95, and 96, and where the light chain variable domain includes an alanine at position 91 in SEQ ID NO: 106. In some examples of any of the ABPCs described herein the first antigen-binding domain includes: a light chain variable domain that is at least 90% (e.g., at least 92%, at least 94%, at least 96%, at least 98%, at least 99%, or 100%) identical to SEQ ID NO: 106, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 106 selected from the group consisting of: 28, 29, 30, 31, 50, 92, 93, 94, 95, and 96, and where the light chain variable domain includes an alanine at position 91 in SEQ ID NO: 106, and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 105 selected from the group consisting of: 29, 33, 34, 50, 51, 52, 53, 55, 56, 57, 101, 102, 103, 108, 109, 110, 111, 112, and 113.

In some examples of any of the ABPCs described herein, a light chain variable domain includes a light chain variable domain that is at least 90% (e.g., at least 92%, at least 94%, at least 96%, at least 98%, at least 99%, or 100%) identical to SEQ ID NO: 106, where the light chain variable domain includes a histidine at any of the specific combinations of one or more amino acid positions in SEQ ID NO: 106 listed in Table 4 and where the light chain variable domain includes an alanine at position 91 of SEQ ID NO: 106.

TABLE 4

Exemplary Combinations of Amino Acid Positions in SEQ
ID NO: 106 that can be Substituted with Histidine 28 + 29, 28 + 30, 28 + 31, 28 + 50, 28 + 92, 28 + 93, 28 + 94, 28 + 95, 28 + 96, 29 + 30,
29 + 31, 29 + 50, 29 + 92, 29 + 93, 29 + 94, 29 + 95, 29 + 96, 30 + 31, 30 + 50, 30 + 92,
30 + 93, 30 + 94, 30 + 95, 30 + 96, 31 + 50, 31 + 92, 31 + 93, 31 + 94, 31 + 95, 31 + 96,
50 + 92, 50 + 93, 50 + 94, 50 + 95, 50 + 96, 92 + 93, 92 + 94, 92 + 95, 92 + 96, 93 + 94,
93 + 95, 93 + 96, 94 + 95, 94 + 96, 95 + 96, 28 + 29 + 30, 28 + 29 + 31, 28 + 29 + 50, 28 +
29 + 92, 28 + 29 + 93, 28 + 29 + 94, 28 + 29 + 95, 28 + 29 + 96, 28 + 30 + 31, 28 + 30 +
50, 28 + 30 + 92, 28 + 30 + 93, 28 + 30 + 94, 28 + 30 + 95, 28 + 30 + 96, 28 + 31 + 50, 28 +
31 + 92, 28 + 31 + 93, 28 + 31 + 94, 28 + 31 + 95, 28 + 31 + 96, 28 + 50 + 92, 28 + 50 +

TABLE 4-continued

Exemplary Combinations of Amino Acid Positions in SEQ
ID NO: 106 that can be Substituted with Histidine 93, 28 + 50 + 94, 28 + 50 + 95, 28 + 50 + 96, 28 + 92 + 93, 28 + 92 + 94, 28 + 92 + 95, 28 +
92 + 96, 28 + 93 + 94, 28 + 93 + 95, 28 + 93 + 96, 28 + 94 + 95, 28 + 94 + 96, 28 + 95 +
96, 29 + 30 + 31, 29 + 30 + 50, 29 + 30 + 92, 29 + 30 + 93, 29 + 30 + 94, 29 + 30 + 95, 29 +
30 + 96, 29 + 31 + 50, 29 + 31 + 92, 29 + 31 + 93, 29 + 31 + 94, 29 + 31 + 95, 29 + 31 +
96, 29 + 50 + 92, 29 + 50 + 93, 29 + 50 + 94, 29 + 50 + 95, 29 + 50 + 96, 29 + 92 + 93, 29 +
92 + 94, 29 + 92 + 95, 29 + 92 + 96, 29 + 93 + 94, 29 + 93 + 95, 29 + 93 + 96, 29 + 94 +
95, 29 + 94 + 96, 29 + 95 + 96, 30 + 31 + 50, 30 + 31 + 92, 30 + 31 + 93, 30 + 31 + 94, 30 +
31 + 95, 30 + 31 + 96, 30 + 50 + 92, 30 + 50 + 93, 30 + 50 + 94, 30 + 50 + 95, 30 + 50 +
96, 30 + 92 + 93, 30 + 92 + 94, 30 + 92 + 95, 30 + 92 + 96, 30 + 93 + 94, 30 + 93 + 95, 30 +
93 + 96, 30 + 94 + 95, 30 + 94 + 96, 30 + 95 + 96, 31 + 50 + 92, 31 + 50 + 93, 31 + 50 +
94, 31 + 50 + 95, 31 + 50 + 96, 31 + 92 + 93, 31 + 92 + 94, 31 + 92 + 95, 31 + 92 + 96, 31 +
93 + 94, 31 + 93 + 95, 31 + 93 + 96, 31 + 94 + 95, 31 + 94 + 96, 31 + 95 + 96, 50 + 92 +
93, 50 + 92 + 94, 50 + 92 + 95, 50 + 92 + 96, 50 + 93 + 94, 50 + 93 + 95, 50 + 93 + 96, 50 +
94 + 95, 50 + 94 + 96, 50 + 95 + 96, 92 + 93 + 94, 92 + 93 + 95, 92 + 93 + 96, 92 + 94 +
95, 92 + 94 + 96, 92 + 95 + 96, 93 + 94 + 95, 93 + 94 + 96, 93 + 95 + 96, 94 + 95 + 96, In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3; and a light chain variable domain that that is at least 90% (e.g., at least 92%, at least 94%, at least 96%, at least 98%, at least 99%, or 100%) identical to SEQ ID NO: 106, where the light chain variable domain includes a histidine at any of the specific combinations of one or more amino acid positions in SEQ ID NO: 106 listed in Table 4.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3, and where the heavy chain variable domain includes an alanine at position 35 in SEQ ID NO: 105; and a light chain variable domain that that is at least 90% (e.g., at least 92%, at least 94%, at least 96%, at least 98%, at least 99%, or 100%) identical to SEQ ID NO: 106, where the light chain variable domain includes a histidine at any of the specific combinations of one or more amino acid positions in SEQ ID NO: 106 listed in Table 4.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 106, where the light chain variable domain includes a histidine at any of the specific combinations of one or more amino acid positions in SEQ ID NO: 106 listed in Table 4, and where the light chain variable domain includes an alanine at position 91 in SEQ ID NO: 106; and a heavy chain variable domain that that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 28 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain comprising SEQ ID NO: 106, and a heavy chain variable domain that is at least 90% identical (e.g., at least 92%, at least 94%, at least 96%, at least 98%, at least 99%, or 100%) identical to SEQ ID NO: 105, where the heavy chain variable domain includes a histidine at any of the specific combinations of one or more (e.g., two, three, four, five, six, seven, eight, nine, or ten) amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 29 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 30 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 31 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 50 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes an alanine at position 91 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 92 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 93 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 94 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 95 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain comprises a light chain variable domain that is at least 90% identical to SEQ ID NO: 106, wherein the light chain variable domain includes a histidine at position 96 in SEQ ID NO: 106; and a heavy chain variable domain that is at least 90% (e.g., at least 92%, at least 94%, at least 96%, at least 98%, at least 99%, or 100%) identical to SEQ ID NO: 105, where the heavy chain variable domain includes a histidine at any of the specific combinations of one or more amino acid positions in SEQ ID NO: 105 listed in Table 3.

In some examples of any of the ABPCs described herein, the first antigen-binding domain includes a heavy chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a light chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a heavy chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) histidines substituted with an alanine; and a light chain variable domain of STRO-002 with one or more (e.g., one, two, three, four, five, six, seven, eight, nine, ten, eleven, twelve, thirteen, fourteen, fifteen, sixteen, seventeen, eighteen, nineteen, or twenty) histidine (s) substituted with an alanine. In some examples of any of the ABPCs described herein, the heavy chain variable domain of STRO-002 comprises SEQ ID NO: 105. In some examples of any of the ABPCs described herein, the light chain variable domain of STRO-002 comprises SEQ ID NO: 106.

In some examples of any of the ABPCs described herein, the first antigen-binding domain comprises a heavy chain variable domain comprising a CDR1, a CDR2, and a CDR3 of SEQ ID NO: 107, SEQ ID NO: 108, and SEQ ID NO: 109, respectively, with collectively a total of one or more (e.g., one, two, three, four, five, six, seven, eight, nine, or ten) histidine(s) in SEQ ID NOs: 107-109 substituted with an alanine. In some examples of any of the ABPCs described herein, the first antigen-binding domain comprises a light chain variable domain comprising a CDR1, a CDR2, and a CDR3 of SEQ ID NO: 110, SEQ ID NO: 111, and SEQ ID NO: 112, respectively, with collectively a total of one or more (e.g., one, two, three, four, five, six, seven, eight, nine, or ten) histidine(s) in SEQ ID NOs: 110-112 substituted with an alanine. In some examples of any of the ABPCs described herein, the first antigen-binding domain includes: a heavy chain variable domain comprising a CDR1, a CDR2, and a CDR3 of SEQ ID NO: 107, SEQ ID NO: 108, and SEQ ID NO: 109, respectively, with collectively a total of one or more (e.g., one, two, three, four, five, six, seven, eight, nine, or ten) histidine(s) in SEQ ID NOs: 107-109 substituted with an alanine; and a light chain variable domain comprising a CDR1, a CDR2, and a CDR3 of SEQ ID NO: 110, SEQ ID NO: 111, and SEQ ID NO: 112, respectively, with collectively a total of one or more (e.g., one, two, three, four, five, six, seven, eight, nine, or ten) histidine(s) in SEQ ID NOs: 110-112 substituted with an alanine.

In some examples of any of the ABPCs described herein, the first antigen-binding domain comprises a heavy chain variable domain of SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain of SEQ ID NO: 106, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, or SEQ ID NO: 183.

In some examples of any of the ABPCs described herein, the first antigen-binding domain includes a light chain variable domain comprising SEQ ID NO: 106, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 157, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 158, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 159, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 160, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 161, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 162, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 163, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 164, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 165, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 166, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 167, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 168, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 169, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 170, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 171, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 172, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 173, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 174, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 175, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 176, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 177, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 178, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 179, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 180, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO:

119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 181, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 182, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a light chain variable domain comprising SEQ ID NO: 183, and a heavy chain variable domain comprising SEQ ID NO: 105, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, or SEQ ID NO: 156.

In some examples of any of the ABPCs described herein, the first antigen-binding domain includes a heavy chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a light chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a heavy chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine; and a light chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the heavy chain variable domain of farletuzumab comprises SEQ ID NO: 184. In some examples of any of the ABPCs described herein, the light chain variable domain of farletuzumab comprises SEQ ID NO: 185.

In some examples of any of the ABPCs described herein, the first antigen-binding domain comprises a heavy chain variable domain comprising a CDR1, a CDR2, and a CDR3 of SEQ ID NO: 186, SEQ ID NO: 187, and SEQ ID NO: 188, respectively, with collectively a total of one or more (e.g., one, two, three, four, five, six, seven, eight, nine, or ten) amino acid positions in SEQ ID NOs: 186-188 substituted with a histidine. In some examples of any of the ABPCs described herein, the first antigen-binding domain comprises a light chain variable domain comprising a CDR1, a CDR2, and a CDR3 of SEQ ID NO: 189, SEQ ID NO: 190, and SEQ ID NO: 191, respectively, with collectively a total of one or more (e.g., one, two, three, four, five, six, seven, eight, nine, or ten) amino acid positions in SEQ ID NOs: 189-191 substituted with a histidine. In some examples of any of the ABPCs described herein, the first antigen-binding domain includes: a heavy chain variable domain comprising a CDR1, a CDR2, and a CDR3 of SEQ ID NO: 186, SEQ ID NO: 187, and SEQ ID NO: 188, respectively, with collectively a total of one or more (e.g., one, two, three, four, five, six, seven, eight, nine, or ten) amino acid positions in SEQ ID NOs: 186-188 substituted with a histidine; and a light chain variable domain comprising a CDR1, a CDR2, and a CDR3 of SEQ ID NO: 189, SEQ ID NO: 190, and SEQ ID NO: 191, respectively, with collectively a total of one or more (e.g., one, two, three, four, five, six, seven, eight, nine, or ten) amino acid positions in SEQ ID NOs: 189-191 substituted with a histidine.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 184 selected from the group consisting of: 26, 27, 28, 29, 30, 32, 33, 34, 53, 56, 57, 59, 62, 63, 103, and 105. In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 185, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 185 selected from the group consisting of: 29, 33, 34, 51, 52, 53, 54, 55, 90, 92, 94, 96, 97, 98, 99, and 100. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 184 selected from the group consisting of: 26, 27, 28, 29, 30, 32, 33, 34, 53, 56, 57, 59, 62, 63, 103, and 105, and a light chain variable domain that is at least 90% (e.g., at least 92%, at least 94%, at least 96%, at least 98%, at least 99%, or 100%) identical to SEQ ID NO: 185, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 185 selected from the group consisting of: 29, 33, 34, 51, 52, 53, 54, 55, 90, 92, 94, 96, 97, 98, 99, and 100.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 184, where the heavy chain variable domain includes an alanine at position 99 in SEQ ID NO: 184.

In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 184, where the heavy chain variable domain includes an alanine at position 99 in SEQ ID NO: 184, and a light chain variable domain that is at least 90% (e.g., at least 92%, at least 94%, at least 96%, at least 98%, at least 99%, or 100%) identical to SEQ ID NO: 185, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 185 selected from the group consisting of: 29, 33, 34, 51, 52, 53, 54, 55, 90, 92, 94, 96, 97, 98, 99, and 100.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 184 selected from the group consisting of: 26, 27, 28, 29, 30, 32, 33, 34, 53, 56, 57, 59, 62, 63, 103, and 105, and where the heavy chain variable domain includes an alanine at position 99 in SEQ ID NO: 184. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 184 selected from the group consisting of: 26, 27, 28, 29, 30, 32, 33, 34, 53, 56, 57, 59, 62, 63, 103, and 105, and where the heavy chain variable domain includes an alanine at position 99 in SEQ ID NO:

184, and a light chain variable domain that is at least 90% (e.g., at least 92%, at least 94%, at least 96%, at least 98%, at least 99%, or 100%) identical to SEQ ID NO: 185, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 185 selected from the group consisting of: 29, 33, 34, 51, 52, 53, 54, 55, 90, 92, 94, 96, 97, 98, 99, and 100.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5 and where the heavy chain variable domain includes an alanine at position 99 of SEQ ID NO: 184.

TABLE 5

Exemplary Combinations of Amino Acid Positions in SEQ
ID NO: 184 that can be Substituted with Histidine 26 + 27, 26 + 28, 26 + 29, 26 + 30, 26 + 32, 26 + 33, 26 + 34, 26 + 53, 26 + 56, 26 + 57,
26 + 59, 26 + 62, 26 + 63, 26 + 103, 26 + 105, 27 + 28, 27 + 29, 27 + 30, 27 + 32, 27 +
33, 27 + 34, 27 + 53, 27 + 56, 27 + 57, 27 + 59, 27 + 62, 27 + 63, 27 + 103, 27 + 105, 28 +
29, 28 + 30, 28 + 32, 28 + 33, 28 + 34, 28 + 53, 28 + 56, 28 + 57, 28 + 59, 28 + 62, 28 +
63, 28 + 103, 28 + 105, 29 + 30, 29 + 32, 29 + 33, 29 + 34, 29 + 53, 29 + 56, 29 + 57,
29 + 59, 29 + 62, 29 + 63, 29 + 103, 29 + 105, 30 + 32, 30 + 33, 30 + 34, 30 + 53, 30 +
56, 30 + 57, 30 + 59, 30 + 62, 30 + 63, 30 + 103, 30 + 105, 32 + 33, 32 + 34, 32 + 53, 32 +
56, 32 + 57, 32 + 59, 32 + 62, 32 + 63, 32 + 103, 32 + 105, 33 + 34, 33 + 53, 33 + 56,
33 + 57, 33 + 59, 33 + 62, 33 + 63, 33 + 103, 33 + 105, 34 + 53, 34 + 56, 34 + 57, 34 +
59, 34 + 62, 34 + 63, 34 + 103, 34 + 105, 53 + 56, 53 + 57, 53 + 59, 53 + 62, 53 + 63, 53 +
103, 53 + 105, 56 + 57, 56 + 59, 56 + 62, 56 + 63, 56 + 103, 56 + 105, 57 + 59, 57 +
62, 57 + 63, 57 + 103, 57 + 105, 59 + 62, 59 + 63, 59 + 103, 59 + 105, 62 + 63, 62 + 103,
62 + 105, 63 + 103, 63 + 105, 103 + 105, 26 + 27 + 28, 26 + 27 + 29, 26 + 27 + 30, 26 +
27 + 32, 26 + 27 + 33, 26 + 27 + 34, 26 + 27 + 53, 26 + 27 + 56, 26 + 27 + 57, 26 + 27 +
59, 26 + 27 + 62, 26 + 27 + 63, 26 + 27 + 103, 26 + 27 + 105, 26 + 28 + 29, 26 + 28 +
30, 26 + 28 + 32, 26 + 28 + 33, 26 + 28 + 34, 26 + 28 + 53, 26 + 28 + 56, 26 + 28 + 57,
26 + 28 + 59, 26 + 28 + 62, 26 + 28 + 63, 26 + 28 + 103, 26 + 28 + 105, 26 + 29 + 30, 26 +
29 + 32, 26 + 29 + 33, 26 + 29 + 34, 26 + 29 + 53, 26 + 29 + 56, 26 + 29 + 57, 26 + 29 +
59, 26 + 29 + 62, 26 + 29 + 63, 26 + 29 + 103, 26 + 29 + 105, 26 + 30 + 32, 26 + 30 +
33, 26 + 30 + 34, 26 + 30 + 53, 26 + 30 + 56, 26 + 30 + 57, 26 + 30 + 59, 26 + 30 + 62,
26 + 30 + 63, 26 + 30 + 103, 26 + 30 + 105, 26 + 32 + 33, 26 + 32 + 34, 26 + 32 + 53, 26 +
32 + 56, 26 + 32 + 57, 26 + 32 + 59, 26 + 32 + 62, 26 + 32 + 63, 26 + 32 + 103, 26 +
32 + 105, 26 + 33 + 34, 26 + 33 + 53, 26 + 33 + 56, 26 + 33 + 57, 26 + 33 + 59, 26 + 33 +
62, 26 + 33 + 63, 26 + 33 + 103, 26 + 33 + 105, 26 + 34 + 53, 26 + 34 + 56, 26 + 34 +
57, 26 + 34 + 59, 26 + 34 + 62, 26 + 34 + 63, 26 + 34 + 103, 26 + 34 + 105, 26 + 53 +
56, 26 + 53 + 57, 26 + 53 + 59, 26 + 53 + 62, 26 + 53 + 63, 26 + 53 + 103, 26 + 53 +
105, 26 + 56 + 57, 26 + 56 + 59, 26 + 56 + 62, 26 + 56 + 63, 26 + 56 + 103, 26 + 56 +
105, 26 + 57 + 59, 26 + 57 + 62, 26 + 57 + 63, 26 + 57 + 103, 26 + 57 + 105, 26 + 59 +
62, 26 + 59 + 63, 26 + 59 + 103, 26 + 59 + 105, 26 + 62 + 63, 26 + 62 + 103, 26 + 62 +
105, 26 + 63 + 103, 26 + 63 + 105, 26 + 103 + 105, 27 + 28 + 29, 27 + 28 + 30, 27 + 28 +
32, 27 + 28 + 33, 27 + 28 + 34, 27 + 28 + 53, 27 + 28 + 56, 27 + 28 + 57, 27 + 28 + 59,
27 + 28 + 62, 27 + 28 + 63, 27 + 28 + 103, 27 + 28 + 105, 27 + 29 + 30, 27 + 29 + 32, 27 +
29 + 33, 27 + 29 + 34, 27 + 29 + 53, 27 + 29 + 56, 27 + 29 + 57, 27 + 29 + 59, 27 + 29 +
62, 27 + 29 + 63, 27 + 29 + 103, 27 + 29 + 105, 27 + 30 + 32, 27 + 30 + 33, 27 + 30 +
34, 27 + 30 + 53, 27 + 30 + 56, 27 + 30 + 57, 27 + 30 + 59, 27 + 30 + 62, 27 + 30 + 63,
27 + 30 + 103, 27 + 30 + 105, 27 + 32 + 33, 27 + 32 + 34, 27 + 32 + 53, 27 + 32 + 56, 27 +
32 + 57, 27 + 32 + 59, 27 + 32 + 62, 27 + 32 + 63, 27 + 32 + 103, 27 + 32 + 105, 27 +
33 + 34, 27 + 33 + 53, 27 + 33 + 56, 27 + 33 + 57, 27 + 33 + 59, 27 + 33 + 62, 27 + 33 +
63, 27 + 33 + 103, 27 + 33 + 105, 27 + 34 + 53, 27 + 34 + 56, 27 + 34 + 57, 27 + 34 +
59, 27 + 34 + 62, 27 + 34 + 63, 27 + 34 + 103, 27 + 34 + 105, 27 + 53 + 56, 27 + 53 +
57, 27 + 53 + 59, 27 + 53 + 62, 27 + 53 + 63, 27 + 53 + 103, 27 + 53 + 105, 27 + 56 +
57, 27 + 56 + 59, 27 + 56 + 62, 27 + 56 + 63, 27 + 56 + 103, 27 + 56 + 105, 27 + 57 +
59, 27 + 57 + 62, 27 + 57 + 63, 27 + 57 + 103, 27 + 57 + 105, 27 + 59 + 62, 27 + 59 +
63, 27 + 59 + 103, 27 + 59 + 105, 27 + 62 + 63, 27 + 62 + 103, 27 + 62 + 105, 27 + 63 +
103, 27 + 63 + 105, 27 + 103 + 105, 28 + 29 + 30, 28 + 29 + 32, 28 + 29 + 33, 28 + 29 +
34, 28 + 29 + 53, 28 + 29 + 56, 28 + 29 + 57, 28 + 29 + 59, 28 + 29 + 62, 28 + 29 + 63,
28 + 29 + 103, 28 + 29 + 105, 28 + 30 + 32, 28 + 30 + 33, 28 + 30 + 34, 28 + 30 + 53, 28 +
30 + 56, 28 + 30 + 57, 28 + 30 + 59, 28 + 30 + 62, 28 + 30 + 63, 28 + 30 + 103, 28 +
30 + 105, 28 + 32 + 33, 28 + 32 + 34, 28 + 32 + 53, 28 + 32 + 56, 28 + 32 + 57, 28 + 32 +
59, 28 + 32 + 62, 28 + 32 + 63, 28 + 32 + 103, 28 + 32 + 105, 28 + 33 + 34, 28 + 33 +
53, 28 + 33 + 56, 28 + 33 + 57, 28 + 33 + 59, 28 + 33 + 62, 28 + 33 + 63, 28 + 33 + 103, TABLE 5-continued Exemplary Combinations of Amino Acid Positions in SEQ
ID NO: 184 that can be Substituted with Histidine 28 + 33 + 105, 28 + 34 + 53, 28 + 34 + 56, 28 + 34 + 57, 28 + 34 + 59, 28 + 34 + 62, 28 +
34 + 63, 28 + 34 + 103, 28 + 34 + 105, 28 + 53 + 56, 28 + 53 + 57, 28 + 53 + 59, 28 +
53 + 62, 28 + 53 + 63, 28 + 53 + 103, 28 + 53 + 105, 28 + 56 + 57, 28 + 56 + 59, 28 + 56 +
62, 28 + 56 + 63, 28 + 56 + 103, 28 + 56 + 105, 28 + 57 + 59, 28 + 57 + 62, 28 + 57 +
63, 28 + 57 + 103, 28 + 57 + 105, 28 + 59 + 62, 28 + 59 + 63, 28 + 59 + 103, 28 + 59 +
105, 28 + 62 + 63, 28 + 62 + 103, 28 + 62 + 105, 28 + 63 + 103, 28 + 63 + 105, 28 + 103 +
105, 29 + 30 + 32, 29 + 30 + 33, 29 + 30 + 34, 29 + 30 + 53, 29 + 30 + 56, 29 + 30 +
57, 29 + 30 + 59, 29 + 30 + 62, 29 + 30 + 63, 29 + 30 + 103, 29 + 30 + 105, 29 + 32 +
33, 29 + 32 + 34, 29 + 32 + 53, 29 + 32 + 56, 29 + 32 + 57, 29 + 32 + 59, 29 + 32 + 62,
29 + 32 + 63, 29 + 32 + 103, 29 + 32 + 105, 29 + 33 + 34, 29 + 33 + 53, 29 + 33 + 56, 29 +
33 + 57, 29 + 33 + 59, 29 + 33 + 62, 29 + 33 + 63, 29 + 33 + 103, 29 + 33 + 105, 29 +
34 + 53, 29 + 34 + 56, 29 + 34 + 57, 29 + 34 + 59, 29 + 34 + 62, 29 + 34 + 63, 29 + 34 +
103, 29 + 34 + 105, 29 + 53 + 56, 29 + 53 + 57, 29 + 53 + 59, 29 + 53 + 62, 29 + 53 +
63, 29 + 53 + 103, 29 + 53 + 105, 29 + 56 + 57, 29 + 56 + 59, 29 + 56 + 62, 29 + 56 +
63, 29 + 56 + 103, 29 + 56 + 105, 29 + 57 + 59, 29 + 57 + 62, 29 + 57 + 63, 29 + 57 +
103, 29 + 57 + 105, 29 + 59 + 62, 29 + 59 + 63, 29 + 59 + 103, 29 + 59 + 105, 29 + 62 +
63, 29 + 62 + 103, 29 + 62 + 105, 29 + 63 + 103, 29 + 63 + 105, 29 + 103 + 105, 30 + 32 +
33, 30 + 32 + 34, 30 + 32 + 53, 30 + 32 + 56, 30 + 32 + 57, 30 + 32 + 59, 30 + 32 + 62,
30 + 32 + 63, 30 + 32 + 103, 30 + 32 + 105, 30 + 33 + 34, 30 + 33 + 53, 30 + 33 + 56, 30 +
33 + 57, 30 + 33 + 59, 30 + 33 + 62, 30 + 33 + 63, 30 + 33 + 103, 30 + 33 + 105, 30 +
34 + 53, 30 + 34 + 56, 30 + 34 + 57, 30 + 34 + 59, 30 + 34 + 62, 30 + 34 + 63, 30 + 34 +
103, 30 + 34 + 105, 30 + 53 + 56, 30 + 53 + 57, 30 + 53 + 59, 30 + 53 + 62, 30 + 53 +
63, 30 + 53 + 103, 30 + 53 + 105, 30 + 56 + 57, 30 + 56 + 59, 30 + 56 + 62, 30 + 56 +
63, 30 + 56 + 103, 30 + 56 + 105, 30 + 57 + 59, 30 + 57 + 62, 30 + 57 + 63, 30 + 57 +
103, 30 + 57 + 105, 30 + 59 + 62, 30 + 59 + 63, 30 + 59 + 103, 30 + 59 + 105, 30 + 62 +
63, 30 + 62 + 103, 30 + 62 + 105, 30 + 63 + 103, 30 + 63 + 105, 30 + 103 + 105, 32 + 33 +
34, 32 + 33 + 53, 32 + 33 + 56, 32 + 33 + 57, 32 + 33 + 59, 32 + 33 + 62, 32 + 33 + 63,
32 + 33 + 103, 32 + 33 + 105, 32 + 34 + 53, 32 + 34 + 56, 32 + 34 + 57, 32 + 34 + 59, 32 +
34 + 62, 32 + 34 + 63, 32 + 34 + 103, 32 + 34 + 105, 32 + 53 + 56, 32 + 53 + 57, 32 +
53 + 59, 32 + 53 + 62, 32 + 53 + 63, 32 + 53 + 103, 32 + 53 + 105, 32 + 56 + 57, 32 + 56 +
59, 32 + 56 + 62, 32 + 56 + 63, 32 + 56 + 103, 32 + 56 + 105, 32 + 57 + 59, 32 + 57 +
62, 32 + 57 + 63, 32 + 57 + 103, 32 + 57 + 105, 32 + 59 + 62, 32 + 59 + 63, 32 + 59 +
103, 32 + 59 + 105, 32 + 62 + 63, 32 + 62 + 103, 32 + 62 + 105, 32 + 63 + 103, 32 + 63 +
105, 32 + 103 + 105, 33 + 34 + 53, 33 + 34 + 56, 33 + 34 + 57, 33 + 34 + 59, 33 + 34 +
62, 33 + 34 + 63, 33 + 34 + 103, 33 + 34 + 105, 33 + 53 + 56, 33 + 53 + 57, 33 + 53 +
59, 33 + 53 + 62, 33 + 53 + 63, 33 + 53 + 103, 33 + 53 + 105, 33 + 56 + 57, 33 + 56 +
59, 33 + 56 + 62, 33 + 56 + 63, 33 + 56 + 103, 33 + 56 + 105, 33 + 57 + 59, 33 + 57 +
62, 33 + 57 + 63, 33 + 57 + 103, 33 + 57 + 105, 33 + 59 + 62, 33 + 59 + 63, 33 + 59 +
103, 33 + 59 + 105, 33 + 62 + 63, 33 + 62 + 103, 33 + 62 + 105, 33 + 63 + 103, 33 + 63 +
105, 33 + 103 + 105, 34 + 53 + 56, 34 + 53 + 57, 34 + 53 + 59, 34 + 53 + 62, 34 + 53 +
63, 34 + 53 + 103, 34 + 53 + 105, 34 + 56 + 57, 34 + 56 + 59, 34 + 56 + 62, 34 + 56 +
63, 34 + 56 + 103, 34 + 56 + 105, 34 + 57 + 59, 34 + 57 + 62, 34 + 57 + 63, 34 + 57 +
103, 34 + 57 + 105, 34 + 59 + 62, 34 + 59 + 63, 34 + 59 + 103, 34 + 59 + 105, 34 + 62 +
63, 34 + 62 + 103, 34 + 62 + 105, 34 + 63 + 103, 34 + 63 + 105, 34 + 103 + 105, 53 + 56 +
57, 53 + 56 + 59, 53 + 56 + 62, 53 + 56 + 63, 53 + 56 + 103, 53 + 56 + 105, 53 + 57 +
59, 53 + 57 + 62, 53 + 57 + 63, 53 + 57 + 103, 53 + 57 + 105, 53 + 59 + 62, 53 + 59 +
63, 53 + 59 + 103, 53 + 59 + 105, 53 + 62 + 63, 53 + 62 + 103, 53 + 62 + 105, 53 + 63 +
103, 53 + 63 + 105, 53 + 103 + 105, 56 + 57 + 59, 56 + 57 + 62, 56 + 57 + 63, 56 + 57 +
103, 56 + 57 + 105, 56 + 59 + 62, 56 + 59 + 63, 56 + 59 + 103, 56 + 59 + 105, 56 + 62 +
63, 56 + 62 + 103, 56 + 62 + 105, 56 + 63 + 103, 56 + 63 + 105, 56 + 103 + 105, 57 + 59 +
62, 57 + 59 + 63, 57 + 59 + 103, 57 + 59 + 105, 57 + 62 + 63, 57 + 62 + 103, 57 + 62 +
105, 57 + 63 + 103, 57 + 63 + 105, 57 + 103 + 105, 59 + 62 + 63, 59 + 62 + 103, 59 + 62 +
105, 59 + 63 + 103, 59 + 63 + 105, 59 + 103 + 105, 62 + 63 + 103, 62 + 63 + 105, 62 +
103 + 105, 63 + 103 + 105, In some examples of any of the ABPCs described herein, a light chain variable domain includes a light chain variable domain that is at least 90% (e.g., at least 92%, at least 94%, at least 96%, at least 98%, at least 99%, or 100%) identical to SEQ ID NO: 185, where the light chain variable domain includes a histidine at any of the specific combinations of one or more amino acid positions in SEQ ID NO: 185 listed in Table 6.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 185, where the light chain variable domain includes an alanine at position 35 in SEQ ID NO: 185.

In some examples of any of the ABPCs described herein the first antigen-binding domain includes: a light chain variable domain that is at least 90% (e.g., at least 92%, at least 94%, at least 96%, at least 98%, at least 99%, or 100%) identical to SEQ ID NO: 185, where the light chain variable domain includes an alanine at position 35 in SEQ ID NO: 185, and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 184 selected from the group consisting of: 26, 27, 28, 29, 30, 32, 33, 34, 53, 56, 57, 59, 62, 63, 103, and 105.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 185, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 185 selected from the group consisting of: 29, 33, 34, 51, 52, 53, 54, 55, 90, 92, 94, 96, 97, 98, 99, and 100, and where the light chain variable domain includes an alanine at position 35 in SEQ ID NO: 185. In some examples of any of the ABPCs described herein the first antigen-binding domain includes: a light chain variable domain that is at least 90% (e.g., at least 92%, at least 94%, at least 96%, at least 98%, at least 99%, or 100%) identical to SEQ ID NO: 185, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 185 selected from the group consisting of: 29, 33, 34, 51, 52, 53, 54, 55, 90, 92, 94, 96, 97, 98, 99, and 100, and where the light chain variable domain includes an alanine at position 35 in SEQ ID NO: 185, and a heavy chain variable domain that is at least 90% (e.g., at least 92%, at least 94%, at least 96%, at least 98%, at least 99%, or 100%) identical to SEQ ID NO: 184, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 184 selected from the group consisting of: 26, 27, 28, 29, 30, 32, 33, 34, 53, 56, 57, 59, 62, 63, 103, and 105.

In some examples of any of the ABPCs described herein, a light chain variable domain includes a light chain variable domain that is at least 90% (e.g., at least 92%, at least 94%, at least 96%, at least 98%, at least 99%, or 100%) identical to SEQ ID NO: 185, where the light chain variable domain includes a histidine at any of the specific combinations of one or more amino acid positions in SEQ ID NO: 185 listed in Table 6 and where the light chain variable domain includes an alanine at position 35 of SEQ ID NO: 185.

TABLE 6

| Exemplary Combinations of Amino Acid Positions in SEQ ID NO: 185 that can be Substituted with Histidine |
| --- |
| 29 + 33, 29 + 34, 29 + 51, 29 + 52, 29 + 53, 29 + 54, 29 + 55, 29 + 90, 29 + 92, 29 + 94, 29 + 96, 29 + 97, 29 + 98, 29 + 99, 29 + 100, 33 + 34, 33 + 51, 33 + 52, 33 + 53, 33 + 54, 33 + 55, 33 + 90, 33 + 92, 33 + 94, 33 + 96, 33 + 97, 33 + 98, 33 + 99, 33 + 100, 34 + 51, 34 + 52, 34 + 53, 34 + 54, 34 + 55, 34 + 90, 34 + 92, 34 + 94, 34 + 96, 34 + 97, 34 + 98, 34 + 99, 34 + 100, 51 + 52, 51 + 53, 51 + 54, 51 + 55, 51 + 90, 51 + 92, 51 + 94, 51 + 96, 51 + 97, 51 + 98, 51 + 99, 51 + 100, 52 + 53, 52 + 54, 52 + 55, 52 + 90, 52 + 92, 52 + 94, 52 + 96, 52 + 97, 52 + 98, 52 + 99, 52 + 100, 53 + 54, 53 + 55, 53 + 90, 53 + 92, 53 + 94, 53 + 96, 53 + 97, 53 + 98, 53 + 99, 53 + 100, 54 + 55, 54 + 90, 54 + 92, 54 + 94, 54 + 96, 54 + 97, 54 + 98, 54 + 99, 54 + 100, 55 + 90, 55 + 92, 55 + 94, 55 + 96, 55 + 97, 55 + 98, 55 + 99, 55 + 100, 90 + 92, 90 + 94, 90 + 96, 90 + 97, 90 + 98, 90 + 99, 90 + 100, 92 + 94, 92 + 96, 92 + 97, 92 + 98, 92 + 99, 92 + 100, 94 + 96, 94 + 97, 94 + 98, 94 + 99, 94 + 100, 96 + 97, 96 + 98, 96 + 99, 96 + 100, 97 + 98, 97 + 99, 97 + 100, 98 + 99, 98 + 100, 99 + 100, 29 + 33 + 34, 29 + 33 + 51, 29 + 33 + 52, 29 + 33 + 53, 29 + 33 + 54, 29 + 33 + 55, 29 + 33 + 90, 29 + 33 + 92, 29 + 33 + 94, 29 + 33 + 96, 29 + 33 + 97, 29 + 33 + 98, 29 + 33 + 99, 29 + 33 + 100, 29 + 34 + 51, 29 + 34 + 52, 29 + 34 + 53, 29 + 34 + 54, 29 + 34 + 55, 29 + 34 + 90, 29 + 34 + 92, 29 + 34 + 94, 29 + 34 + 96, 29 + 34 + 97, 29 + 34 + 98, 29 + 34 + 99, 29 + 34 + 100, 29 + 51 + 52, 29 + 51 + 53, 29 + 51 + 54, 29 + 51 + 55, 29 + 51 + 90, 29 + 51 + 92, 29 + 51 + 94, 29 + 51 + 96, 29 + 51 + 97, 29 + 51 + 98, 29 + 51 + 99, 29 + 51 + 100, 29 + 52 + 53, 29 + 52 + 54, 29 + 52 + 55, 29 + 52 + 90, 29 + 52 + 92, 29 + 52 + 94, 29 + 52 + 96, 29 + 52 + 97, 29 + 52 + 98, 29 + 52 + 99, 29 + 52 + 100, 29 + 53 + 54, 29 + 53 + 55, 29 + 53 + 90, 29 + 53 + 92, 29 + 53 + 94, 29 + 53 + 96, 29 + 53 + 97, 29 + 53 + 98, 29 + 53 + 99, 29 + 53 + 100, 29 + 54 + 55, 29 + 54 + 90, 29 + 54 + 92, 29 + 54 + 94, 29 + 54 + 96, 29 + 54 + 97, 29 + 54 + 98, 29 + 54 + 99, 29 + 54 + 100, 29 + 55 + 90, 29 + 55 + 92, 29 + 55 + 94, 29 + 55 + 96, 29 + 55 + 97, 29 + 55 + 98, 29 + 55 + 99, 29 + 55 + 100, 29 + 90 + 92, 29 + 90 + 94, 29 + 90 + 96, 29 + 90 + 97, 29 + 90 + 98, 29 + 90 + 99, 29 + 90 + 100, 29 + 92 + 94, 29 + 92 + 96, 29 + 92 + 97, 29 + 92 + 98, 29 + 92 + 99, 29 + 92 + 100, 29 + 94 + 96, 29 + 94 + 97, 29 + 94 + 98, 29 + 94 + 99, 29 + 94 + 100, 29 + 96 + 97, 29 + 96 + 98, 29 + 96 + 99, 29 + 96 + 100, 29 + 97 + 98, 29 + 97 + 99, 29 + 97 + 100, 29 + 98 + 99, 29 + 98 + 100, 29 + 99 + 100, 33 + 34 + 51, 33 + 34 + 52, 33 + 34 + 53, 33 + 34 + 54, 33 + 34 + 55, 33 + 34 + 90, 33 + 34 + 92, 33 + 34 + 94, 33 + 34 + 96, 33 + 34 + 97, 33 + 34 + 98, 33 + 34 + 99, 33 + 34 + 100, 33 + 51 + 52, 33 + 51 + 53, 33 + 51 + 54, 33 + 51 + 55, 33 + 51 + 90, 33 + 51 + 92, 33 + 51 + 94, 33 + 51 + 96, 33 + 51 + 97, 33 + 51 + 98, 33 + 51 + 99, 33 + 51 + 100, 33 + 52 + 53, 33 + 52 + 54, 33 + 52 + 55, 33 + 52 + 90, 33 + 52 + 92, 33 + 52 + 94, 33 + 52 + 96, 33 + 52 + 97, 33 + 52 + 98, 33 + 52 + 99, 33 + 52 + 100, 33 + 53 + 54, 33 + 53 + 55, 33 + 53 + 90, 33 + 53 + 92, 33 + 53 + 94, 33 + 53 + 96, 33 + 53 + 97, 33 + 53 + 98, 33 + 53 + 99, 33 + 53 + 100, 33 + 54 + 55, 33 + 54 + 90, 33 + 54 + 92, 33 + 54 + 94, 33 + 54 + 96, 33 + 54 + 97, 33 + 54 + 98, 33 + 54 + 99, 33 + 54 + 100, 33 + 55 + 90, 33 + 55 + 92, 33 + 55 + 94, 33 + 55 + 96, 33 + 55 + 97, 33 + 55 + 98, 33 + 55 + 99, 33 + 55 + 100, 33 + 90 + 92, 33 + 90 + 94, 33 + 90 + 96, 33 + 90 + 97, 33 + 90 + 98, 33 + 90 + 99, 33 + 90 + 100, 33 + 92 + 94, 33 + 92 + 96, 33 + 92 + 97, 33 + 92 + 98, 33 + 92 + 99, 33 + 92 + 100, 33 + 94 + 96, 33 + 94 + 97, 33 + 94 + 98, 33 + 94 + 99, 33 + 94 + 100, 33 + 96 + 97, 33 + 96 + 98, 33 + 96 + 99, 33 + 96 + 100, 33 + 97 + 98, 33 + 97 + 99, 33 + 97 + 100, 33 + 98 + 99, 33 + 98 + 100, 33 + 99 + 100, 34 + 51 + 52, 34 + 51 + 53, 34 + 51 + 54, 34 + 51 + 55, 34 + 51 + 90, 34 + 51 + 92, 34 + 51 + 94, 34 + 51 + 96, 34 + 51 + 97, 34 + 51 + 98, 34 + 51 + 99, 34 + 51 + 100, 34 + 52 + 53, 34 + 52 + 54, 34 + 52 + 55, 34 + 52 + 90, 34 + 52 + 92, 34 + 52 + 94, 34 + 52 + 96, 34 + 52 + 97, 34 + 52 + 98, 34 + 52 + 99, 34 + 52 + 100, 34 + 53 + 54, 34 + 53 + 55, 34 + 53 + 90, 34 + 53 + 92, 34 + 53 + 94, 34 + 53 + 96, 34 + 53 + 97, 34 + 53 + 98, 34 + 53 + 99, 34 + 53 + 100, 34 + 54 + 55, 34 + 54 + 90, 34 + 54 + 92, 34 + 54 + 94, 34 + 54 + 96, 34 + 54 + 97, 34 + 54 + 98, 34 + 54 + 99, 34 + 54 + 100, 34 + 55 + 90, 34 + 55 + 92, 34 + 55 + 94, 34 + 55 + 96, 34 + 55 + 97, 34 + 55 + 98, 34 + 55 + 99, 34 + 55 + 100, 34 + 90 + 92, 34 + |

TABLE 6-continued

Exemplary Combinations of Amino Acid Positions in SEQ
ID NO: 185 that can be Substituted with Histidine 90 + 94, 34 + 90 + 96, 34 + 90 + 97, 34 + 90 + 98, 34 + 90 + 99, 34 + 90 + 100, 34 + 92 +
94, 34 + 92 + 96, 34 + 92 + 97, 34 + 92 + 98, 34 + 92 + 99, 34 + 92 + 100, 34 + 94 + 96,
34 + 94 + 97, 34 + 94 + 98, 34 + 94 + 99, 34 + 94 + 100, 34 + 96 + 97, 34 + 96 + 98, 34 +
96 + 99, 34 + 96 + 100, 34 + 97 + 98, 34 + 97 + 99, 34 + 97 + 100, 34 + 98 + 99, 34 + 98 +
100, 34 + 99 + 100, 51 + 52 + 53, 51 + 52 + 54, 51 + 52 + 55, 51 + 52 + 90, 51 + 52 +
92, 51 + 52 + 94, 51 + 52 + 96, 51 + 52 + 97, 51 + 52 + 98, 51 + 52 + 99, 51 + 52 + 100,
51 + 53 + 54, 51 + 53 + 55, 51 + 53 + 90, 51 + 53 + 92, 51 + 53 + 94, 51 + 53 + 96, 51 +
53 + 97, 51 + 53 + 98, 51 + 53 + 99, 51 + 53 + 100, 51 + 54 + 55, 51 + 54 + 90, 51 + 54 +
92, 51 + 54 + 94, 51 + 54 + 96, 51 + 54 + 97, 51 + 54 + 98, 51 + 54 + 99, 51 + 54 + 100,
51 + 55 + 90, 51 + 55 + 92, 51 + 55 + 94, 51 + 55 + 96, 51 + 55 + 97, 51 + 55 + 98, 51 +
55 + 99, 51 + 55 + 100, 51 + 90 + 92, 51 + 90 + 94, 51 + 90 + 96, 51 + 90 + 97, 51 + 90 +
98, 51 + 90 + 99, 51 + 90 + 100, 51 + 92 + 94, 51 + 92 + 96, 51 + 92 + 97, 51 + 92 + 98,
51 + 92 + 99, 51 + 92 + 100, 51 + 94 + 96, 51 + 94 + 97, 51 + 94 + 98, 51 + 94 + 99, 51 +
94 + 100, 51 + 96 + 97, 51 + 96 + 98, 51 + 96 + 99, 51 + 96 + 100, 51 + 97 + 98, 51 + 97 +
99, 51 + 97 + 100, 51 + 98 + 99, 51 + 98 + 100, 51 + 99 + 100, 52 + 53 + 54, 52 + 53 +
55, 52 + 53 + 90, 52 + 53 + 92, 52 + 53 + 94, 52 + 53 + 96, 52 + 53 + 97, 52 + 53 + 98, 52 +
53 + 99, 52 + 53 + 100, 52 + 54 + 55, 52 + 54 + 90, 52 + 54 + 92, 52 + 54 + 94, 52 + 54 +
96, 52 + 54 + 97, 52 + 54 + 98, 52 + 54 + 99, 52 + 54 + 100, 52 + 55 + 90, 52 + 55 + 92,
52 + 55 + 94, 52 + 55 + 96, 52 + 55 + 97, 52 + 55 + 98, 52 + 55 + 99, 52 + 55 + 100, 52 +
90 + 92, 52 + 90 + 94, 52 + 90 + 96, 52 + 90 + 97, 52 + 90 + 98, 52 + 90 + 99, 52 + 90 +
100, 52 + 92 + 94, 52 + 92 + 96, 52 + 92 + 97, 52 + 92 + 98, 52 + 92 + 99, 52 + 92 + 100,
52 + 94 + 96, 52 + 94 + 97, 52 + 94 + 98, 52 + 94 + 99, 52 + 94 + 100, 52 + 96 + 97, 52 +
96 + 98, 52 + 96 + 99, 52 + 96 + 100, 52 + 97 + 98, 52 + 97 + 99, 52 + 97 + 100, 52 + 98 +
99, 52 + 98 + 100, 52 + 99 + 100, 53 + 54 + 55, 53 + 54 + 90, 53 + 54 + 92, 53 + 54 +
94, 53 + 54 + 96, 53 + 54 + 97, 53 + 54 + 98, 53 + 54 + 99, 53 + 54 + 100, 53 + 55 + 90,
53 + 55 + 92, 53 + 55 + 94, 53 + 55 + 96, 53 + 55 + 97, 53 + 55 + 98, 53 + 55 + 99, 53 +
55 + 100, 53 + 90 + 92, 53 + 90 + 94, 53 + 90 + 96, 53 + 90 + 97, 53 + 90 + 98, 53 + 90 +
99, 53 + 90 + 100, 53 + 92 + 94, 53 + 92 + 96, 53 + 92 + 97, 53 + 92 + 98, 53 + 92 + 99,
53 + 92 + 100, 53 + 94 + 96, 53 + 94 + 97, 53 + 94 + 98, 53 + 94 + 99, 53 + 94 + 100, 53 +
96 + 97, 53 + 96 + 98, 53 + 96 + 99, 53 + 96 + 100, 53 + 97 + 98, 53 + 97 + 99, 53 + 97 +
100, 53 + 98 + 99, 53 + 98 + 100, 53 + 99 + 100, 54 + 55 + 90, 54 + 55 + 92, 54 + 55 +
94, 54 + 55 + 96, 54 + 55 + 97, 54 + 55 + 98, 54 + 55 + 99, 54 + 55 + 100, 54 + 90 + 92,
54 + 90 + 94, 54 + 90 + 96, 54 + 90 + 97, 54 + 90 + 98, 54 + 90 + 99, 54 + 90 + 100, 54 +
92 + 94, 54 + 92 + 96, 54 + 92 + 97, 54 + 92 + 98, 54 + 92 + 99, 54 + 92 + 100, 54 + 94 +
96, 54 + 94 + 97, 54 + 94 + 98, 54 + 94 + 99, 54 + 94 + 100, 54 + 96 + 97, 54 + 96 + 98,
54 + 96 + 99, 54 + 96 + 100, 54 + 97 + 98, 54 + 97 + 99, 54 + 97 + 100, 54 + 98 + 99, 54 +
98 + 100, 54 + 99 + 100, 55 + 90 + 92, 55 + 90 + 94, 55 + 90 + 96, 55 + 90 + 97, 55 +
90 + 98, 55 + 90 + 99, 55 + 90 + 100, 55 + 92 + 94, 55 + 92 + 96, 55 + 92 + 97, 55 + 92 +
98, 55 + 92 + 99, 55 + 92 + 100, 55 + 94 + 96, 55 + 94 + 97, 55 + 94 + 98, 55 + 94 + 99,
55 + 94 + 100, 55 + 96 + 97, 55 + 96 + 98, 55 + 96 + 99, 55 + 96 + 100, 55 + 97 + 98, 55 +
97 + 99, 55 + 97 + 100, 55 + 98 + 99, 55 + 98 + 100, 55 + 99 + 100, 90 + 92 + 94, 90 +
92 + 96, 90 + 92 + 97, 90 + 92 + 98, 90 + 92 + 99, 90 + 92 + 100, 90 + 94 + 96, 90 + 94 +
97, 90 + 94 + 98, 90 + 94 + 99, 90 + 94 + 100, 90 + 96 + 97, 90 + 96 + 98, 90 + 96 + 99,
90 + 96 + 100, 90 + 97 + 98, 90 + 97 + 99, 90 + 97 + 100, 90 + 98 + 99, 90 + 98 + 100, 90 +
99 + 100, 92 + 94 + 96, 92 + 94 + 97, 92 + 94 + 98, 92 + 94 + 99, 92 + 94 + 100, 92 +
96 + 97, 92 + 96 + 98, 92 + 96 + 99, 92 + 96 + 100, 92 + 97 + 98, 92 + 97 + 99, 92 + 97 +
100, 92 + 98 + 99, 92 + 98 + 100, 92 + 99 + 100, 94 + 96 + 97, 94 + 96 + 98, 94 + 96 +
99, 94 + 96 + 100, 94 + 97 + 98, 94 + 97 + 99, 94 + 97 + 100, 94 + 98 + 99, 94 + 98 +
100, 94 + 99 + 100, 96 + 97 + 98, 96 + 97 + 99, 96 + 97 + 100, 96 + 98 + 99, 96 + 98 +
100, 96 + 99 + 100, 97 + 98 + 99, 97 + 98 + 100, 97 + 99 + 100, 98 + 99 + 100

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5; and a light chain variable domain that that is at least 90% (e.g., at least 92%, at least 94%, at least 96%, at least 98%, at least 99%, or 100%) identical to SEQ ID NO: 186, where the light chain variable domain includes a histidine at any of the specific combinations of one or more amino acid positions in SEQ ID NO: 185 listed in Table 6.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5, and where the heavy chain variable domain includes an alanine at position 99 in SEQ ID NO: 184; and a light chain variable domain that that is at least 90% (e.g., at least 92%, at least 94%, at least 96%, at least 98%, at least 99%, or 100%) identical to SEQ ID NO: 185, where the light chain variable domain includes a histidine at any of the specific combinations of one or more amino acid positions in SEQ ID NO: 185 listed in Table 6.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5, and where the heavy chain variable domain includes an alanine at position 99 in SEQ ID NO: 184; and a light chain variable domain that that is at least 90% (e.g., at least 92%, at least 94%, at least 96%, at least 98%, at least 99%, or 100%) identical to SEQ ID NO: 185, where the light chain variable domain includes a histidine at any of the specific combinations of one or more amino acid positions in SEQ ID NO: 185 listed in Table 6.

In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 185, where the light chain variable domain includes a histidine at any of the specific combinations of one or more amino acid positions in SEQ ID NO: 185 listed in Table 6, and where the light chain variable domain includes an alanine at position 35 in SEQ ID NO: 185; and a heavy chain variable domain that that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 29 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain comprising SEQ ID NO: 185, and a heavy chain variable domain that is at least 90% identical (e.g., at least 92%, at least 94%, at least 96%, at least 98%, at least 99%, or 100%) identical to SEQ ID NO: 184, where the heavy chain variable domain includes a histidine at any of the specific combinations of one or more (e.g., two, three, four, five, six, seven, eight, nine, or ten) amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 33 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 34 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes an alanine at position 35 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 51 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 52 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 53 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 54 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 55 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 90 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 92 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 94 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 96 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 97 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 98 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 99 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain comprises a light chain variable domain that is at least 90% identical to SEQ ID NO: 185, wherein the light chain variable domain includes a histidine at position 100 in SEQ ID NO: 185; and a heavy chain variable domain that is at least 90% (e.g., at least 92%, at least 94%, at least 96%, at least 98%, at least 99%, or 100%) identical to SEQ ID NO: 184, where the heavy chain variable domain includes a histidine at any of the specific combinations of one or more amino acid positions in SEQ ID NO: 184 listed in Table 5.

In some examples of any of the ABPCs described herein, the first antigen-binding domain includes a heavy chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a light chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a heavy chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) histidines substituted with an alanine; and a light chain variable domain of farletuzumab with one or more (e.g., one, two, three, four, five, six, seven, eight, nine, ten, eleven, twelve, thirteen, fourteen, fifteen, sixteen, seventeen, eighteen, nineteen, or twenty) histidine (s) substituted with an alanine. In some examples of any of the ABPCs described herein, the heavy chain variable domain of farletuzumab comprises SEQ ID NO: 184. In some examples of any of the ABPCs described herein, the light chain variable domain of farletuzumab comprises SEQ ID NO: 185.

In some examples of any of the ABPCs described herein, the first antigen-binding domain comprises a heavy chain variable domain comprising a CDR1, a CDR2, and a CDR3 of SEQ ID NO: 186, SEQ ID NO: 187, and SEQ ID NO: 188, respectively, with collectively a total of one or more (e.g., one, two, three, four, five, six, seven, eight, nine, or ten) histidine(s) in SEQ ID NOs: 186-188 substituted with an alanine. In some examples of any of the ABPCs described herein, the first antigen-binding domain comprises a light chain variable domain comprising a CDR1, a CDR2, and a CDR3 of SEQ ID NO: 189, SEQ ID NO: 190, and SEQ ID NO: 191, respectively, with collectively a total of one or more (e.g., one, two, three, four, five, six, seven, eight, nine, or ten) histidine(s) in SEQ ID NOs: 189-191 substituted with an alanine. In some examples of any of the ABPCs described herein, the first antigen-binding domain includes: a heavy chain variable domain comprising a CDR1, a CDR2, and a CDR3 of SEQ ID NO: 186, SEQ ID NO: 187, and SEQ ID NO: 188, respectively, with collectively a total of one or more (e.g., one, two, three, four, five, six, seven, eight, nine, or ten) histidine(s) in SEQ ID NOs: 186-188 substituted with an alanine; and a light chain variable domain comprising a CDR1, a CDR2, and a CDR3 of SEQ ID NO: 189, SEQ ID NO: 190, and SEQ ID NO: 191, respectively, with collectively a total of one or more (e.g., one, two, three, four, five, six, seven, eight, nine, or ten) histidine(s) in SEQ ID NOs: 189-191 substituted with an alanine.

In some examples of any of the ABPCs described herein, the first antigen-binding domain comprises a heavy chain variable domain of SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain of SEQ ID NO: 185, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, or SEQ ID NO: 257.

In some examples of any of the ABPCs described herein, the first antigen-binding domain includes a light chain variable domain comprising SEQ ID NO: 185, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 231, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 232, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO:

198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 233, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 234, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 235, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 236, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 237, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 238, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 239, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 240, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 241, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 242, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 243, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 244, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO:

224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 245, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 246, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 247, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 248, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 249, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 250, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 251, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 252, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 253, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 254, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 255, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 256, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

In some examples of any of the ABPCs described herein, the first antigen-binding domain includes a light chain variable domain comprising SEQ ID NO: 257, and a heavy chain variable domain comprising SEQ ID NO: 184, SEQ ID NO: 192, SEQ ID NO: 193, SEQ ID NO: 194, SEQ ID NO: 195, SEQ ID NO: 196, SEQ ID NO: 197, SEQ ID NO:

198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, or SEQ ID NO: 230.

Also provided herein are pharmaceutical compositions including any of the ABPCs described herein. Also provided herein are methods of treating a subject in need thereof that include administering a therapeutically effective amount of any of the ABPCs described herein to the subject.

In some examples of any of the ABPCs described herein, a composition including the ABPC (e.g., any of the ABPCs described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at a least a 9,000% increase, or at least a 10,000% increase, or about a 1% increase to about 10,000% increase, about a 1% increase to about a 9,000% increase, about a 1% increase to about a 8,000% increase, about a 1% increase to about a 7,000% increase, about a 1% increase to about a 6,000% increase, about a 1% increase to about a 5,000% increase, about a 1% increase to about a 4,000% increase, about a 1% increase to about a 3,000% increase, about a 1% increase to about a 2,000% increase, about a 1% increase to about a 1,000% increase, about a 1% increase to about a 500% increase, about a 1% increase to about a 450% increase, about a 1% increase to about a 400% increase, about a 1% increase to about a 350% increase, about a 1% increase to about a 300% increase, about a 1% increase to about a 250% increase, about a 1% increase to about a 200% increase, about a 1% increase to about a 180% increase, about a 1% increase to about a 160% increase, about a 1% increase to about a 140% increase, about a 1% increase to about a 120% increase, about a 1% increase to about a 100% increase, about a 1% increase to about a 95% increase, about a 1% increase to about a 90% increase, about a 1% increase to about a 85% increase, about a 1% increase to about a 80% increase, about a 1% increase to about a 75% increase, about a 1% increase to about a 70% increase, about a 1% increase to about a 65% increase, about a 1% increase to about a 60% increase, about a 1% increase to about a 55% increase, about a 1% increase to about a 50% increase, about a 1% increase to about a 45% increase, about a 1% increase to about a 40% increase, about a 1% increase to about a 35% increase, about a 1% increase to about a 25% increase, about a 1% increase to about a 20% increase, about a 1% increase to about a 15% increase, about a 1% increase to about a 10% increase, about a 1% increase to about a 5% increase, about a 2% increase to about 10,000% increase, about a 2% increase to about a 9,000% increase, about a 2% increase to about a 8,000% increase, about a 2% increase to about a 7,000% increase, about a 2% increase to about a 6,000% increase, about a 2% increase to about a 5,000% increase, about a 2% increase to about a 4,000% increase, about a 2% increase to about a 3,000% increase, about a 2% increase to about a 2,000% increase, about a 2% increase to about a 1,000% increase, about a 2% increase to about a 500% increase, about a 2% increase to about a 450% increase, about a 2% increase to about a 400% increase, about a 2% increase to about a 350% increase, about a 2% increase to about a 300% increase, about a 2% increase to about a 250% increase, about a 2% increase to about a 200% increase, about a 2% increase to about a 180% increase, about a 2% increase to about a 160% increase, about a 2% increase to about a 140% increase, about a 2% increase to about a 120% increase, about a 2% increase to about a 100% increase, about a 2% increase to about a 95% increase, about a 2% increase to about a 90% increase, about a 2% increase to about a 85% increase, about a 2% increase to about a 80% increase, about a 2% increase to about a 75% increase, about a 2% increase to about a 70% increase, about a 2% increase to about a 65% increase, about a 2% increase to about a 60% increase, about a 2% increase to about a 55% increase, about a 2% increase to about a 50% increase, about a 2% increase to about a 45% increase, about a 2% increase to about a 40% increase, about a 2% increase to about a 35% increase, about a 2% increase to about a 25% increase, about a 2% increase to about a 20% increase, about a 2% increase to about a 15% increase, about a 2% increase to about a 10% increase, about a 2% increase to about a 5% increase, about a 5% increase to about 10,000% increase, about a 5% increase to about a 9,000% increase, about a 5% increase to about a 8,000% increase, about a 5% increase to about a 7,000% increase, about a 5% increase to about a 6,000% increase, about a 5% increase to about a 5,000% increase, about a 5% increase to about a 4,000% increase, about a 5% increase to about a 3,000% increase, about a 5% increase to about a 2,000% increase, about a 5% increase to about a 1,000% increase, about a 5% increase to about a 500% increase, about a 5% increase to about a 450% increase, about a 5% increase to about a 400% increase, about a 5% increase to about a 350% increase, about a 5% increase to about a 300% increase, about a 5% increase to about a 250% increase, about a 5% increase to about a 200% increase, about a 5% increase to about a 180% increase, about a 5% increase to about a 160% increase, about a 5% increase to about a 140% increase, about a 5% increase to about a 120% increase, about a 5% increase to about a 100% increase, about a 5% increase to about a 95% increase, about a 5% increase to about a 90% increase, about a 5% increase to about a 85% increase, about a 5% increase to about a 80% increase, about a 5% increase to about a 75% increase, about a 5% increase to about a 70% increase, about a 5% increase to about a 65% increase, about a 5% increase to about a 60% increase, about a 5% increase to about a 55% increase, about a 5% increase to about a 50% increase, about a 5% increase to about a 45% increase, about a 5% increase to about a 40% increase, about a 5% increase to about a 35% increase, about a 5% increase to about a 25% increase, about a 5% increase to about a 20% increase, about a 5% increase to about a 15% increase, about a 5% increase to about a 10% increase, about a 10% increase to about 10,000% increase, about a 10% increase to about a 9,000% increase, about a 10% increase to about a 8,000% increase, about a 10% increase to about a 7,000% increase, about a 10% increase to about a 6,000% increase, about a 10% increase to about a 5,000% increase, about a 10% increase to about a 4,000% increase, about a 10% increase to about a 3,000% increase, about a 10% increase to about a 2,000% increase, about a 10% increase to about a 1,000% increase, about a 10% increase to about a 500% increase, about a 10% increase to about a 450% increase, about a 10% increase to about a 400% increase, about a 10% increase to about a 350% increase, about a 10% increase to about a 300% increase, about a 10% increase to about a 250% increase, about a 10% increase to about a 200% increase, about a 10% increase to about a 180% increase, about a 10% increase to about a 160% increase, about a 10% increase to about a 140% increase, about a 10% increase to about a 120% increase, about a 10% increase to about a 100% increase, about a 10% increase to about a 95% increase, about a 10% increase to about a 90% increase, about a 10% increase to about a 85% increase, about a 10% increase to about a 80% increase, about a 10% increase to about a 75% increase, about a 10% increase to about a 70% increase, about a 10% increase to about a 65% increase, about a 10% increase to about a 60% increase, about a 10% increase to about a 55% increase, about a 10% increase to about a 50% increase, about a 10% increase to about a 45% increase, about a 10% increase to about a 40% increase, about a 10% increase to about a 35% increase, about a 10% increase to about a 30% increase, about a 10% increase to about a 25% increase, about a 10% increase to about a 20% increase, about a 10% increase to about a 15% increase, about a 15% increase to about 10,000% increase, about a 15% increase to about a 9,000% increase, about a 15% increase to about a 8,000% increase, about a 15% increase to about a 7,000% increase, about a 15% increase to about a 6,000% increase, about a 15% increase to about a 5,000% increase, about a 15% increase to about a 4,000% increase, about a 15% increase to about a 3,000% increase, about a 15% increase to about a 2,000% increase, about a 15% increase to about a 1,000% increase, about a 15% increase to about a 500% increase, about a 15% increase to about a 450% increase, about a 15% increase to about a 400% increase, about a 15% increase to about a 350% increase, about a 15% increase to about a 300% increase, about a 15% increase to about a 250% increase, about a 15% increase to about a 200% increase, about a 15% increase to about a 180% increase, about a 15% increase to about a 160% increase, about a 15% increase to about a 140% increase, about a 15% increase to about a 120% increase, about a 15% increase to about a 100% increase, about a 15% increase to about a 95% increase, about a 15% increase to about a 90% increase, about a 15% increase to about a 85% increase, about a 15% increase to about a 80% increase, about a 15% increase to about a 75% increase, about a 15% increase to about a 70% increase, about a 15% increase to about a 65% increase, about a 15% increase to about a 60% increase, about a 15% increase to about a 55% increase, about a 15% increase to about a 50% increase, about a 15% increase to about a 45% increase, about a 15% increase to about a 40% increase, about a 15% increase to about a 35% increase, about a 15% increase to about a 30% increase, about a 15% increase to about a 25% increase, about a 15% increase to about a 20% increase, about a 20% increase to about 10,000% increase, about a 20% increase to about a 9,000% increase, about a 20% increase to about a 8,000% increase, about a 20% increase to about a 7,000% increase, about a 20% increase to about a 6,000% increase, about a 20% increase to about a 5,000% increase, about a 20% increase to about a 4,000% increase, about a 20% increase to about a 3,000% increase, about a 20% increase to about a 2,000% increase, about a 20% increase to about a 1,000% increase, about a 20% increase to about a 500% increase, about a 20% increase to about a 450% increase, about a 20% increase to about a 400% increase, about a 20% increase to about a 350% increase, about a 20% increase to about a 300% increase, about a 20% increase to about a 250% increase, about a 20% increase to about a 200% increase, about a 20% increase to about a 180% increase, about a 20% increase to about a 160% increase, about a 20% increase to about a 140% increase, about a 20% increase to about a 120% increase, about a 20% increase to about a 100% increase, about a 20% increase to about a 95% increase, about a 20% increase to about a 90% increase, about a 20% increase to about a 85% increase, about a 20% increase to about a 80% increase, about a 20% increase to about a 75% increase, about a 20% increase to about a 70% increase, about a 20% increase to about a 65% increase, about a 20% increase to about a 60% increase, about a 20% increase to about a 55% increase, about a 20% increase to about a 50% increase, about a 20% increase to about a 45% increase, about a 20% increase to about a 40% increase, about a 20% increase to about a 35% increase, about a 20% increase to about a 30% increase, about a 20% increase to about a 25% increase, about a 25% increase to about 10,000% increase, about a 25% increase to about a 9,000% increase, about a 25% increase to about a 8,000% increase, about a 25% increase to about a 7,000% increase, about a 25% increase to about a 6,000% increase, about a 25% increase to about a 5,000% increase, about a 25% increase to about a 4,000% increase, about a 25% increase to about a 3,000% increase, about a 25% increase to about a 2,000% increase, about a 25% increase to about a 1,000% increase, about a 25% increase to about a 500% increase, about a 25% increase to about a 450% increase, about a 25% increase to about a 400% increase, about a 25% increase to about a 350% increase, about a 25% increase to about a 300% increase, about a 25% increase to about a 250% increase, about a 25% increase to about a 200% increase, about a 25% increase to about a 180% increase, about a 25% increase to about a 160% increase, about a 25% increase to about a 140% increase, about a 25% increase to about a 120% increase, about a 25% increase to about a 100% increase, about a 25% increase to about a 95% increase, about a 25% increase to about a 90% increase, about a 25% increase to about a 85% increase, about a 25% increase to about a 80% increase, about a 25% increase to about a 75% increase, about a 25% increase to about a 70% increase, about a 25% increase to about a 65% increase, about a 25% increase to about a 60% increase, about a 25% increase to about a 55% increase, about a 25% increase to about a 50% increase, about a 25% increase to about a 45% increase, about a 25% increase to about a 40% increase, about a 25% increase to about a 35% increase, about a 25% increase to about a 30% increase, about a 30% increase to about 10,000% increase, about a 30% increase to about a 9,000% increase, about a 30% increase to about a 8,000% increase, about a 30% increase to about a 7,000% increase, about a 30% increase to about a 6,000% increase, about a 30% increase to about a 5,000% increase, about a 30% increase to about a 4,000% increase, about a 30% increase to about a 3,000% increase, about a 30% increase to about a 2,000% increase, about a 30% increase to about a 1,000% increase, about a 30% increase to about a 500% increase, about a 30% increase to about a 450% increase, about a 30% increase to about a 400% increase, about a 30% increase to about a 350% increase, about a 30% increase to about a 300% increase, about a 30% increase to about a 250% increase, about a 30% increase to about a 200% increase, about a 30% increase to about a 180% increase, about a 30% increase to about a 160% increase, about a 30% increase to about a 140% increase, about a 30% increase to about a 120% increase, about a 30% increase to about a 100% increase, about a 30% increase to about a 95% increase, about a 30% increase to about a 90% increase, about a 30% increase to about a 85% increase, about a 30% increase to about a 80% increase, about a 30% increase to about a 75% increase, about a 30% increase to about a 70% increase, about a 30% increase to about a 65% increase, about a 30% increase to about a 60% increase, about a 30% increase to about a 55% increase, about a 30% increase to about a 50% increase, about a 30% increase to about a 45% increase, about a 30% increase to about a 40% increase, about a 30% increase to about a 35% increase, about a 35% increase to about 10,000% increase, about a 35% increase to about a 9,000% increase, about a 35% increase to about a 8,000% increase, about a 35% increase to about a 7,000% increase, about a 35% increase to about a 6,000% increase, about a 35% increase to about a 5,000% increase, about a 35% increase to about a 4,000% increase, about a 35% increase to about a 3,000% increase, about a 35% increase to about a 2,000% increase, about a 35% increase to about a 1,000% increase, about a 35% increase to about a 500% increase, about a 35% increase to about a 450% increase, about a 35% increase to about a 400% increase, about a 35% increase to about a 350% increase, about a 35% increase to about a 300% increase, about a 35% increase to about a 250% increase, about a 35% increase to about a 200% increase, about a 35% increase to about a 180% increase, about a 35% increase to about a 160% increase, about a 35% increase to about a 140% increase, about a 35% increase to about a 120% increase, about a 35% increase to about a 100% increase, about a 35% increase to about a 95% increase, about a 35% increase to about a 90% increase, about a 35% increase to about a 85% increase, about a 35% increase to about a 80% increase, about a 35% increase to about a 75% increase, about a 35% increase to about a 70% increase, about a 35% increase to about a 65% increase, about a 35% increase to about a 60% increase, about a 35% increase to about a 55% increase, about a 35% increase to about a 50% increase, about a 35% increase to about a 45% increase, about a 35% increase to about a 40% increase, about a 40% increase to about 10,000% increase, about a 40% increase to about a 9,000% increase, about a 40% increase to about a 8,000% increase, about a 40% increase to about a 7,000% increase, about a 40% increase to about a 6,000% increase, about a 40% increase to about a 5,000% increase, about a 40% increase to about a 4,000% increase, about a 40% increase to about a 3,000% increase, about a 40% increase to about a 2,000% increase, about a 40% increase to about a 1,000% increase, about a 40% increase to about a 500% increase, about a 40% increase to about a 450% increase, about a 40% increase to about a 400% increase, about a 40% increase to about a 350% increase, about a 40% increase to about a 300% increase, about a 40% increase to about a 250% increase, about a 40% increase to about a 200% increase, about a 40% increase to about a 180% increase, about a 40% increase to about a 160% increase, about a 40% increase to about a 140% increase, about a 40% increase to about a 120% increase, about a 40% increase to about a 100% increase, about a 40% increase to about a 95% increase, about a 40% increase to about a 90% increase, about a 40% increase to about a 85% increase, about a 40% increase to about a 80% increase, about a 40% increase to about a 75% increase, about a 40% increase to about a 70% increase, about a 40% increase to about a 65% increase, about a 40% increase to about a 60% increase, about a 40% increase to about a 55% increase, about a 40% increase to about a 50% increase, about a 40% increase to about a 45% increase, about a 45% increase to about 10,000% increase, about a 45% increase to about a 9,000% increase, about a 45% increase to about a 8,000% increase, about a 45% increase to about a 7,000% increase, about a 45% increase to about a 6,000% increase, about a 45% increase to about a 5,000% increase, about a 45% increase to about a 4,000% increase, about a 45% increase to about a 3,000% increase, about a 45% increase to about a 2,000% increase, about a 45% increase to about a 1,000% increase, about a 45% increase to about a 500% increase, about a 45% increase to about a 450% increase, about a 45% increase to about a 400% increase, about a 45% increase to about a 350% increase, about a 45% increase to about a 300% increase, about a 45% increase to about a 250% increase, about a 45% increase to about a 200% increase, about a 45% increase to about a 180% increase, about a 45% increase to about a 160% increase, about a 45% increase to about a 140% increase, about a 45% increase to about a 120% increase, about a 45% increase to about a 100% increase, about a 45% increase to about a 95% increase, about a 45% increase to about a 90% increase, about a 45% increase to about a 85% increase, about a 45% increase to about a 80% increase, about a 45% increase to about a 75% increase, about a 45% increase to about a 70% increase, about a 45% increase to about a 65% increase, about a 45% increase to about a 60% increase, about a 45% increase to about a 55% increase, about a 45% increase to about a 50% increase, about a 50% increase to about 10,000% increase, about a 50% increase to about a 9,000% increase, about a 50% increase to about a 8,000% increase, about a 50% increase to about a 7,000% increase, about a 50% increase to about a 6,000% increase, about a 50% increase to about a 5,000% increase, about a 50% increase to about a 4,000% increase, about a 50% increase to about a 3,000% increase, about a 50% increase to about a 2,000% increase, about a 50% increase to about a 1,000% increase, about a 50% increase to about a 500% increase, about a 50% increase to about a 450% increase, about a 50% increase to about a 400% increase, about a 50% increase to about a 350% increase, about a 50% increase to about a 300% increase, about a 50% increase to about a 250% increase, about a 50% increase to about a 200% increase, about a 50% increase to about a 180% increase, about a 50% increase to about a 160% increase, about a 50% increase to about a 140% increase, about a 50% increase to about a 120% increase, about a 50% increase to about a 100% increase, about a 50% increase to about a 95% increase, about a 50% increase to about a 90% increase, about a 50% increase to about a 85% increase, about a 50% increase to about a 80% increase, about a 50% increase to about a 75% increase, about a 50% increase to about a 70% increase, about a 50% increase to about a 65% increase, about a 50% increase to about a 60% increase, about a 50% increase to about a 55% increase, about a 55% increase to about 10,000% increase, about a 55% increase to about a 9,000% increase, about a 55% increase to about a 8,000% increase, about a 55% increase to about a 7,000% increase, about a 55% increase to about a 6,000% increase, about a 55% increase to about a 5,000% increase, about a 55% increase to about a 4,000% increase, about a 55% increase to about a 3,000% increase, about a 55% increase to about a 2,000% increase, about a 55% increase to about a 1,000% increase, about a 55% increase to about a 500% increase, about a 55% increase to about a 450% increase, about a 55% increase to about a 400% increase, about a 55% increase to about a 350% increase, about a 55% increase to about a 300% increase, about a 55% increase to about a 250% increase, about a 55% increase to about a 200% increase, about a 55% increase to about a 180% increase, about a 55% increase to about a 160% increase, about a 55% increase to about a 140% increase, about a 55% increase to about a 120% increase, about a 55% increase to about a 100% increase, about a 55% increase to about a 95% increase, about a 55% increase to about a 90% increase, about a 55% increase to about a 85% increase, about a 55% increase to about a 80% increase, about a 55% increase to about a 75% increase, about a 55% increase to about a 70% increase, about a 55% increase to about a 65% increase, about a 55% increase to about a 60% increase, about a 60% increase to about 10,000% increase, about a 60% increase to about a 9,000% increase, about a 60% increase to about a 8,000% increase, about a 60% increase to about a 7,000% increase, about a 60% increase to about a 6,000% increase, about a 60% increase to about a 5,000% increase, about a 60% increase to about a 4,000% increase, about a 60% increase to about a 3,000% increase, about a 60% increase to about a 2,000% increase, about a 60% increase to about a 1,000% increase, about a 60% increase to about a 500% increase, about a 60% increase to about a 450% increase, about a 60% increase to about a 400% increase, about a 60% increase to about a 350% increase, about a 60% increase to about a 300% increase, about a 60% increase to about a 250% increase, about a 60% increase to about a 200% increase, about a 60% increase to about a 180% increase, about a 60% increase to about a 160% increase, about a 60% increase to about a 140% increase, about a 60% increase to about a 120% increase, about a 60% increase to about a 100% increase, about a 60% increase to about a 95% increase, about a 60% increase to about a 90% increase, about a 60% increase to about a 85% increase, about a 60% increase to about a 80% increase, about a 60% increase to about a 75% increase, about a 60% increase to about a 70% increase, about a 60% increase to about a 65% increase, about a 65% increase to about 10,000% increase, about a 65% increase to about a 9,000% increase, about a 65% increase to about a 8,000% increase, about a 65% increase to about a 7,000% increase, about a 65% increase to about a 6,000% increase, about a 65% increase to about a 5,000% increase, about a 65% increase to about a 4,000% increase, about a 65% increase to about a 3,000% increase, about a 65% increase to about a 2,000% increase, about a 65% increase to about a 1,000% increase, about a 65% increase to about a 500% increase, about a 65% increase to about a 450% increase, about a 65% increase to about a 400% increase, about a 65% increase to about a 350% increase, about a 65% increase to about a 300% increase, about a 65% increase to about a 250% increase, about a 65% increase to about a 200% increase, about a 65% increase to about a 180% increase, about a 65% increase to about a 160% increase, about a 65% increase to about a 140% increase, about a 65% increase to about a 120% increase, about a 65% increase to about a 100% increase, about a 65% increase to about a 95% increase, about a 65% increase to about a 90% increase, about a 65% increase to about a 85% increase, about a 65% increase to about a 80% increase, about a 65% increase to about a 75% increase, about a 65% increase to about a 70% increase, about a 70% increase to about 10,000% increase, about a 70% increase to about a 9,000% increase, about a 70% increase to about a 8,000% increase, about a 70% increase to about a 7,000% increase, about a 70% increase to about a 6,000% increase, about a 70% increase to about a 5,000% increase, about a 70% increase to about a 4,000% increase, about a 70% increase to about a 3,000% increase, about a 70% increase to about a 2,000% increase, about a 70% increase to about a 1,000% increase, about a 70% increase to about a 500% increase, about a 70% increase to about a 450% increase, about a 70% increase to about a 400% increase, about a 70% increase to about a 350% increase, about a 70% increase to about a 300% increase, about a 70% increase to about a 250% increase, about a 70% increase to about a 200% increase, about a 70% increase to about a 180% increase, about a 70% increase to about a 160% increase, about a 70% increase to about a 140% increase, about a 70% increase to about a 120% increase, about a 70% increase to about a 100% increase, about a 70% increase to about a 95% increase, about a 70% increase to about a 90% increase, about a 70% increase to about a 85% increase, about a 70% increase to about a 80% increase, about a 70% increase to about a 75% increase, about a 75% increase to about 10,000% increase, about a 75% increase to about a 9,000% increase, about a 75% increase to about a 8,000% increase, about a 75% increase to about a 7,000% increase, about a 75% increase to about a 6,000% increase, about a 75% increase to about a 5,000% increase, about a 75% increase to about a 4,000% increase, about a 75% increase to about a 3,000% increase, about a 75% increase to about a 2,000% increase, about a 75% increase to about a 1,000% increase, about a 75% increase to about a 500% increase, about a 75% increase to about a 450% increase, about a 75% increase to about a 400% increase, about a 75% increase to about a 350% increase, about a 75% increase to about a 300% increase, about a 75% increase to about a 250% increase, about a 75% increase to about a 200% increase, about a 75% increase to about a 180% increase, about a 75% increase to about a 160% increase, about a 75% increase to about a 140% increase, about a 75% increase to about a 120% increase, about a 75% increase to about a 100% increase, about a 75% increase to about a 95% increase, about a 75% increase to about a 90% increase, about a 75% increase to about a 85% increase, about a 75% increase to about a 80%, about a 80% increase to about 10,000% increase, about a 80% increase to about a 9,000% increase, about a 80% increase to about a 8,000% increase, about a 80% increase to about a 7,000% increase, about a 80% increase to about a 6,000% increase, about a 80% increase to about a 5,000% increase, about a 80% increase to about a 4,000% increase, about a 80% increase to about a 3,000% increase, about a 80% increase to about a 2,000% increase, about a 80% increase to about a 1,000% increase, increase, about a 80% increase to about a 500% increase, about a 80% increase to about a 450% increase, about a 80% increase to about a 400% increase, about a 80% increase to about a 350% increase, about a 80% increase to about a 300% increase, about a 80% increase to about a 250% increase, about a 80% increase to about a 200% increase, about a 80% increase to about a 180% increase, about a 80% increase to about a 160% increase, about a 80% increase to about a 140% increase, about a 80% increase to about a 120% increase, about a 80% increase to about a 100% increase, about a 80% increase to about a 95% increase, about a 80% increase to about a 90% increase, about a 80% increase to about a 85% increase, about a 85% increase to about 10,000% increase, about a 85% increase to about a 9,000% increase, about a 85% increase to about a 8,000% increase, about a 85% increase to about a 7,000% increase, about a 85% increase to about a 6,000% increase, about a 85% increase to about a 5,000% increase, about a 85% increase to about a 4,000% increase, about a 85% increase to about a 3,000% increase, about a 85% increase to about a 2,000% increase, about a 85% increase to about a 1,000% increase, about a 85% increase to about a 500% increase, about a 85% increase to about a 450% increase, about a 85% increase to about a 400% increase, about a 85% increase to about a 350% increase, about a 85% increase to about a 300% increase, about a 85% increase to about a 250% increase, about a 85% increase to about a 200% increase, about a 85% increase to about a 180% increase, about a 85% increase to about a 160% increase, about a 85% increase to about a 140% increase, about a 85% increase to about a 120% increase, about a 85% increase to about a 100% increase, about a 85% increase to about a 95% increase, about a 85% increase to about a 90% increase, about a 90% increase to about 10,000% increase, about a 90% increase to about a 9,000% increase, about a 90% increase to about a 8,000% increase, about a 90% increase to about a 7,000% increase, about a 90% increase to about a 6,000% increase, about a 90% increase to about a 5,000% increase, about a 90% increase to about a 4,000% increase, about a 90% increase to about a 3,000% increase, about a 90% increase to about a 2,000% increase, about a 90% increase to about a 1,000% increase, about a 90% increase to about a 500% increase, about a 90% increase to about a 450% increase, about a 90% increase to about a 400% increase, about a 90% increase to about a 350% increase, about a 90% increase to about a 300% increase, about a 90% increase to about a 250% increase, about a 90% increase to about a 200% increase, about a 90% increase to about a 180% increase, about a 90% increase to about a 160% increase, about a 90% increase to about a 140% increase, about a 90% increase to about a 120% increase, about a 90% increase to about a 100% increase, about a 90% increase to about a 95% increase, about a 95% increase to about 10,000% increase, about a 95% increase to about a 9,000% increase, about a 95% increase to about a 8,000% increase, about a 95% increase to about a 7,000% increase, about a 95% increase to about a 6,000% increase, about a 95% increase to about a 5,000% increase, about a 95% increase to about a 4,000% increase, about a 95% increase to about a 3,000% increase, about a 95% increase to about a 2,000% increase, about a 95% increase to about a 1,000% increase, about a 95% increase to about a 500% increase, about a 95% increase to about a 450% increase, about a 95% increase to about a 400% increase, about a 95% increase to about a 350% increase, about a 95% increase to about a 300% increase, about a 95% increase to about a 250% increase, about a 95% increase to about a 200% increase, about a 95% increase to about a 180% increase, about a 95% increase to about a 160% increase, about a 95% increase to about a 140% increase, about a 95% increase to about a 120% increase, about a 95% increase to about a 100% increase, about a 100% increase to about 10,000% increase, about a 100% increase to about a 9,000% increase, about a 100% increase to about a 8,000% increase, about a 100% increase to about a 7,000% increase, about a 100% increase to about a 6,000% increase, about a 100% increase to about a 5,000% increase, about a 100% increase to about a 4,000% increase, about a 100% increase to about a 3,000% increase, about a 100% increase to about a 2,000% increase, about a 100% increase to about a 1,000% increase, about a 100% increase to about a 500% increase, about a 100% increase to about a 450% increase, about a 100% increase to about a 400% increase, about a 100% increase to about a 350% increase, about a 100% increase to about a 300% increase, about a 100% increase to about a 250% increase, about a 100% increase to about a 200% increase, about a 100% increase to about a 180% increase, about a 100% increase to about a 160% increase, about a 100% increase to about a 140% increase, about a 100% increase to about a 120% increase, about a 120% increase to about 10,000% increase, about a 120% increase to about a 9,000% increase, about a 120% increase to about a 8,000% increase, about a 120% increase to about a 7,000% increase, about a 120% increase to about a 6,000% increase, about a 120% increase to about a 5,000% increase, about a 120% increase to about a 4,000% increase, about a 120% increase to about a 3,000% increase, about a 120% increase to about a 2,000% increase, about a 120% increase to about a 1,000% increase, about a 120% increase to about a 500% increase, about a 120% increase to about a 450% increase, about a 120% increase to about a 400% increase, about a 120% increase to about a 350% increase, about a 120% increase to about a 300% increase, about a 120% increase to about a 250% increase, about a 120% increase to about a 200% increase, about a 120% increase to about a 180% increase, about a 120% increase to about a 160% increase, about a 120% increase to about a 140% increase, about a 140% increase to about 10,000% increase, about a 140% increase to about a 9,000% increase, about a 140% increase to about a 8,000% increase, about a 140% increase to about a 7,000% increase, about a 140% increase to about a 6,000% increase, about a 140% increase to about a 5,000% increase, about a 140% increase to about a 4,000% increase, about a 140% increase to about a 3,000% increase, about a 140% increase to about a 2,000% increase, about a 140% increase to about a 1,000% increase, about a 140% increase to about a 500% increase, about a 140% increase to about a 450% increase, about a 140% increase to about a 400% increase, about a 140% increase to about a 350% increase, about a 140% increase to about a 300% increase, about a 140% increase to about a 250% increase, about a 140% increase to about a 200% increase, about a 140% increase to about a 180% increase, about a 140% increase to about a 160% increase, about a 160% increase to about 10,000% increase, about a 160% increase to about a 9,000% increase, about a 160% increase to about a 8,000% increase, about a 160% increase to about a 7,000% increase, about a 160% increase to about a 6,000% increase, about a 160% increase to about a 5,000% increase, about a 160% increase to about a 4,000% increase, about a 160% increase to about a 3,000% increase, about a 160% increase to about a 2,000% increase, about a 160% increase to about a 1,000% increase, about a 160% increase to about a 500% increase, about a 160% increase to about a 450% increase, about a 160% increase to about a 400% increase, about a 160% increase to about a 350% increase, about a 160% increase to about a 300% increase, about a 160% increase to about a 250% increase, about a 160% increase to about a 200% increase, about a 160% increase to about a 180% increase, about a 180% increase to about 10,000% increase, about a 180% increase to about a 9,000% increase, about a 180% increase to about a 8,000% increase, about a 180% increase to about a 7,000% increase, about a 180% increase to about a 6,000% increase, about a 180% increase to about a 5,000% increase, about a 180% increase to about a 4,000% increase, about a 180% increase to about a 3,000% increase, about a 180% increase to about a 2,000% increase, about a 180% increase to about a 1,000% increase, about a 180% increase to about a 500% increase, about a 180% increase to about a 450% increase, about a 180% increase to about a 400% increase, about a 180% increase to about a 350% increase, about a 180% increase to about a 300% increase, about a 180% increase to about a 250% increase, about a 180% increase to about a 200% increase, about a 200% increase to about 10,000% increase, about a 200% increase to about a 9,000% increase, about a 200% increase to about a 8,000% increase, about a 200% increase to about a 7,000% increase, about a 200% increase to about a 6,000% increase, about a 200% increase to about a 5,000% increase, about a 200% increase to about a 4,000% increase, about a 200% increase to about a 3,000% increase, about a 200% increase to about a 2,000% increase, about a 200% increase to about a 1,000% increase, about a 200% increase to about a 500% increase, about a 200% increase to about a 450% increase, about a 200% increase to about a 400% increase, about a 200% increase to about a 350% increase, about a 200% increase to about a 300% increase, about a 200% increase to about a 250% increase, about a 250% increase to about 10,000% increase, about a 250% increase to about a 9,000% increase, about a 250% increase to about a 8,000% increase, about a 250% increase to about a 7,000% increase, about a 250% increase to about a 6,000% increase, about a 250% increase to about a 5,000% increase, about a 250% increase to about a 4,000% increase, about a 250% increase to about a 3,000% increase, about a 250% increase to about a 2,000% increase, about a 250% increase to about a 1,000% increase, about a 250% increase to about a 500% increase, about a 250% increase to about a 450% increase, about a 250% increase to about a 400% increase, about a 250% increase to about a 350% increase, about a 250% increase to about a 300% increase, about a 300% increase to about 10,000% increase, about a 300% increase to about a 9,000% increase, about a 300% increase to about a 8,000% increase, about a 300% increase to about a 7,000% increase, about a 300% increase to about a 6,000% increase, about a 300% increase to about a 5,000% increase, about a 300% increase to about a 4,000% increase, about a 300% increase to about a 3,000% increase, about a 300% increase to about a 2,000% increase, about a 300% increase to about a 1,000% increase, about a 300% increase to about a 500% increase, about a 300% increase to about a 450% increase, about a 300% increase to about a 400% increase, about a 300% increase to about a 350% increase, about a 350% increase to about 10,000% increase, about a 350% increase to about a 9,000% increase, about a 350% increase to about a 8,000% increase, about a 350% increase to about a 7,000% increase, about a 350% increase to about a 6,000% increase, about a 350% increase to about a 5,000% increase, about a 350% increase to about a 4,000% increase, about a 350% increase to about a 3,000% increase, about a 350% increase to about a 2,000% increase, about a 350% increase to about a 1,000% increase, about a 350% increase to about a 500% increase, about a 350% increase to about a 450% increase, about a 350% increase to about a 400% increase, about a 400% increase to about 10,000% increase, about a 400% increase to about a 9,000% increase, about a 400% increase to about a 8,000% increase, about a 400% increase to about a 7,000% increase, about a 400% increase to about a 6,000% increase, about a 400% increase to about a 5,000% increase, about a 400% increase to about a 4,000% increase, about a 400% increase to about a 3,000% increase, about a 400% increase to about a 2,000% increase, about a 400% increase to about a 1,000% increase, about a 400% increase to about a 500% increase, about a 400% increase to about a 450% increase, about a 450% increase to about 10,000% increase, about a 450% increase to about a 9,000% increase, about a 450% increase to about a 8,000% increase, about a 450% increase to about a 7,000% increase, about a 450% increase to about a 6,000% increase, about a 450% increase to about a 5,000% increase, about a 450% increase to about a 4,000% increase, about a 450% increase to about a 3,000% increase, about a 450% increase to about a 2,000% increase, about a 450% increase to about a 1,000% increase, about a 450% increase to about a 500% increase, about a 500% increase to about 10,000% increase, about a 500% increase to about a 9,000% increase, about a 500% increase to about a 8,000% increase, about a 500% increase to about a 7,000% increase, about a 500% increase to about a 6,000% increase, about a 500% increase to about a 5,000% increase, about a 500% increase to about a 4,000% increase, about a 500% increase to about a 3,000% increase, about a 500% increase to about a 2,000% increase, about a 500% increase to about a 1,000% increase, about a 1,000% increase to about 10,000% increase, about a 1,000% increase to about a 9,000% increase, about a 1,000% increase to about a 8,000% increase, about a 1,000% increase to about a 7,000% increase, about a 1,000% increase to about a 6,000% increase, about a 1,000% increase to about a 5,000% increase, about a 1,000% increase to about a 4,000% increase, about a 1,000% increase to about a 3,000% increase, about a 1,000% increase to about a 2,000% increase, about a 2,000% increase to about 10,000% increase, about a 2,000% increase to about a 9,000% increase, about a 2,000% increase to about a 8,000% increase, about a 2,000% increase to about a 7,000% increase, about a 2,000% increase to about a 6,000% increase, about a 2,000% increase to about a 5,000% increase, about a 2,000% increase to about a 4,000% increase, about a 2,000% increase to about a 3,000% increase, about a 3,000% increase to about 10,000% increase, about a 3,000% increase to about a 9,000% increase, about a 3,000% increase to about a 8,000% increase, about a 3,000% increase to about a 7,000% increase, about a 3,000% increase to about a 6,000% increase, about a 3,000% increase to about a 5,000% increase, about a 3,000% increase to about a 4,000% increase, about a 4,000% increase to about 10,000% increase, about a 4,000% increase to about a 9,000% increase, about a 4,000% increase to about a 8,000% increase, about a 4,000% increase to about a 7,000% increase, about a 4,000% increase to about a 6,000% increase, about a 4,000% increase to about a 5,000% increase, about a 5,000% increase to about 10,000% increase, about a 5,000% increase to about a 9,000% increase, about a 5,000% increase to about a 8,000% increase, about a 5,000% increase to about a 7,000% increase, about a 5,000% increase to about a 6,000% increase, about a 6,000% increase to about 10,000% increase, about a 6,000% increase to about a 9,000% increase, about a 6,000% increase to about a 8,000% increase, about a 6,000% increase to about a 7,000% increase, about a 7,000% increase to about 10,000% increase, about a 7,000% increase to about a 9,000% increase, about a 7,000% increase to about a 8,000% increase, about a 8,000% increase to about 10,000% increase, about a 8,000% increase to about a 9,000% increase, or about a 9,000% increase to about 10,000%) in toxin liberation in the target mammalian cell (e.g., any of the target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about a 100-fold increase, about 0.1-fold increase to about a 90-fold increase, about 0.1-fold increase to about a 80-fold increase, about a 0.1-fold increase to about a 70-fold increase, about a 0.1-fold increase to about a 60-fold increase, about a 0.1-fold increase to about a 50-fold increase, about a 0.1-fold increase to about a 40-fold increase, about a 0.1-fold increase to about a 30-fold increase, about 0.1-fold increase to about 20-fold increase, about a 0.1-fold increase to about a 10-fold increase, about a 0.1-fold increase to about a 9.5-fold increase, about a 0.1-fold increase to about a 9.0-fold increase, about a 0.1-fold increase to about a 8.5-fold increase, about a 0.1-fold increase to about a 8.0-fold increase, about a 0.1-fold increase to about a 7.5-fold increase, about a 0.1-fold increase to about a 7.0-fold increase, about a 0.1-fold increase to about a 6.5-fold increase, about a 0.1-fold increase to about a 6.0-fold increase, about a 0.1-fold increase to about a 5.5-fold increase, about a 0.1-fold increase to about a 5.0-fold increase, about a 0.1-fold increase to about a 4.5-fold increase, about a 0.1-fold increase to about a 4.0-fold increase, about a 0.1-fold increase to about a 3.5-fold increase, about 0.1-fold increase to about a 3.0-fold increase, about a 0.1-fold increase to about a 2.8-fold increase, about a 0.1-fold increase to about a 2.6-fold increase, about a 0.1-fold increase to about a 2.5-fold increase, about a 0.1-fold increase to about a 2.4-fold increase, about a 0.1-fold increase to about a 2.2-fold increase, about a 0.1-fold increase to about a 2.0-fold increase, about a 0.1-fold increase to about a 1.8-fold increase, about a 0.1-fold increase to about a 1.6-fold increase, about a 0.1-fold increase to about a 1.5-fold increase, about a 0.1-fold increase to about a 1.4-fold increase, about a 0.1-fold increase to about a 1.2-fold increase, about a 0.1-fold increase to about a 1.0-fold increase, about a 0.1-fold increase to about a 0.9-fold increase, about a 0.1-fold increase to about a 0.8-fold increase, about a 0.1-fold increase to about a 0.7-fold increase, about a 0.1-fold increase to about a 0.6-fold increase, about a 0.1-fold increase to about a 0.5-fold increase, about a 0.1-fold increase to about a 0.4-fold increase, about a 0.1-fold increase to about a 0.3-fold increase, about a 0.2-fold increase to about a 100-fold increase, about 0.2-fold increase to about a 90-fold increase, about 0.2-fold increase to about a 80-fold increase, about a 0.2-fold increase to about a 70-fold increase, about a 0.2-fold increase to about a 60-fold increase, about a 0.2-fold increase to about a 50-fold increase, about a 0.2-fold increase to about a 40-fold increase, about a 0.2-fold increase to about a 30-fold increase, about 0.2-fold increase to about 20-fold increase, about a 0.2-fold increase to about a 10-fold increase, about a 0.2-fold increase to about a 9.5-fold increase, about a 0.2-fold increase to about a 9.0-fold increase, about a 0.2-fold increase to about a 8.5-fold increase, about a 0.2-fold increase to about a 8.0-fold increase, about a 0.2-fold increase to about a 7.5-fold increase, about a 0.2-fold increase to about a 7.0-fold increase, about a 0.2-fold increase to about a 6.5-fold increase, about a 0.2-fold increase to about a 6.0-fold increase, about a 0.2-fold increase to about a 5.5-fold increase, about a 0.2-fold increase to about a 5.0-fold increase, about a 0.2-fold increase to about a 4.5-fold increase, about a 0.2-fold increase to about a 4.0-fold increase, about a 0.2-fold increase to about a 3.5-fold increase, about 0.2-fold increase to about a 3.0-fold increase, about a 0.2-fold increase to about a 2.8-fold increase, about a 0.2-fold increase to about a 2.6-fold increase, about a 0.2-fold increase to about a 2.5-fold increase, about a 0.2-fold increase to about a 2.4-fold increase, about a 0.2-fold increase to about a 2.2-fold increase, about a 0.2-fold increase to about a 2.0-fold increase, about a 0.2-fold increase to about a 1.8-fold increase, about a 0.2-fold increase to about a 1.6-fold increase, about a 0.2-fold increase to about a 1.5-fold increase, about a 0.2-fold increase to about a 1.4-fold increase, about a 0.2-fold increase to about a 1.2-fold increase, about a 0.2-fold increase to about a 1.0-fold increase, about a 0.2-fold increase to about a 0.9-fold increase, about a 0.2-fold increase to about a 0.8-fold increase, about a 0.2-fold increase to about a 0.7-fold increase, about a 0.2-fold increase to about a 0.6-fold increase, about a 0.2-fold increase to about a 0.5-fold increase, about a 0.2-fold increase to about a 0.4-fold increase, about a 0.3-fold increase to about a 100-fold increase, about 0.3-fold increase to about a 90-fold increase, about 0.3-fold increase to about a 80-fold increase, about a 0.3-fold increase to about a 70-fold increase, about a 0.3-fold increase to about a 60-fold increase, about a 0.3-fold increase to about a 50-fold increase, about a 0.3-fold increase to about a 40-fold increase, about a 0.3-fold increase to about a 30-fold increase, about 0.3-fold increase to about 20-fold increase, about a 0.3-fold increase to about a 10-fold increase, about a 0.3-fold increase to about a 9.5-fold increase, about a 0.3-fold increase to about a 9.0-fold increase, about a 0.3-fold increase to about a 8.5-fold increase, about a 0.3-fold increase to about a 8.0-fold increase, about a 0.3-fold increase to about a 7.5-fold increase, about a 0.3-fold increase to about a 7.0-fold increase, about a 0.3-fold increase to about a 6.5-fold increase, about a 0.3-fold increase to about a 6.0-fold increase, about a 0.3-fold increase to about a 5.5-fold increase, about a 0.3-fold increase to about a 5.0-fold increase, about a 0.3-fold increase to about a 4.5-fold increase, about a 0.3-fold increase to about a 4.0-fold increase, about a 0.3-fold increase to about a 3.5-fold increase, about 0.3-fold increase to about a 3.0-fold increase, about a 0.3-fold increase to about a 2.8-fold increase, about a 0.3-fold increase to about a 2.6-fold increase, about a 0.3-fold increase to about a 2.5-fold increase, about a 0.3-fold increase to about a 2.4-fold increase, about a 0.3-fold increase to about a 2.2-fold increase, about a 0.3-fold increase to about a 2.0-fold increase, about a 0.3-fold increase to about a 1.8-fold increase, about a 0.3-fold increase to about a 1.6-fold increase, about a 0.3-fold increase to about a 1.5-fold increase, about a 0.3-fold increase to about a 1.4-fold increase, about a 0.3-fold increase to about a 1.2-fold increase, about a 0.3-fold increase to about a 1.0-fold increase, about a 0.3-fold increase to about a 0.9-fold increase, about a 0.3-fold increase to about a 0.8-fold increase, about a 0.3-fold increase to about a 0.7-fold increase, about a 0.3-fold increase to about a 0.6-fold increase, about a 0.3-fold increase to about a 0.5-fold increase, about a 0.4-fold increase to about a 100-fold increase, about 0.4-fold increase to about a 90-fold increase, about 0.4-fold increase to about a 80-fold increase, about a 0.4-fold increase to about a 70-fold increase, about a 0.4-fold increase to about a 60-fold increase, about a 0.4-fold increase to about a 50-fold increase, about a 0.4-fold increase to about a 40-fold increase, about a 0.4-fold increase to about a 30-fold increase, about 0.4-fold increase to about 20-fold increase, about a 0.4-fold increase to about a 10-fold increase, about a 0.4-fold increase to about a 9.5-fold increase, about a 0.4-fold increase to about a 9.0-fold increase, about a 0.4-fold increase to about a 8.5-fold increase, about a 0.4-fold increase to about a 8.0-fold increase, about a 0.4-fold increase to about a 7.5-fold increase, about a 0.4-fold increase to about a 7.0-fold increase, about a 0.4-fold increase to about a 6.5-fold increase, about a 0.4-fold increase to about a 6.0-fold increase, about a 0.4-fold increase to about a 5.5-fold increase, about a 0.4-fold increase to about a 5.0-fold increase, about a 0.4-fold increase to about a 4.5-fold increase, about a 0.4-fold increase to about a 4.0-fold increase, about a 0.4-fold increase to about a 3.5-fold increase, about 0.4-fold increase to about a 3.0-fold increase, about a 0.4-fold increase to about a 2.8-fold increase, about a 0.4-fold increase to about a 2.6-fold increase, about a 0.4-fold increase to about a 2.5-fold increase, about a 0.4-fold increase to about a 2.4-fold increase, about a 0.4-fold increase to about a 2.2-fold increase, about a 0.4-fold increase to about a 2.0-fold increase, about a 0.4-fold increase to about a 1.8-fold increase, about a 0.4-fold increase to about a 1.6-fold increase, about a 0.4-fold increase to about a 1.5-fold increase, about a 0.4-fold increase to about a 1.4-fold increase, about a 0.4-fold increase to about a 1.2-fold increase, about a 0.4-fold increase to about a 1.0-fold increase, about a 0.4-fold increase to about a 0.9-fold increase, about a 0.4-fold increase to about a 0.8-fold increase, about a 0.4-fold increase to about a 0.7-fold increase, about a 0.4-fold increase to about a 0.6-fold increase, about a 0.5-fold increase to about a 100-fold increase, about 0.5-fold increase to about a 90-fold increase, about 0.5-fold increase to about a 80-fold increase, about a 0.5-fold increase to about a 70-fold increase, about a 0.5-fold increase to about a 60-fold increase, about a 0.5-fold increase to about a 50-fold increase, about a 0.5-fold increase to about a 40-fold increase, about a 0.5-fold increase to about a 30-fold increase, about 0.5-fold increase to about 20-fold increase, about a 0.5-fold increase to about a 10-fold increase, about a 0.5-fold increase to about a 9.5-fold increase, about a 0.5-fold increase to about a 9.0-fold increase, about a 0.5-fold increase to about a 8.5-fold increase, about a 0.5-fold increase to about a 8.0-fold increase, about a 0.5-fold increase to about a 7.5-fold increase, about a 0.5-fold increase to about a 7.0-fold increase, about a 0.5-fold increase to about a 6.5-fold increase, about a 0.5-fold increase to about a 6.0-fold increase, about a 0.5-fold increase to about a 5.5-fold increase, about a 0.5-fold increase to about a 5.0-fold increase, about a 0.5-fold increase to about a 4.5-fold increase, about a 0.5-fold increase to about a 4.0-fold increase, about a 0.5-fold increase to about a 3.5-fold increase, about 0.5-fold increase to about a 3.0-fold increase, about a 0.5-fold increase to about a 2.8-fold increase, about a 0.5-fold increase to about a 2.6-fold increase, about a 0.5-fold increase to about a 2.5-fold increase, about a 0.5-fold increase to about a 2.4-fold increase, about a 0.5-fold increase to about a 2.2-fold increase, about a 0.5-fold increase to about a 2.0-fold increase, about a 0.5-fold increase to about a 1.8-fold increase, about a 0.5-fold increase to about a 1.6-fold increase, about a 0.5-fold increase to about a 1.5-fold increase, about a 0.5-fold increase to about a 1.4-fold increase, about a 0.5-fold increase to about a 1.2-fold increase, about a 0.5-fold increase to about a 1.0-fold increase, about a 0.5-fold increase to about a 0.9-fold increase, about a 0.5-fold increase to about a 0.8-fold increase, about a 0.5-fold increase to about a 0.7-fold increase, about a 0.6-fold increase to about a 100-fold increase, about 0.6-fold increase to about a 90-fold increase, about 0.6-fold increase to about a 80-fold increase, about a 0.6-fold increase to about a 70-fold increase, about a 0.6-fold increase to about a 60-fold increase, about a 0.6-fold increase to about a 50-fold increase, about a 0.6-fold increase to about a 40-fold increase, about a 0.6-fold increase to about a 30-fold increase, about 0.6-fold increase to about 20-fold increase, about a 0.6-fold increase to about a 10-fold increase, about a 0.6-fold increase to about a 9.5-fold increase, about a 0.6-fold increase to about a 9.0-fold increase, about a 0.6-fold increase to about a 8.5-fold increase, about a 0.6-fold increase to about a 8.0-fold increase, about a 0.6-fold increase to about a 7.5-fold increase, about a 0.6-fold increase to about a 7.0-fold increase, about a 0.6-fold increase to about a 6.5-fold increase, about a 0.6-fold increase to about a 6.0-fold increase, about a 0.6-fold increase to about a 5.5-fold increase, about a 0.6-fold increase to about a 5.0-fold increase, about a 0.6-fold increase to about a 4.5-fold increase, about a 0.6-fold increase to about a 4.0-fold increase, about a 0.6-fold increase to about a 3.5-fold increase, about 0.6-fold increase to about a 3.0-fold increase, about a 0.6-fold increase to about a 2.8-fold increase, about a 0.6-fold increase to about a 2.6-fold increase, about a 0.6-fold increase to about a 2.5-fold increase, about a 0.6-fold increase to about a 2.4-fold increase, about a 0.6-fold increase to about a 2.2-fold increase, about a 0.6-fold increase to about a 2.0-fold increase, about a 0.6-fold increase to about a 1.8-fold increase, about a 0.6-fold increase to about a 1.6-fold increase, about a 0.6-fold increase to about a 1.5-fold increase, about a 0.6-fold increase to about a 1.4-fold increase, about a 0.6-fold increase to about a 1.2-fold increase, about a 0.6-fold increase to about a 1.0-fold increase, about a 0.6-fold increase to about a 0.9-fold increase, about a 0.6-fold increase to about a 0.8-fold increase, about a 0.7-fold increase to about a 100-fold increase, about 0.7-fold increase to about a 90-fold increase, about 0.7-fold increase to about a 80-fold increase, about a 0.7-fold increase to about a 70-fold increase, about a 0.7-fold increase to about a 60-fold increase, about a 0.7-fold increase to about a 50-fold increase, about a 0.7-fold increase to about a 40-fold increase, about a 0.7-fold increase to about a 30-fold increase, about 0.7-fold increase to about 20-fold increase, about a 0.7-fold increase to about a 10-fold increase, about a 0.7-fold increase to about a 9.5-fold increase, about a 0.7-fold increase to about a 9.0-fold increase, about a 0.7-fold increase to about a 8.5-fold increase, about a 0.7-fold increase to about a 8.0-fold increase, about a 0.7-fold increase to about a 7.5-fold increase, about a 0.7-fold increase to about a 7.0-fold increase, about a 0.7-fold increase to about a 6.5-fold increase, about a 0.7-fold increase to about a 6.0-fold increase, about a 0.7-fold increase to about a 5.5-fold increase, about a 0.7-fold increase to about a 5.0-fold increase, about a 0.7-fold increase to about a 4.5-fold increase, about a 0.7-fold increase to about a 4.0-fold increase, about a 0.7-fold increase to about a 3.5-fold increase, about 0.7-fold increase to about a 3.0-fold increase, about a 0.7-fold increase to about a 2.8-fold increase, about a 0.7-fold increase to about a 2.6-fold increase, about a 0.7-fold increase to about a 2.5-fold increase, about a 0.7-fold increase to about a 2.4-fold increase, about a 0.7-fold increase to about a 2.2-fold increase, about a 0.7-fold increase to about a 2.0-fold increase, about a 0.7-fold increase to about a 1.8-fold increase, about a 0.7-fold increase to about a 1.6-fold increase, about a 0.7-fold increase to about a 1.5-fold increase, about a 0.7-fold increase to about a 1.4-fold increase, about a 0.7-fold increase to about a 1.2-fold increase, about a 0.7-fold increase to about a 1.0-fold increase, about a 0.7-fold increase to about a 0.9-fold increase, about a 0.8-fold increase to about a 100-fold increase, about 0.8-fold increase to about a 90-fold increase, about 0.8-fold increase to about a 80-fold increase, about a 0.8-fold increase to about a 70-fold increase, about a 0.8-fold increase to about a 60-fold increase, about a 0.8-fold increase to about a 50-fold increase, about a 0.8-fold increase to about a 40-fold increase, about a 0.8-fold increase to about a 30-fold increase, about 0.8-fold increase to about 20-fold increase, about a 0.8-fold increase to about a 10-fold increase, about a 0.8-fold increase to about a 9.5-fold increase, about a 0.8-fold increase to about a 9.0-fold increase, about a 0.8-fold increase to about a 8.5-fold increase, about a 0.8-fold increase to about a 8.0-fold increase, about a 0.8-fold increase to about a 7.5-fold increase, about a 0.8-fold increase to about a 7.0-fold increase, about a 0.8-fold increase to about a 6.5-fold increase, about a 0.8-fold increase to about a 6.0-fold increase, about a 0.8-fold increase to about a 5.5-fold increase, about a 0.8-fold increase to about a 5.0-fold increase, about a 0.8-fold increase to about a 4.5-fold increase, about a 0.8-fold increase to about a 4.0-fold increase, about a 0.8-fold increase to about a 3.5-fold increase, about 0.8-fold increase to about a 3.0-fold increase, about a 0.8-fold increase to about a 2.8-fold increase, about a 0.8-fold increase to about a 2.6-fold increase, about a 0.8-fold increase to about a 2.5-fold increase, about a 0.8-fold increase to about a 2.4-fold increase, about a 0.8-fold increase to about a 2.2-fold increase, about a 0.8-fold increase to about a 2.0-fold increase, about a 0.8-fold increase to about a 1.8-fold increase, about a 0.8-fold increase to about a 1.6-fold increase, about a 0.8-fold increase to about a 1.5-fold increase, about a 0.8-fold increase to about a 1.4-fold increase, about a 0.8-fold increase to about a 1.2-fold increase, about a 0.8-fold increase to about a 1.0-fold increase, about a 1.0-fold increase to about a 100-fold increase, about 1.0-fold increase to about a 90-fold increase, about 1.0-fold increase to about a 80-fold increase, about a 1.0-fold increase to about a 70-fold increase, about a 1.0- fold increase to about a 60-fold increase, about a 1.0-fold increase to about a 50-fold increase, about a 1.0-fold increase to about a 40-fold increase, about a 1.0-fold increase to about a 30-fold increase, about 1.0-fold increase to about 20-fold increase, about a 1.0-fold increase to about a 10-fold increase, about a 1.0-fold increase to about a 9.5-fold increase, about a 1.0-fold increase to about a 9.0-fold increase, about a 1.0-fold increase to about a 8.5-fold increase, about a 1.0-fold increase to about a 8.0-fold increase, about a 1.0-fold increase to about a 7.5-fold increase, about a 1.0-fold increase to about a 7.0-fold increase, about a 1.0-fold increase to about a 6.5-fold increase, about a 1.0-fold increase to about a 6.0-fold increase, about a 1.0-fold increase to about a 5.5-fold increase, about a 1.0-fold increase to about a 5.0-fold increase, about a 1.0-fold increase to about a 4.5-fold increase, about a 1.0-fold increase to about a 4.0-fold increase, about a 1.0-fold increase to about a 3.5-fold increase, about 1.0-fold increase to about a 3.0-fold increase, about a 1.0-fold increase to about a 2.8-fold increase, about a 1.0-fold increase to about a 2.6-fold increase, about a 1.0-fold increase to about a 2.5-fold increase, about a 1.0-fold increase to about a 2.4-fold increase, about a 1.0-fold increase to about a 2.2-fold increase, about a 1.0-fold increase to about a 2.0-fold increase, about a 1.0-fold increase to about a 1.8-fold increase, about a 1.0-fold increase to about a 1.6-fold increase, about a 1.0-fold increase to about a 1.5-fold increase, about a 1.0-fold increase to about a 1.4-fold increase, about a 1.0-fold increase to about a 1.2-fold increase, about a 1.2-fold increase to about a 100-fold increase, about 1.2-fold increase to about a 90-fold increase, about 1.2-fold increase to about a 80-fold increase, about a 1.2-fold increase to about a 70-fold increase, about a 1.2-fold increase to about a 60-fold increase, about a 1.2-fold increase to about a 50-fold increase, about a 1.2-fold increase to about a 40-fold increase, about a 1.2-fold increase to about a 30-fold increase, about 1.2-fold increase to about 20-fold increase, about a 1.2-fold increase to about a 10-fold increase, about a 1.2-fold increase to about a 9.5-fold increase, about a 1.2-fold increase to about a 9.0-fold increase, about a 1.2-fold increase to about a 8.5-fold increase, about a 1.2-fold increase to about a 8.0-fold increase, about a 1.2-fold increase to about a 7.5-fold increase, about a 1.2-fold increase to about a 7.0-fold increase, about a 1.2-fold increase to about a 6.5-fold increase, about a 1.2-fold increase to about a 6.0-fold increase, about a 1.2-fold increase to about a 5.5-fold increase, about a 1.2-fold increase to about a 5.0-fold increase, about a 1.2-fold increase to about a 4.5-fold increase, about a 1.2-fold increase to about a 4.0-fold increase, about a 1.2-fold increase to about a 3.5-fold increase, about 1.2-fold increase to about a 3.0-fold increase, about a 1.2-fold increase to about a 2.8-fold increase, about a 1.2-fold increase to about a 2.6-fold increase, about a 1.2-fold increase to about a 2.5-fold increase, about a 1.2-fold increase to about a 2.4-fold increase, about a 1.2-fold increase to about a 2.2-fold increase, about a 1.2-fold increase to about a 2.0-fold increase, about a 1.2-fold increase to about a 1.8-fold increase, about a 1.2-fold increase to about a 1.6-fold increase, about a 1.2-fold increase to about a 1.5-fold increase, about a 1.2-fold increase to about a 1.4-fold increase, about a 1.4-fold increase to about a 100-fold increase, about 1.4-fold increase to about a 90-fold increase, about 1.4-fold increase to about a 80-fold increase, about a 1.4-fold increase to about a 70-fold increase, about a 1.4- fold increase to about a 60-fold increase, about a 1.4-fold increase to about a 50-fold increase, about a 1.4-fold increase to about a 40-fold increase, about a 1.4-fold increase to about a 30-fold increase, about 1.4-fold increase to about 20-fold increase, about a 1.4-fold increase to about a 10-fold increase, about a 1.4-fold increase to about a 9.5-fold increase, about a 1.4-fold increase to about a 9.0-fold increase, about a 1.4-fold increase to about a 8.5-fold increase, about a 1.4-fold increase to about a 8.0-fold increase, about a 1.4-fold increase to about a 7.5-fold increase, about a 1.4-fold increase to about a 7.0-fold increase, about a 1.4-fold increase to about a 6.5-fold increase, about a 1.4-fold increase to about a 6.0-fold increase, about a 1.4-fold increase to about a 5.5-fold increase, about a 1.4-fold increase to about a 5.0-fold increase, about a 1.4-fold increase to about a 4.5-fold increase, about a 1.4-fold increase to about a 4.0-fold increase, about a 1.4-fold increase to about a 3.5-fold increase, about 1.4-fold increase to about a 3.0-fold increase, about a 1.4-fold increase to about a 2.8-fold increase, about a 1.4-fold increase to about a 2.6-fold increase, about a 1.4-fold increase to about a 2.5-fold increase, about a 1.4-fold increase to about a 2.4-fold increase, about a 1.4-fold increase to about a 2.2-fold increase, about a 1.4-fold increase to about a 2.0-fold increase, about a 1.4-fold increase to about a 1.8-fold increase, about a 1.4-fold increase to about a 1.6-fold increase, about a 1.6-fold increase to about a 10-fold increase, about a 1.6-fold increase to about a 100-fold increase, about 1.6-fold increase to about a 90-fold increase, about 1.6-fold increase to about a 80-fold increase, about a 1.6-fold increase to about a 70-fold increase, about a 1.6-fold increase to about a 60-fold increase, about a 1.6-fold increase to about a 50-fold increase, about a 1.6-fold increase to about a 40-fold increase, about a 1.6-fold increase to about a 30-fold increase, about 1.6-fold increase to about 20-fold increase, about a 1.6-fold increase to about a 9.5-fold increase, about a 1.6-fold increase to about a 9.0-fold increase, about a 1.6-fold increase to about a 8.5-fold increase, about a 1.6-fold increase to about a 8.0-fold increase, about a 1.6-fold increase to about a 7.5-fold increase, about a 1.6-fold increase to about a 7.0-fold increase, about a 1.6-fold increase to about a 6.5-fold increase, about a 1.6-fold increase to about a 6.0-fold increase, about a 1.6-fold increase to about a 5.5-fold increase, about a 1.6-fold increase to about a 5.0-fold increase, about a 1.6-fold increase to about a 4.5-fold increase, about a 1.6-fold increase to about a 4.0-fold increase, about a 1.6-fold increase to about a 3.5-fold increase, about 1.6-fold increase to about a 3.0-fold increase, about a 1.6-fold increase to about a 2.8-fold increase, about a 1.6-fold increase to about a 2.6-fold increase, about a 1.6-fold increase to about a 2.5-fold increase, about a 1.6-fold increase to about a 2.4-fold increase, about a 1.6-fold increase to about a 2.2-fold increase, about a 1.6-fold increase to about a 2.0-fold increase, about a 1.6-fold increase to about a 1.8-fold increase, about a 1.8-fold increase to about a 100-fold increase, about 1.8-fold increase to about a 90-fold increase, about 1.8-fold increase to about a 80-fold increase, about a 1.8-fold increase to about a 70-fold increase, about a 1.8-fold increase to about a 60-fold increase, about a 1.8-fold increase to about a 50-fold increase, about a 1.8-fold increase to about a 40-fold increase, about a 1.8-fold increase to about a 30-fold increase, about 1.8-fold increase to about 20-fold increase, about a 1.8-fold increase to about a 10-fold increase, about a 1.8-fold increase to about a 9.5-fold increase, about a 1.8-fold increase to about a 9.0-fold increase, about a 1.8-fold increase to about a 8.5-fold increase, about a 1.8-fold increase to about a 8.0-fold increase, about a 1.8-fold increase to about a 7.5-fold increase, about a 1.8-fold increase to about a 7.0-fold increase, about a 1.8-fold increase to about a 6.5-fold increase, about a 1.8-fold increase to about a 6.0-fold increase, about a 1.8-fold increase to about a 5.5-fold increase, about a 1.8-fold increase to about a 5.0-fold increase, about a 1.8-fold increase to about a 4.5-fold increase, about a 1.8-fold increase to about a 4.0-fold increase, about a 1.8-fold increase to about a 3.5-fold increase, about 1.8-fold increase to about a 3.0-fold increase, about a 1.8-fold increase to about a 2.8-fold increase, about a 1.8-fold increase to about a 2.6-fold increase, about a 1.8-fold increase to about a 2.5-fold increase, about a 1.8-fold increase to about a 2.4-fold increase, about a 1.8-fold increase to about a 2.2-fold increase, about a 1.8-fold increase to about a 2.0-fold increase, about a 2.0-fold increase to about a 100-fold increase, about 2.0-fold increase to about a 90-fold increase, about 2.0-fold increase to about a 80-fold increase, about a 2.0-fold increase to about a 70-fold increase, about a 2.0-fold increase to about a 60-fold increase, about a 2.0-fold increase to about a 50-fold increase, about a 2.0-fold increase to about a 40-fold increase, about a 2.0-fold increase to about a 30-fold increase, about 2.0-fold increase to about 20-fold increase, about a 2.0-fold increase to about a 10-fold increase, about a 2.0-fold increase to about a 9.5-fold increase, about a 2.0-fold increase to about a 9.0-fold increase, about a 2.0-fold increase to about a 8.5-fold increase, about a 2.0-fold increase to about a 8.0-fold increase, about a 2.0-fold increase to about a 7.5-fold increase, about a 2.0-fold increase to about a 7.0-fold increase, about a 2.0-fold increase to about a 6.5-fold increase, about a 2.0-fold increase to about a 6.0-fold increase, about a 2.0-fold increase to about a 5.5-fold increase, about a 2.0-fold increase to about a 5.0-fold increase, about a 2.0-fold increase to about a 4.5-fold increase, about a 2.0-fold increase to about a 4.0-fold increase, about a 2.0-fold increase to about a 3.5-fold increase, about 2.0-fold increase to about a 3.0-fold increase, about a 2.0-fold increase to about a 2.8-fold increase, about a 2.0-fold increase to about a 2.6-fold increase, about a 2.0-fold increase to about a 2.5-fold increase, about a 2.0-fold increase to about a 2.4-fold increase, about a 2.0-fold increase to about a 2.2-fold increase, about a 2.2-fold increase to about a 100-fold increase, about 2.2-fold increase to about a 90-fold increase, about 2.2-fold increase to about a 80-fold increase, about a 2.2-fold increase to about a 70-fold increase, about a 2.2-fold increase to about a 60-fold increase, about a 2.2-fold increase to about a 50-fold increase, about a 2.2-fold increase to about a 40-fold increase, about a 2.2-fold increase to about a 30-fold increase, about 2.2-fold increase to about 20-fold increase, about a 2.2-fold increase to about a 10-fold increase, about a 2.2-fold increase to about a 9.5-fold increase, about a 2.2-fold increase to about a 9.0-fold increase, about a 2.2-fold increase to about a 8.5-fold increase, about a 2.2-fold increase to about a 8.0-fold increase, about a 2.2-fold increase to about a 7.5-fold increase, about a 2.2-fold increase to about a 7.0-fold increase, about a 2.2-fold increase to about a 6.5-fold increase, about a 2.2-fold increase to about a 6.0-fold increase, about a 2.2-fold increase to about a 5.5-fold increase, about a 2.2-fold increase to about a 5.0-fold increase, about a 2.2-fold increase to about a 4.5-fold increase, about a 2.2-fold increase to about a 4.0-fold increase, about a 2.2-fold increase to about a 3.5-fold increase, about 2.2-fold increase to about a 3.0-fold increase, about a 2.2-fold increase to about a 2.8-fold increase, about a 2.2-fold increase to about a 2.6-fold increase, about a 2.2-fold increase to about a 2.5-fold increase, about a 2.2-fold increase to about a 2.4-fold increase, about a 2.4-fold increase to about a 100-fold increase, about 2.4-fold increase to about a 90-fold increase, about 2.4-fold increase to about a 80-fold increase, about a 2.4-fold increase to about a 70-fold increase, about a 2.4-fold increase to about a 60-fold increase, about a 2.4-fold increase to about a 50-fold increase, about a 2.4-fold increase to about a 40-fold increase, about a 2.4-fold increase to about a 30-fold increase, about 2.4-fold increase to about 20-fold increase, about a 2.4-fold increase to about a 10-fold increase, about a 2.4-fold increase to about a 9.5-fold increase, about a 2.4-fold increase to about a 9.0-fold increase, about a 2.4-fold increase to about a 8.5-fold increase, about a 2.4-fold increase to about a 8.0-fold increase, about a 2.4-fold increase to about a 7.5-fold increase, about a 2.4-fold increase to about a 7.0-fold increase, about a 2.4-fold increase to about a 6.5-fold increase, about a 2.4-fold increase to about a 6.0-fold increase, about a 2.4-fold increase to about a 5.5-fold increase, about a 2.4-fold increase to about a 5.0-fold increase, about a 2.4-fold increase to about a 4.5-fold increase, about a 2.4-fold increase to about a 4.0-fold increase, about a 2.4-fold increase to about a 3.5-fold increase, about 2.4-fold increase to about a 3.0-fold increase, about a 2.4-fold increase to about a 2.8-fold increase, about a 2.4-fold increase to about a 2.6-fold increase, about a 2.6-fold increase to about a 100-fold increase, about 2.6-fold increase to about a 90-fold increase, about 2.6-fold increase to about a 80-fold increase, about a 2.6-fold increase to about a 70-fold increase, about a 2.6-fold increase to about a 60-fold increase, about a 2.6-fold increase to about a 50-fold increase, about a 2.6-fold increase to about a 40-fold increase, about a 2.6-fold increase to about a 30-fold increase, about 2.6-fold increase to about 20-fold increase, about a 2.6-fold increase to about a 10-fold increase, about a 2.6-fold increase to about a 9.5-fold increase, about a 2.6-fold increase to about a 9.0-fold increase, about a 2.6-fold increase to about a 8.5-fold increase, about a 2.6-fold increase to about a 8.0-fold increase, about a 2.6-fold increase to about a 7.5-fold increase, about a 2.6-fold increase to about a 7.0-fold increase, about a 2.6-fold increase to about a 6.5-fold increase, about a 2.6-fold increase to about a 6.0-fold increase, about a 2.6-fold increase to about a 5.5-fold increase, about a 2.6-fold increase to about a 5.0-fold increase, about a 2.6-fold increase to about a 4.5-fold increase, about a 2.6-fold increase to about a 4.0-fold increase, about a 2.6-fold increase to about a 3.5-fold increase, about 2.6-fold increase to about a 3.0-fold increase, about a 2.6-fold increase to about a 2.8-fold increase, about a 2.8-fold increase to about a 100-fold increase, about 2.8-fold increase to about a 90-fold increase, about 2.8-fold increase to about a 80-fold increase, about a 2.8-fold increase to about a 70-fold increase, about a 2.8-fold increase to about a 60-fold increase, about a 2.8-fold increase to about a 50-fold increase, about a 2.8-fold increase to about a 40-fold increase, about a 2.8-fold increase to about a 30-fold increase, about 2.8-fold increase to about 20-fold increase, about a 2.8-fold increase to about a 10-fold increase, about a 2.8-fold increase to about a 9.5-fold increase, about a 2.8-fold increase to about a 9.0-fold increase, about a 2.8-fold increase to about a 8.5-fold increase, about a 2.8-fold increase to about a 8.0-fold increase, about a 2.8-fold increase to about a 7.5-fold increase, about a 2.8-fold increase to about a 7.0-fold increase, about a 2.8-fold increase to about a 6.5-fold increase, about a 2.8-fold increase to about a 6.0-fold increase, about a 2.8-fold increase to about a 5.5-fold increase, about a 2.8-fold increase to about a 5.0-fold increase, about a 2.8-fold increase to about a 4.5-fold increase, about a 2.8-fold increase to about a 4.0-fold increase, about a 2.8-fold increase to about a 3.5-fold increase, about 2.8-fold increase to about a 3.0-fold increase, about a 3.0-fold increase to about a 100-fold increase, about 3.0-fold increase to about a 90-fold increase, about 3.0-fold increase to about a 80-fold increase, about a 3.0-fold increase to about a 70-fold increase, about a 3.0-fold increase to about a 60-fold increase, about a 3.0-fold increase to about a 50-fold increase, about a 3.0-fold increase to about a 40-fold increase, about a 3.0-fold increase to about a 30-fold increase, about 3.0-fold increase to about 20-fold increase, about a 3.0-fold increase to about a 10-fold increase, about a 3.0-fold increase to about a 9.5-fold increase, about a 3.0-fold increase to about a 9.0-fold increase, about a 3.0-fold increase to about a 8.5-fold increase, about a 3.0-fold increase to about a 8.0-fold increase, about a 3.0-fold increase to about a 7.5-fold increase, about a 3.0-fold increase to about a 7.0-fold increase, about a 3.0-fold increase to about a 6.5-fold increase, about a 3.0-fold increase to about a 6.0-fold increase, about a 3.0-fold increase to about a 5.5-fold increase, about a 3.0-fold increase to about a 5.0-fold increase, about a 3.0-fold increase to about a 4.5-fold increase, about a 3.0-fold increase to about a 4.0-fold increase, about a 3.0-fold increase to about a 3.5-fold increase, about a 3.5-fold increase to about a 100-fold increase, about 3.5-fold increase to about a 90-fold increase, about 3.5-fold increase to about a 80-fold increase, about a 3.5-fold increase to about a 70-fold increase, about a 3.5-fold increase to about a 60-fold increase, about a 3.5-fold increase to about a 50-fold increase, about a 3.5-fold increase to about a 40-fold increase, about a 3.5-fold increase to about a 30-fold increase, about 3.5-fold increase to about 20-fold increase, about a 3.5-fold increase to about a 10-fold increase, about a 3.5-fold increase to about a 9.5-fold increase, about a 3.5-fold increase to about a 9.0-fold increase, about a 3.5-fold increase to about a 8.5-fold increase, about a 3.5-fold increase to about a 8.0-fold increase, about a 3.5-fold increase to about a 7.5-fold increase, about a 3.5-fold increase to about a 7.0-fold increase, about a 3.5-fold increase to about a 6.5-fold increase, about a 3.5-fold increase to about a 6.0-fold increase, about a 3.5-fold increase to about a 5.5-fold increase, about a 3.5-fold increase to about a 5.0-fold increase, about a 3.5-fold increase to about a 4.5-fold increase, about a 3.5-fold increase to about a 4.0-fold increase, about a 4.0-fold increase to about a 100-fold increase, about 4.0-fold increase to about a 90-fold increase, about 4.0-fold increase to about a 80-fold increase, about a 4.0-fold increase to about a 70-fold increase, about a 4.0-fold increase to about a 60-fold increase, about a 4.0-fold increase to about a 50-fold increase, about a 4.0-fold increase to about a 40-fold increase, about a 4.0-fold increase to about a 30-fold increase, about 4.0-fold increase to about 20-fold increase, about a 4.0-fold increase to about a 10-fold increase, about a 4.0-fold increase to about a 9.5-fold increase, about a 4.0-fold increase to about a 9.0-fold increase, about a 4.0-fold increase to about a 8.5-fold increase, about a 4.0-fold increase to about a 8.0-fold increase, about a 4.0-fold increase to about a 7.5-fold increase, about a 4.0-fold increase to about a 7.0-fold increase, about a 4.0-fold increase to about a 6.5-fold increase, about a 4.0-fold increase to about a 6.0-fold increase, about a 4.0-fold increase to about a 5.5-fold increase, about a 4.0-fold increase to about a 5.0-fold increase, about a 4.0-fold increase to about a 4.5-fold increase, about a 4.5-fold increase to about a 100-fold increase, about 4.5-fold increase to about a 90-fold increase, about 4.5-fold increase to about a 80-fold increase, about a 4.5-fold increase to about a 70-fold increase, about a 4.5-fold increase to about a 60-fold increase, about a 4.5-fold increase to about a 50-fold increase, about a 4.5-fold increase to about a 40-fold increase, about a 4.5-fold increase to about a 30-fold increase, about 4.5-fold increase to about 20-fold increase, about a 4.5-fold increase to about a 10-fold increase, about a 4.5-fold increase to about a 9.5-fold increase, about a 4.5-fold increase to about a 9.0-fold increase, about a 4.5-fold increase to about a 8.5-fold increase, about a 4.5-fold increase to about a 8.0-fold increase, about a 4.5-fold increase to about a 7.5-fold increase, about a 4.5-fold increase to about a 7.0-fold increase, about a 4.5-fold increase to about a 6.5-fold increase, about a 4.5-fold increase to about a 6.0-fold increase, about a 4.5-fold increase to about a 5.5-fold increase, about a 4.5-fold increase to about a 5.0-fold increase, about a 5.0-fold increase to about a 100-fold increase, about 5.0-fold increase to about a 90-fold increase, about 5.0-fold increase to about a 80-fold increase, about a 5.0-fold increase to about a 70-fold increase, about a 5.0-fold increase to about a 60-fold increase, about a 5.0-fold increase to about a 50-fold increase, about a 5.0-fold increase to about a 40-fold increase, about a 5.0-fold increase to about a 30-fold increase, about 5.0-fold increase to about 20-fold increase, about a 5.0-fold increase to about a 10-fold increase, about a 5.0-fold increase to about a 9.5-fold increase, about a 5.0-fold increase to about a 9.0-fold increase, about a 5.0-fold increase to about a 8.5-fold increase, about a 5.0-fold increase to about a 8.0-fold increase, about a 5.0-fold increase to about a 7.5-fold increase, about a 5.0-fold increase to about a 7.0-fold increase, about a 5.0-fold increase to about a 6.5-fold increase, about a 5.0-fold increase to about a 6.0-fold increase, about a 5.0-fold increase to about a 5.5-fold increase, about a 5.5-fold increase to about a 100-fold increase, about 5.5-fold increase to about a 90-fold increase, about 5.5-fold increase to about a 80-fold increase, about a 5.5-fold increase to about a 70-fold increase, about a 5.5-fold increase to about a 60-fold increase, about a 5.5-fold increase to about a 50-fold increase, about a 5.5-fold increase to about a 40-fold increase, about a 5.5-fold increase to about a 30-fold increase, about 5.5-fold increase to about 20-fold increase, about a 5.5-fold increase to about a 10-fold increase, about a 5.5-fold increase to about a 9.5-fold increase, about a 5.5-fold increase to about a 9.0-fold increase, about a 5.5-fold increase to about a 8.5-fold increase, about a 5.5-fold increase to about a 8.0-fold increase, about a 5.5-fold increase to about a 7.5-fold increase, about a 5.5-fold increase to about a 7.0-fold increase, about a 5.5-fold increase to about a 6.5-fold increase, about a 5.5-fold increase to about a 6.0-fold increase, about a 6.0-fold increase to about a 100-fold increase, about 6.0-fold increase to about a 90-fold increase, about 6.0-fold increase to about a 80-fold increase, about a 6.0-fold increase to about a 70-fold increase, about a 6.0-fold increase to about a 60-fold increase, about a 6.0-fold increase to about a 50-fold increase, about a 6.0-fold increase to about a 40-fold increase, about a 6.0-fold increase to about a 30-fold increase, about 6.0-fold increase to about 20-fold increase, about a 6.0-fold increase to about a 10-fold increase, about a 6.0-fold increase to about a 9.5-fold increase, about a 6.0-fold increase to about a 9.0-fold increase, about a 6.0-fold increase to about a 8.5-fold increase, about a 6.0-fold increase to about a 8.0-fold increase, about a 6.0-fold increase to about a 7.5-fold increase, about a 6.0-fold increase to about a 7.0-fold increase, about a 6.0-fold increase to about a 6.5-fold increase, about a 6.5-fold increase to about a 100-fold increase, about 6.5-fold increase to about a 90-fold increase, about 6.5-fold increase to about a 80-fold increase, about a 6.5-fold increase to about a 70-fold increase, about a 6.5-fold increase to about a 60-fold increase, about a 6.5-fold increase to about a 50-fold increase, about a 6.5-fold increase to about a 40-fold increase, about a 6.5-fold increase to about a 30-fold increase, about 6.5-fold increase to about 20-fold increase, about a 6.5-fold increase to about a 10-fold increase, about a 6.5-fold increase to about a 9.5-fold increase, about a 6.5-fold increase to about a 9.0-fold increase, about a 6.5-fold increase to about a 8.5-fold increase, about a 6.5-fold increase to about a 8.0-fold increase, about a 6.5-fold increase to about a 7.5-fold increase, about a 6.5-fold increase to about a 7.0-fold increase, about a 7.0-fold increase to about a 100-fold increase, about 7.0-fold increase to about a 90-fold increase, about 7.0-fold increase to about a 80-fold increase, about a 7.0-fold increase to about a 70-fold increase, about a 7.0-fold increase to about a 60-fold increase, about a 7.0-fold increase to about a 50-fold increase, about a 7.0-fold increase to about a 40-fold increase, about a 7.0-fold increase to about a 30-fold increase, about 7.0-fold increase to about 20-fold increase, about a 7.0-fold increase to about a 10-fold increase, about a 7.0-fold increase to about a 9.5-fold increase, about a 7.0-fold increase to about a 9.0-fold increase, about a 7.0-fold increase to about a 8.5-fold increase, about a 7.0-fold increase to about a 8.0-fold increase, about a 7.0-fold increase to about a 7.5-fold increase, about a 7.5-fold increase to about a 100-fold increase, about 7.5-fold increase to about a 90-fold increase, about 7.5-fold increase to about a 80-fold increase, about a 7.5-fold increase to about a 70-fold increase, about a 7.5-fold increase to about a 60-fold increase, about a 7.5-fold increase to about a 50-fold increase, about a 7.5-fold increase to about a 40-fold increase, about a 7.5-fold increase to about a 30-fold increase, about 7.5-fold increase to about 20-fold increase, about a 7.5-fold increase to about a 10-fold increase, about a 7.5-fold increase to about a 9.5-fold-increase, about a 7.5-fold increase to about a 9.0-fold increase, about a 7.5-fold increase to about a 8.5-fold increase, about a 7.5-fold increase to about a 8.0-fold increase, about a 8.0-fold increase to about a 100-fold increase, about 8.0-fold increase to about a 90-fold increase, about 8.0-fold increase to about a 80-fold increase, about a 8.0-fold increase to about a 70-fold increase, about a 8.0-fold increase to about a 60-fold increase, about a 8.0-fold increase to about a 50-fold increase, about a 8.0-fold increase to about a 40-fold increase, about a 8.0-fold increase to about a 30-fold increase, about 8.0-fold increase to about 20-fold increase, about a 8.0-fold increase to about a 10-fold increase, about a 8.0-fold increase to about a 9.5-fold increase, about a 8.0-fold increase to about a 9.0-fold increase, about a 8.0-fold increase to about a 8.5-fold increase, about a 8.5-fold increase to about a 100-fold increase, about 8.5-fold increase to about a 90-fold increase, about 8.5-fold increase to about a 80-fold increase, about a 8.5-fold increase to about a 70-fold increase, about a 8.5-fold increase to about a 60-fold increase, about a 8.5-fold increase to about a 50-fold increase, about a 8.5-fold increase to about a 40-fold increase, about a 8.5-fold increase to about a 30-fold increase, about 8.5-fold increase to about 20-fold increase, about a 8.5-fold increase to about a 10-fold increase, about a 8.5-fold increase to about a 9.5-fold increase, about a 8.5-fold increase to about a 9.0-fold increase, about a 9.0-fold increase to about a 100-fold increase, about 9.0-fold increase to about a 90-fold increase, about 9.0-fold increase to about a 80-fold increase, about a 9.0-fold increase to about a 70-fold increase, about a 9.0-fold increase to about a 60-fold increase, about a 9.0-fold increase to about a 50-fold increase, about a 9.0-fold increase to about a 40-fold increase, about a 9.0-fold increase to about a 30-fold increase, about 9.0-fold increase to about 20-fold increase, about a 9.0-fold increase to about a 10-fold increase, about a 9.0-fold increase to about a 9.5-fold increase, about a 9.5-fold increase to about a 100-fold increase, about 9.5-fold increase to about a 90-fold increase, about 9.5-fold increase to about a 80-fold increase, about a 9.5-fold increase to about a 70-fold increase, about a 9.5-fold increase to about a 60-fold increase, about a 9.5-fold increase to about a 50-fold increase, about a 9.5-fold increase to about a 40-fold increase, about a 9.5-fold increase to about a 30-fold increase, about 9.5-fold increase to about 20-fold increase, about a 9.5-fold increase to about a 10-fold increase, about a 10-fold increase to about a 100-fold increase, about 10-fold increase to about a 90-fold increase, about 10-fold increase to about a 80-fold increase, about a 10-fold increase to about a 70-fold increase, about a 10-fold increase to about a 60-fold increase, about a 10-fold increase to about a 50-fold increase, about a 10-fold increase to about a 40-fold increase, about a 10-fold increase to about a 30-fold increase, about 10-fold increase to about 20-fold increase, about a 20-fold increase to about a 100-fold increase, about 20-fold increase to about a 90-fold increase, about 20-fold increase to about a 80-fold increase, about a 20-fold increase to about a 70-fold increase, about a 20-fold increase to about a 60-fold increase, about a 20-fold increase to about a 50-fold increase, about a 20-fold increase to about a 40-fold increase, about a 20-fold increase to about a 30-fold increase to about a 30-fold increase to about a 100-fold increase, about 30-fold increase to about a 90-fold increase, about 30-fold increase to about a 80-fold increase, about a 30-fold increase to about a 70-fold increase, about a 30-fold increase to about a 60-fold increase, about a 30-fold increase to about a 50-fold increase, about a 30-fold increase to about a 40-fold increase, about a 40-fold increase to about a 100-fold increase, about 40-fold increase to about a 90-fold increase, about 40-fold increase to about a 80-fold increase, about a 40-fold increase to about a 70-fold increase, about a 40-fold increase to about a 60-fold increase, about a 40-fold increase to about a 50-fold increase, about a 50-fold increase to about a 100-fold increase, about 50-fold increase to about a 90-fold increase, about 50-fold increase to about a 80-fold increase, about a 50-fold increase to about a 70-fold increase, about a 50-fold increase to about a 60-fold increase, about a 60-fold increase to about a 100-fold increase, about 60-fold increase to about a 90-fold increase, about 60-fold increase to about a 80-fold increase, about a 60-fold increase to about a 70-fold increase, about a 70-fold increase to about a 100-fold increase, about 70-fold increase to about a 90-fold increase, about 70-fold increase to about a 80-fold increase, about a 80-fold increase to about a 100-fold increase, about 80-fold increase to about a 90-fold increase, or about a 90-fold increase to about a 100-fold increase) in toxin liberation in the target mammalian cell (e.g., any of the target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at a least a 9,000% increase, or at least a 10,000% increase, or about a 1% increase to about a 10,000% increase (e.g., or any of the subranges of this range described herein)) in target mammalian cell killing (e.g., any of the exemplary target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 40-fold increase, at least a 45-fold increase, at least a 50-fold increase, at least a 55-fold increase, at least a 60-fold increase, at least a 65-fold increase, at least a 70-fold increase, at least a 80-fold increase, at least a 85-fold increase, at least a 90-fold increase, at least a 95-fold increase, or at least a 100-fold increase, or about a 0.1-fold increase to about a 100-fold increase (or any of the subranges of this range described herein)) in target mammalian cell killing (e.g., any of the exemplary target mammalian cells described herein) as compared to a composition including the same amount of a control ABPC (e.g., any of the exemplary control ABPCs described herein).

In some examples of any of the ABPCs described herein, a composition including any of the ABPCs described herein (e.g., upon contacting target mammalian cells presenting FOLR1 on their surface) results in decreased (e.g., at least a 1% decrease, at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease, about a 1% decrease to about a 99% decrease, or any of the subranges of this range described herein) IC50 (for target mammalian cell killing) as compared to the $IC_{50}$ for a composition including the same amount of a control ABPC (e.g., any of the control ABPCs described herein) (e.g., upon contacting the same target mammalian cells).

In some examples of any of the ABPCs described herein, a composition including any of the ABPCs described herein (e.g., upon contacting target mammalian cells presenting FOLR1 on their surface) can provide for an increase (e.g., at least a 0.1-fold increase, at least a 0.2-fold increase, at least a 0.4-fold increase, at least a 0.6-fold increase, at least a 0.8-fold increase, at least a 1-fold increase, at least a 2-fold increase, at least a 5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about 500-fold increase (or any of the subranges of this range described herein) in the ratio of $K_D$ on target mammalian cells presenting FOLR1 on their surface at a neutral pH (a pH of about 7.0 to about 8.0) to IC50 at the neutral pH on the same target cells, e.g., as compared to a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at least a 9,000% increase, or at least a 10,000% increase, or about a 1% increase to about a 10,000% increase (e.g., or any of the subranges of this range described herein)) in endolysosomal delivery in the target mammalian cell (e.g., any of the exemplary target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about a 100-fold increase (or any of the subranges of this range described herein)) in endolysosomal delivery in the target mammalian cell (e.g., any of the exemplary target mammalian cells described herein) as compared to a composition including the same amount of a control ABPC (e.g., any of the exemplary control ABPCs described herein).

In examples of any of the ABPCs described herein, the target mammalian cell does not express an FcRn receptor, or expresses a lower (e.g., a detectably lower) level (e.g., at least a 1% decreased, at least a 2% decreased, at least a 5% decreased, at least a 10% decrease, at least a 15% decreased, at least a 20% decreased, at least a 25% decreased, at least a 30% decreased, at least a 35% decreased, at least a 40% decreased, at least a 45% decreased, at least a 50% decreased, at least a 55% decreased, at least a 60% decreased, at least a 65% decreased, at least a 70% decreased, at least a 75% decreased, at least a 80% decreased, at least a 85% decreased, at least a 90% decreased, at least a 95% decreased, or at least a 99% decreased level) of FcRn receptor as compared to a FcRn expressing control cell (e.g., HUVEC—ThermoFisher #C0035C). In some examples of any of the ABPCs described herein, the target mammalian cell is a cancer cell. In some examples of any of the ABPCs described herein, the ABPC is cytotoxic or cytostatic to the target mammalian cell.

In some examples of any of the ABPCs described herein, a composition including any of the ABPCs described herein (e.g., upon administration to a subject) results in less (e.g., a 1% decrease to about a 99% decrease, or any of the subranges of this range described herein)) of a reduction in the level of FOLR1 presented on the surface of the target cell as compared to a composition including the same amount of a control ABPC (e.g., any of the control ABPCs described herein). In some examples of any of the ABPCs described herein, the composition does not result in a detectable reduction in the level of the FOLR1 presented on the surface of the target mammalian cell.

In some examples of any of the ABPCs described herein, the ABPC is cross-reactive with a non-human primate FOLR1 and a human FOLR1. In some examples of any of the ABPCs described herein, the ABPC is cross-reactive with a non-human primate FOLR1, a human FOLR1, and one or both of rat FOLR1 and a mouse FOLR1. In some examples of any of the ABPCs described herein, the ABPC is cross-reactive with a non-human primate FOLR1, a human FOLR1, a rat FOLR1, and a mouse FOLR1. In some examples of any of the ABPCs described herein, the ABPC is cross-reactive with mouse FOLR1 and rat FOLR1. In some examples of any of the ABPCs described herein, the antigen-binding domain binds to an epitope of FOLR1 that is present on the surface of cells from an Old World Monkey.

Some examples of any of the ABPCs described herein can further include a second antigen-binding domain (e.g., any of the exemplary antigen-binding domains described herein). Non-limiting aspects of these methods are described below, and can be used in any combination without limitation. Additional aspects of these methods are known in the art.

FOLR1 or Epitope of FOLR1

Folate Receptor 1 (FOLR1) is a tumor antigen that is known in the art, and is the target of therapeutic antibodies in oncology (Cheung A et al (2016) "Targeting folate receptor alpha for cancer treatment" Oncotarget 7(32): 52553-52574). The sequence of the mature Human FOLR1 can be found in SEQ ID NO: 9. The sequence of the cDNA encoding the mature Human FOLR1 can be found in SEQ ID NO: 10. The sequence of the extracellular domain of FOLR1 can be found in SEQ ID NO: 11. The sequence of the cDNA encoding the extracellular domain of FOLR1 can be found in SEQ ID NO: 12.

Antigen-Binding Protein Constructs

Any of the antigen-binding protein constructs (ABPCs) described herein can be a single polypeptide, or can include two, three, four, five, six, seven, eight, nine, or ten (the same or different) polypeptides. In some embodiments where the ABPC is a single polypeptide, the ABPC can include a single antigen-binding domain or two antigen-binding domains. In some embodiments where the ABPC is a single polypeptide and includes two antigen-binding domains, the first and second antigen-binding domains can be identical or different from each other (and can specifically bind to the same or different antigens or epitopes).

In some embodiments where the ABPC is a single polypeptide, the first antigen-binding domain and the second antigen-binding domain (if present) can each be independently selected from the group of: a VH domain, a VHH domain, a VNAR domain, and a scFv. In some embodiments where the ABPC is a single polypeptide, the antigen-binding protein construct can be a BITE® (bispecific T-cell engagers), a (scFv)2, a NANOBODY® (single-domain antibodies), a NANOBODY® (single-domain antibodies)-HSA, a DART® (proteins comprising two engineered scFv fragments which have their VH and VL domains exchanged), a TANDAB® (tetravalent bispecific molecules comprising antibody variable domains with two binding sites for each antigen), a scDiabody, a scDiabody-CH3, scFv-CH-CL-scFv, a HSAbody, scDiabody-HAS, a tandem-scFv, an Adnectin, a DARPIN™ (genetically engineered antibody mimetic proteins), a fibronectin, and a DEP conjugate. Additional examples of antigen-binding domains that can be used when the ABPC is a single polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., Med. Microbiol. Immunol. 198:157-174, 2009.

In some embodiments where the ABPC is a single polypeptide and includes two antigen-binding domains, the first antigen-binding domain and the second antigen-binding domain can both be VHH domains, or at least one antigen-binding domain can be a VHH domain. In some embodiments where the ABPC is a single polypeptide and includes two antigen-binding domains, the first antigen-binding domain and the second antigen-binding domain are both VNAR domains, or at least one antigen-binding domain is a VNAR domain. In some embodiments where the ABPC is a single polypeptide, the first antigen-binding domain is a scFv domain. In some embodiments where the ABPC is a single polypeptide and includes two antigen-binding domains, the first antigen-binding domain and the second antigen-binding domain can both be scFv domains, or at least one antigen-binding domain can be a scFv domain.

In some embodiments, the ABPC can include two or more polypeptides (e.g., two, three, four, five, six, seven, eight, nine, or ten polypeptides). In some embodiments where the ABPC includes two or more polypeptides, two, three, four, five or six of the polypeptides of the two or more polypeptides can be identical.

In some embodiments where the ABPC includes two or more polypeptides (e.g., two, three, four, five, six, seven, eight, nine, or ten polypeptides), two or more of the polypeptides of the ABPC can assemble (e.g., non-covalently assemble) to form one or more antigen-binding domains, e.g., an antigen-binding fragment of an antibody (e.g., any of the antigen-binding fragments of an antibody described herein), a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IG™ (dual variable domain immunoglobulins), a IgG(H)-scFv, a scFv-(H)IgG, IgG(L)-scFv, scFv-(L)IgG, IgG(L,H)-Fv, IgG(H)-V, V(H)-

IgG, IgG(L)-V, V(L)-IgG, KIH IgG-scFab, 2scFv-IgG, IgG-2scFv, scFv4-Ig, ZYBODY™ (engineered proteins comprising multiple modular recognition domains), DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fe, a tandem scFv-Fc, a VHH-Fc, a tandem VHH-Fc, a VHH-Fc KiH, a Fab-VHH-Fc, an Intrabody, a dock and lock, an IMMTAC® (engineered fusion proteins that comprise an engineered T cell receptor based targeting system with a single chain antibody fragment), an IgG-IgG conjugate, a Cov-X-Body, a scFv1-PEG-scFv2, an Adnectin, a DARPIN™ (genetically engineered antibody mimetic proteins), a fibronectin, and a DEP conjugate. See, e.g., Spiess et al., Mol. Immunol. 67:95-106, 2015, incorporated in its entirety herewith, for a description of these elements. Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

A "Fv" fragment includes a non-covalently-linked dimer of one heavy chain variable domain and one light chain variable domain.

A "Fab" fragment includes, the constant domain of the light chain and the first constant domain (CHI) of the heavy chain, in addition to the heavy and light chain variable domains of the Fv fragment.

A "F(ab')2" fragment includes two Fab fragments joined, near the hinge region, by disulfide bonds.

A "dual variable domain immunoglobulin" or "DVD-IG™" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

A DART® (proteins comprising two engineered scFv fragments which have their VH and VL domains exchanged) is described in, e.g., Garber, Nature Reviews Drug Discovery 13:799-801, 2014. Additional aspects of ABPCs are known in the art.

Antigen-Binding Domains

In some embodiments of any of the antigen-binding protein constructs (ABPCs) described herein, the dissociation rate of the first antigen-binding domain (and optionally the second antigen-binding domain, if present) at a pH of about 4.0 to about 6.5 (e.g., about 4.0 to about 6.4, about 4.0 to about 6.3, about 4.0 to about 6.2, about 4.0 to about 6.1, about 4.0 to about 6.0, about 4.0 to about 5.9, about 4.0 to about 5.8, about 4.0 to about 5.7, about 4.0 to about 5.6, about 4.0 to about 5.5, about 4.0 to about 5.4, about 4.0 to about 5.3, about 4.0 to about 5.2, about 4.0 to about 5.1, about 4.0 to about 5.0, about 4.0 to about 4.9, about 4.0 to about 4.8, about 4.0 to about 4.7, about 4.0 to about 4.6, about 4.0 to about 4.5, about 4.0 to about 4.4, about 4.0 to about 4.3, about 4.0 to about 4.2, about 4.0 to about 4.1, about 4.1 to about 6.5, about 4.1 to about 6.4, about 4.1 to about 6.3, about 4.1 to about 6.2, about 4.1 to about 6.1, about 4.1 to about 6.0, about 4.1 to about 5.9, about 4.1 to about 5.8, about 4.1 to about 5.7, about 4.1 to about 5.6, about 4.1 to about 5.5, about 4.1 to about 5.4, about 4.1 to about 5.3, about 4.1 to about 5.2, about 4.1 to about 5.1, about 4.1 to about 5.0, about 4.1 to about 4.9, about 4.1 to about 4.8, about 4.1 to about 4.7, about 4.1 to about 4.6, about 4.1 to about 4.5, about 4.1 to about 4.4, about 4.1 to about 4.3, about 4.1 to about 4.2, about 4.2 to about 6.5, about 4.2 to about 6.4, about 4.2 to about 6.3, about 4.2 to about 6.2, about 4.2 to about 6.1, about 4.2 to about 6.0, about 4.2 to about 5.9, about 4.2 to about 5.8, about 4.2 to about 5.7, about 4.2 to about 5.6, about 4.2 to about 5.5, about 4.2 to about 5.4, about 4.2 to about 5.3, about 4.2 to about 5.2, about 4.2 to about 5.1, about 4.2 to about 5.0, about 4.2 to about 4.9, about 4.2 to about 4.8, about 4.2 to about 4.7, about 4.2 to about 4.6, about 4.2 to about 4.5, about 4.2 to about 4.4, about 4.2 to about 4.3, about 4.3 to about 6.5, about 4.3 to about 6.4, about 4.3 to about 6.3, about 4.3 to about 6.2, about 4.3 to about 6.1, about 4.3 to about 6.0, about 4.3 to about 5.9, about 4.3 to about 5.8, about 4.3 to about 5.7, about 4.3 to about 5.6, about 4.3 to about 5.5, about 4.3 to about 5.4, about 4.3 to about 5.3, about 4.3 to about 5.2, about 4.3 to about 5.1, about 4.3 to about 5.0, about 4.3 to about 4.9, about 4.3 to about 4.8, about 4.3 to about 4.7, about 4.3 to about 4.6, about 4.3 to about 4.5, about 4.3 to about 4.4, about 4.4 to about 6.5, about 4.4 to about 6.4, about 4.4 to about 6.3, about 4.4 to about 6.2, about 4.4 to about 6.1, about 4.4 to about 6.0, about 4.4 to about 5.9, about 4.4 to about 5.8, about 4.4 to about 5.7, about 4.4 to about 5.6, about 4.4 to about 5.5, about 4.4 to about 5.4, about 4.4 to about 5.3, about 4.4 to about 5.2, about 4.4 to about 5.1, about 4.4 to about 5.0, about 4.4 to about 4.9, about 4.4 to about 4.8, about 4.4 to about 4.7, about 4.4 to about 4.6, about 4.4 to about 4.5, about 4.5 to about 6.5, about 4.5 to about 6.4, about 4.5 to about 6.3, about 4.5 to about 6.2, about 4.5 to about 6.1, about 4.5 to about 6.0, about 4.5 to about 5.9, about 4.5 to about 5.8, about 4.5 to about 5.7, about 4.5 to about 5.6, about 4.5 to about 5.5, about 4.5 to about 5.4, about 4.5 to about 5.3, about 4.5 to about 5.2, about 4.5 to about 5.1, about 4.5 to about 5.0, about 4.5 to about 4.9, about 4.5 to about 4.8, about 4.5 to about 4.7, about 4.5 to about 4.6, about 4.6 to about 6.5, about 4.6 to about 6.4, about 4.6 to about 6.3, about 4.6 to about 6.2, about 4.6 to about 6.1, about 4.6 to about 6.0, about 4.6 to about 5.9, about 4.6 to about 5.8, about 4.6 to about 5.7, about 4.6 to about 5.6, about 4.6 to about 5.5, about 4.6 to about 5.4, about 4.6 to about 5.3, about 4.6 to about 5.2, about 4.6 to about 5.1, about 4.6 to about 5.0, about 4.6 to about 4.9, about 4.6 to about 4.8, about 4.6 to about 4.7, about 4.7 to about 6.5, about 4.7 to about 6.4, about 4.7 to about 6.3, about 4.7 to about 6.2, about 4.7 to about 6.1, about 4.7 to about 6.0, about 4.7 to about 5.9, about 4.7 to about 5.8, about 4.7 to about 5.7, about 4.7 to about 5.6, about 4.7 to about 5.5, about 4.7 to about 5.4, about 4.7 to about 5.3, about 4.7 to about 5.2, about 4.7 to about 5.1, about 4.7 to about 5.0, about 4.7 to about 4.9, about 4.7 to about 4.8, about 4.8 to about 6.5, about 4.8 to about 6.4, about 4.8 to about 6.3, about 4.8 to about 6.2, about 4.8 to about 6.1, about 4.8 to about 6.0, about 4.8 to about 5.9, about 4.8 to about 5.8, about 4.8 to about 5.7, about 4.8 to about 5.6, about 4.8 to about 5.5, about 4.8 to about 5.4, about 4.8 to about 5.3, about 4.8 to about 5.2, about 4.8 to about 5.1, about 4.8 to about 5.0, about 4.8 to about 4.9, about 4.9 to about 6.5, about 4.9 to about 6.4, about 4.9 to about 6.3, about 4.9 to about 6.2, about 4.9 to about 6.1, about 4.9 to about 6.0, about 4.9 to about 5.9, about 4.9 to about 5.8, about 4.9 to about 5.7, about 4.9 to about 5.6, about 4.9 to about 5.5, about 4.9 to about 5.4, about 4.9 to about 5.3, about 4.9 to about 5.2, about 4.9 to about 5.1, about 4.9 to about 5.0, about 5.0 to about 6.5, about 5.0 to about 6.4, about 5.0 to about 6.3, about 5.0 to about 6.2, about 5.0 to about 6.1, about 5.0 to about 6.0, about 5.0 to about 5.9, about 5.0 to about 5.8, about 5.0 to about 5.7, about 5.0 to about 5.6, about 5.0 to about 5.5, about 5.0 to about 5.4, about 5.0 to about 5.3, about 5.0 to about 5.2, about 5.0 to about 5.1, about 5.1 to about 6.5, about 5.1 to about 6.4, about 5.1 to about 6.3, about 5.1 to about 6.2, about 5.1 to about 6.1, about 5.1 to about 6.0, about 5.1 to about 5.9, about 5.1 to about 5.8, about 5.1 to about 5.7, about 5.1 to about 5.6, about 5.1 to about 5.5, about 5.1 to about 5.4, about 5.1 to about 5.3, about 5.1 to about 5.2, about 5.2 to about 6.5, about 5.2 to about 6.4, about 5.2 to about 6.3, about 5.2 to about 6.2, about 5.2 to about 6.1, about 5.2 to about 6.0, about 5.2 to about 5.9, about 5.2 to about 5.8, about 5.2 to about 5.7, about 5.2 to about 5.6, about 5.2 to about 5.5, about 5.2 to about 5.4, about 5.2 to about 5.3, about 5.3 to about 6.5, about 5.3 to about 6.4, about 5.3 to about 6.3, about 5.3 to about 6.2, about 5.3 to about 6.1, about 5.3 to about 6.0, about 5.3 to about 5.9, about 5.3 to about 5.8, about 5.3 to about 5.7, about 5.3 to about 5.6, about 5.3 to about 5.5, about 5.3 to about 5.4, about 5.4 to about 6.5, about 5.4 to about 6.4, about 5.4 to about 6.3, about 5.4 to about 6.2, about 5.4 to about 6.1, about 5.4 to about 6.0, about 5.4 to about 5.9, about 5.4 to about 5.8, about 5.4 to about 5.7, about 5.4 to about 5.6, about 5.4 to about 5.5, about 5.5 to about 6.5, about 5.5 to about 6.4, about 5.5 to about 6.3, about 5.5 to about 6.2, about 5.5 to about 6.1, about 5.5 to about 6.0, about 5.5 to about 5.9, about 5.5 to about 5.8, about 5.5 to about 5.7, about 5.5 to about 5.6, about 5.6 to about 6.5, about 5.6 to about 6.4, about 5.6 to about 6.3, about 5.6 to about 6.2, about 5.6 to about 6.1, about 5.6 to about 6.0, about 5.6 to about 5.9, about 5.6 to about 5.8, about 5.6 to about 5.7, about 5.7 to about 6.5, about 5.7 to about 6.4, about 5.7 to about 6.3, about 5.7 to about 6.2, about 5.7 to about 6.1, about 5.7 to about 6.0, about 5.7 to about 5.9, about 5.7 to about 5.8, about 5.8 to about 6.5, about 5.8 to about 6.4, about 5.8 to about 6.3, about 5.8 to about 6.2, about 5.8 to about 6.1, about 5.8 to about 6.0, about 5.8 to about 5.9, about 5.9 to about 6.5, about 5.9 to about 6.4, about 5.9 to about 6.3, about 5.9 to about 6.2, about 5.9 to about 6.1, about 5.9 to about 6.0, about 6.0 to about 6.5, about 6.0 to about 6.4, about 6.0 to about 6.3, about 6.0 to about 6.2, about 6.0 to about 6.1, about 6.1 to about 6.5, about 6.1 to about 6.4, about 6.1 to about 6.3, about 6.1 to about 6.2, about 6.2 to about 6.5, about 6.2 to about 6.4, about 6.2 to about 6.3, about 6.3 to about 6.5, about 6.3 to about 6.4, or about 6.4 to about 6.5) is faster (e.g., (e.g., at least 5% faster, at least 10% faster, at least 15% faster, at least 20%, at least 25% faster, at least 30% faster, at least 35% faster, at least 40% faster, at least 45% faster, at least 50% faster, at least 55% faster, at least 60% faster, at least 65% faster, at least 70% faster, at least 75% faster, at least 80% faster, at least 85% faster, at least 90% faster, at least 95% faster, at least 100% faster, at least 120% faster, at least 140% faster, at least 160% faster, at least 180% faster, at least 200% faster, at least 220% faster at least 240% faster at least 260% faster at least 280% faster at least 300% faster at least 320% faster at least 340% faster at least 360% faster at least 380% faster at least 400% faster at least 420% faster at least 440% faster at least 460% faster at least 480% faster, at least 500% faster, at least 1,000% faster, at least 2,000% faster, at least 3,000% faster, at least 4,000% faster, at least 5,000%, at least 6,000% faster, at least 7,000% faster, at least 8,000% faster, at least 9,000% faster, or at least 10,000% faster, or about 5% faster to about 10,000% faster, about 5% faster to about 9,000% faster, about 5% faster to about 8,000% faster, about 5% faster to about 7,000% faster, about 5% faster to about 6,000% faster, about 5% faster to about 5,000% faster, about 5% faster to about 4,000% faster, about 5% faster to about 3,000% faster, about 5% faster to about 2,000% faster, about 5% faster to about 1,000% faster, about 5% faster to about 500% faster, about 5% faster to about 480% faster, about 5% faster to about 460% faster, about 5% faster to about 440% faster, about 5% faster to about 420% faster, about 5% faster to about 400% faster, about 5% faster to about 380% faster, about 5% faster to about 360% faster, about 5% faster to about 340% faster, about 5% faster to about 320% faster, about 5% faster to about 300% faster, about 5% faster to about 280% faster, about 5% faster to about 260% faster, about 5% faster to about 240% faster, about 5% faster to about 220% faster, about 5% faster to about 200% faster, about 5% faster to about 180% faster, about 5% faster to about 160% faster, about 5% faster to about 140% faster, about 5% faster to about 120% faster, about 5% faster to about 100% faster, about 5% faster to about 95% faster, about 5% faster to about 90% faster, about 5% faster to about 85% faster, about 5% faster to about 80% faster, about 5% faster to about 75% faster, about 5% faster to about 70% faster, about 5% faster to about 65% faster, about 5% faster to about 60% faster, about 5% faster to about 55% faster, about 5% faster to about 50% faster, about 5% faster to about 45% faster, about 5% faster to about 40% faster, about 5% faster to about 35% faster, about 5% faster to about 30% faster, about 5% faster to about 25% faster, about 5% faster to about 20% faster, about 5% faster to about 15% faster, about 5% faster to about 10% faster, about 10% faster to about 10,000% faster, about 10% faster to about 9,000% faster, about 10% faster to about 8,000% faster, about 10% faster to about 7,000% faster, about 10% faster to about 6,000% faster, about 10% faster to about 5,000% faster, about 10% faster to about 4,000% faster, about 10% faster to about 3,000% faster, about 10% faster to about 2,000% faster, about 10% faster to about 1,000% faster, about 10% faster to about 500% faster, about 10% faster to about 480% faster, about 10% faster to about 460% faster, about 10% faster to about 440% faster, about 10% faster to about 420% faster, about 10% faster to about 400% faster, about 10% faster to about 380% faster, about 10% faster to about 360% faster, about 10% faster to about 340% faster, about 10% faster to about 320% faster, about 10% faster to about 300% faster, about 10% faster to about 280% faster, about 10% faster to about 260% faster, about 10% faster to about 240% faster, about 10% faster to about 220% faster, about 10% faster to about 200% faster, about 10% faster to about 180% faster, about 10% faster to about 160% faster, about 10% faster to about 140% faster, about 10% faster to about 120% faster, about 10% faster to about 100% faster, about 10% faster to about 95% faster, about 10% faster to about 90% faster, about 10% faster to about 85% faster, about 10% faster to about 80% faster, about 10% faster to about 75% faster, about 10% faster to about 70% faster, about 10% faster to about 65% faster, about 10% faster to about 60% faster, about 10% faster to about 55% faster, about 10% faster to about 50% faster, about 10% faster to about 45% faster, about 10% faster to about 40% faster, about 10% faster to about 35% faster, about 10% faster to about 30% faster, about 10% faster to about 25% faster, about 10% faster to about 20% faster, about 10% faster to about 15% faster, about 15% faster to about 10,000% faster, about 15% faster to about 9,000% faster, about 15% faster to about 8,000% faster, about 15% faster to about 7,000% faster, about 15% faster to about 6,000% faster, about 15% faster to about 5,000% faster, about 15% faster to about 4,000% faster, about 15% faster to about 3,000% faster, about 15% faster to about 2,000% faster, about 15% faster to about 1,000% faster, about 15% faster to about 500% faster, about 15% faster to about 480% faster, about 15% faster to about 460% faster, about 15% faster to about 440% faster, about 15% faster to about 420% faster, about 15% faster to about 400% faster, about 15% faster to about 380% faster, about 15% faster to about 360% faster, about 15% faster to about 340% faster, about 15% faster to about 320% faster, about 15% faster to about 300% faster, about 15% faster to about 280% faster, about 15% faster to about 260% faster, about 15% faster to about 240% faster, about 15% faster to about 220% faster, about 15% faster to about 200% faster, about 15% faster to about 180% faster, about 15% faster to about 160% faster, about 15% faster to about 140% faster, about 15% faster to about 120% faster, about 15% faster to about 100% faster, about 15% faster to about 95% faster, about 15% faster to about 90% faster, about 15% faster to about 85% faster, about 15% faster to about 80% faster, about 15% faster to about 75% faster, about 15% faster to about 70% faster, about 15% faster to about 65% faster, about 15% faster to about 60% faster, about 15% faster to about 55% faster, about 15% faster to about 50% faster, about 15% faster to about 45% faster, about 15% faster to about 40% faster, about 15% faster to about 35% faster, about 15% faster to about 30% faster, about 15% faster to about 25% faster, about 15% faster to about 20% faster, about 20% faster to about 10,000% faster, about 20% faster to about 9,000% faster, about 20% faster to about 8,000% faster, about 20% faster to about 7,000% faster, about 20% faster to about 6,000% faster, about 20% faster to about 5,000% faster, about 20% faster to about 4,000% faster, about 20% faster to about 3,000% faster, about 20% faster to about 2,000% faster, about 20% faster to about 1,000% faster, about 20% faster to about 500% faster, about 20% faster to about 480% faster, about 20% faster to about 460% faster, about 20% faster to about 440% faster, about 20% faster to about 420% faster, about 20% faster to about 400% faster, about 20% faster to about 380% faster, about 20% faster to about 360% faster, about 20% faster to about 340% faster, about 20% faster to about 320% faster, about 20% faster to about 300% faster, about 20% faster to about 280% faster, about 20% faster to about 260% faster, about 20% faster to about 240% faster, about 20% faster to about 220% faster, about 20% faster to about 200% faster, about 20% faster to about 180% faster, about 20% faster to about 160% faster, about 20% faster to about 140% faster, about 20% faster to about 120% faster, about 20% faster to about 100% faster, about 20% faster to about 95% faster, about 20% faster to about 90% faster, about 20% faster to about 85% faster, about 20% faster to about 80% faster, about 20% faster to about 75% faster, about 20% faster to about 70% faster, about 20% faster to about 65% faster, about 20% faster to about 60% faster, about 20% faster to about 55% faster, about 20% faster to about 50% faster, about 20% faster to about 45% faster, about 20% faster to about 40% faster, about 20% faster to about 35% faster, about 20% faster to about 30% faster, about 20% faster to about 25% faster, about 25% faster to about 10,000% faster, about 25% faster to about 9,000% faster, about 25% faster to about 8,000% faster, about 25% faster to about 7,000% faster, about 25% faster to about 6,000% faster, about 25% faster to about 5,000% faster, about 25% faster to about 4,000% faster, about 25% faster to about 3,000% faster, about 25% faster to about 2,000% faster, about 25% faster to about 1,000% faster, about 25% faster to about 500% faster, about 25% faster to about 480% faster, about 25% faster to about 460% faster, about 25% faster to about 440% faster, about 25% faster to about 420% faster, about 25% faster to about 400% faster, about 25% faster to about 380% faster, about 25% faster to about 360% faster, about 25% faster to about 340% faster, about 25% faster to about 320% faster, about 25% faster to about 300% faster, about 25% faster to about 280% faster, about 25% faster to about 260% faster, about 25% faster to about 240% faster, about 25% faster to about 220% faster, about 25% faster to about 200% faster, about 25% faster to about 180% faster, about 25% faster to about 160% faster, about 25% faster to about 140% faster, about 25% faster to about 120% faster, about 25% faster to about 100% faster, about 25% faster to about 95% faster, about 25% faster to about 90% faster, about 25% faster to about 85% faster, about 25% faster to about 80% faster, about 25% faster to about 75% faster, about 25% faster to about 70% faster, about 25% faster to about 65% faster, about 25% faster to about 60% faster, about 25% faster to about 55% faster, about 25% faster to about 50% faster, about 25% faster to about 45% faster, about 25% faster to about 40% faster, about 25% faster to about 35% faster, about 25% faster to about 30% faster, about 30% faster to about 10,000% faster, about 30% faster to about 9,000% faster, about 30% faster to about 8,000% faster, about 30% faster to about 7,000% faster, about 30% faster to about 6,000% faster, about 30% faster to about 5,000% faster, about 30% faster to about 4,000% faster, about 30% faster to about 3,000% faster, about 30% faster to about 2,000% faster, about 30% faster to about 1,000% faster, about 30% faster to about 500% faster, about 30% faster to about 480% faster, about 30% faster to about 460% faster, about 30% faster to about 440% faster, about 30% faster to about 420% faster, about 30% faster to about 400% faster, about 30% faster to about 380% faster, about 30% faster to about 360% faster, about 30% faster to about 340% faster, about 30% faster to about 320% faster, about 30% faster to about 300% faster, about 30% faster to about 280% faster, about 30% faster to about 260% faster, about 30% faster to about 240% faster, about 30% faster to about 220% faster, about 30% faster to about 200% faster, about 30% faster to about 180% faster, about 30% faster to about 160% faster, about 30% faster to about 140% faster, about 30% faster to about 120% faster, about 30% faster to about 100% faster, about 30% faster to about 95% faster, about 30% faster to about 90% faster, about 30% faster to about 85% faster, about 30% faster to about 80% faster, about 30% faster to about 75% faster, about 30% faster to about 70% faster, about 30% faster to about 65% faster, about 30% faster to about 60% faster, about 30% faster to about 55% faster, about 30% faster to about 50% faster, about 30% faster to about 45% faster, about 30% faster to about 40% faster, about 30% faster to about 35% faster, about 35% faster to about 10,000% faster, about 35% faster to about 9,000% faster, about 35% faster to about 8,000% faster, about 35% faster to about 7,000% faster, about 35% faster to about 6,000% faster, about 35% faster to about 5,000% faster, about 35% faster to about 4,000% faster, about 35% faster to about 3,000% faster, about 35% faster to about 2,000% faster, about 35% faster to about 1,000% faster, about 35% faster to about 500% faster, about 35% faster to about 480% faster, about 35% faster to about 460% faster, about 35% faster to about 440% faster, about 35% faster to about 420% faster, about 35% faster to about 400% faster, about 35% faster to about 380% faster, about 35% faster to about 360% faster, about 35% faster to about 340% faster, about 35% faster to about 320% faster, about 35% faster to about 300% faster, about 35% faster to about 280% faster, about 35% faster to about 260% faster, about 35% faster to about 240% faster, about 35% faster to about 220% faster, about 35% faster to about 200% faster, about 35% faster to about 180% faster, about 35% faster to about 160% faster, about 35% faster to about 140% faster, about 35% faster to about 120% faster, about 35% faster to about 100% faster, about 35% faster to about 95% faster, about 35% faster to about 90% faster, about 35% faster to about 85% faster, about 35% faster to about 80% faster, about 35% faster to about 75% faster, about 35% faster to about 70% faster, about 35% faster to about 65% faster, about 35% faster to about 60% faster, about 35% faster to about 55% faster, about 35% faster to about 50% faster, about 35% faster to about 45% faster, about 35% faster to about 40% faster, about 40% faster to about 10,000% faster, about 40% faster to about 9,000% faster, about 40% faster to about 8,000% faster, about 40% faster to about 7,000% faster, about 40% faster to about 6,000% faster, about 40% faster to about 5,000% faster, about 40% faster to about 4,000% faster, about 40% faster to about 3,000% faster, about 40% faster to about 2,000% faster, about 40% faster to about 1,000% faster, about 40% faster to about 500% faster, about 40% faster to about 480% faster, about 40% faster to about 460% faster, about 40% faster to about 440% faster, about 40% faster to about 420% faster, about 40% faster to about 400% faster, about 40% faster to about 380% faster, about 40% faster to about 360% faster, about 40% faster to about 340% faster, about 40% faster to about 320% faster, about 40% faster to about 300% faster, about 40% faster to about 280% faster, about 40% faster to about 260% faster, about 40% faster to about 240% faster, about 40% faster to about 220% faster, about 40% faster to about 200% faster, about 40% faster to about 180% faster, about 40% faster to about 160% faster, about 40% faster to about 140% faster, about 40% faster to about 120% faster, about 40% faster to about 100% faster, about 40% faster to about 95% faster, about 40% faster to about 90% faster, about 40% faster to about 85% faster, about 40% faster to about 80% faster, about 40% faster to about 75% faster, about 40% faster to about 70% faster, about 40% faster to about 65% faster, about 40% faster to about 60% faster, about 40% faster to about 55% faster, about 40% faster to about 50% faster, about 40% faster to about 45% faster, about 45% faster to about 10,000% faster, about 45% faster to about 9,000% faster, about 45% faster to about 8,000% faster, about 45% faster to about 7,000% faster, about 45% faster to about 6,000% faster, about 45% faster to about 5,000% faster, about 45% faster to about 4,000% faster, about 45% faster to about 3,000% faster, about 45% faster to about 2,000% faster, about 45% faster to about 1,000% faster, about 45% faster to about 500% faster, about 45% faster to about 480% faster, about 45% faster to about 460% faster, about 45% faster to about 440% faster, about 45% faster to about 420% faster, about 45% faster to about 400% faster, about 45% faster to about 380% faster, about 45% faster to about 360% faster, about 45% faster to about 340% faster, about 45% faster to about 320% faster, about 45% faster to about 300% faster, about 45% faster to about 280% faster, about 45% faster to about 260% faster, about 45% faster to about 240% faster, about 45% faster to about 220% faster, about 45% faster to about 200% faster, about 45% faster to about 180% faster, about 45% faster to about 160% faster, about 45% faster to about 140% faster, about 45% faster to about 120% faster, about 45% faster to about 100% faster, about 45% faster to about 95% faster, about 45% faster to about 90% faster, about 45% faster to about 85% faster, about 45% faster to about 80% faster, about 45% faster to about 75% faster, about 45% faster to about 70% faster, about 45% faster to about 65% faster, about 45% faster to about 60% faster, about 45% faster to about 55% faster, about 45% faster to about 50% faster, about 50% faster to about 10,000% faster, about 50% faster to about 9,000% faster, about 50% faster to about 8,000% faster, about 50% faster to about 7,000% faster, about 50% faster to about 6,000% faster, about 50% faster to about 5,000% faster, about 50% faster to about. 4,000% faster, about 50% faster to about 3,000% faster, about 50% faster to about 2,000% faster, about 50% faster to about 1,000% faster, about 50% faster to about 500% faster, about 50% faster to about 480% faster, about 50% faster to about 460% faster, about 50% faster to about 440% faster, about 50% faster to about 420% faster, about 50% faster to about 400% faster, about 50% faster to about 380% faster, about 50% faster to about 360% faster, about 50% faster to about 340% faster, about 50% faster to about 320% faster, about 50% faster to about 300% faster, about 50% faster to about 280% faster, about 50% faster to about 260% faster, about 50% faster to about 240% faster, about 50% faster to about 220% faster, about 50% faster to about 200% faster, about 50% faster to about 180% faster, about 50% faster to about 160% faster, about 50% faster to about 140% faster, about 50% faster to about 120% faster, about 50% faster to about 100% faster, about 50% faster to about 95% faster, about 50% faster to about 90% faster, about 50% faster to about 85% faster, about 50% faster to about 80% faster, about 50% faster to about 75% faster, about 50% faster to about 70% faster, about 50% faster to about 65% faster, about 50% faster to about 60% faster, about 50% faster to about 55% faster, about 55% faster to about 10,000% faster, about 55% faster to about 9,000% faster, about 55% faster to about 8,000% faster, about 55% faster to about 7,000% faster, about 55% faster to about 6,000% faster, about 55% faster to about 5,000% faster, about 55% faster to about 4,000% faster, about 55% faster to about 3,000% faster, about 55% faster to about 2,000% faster, about 55% faster to about 1,000% faster, about 55% faster to about 500% faster, about 55% faster to about 480% faster, about 55% faster to about 460% faster, about 55% faster to about 440% faster, about 55% faster to about 420% faster, about 55% faster to about 400% faster, about 55% faster to about 380% faster, about 55% faster to about 360% faster, about 55% faster to about 340% faster, about 55% faster to about 320% faster, about 55% faster to about 300% faster, about 55% faster to about 280% faster, about 55% faster to about 260% faster, about 55% faster to about 240% faster, about 55% faster to about 220% faster, about 55% faster to about 200% faster, about 55% faster to about 180% faster, about 55% faster to about 160% faster, about 55% faster to about 140% faster, about 55% faster to about 120% faster, about 55% faster to about 100% faster, about 55% faster to about 95% faster, about 55% faster to about 90% faster, about 55% faster to about 85% faster, about 55% faster to about 80% faster, about 55% faster to about 75% faster, about 55% faster to about 70% faster, about 55% faster to about 65% faster, about 55% faster to about 60% faster, about 60% faster to about 10,000% faster, about 60% faster to about 9,000% faster, about 60% faster to about 8,000% faster, about 60% faster to about 7,000% faster, about 60% faster to about 6,000% faster, about 60% faster to about 5,000% faster, about 60% faster to about 4,000% faster, about 60% faster to about 3,000% faster, about 60% faster to about 2,000% faster, about 60% faster to about 1,000% faster, about 60% faster to about 500% faster, about 60% faster to about 480% faster, about 60% faster to about 460% faster, about 60% faster to about 440% faster, about 60% faster to about 420% faster, about 60% faster to about 400% faster, about 60% faster to about 380% faster, about 60% faster to about 360% faster, about 60% faster to about 340% faster, about 60% faster to about 320% faster, about 60% faster to about 300% faster, about 60% faster to about 280% faster, about 60% faster to about 260% faster, about 60% faster to about 240% faster, about 60% faster to about 220% faster, about 60% faster to about 200% faster, about 60% faster to about 180% faster, about 60% faster to about 160% faster, about 60% faster to about 140% faster, about 60% faster to about 120% faster, about 60% faster to about 100% faster, about 60% faster to about 95% faster, about 60% faster to about 90% faster, about 60% faster to about 85% faster, about 60% faster to about 80% faster, about 60% faster to about 75% faster, about 60% faster to about 70% faster, about 60% faster to about 65% faster, about 65% faster to about 10,000% faster, about 65% faster to about 9,000% faster, about 65% faster to about 8,000% faster, about 65% faster to about 7,000% faster, about 65% faster to about 6,000% faster, about 65% faster to about 5,000% faster, about 65% faster to about 4,000% faster, about 65% faster to about 3,000% faster, about 65% faster to about 2,000% faster, about 65% faster to about 1,000% faster, about 65% faster to about 500% faster, about 65% faster to about 480% faster, about 65% faster to about 460% faster, about 65% faster to about 440% faster, about 65% faster to about 420% faster, about 65% faster to about 400% faster, about 65% faster to about 380% faster, about 65% faster to about 360% faster, about 65% faster to about 340% faster, about 65% faster to about 320% faster, about 65% faster to about 300% faster, about 65% faster to about 280% faster, about 65% faster to about 260% faster, about 65% faster to about 240% faster, about 65% faster to about 220% faster, about 65% faster to about 200% faster, about 65% faster to about 180% faster, about 65% faster to about 160% faster, about 65% faster to about 140% faster, about 65% faster to about 120% faster, about 65% faster to about 100% faster, about 65% faster to about 95% faster, about 65% faster to about 90% faster, about 65% faster to about 85% faster, about 65% faster to about 80% faster, about 65% faster to about 75% faster, about 65% faster to about 70% faster, about 70% faster to about 10,000% faster, about 70% faster to about 9,000% faster, about 70% faster to about 8,000% faster, about 70% faster to about 7,000% faster, about 70% faster to about 6,000% faster, about 70% faster to about 5,000% faster, about 70% faster to about 4,000% faster, about 70% faster to about 3,000% faster, about 70% faster to about 2,000% faster, about 70% faster to about 1,000% faster, about 70% faster to about 500% faster, about 70% faster to about 480% faster, about 70% faster to about 460% faster, about 70% faster to about 440% faster, about 70% faster to about 420% faster, about 70% faster to about 400% faster, about 70% faster to about 380% faster, about 70% faster to about 360% faster, about 70% faster to about 340% faster, about 70% faster to about 320% faster, about 70% faster to about 300% faster, about 70% faster to about 280% faster, about 70% faster to about 260% faster, about 70% faster to about 240% faster, about 70% faster to about 220% faster, about 70% faster to about 200% faster, about 70% faster to about 180% faster, about 70% faster to about 160% faster, about 70% faster to about 140% faster, about 70% faster to about 120% faster, about 70% faster to about 100% faster, about 70% faster to about 95% faster, about 70% faster to about 90% faster, about 70% faster to about 85% faster, about 70% faster to about 80% faster, about 70% faster to about 75% faster, about 75% faster to about 10,000% faster, about 75% faster to about 9,000% faster, about 75% faster to about 8,000% faster, about 75% faster to about 7,000% faster, about 75% faster to about 6,000% faster, about 75% faster to about 5,000% faster, about 75% faster to about 4,000% faster, about 75% faster to about 3,000% faster, about 75% faster to about 2,000% faster, about 75% faster to about 1,000% faster, about 75% faster to about 500% faster, about 75% faster to about 480% faster, about 75% faster to about 460% faster, about 75% faster to about 440% faster, about 75% faster to about 420% faster, about 75% faster to about 400% faster, about 75% faster to about 380% faster, about 75% faster to about 360% faster, about 75% faster to about 340% faster, about 75% faster to about 320% faster, about 75% faster to about 300% faster, about 75% faster to about 280% faster, about 75% faster to about 260% faster, about 75% faster to about 240% faster, about 75% faster to about 220% faster, about 75% faster to about 200% faster, about 75% faster to about 180% faster, about 75% faster to about 160% faster, about 75% faster to about 140% faster, about 75% faster to about 120% faster, about 75% faster to about 100% faster, about 75% faster to about 95% faster, about 75% faster to about 90% faster, about 75% faster to about 85% faster, about 75% faster to about 80% faster, about 80% faster to about 10,000% faster, about 80% faster to about 9,000% faster, about 80% faster to about 8,000% faster, about 80% faster to about 7,000% faster, about 80% faster to about 6,000% faster, about 80% faster to about 5,000% faster, about 80% faster to about 4,000% faster, about 80% faster to about 3,000% faster, about 80% faster to about 2,000% faster, about 80% faster to about 1,000% faster, about 80% faster to about 500% faster, about 80% faster to about 480% faster, about 80% faster to about 460% faster, about 80% faster to about 440% faster, about 80% faster to about 420% faster, about 80% faster to about 400% faster, about 80% faster to about 380% faster, about 80% faster to about 360% faster, about 80% faster to about 340% faster, about 80% faster to about 320% faster, about 80% faster to about 300% faster, about 80% faster to about 280% faster, about 80% faster to about 260% faster, about 80% faster to about 240% faster, about 80% faster to about 220% faster, about 80% faster to about 200% faster, about 80% faster to about 180% faster, about 80% faster to about 160% faster, about 80% faster to about 140% faster, about 80% faster to about 120% faster, about 80% faster to about 100% faster, about 80% faster to about 95% faster, about 80% faster to about 90% faster, about 80% faster to about 85% faster, about 85% faster to about 10,000% faster, about 85% faster to about 9,000% faster, about 85% faster to about 8,000% faster, about 85% faster to about 7,000% faster, about 85% faster to about 6,000% faster, about 85% faster to about 5,000% faster, about 85% faster to about 4,000% faster, about 85% faster to about 3,000% faster, about 85% faster to about 2,000% faster, about 85% faster to about 1,000% faster, about 85% faster to about 500% faster, about 85% faster to about 480% faster, about 85% faster to about 460% faster, about 85% faster to about 440% faster, about 85% faster to about 420% faster, about 85% faster to about 400% faster, about 85% faster to about 380% faster, about 85% faster to about 360% faster, about 85% faster to about 340% faster, about 85% faster to about 320% faster, about 85% faster to about 300% faster, about 85% faster to about 280% faster, about 85% faster to about 260% faster, about 85% faster to about 240% faster, about 85% faster to about 220% faster, about 85% faster to about 200% faster, about 85% faster to about 180% faster, about 85% faster to about 160% faster, about 85% faster to about 140% faster, about 85% faster to about 120% faster, about 85% faster to about 100% faster, about 85% faster to about 95% faster, about 85% faster to about 90% faster, about 90% faster to about 10,000% faster, about 90% faster to about 9,000% faster, about 90% faster to about 8,000% faster, about 90% faster to about 7,000% faster, about 90% faster to about 6,000% faster, about 90% faster to about 5,000% faster, about 90% faster to about 4,000% faster, about 90% faster to about 3,000% faster, about 90% faster to about 2,000% faster, about 90% faster to about 1,000% faster, about 90% faster to about 500% faster, about 90% faster to about 480% faster, about 90% faster to about 460% faster, about 90% faster to about 440% faster, about 90% faster to about 420% faster, about 90% faster to about 400% faster, about 90% faster to about 380% faster, about 90% faster to about 360% faster, about 90% faster to about 340% faster, about 90% faster to about 320% faster, about 90% faster to about 300% faster, about 90% faster to about 280% faster, about 90% faster to about 260% faster, about 90% faster to about 240% faster, about 90% faster to about 220% faster, about 90% faster to about 200% faster, about 90% faster to about 180% faster, about 90% faster to about 160% faster, about 90% faster to about 140% faster, about 90% faster to about 120% faster, about 90% faster to about 100% faster, about 90% faster to about 95% faster, about 95% faster to about 10,000% faster, about 95% faster to about 9,000% faster, about 95% faster to about 8,000% faster, about 95% faster to about 7,000% faster, about 95% faster to about 6,000% faster, about 95% faster to about 5,000% faster, about 95% faster to about 4,000% faster, about 95% faster to about 3,000% faster, about 95% faster to about 2,000% faster, about 95% faster to about 1,000% faster, about 95% faster to about 500% faster, about 95% faster to about 480% faster, about 95% faster to about 460% faster, about 95% faster to about 440% faster, about 95% faster to about 420% faster, about 95% faster to about 400% faster, about 95% faster to about 380% faster, about 95% faster to about 360% faster, about 95% faster to about 340% faster, about 95% faster to about 320% faster, about 95% faster to about 300% faster, about 95% faster to about 280% faster, about 95% faster to about 260% faster, about 95% faster to about 240% faster, about 95% faster to about 220% faster, about 95% faster to about 200% faster, about 95% faster to about 180% faster, about 95% faster to about 160% faster, about 95% faster to about 140% faster, about 95% faster to about 120% faster, about 95% faster to about 100% faster, about 100% faster to about 10,000% faster, about 100% faster to about 9,000% faster, about 100% faster to about 8,000% faster, about 100% faster to about 7,000% faster, about 100% faster to about 6,000% faster, about 100% faster to about 5,000% faster, about 100% faster to about 4,000% faster, about 100% faster to about 3,000% faster, about 100% faster to about 2,000% faster, about 100% faster to about 1,000% faster, about 100% faster to about 500% faster, about 100% faster to about 480% faster, about 100% faster to about 460% faster, about 100% faster to about 440% faster, about 100% faster to about 420% faster, about 100% faster to about 400% faster, about 100% faster to about 380% faster, about 100% faster to about 360% faster, about 100% faster to about 340% faster, about 100% faster to about 320% faster, about 100% faster to about 300% faster, about 100% faster to about 280% faster, about 100% faster to about 260% faster, about 100% faster to about 240% faster, about 100% faster to about 220% faster, about 100% faster to about 200% faster, about 100% faster to about 180% faster, about 100% faster to about 160% faster, about 100% faster to about 140% faster, about 100% faster to about 120% faster, about 120% faster to about 10,000% faster, about 120% faster to about 9,000% faster, about 120% faster to about 8,000% faster, about 120% faster to about 7,000% faster, about 120% faster to about 6,000% faster, about 120% faster to about 5,000% faster, about 120% faster to about 4,000% faster, about 120% faster to about 3,000% faster, about 120% faster to about 2,000% faster, about 120% faster to about 1,000% faster, about 120% faster to about 500% faster, about 120% faster to about 480% faster, about 120% faster to about 460% faster, about 120% faster to about 440% faster, about 120% faster to about 420% faster, about 120% faster to about 400% faster, about 120% faster to about 380% faster, about 120% faster to about 360% faster, about 120% faster to about 340% faster, about 120% faster to about 320% faster, about 120% faster to about 300% faster, about 120% faster to about 280% faster, about 120% faster to about 260% faster, about 120% faster to about 240% faster, about 120% faster to about 220% faster, about 120% faster to about 200% faster, about 120% faster to about 180% faster, about 120% faster to about 160% faster, about 120% faster to about 140% faster, about 140% faster to about 10,000% faster, about 140% faster to about 9,000% faster, about 140% faster to about 8,000% faster, about 140% faster to about 7,000% faster, about 140% faster to about 6,000% faster, about 140% faster to about 5,000% faster, about 140% faster to about 4,000% faster, about 140% faster to about 3,000% faster, about 140% faster to about 2,000% faster, about 140% faster to about 1,000% faster, about 140% faster to about 500% faster, about 140% faster to about 480% faster, about 140% faster to about 460% faster, about 140% faster to about 440% faster, about 140% faster to about 420% faster, about 140% faster to about 400% faster, about 140% faster to about 380% faster, about 140% faster to about 360% faster, about 140% faster to about 340% faster, about 140% faster to about 320% faster, about 140% faster to about 300% faster, about 140% faster to about 280% faster, about 140% faster to about 260% faster, about 140% faster to about 240% faster, about 140% faster to about 220% faster, about 140% faster to about 200% faster, about 140% faster to about 180% faster, about 140% faster to about 160% faster, about 160% faster to about 10,000% faster, about 160% faster to about 9,000% faster, about 160% faster to about 8,000% faster, about 160% faster to about 7,000% faster, about 160% faster to about 6,000% faster, about 160% faster to about 5,000% faster, about 160% faster to about 4,000% faster, about 160% faster to about 3,000% faster, about 160% faster to about 2,000% faster, about 160% faster to about 1,000% faster, about 160% faster to about 500% faster, about 160% faster to about 480% faster, about 160% faster to about 460% faster, about 160% faster to about 440% faster, about 160% faster to about 420% faster, about 160% faster to about 400% faster, about 160% faster to about 380% faster, about 160% faster to about 360% faster, about 160% faster to about 340% faster, about 160% faster to about 320% faster, about 160% faster to about 300% faster, about 160% faster to about 280% faster, about 160% faster to about 260% faster, about 160% faster to about 240% faster, about 160% faster to about 220% faster, about 160% faster to about 200% faster, about 160% faster to about 180% faster, about 180% faster to about 10,000% faster, about 180% faster to about 9,000% faster, about 180% faster to about 8,000% faster, about 180% faster to about 7,000% faster, about 180% faster to about 6,000% faster, about 180% faster to about 5,000% faster, about 180% faster to about 4,000% faster, about 180% faster to about 3,000% faster, about 180% faster to about 2,000% faster, about 180% faster to about 1,000% faster, about 180% faster to about 500% faster, about 180% faster to about 480% faster, about 180% faster to about 460% faster, about 180% faster to about 440% faster, about 180% faster to about 420% faster, about 180% faster to about 400% faster, about 180% faster to about 380% faster, about 180% faster to about 360% faster, about 180% faster to about 340% faster, about 180% faster to about 320% faster, about 180% faster to about 300% faster, about 180% faster to about 280% faster, about 180% faster to about 260% faster, about 180% faster to about 240% faster, about 180% faster to about 220% faster, about 180% faster to about 200% faster, about 200% faster to about 10,000% faster, about 200% faster to about 9,000% faster, about 200% faster to about 8,000% faster, about 200% faster to about 7,000% faster, about 200% faster to about 6,000% faster, about 200% faster to about 5,000% faster, about 200% faster to about 4,000% faster, about 200% faster to about 3,000% faster, about 200% faster to about 2,000% faster, about 200% faster to about 1,000% faster, about 200% faster to about 500% faster, about 200% faster to about 480% faster, about 200% faster to about 460% faster, about 200% faster to about 440% faster, about 200% faster to about 420% faster, about 200% faster to about 400% faster, about 200% faster to about 380% faster, about 200% faster to about 360% faster, about 200% faster to about 340% faster, about 200% faster to about 320% faster, about 200% faster to about 300% faster, about 200% faster to about 280% faster, about 200% faster to about 260% faster, about 200% faster to about 240% faster, about 200% faster to about 220% faster, about 220% faster to about 10,000% faster, about 220% faster to about 9,000% faster, about 220% faster to about 8,000% faster, about 220% faster to about 7,000% faster, about 220% faster to about 6,000% faster, about 220% faster to about 5,000% faster, about 220% faster to about 4,000% faster, about 220% faster to about 3,000% faster, about 220% faster to about 2,000% faster, about 220% faster to about 1,000% faster, about 220% faster to about 500% faster, about 220% faster to about 480% faster, about 220% faster to about 460% faster, about 220% faster to about 440% faster, about 220% faster to about 420% faster, about 220% faster to about 400% faster, about 220% faster to about 380% faster, about 220% faster to about 360% faster, about 220% faster to about 340% faster, about 220% faster to about 320% faster, about 220% faster to about 300% faster, about 220% faster to about 280% faster, about 220% faster to about 260% faster, about 220% faster to about 240% faster, about 240% faster to about 10,000% faster, about 240% faster to about 9,000% faster, about 240% faster to about 8,000% faster, about 240% faster to about 7,000% faster, about 240% faster to about 6,000% faster, about 240% faster to about 5,000% faster, about 240% faster to about 4,000% faster, about 240% faster to about 3,000% faster, about 240% faster to about 2,000% faster, about 240% faster to about 1,000% faster, about 240% faster to about 500% faster, about 240% faster to about 480% faster, about 240% faster to about 460% faster, about 240% faster to about 440% faster, about 240% faster to about 420% faster, about 240% faster to about 400% faster, about 240% faster to about 380% faster, about 240% faster to about 360% faster, about 240% faster to about 340% faster, about 240% faster to about 320% faster, about 240% faster to about 300% faster, about 240% faster to about 280% faster, about 240% faster to about 260% faster, about 260% faster to about 10,000% faster, about 260% faster to about 9,000% faster, about 260% faster to about 8,000% faster, about 260% faster to about 7,000% faster, about 260% faster to about 6,000% faster, about 260% faster to about 5,000% faster, about 260% faster to about 4,000% faster, about 260% faster to about 3,000% faster, about 260% faster to about 2,000% faster, about 260% faster to about 1,000% faster, about 260% faster to about 500% faster, about 260% faster to about 480% faster, about 260% faster to about 460% faster, about 260% faster to about 440% faster, about 260% faster to about 420% faster, about 260% faster to about 400% faster, about 260% faster to about 380% faster, about 260% faster to about 360% faster, about 260% faster to about 340% faster, about 260% faster to about 320% faster, about 260% faster to about 300% faster, about 260% faster to about 280% faster, about 280% faster to about 10,000% faster, about 280% faster to about 9,000% faster, about 280% faster to about 8,000% faster, about 280% faster to about 7,000% faster, about 280% faster to about 6,000% faster, about 280% faster to about 5,000% faster, about 280% faster to about 4,000% faster, about 280% faster to about 3,000% faster, about 280% faster to about 2,000% faster, about 280% faster to about 1,000% faster, about 280% faster to about 500% faster, about 280% faster to about 480% faster, about 280% faster to about 460% faster, about 280% faster to about 440% faster, about 280% faster to about 420% faster, about 280% faster to about 400% faster, about 280% faster to about 380% faster, about 280% faster to about 360% faster, about 280% faster to about 340% faster, about 280% faster to about 320% faster, about 280% faster to about 300% faster, about 300% faster to about 10,000% faster, about 300% faster to about 9,000% faster, about 300% faster to about 8,000% faster, about 300% faster to about 7,000% faster, about 300% faster to about 6,000% faster, about 300% faster to about 5,000% faster, about 300% faster to about 4,000% faster, about 300% faster to about 3,000% faster, about 300% faster to about 2,000% faster, about 300% faster to about 1,000% faster, about 300% faster to about 500% faster, about 300% faster to about 480% faster, about 300% faster to about 460% faster, about 300% faster to about 440% faster, about 300% faster to about 420% faster, about 300% faster to about 400% faster, about 300% faster to about 380% faster, about 300% faster to about 360% faster, about 300% faster to about 340% faster, about 300% faster to about 320% faster, about 320% faster to about 10,000% faster, about 320% faster to about 9,000% faster, about 320% faster to about 8,000% faster, about 320% faster to about 7,000% faster, about 320% faster to about 6,000% faster, about 320% faster to about 5,000% faster, about 320% faster to about 4,000% faster, about 320% faster to about 3,000% faster, about 320% faster to about 2,000% faster, about 320% faster to about 1,000% faster, about 320% faster to about 500% faster, about 320% faster to about 480% faster, about 320% faster to about 460% faster, about 320% faster to about 440% faster, about 320% faster to about 420% faster, about 320% faster to about 400% faster, about 320% faster to about 380% faster, about 320% faster to about 360% faster, about 320% faster to about 340% faster, about 340% faster to about 10,000% faster, about 340% faster to about 9,000% faster, about 340% faster to about 8,000% faster, about 340% faster to about 7,000% faster, about 340% faster to about 6,000% faster, about 340% faster to about 5,000% faster, about 340% faster to about 4,000% faster, about 340% faster to about 3,000% faster, about 340% faster to about 2,000% faster, about 340% faster to about 1,000% faster, about 340% faster to about 500% faster, about 340% faster to about 480% faster, about 340% faster to about 460% faster, about 340% faster to about 440% faster, about 340% faster to about 420% faster, about 340% faster to about 400% faster, about 340% faster to about 380% faster, about 340% faster to about 360% faster, about 360% faster to about 10,000% faster, about 360% faster to about 9,000% faster, about 360% faster to about 8,000% faster, about 360% faster to about 7,000% faster, about 360% faster to about 6,000% faster, about 360% faster to about 5,000% faster, about 360% faster to about 4,000% faster, about 360% faster to about 3,000% faster, about 360% faster to about 2,000% faster, about 360% faster to about 1,000% faster, about 360% faster to about 500% faster, about 360% faster to about 480% faster, about 360% faster to about 460% faster, about 360% faster to about 440% faster, about 360% faster to about 420% faster, about 360% faster to about 400% faster, about 360% faster to about 380% faster, about 380% faster to about 10,000% faster, about 380% faster to about 9,000% faster, about 380% faster to about 8,000% faster, about 380% faster to about 7,000% faster, about 380% faster to about 6,000% faster, about 380% faster to about 5,000% faster, about 380% faster to about 4,000% faster, about 380% faster to about 3,000% faster, about 380% faster to about 2,000% faster, about 380% faster to about 1,000% faster, about 380% faster to about 500% faster, about 380% faster to about 480% faster, about 380% faster to about 460% faster, about 380% faster to about 440% faster, about 380% faster to about 420% faster, about 380% faster to about 400% faster, about 400% faster to about 10,000% faster, about 400% faster to about 9,000% faster, about 400% faster to about 8,000% faster, about 400% faster to about 7,000% faster, about 400% faster to about 6,000% faster, about 400% faster to about 5,000% faster, about 400% faster to about 4,000% faster, about 400% faster to about 3,000% faster, about 400% faster to about 2,000% faster, about 400% faster to about 1,000% faster, about 400% faster to about 500% faster, about 400% faster to about 480% faster, about 400% faster to about 460% faster, about 400% faster to about 440% faster, about 400% faster to about 420% faster, about 420% faster to about 10,000% faster, about 420% faster to about 9,000% faster, about 420% faster to about 8,000% faster, about 420% faster to about 7,000% faster, about 420% faster to about 6,000% faster, about 420% faster to about 5,000% faster, about 420% faster to about 4,000% faster, about 420% faster to about 3,000% faster, about 420% faster to about 2,000% faster, about 420% faster to about 1,000% faster, about 420% faster to about 500% faster, about 420% faster to about 480% faster, about 420% faster to about 460% faster, about 420% faster to about 440% faster, about 440% faster to about 10,000% faster, about 440% faster to about 9,000% faster, about 440% faster to about 8,000% faster, about 440% faster to about 7,000% faster, about 440% faster to about 6,000% faster, about 440% faster to about 5,000% faster, about 440% faster to about 4,000% faster, about 440% faster to about 3,000% faster, about 440% faster to about 2,000% faster, about 440% faster to about 1,000% faster, about 440% faster to about 500% faster, about 440% faster to about 480% faster, about 440% faster to about 460% faster, about 460% faster to about 10,000% faster, about 460% faster to about 9,000% faster, about 460% faster to about 8,000% faster, about 460% faster to about 7,000% faster, about 460% faster to about 6,000% faster, about 460% faster to about 5,000% faster, about 460% faster to about 4,000% faster, about 460% faster to about 3,000% faster, about 460% faster to about 2,000% faster, about 460% faster to about 1,000% faster, about 460% faster to about 500% faster, about 460% faster to about 480% faster, about 480% faster to about 10,000% faster, about 480% faster to about 9,000% faster, about 480% faster to about 8,000% faster, about 480% faster to about 7,000% faster, about 480% faster to about 6,000% faster, about 480% faster to about 5,000% faster, about 480% faster to about 4,000% faster, about 480% faster to about 3,000% faster, about 480% faster to about 2,000% faster, about 480% faster to about 1,000% faster, about 480% faster to about 500% faster, about 500% faster to about 10,000% faster, about 500% faster to about 9,000% faster, about 500% faster to about 8,000% faster, about 500% faster to about 7,000% faster, about 500% faster to about 6,000% faster, about 500% faster to about 5,000% faster, about 500% faster to about 4,000% faster, about 500% faster to about 3,000% faster, about 500% faster to about 2,000% faster, about 500% faster to about 1,000% faster, about 1,000% faster to about 10,000% faster, about 1,000% faster to about 9,000% faster, about 1,000% faster to about 8,000% faster, about 1,000% faster to about 7,000% faster, about 1,000% faster to about 6,000% faster, about 1,000% faster to about 5,000% faster, about 1,000% faster to about 4,000% faster, about 1,000% faster to about 3,000% faster, about 1,000% faster to about 2,000% faster, about 2,000% faster to about 10,000% faster, about 2,000% faster to about 9,000% faster, about 2,000% faster to about 8,000% faster, about 2,000% faster to about 7,000% faster, about 2,000% faster to about 6,000% faster, about 2,000% faster to about 5,000% faster, about 2,000% faster to about 4,000% faster, about 2,000% faster to about 3,000% faster, about 3,000% faster to about 10,000% faster, about 3,000% faster to about 9,000% faster, about 3,000% faster to about 8,000% faster, about 3,000% faster to about 7,000% faster, about 3,000% faster to about 6,000% faster, about 3,000% faster to about 5,000% faster, about 3,000% faster to about 4,000% faster, about 4,000% faster to about 10,000% faster, about 4,000% faster to about 9,000% faster, about 4,000% faster to about 8,000% faster, about 4,000% faster to about 7,000% faster, about 4,000% faster to about 6,000% faster, about 4,000% faster to about 5,000% faster, about 5,000% faster to about 10,000% faster, about 5,000% faster to about 9,000% faster, about 5,000% faster to about 8,000% faster, about 5,000% faster to about 7,000% faster, about 5,000% faster to about 6,000% faster, about 6,000% faster to about 10,000% faster, about 6,000% faster to about 9,000% faster, about 6,000% faster to about 8,000% faster, about 6,000% faster to about 7,000% faster, about 7,000% faster to about 10,000% faster, about 7,000% faster to about 9,000% faster, about 7,000% faster to about 8,000% faster, about 8,000% faster to about 10,000% faster, about 8,000% faster to about 9,000% faster, or about 9,000% faster to about 10,000% faster) than the dissociation rate at a pH of about 7.0 to about 8.0 (e.g., about 7.0 to about 7.9, about 7.0 to about 7.8, about 7.0 to about 7.7, about 7.0 to about 7.6, about 7.0 to about 7.5, about 7.0 to about 7.4, about 7.0 to about 7.3, about 7.0 to about 7.2, about 7.0 to about 7.1, about 7.1 to about 8.0, about 7.1 to about 7.9, about 7.1 to about 7.8, about 7.1 to about 7.7, about 7.1 to about 7.6, about 7.1 to about 7.5, about 7.1 to about 7.4, about 7.1 to about 7.3, about 7.1 to about 7.2, about 7.2 to about 8.0, about 7.2 to about 7.9, about 7.2 to about 7.8, about 7.2 to about 7.7, about 7.2 to about 7.6, about 7.2 to about 7.5, about 7.2 to about 7.4, about 7.2 to about 7.3, about 7.3 to about 8.0, about 7.3 to about 7.9, about 7.3 to about 7.8, about 7.3 to about 7.7, about 7.3 to about 7.6, about 7.3 to about 7.5, about 7.3 to about 7.4, about 7.4 to about 8.0, about 7.4 to about 7.9, about 7.4 to about 7.8, about 7.4 to about 7.7, about 7.4 to about 7.6, about 7.4 to about 7.5, about 7.5 to about 8.0, about 7.5 to about 7.9, about 7.5 to about 7.8, about 7.5 to about 7.7, about 7.5 to about 7.6, about 7.6 to about 8.0, about 7.6 to about 7.9, about 7.6 to about 7.8, about 7.6 to about 7.7, about 7.7 to about 8.0, about 7.7 to about 7.9, about 7.7 to about 7.8, about 7.8 to about 8.0, about 7.8 to about 7.9, or about 7.9 to about 8.0).

In some embodiments of any of the antigen-binding protein constructs (ABPCs) described herein, the dissociation constant (KD) of the first antigen-binding domain (and optionally the second antigen-binding domain, if present) at a pH of about 4.0 to about 6.5 (e.g., any of the subranges of this range described herein) is greater (e.g., detectably greater) (e.g., at least 5% greater, at least 10% greater, at least 15% greater, at least 20% greater, at least 25% greater, at least 30% greater, at least 35% greater, at least 40% greater, at least 45% greater, at least 50% greater, at least 55% greater, at least 60% greater, at least 65% greater, at least 70% greater, at least 80% greater, at least 85% greater, at least 90% greater, at least 95% greater, at least 100% greater, at least 120% greater, at least 140% greater, at least 160% greater, at least 180% greater, at least 200% greater, at least 220% greater, at least 240% greater, at least 260% greater, at least 280% greater, at least 300% greater, at least 320% greater, at least 340% greater, at least 360% greater, at least 380% greater, at least 400% greater, at least 420% greater, at least 440% greater, at least 460% greater, at least 480% greater, at least 500% greater, at least 1,000% greater, at least 2,000% greater, at least 3,000% greater, at least 4,000% greater, at least 5,000% greater, at least 6,000% greater, at least 7,000% greater, at least 8,000% greater, at least 9,000% greater, or at least 10,000% greater, or about 5% greater to about 10,000% greater, about 5% greater to about 9,000% greater, about 5% greater to about 8,000% greater, about 5% greater to about 7,000% greater, about 5% greater to about 6,000% greater, about 5% greater to about 5,000% greater, about 5% greater to about 4,000% greater, about 5% greater to about 3,000% greater, about 5% greater to about 2,000% greater, about 5% greater to about 1,000% greater, about 5% greater to about 500% greater, about 5% greater to about 480% greater, about 5% greater to about 460% greater, about 5% greater to about 440% greater, about 5% greater to about 420% greater, about 5% greater to about 400% greater, about 5% greater to about 380% greater, about 5% greater to about 360% greater, about 5% greater to about 340% greater, about 5% greater to about 320% greater, about 5% greater to about 300% greater, about 5% greater to about 280% greater, about 5% greater to about 260% greater, about 5% greater to about 240% greater, about 5% greater to about 220% greater, about 5% greater to about 200% greater, about 5% greater to about 180% greater, about 5% greater to about 160% greater, about 5% greater to about 140% greater, about 5% greater to about 120% greater, about 5% greater to about 100% greater, about 5% greater to about 95% greater, about 5% greater to about 90% greater, about 5% greater to about 85% greater, about 5% greater to about 80% greater, about 5% greater to about 75% greater, about 5% greater to about 70% greater, about 5% greater to about 65% greater, about 5% greater to about 60% greater, about 5% greater to about 55% greater, about 5% greater to about 50% greater, about 5% greater to about 45% greater, about 5% greater to about 40% greater, about 5% greater to about 35% greater, about 5% greater to about 30% greater, about 5% greater to about 25% greater, about 5% greater to about 20% greater, about 5% greater to about 15% greater, about 5% greater to about 10% greater, about 10% greater to about 10,000% greater, about 10% greater to about 9,000% greater, about 10% greater to about 8,000% greater, about 10% greater to about 7,000% greater, about 10% greater to about 6,000% greater, about 10% greater to about 5,000% greater, about 10% greater to about 4,000% greater, about 10% greater to about 3,000% greater, about 10% greater to about 2,000% greater, about 10% greater to about 1,000% greater, about 10% greater to about 500% greater, about 10% greater to about 480% greater, about 10% greater to about 460% greater, about 10% greater to about 440% greater, about 10% greater to about 420% greater, about 10% greater to about 400% greater, about 10% greater to about 380% greater, about 10% greater to about 360% greater, about 10% greater to about 340% greater, about 10% greater to about 320% greater, about 10% greater to about 300% greater, about 10% greater to about 280% greater, about 10% greater to about 260% greater, about 10% greater to about 240% greater, about 10% greater to about 220% greater, about 10% greater to about 200% greater, about 10% greater to about 180% greater, about 10% greater to about 160% greater, about 10% greater to about 140% greater, about 10% greater to about 120% greater, about 10% greater to about 100% greater, about 10% greater to about 95% greater, about 10% greater to about 90% greater, about 10% greater to about 85% greater, about 10% greater to about 80% greater, about 10% greater to about 75% greater, about 10% greater to about 70% greater, about 10% greater to about 65% greater, about 10% greater to about 60% greater, about 10% greater to about 55% greater, about 10% greater to about 50% greater, about 10% greater to about 45% greater, about 10% greater to about 40% greater, about 10% greater to about 35% greater, about 10% greater to about 30% greater, about 10% greater to about 25% greater, about 10% greater to about 20% greater, about 10% greater to about 15% greater, about 15% greater to about 10,000% greater, about 15% greater to about 9,000% greater, about 15% greater to about 8,000% greater, about 15% greater to about 7,000% greater, about 15% greater to about 6,000% greater, about 15% greater to about 5,000% greater, about 15% greater to about 4,000% greater, about 15% greater to about 3,000% greater, about 15% greater to about 2,000% greater, about 15% greater to about 1,000% greater, about 15% greater to about 500% greater, about 15% greater to about 480% greater, about 15% greater to about 460% greater, about 15% greater to about 440% greater, about 15% greater to about 420% greater, about 15% greater to about 400% greater, about 15% greater to about 380% greater, about 15% greater to about 360% greater, about 15% greater to about 340% greater, about 15% greater to about 320% greater, about 15% greater to about 300% greater, about 15% greater to about 280% greater, about 15% greater to about 260% greater, about 15% greater to about 240% greater, about 15% greater to about 220% greater, about 15% greater to about 200% greater, about 15% greater to about 180% greater, about 15% greater to about 160% greater, about 15% greater to about 140% greater, about 15% greater to about 120% greater, about 15% greater to about 100% greater, about 15% greater to about 95% greater, about 15% greater to about 90% greater, about 15% greater to about 85% greater, about 15% greater to about 80% greater, about 15% greater to about 75% greater, about 15% greater to about 70% greater, about 15% greater to about 65% greater, about 15% greater to about 60% greater, about 15% greater to about 55% greater, about 15% greater to about 50% greater, about 15% greater to about 45% greater, about 15% greater to about 40% greater, about 15% greater to about 35% greater, about 15% greater to about 30% greater, about 15% greater to about 25% greater, about 15% greater to about 20% greater, about 20% greater to about 10,000% greater, about 20% greater to about 9,000% greater, about 20% greater to about 8,000% greater, about 20% greater to about 7,000% greater, about 20% greater to about 6,000% greater, about 20% greater to about 5,000% greater, about 20% greater to about 4,000% greater, about 20% greater to about 3,000% greater, about 20% greater to about 2,000% greater, about 20% greater to about 1,000% greater, about 20% greater to about 500% greater, about 20% greater to about 480% greater, about 20% greater to about 460% greater, about 20% greater to about 440% greater, about 20% greater to about 420% greater, about 20% greater to about 400% greater, about 20% greater to about 380% greater, about 20% greater to about 360% greater, about 20% greater to about 340% greater, about 20% greater to about 320% greater, about 20% greater to about 300% greater, about 20% greater to about 280% greater, about 20% greater to about 260% greater, about 20% greater to about 240% greater, about 20% greater to about 220% greater, about 20% greater to about 200% greater, about 20% greater to about 180% greater, about 20% greater to about 160% greater, about 20% greater to about 140% greater, about 20% greater to about 120% greater, about 20% greater to about 100% greater, about 20% greater to about 95% greater, about 20% greater to about 90% greater, about 20% greater to about 85% greater, about 20% greater to about 80% greater, about 20% greater to about 75% greater, about 20% greater to about 70% greater, about 20% greater to about 65% greater, about 20% greater to about 60% greater, about 20% greater to about 55% greater, about 20% greater to about 50% greater, about 20% greater to about 45% greater, about 20% greater to about 40% greater, about 20% greater to about 35% greater, about 20% greater to about 30% greater, about 20% greater to about 25% greater, about 25% greater to about 10,000% greater, about 25% greater to about 9,000% greater, about 25% greater to about 8,000% greater, about 25% greater to about 7,000% greater, about 25% greater to about 6,000% greater, about 25% greater to about 5,000% greater, about 25% greater to about 4,000% greater, about 25% greater to about 3,000% greater, about 25% greater to about 2,000% greater, about 25% greater to about 1,000% greater, about 25% greater to about 500% greater, about 25% greater to about 480% greater, about 25% greater to about 460% greater, about 25% greater to about 440% greater, about 25% greater to about 420% greater, about 25% greater to about 400% greater, about 25% greater to about 380% greater, about 25% greater to about 360% greater, about 25% greater to about 340% greater, about 25% greater to about 320% greater, about 25% greater to about 300% greater, about 25% greater to about 280% greater, about 25% greater to about 260% greater, about 25% greater to about 240% greater, about 25% greater to about 220% greater, about 25% greater to about 200% greater, about 25% greater to about 180% greater, about 25% greater to about 160% greater, about 25% greater to about 140% greater, about 25% greater to about 120% greater, about 25% greater to about 100% greater, about 25% greater to about 95% greater, about 25% greater to about 90% greater, about 25% greater to about 85% greater, about 25% greater to about 80% greater, about 25% greater to about 75% greater, about 25% greater to about 70% greater, about 25% greater to about 65% greater, about 25% greater to about 60% greater, about 25% greater to about 55% greater, about 25% greater to about 50% greater, about 25% greater to about 45% greater, about 25% greater to about 40% greater, about 25% greater to about 35% greater, about 25% greater to about 30% greater, about 30% greater to about 10,000% greater, about 30% greater to about 9,000% greater, about 30% greater to about 8,000% greater, about 30% greater to about 7,000% greater, about 30% greater to about 6,000% greater, about 30% greater to about 5,000% greater, about 30% greater to about 4,000% greater, about 30% greater to about 3,000% greater, about 30% greater to about 2,000% greater, about 30% greater to about 1,000% greater, about 30% greater to about 500% greater, about 30% greater to about 480% greater, about 30% greater to about 460% greater, about 30% greater to about 440% greater, about 30% greater to about 420% greater, about 30% greater to about 400% greater, about 30% greater to about 380% greater, about 30% greater to about 360% greater, about 30% greater to about 340% greater, about 30% greater to about 320% greater, about 30% greater to about 300% greater, about 30% greater to about 280% greater, about 30% greater to about 260% greater, about 30% greater to about 240% greater, about 30% greater to about 220% greater, about 30% greater to about 200% greater, about 30% greater to about 180% greater, about 30% greater to about 160% greater, about 30% greater to about 140% greater, about 30% greater to about 120% greater, about 30% greater to about 100% greater, about 30% greater to about 95% greater, about 30% greater to about 90% greater, about 30% greater to about 85% greater, about 30% greater to about 80% greater, about 30% greater to about 75% greater, about 30% greater to about 70% greater, about 30% greater to about 65% greater, about 30% greater to about 60% greater, about 30% greater to about 55% greater, about 30% greater to about 50% greater, about 30% greater to about 45% greater, about 30% greater to about 40% greater, about 30% greater to about 35% greater, about 35% greater to about 10,000% greater, about 35% greater to about 9,000% greater, about 35% greater to about 8,000% greater, about 35% greater to about 7,000% greater, about 35% greater to about 6,000% greater, about 35% greater to about 5,000% greater, about 35% greater to about 4,000% greater, about 35% greater to about 3,000% greater, about 35% greater to about 2,000% greater, about 35% greater to about 1,000% greater, about 35% greater to about 500% greater, about 35% greater to about 480% greater, about 35% greater to about 460% greater, about 35% greater to about 440% greater, about 35% greater to about 420% greater, about 35% greater to about 400% greater, about 35% greater to about 380% greater, about 35% greater to about 360% greater, about 35% greater to about 340% greater, about 35% greater to about 320% greater, about 35% greater to about 300% greater, about 35% greater to about 280% greater, about 35% greater to about 260% greater, about 35% greater to about 240% greater, about 35% greater to about 220% greater, about 35% greater to about 200% greater, about 35% greater to about 180% greater, about 35% greater to about 160% greater, about 35% greater to about 140% greater, about 35% greater to about 120% greater, about 35% greater to about 100% greater, about 35% greater to about 95% greater, about 35% greater to about 90% greater, about 35% greater to about 85% greater, about 35% greater to about 80% greater, about 35% greater to about 75% greater, about 35% greater to about 70% greater, about 35% greater to about 65% greater, about 35% greater to about 60% greater, about 35% greater to about 55% greater, about 35% greater to about 50% greater, about 35% greater to about 45% greater, about 35% greater to about 40% greater, about 40% greater to about 10,000% greater, about 40% greater to about 9,000% greater, about 40% greater to about 8,000% greater, about 40% greater to about 7,000% greater, about 40% greater to about 6,000% greater, about 40% greater to about 5,000% greater, about 40% greater to about 4,000% greater, about 40% greater to about 3,000% greater, about 40% greater to about 2,000% greater, about 40% greater to about 1,000% greater, about 40% greater to about 500% greater, about 40% greater to about 480% greater, about 40% greater to about 460% greater, about 40% greater to about 440% greater, about 40% greater to about 420% greater, about 40% greater to about 400% greater, about 40% greater to about 380% greater, about 40% greater to about 360% greater, about 40% greater to about 340% greater, about 40% greater to about 320% greater, about 40% greater to about 300% greater, about 40% greater to about 280% greater, about 40% greater to about 260% greater, about 40% greater to about 240% greater, about 40% greater to about 220% greater, about 40% greater to about 200% greater, about 40% greater to about 180% greater, about 40% greater to about 160% greater, about 40% greater to about 140% greater, about 40% greater to about 120% greater, about 40% greater to about 100% greater, about 40% greater to about 95% greater, about 40% greater to about 90% greater, about 40% greater to about 85% greater, about 40% greater to about 80% greater, about 40% greater to about 75% greater, about 40% greater to about 70% greater, about 40% greater to about 65% greater, about 40% greater to about 60% greater, about 40% greater to about 55% greater, about 40% greater to about 50% greater, about 40% greater to about 45% greater, about 45% greater to about 10,000% greater, about 45% greater to about 9,000% greater, about 45% greater to about 8,000% greater, about 45% greater to about 7,000% greater, about 45% greater to about 6,000% greater, about 45% greater to about 5,000% greater, about 45% greater to about 4,000% greater, about 45% greater to about 3,000% greater, about 45% greater to about 2,000% greater, about 45% greater to about 1,000% greater, about 45% greater to about 500% greater, about 45% greater to about 480% greater, about 45% greater to about 460% greater, about 45% greater to about 440% greater, about 45% greater to about 420% greater, about 45% greater to about 400% greater, about 45% greater to about 380% greater, about 45% greater to about 360% greater, about 45% greater to about 340% greater, about 45% greater to about 320% greater, about 45% greater to about 300% greater, about 45% greater to about 280% greater, about 45% greater to about 260% greater, about 45% greater to about 240% greater, about 45% greater to about 220% greater, about 45% greater to about 200% greater, about 45% greater to about 180% greater, about 45% greater to about 160% greater, about 45% greater to about 140% greater, about 45% greater to about 120% greater, about 45% greater to about 100% greater, about 45% greater to about 95% greater, about 45% greater to about 90% greater, about 45% greater to about 85% greater, about 45% greater to about 80% greater, about 45% greater to about 75% greater, about 45% greater to about 70% greater, about 45% greater to about 65% greater, about 45% greater to about 60% greater, about 45% greater to about 55% greater, about 45% greater to about 50% greater, about 50% greater to about 10,000% greater, about 50% greater to about 9,000% greater, about 50% greater to about 8,000% greater, about 50% greater to about 7,000% greater, about 50% greater to about 6,000% greater, about 50% greater to about 5,000% greater, about 50% greater to about 4,000% greater, about 50% greater to about 3,000% greater, about 50% greater to about 2,000% greater, about 50% greater to about 1,000% greater, about 50% greater to about 500% greater, about 50% greater to about 480% greater, about 50% greater to about 460% greater, about 50% greater to about 440% greater, about 50% greater to about 420% greater, about 50% greater to about 400% greater, about 50% greater to about 380% greater, about 50% greater to about 360% greater, about 50% greater to about 340% greater, about 50% greater to about 320% greater, about 50% greater to about 300% greater, about 50% greater to about 280% greater, about 50% greater to about 260% greater, about 50% greater to about 240% greater, about 50% greater to about 220% greater, about 50% greater to about 200% greater, about 50% greater to about 180% greater, about 50% greater to about 160% greater, about 50% greater to about 140% greater, about 50% greater to about 120% greater, about 50% greater to about 100% greater, about 50% greater to about 95% greater, about 50% greater to about 90% greater, about 50% greater to about 85% greater, about 50% greater to about 80% greater, about 50% greater to about 75% greater, about 50% greater to about 70% greater, about 50% greater to about 65% greater, about 50% greater to about 60% greater, about 50% greater to about 55% greater, about 55% greater to about 10,000% greater, about 55% greater to about 9,000% greater, about 55% greater to about 8,000% greater, about 55% greater to about 7,000% greater, about 55% greater to about 6,000% greater, about 55% greater to about 5,000% greater, about 55% greater to about 4,000% greater, about 55% greater to about 3,000% greater, about 55% greater to about 2,000% greater, about 55% greater to about 1,000% greater, about 55% greater to about 500% greater, about 55% greater to about 480% greater, about 55% greater to about 460% greater, about 55% greater to about 440% greater, about 55% greater to about 420% greater, about 55% greater to about 400% greater, about 55% greater to about 380% greater, about 55% greater to about 360% greater, about 55% greater to about 340% greater, about 55% greater to about 320% greater, about 55% greater to about 300% greater, about 55% greater to about 280% greater, about 55% greater to about 260% greater, about 55% greater to about 240% greater, about 55% greater to about 220% greater, about 55% greater to about 200% greater, about 55% greater to about 180% greater, about 55% greater to about 160% greater, about 55% greater to about 140% greater, about 55% greater to about 120% greater, about 55% greater to about 100% greater, about 55% greater to about 95% greater, about 55% greater to about 90% greater, about 55% greater to about 85% greater, about 55% greater to about 80% greater, about 55% greater to about 75% greater, about 55% greater to about 70% greater, about 55% greater to about 65% greater, about 55% greater to about 60% greater, about 60% greater to about 10,000% greater, about 60% greater to about 9,000% greater, about 60% greater to about 8,000% greater, about 60% greater to about 7,000% greater, about 60% greater to about 6,000% greater, about 60% greater to about 5,000% greater, about 60% greater to about 4,000% greater, about 60% greater to about 3,000% greater, about 60% greater to about 2,000% greater, about 60% greater to about 1,000% greater, about 60% greater to about 500% greater, about 60% greater to about 480% greater, about 60% greater to about 460% greater, about 60% greater to about 440% greater, about 60% greater to about 420% greater, about 60% greater to about 400% greater, about 60% greater to about 380% greater, about 60% greater to about 360% greater, about 60% greater to about 340% greater, about 60% greater to about 320% greater, about 60% greater to about 300% greater, about 60% greater to about 280% greater, about 60% greater to about 260% greater, about 60% greater to about 240% greater, about 60% greater to about 220% greater, about 60% greater to about 200% greater, about 60% greater to about 180% greater, about 60% greater to about 160% greater, about 60% greater to about 140% greater, about 60% greater to about 120% greater, about 60% greater to about 100% greater, about 60% greater to about 95% greater, about 60% greater to about 90% greater, about 60% greater to about 85% greater, about 60% greater to about 80% greater, about 60% greater to about 75% greater, about 60% greater to about 70% greater, about 60% greater to about 65% greater, about 65% greater to about 10,000% greater, about 65% greater to about 9,000% greater, about 65% greater to about 8,000% greater, about 65% greater to about 7,000% greater, about 65% greater to about 6,000% greater, about 65% greater to about 5,000% greater, about 65% greater to about 4,000% greater, about 65% greater to about 3,000% greater, about 65% greater to about 2,000% greater, about 65% greater to about 1,000% greater, about 65% greater to about 500% greater, about 65% greater to about 480% greater, about 65% greater to about 460% greater, about 65% greater to about 440% greater, about 65% greater to about 420% greater, about 65% greater to about 400% greater, about 65% greater to about 380% greater, about 65% greater to about 360% greater, about 65% greater to about 340% greater, about 65% greater to about 320% greater, about 65% greater to about 300% greater, about 65% greater to about 280% greater, about 65% greater to about 260% greater, about 65% greater to about 240% greater, about 65% greater to about 220% greater, about 65% greater to about 200% greater, about 65% greater to about 180% greater, about 65% greater to about 160% greater, about 65% greater to about 140% greater, about 65% greater to about 120% greater, about 65% greater to about 100% greater, about 65% greater to about 95% greater, about 65% greater to about 90% greater, about 65% greater to about 85% greater, about 65% greater to about 80% greater, about 65% greater to about 75% greater, about 65% greater to about 70% greater, about 70% greater to about 10,000% greater, about 70% greater to about 9,000% greater, about 70% greater to about 8,000% greater, about 70% greater to about 7,000% greater, about 70% greater to about 6,000% greater, about 70% greater to about 5,000% greater, about 70% greater to about 4,000% greater, about 70% greater to about 3,000% greater, about 70% greater to about 2,000% greater, about 70% greater to about 1,000% greater, about 70% greater to about 500% greater, about 70% greater to about 480% greater, about 70% greater to about 460% greater, about 70% greater to about 440% greater, about 70% greater to about 420% greater, about 70% greater to about 400% greater, about 70% greater to about 380% greater, about 70% greater to about 360% greater, about 70% greater to about 340% greater, about 70% greater to about 320% greater, about 70% greater to about 300% greater, about 70% greater to about 280% greater, about 70% greater to about 260% greater, about 70% greater to about 240% greater, about 70% greater to about 220% greater, about 70% greater to about 200% greater, about 70% greater to about 180% greater, about 70% greater to about 160% greater, about 70% greater to about 140% greater, about 70% greater to about 120% greater, about 70% greater to about 100% greater, about 70% greater to about 95% greater, about 70% greater to about 90% greater, about 70% greater to about 85% greater, about 70% greater to about 80% greater, about 70% greater to about 75% greater, about 75% greater to about 10,000% greater, about 75% greater to about 9,000% greater, about 75% greater to about 8,000% greater, about 75% greater to about 7,000% greater, about 75% greater to about 6,000% greater, about 75% greater to about 5,000% greater, about 75% greater to about 4,000% greater, about 75% greater to about 3,000% greater, about 75% greater to about 2,000% greater, about 75% greater to about 1,000% greater, about 75% greater to about 500% greater, about 75% greater to about 480% greater, about 75% greater to about 460% greater, about 75% greater to about 440% greater, about 75% greater to about 420% greater, about 75% greater to about 400% greater, about 75% greater to about 380% greater, about 75% greater to about 360% greater, about 75% greater to about 340% greater, about 75% greater to about 320% greater, about 75% greater to about 300% greater, about 75% greater to about 280% greater, about 75% greater to about 260% greater, about 75% greater to about 240% greater, about 75% greater to about 220% greater, about 75% greater to about 200% greater, about 75% greater to about 180% greater, about 75% greater to about 160% greater, about 75% greater to about 140% greater, about 75% greater to about 120% greater, about 75% greater to about 100% greater, about 75% greater to about 95% greater, about 75% greater to about 90% greater, about 75% greater to about 85% greater, about 75% greater to about 80% greater, about 80% greater to about 10,000% greater, about 80% greater to about 9,000% greater, about 80% greater to about 8,000% greater, about 80% greater to about 7,000% greater, about 80% greater to about 6,000% greater, about 80% greater to about 5,000% greater, about 80% greater to about 4,000% greater, about 80% greater to about 3,000% greater, about 80% greater to about 2,000% greater, about 80% greater to about 1,000% greater, about 80% greater to about 500% greater, about 80% greater to about 480% greater, about 80% greater to about 460% greater, about 80% greater to about 440% greater, about 80% greater to about 420% greater, about 80% greater to about 400% greater, about 80% greater to about 380% greater, about 80% greater to about 360% greater, about 80% greater to about 340% greater, about 80% greater to about 320% greater, about 80% greater to about 300% greater, about 80% greater to about 280% greater, about 80% greater to about 260% greater, about 80% greater to about 240% greater, about 80% greater to about 220% greater, about 80% greater to about 200% greater, about 80% greater to about 180% greater, about 80% greater to about 160% greater, about 80% greater to about 140% greater, about 80% greater to about 120% greater, about 80% greater to about 100% greater, about 80% greater to about 95% greater, about 80% greater to about 90% greater, about 80% greater to about 85% greater, about 85% greater to about 10,000% greater, about 85% greater to about 9,000% greater, about 85% greater to about 8,000% greater, about 85% greater to about 7,000% greater, about 85% greater to about 6,000% greater, about 85% greater to about 5,000% greater, about 85% greater to about 4,000% greater, about 85% greater to about 3,000% greater, about 85% greater to about 2,000% greater, about 85% greater to about 1,000% greater, about 85% greater to about 500% greater, about 85% greater to about 480% greater, about 85% greater to about 460% greater, about 85% greater to about 440% greater, about 85% greater to about 420% greater, about 85% greater to about 400% greater, about 85% greater to about 380% greater, about 85% greater to about 360% greater, about 85% greater to about 340% greater, about 85% greater to about 320% greater, about 85% greater to about 300% greater, about 85% greater to about 280% greater, about 85% greater to about 260% greater, about 85% greater to about 240% greater, about 85% greater to about 220% greater, about 85% greater to about 200% greater, about 85% greater to about 180% greater, about 85% greater to about 160% greater, about 85% greater to about 140% greater, about 85% greater to about 120% greater, about 85% greater to about 100% greater, about 85% greater to about 95% greater, about 85% greater to about 90% greater, about 90% greater to about 10,000% greater, about 90% greater to about 9,000% greater, about 90% greater to about 8,000% greater, about 90% greater to about 7,000% greater, about 90% greater to about 6,000% greater, about 90% greater to about 5,000% greater, about 90% greater to about 4,000% greater, about 90% greater to about 3,000% greater, about 90% greater to about 2,000% greater, about 90% greater to about 1,000% greater, about 90% greater to about 500% greater, about 90% greater to about 480% greater, about 90% greater to about 460% greater, about 90% greater to about 440% greater, about 90% greater to about 420% greater, about 90% greater to about 400% greater, about 90% greater to about 380% greater, about 90% greater to about 360% greater, about 90% greater to about 340% greater, about 90% greater to about 320% greater, about 90% greater to about 300% greater, about 90% greater to about 280% greater, about 90% greater to about 260% greater, about 90% greater to about 240% greater, about 90% greater to about 220% greater, about 90% greater to about 200% greater, about 90% greater to about 180% greater, about 90% greater to about 160% greater, about 90% greater to about 140% greater, about 90% greater to about 120% greater, about 90% greater to about 100% greater, about 90% greater to about 95% greater, about 95% greater to about 10,000% greater, about 95% greater to about 9,000% greater, about 95% greater to about 8,000% greater, about 95% greater to about 7,000% greater, about 95% greater to about 6,000% greater, about 95% greater to about 5,000% greater, about 95% greater to about 4,000% greater, about 95% greater to about 3,000% greater, about 95% greater to about 2,000% greater, about 95% greater to about 1,000% greater, about 95% greater to about 500% greater, about 95% greater to about 480% greater, about 95% greater to about 460% greater, about 95% greater to about 440% greater, about 95% greater to about 420% greater, about 95% greater to about 400% greater, about 95% greater to about 380% greater, about 95% greater to about 360% greater, about 95% greater to about 340% greater, about 95% greater to about 320% greater, about 95% greater to about 300% greater, about 95% greater to about 280% greater, about 95% greater to about 260% greater, about 95% greater to about 240% greater, about 95% greater to about 220% greater, about 95% greater to about 200% greater, about 95% greater to about 180% greater, about 95% greater to about 160% greater, about 95% greater to about 140% greater, about 95% greater to about 120% greater, about 95% greater to about 100% greater, about 100% greater to about 10,000% greater, about 100% greater to about 9,000% greater, about 100% greater to about 8,000% greater, about 100% greater to about 7,000% greater, about 100% greater to about 6,000% greater, about 100% greater to about 5,000% greater, about 100% greater to about 4,000% greater, about 100% greater to about 3,000% greater, about 100% greater to about 2,000% greater, about 100% greater to about 1,000% greater, about 100% greater to about 500% greater, about 100% greater to about 480% greater, about 100% greater to about 460% greater, about 100% greater to about 440% greater, about 100% greater to about 420% greater, about 100% greater to about 400% greater, about 100% greater to about 380% greater, about 100% greater to about 360% greater, about 100% greater to about 340% greater, about 100% greater to about 320% greater, about 100% greater to about 300% greater, about 100% greater to about 280% greater, about 100% greater to about 260% greater, about 100% greater to about 240% greater, about 100% greater to about 220% greater, about 100% greater to about 200% greater, about 100% greater to about 180% greater, about 100% greater to about 160% greater, about 100% greater to about 140% greater, about 100% greater to about. 120% greater, about 120% greater to about 10,000% greater, about 120% greater to about 9,000% greater, about 120% greater to about 8,000% greater, about 120% greater to about 7,000% greater, about 120% greater to about 6,000% greater, about 120% greater to about 5,000% greater, about 120% greater to about 4,000% greater, about 120% greater to about 3,000% greater, about 120% greater to about 2,000% greater, about 120% greater to about 1,000% greater, about 120% greater to about 500% greater, about 120% greater to about 480% greater, about 120% greater to about 460% greater, about 120% greater to about 440% greater, about 120% greater to about 420% greater, about 120% greater to about 400% greater, about 120% greater to about 380% greater, about 120% greater to about 360% greater, about 120% greater to about 340% greater, about 120% greater to about 320% greater, about 120% greater to about 300% greater, about 120% greater to about 280% greater, about 120% greater to about 260% greater, about 120% greater to about 240% greater, about 120% greater to about 220% greater, about 120% greater to about 200% greater, about 120% greater to about 180% greater, about 120% greater to about 160% greater, about 120% greater to about 140% greater, about 140% greater to about 10,000% greater, about 140% greater to about 9,000% greater, about 140% greater to about 8,000% greater, about 140% greater to about 7,000% greater, about 140% greater to about 6,000% greater, about 140% greater to about 5,000% greater, about 140% greater to about 4,000% greater, about 140% greater to about 3,000% greater, about 140% greater to about 2,000% greater, about 140% greater to about 1,000% greater, about 140% greater to about 500% greater, about 140% greater to about 480% greater, about 140% greater to about 460% greater, about 140% greater to about 440% greater, about 140% greater to about 420% greater, about 140% greater to about 400% greater, about 140% greater to about 380% greater, about 140% greater to about 360% greater, about 140% greater to about 340% greater, about 140% greater to about 320% greater, about 140% greater to about 300% greater, about 140% greater to about 280% greater, about 140% greater to about 260% greater, about 140% greater to about 240% greater, about 140% greater to about 220% greater, about 140% greater to about 200% greater, about 140% greater to about 180% greater, about 140% greater to about 160% greater, about 160% greater to about 10,000% greater, about 160% greater to about 9,000% greater, about 160% greater to about 8,000% greater, about 160% greater to about 7,000% greater, about 160% greater to about 6,000% greater, about 160% greater to about 5,000%-greater, about 160% greater to about 4,000% greater, about 160% greater to about 3,000% greater, about 160% greater to about 2,000% greater, about 160% greater to about 1,000% greater, about 160% greater to about 500% greater, about 160% greater to about 480% greater, about 160% greater to about 460% greater, about 160% greater to about 440% greater, about 160% greater to about 420% greater, about 160% greater to about 400% greater, about 160% greater to about 380% greater, about 160% greater to about 360% greater, about 160% greater to about 340% greater, about 160% greater to about 320% greater, about 160% greater to about 300% greater, about 160% greater to about 280% greater, about 160% greater to about 260% greater, about 160% greater to about 240% greater, about 160% greater to about 220% greater, about 160% greater to about 200% greater, about 160% greater to about 180% greater, about 180% greater to about 10,000% greater, about 180% greater to about 9,000% greater, about 180% greater to about 8,000% greater, about 180% greater to about 7,000% greater, about 180% greater to about 6,000% greater, about 180% greater to about 5,000% greater, about 180% greater to about 4,000% greater, about 180% greater to about 3,000% greater, about 180% greater to about 2,000% greater, about 180% greater to about 1,000% greater, about 180% greater to about 500% greater, about 180% greater to about 480% greater, about 180% greater to about 460% greater, about 180% greater to about 440% greater, about 180% greater to about 420% greater, about 180% greater to about 400% greater, about 180% greater to about 380% greater, about 180% greater to about 360% greater, about 180% greater to about 340% greater, about 180% greater to about 320% greater, about 180% greater to about 300% greater, about 180% greater to about 280% greater, about 180% greater to about 260% greater, about 180% greater to about 240% greater, about 180% greater to about 220% greater, about 180% greater to about 200% greater, about 200% greater to about 10,000% greater, about 200% greater to about 9,000% greater, about 200% greater to about 8,000% greater, about 200% greater to about 7,000% greater, about 200% greater to about 6,000% greater, about 200% greater to about 5,000% greater, about 200% greater to about 4,000% greater, about 200% greater to about 3,000% greater, about 200% greater to about 2,000% greater, about 200% greater to about 1,000% greater, about 200% greater to about 500% greater, about 200% greater to about 480% greater, about 200% greater to about 460% greater, about 200% greater to about 440% greater, about 200% greater to about 420% greater, about 200% greater to about 400% greater, about 200% greater to about 380% greater, about 200% greater to about 360% greater, about 200% greater to about 340% greater, about 200% greater to about 320% greater, about 200% greater to about 300% greater, about 200% greater to about 280% greater, about 200% greater to about 260% greater, about 200% greater to about 240% greater, about 200% greater to about 220% greater, about 220% greater to about 10,000% greater, about 220% greater to about 9,000% greater, about 220% greater to about 8,000% greater, about 220% greater to about 7,000% greater, about 220% greater to about 6,000% greater, about 220% greater to about 5,000% greater, about 220% greater to about 4,000% greater, about 220% greater to about 3,000% greater, about 220% greater to about 2,000% greater, about 220% greater to about 1,000% greater, about 220% greater to about 500% greater, about 220% greater to about 480% greater, about 220% greater to about 460% greater, about 220% greater to about 440% greater, about 220% greater to about 420% greater, about 220% greater to about 400% greater, about 220% greater to about 380% greater, about 220% greater to about 360% greater, about 220% greater to about 340% greater, about 220% greater to about 320% greater, about 220% greater to about 300% greater, about 220% greater to about 280% greater, about 220% greater to about 260% greater, about 220% greater to about 240% greater, about 240% greater to about 10,000% greater, about 240% greater to about 9,000% greater, about 240% greater to about 8,000% greater, about 240% greater to about 7,000% greater, about 240% greater to about 6,000% greater, about 240% greater to about 5,000% greater, about 240% greater to about 4,000% greater, about 240% greater to about 3,000% greater, about 240% greater to about 2,000% greater, about 240% greater to about 1,000% greater, about 240% greater to about 500% greater, about 240% greater to about 480% greater, about 240% greater to about 460% greater, about 240% greater to about 440% greater, about 240% greater to about 420% greater, about 240% greater to about 400% greater, about 240% greater to about 380% greater, about 240% greater to about 360% greater, about 240% greater to about-340% greater, about 240% greater to about 320% greater, about 240% greater to about 300% greater, about 240% greater to about 280% greater, about 240% greater to about 260% greater, about 260% greater to about 10,000% greater, about 260% greater to about 9,000% greater, about 260% greater to about 8,000% greater, about 260% greater to about 7,000% greater, about 260% greater to about 6,000% greater, about 260% greater to about 5,000% greater, about 260% greater to about 4,000% greater, about 260% greater to about 3,000% greater, about 260% greater to about 2,000% greater, about 260% greater to about 1,000% greater, about 260% greater to about 500% greater, about 260% greater to about 480% greater, about 260% greater to about 460% greater, about 260% greater to about 440% greater, about 260% greater to about 420% greater, about 260% greater to about 400% greater, about 260% greater to about 380% greater, about 260% greater to about 360% greater, about 260% greater to about 340% greater, about 260% greater to about 320% greater, about 260% greater to about 300% greater, about 260% greater to about 280% greater, about 280% greater to about 10,000% greater, about 280% greater to about 9,000% greater, about 280% greater to about 8,000% greater, about 280% greater to about 7,000% greater, about 280% greater to about 6,000% greater, about 280% greater to about 5,000% greater, about 280% greater to about 4,000% greater, about 280% greater to about 3,000% greater, about 280% greater to about 2,000% greater, about 280% greater to about 1,000% greater, about 280% greater to about 500% greater, about 280% greater to about 480% greater, about 280% greater to about 460% greater, about 280% greater to about 440% greater, about 280% greater to about 420% greater, about 280% greater to about 400% greater, about 280% greater to about 380% greater, about 280% greater to about 360% greater, about 280% greater to about 340% greater, about 280% greater to about 320% greater, about 280% greater to about 300% greater, about 300% greater to about 10,000% greater, about 300% greater to about 9,000% greater, about 300% greater to about 8,000% greater, about 300% greater to about 7,000% greater, about 300% greater to about 6,000% greater, about 300% greater to about 5,000% greater, about 300% greater to about 4,000% greater, about 300% greater to about 3,000% greater, about 300% greater to about 2,000% greater, about 300% greater to about 1,000% greater, about 300% greater to about 500% greater, about 300% greater to about 480% greater, about 300% greater to about 460% greater, about 300% greater to about 440% greater, about 300% greater to about 420% greater, about 300% greater to about 400% greater, about 300% greater to about 380% greater, about 300% greater to about 360% greater, about 300% greater to about 340% greater, about 300% greater to about 320% greater, about 320% greater to about 10,000% greater, about 320% greater to about 9,000% greater, about 320% greater to about 8,000% greater, about 320% greater to about 7,000% greater, about 320% greater to about 6,000% greater, about 320% greater to about 5,000% greater, about 320% greater to about 4,000% greater, about 320% greater to about 3,000% greater, about 320% greater to about 2,000% greater, about 320% greater to about 1,000% greater, about 320% greater to about 500% greater, about 320% greater to about 480% greater, about 320% greater to about 460% greater, about 320% greater to about 440% greater, about 320% greater to about 420% greater, about 320% greater to about 400% greater, about 320% greater to about 380% greater, about 320% greater to about 360% greater, about 320% greater to about 340% greater, about 340% greater to about 10,000% greater, about 340% greater to about 9,000% greater, about 340% greater to about 8,000% greater, about 340% greater to about 7,000% greater, about 340% greater to about 6,000% greater, about 340% greater to about 5,000% greater, about 340% greater to about 4,000% greater, about 340% greater to about 3,000% greater, about 340% greater to about 2,000% greater, about 340% greater to about 1,000% greater, about 340% greater to about 500% greater, about 340% greater to about 480% greater, about 340% greater to about 460% greater, about 340% greater to about 440% greater, about 340% greater to about 420% greater, about 340% greater to about 400% greater, about 340% greater to about 380% greater, about 340% greater to about 360% greater, about 360% greater to about 10,000% greater, about 360% greater to about 9,000% greater, about 360% greater to about 8,000% greater, about 360% greater to about 7,000% greater, about 360% greater to about 6,000% greater, about 360% greater to about 5,000% greater, about 360% greater to about 4,000% greater, about 360% greater to about 3,000% greater, about 360% greater to about 2,000% greater, about 360% greater to about 1,000% greater, about 360% greater to about 500% greater, about 360% greater to about 480% greater, about 360% greater to about 460% greater, about 360% greater to about 440% greater, about 360% greater to about 420% greater, about 360% greater to about 400% greater, about 360% greater to about 380% greater, about 380% greater to about 10,000% greater, about 380% greater to about 9,000% greater, about 380% greater to about 8,000% greater, about 380% greater to about 7,000% greater, about 380% greater to about 6,000% greater, about 380% greater to about 5,000% greater, about 380% greater to about 4,000% greater, about 380% greater to about 3,000% greater, about 380% greater to about 2,000% greater, about 380% greater to about 1,000% greater, about 380% greater to about 500% greater, about 380% greater to about 480% greater, about 380% greater to about 460% greater, about 380% greater to about 440% greater, about 380% greater to about 420% greater, about 380% greater to about 400% greater, about 400% greater to about 10,000% greater, about 400% greater to about 9,000% greater, about 400% greater to about 8,000% greater, about 400% greater to about 7,000% greater, about 400% greater to about 6,000% greater, about 400% greater to about 5,000% greater, about 400% greater to about 4,000% greater, about 400% greater to about 3,000% greater, about 400% greater to about 2,000% greater, about 400% greater to about 1,000% greater, about 400% greater to about 500% greater, about 400% greater to about 480% greater, about 400% greater to about 460% greater, about 400% greater to about 440% greater, about 400% greater to about 420% greater, about 420% greater to about 10,000% greater, about 420% greater to about 9,000% greater, about 420% greater to about 8,000% greater, about 420% greater to about 7,000% greater, about 420% greater to about 6,000% greater, about 420% greater to about 5,000% greater, about 420% greater to about 4,000% greater, about 420% greater to about 3,000% greater, about 420% greater to about 2,000% greater, about 420% greater to about 1,000% greater, about 420% greater to about 500% greater, about 420% greater to about 480% greater, about 420% greater to about 460% greater, about 420% greater to about 440% greater, about 440% greater to about 10,000% greater, about 440% greater to about 9,000% greater, about 440% greater to about 8,000% greater, about 440% greater to about 7,000% greater, about 440% greater to about 6,000% greater, about 440% greater to about 5,000% greater, about 440% greater to about 4,000% greater, about 440% greater to about 3,000% greater, about 440% greater to about 2,000% greater, about 440% greater to about 1,000% greater, about 440% greater to about 500% greater, about 440% greater to about 480% greater, about 440% greater to about 460% greater, about 460% greater to about 10,000% greater, about 460% greater to about 9,000% greater, about 460% greater to about 8,000% greater, about 460% greater to about 7,000% greater, about 460% greater to about 6,000% greater, about 460% greater to about 5,000% greater, about 460% greater to about 4,000% greater, about 460% greater to about 3,000% greater, about 460% greater to about 2,000% greater, about 460% greater to about 1,000% greater, about 460% greater to about 500% greater, about 460% greater to about 480% greater, about 480% greater to about 10,000% greater, about 480% greater to about 9,000% greater, about 480% greater to about 8,000% greater, about 480% greater to about 7,000% greater, about 480% greater to about 6,000% greater, about 480% greater to about 5,000% greater, about 480% greater to about 4,000% greater, about 480% greater to about 3,000% greater, about 480% greater to about 2,000% greater, about 480% greater to about 1,000% greater, about 480% greater to about 500% greater, about 500% greater to about 10,000% greater, about 500% greater to about 9,000% greater, about 500% greater to about 8,000% greater, about 500% greater to about 7,000% greater, about 500% greater to about 6,000% greater, about 500% greater to about 5,000% greater, about 500% greater to about 4,000% greater, about 500% greater to about 3,000% greater, about 500% greater to about 2,000% greater, about 500% greater to about 1,000% greater, about 1,000% greater to about 10,000% greater, about 1,000% greater to about 9,000% greater, about 1,000% greater to about 8,000% greater, about 1,000% greater to about 7,000% greater, about 1,000% greater to about 6,000% greater, about 1,000% greater to about 5,000% greater, about 1,000% greater to about 4,000% greater, about 1,000% greater to about 3,000% greater, about 1,000% greater to about 2,000% greater, about 2,000% greater to about 10,000% greater, about 2,000% greater to about 9,000% greater, about 2,000% greater to about 8,000% greater, about 2,000% greater to about 7,000% greater, about 2,000% greater to about 6,000% greater, about 2,000% greater to about 5,000% greater, about 2,000% greater to about 4,000% greater, about 2,000% greater to about 3,000% greater, about 3,000% greater to about 10,000% greater, about 3,000% greater to about 9,000% greater, about 3,000% greater to about 8,000% greater, about 3,000% greater to about 7,000% greater, about 3,000% greater to about 6,000% greater, about 3,000% greater to about 5,000% greater, about 3,000% greater to about 4,000% greater, about 4,000% greater to about 10,000% greater, about 4,000% greater to about 9,000% greater, about 4,000% greater to about 8,000% greater, about 4,000% greater to about 7,000% greater, about 4,000% greater to about 6,000% greater, about 4,000% greater to about 5,000% greater, about 5,000% greater to about 10,000% greater, about 5,000% greater to about 9,000% greater, about 5,000% greater to about 8,000% greater, about 5,000% greater to about 7,000% greater, about 5,000% greater to about 6,000% greater, about 6,000% greater to about 10,000% greater, about 6,000% greater to about 9,000% greater, about 6,000% greater to about 8,000% greater, about 6,000% greater to about 7,000% greater, about 7,000% greater to about 10,000% greater, about 7,000% greater to about 9,000% greater, about 7,000% greater to about 8,000% greater, about 8,000% greater to about 10,000% greater, about 8,000% greater to about 9,000% greater, or about 9,000% greater to about 10,000% greater) than the KD at a pH of about 7.0 to about 8.0 (e.g., any of the subranges of this range described herein).

In some embodiments of any of the antigen-binding protein constructs (ABPCs) described herein, the dissociation rate of the first antigen-binding domain (and optionally the second antigen-binding domain, if present) at a pH of about 4.0 to about 6.5 (e.g., any of the subranges of this range described herein) is faster (e.g., at least 0.2-fold faster, at least 0.3-fold, at least 0.4-fold, at least 0.5-fold, at least 0.6-fold, at least 0.7-fold, at least 0.8-fold, at least 0.9-fold, at least 1.0-fold, at least 1.5-fold, at least 2.0-fold, at least 2.5-fold, at least 3.0 fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, at least 10.0-fold, at least 10.5-fold, at least 11.0-fold, at least 11.5-fold, at least 12.0-fold, at least 12.5-fold, at least 13.0-fold, at least 13.5-fold, at least 14.0-fold, at least 14.5-fold, at least 15.0-fold, at least 15.5-fold, at least 16.0-fold, at least 16.5-fold, at least 17.0-fold, at least 17.5-fold, at least 18.0-fold, at least 18.5-fold, at least 19.0-fold, at least 19.5-fold, at least 20-fold, at least 25-fold, at least 30-fold, at least 35-fold, at least 40-fold, at least 45-fold, at least 50-fold, at least 55-fold, at least 60-fold, at least 65-fold, at least 70-fold, at least 75-fold, at least 80-fold, at least 85-fold, at least 90-fold, at least 95-fold, or at least 100-fold faster or about 0.2-fold to about 100-fold faster, about 0.2-fold to about 90-fold faster, about 0.2-fold to about 80-fold faster, about 0.2-fold to about 70-fold faster, about 0.2-fold to about 60-fold faster, about 0.2-fold to about 50-fold faster, about 0.2-fold to about 40-fold faster, about 0.2-fold to about 30-fold faster, about 0.2-fold to about 20-fold faster, about 0.2-fold to about 15=fold faster, about 0.2-fold to about 10-fold faster, about 0.2-fold to about 5-fold, about 0.2-fold to about 2-fold faster, about 0.2-fold to about 1-fold faster, about 0.2-fold to about 0.5-fold faster, about 0.5-fold to about 100-fold faster, about 0.5-fold to about 90-fold faster, about 0.5-fold to about 80-fold faster, about 0.5-fold to about 70-fold faster, about 0.5-fold to about 60-fold faster, about 0.5-fold to about 50-fold faster, about 0.5-fold to about 40-fold faster, about 0.5-fold to about 30-fold faster, about 0.5-fold to about 20-fold faster, about 0.5-fold to about 15-fold faster, about 0.5-fold to about 10-fold faster, about 0.5-fold to about 5-fold, about 0.5-fold to about 2-fold faster, about 0.5-fold to about 1-fold faster, about 1-fold to about 100-fold faster, about 1-fold to about 90-fold faster, about 1-fold to about 80-fold faster, about 1-fold to about 70-fold faster, about 1-fold to about 60-fold faster, about 1-fold to about 50-fold faster, about 1-fold to about 40-fold faster, about 1-fold to about 30-fold faster, about 1-fold to about 20-fold faster, about 1-fold to about 15-fold faster, about 1-fold to about 10-fold faster, about 1-fold to about 5-fold, about 1-fold to about 2-fold faster, about 2-fold to about 100-fold faster, about 2-fold to about 90-fold faster, about 2-fold to about 80-fold faster, about 2-fold to about 70-fold faster, about 2-fold to about 60-fold faster, about 2-fold to about 50-fold faster, about 2-fold to about 40-fold faster, about 2-fold to about 30-fold faster, about 2-fold to about 20-fold faster, about 2-fold to about 15-fold faster, about 2-fold to about 10-fold faster, about 2-fold to about 5-fold, about 5-fold to about 100-fold faster, about 5-fold to about 90-fold faster, about 5-fold to about 80-fold faster, about 5-fold to about 70-fold faster, about 5-fold to about 60-fold faster, about 5-fold to about 50-fold faster, about 5-fold to about 40-fold faster, about 5-fold to about 30-fold faster, about 5-fold to about 20-fold faster, about 5-fold to about 15-fold faster, about 5-fold to about 10-fold faster, about 10-fold to about 100-fold faster, about 10-fold to about 90-fold faster, about 10-fold to about 80-fold faster, about 10-fold to about 70-fold faster, about 10-fold to about 60-fold faster, about 10-fold to about 50-fold faster, about 10-fold to about 40-fold faster, about 10-fold to about 30-fold faster, about 10-fold to about 20-fold faster, about 10-fold to about 15-fold faster, about 15-fold to about 100-fold faster, about 15-fold to about 90-fold faster, about 15-fold to about 80-fold faster, about 15-fold to about 70-fold faster, about 15-fold to about 60-fold faster, about 15-fold to about 50-fold faster, about 15-fold to about 40-fold faster, about 15-fold to about 30-fold faster, about 15-fold to about 20-fold faster, about 20-fold to about 100-fold faster, about 20-fold to about 90-fold faster, about 20-fold to about 80-fold faster, about 20-fold to about 70-fold faster, about 20-fold to about 60-fold faster, about 20-fold to about 50-fold faster, about 20-fold to about 40-fold faster, about 20-fold to about 30-fold faster, about 30-fold to about 100-fold faster, about 30-fold to about 90-fold faster, about 30-fold to about 80-fold faster, about 30-fold to about 70-fold faster, about 30-fold to about 60-fold faster, about 30-fold to about 50-fold faster, about 30-fold to about 40-fold faster, about 40-fold to about 100-fold faster, about 40-fold to about 90-fold faster, about 40-fold to about 80-fold faster, about 40-fold to about 70-fold faster, about 40-fold to about 60-fold faster, about 40-fold to about 50-fold faster, about 50-fold to about 100-fold faster, about 50-fold to about 90-fold faster, about 50-fold to about 80-fold faster, about 50-fold to about 70-fold faster, about 50-fold to about 60-fold faster, about 60-fold to about 100-fold faster, about 60-fold to about 90-fold faster, about 60-fold to about 80-fold faster, about 60-fold to about 70-fold faster, about 70-fold to about 100-fold faster, about 70-fold to about 90-fold faster, about 70-fold to about 80-fold faster, about 80-fold to about 100-fold faster, about 80-fold to about 90-fold faster, or about 90-fold to about 100-fold faster) than the dissociation rate at a pH of about 7.0 to about 8.0 (e.g., or any of the subranges of this range described herein).

In some embodiments of any of the antigen-binding protein constructs (ABPCs) described herein, the dissociation constant (KD) of the first antigen-binding domain (and optionally the second antigen-binding domain, if present) at a pH of about 4.0 to about 6.5 (e.g., any of the subranges of this range described herein) is greater (e.g., detectably greater) (e.g., at least 0.2-fold greater, at least 0.3-fold, at least 0.4-fold, at least 0.5-fold, at least 0.6-fold, at least 0.7-fold, at least 0.8-fold, at least 0.9-fold, at least 1.0-fold, at least 1.5-fold, at least 2.0-fold, at least 2.5-fold, at least 3.0 fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, at least 10.0-fold, at least 10.5-fold, at least 11.0-fold, at least 11.5-fold, at least 12.0-fold, at least 12.5-fold, at least 13.0-fold, at least 13.5-fold, at least 14.0-fold, at least 14.5-fold, at least 15.0-fold, at least 15.5-fold, at least 16.0-fold, at least 16.5-fold, at least 17.0-fold, at least 17.5-fold, at least 18.0-fold, at least 18.5-fold, at least 19.0-fold, at least 19.5-fold, at least 20-fold greater, at least 25-fold greater, at least 30-fold greater, at least 35-fold greater, at least 40-fold greater, at least 45-fold greater, at least 50-fold greater, at least 55-fold greater, at least 60-fold greater, at least 65-fold greater, at least 70-fold greater, at least 75-fold greater, at least 80-fold greater, at least 85-fold greater, at least 90-fold greater, at least 95-fold greater, or at least 100-fold greater, or about 0.2-fold to about 100-fold greater, about 0.2-fold to about 90-fold greater, about 0.2-fold to about 80-fold greater, about 0.2-fold to about 70-fold greater, about 0.2-fold to about 60-fold greater, about 0.2-fold to about 50-fold greater, about 0.2-fold to about 40-fold greater, about 0.2-fold to about 30-fold greater, about 0.2-fold to about 25-fold greater, about 0.2-fold to about 20-fold greater, about 0.2-fold to about 15-fold greater, about 0.2-fold to about 10-fold greater, about 0.2-fold to about 8-fold greater, about 0.2-fold to about 5-fold greater, about 0.2-fold to about 2-fold greater, about 0.2-fold to about 1-fold greater, about 0.2-fold to about 0.5-fold greater, about 0.5-fold to about 100-fold greater, about 0.5-fold to about 90-fold greater, about 0.5-fold to about 80-fold greater, about 0.5-fold to about 70-fold greater, about 0.5-fold to about 60-fold greater, about 0.5-fold to about 50-fold greater, about 0.5-fold to about 40-fold greater, about 0.5-fold to about 30-fold greater, about 0.5-fold to about 25-fold greater, about 0.5-fold to about 20-fold greater, about 0.5-fold to about 15-fold greater, about 0.5-fold to about 10-fold greater, about 0.5-fold to about 8-fold greater, about 0.5-fold to about 5-fold greater, about 0.5-fold to about 2-fold greater, about 0.5-fold to about 1-fold greater, about 1-fold to about 100-fold greater, about 1-fold to about 90-fold greater, about 1-fold to about 80-fold greater, about 1-fold to about 70-fold greater, about 1-fold to about 60-fold greater, about 1-fold to about 50-fold greater, about 1-fold to about 40-fold greater, about 1-fold to about 30-fold greater, about 1-fold to about 25-fold greater, about 1-fold to about 20-fold greater, about 1-fold to about 15-fold greater, about 1-fold to about 10-fold greater, about 1-fold to about 8-fold greater, about 1-fold to about 5-fold greater, about 1-fold to about 2-fold greater, about 2-fold to about 100-fold greater, about 2-fold to about 90-fold greater, about 2-fold to about 80-fold greater, about 2-fold to about 70-fold greater, about 2-fold to about 60-fold greater, about 2-fold to about 50-fold greater, about 2-fold to about 40-fold greater, about 2-fold to about 30-fold greater, about 2-fold to about 25-fold greater, about 2-fold to about 20-fold greater, about 2-fold to about 15-fold greater, about 2-fold to about 10-fold greater, about 2-fold to about 8-fold greater, about 2-fold to about 5-fold greater, about 5-fold to about 100-fold greater, about 5-fold to about 90-fold greater, about 5-fold to about 80-fold greater, about 5-fold to about 70-fold greater, about 5-fold to about 60-fold greater, about 5-fold to about 50-fold greater, about 5-fold to about 40-fold greater, about 5-fold to about 30-fold greater, about 5-fold to about 25-fold greater, about 5-fold to about 20-fold greater, about 5-fold to about 15-fold greater, about 5-fold to about 10-fold greater, about 5-fold to about 8-fold greater, about 8-fold to about 100-fold greater, about 8-fold to about 90-fold greater, about 8-fold to about 80-fold greater, about 8-fold to about 70-fold greater, about 8-fold to about 60-fold greater, about 8-fold to about 50-fold greater, about 8-fold to about 40-fold greater, about 8-fold to about 30-fold greater, about 8-fold to about 25-fold greater, about 8-fold to about 20-fold greater, about 8-fold to about 15-fold greater, about 8-fold to about 10-fold greater, about 10-fold to about 100-fold greater, about 10-fold to about 90-fold greater, about 10-fold to about 80-fold greater, about 10-fold to about 70-fold greater, about 10-fold to about 60-fold greater, about 10-fold to about 50-fold greater, about 10-fold to about 40-fold greater, about 10-fold to about 30-fold greater, about 10-fold to about 25-fold greater, about 10-fold to about 20-fold greater, about 10-fold to about 15-fold greater, about 15-fold to about 100-fold greater, about 15-fold to about 90-fold greater, about 15-fold to about 80-fold greater, about 15-fold to about 70-fold greater, about 15-fold to about 60-fold greater, about 15-fold to about 50-fold greater, about 15-fold to about 40-fold greater, about 15-fold to about 30-fold greater, about 15-fold to about 25-fold greater, about 15-fold to about 20-fold greater, about 20-fold to about 100-fold greater, about 20-fold to about 90-fold greater, about 20-fold to about 80-fold greater, about 20-fold to about 70-fold greater, about 20-fold to about 60-fold greater, about 20-fold to about 50-fold greater, about 20-fold to about 40-fold greater, about 20-fold to about 30-fold greater, about 20-fold to about 25-fold greater, about 25-fold to about 100-fold greater, about 25-fold to about 90-fold greater, about 25-fold to about 80-fold greater, about 25-fold to about 70-fold greater, about 25-fold to about 60-fold greater, about 25-fold to about 50-fold greater, about 25-fold to about 40-fold greater, about 25-fold to about 30-fold greater, about 30-fold to about 100-fold greater, about 30-fold to about 90-fold greater, about 30-fold to about 80-fold greater, about 30-fold to about 70-fold greater, about 30-fold to about 60-fold greater, about 30-fold to about 50-fold greater, about 30-fold to about 40-fold greater, about 40-fold to about 100-fold greater, about 40-fold to about 90-fold greater, about 40-fold to about 80-fold greater, about 40-fold to about 70-fold greater, about 40-fold to about 60-fold greater, about 40-fold to about 50-fold greater, about 50-fold to about 100-fold greater, about 50-fold to about 90-fold greater, about 50-fold to about 80-fold greater, about 50-fold to about 70-fold greater, about 50-fold to about 60-fold greater, about 60-fold to about 100-fold greater, about 60-fold to about 90-fold greater, about 60-fold to about 80-fold greater, about 60-fold to about 70-fold greater, about 70-fold to about 100-fold greater, about 70-fold to about 90-fold greater, about 70-fold to about 80-fold greater, about 80-fold to about 100-fold greater, about 80-fold to about 90-fold greater, or about 90-fold to about 100-fold greater), than the KD at a pH of about 7.0 to about 8.0 (e.g., any of the subranges of this range described herein).

In some embodiments of the ABPCs that include a first antigen-binding domain and a second antigen-binding domain, the first and second antigen-binding domains are identical or are at least 80% identical (e.g., at least 82%, at least 84%, at least 86%, at least 88%, at least 90%, at least 91%, at least 92%, at least 93%, at least 94%, at least 95%, at least 96%, at least 97%, at least 98%, or at least 99% identical) in amino acid sequence to each other. In some embodiments, the ABPCs that include a first antigen-binding domain and a second antigen-binding domain, the first antigen-binding domain and the second antigen-binding domain have a sequence that is less than 80% identical (e.g., less than 75% identical, less than 70% identical, less than 65% identical, less than 60% identical, less than 55% identical, less than 50% identical, less than 45% identical, less than 40% identical, less than 35% identical, less than 30% identical, less than 25% identical, less than 20% identical, less than 15% identical, less than 10% identical, or less than 5% identical) to each other. In some embodiments of ABPCs that include a first and a second antigen-binding domain, the first and second antigen-binding domain binds two different epitopes (e.g., two different epitopes on FOLR1 or the first antigen-binding domain binding specifically to FOLR1 and the second antigen-binding domain binding to an antigen other than FOLR1).

In some embodiments of any of the ABPCs described herein, the $K_D$ of the first antigen-binding domain (and optionally, the second antigen-binding domain if present) at a pH of about 7.0 to about 8.0 (e.g., any of the subranges of this range described herein) is between about 1 pM to about 5 μM (e.g., about 1 pM to about 2 μM, about 1 pM to about 1 μM, about 1 pM to about 500 nM, about 1 pM to about 250 nM, about 1 pM to about 240 nM, about 1 pM to about 230 nM, about 1 pM to about 220 nM, about 1 pM to about 210 nM, about 1 pM to about 200 nM, about 1 pM to about 190 nM, about 1 pM to about 180 nM, about 1 pM to about 170 nM, about 1 pM to about 160 nM, about 1 pM to about 150 nM, about 1 pM to about 140 nM, about 1 pM to about 130 nM, about 1 pM to about 120 nM, about 1 pM to about 110 nM, about 1 pM to about 100 nM, about 1 pM to about 95 nM, about 1 pM to about 90 nM, about 1 pM to about 85 nM, about 1 pM to about 80 nM, about 1 pM to about 75 nM, about 1 pM to about 70 nM, about 1 pM to about 65 nM, about 1 pM to about 60 nM, about 1 pM to about 55 nM, about 1 pM to about 50 nM, about 1 pM to about 45 nM, about 1 pM to about 40 nM, about 1 pM to about 35 nM, about 1 pM to about 30 nM, about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 5 μM, about 2 pM to about 2 μM, about 2 pM to about 1 μM, about 2 pM to about 500 nM, about 2 pM to about 250 nM, about 2 pM to about 240 nM, about 2 pM to about 230 nM, about 2 pM to about 220 nM, about 2 pM to about 210 nM, about 2 pM to about 200 nM, about 2 pM to about 190 nM, about 2 pM to about 180 nM, about 2 pM to about 170 nM, about 2 pM to about 160 nM, about 2 pM to about 150 nM, about 2 pM to about 140 nM, about 2 pM to about 130 nM, about 2 pM to about 120 nM, about 2 pM to about 110 nM, about 2 pM to about 100 nM, about 2 pM to about 95 nM, about 2 pM to about 90 nM, about 2 pM to about 85 nM, about 2 pM to about 80 nM, about 2 pM to about 75 nM, about 2 pM to about 70 nM, about 2 pM to about 65 nM, about 2 pM to about 60 nM, about 2 pM to about 55 nM, about 2 pM to about 50 nM, about 2 pM to about 45 nM, about 2 pM to about 40 nM, about 2 pM to about 35 nM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 5 μM, about 5 pM to about 2 μM, about 5 pM to about 1 μM, about 5 pM to about 500 nM, about 5 pM to about 250 nM, about 5 pM to about 240 nM, about 5 pM to about 230 nM, about 5 pM to about 220 nM, about 5 pM to about 210 nM, about 5 pM to about 200 nM, about 5 pM to about 190 nM, about 5 pM to about 180 nM, about 5 pM to about 170 nM, about 5 pM to about 160 nM, about 5 pM to about 150 nM, about 5 pM to about 140 nM, about 5 pM to about 130 nM, about 5 pM to about 120 nM, about 5 pM to about 110 nM, about 5 pM to about 100 nM, about 5 pM to about 95 nM, about 5 pM to about 90 nM, about 5 pM to about 85 nM, about 5 pM to about 80 nM, about 5 pM to about 75 nM, about 5 pM to about 70 nM, about 5 pM to about 65 nM, about 5 pM to about 60 nM, about 5 pM to about 55 nM, about 5 pM to about 50 nM, about 5 pM to about 45 nM, about 5 pM to about 40 nM, about 5 pM to about 35 nM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 5 μM, about 10 pM to about 2 μM, about 10 pM to about 1 μM, about 10 pM to about 500 nM, about 10 pM to about 250 nM, about 10 pM to about 240 nM, about 10 pM to about 230 nM, about 10 pM to about 220 nM, about 10 pM to about 210 nM, about 10 pM to about 200 nM, about 10 pM to about 190 nM, about 10 pM to about 180 nM, about 10 pM to about 170 nM, about 10 pM to about 160 nM, about 10 pM to about 150 nM, about 10 pM to about 140 nM, about 10 pM to about 130 nM, about 10 pM to about 120 nM, about 10 pM to about 110 nM, about 10 pM to about 100 nM, about 10 pM to about 95 nM, about 10 pM to about 90 nM, about 10 pM to about 85 nM, about 10 pM to about 80 nM, about 10 pM to about 75 nM, about 10 pM to about 70 nM, about 10 pM to about 65 nM, about 10 pM to about 60 nM, about 10 pM to about 55 nM, about 10 pM to about 50 nM, about 10 pM to about 45 nM, about 10 pM to about 40 nM, about 10 pM to about 35 nM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 5 μM, about 15 pM to about 2 μM, about 15 pM to about 1 μM, about 15 pM to about 500 nM, about 15 pM to about 250 nM, about 15 pM to about 240 nM, about 15 pM to about 230 nM, about 15 pM to about 220 nM, about 15 pM to about 210 nM, about 15 pM to about 200 nM, about 15 pM to about 190 nM, about 15 pM to about 180 nM, about 15 pM to about 170 nM, about 15 pM to about 160 nM, about 15 pM to about 150 nM, about 15 pM to about 140 nM, about 15 pM to about 130 nM, about 15 pM to about 120 nM, about 15 pM to about 110 nM, about 15 pM to about 100 nM, about 15 pM to about 95 nM, about 15 pM to about 90 nM, about 15 pM to about 85 nM, about 15 pM to about 80 nM, about 15 pM to about 75 nM, about 15 pM to about 70 nM, about 15 pM to about 65 nM, about 15 pM to about 60 nM, about 15 pM to about 55 nM, about 15 pM to about 50 nM, about 15 pM to about 45 nM, about 15 pM to about 40 nM, about 15 pM to about 35 nM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 5 μM, about 20 pM to about 2 μM, about 20 pM to about 1 μM, about 20 pM to about 500 nM, about 20 pM to about 250 nM, about 20 pM to about 240 nM, about 20 pM to about 230 nM, about 20 pM to about 220 nM, about 20 pM to about 210 nM, about 20 pM to about 200 nM, about 20 pM to about 190 nM, about 20 pM to about 180 nM, about 20 pM to about 170 nM, about 20 pM to about 160 nM, about 20 pM to about 150 nM, about 20 pM to about 140 nM, about 20 pM to about 130 nM, about 20 pM to about 120 nM, about 20 pM to about 110 nM, about 20 pM to about 100 nM, about 20 pM to about 95 nM, about 20 pM to about 90 nM, about 20 pM to about 85 nM, about 20 pM to about 80 nM, about 20 pM to about 75 nM, about 20 pM to about 70 nM, about 20 pM to about 65 nM, about 20 pM to about 60 nM, about 20 pM to about 55 nM, about 20 pM to about 50 nM, about 20 pM to about 45 nM, about 20 pM to about 40 nM, about 20 pM to about 35 nM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 5 µM, about 30 pM to about 2 µM, about 30 pM to about 1 µM, about 30 pM to about 500 nM, about 30 pM to about 250 nM, about 30 pM to about 240 nM, about 30 pM to about 230 nM, about 30 pM to about 220 nM, about 30 pM to about 210 nM, about 30 pM to about 200 nM, about 30 pM to about 190 nM, about 30 pM to about 180 nM, about 30 pM to about 170 nM, about 30 pM to about 160 nM, about 30 pM to about 150 nM, about 30 pM to about 140 nM, about 30 pM to about 130 nM, about 30 pM to about 120 nM, about 30 pM to about 110 nM, about 30 pM to about 100 nM, about 30 pM to about 95 nM, about 30 pM to about 90 nM, about 30 pM to about 85 nM, about 30 pM to about 80 nM, about 30 pM to about 75 nM, about 30 pM to about 70 nM, about 30 pM to about 65 nM, about 30 pM to about 60 nM, about 30 pM to about 55 nM, about 30 pM to about 50 nM, about 30 pM to about 45 nM, about 30 pM to about 40 nM, about 30 pM to about 35 nM, about 30 pM to about 30 nM, about 30 pM to about 25 nM, about 30 pM to about 20 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 5 µM, about 40 pM to about 2 µM, about 40 pM to about 1 pM, about 40 pM to about 500 nM, about 40 pM to about 250 nM, about 40 pM to about 240 nM, about 40 pM to about 230 nM, about 40 pM to about 220 nM, about 40 pM to about 210 nM, about 40 pM to about 200 nM, about 40 pM to about 190 nM, about 40 pM to about 180 nM, about 40 pM to about 170 nM, about 40 pM to about 160 nM, about 40 pM to about 150 nM, about 40 pM to about 140 nM, about 40 pM to about 130 nM, about 40 pM to about 120 nM, about 40 pM to about 110 nM, about 40 pM to about 100 nM, about 40 pM to about 95 nM, about 40 pM to about 90 nM, about 40 pM to about 85 nM, about 40 pM to about 80 nM, about 40 pM to about 75 nM, about 40 pM to about 70 nM, about 40 pM to about 65 nM, about 40 pM to about 60 nM, about 40 pM to about 55 nM, about 40 pM to about 50 nM, about 40 pM to about 45 nM, about 40 pM to about 40 nM, about 40 pM to about 35 nM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 5 µM, about 50 pM to about 2 µM, about 50 pM to about 1 µM, about 50 pM to about 500 nM, about 50 pM to about 250 nM, about 50 pM to about 240 nM, about 50 pM to about 230 nM, about 50 pM to about 220 nM, about 50 pM to about 210 nM, about 50 pM to about 200 nM, about 50 pM to about 190 nM, about 50 pM to about 180 nM, about 50 pM to about 170 nM, about 50 pM to about 160 nM, about 50 pM to about 150 nM, about 50 pM to about 140 nM, about 50 pM to about 130 nM, about 50 pM to about 120 nM, about 50 pM to about 110 nM, about 50 pM to about 100 nM, about 50 pM to about 95 nM, about 50 pM to about 90 nM, about 50 pM to about 85 nM, about 50 pM to about 80 nM, about 50 pM to about 75 nM, about 50 pM to about 70 nM, about 50 pM to about 65 nM, about 50 pM to about 60 nM, about 50 pM to about 55 nM, about 50 pM to about 50 nM, about 50 pM to about 45 nM, about 50 pM to about 40 nM, about 50 pM to about 35 nM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 5 µM, about 60 pM to about 2 µM, about 60 pM to about 1 µM, about 60 pM to about 500 nM, about 60 pM to about 250 nM, about 60 pM to about 240 nM, about 60 pM to about 230 nM, about 60 pM to about 220 nM, about 60 pM to about 210 nM, about 60 pM to about 200 nM, about 60 pM to about 190 nM, about 60 pM to about 180 nM, about 60 pM to about 170 nM, about 60 pM to about 160 nM, about 60 pM to about 150 nM, about 60 pM to about 140 nM, about 60 pM to about 130 nM, about 60 pM to about 120 nM, about 60 pM to about 110 nM, about 60 pM to about 100 nM, about 60 pM to about 95 nM, about 60 pM to about 90 nM, about 60 pM to about 85 nM, about 60 pM to about 80 nM, about 60 pM to about 75 nM, about 60 pM to about 70 nM, about 60 pM to about 65 nM, about 60 pM to about 60 nM, about 60 pM to about 55 nM, about 60 pM to about 50 nM, about 60 pM to about 45 nM, about 60 pM to about 40 nM, about 60 pM to about 35 nM, about 60 pM to about 30 nM, about 60 pM to about 25 nM, about 60 pM to about 20 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 5 μM, about 70 pM to about 2 μM, about 70 pM to about 1 μM, about 70 pM to about 500 nM, about 70 pM to about 250 nM, about 70 pM to about 240 nM, about 70 pM to about 230 nM, about 70 pM to about 220 nM, about 70 pM to about 210 nM, about 70 pM to about 200 nM, about 70 pM to about 190 nM, about 70 pM to about 180 nM, about 70 pM to about 170 nM, about 70 pM to about 160 nM, about 70 pM to about 150 nM, about 70 pM to about 140 nM, about 70 pM to about 130 nM, about 70 pM to about 120 nM, about 70 pM to about 110 nM, about 70 pM to about 100 nM, about 70 pM to about 95 nM, about 70 pM to about 90 nM, about 70 pM to about 85 nM, about 70 pM to about 80 nM, about 70 pM to about 75 nM, about 70 pM to about 70 nM, about 70 pM to about 65 nM, about 70 pM to about 60 nM, about 70 pM to about 55 nM, about 70 pM to about 50 nM, about 70 pM to about 45 nM, about 70 pM to about 40 nM, about 70 pM to about 35 nM, about 70 pM to about 30 nM, about 70 pM to about 25 nM, about 70 pM to about 20 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 5 μM, about 80 pM to about 2 μM, about 80 pM to about 1 μM, about 80 pM to about 500 nM, about 80 pM to about 250 nM, about 80 pM to about 240 nM, about 80 pM to about 230 nM, about 80 pM to about 220 nM, about 80 pM to about 210 nM, about 80 pM to about 200 nM, about 80 pM to about 190 nM, about 80 pM to about 180 nM, about 80 pM to about 170 nM, about 80 pM to about 160 nM, about 80 pM to about 150 nM, about 80 pM to about 140 nM, about 80 pM to about 130 nM, about 80 pM to about 120 nM, about 80 pM to about 110 nM, about 80 pM to about 100 nM, about 80 pM to about 95 nM, about 80 pM to about 90 nM, about 80 pM to about 85 nM, about 80 pM to about 80 nM, about 80 pM to about 75 nM, about 80 pM to about 70 nM, about 80 pM to about 65 nM, about 80 pM to about 60 nM, about 80 pM to about 55 nM, about 80 pM to about 50 nM, about 80 pM to about 45 nM, about 80 pM to about 40 nM, about 80 pM to about 35 nM, about 80 pM to about 30 nM, about 80 pM to about 25 nM, about 80 pM to about 20 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 5 μM, about 90 pM to about 2 μM, about 90 pM to about 1 μM, about 90 pM to about 500 nM, about 90 pM to about 250 nM, about 90 pM to about 240 nM, about 90 pM to about 230 nM, about 90 pM to about 220 nM, about 90 pM to about 210 nM, about 90 pM to about 200 nM, about 90 pM to about 190 nM, about 90 pM to about 180 nM, about 90 pM to about 170 nM, about 90 pM to about 160 nM, about 90 pM to about 150 nM, about 90 pM to about 140 nM, about 90 pM to about 130 nM, about 90 pM to about 120 nM, about 90 pM to about 110 nM, about 90 pM to about 100 nM, about 90 pM to about 95 nM, about 90 pM to about 90 nM, about 90 pM to about 85 nM, about 90 pM to about 80 nM, about 90 pM to about 75 nM, about 90 pM to about 70 nM, about 90 pM to about 65 nM, about 90 pM to about 60 nM, about 90 pM to about 55 nM, about 90 pM to about 50 nM, about 90 pM to about 45 nM, about 90 pM to about 40 nM, about 90 pM to about 35 nM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 5 μM, about 100 pM to about 2 μM, about 100 pM to about 1 μM, about 100 pM to about 500 nM, about 100 pM to about 250 nM, about 100 pM to about 240 nM, about 100 pM to about 230 nM, about 100 pM to about 220 nM, about 100 pM to about 210 nM, about 100 pM to about 200 nM, about 100 pM to about 190 nM, about 100 pM to about 180 nM, about 100 pM to about 170 nM, about 100 pM to about 160 nM, about 100 pM to about 150 nM, about 100 pM to about 140 nM, about 100 pM to about 130 nM, about 100 pM to about 120 nM, about 100 pM to about 110 nM, about 100 pM to about 100 nM, about 100 pM to about 95 nM, about 100 pM to about 90 nM, about 100 pM to about 85 nM, about 100 pM to about 80 nM, about 100 pM to about 75 nM, about 100 pM to about 70 nM, about 100 pM to about 65 nM, about 100 pM to about 60 nM, about 100 pM to about 55 nM, about 100 pM to about 50 nM, about 100 pM to about 45 nM, about 100 pM to about 40 nM, about 100 pM to about 35 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 5 μM, about 150 pM to about 2 μM, about 150 pM to about 1 μM, about 150 pM to about 500 nM, about 150 pM to about 250 nM, about 150 pM to about 240 nM, about 150 pM to about 230 nM, about 150 pM to about 220 nM, about 150 pM to about 210 nM, about 150 pM to about 200 nM, about 150 pM to about 190 nM, about 150 pM to about 180 nM, about 150 pM to about 170 nM, about 150 pM to about 160 nM, about 150 pM to about 150 nM, about 150 pM to about 140 nM, about 150 pM to about 130 nM, about 150 pM to about 120 nM, about 150 pM to about 110 nM, about 150 pM to about 100 nM, about 150 pM to about 95 nM, about 150 pM to about 90 nM, about 150 pM to about 85 nM, about 150 pM to about 80 nM, about 150 pM to about 75 nM, about 150 pM to about 70 nM, about 150 pM to about 65 nM, about 150 pM to about 60 nM, about 150 pM to about 55 nM, about 150 pM to about 50 nM, about 150 pM to about 45 nM, about 150 pM to about 40 nM, about 150 pM to about 35 nM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 5 μM, about 200 pM to about 2 μM, about 200 pM to about 1 μM, about 200 pM to about 500 nM, about 200 pM to about 250 nM, about 200 pM to about 240 nM, about 200 pM to about 230 nM, about 200 pM to about 220 nM, about 200 pM to about 210 nM, about 200 pM to about 200 nM, about 200 pM to about 190 nM, about 200 pM to about 180 nM, about 200 pM to about 170 nM, about 200 pM to about 160 nM, about 200 pM to about 150 nM, about 200 pM to about 140 nM, about 200 pM to about 130 nM, about 200 pM to about 120 nM, about 200 pM to about 110 nM, about 200 pM to about 100 nM, about 200 pM to about 95 nM, about 200 pM to about 90 nM, about 200 pM to about 85 nM, about 200 pM to about 80 nM, about 200 pM to about 75 nM, about 200 pM to about 70 nM, about 200 pM to about 65 nM, about 200 pM to about 60 nM, about 200 pM to about 55 nM, about 200 pM to about 50 nM, about 200 pM to about 45 nM, about 200 pM to about 40 nM, about 200 pM to about 35 nM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 5 μM, about 300 pM to about 2 μM, about 300 pM to about 1 pM, about 300 pM to about 500 nM, about 300 pM to about 250 nM, about 300 pM to about 240 nM, about 300 pM to about 230 nM, about 300 pM to about 220 nM, about 300 pM to about 210 nM, about 300 pM to about 200 nM, about 300 pM to about 190 nM, about 300 pM to about 180 nM, about 300 pM to about 170 nM, about 300 pM to about 160 nM, about 300 pM to about 150 nM, about 300 pM to about 140 nM, about 300 pM to about 130 nM, about 300 pM to about 120 nM, about 300 pM to about 110 nM, about 300 pM to about 100 nM, about 300 pM to about 95 nM, about 300 pM to about 90 nM, about 300 pM to about 85 nM, about 300 pM to about 80 nM, about 300 pM to about 75 nM, about 300 pM to about 70 nM, about 300 pM to about 65 nM, about 300 pM to about 60 nM, about 300 pM to about 55 nM, about 300 pM to about 50 nM, about 300 pM to about 45 nM, about 300 pM to about 40 nM, about 300 pM to about 35 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 5 μM, about 400 pM to about 2 μM, about 400 pM to about 1 μM, about 400 pM to about 500 nM, about 400 pM to about 250 nM, about 400 pM to about 240 nM, about 400 pM to about 230 nM, about 400 pM to about 220 nM, about 400 pM to about 210 nM, about 400 pM to about 200 nM, about 400 pM to about 190 nM, about 400 pM to about 180 nM, about 400 pM to about 170 nM, about 400 pM to about 160 nM, about 400 pM to about 150 nM, about 400 pM to about 140 nM, about 400 pM to about 130 nM, about 400 pM to about 120 nM, about 400 pM to about 110 nM, about 400 pM to about 100 nM, about 400 pM to about 95 nM, about 400 pM to about 90 nM, about 400 pM to about 85 nM, about 400 pM to about 80 nM, about 400 pM to about 75 nM, about 400 pM to about 70 nM, about 400 pM to about 65 nM, about 400 pM to about 60 nM, about 400 pM to about 55 nM, about 400 pM to about 50 nM, about 400 pM to about 45 nM, about 400 pM to about 40 nM, about 400 pM to about 35 nM, about 400 pM to about 30 nM, about 400 pM to about 25 nM, about 400 pM to about 20 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 5 μM, about 500 pM to about 2 μM, about 500 pM to about 1 μM, about 500 pM to about 500 nM, about 500 pM to about 250 nM, about 500 pM to about 240 nM, about 500 pM to about 230 nM, about 500 pM to about 220 nM, about 500 pM to about 210 nM, about 500 pM to about 200 nM, about 500 pM to about 190 nM, about 500 pM to about 180 nM, about 500 pM to about 170 nM, about 500 pM to about 160 nM, about 500 pM to about 150 nM, about 500 pM to about 140 nM, about 500 pM to about 130 nM, about 500 pM to about 120 nM, about 500 pM to about 110 nM, about 500 pM to about 100 nM, about 500 pM to about 95 nM, about 500 pM to about 90 nM, about 500 pM to about 85 nM, about 500 pM to about 80 nM, about 500 pM to about 75 nM, about 500 pM to about 70 nM, about 500 pM to about 65 nM, about 500 pM to about 60 nM, about 500 pM to about 55 nM, about 500 pM to about 50 nM, about 500 pM to about 45 nM, about 500 pM to about 40 nM, about 500 pM to about 35 nM, about 500 pM to about 30 nM, about 500 pM to about 25 nM, about 500 pM to about 20 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 5 µM, about 600 pM to about 2 µM, about 600 pM to about 1 µM, about 600 pM to about 500 nM, about 600 pM to about 250 nM, about 600 pM to about 240 nM, about 600 pM to about 230 nM, about 600 pM to about 220 nM, about 600 pM to about 210 nM, about 600 pM to about 200 nM, about 600 pM to about 190 nM, about 600 pM to about 180 nM, about 600 pM to about 170 nM, about 600 pM to about 160 nM, about 600 pM to about 150 nM, about 600 pM to about 140 nM, about 600 pM to about 130 nM, about 600 pM to about 120 nM, about 600 pM to about 110 nM, about 600 pM to about 100 nM, about 600 pM to about 95 nM, about 600 pM to about 90 nM, about 600 pM to about 85 nM, about 600 pM to about 80 nM, about 600 pM to about 75 nM, about 600 pM to about 70 nM, about 600 pM to about 65 nM, about 600 pM to about 60 nM, about 600 pM to about 55 nM, about 600 pM to about 50 nM, about 600 pM to about 45 nM, about 600 pM to about 40 nM, about 600 pM to about 35 nM, about 600 pM to about 30 nM, about 600 pM to about 25 nM, about 600 pM to about 20 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 5 µM, about 700 pM to about 2 µM, about 700 pM to about 1 µM, about 700 pM to about 500 nM, about 700 pM to about 250 nM, about 700 pM to about 240 nM, about 700 pM to about 230 nM; about 700 pM to about 220 nM, about 700 pM to about 210 nM, about 700 pM to about 200 nM, about 700 pM to about 190 nM, about 700 pM to about 180 nM, about 700 pM to about 170 nM, about 700 pM to about 160 nM, about 700 pM to about 150 nM, about 700 pM to about 140 nM, about 700 pM to about 130 nM, about 700 pM to about 120 nM, about 700 pM to about 110 nM, about 700 pM to about 100 nM, about 700 pM to about 95 nM, about 700 pM to about 90 nM, about 700 pM to about 85 nM, about 700 pM to about 80 nM, about 700 pM to about 75 nM, about 700 pM to about 70 nM, about 700 pM to about 65 nM, about 700 pM to about 60 nM, about 700 pM to about 55 nM, about 700 pM to about 50 nM, about 700 pM to about 45 nM, about 700 pM to about 40 nM, about 700 pM to about 35 nM, about 700 pM to about 30 nM, about 700 pM to about 25 nM, about 700 pM to about 20 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 5 µM, about 800 pM to about 2 µM, about 800 pM to about 1 µM, about 800 pM to about 500 nM, about 800 pM to about 250 nM, about 800 pM to about 240 nM, about 800 pM to about 230 nM, about 800 pM to about 220 nM, about 800 pM to about 210 nM, about 800 pM to about 200 nM, about 800 pM to about 190 nM, about 800 pM to about 180 nM, about 800 pM to about 170 nM, about 800 pM to about 160 nM, about 800 pM to about 150 nM, about 800 pM to about 140 nM, about 800 pM to about 130 nM, about 800 pM to about 120 nM, about 800 pM to about 110 nM, about 800 pM to about 100 nM, about 800 pM to about 95 nM, about 800 pM to about 90 nM, about 800 pM to about 85 nM, about 800 pM to about 80 nM, about 800 pM to about 75 nM, about 800 pM to about 70 nM, about 800 pM to about 65 nM, about 800 pM to about 60 nM, about 800 pM to about 55 nM, about 800 pM to about 50 nM, about 800 pM to about 45 nM, about 800 pM to about 40 nM, about 800 pM to about 35 nM, about 800 pM to about 30 nM, about 800 pM to about 25 nM, about 800 pM to about 20 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 5 µM, about 900 pM to about 2 µM, about 900 pM to about 1 µM, about 900 pM to about 500 nM, about 900 pM to about 250 nM, about 900 pM to about 240 nM, about 900 pM to about 230 nM, about 900 pM to about 220 nM, about 900 pM to about 210 nM, about 900 pM to about 200 nM, about 900 pM to about 190 nM, about 900 pM to about 180 nM, about 900 pM to about 170 nM, about 900 pM to about 160 nM, about 900 pM to about 150 nM, about 900 pM to about 140 nM, about 900 pM to about 130 nM, about 900 pM to about 120 nM, about 900 pM to about 110 nM, about 900 pM to about 100 nM, about 900 pM to about 95 nM, about 900 pM to about 90 nM, about 900 pM to about 85 nM, about 900 pM to about 80 nM, about 900 pM to about 75 nM, about 900 pM to about 70 nM, about 900 pM to about 65 nM, about 900 pM to about 60 nM, about 900 pM to about 55 nM, about 900 pM to about 50 nM, about 900 pM to about 45 nM, about 900 pM to about 40 nM, about 900 pM to about 35 nM, about 900 pM to about 30 nM, about 900 pM to about 25 nM, about 900 pM to about 20 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 5 µM, about 1 nM to about 2 µM, about 1 nM to about 1 µM, about 1 nM to about 500 nM, about 1 nM to about 250 nM, about 1 nM to about 240 nM, about 1 nM to about 230 nM, about 1 nM to about 220 nM, about 1 nM to about 210 nM, about 1 nM to about 200 nM, about 1 nM to about 190 nM, about 1 nM to about 180 nM, about 1 nM to about 170 nM, about 1 nM to about 160 nM, about 1 nM to about 150 nM, about 1 nM to about 140 nM, about 1 nM to about 130 nM, about 1 nM to about 120 nM, about 1 nM to about 110 nM, about 1 nM to about 100 nM, about 1 nM to about 95 nM, about 1 nM to about 90 nM, about 1 nM to about 85 nM, about 1 nM to about 80 nM, about 1 nM to about 75 nM, about 1 nM to about 70 nM, about 1 nM to about 65 nM, about 1 nM to about 60 nM, about 1 nM to about 55 nM, about 1 nM to about 50 nM, about 1 nM to about 45 nM, about 1 nM to about 40 nM, about 1 nM to about 35 nM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 5 µM, about 2 nM to about 2 µM, about 2 nM to about 1 µM, about 2 nM to about 500 nM, about 2 nM to about 250 nM, about 2 nM to about 240 nM, about 2 nM to about 230 nM, about 2 nM to about 220 nM, about 2 nM to about 210 nM, about 2 nM to about 200 nM, about 2 nM to about 190 nM, about 2 nM to about 180 nM, about 2 nM to about 170 nM, about 2 nM to about 160 nM, about 2 nM to about 150 nM, about 2 nM to about 140 nM, about 2 nM to about 130 nM, about 2 nM to about 120 nM, about 2 nM to about 110 nM, about 2 nM to about 100 nM, about 2 nM to about 95 nM, about 2 nM to about 90 nM, about 2 nM to about 85 nM, about 2 nM to about 80 nM, about 2 nM to about 75 nM, about 2 nM to about 70 nM, about 2 nM to about 65 nM, about 2 nM to about 60 nM, about 2 nM to about 55 nM, about 2 nM to about 50 nM, about 2 nM to about 45 nM, about 2 nM to about 40 nM, about 2 nM to about 35 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 5 µM, about 4 nM to about 2 µM, about 4 nM to about 1 µM, about 4 nM to about 500 nM, about 4 nM to about 250 nM, about 4 nM to about 240 nM, about 4 nM to about 230 nM, about 4 nM to about 220 nM, about 4 nM to about 210 nM, about 4 nM to about 200 nM, about 4 nM to about 190 nM, about 4 nM to about 180 nM, about 4 nM to about 170 nM, about 4 nM to about 160 nM, about 4 nM to about 150 nM, about 4 nM to about 140 nM, about 4 nM to about 130 nM, about 4 nM to about 120 nM, about 4 nM to about 110 nM, about 4 nM to about 100 nM, about 4 nM to about 95 nM, about 4 nM to about 90 nM, about 4 nM to about 85 nM, about 4 nM to about 80 nM, about 4 nM to about 75 nM, about 4 nM to about 70 nM, about 4 nM to about 65 nM, about 4 nM to about 60 nM, about 4 nM to about 55 nM, about 4 nM to about 50 nM, about 4 nM to about 45 nM, about 4 nM to about 40 nM, about 4 nM to about 35 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 5 µM, about 5 nM to about 2 µM, about 5 nM to about 1 µM, about 5 nM to about 500 nM, about 5 nM to about 250 nM, about 5 nM to about 240 nM, about 5 nM to about 230 nM, about 5 nM to about 220 nM, about 5 nM to about 210 nM, about 5 nM to about 200 nM, about 5 nM to about 190 nM, about 5 nM to about 180 nM, about 5 nM to about 170 nM, about 5 nM to about 160 nM, about 5 nM to about 150 nM, about 5 nM to about 140 nM, about 5 nM to about 130 nM, about 5 nM to about 120 nM, about 5 nM to about 110 nM, about 5 nM to about 100 nM, about 5 nM to about 95 nM, about 5 nM to about 90 nM, about 5 nM to about 85 nM, about 5 nM to about 80 nM, about 5 nM to about 75 nM, about 5 nM to about 70 nM, about 5 nM to about 65 nM, about 5 nM to about 60 nM, about 5 nM to about 55 nM, about 5 nM to about 50 nM, about 5 nM to about 45 nM, about 5 nM to about 40 nM, about 5 nM to about 35 nM, about 5 nM to about 30 nM, about 5 nM to about 25 nM, about 5 nM to about 20 nM, about 5 nM to about 15 nM, about 5 nM to about 10 nM, about 10 nM to about 5 µM, about 10 nM to about 2 µM, about 10 nM to about 1 µM, about 10 nM to about 500 nM, about 10 nM to about 250 nM, about 10 nM to about 240 nM, about 10 nM to about 230 nM, about 10 nM to about 220 nM, about 10 nM to about 210 nM, about 10 nM to about 200 nM, about 10 nM to about 190 nM, about 10 nM to about 180 nM, about 10 nM to about 170 nM, about 10 nM to about 160 nM, about 10 nM to about 150 nM, about 10 nM to about 140 nM, about 10 nM to about 130 nM, about 10 nM to about 120 nM, about 10 nM to about 110 nM, about 10 nM to about 100 nM, about 10 nM to about 95 nM, about 10 nM to about 90 nM, about 10 nM to about 85 nM, about 10 nM to about 80 nM, about 10 nM to about 75 nM, about 10 nM to about 70 nM, about 10 nM to about 65 nM, about 10 nM to about 60 nM, about 10 nM to about 55 nM, about 10 nM to about 50 nM, about 10 nM to about 45 nM, about 10 nM to about 40 nM, about 10 nM to about 35 nM, about 10 nM to about 30 nM, about 10 nM to about 25 nM, about 10 nM to about 20 nM, about 10 nM to about 15 nM, about 15 nM to about 5 µM, about 15 nM to about 2 µM, about 15 nM to about 1 µM, about 15 nM to about 500 nM, about 15 nM to about 250 nM, about 15 nM to about 240 nM, about 15 nM to about 230 nM, about 15 nM to about 220 nM, about 15 nM to about 210 nM, about 15 nM to about 200 nM, about 15 nM to about 190 nM, about 15 nM to about 180 nM, about 15 nM to about 170 nM, about 15 nM to about 160 nM, about 15 nM to about 150 nM, about 15 nM to about 140 nM, about 15 nM to about 130 nM, about 15 nM to about 120 nM, about 15 nM to about 110 nM, about 15 nM to about 100 nM, about 15 nM to about 95 nM, about 15 nM to about 90 nM, about 15 nM to about 85 nM, about 15 nM to about 80 nM, about 15 nM to about 75 nM, about 15 nM to about 70 nM, about 15 nM to about 65 nM, about 15 nM to about 60 nM, about 15 nM to about 55 nM, about 15 nM to about 50 nM, about 15 nM to about 45 nM, about 15 nM to about 40 nM, about 15 nM to about 35 nM, about 15 nM to about 30 nM, about 15 nM to about 25 nM, about 15 nM to about 20 nM, about 20 nM to about 5 µM, about 20 nM to about 2 µM, about 20 nM to about 1 µM, about 20 nM to about 500 nM, about 20 nM to about 250 nM, about 20 nM to about 240 nM, about 20 nM to about 230 nM, about 20 nM to about 220 nM, about 20 nM to about 210 nM, about 20 nM to about 200 nM, about 20 nM to about 190 nM, about 20 nM to about 180 nM, about 20 nM to about 170 nM, about 20 nM to about 160 nM, about 20 nM to about 150 nM, about 20 nM to about 140 nM, about 20 nM to about 130 nM, about 20 nM to about 120 nM, about 20 nM to about 110 DM, about 20 nM to about 100 nM, about 20 nM to about 95 nM, about 20 nM to about 90 nM, about 20 nM to about 85 nM, about 20 nM to about 80 nM, about 20 nM to about 75 nM, about 20 nM to about 70 nM, about 20 nM to about 65 nM, about 20 nM to about 60 nM, about 20 nM to about 55 nM, about 20 nM to about 50 nM, about 20 nM to about 45 nM, about 20 nM to about 40 nM, about 20 nM to about 35 nM, about 20 nM to about 30 nM, about 20 nM to about 25 nM, about 25 nM to about 5 µM, about 25 nM to about 2 µM, about 25 nM to about 1 µM, about 25 nM to about 500 nM, about 25 nM to about 250 nM, about 25 nM to about 240 nM, about 25 nM to about 230 nM, about 25 nM to about 220 nM, about 25 nM to about 210 nM, about 25 nM to about 200 nM, about 25 nM to about 190 nM, about 25 nM to about 180 nM, about 25 nM to about 170 nM, about 25 nM to about 160 nM, about 25 nM to about 150 nM, about 25 nM to about 140 nM, about 25 nM to about 130 nM, about 25 nM to about 120 nM, about 25 nM to about 110 nM, about 25 nM to about 100 nM, about 25 nM to about 95 nM, about 25 nM to about 90 nM, about 25 nM to about 85 nM, about 25 nM to about 80 nM, about 25 nM to about 75 nM, about 25 nM to about 70 nM, about 25 nM to about 65 nM, about 25 nM to about 60 nM, about 25 nM to about 55 nM, about 25 nM to about 50 nM, about 25 nM to about 45 nM, about 25 nM to about 40 nM, about 25 nM to about 35 nM, about 25 nM to about 30 nM, about 30 nM to about 5 µM, about 30 nM to about 2 µM, about 30 nM to about 1 µM, about 30 nM to about 500 nM, about 30 nM to about 250 nM, about 30 nM to about 240 nM, about 30 nM to about 230 nM, about 30 nM to about 220 nM, about 30 nM to about 210 nM, about 30 nM to about 200 nM, about 30 nM to about 190 nM, about 30 nM to about 180 nM, about 30 nM to about 170 nM, about 30 nM to about 160 nM, about 30 nM to about 150 nM, about 30 nM to about 140 nM, about 30 nM to about 130 nM, about 30 nM to about 120 nM, about 30 nM to about 110 nM, about 30 nM to about 100 nM, about 30 nM to about 95 nM, about 30 nM to about 90 nM, about 30 nM to about 85 nM, about 30 nM to about 80 nM, about 30 nM to about 75 nM, about 30 nM to about 70 nM, about 30 nM to about 65 nM, about 30 nM to about 60 nM, about 30 nM to about 55 nM, about 30 nM to about 50 nM, about 30 nM to about 45 nM, about 30 nM to about 40 nM, about 30 nM to about 35 nM, about 40 nM to about 5 μM, about 40 nM to about 2 μM, about 40 nM to about 1 μM, about 40 nM to about 500 nM, about 40 nM to about 250 nM, about 40 nM to about 240 nM, about 40 nM to about 230 nM, about 40 nM to about 220 nM, about 40 nM to about 210 nM, about 40 nM to about 200 nM, about 40 nM to about 190 nM, about 40 nM to about 180 nM, about 40 nM to about 170 nM, about 40 nM to about 160 nM, about 40 nM to about 150 nM, about 40 nM to about 140 nM, about 40 nM to about 130 nM, about 40 nM to about 120 nM, about 40 nM to about 110 nM, about 40 nM to about 100 nM, about 40 nM to about 95 nM, about 40 nM to about 90 nM, about 40 nM to about 85 nM, about 40 nM to about 80 nM, about 40 nM to about 75 nM, about 40 nM to about 70 nM, about 40 nM to about 65 nM, about 40 nM to about 60 nM, about 40 nM to about 55 nM, about 40 nM to about 50 nM, about 40 nM to about 45 nM, about 50 nM to about 5 μM, about 50 nM to about 2 μM, about 50 nM to about 1 μM, about 50 nM to about 500 nM, about 50 nM to about 250 nM, about 50 nM to about 240 nM, about 50 nM to about 230 nM, about 50 nM to about 220 nM, about 50 nM to about 210 nM, about 50 nM to about 200 nM, about 50 nM to about 190 nM, about 50 nM to about 180 nM, about 50 nM to about 170 nM, about 50 nM to about 160 nM, about 50 nM to about 150 nM, about 50 nM to about 140 nM, about 50 nM to about 130 nM, about 50 nM to about 120 nM, about 50 nM to about 110 nM, about 50 nM to about 100 nM, about 50 nM to about 95 nM, about 50 nM to about 90 nM, about 50 nM to about 85 nM, about 50 nM to about 80 nM, about 50 nM to about 75 nM, about 50 nM to about 70 nM, about 50 nM to about 65 nM, about 50 nM to about 60 nM, about 50 nM to about 55 nM, about 60 nM to about 5 μM, about 60 nM to about 2 μM, about 60 nM to about 1 μM, about 60 nM to about 500 nM, about 60 nM to about 250 nM, about 60 nM to about 240 nM, about 60 nM to about 230 nM, about 60 nM to about 220 nM, about 60 nM to about 210 nM, about 60 nM to about 200 nM, about 60 nM to about 190 nM, about 60 nM to about 180 nM, about 60 nM to about 170 nM, about 60 nM to about 160 nM, about 60 nM to about 150 nM, about 60 nM to about 140 nM, about 60 nM to about 130 nM, about 60 nM to about 120 nM, about 60 nM to about 110 nM, about 60 nM to about 100 nM, about 60 nM to about 95 nM, about 60 nM to about 90 nM, about 60 nM to about 85 nM, about 60 nM to about 80 nM, about 60 nM to about 75 nM, about 60 nM to about 70 nM, about 60 nM to about 65 nM, about 70 nM to about 5 μM, about 70 nM to about 2 μM, about 70 nM to about 1 μM, about 70 nM to about 500 nM, about 70 nM to about 250 nM, about 70 nM to about 240 nM, about 70 nM to about 230 nM, about 70 nM to about 220 nM, about 70 nM to about 210 nM, about 70 nM to about 200 nM, about 70 nM to about 190 nM, about 70 nM to about 180 nM, about 70 nM to about 170 nM, about 70 nM to about 160 nM, about 70 nM to about 150 nM, about 70 nM to about 140 nM, about 70 nM to about 130 nM, about 70 nM to about 120 nM, about 70 nM to about 110 nM, about 70 nM to about 100 nM, about 70 nM to about 95 nM, about 70 nM to about 90 nM, about 70 nM to about 85 nM, about 70 nM to about 80 nM, about 70 nM to about 75 nM, about 80 nM to about 5 μM, about 80 nM to about 2 μM, about 80 nM to about 1 μM, about 80 nM to about 500 nM, about 80 nM to about 250 nM, about 80 nM to about 240 nM, about 80 nM to about 230 nM, about 80 nM to about 220 nM, about 80 nM to about 210 nM, about 80 nM to about 200 nM, about 80 nM to about 190 nM, about 80 nM to about 180 nM, about 80 nM to about 170 nM, about 80 nM to about 160 nM, about 80 nM to about 150 nM, about 80 nM to about 140 nM, about 80 nM to about 130 nM, about 80 nM to about 120 nM, about 80 nM to about 110 nM, about 80 nM to about 100 nM, about 80 nM to about 95 nM, about 80 nM to about 90 nM, about 80 nM to about 85 nM, about 90 nM to about 5 μM, about 90 nM to about 2 μM, about 90 mM to about 1 μM, about 90 nM to about 500 nM, about 90 nM to about 250 nM, about 90 nM to about 240 nM, about 90 nM to about 230 nM, about 90 nM to about 220 nM, about 90 nM to about 210 nM, about 90 nM to about 200 nM, about 90 nM to about 190 nM, about 90 nM to about 180 nM, about 90 nM to about 170 nM, about 90 nM to about 160 nM, about 90 nM to about 150 nM, about 90 nM to about 140 nM, about 90 nM to about 130 nM, about 90 nM to about 120 nM, about 90 nM to about 110 nM, about 90 nM to about 100 nM, about 90 nM to about 95 nM, about 100 nM to about 5 μM, about 100 nM to about 2 μM, about 100 nM to about 1 μM, about 100 nM to about 500 nM, about 100 nM to about 250 nM, about 100 nM to about 240 nM, about 100 nM to about 230 nM, about 100 nM to about 220 nM, about 100 nM to about 210 nM, about 100 nM to about 200 nM, about 100 nM to about 190 nM, about 100 nM to about 180 nM, about 100 nM to about 170 nM, about 100 nM to about 160 nM, about 100 nM to about 150 nM, about 100 nM to about 140 nM, about 100 nM to about 130 nM, about 100 nM to about 120 nM, about 100 nM to about 110 nM, about 110 nM to about 5 μM, about 110 nM to about 2 μM, about 110 nM to about 1 μM, about 110 nM to about 500 nM, about 110 nM to about 250 nM, about 110 nM to about 240 nM, about 110 nM to about 230 nM, about 110 nM to about 220 nM, about 110 nM to about 210 nM, about 110 nM to about 200 nM, about 110 nM to about 190 nM, about 110 nM to about 180 nM, about 110 nM to about 170 nM, about 110 nM to about 160 nM, about 110 nM to about 150 nM, about 110 nM to about 140 nM, about 110 nM to about 130 nM, about 110 nM to about 120 nM, about 120 nM to about 5 μM, about 120 nM to about 2 μM, about 120 nM to about 1 μM, about 120 nM to about 500 nM, about 120 nM to about 250 nM, about 120 nM to about 240 nM, about 120 nM to about 230 nM, about 120 nM to about 220 nM, about 120 nM to about 210 nM, about 120 nM to about 200 nM, about 120 nM to about 190 nM, about 120 nM to about 180 nM, about 120 nM to about 170 nM, about 120 nM to about 160 nM, about 120 nM to about 150 nM, about 120 nM to about 140 nM, about 120 nM to about 130 nM, about 130 nM to about 5 μM, about 130 nM to about 2 μM, about 130 nM to about 1 μM, about 130 nM to about 500 nM, about 130 nM to about 250 nM, about 130 nM to about 240 nM, about 130 nM to about 230 nM, about 130 nM to about 220 nM, about 130 nM to about 210 nM, about 130 nM to about 200 nM, about 130 nM to about 190 nM, about 130 nM to about 180 nM, about 130 nM to about 170 nM, about 130 nM to about 160 nM, about 130 nM to about 150 nM, about 130 nM to about 140 nM, about 140 nM to about 5 μM, about 140 nM to about 2 μM, about 140 nM to about 1 μM, about 140 nM to about 500 nM, about 140 nM to about 250 nM, about 140 nM to about 240 nM, about 140 nM to about 230 nM, about 140 nM to about 220 nM, about 140 nM to about 210 nM, about 140 nM to about 200 nM, about 140 nM to about 190 nM, about 140 nM to about 180 nM, about 140 nM to about 170 nM, about 140 nM to about 160 nM, about 140 nM to about 150 nM, about 150 nM to about 5 μM, about 150 nM to about 2 μM, about 150 nM to about 1 μM, about 150 nM to about 500 nM, about 150 nM to about 250 nM, about 150 nM to about 240 nM, about 150 nM to about 230 nM, about 150 nM to about 220 nM, about 150 nM to about 210 nM, about 150 nM to about 200 nM, about 150 nM to about 190 nM, about 150 nM to about 180 nM, about 150 nM to about 170 nM, about 150 nM to about 160 nM, about 160 nM to about 5 µM, about 160 nM to about 2 µM, about 160 nM to about 1 µM, about 160 nM to about 500 nM, about 160 nM to about 250 nM, about 160 nM to about 240 nM, about 160 nM to about 230 nM, about 160 nM to about 220 nM, about 160 nM to about 210 nM, about 160 nM to about 200 nM, about 160 nM to about 190 nM, about 160 nM to about 180 nM, about 160 nM to about 170 nM, about 170 nM to about 5 µM, about 170 nM to about 2 µM, about 170 nM to about 1 µM, about 170 nM to about 500 nM, about 170 nM to about 250 nM, about 170 nM to about 240 nM, about 170 nM to about 230 nM, about 170 nM to about 220 nM, about 170 nM to about 210 nM, about 170 nM to about 200 nM, about 170 nM to about 190 nM, about 170 nM to about 180 nM, about 180 nM to about 5 µM, about 180 nM to about 2 µM, about 180 nM to about 1 µM, about 180 nM to about 500 nM, about 180 nM to about 250 nM, about 180 nM to about 240 nM, about 180 nM to about 230 nM, about 180 nM to about 220 nM, about 180 nM to about 210 nM, about 180 nM to about 200 nM, about 180 nM to about 190 nM, about 190 nM to about 5 µM, about 190 nM to about 2 µM, about 190 nM to about 1 µM, about 190 nM to about 500 nM, about 190 nM to about 250 nM, about 190 nM to about 240 nM, about 190 nM to about 230 nM, about 190 nM to about 220 nM, about 190 nM to about 210 nM, about 190 nM to about 200 nM, about 200 nM to about 5 µM, about 200 nM to about 2 µM, about 200 nM to about 1 µM, about 200 nM to about 500 nM, about 200 nM to about 250 nM, about 200 nM to about 240 nM, about 200 nM to about 230 nM, about 200 nM to about 220 nM, about 200 nM to about 210 nM, about 210 nM to about 5 µM, about 210 nM to about 2 µM, about 210 nM to about 1 pM, about 210 nM to about 500 nM, about 210 nM to about 250 nM, about 210 nM to about 240 nM, about 210 nM to about 230 nM, about 210 nM to about 220 nM, about 220 nM to about 5 µM, about 220 nM to about 2 µM, about 220 nM to about 1 µM, about 220 nM to about 500 nM, about 220 nM to about 250 nM, about 220 nM to about 240 nM, about 220 nM to about 230 nM, about 230 nM to about 5 µM, about 230 nM to about 2 µM, about 230 nM to about 1 µM, about 230 nM to about 500 nM, about 230 nM to about 250 nM, about 230 nM to about 240 nM, about 240 nM to about 5 µM, about 240 nM to about 2 µM, about 240 nM to about 1 µM, about 240 nM to about 500 nM, about 240 nM to about 250 nM, about 250 nM to about 5 µM, about 250 nM to about 2 µM, about 250 nM to about 1 µM, about 250 nM to about 500 nM, about 500 nM to about 5 µM, about 500 nM to about 2 µM, about 500 nM to about 1 µM, about 1 µM to about 5 µM, about 1 µM to about 2 µM, or about 2 µM to about 5 µM).

In some embodiments of any of the ABPCs described herein, the $K_D$ of the first antigen-binding domain (and optionally, the second antigen-binding domain, if present) at a pH of about 4.0 to about 6.5 (e.g., any of the subranges of this range described herein) can be greater than 1 nM (e.g., between about 1 nM to about 1 mM, about 1 nM to about 900 µM, about 1 nM to about 800 µM, about 1 nM to about 700 µM, about 1 nM to about 600 µM, about 1 nM to about 500 µM, about 1 nM to about 400 µM, about 1 nM to about 300 µM, about 1 nM to about 200 µM, about 1 nM to about 100 µM, about 1 nM to about 90 µM, about 1 nM to about 80 µM, about 1 nM to about 70 µM, about 1 nM to about 60 µM, about 1 nM to about 50 µM, about 1 nM to about 40 µM, about 1 nM to about 30 µM, about 1 nM to about 20 µM, about 1 nM to about 10 µM, about 1 nM to about 5 µM, about 1 nM to about 4 µM, about 1 nM to about 2 µM, about 1 nM to about 1 µM, about 1 nM to about 900 nM, about 1 nM to about 800 nM, about 1 nM to about 700 nM, about 1 nM to about 600 nM, about 1 nM to about 500 nM, about 1 nM to about 400 nM, about 1 nM to about 300 nM, about 1 nM to about 200 nM, about 1 nM to about 100 nM, about 1 nM to about 90 nM, about 1 nM to about 80 nM, about 1 nM to about 70 nM, about 1 nM to about 60 nM, about 1 nM to about 50 nM, about 1 nM to about 40 nM, about 1 nM to about 30 nM, about 2 nM to about 1 mM, about 2 nM to about 900 µM, about 2 nM to about 800 µM, about 2 nM to about 700 µM, about 2 nM to about 600 µM, about 2 nM to about 500 µM, about 2 nM to about 400 µM, about 2 nM to about 300 µM, about 2 nM to about 200 µM, about 2 nM to about 100 µM, about 2 nM to about 90 µM, about 2 nM to about 80 µM, about 2 nM to about 70 µM, about 2 nM to about 60 µM, about 2 nM to about 50 µM, about 2 nM to about 40 µM, about 2 nM to about 30 µM, about 2 nM to about 20 µM, about 2 nM to about 10 µM, about 2 nM to about 5 µM, about 2 nM to about 4 µM, about 2 nM to about 2 µM, about 2 nM to about 1 µM, about 2 nM to about 900 nM, about 2 nM to about 800 nM, about 2 nM to about 700 nM, about 2 nM to about 600 nM, about 2 nM to about 500 nM, about 2 nM to about 400 nM, about 2 nM to about 300 nM, about 2 nM to about 200 nM, about 2 nM to about 100 nM, about 2 nM to about 90 nM, about 2 nM to about 80 nM, about 2 nM to about 70 nM, about 2 nM to about 60 nM, about 2 nM to about 50 nM, about 2 nM to about 40 nM, about 2 nM to about 30 nM, about 5 nM to about 1 mM, about 5 nM to about 900 µM, about 5 nM to about 800 µM, about 5 nM to about 700 µM, about 5 nM to about 600 µM, about 5 nM to about 500 µM, about 5 nM to about 400 µM, about 5 nM to about 300 µM, about 5 nM to about 200 µM, about 5 nM to about 100 µM, about 5 nM to about 90 µM, about 5 nM to about 80 µM, about 5 nM to about 70 µM, about 5 nM to about 60 µM, about 5 nM to about 50 µM, about 5 nM to about 40 µM, about 5 nM to about 30 µM, about 5 nM to about 20 µM, about 5 nM to about 10 µM, about 5 nM to about 5 µM, about 5 nM to about 4 µM, about 5 nM to about 2 µM, about 5 nM to about 1 µM, about 5 nM to about 900 nM, about 5 nM to about 800 nM, about 5 nM to about 700 nM, about 5 nM to about 600 nM, about 5 nM to about 500 nM, about 5 nM to about 400 nM, about 5 nM to about 300 nM, about 5 nM to about 200 nM, about 5 nM to about 100 nM, about 5 nM to about 90 nM, about 5 nM to about 80 nM, about 5 nM to about 70 nM, about 5 nM to about 60 nM, about 5 nM to about 50 nM, about 5 nM to about 40 nM, about 5 nM to about 30 nM, about 10 nM to about 1 mM, about 10 nM to about 900 µM, about 10 nM to about 800 µM, about 10 nM to about 700 µM, about 10 nM to about 600 µM, about 10 nM to about 500 µM, about 10 nM to about 400 µM, about 10 nM to about 300 µM, about 10 nM to about 200 µM, about 10 nM to about 100 µM, about 10 nM to about 90 µM, about 10 nM to about 80 µM, about 10 nM to about 70 µM, about 10 nM to about 60 µM, about 10 nM to about 50 µM, about 10 nM to about 40 µM, about 10 nM to about 30 µM, about 10 nM to about 20 µM, about 10 nM to about 10 µM, about 10 nM to about 5 µM, about 10 nM to about 4 µM, about 10 nM to about 2 µM, about 10 nM to about 1 µM, about 10 nM to about 900 nM, about 10 nM to about 800 nM, about 10 nM to about 700 nM, about 10 nM to about 600 nM, about 10 nM to about 500 nM, about 10 nM to about 400 nM, about 10 nM to about 300 nM, about 10 nM to about 200 nM, about 10 nM to about 100 nM, about 10 nM to about 90 nM, about 10 nM to about 80 nM, about 10 nM to about 70 nM, about 10 nM to about 60 nM, about 10 nM to about 50 nM, about 10 nM to about 40 nM, about 10 nM to about 30 nM, about 20 nM to about 1 mM, about 20 nM to about 900 μM, about 20 nM to about 800 μM, about 20 nM to about 700 μM, about 20 nM to about 600 μM, about 20 nM to about 500 μM, about 20 nM to about 400 μM, about 20 nM to about 300 μM, about 20 nM to about 200 μM, about 20 nM to about 100 μM, about 20 nM to about 90 μM, about 20 nM to about 80 μM, about 20 nM to about 70 μM, about 20 nM to about 60 μM, about 20 nM to about 50 μM, about 20 nM to about 40 μM, about 20 nM to about 30 μM, about 20 nM to about 20 μM, about 20 nM to about 10 μM, about 20 nM to about 5 μM, about 20 nM to about 4 μM, about 20 nM to about 2 μM, about 20 nM to about 1 μM, about 20 nM to about 900 nM, about 20 nM to about 800 nM, about 20 nM to about 700 nM, about 20 nM to about 600 nM, about 20 nM to about 500 nM, about 20 nM to about 400 nM, about 20 nM to about 300 nM, about 20 nM to about 200 nM, about 20 nM to about 100 nM, about 20 nM to about 90 nM, about 20 nM to about 80 nM, about 20 nM to about 70 nM, about 20 nM to about 60 nM, about 20 nM to about 50 nM, about 20 nM to about 40 nM, about 20 nM to about 30 nM; about 1 μM to about 1 mM, about 1 μM to about 900 μM, about 1 μM to about 800 μM, about 1 μM to about 700 μM, about 1 μM to about 600 μM, about 1 μM to about 500 μM, about 1 μM to about 400 μM, about 1 μM to about 300 μM, about 1 μM to about 200 μM, about 1 μM to about 100 μM, about 1 μM to about 90 μM, about 1 μM to about 80 μM, about 1 μM to about 70 μM, about 1 μM to about 60 μM, about 1 μM to about 50 μM, about 1 μM to about 40 μM, about 1 μM to about 30 μM, about 1 μM to about 20 μM, about 1 μM to about 10 μM, about 1 μM to about 5 μM, about 1 μM to about 4 μM, about 1 μM to about 3 μM, about 1 μM to about 2 μM, about 2 μM to about 1 mM, about 2 μM to about 900 μM, about 2 μM to about 800 μM, about 2 μM to about 700 μM, about 2 μM to about 600 μM, about 2 μM to about 500 μM, about 2 μM to about 400 μM, about 2 μM to about 300 μM, about 2 μM to about 200 μM, about 2 μM to about 100 μM, about 2 μM to about 90 μM, about 2 μM to about 80 μM, about 2 μM to about 70 μM, about 2 μM to about 60 μM, about 2 μM to about 50 μM, about 2 μM to about 40 μM, about 2 μM to about 30 μM, about 2 μM to about 20 μM, about 2 μM to about 10 μM, about 2 μM to about 5 μM, about 2 μM to about 4 μM, about 2 μM to about 3 μM, about 5 μM to about 1 mM, about 5 μM to about 900 μM, about 5 μM to about 800 μM, about 5 μM to about 700 μM, about 5 μM to about 600 μM, about 5 μM to about 500 μM, about 5 μM to about 400 μM, about 5 μM to about 300 μM, about 5 μM to about 200 μM, about 5 μM to about 100 μM, about 5 μM to about 90 μM, about 5 μM to about 80 μM, about 5 μM to about 70 μM, about 5 μM to about 60 μM, about 5 μM to about 50 μM, about 5 μM to about 40 μM, about 30 μM to about 5 μM, about 5 μM to about 20 μM, about 5 μM to about 10 μM, about 10 μM to about 1 mM, about 10 μM to about 900 μM, about 10 μM to about 800 μM, about 10 μM to about 700 μM, about 10 μM to about 600 μM, about 10 μM to about 500 μM, about 10 μM to about 400 μM, about 10 μM to about 300 μM, about 10 μM to about 200 μM, about 10 μM to about 100 μM, about 10 μM to about 90 μM, about 10 μM to about 80 μM, about 10 μM to about 70 μM, about 10 μM to about 60 μM, about 10 μM to about 50 μM, about 10 μM to about 40 μM, about 10 μM to about 30 μM, about 10 μM to about 20 μM, about 20 μM to about 1 mM, about 20 μM to about 900 μM, about 20 μM to about 800 μM, about 20 μM to about 700 μM, about 20 μM to about 600 μM, about 20 μM to about 500 μM, about 20 μM to about 400 μM, about 20 μM to about 300 μM, about 20 μM to about 200 μM, about 20 μM to about 100 μM, about 20 μM to about 90 μM, about 20 μM to about 80 μM, about 20 μM to about 70 μM, about 20 μM to about 60 μM, about 20 μM to about 50 μM, about 20 μM to about 40 μM, about 20 μM to about 30 μM, about 30 μM to about 1 mM, about 30 μM to about 900 μM, about 30 μM to about 800 μM, about 30 μM to about 700 μM, about 30 μM to about 600 μM, about 30 μM to about 500 μM, about 30 μM to about 400 μM, about 30 μM to about 300 μM, about 30 μM to about 200 μM, about 30 μM to about 100 μM, about 30 μM to about 90 μM, about 30 μM to about 80 μM, about 30 μM to about 70 μM, about 30 μM to about 60 μM, about 30 μM to about 50 μM, about 30 μM to about 40 μM, about 40 μM to about 1 mM, about 40 μM to about 900 μM, about 40 μM to about 800 μM, about 40 μM to about 700 μM, about 40 μM to about 600 μM, about 40 μM to about 500 μM, about 40 μM to about 400 μM, about 40 μM to about 300 μM, about 40 μM to about 200 μM, about 40 μM to about 100 μM, about 40 μM to about 90 μM, about 40 μM to about 80 μM, about 40 μM to about 70 μM, about 40 μM to about 60 μM, about 40 μM to about 50 μM, about 50 μM to about 1 mM, about 50 μM to about 900 μM, about 50 μM to about 800 μM, about 50 μM to about 700 μM, about 50 μM to about 600 μM, about 50 μM to about 500 μM, about 50 μM to about 400 μM, about 50 μM to about 300 μM, about 50 μM to about 200 μM, about 50 μM to about 100 μM, about 50 μM to about 90 μM, about 50 μM to about 80 μM, about 50 μM to about 70 μM, about 50 μM to about 60 μM, about 60 μM to about 1 mM, about 60 μM to about 900 μM, about 60 μM to about 800 μM, about 60 μM to about 700 μM, about 60 μM to about 600 μM, about 60 μM to about 500 μM, about 60 μM to about 400 μM, about 60 μM to about 300 μM, about 60 μM to about 200 μM, about 60 μM to about 100 μM, about 60 μM to about 90 μM, about 60 μM to about 80 μM, about 60 μM to about 70 μM, about 70 μM to about 1 mM, about 70 μM to about 900 μM, about 70 μM to about 800 μM, about 70 μM to about 700 μM, about 70 μM to about 600 μM, about 70 μM to about 500 μM, about 70 μM to about 400 μM, about 70 μM to about 300 μM, about 70 μM to about 200 μM, about 70 μM to about 100 μM, about 70 μM to about 90 μM, about 70 μM to about 80 μM, about 80 μM to about 1 mM, about 80 μM to about 900 μM, about 80 μM to about 800 μM, about 80 μM to about 700 μM, about 80 μM to about 600 μM, about 80 μM to about 500 μM, about 80 μM to about 400 μM, about 80 μM to about 300 μM, about 80 μM to about 200 μM, about 80 μM to about 100 μM, about 80 μM to about 90 μM, about 90 μM to about 1 mM, about 90 μM to about 900 μM, about 90 μM to about 800 μM, about 90 μM to about 700 μM, about 90 μM to about 600 μM, about 90 μM to about 500 μM, about 90 μM to about 400 μM, about 90 μM to about 300 μM, about 90 μM to about 200 μM, about 90 μM to about 100 μM, about 100 μM to about 1 mM, about 100 μM to about 900 μM, about 100 μM to about 800 μM, about 100 μM to about 700 μM, about 100 μM to about 600 μM, about 100 μM to about 500 μM, about 100 μM to about 400 μM, about 100 μM to about 300 μM, about 100 μM to about 200 μM, about 200 μM to about 1 mM, about 200 μM to about 900 μM, about 200 μM to about 800 μM, about 200 μM to about 700 μM, about 200 μM to about 600 μM, about 200 μM to about 500 μM, about 200 μM to about 400 μM, about 200 μM to about 300 μM, about 300 μM to about 1 mM, about 300 μM to about 900 μM, about 300 μM to about 800 μM, about 300 μM to about 700 μM, about 300 μM to about 600 μM, about 300 μM to about 500 μM, about 300 μM to about 400 μM, about 400 μM to about 1 mM, about 400 μM to about 900 μM, about 400 μM to about 800 μM, about 400

µM to about 700 µM, about 400 µM to about 600 µM, about 400 µM to about 500 µM, about 500 µM to about 1 mM, about 500 µM to about 900 µM, about 500 µM to about 800 µM, about 500 µM to about 700 µM, about 500 µM to about 600 µM, about 600 µM to about 1 mM, about 600 µM to about 900 µM, about 600 µM to about 800 µM, about 600 µM to about 700 µM, about 700 µM to about 1 mM, about 700 µM to about 900 µM, about 700 µM to about 800 µM, about 800 µM to about 1 mM, about 800 µM to about 900 µM, or about 900 µM to about 1 mM).

A variety of different methods known in the art can be used to determine the $K_D$ values of any of the antigen-binding protein constructs described herein (e.g., an electrophoretic mobility shift assay, a filter binding assay, surface plasmon resonance, a biomolecular binding kinetics assay, in vitro binding assay on antigen-expressing cells, etc.).

In some examples of any of the ABPCs described herein, the half-life of the ABPC in vivo is decreased (e.g., a detectable decrease) (e.g., at least a 1% decrease, at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease, or about a 1% decrease to about a 99% decrease, about a 1% decrease to about a 95% decrease, about a 1% decrease to about a 90% decrease, about a 1% decrease to about a 85% decrease, about a 1% decrease to about a 80% decrease, about a 1% decrease to about a 75% decrease, about a 1% decrease to about a 70% decrease, about a 1% decrease to about a 65% decrease, about a 1% decrease to about a 60% decrease, about a 1% decrease to about a 55% decrease, about a 1% decrease to about a 50% decrease, about a 1% decrease to about a 45% decrease, about a 1% decrease to about a 40% decrease, about a 1% decrease to about a 35% decrease, about a 1% decrease to about a 30% decrease, about a 1% decrease to about a 25% decrease, about a 1% decrease to about a 20% decrease, about a 1% decrease to about a 15% decrease, about a 1% decrease to about a 10% decrease, about a 1% decrease to about a 5% decrease, about a 5% decrease to about a 99% decrease, about a 5% decrease to about a 95% decrease, about a 5% decrease to about a 90% decrease, about a 5% decrease to about a 85% decrease, about a 5% decrease to about a 80% decrease, about a 5% decrease to about a 75% decrease, about a 5% decrease to about a 70% decrease, about a 5% decrease to about a 65% decrease, about a 5% decrease to about a 60% decrease, about a 5% decrease to about a 55% decrease, about a 5% decrease to about a 50% decrease, about a 5% decrease to about a 45% decrease, about a 5% decrease to about a 40% decrease, about a 5% decrease to about a 35% decrease, about a 5% decrease to about a 30% decrease, about a 5% decrease to about a 25% decrease, about a 5% decrease to about a 20% decrease, about a 5% decrease to about a 15% decrease, about a 5% decrease to about a 10% decrease, about a 10% decrease to about a 99% decrease, about a 10% decrease to about a 95% decrease, about a 10% decrease to about a 90% decrease, about a 10% decrease to about a 85% decrease, about a 10% decrease to about a 80% decrease, about a 10% decrease to about a 75% decrease, about a 10% decrease to about a 70% decrease, about a 10% decrease to about a 65% decrease, about a 10% decrease to about a 60% decrease, about a 10% decrease to about a 55% decrease, about a 10% decrease to about a 50% decrease, about a 10% decrease to about a 45% decrease, about a 10% decrease to about a 40% decrease, about a 10% decrease to about a 35% decrease, about a 10% decrease to about a 30% decrease, about a 10% decrease to about a 25% decrease, about a 10% decrease to about a 20% decrease, about a 10% decrease to about a 15% decrease, about a 15% decrease to about a 99% decrease, about a 15% decrease to about a 95% decrease, about a 15% decrease to about a 90% decrease, about a 15% decrease to about a 85% decrease, about a 15% decrease to about a 80% decrease, about a 15% decrease to about a 75% decrease, about a 15% decrease to about a 70% decrease, about a 15% decrease to about a 65% decrease, about a 15% decrease to about a 60% decrease, about a 15% decrease to about a 55% decrease, about a 15% decrease to about a 50% decrease, about a 15% decrease to about a 45% decrease, about a 15% decrease to about a 40% decrease, about a 15% decrease to about a 35% decrease, about a 15% decrease to about a 30% decrease, about a 15% decrease to about a 25% decrease, about a 15% decrease to about a 20% decrease, about a 20% decrease to about a 99% decrease, about a 20% decrease to about a 95% decrease, about a 20% decrease to about a 90% decrease, about a 20% decrease to about a 85% decrease, about a 20% decrease to about a 80% decrease, about a 20% decrease to about a 75% decrease, about a 20% decrease to about a 70% decrease, about a 20% decrease to about a 65% decrease, about a 20% decrease to about a 60% decrease, about a 20% decrease to about a 55% decrease, about a 20% decrease to about a 50% decrease, about a 20% decrease to about a 45% decrease, about a 20% decrease to about a 40% decrease, about a 20% decrease to about a 35% decrease, about a 20% decrease to about a 30% decrease, about a 20% decrease to about a 25% decrease, about a 25% decrease to about a 99% decrease, about a 25% decrease to about a 95% decrease, about a 25% decrease to about a 90% decrease, about a 25% decrease to about a 85% decrease, about a 25% decrease to about a 80% decrease, about a 25% decrease to about a 75% decrease, about a 25% decrease to about a 70% decrease, about a 25% decrease to about a 65% decrease, about a 25% decrease to about a 60% decrease, about a 25% decrease to about a 55% decrease, about a 25% decrease to about a 50% decrease, about a 25% decrease to about a 45% decrease, about a 25% decrease to about a 40% decrease, about a 25% decrease to about a 35% decrease, about a 25% decrease to about a 30% decrease, about a 30% decrease to about a 99% decrease, about a 30% decrease to about a 95% decrease, about a 30% decrease to about a 90% decrease, about a 30% decrease to about a 85% decrease, about a 30% decrease to about a 80% decrease, about a 30% decrease to about a 75% decrease, about a 30% decrease to about a 70% decrease, about a 30% decrease to about a 65% decrease, about a 30% decrease to about a 60% decrease, about a 30% decrease to about a 55% decrease, about a 30% decrease to about a 50% decrease, about a 30% decrease to about a 45% decrease, about a 30% decrease to about a 40% decrease, about a 30% decrease to about a 35% decrease, about a 35% decrease to about a 99% decrease, about a 35% decrease to about a 95% decrease, about a 35% decrease to about a 90% decrease, about a 35% decrease to about a 85% decrease, about a 35% decrease to about a 80% decrease, about a 35% decrease to about a 75% decrease, about a 35% decrease to about a 70% decrease, about a 35% decrease to about a 65% decrease, about a 35% decrease to about a 60% decrease, about a 35% decrease to about a 55% decrease, about a 35% decrease to about a 50% decrease, about a 35% decrease to about a 45% decrease, about a 35% decrease to about a 40% decrease, about a 40% decrease to about a 99% decrease, about a 40% decrease to about a 95% decrease, about a 40% decrease to about a 90% decrease, about a 40% decrease to about a 85% decrease, about a 40% decrease to about a 80% decrease, about a 40% decrease to about a 75% decrease, about a 40% decrease to about a 70% decrease, about a 40% decrease to about a 65% decrease, about a 40% decrease to about a 60% decrease, about a 40% decrease to about a 55% decrease, about a 40% decrease to about a 50% decrease, about a 40% decrease to about a 45% decrease, about a 45% decrease to about a 99% decrease, about a 45% decrease to about a 95% decrease, about a 45% decrease to about a 90% decrease, about a 45% decrease to about a 85% decrease, about a 45% decrease to about a 80% decrease, about a 45% decrease to about a 75% decrease, about a 45% decrease to about a 70% decrease, about a 45% decrease to about a 65% decrease, about a 45% decrease to about a 60% decrease, about a 45% decrease to about a 55% decrease, about a 45% decrease to about a 50% decrease, about a 50% decrease to about a 99% decrease, about a 50% decrease to about a 95% decrease, about a 50% decrease to about a 90% decrease, about a 50% decrease to about a 85% decrease, about a 50% decrease to about a 80% decrease, about a 50% decrease to about a 75% decrease, about a 50% decrease to about a 70% decrease, about a 50% decrease to about a 65% decrease, about a 50% decrease to about a 60% decrease, about a 50% decrease to about a 55% decrease, about a 55% decrease to about a 99% decrease, about a 55% decrease to about a 95% decrease, about a 55% decrease to about a 90% decrease, about a 55% decrease to about a 85% decrease, about a 55% decrease to about a 80% decrease, about a 55% decrease to about a 75% decrease, about a 55% decrease to about a 70% decrease, about a 55% decrease to about a 65% decrease, about a 55% decrease to about a 60% decrease, about a 60% decrease to about a 99% decrease, about a 60% decrease to about a 95% decrease, about a 60% decrease to about a 90% decrease, about a 60% decrease to about a 85% decrease, about a 60% decrease to about a 80% decrease, about a 60% decrease to about a 75% decrease, about a 60% decrease to about a 70% decrease, about a 60% decrease to about a 65% decrease, about a 65% decrease to about a 99% decrease, about a 65% decrease to about a 95% decrease, about a 65% decrease to about a 90% decrease, about a 65% decrease to about a 85% decrease, about a 65% decrease to about a 80% decrease, about a 65% decrease to about a 75% decrease, about a 65% decrease to about a 70% decrease, about a 70% decrease to about a 99% decrease, about a 70% decrease to about a 95% decrease, about a 70% decrease to about a 90% decrease, about a 70% decrease to about a 85% decrease, about a 70% decrease to about a 80% decrease, about a 70% decrease to about a 75% decrease, about a 75% decrease to about a 99% decrease, about a 75% decrease to about a 95% decrease, about a 75% decrease to about a 90% decrease, about a 75% decrease to about a 85% decrease, about a 75% decrease to about a 80% decrease, about a 80% decrease to about a 99% decrease, about a 80% decrease to about a 95% decrease, about a 80% decrease to about a 90% decrease, about a 80% decrease to about a 85% decrease, about a 85% decrease to about a 99% decrease, about a 85% decrease to about a 95% decrease, about a 85% decrease to about a 90% decrease, about a 90% decrease to about a 99% decrease, about a 90% decrease to about a 95% decrease, or about a 95% decrease to about a 99% decrease) as compared to the half-life of a control ABPC (e.g., any of the exemplary control ABPCs described herein).

Conjugation

In some embodiments, the ABPCs provided herein can be conjugated to a drug (e.g., a chemotherapeutic drug, a small molecule), a toxin, or a radioisotope. Non-limiting examples of drugs, toxins, and radioisotopes (e.g., known to be useful for the treatment of cancer) are known in the art.

In some embodiments, at least one polypeptide of any of the ABPCs described herein is conjugated to the toxin, the radioisotope, or the drug via a cleavable linker. In some embodiments, the cleavable linker includes a protease cleavage site. In some embodiments, the cleavable linker is cleaved on the ABPC once it is transported to the lysosome or late endosome by the target mammalian cell. In some embodiments, cleavage of the linker functionally activates the drug or toxin.

In some embodiments, at least one polypeptide of any of the ABPCs described herein is conjugated to the toxin, the radioisotope, or the drug via a non-cleavable linker. In some embodiments, the conjugated toxin, radioisotope, or drug is released during lysosomal and/or late endosomal degradation of the ABPC.

Non-limiting examples of cleavable linkers include: hydrazone linkers, peptide linkers, disulfide linkers, and thioether linkers. See, e.g., Carter et al., *Cancer J.* 14(3): 154-169, 2008; Sanderson et al., *Clin. Cancer Res.* 11(2 Ptl):843-852, 2005; Chari et al., *Acc. Chem. Res.* 41(1):98-107, 2008; Oflazoglu et al., *Clin. Cancer Res.* 14(19): 6171-6180, 2008; and Lu et al., *Int. J. Mol. Sci.* 17(4): 561, 2016.

Non-limiting examples of non-cleavable linkers include: maleimide alkane-linkers and meleimide cyclohexane linker (MMC) (see, e.g., those described in McCombs et al., *AAPS J.* 17(2):339-351, 2015).

In some embodiments, any of the ABPCs described herein is cytotoxic or cytostatic to the target mammalian cell.

Expression of an Antigen-Binding Protein Construct in a Cell

Also provided herein are methods of generating a recombinant cell that expresses an ABPC (e.g., any of the ABPCs described herein) that include: introducing into a cell a nucleic acid encoding the ABPC to produce a recombinant cell; and culturing the recombinant cell under conditions sufficient for the expression of the ABPC. In some embodiments, the introducing step includes introducing into a cell an expression vector including a nucleic acid encoding the ABPC to produce a recombinant cell.

Any of the ABPCs described herein can be produced by any cell, e.g., a eukaryotic cell or a prokaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. As used herein, the term "prokaryotic cell" refers to a cell that does not have a distinct, membrane-bound nucleus. In some embodiments, the prokaryotic cell is a bacterial cell.

Methods of culturing cells are well known in the art. Cells can be maintained in vitro under conditions that favor proliferation, differentiation, and growth. Briefly, cells can be cultured by contacting a cell (e.g., any cell) with a cell culture medium that includes the necessary growth factors and supplements to support cell viability and growth.

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection.

Provided herein are methods that further include isolation of the ABPCs from a cell (e.g., a eukaryotic cell) using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of Treatment

Provided herein are methods of treating a cancer characterized by having a population of cancer cells that have FOLR1 or an epitope of FOLR1 presented on their surface, that include: administering a therapeutically effective amount of any of the pharmaceutical compositions described herein or any of the ABPCs described herein to a subject identified as having a cancer characterized by having the population of cancer cells.

Also provided herein are methods of reducing the volume of a tumor in a subject, wherein the tumor is characterized by having a population of cancer cells that have FOLR1 or an epitope of FOLR1 presented on their surface, that include: administering a therapeutically effective amount of any of the pharmaceutical compositions described herein or any of the ABPCs described herein to a subject identified as having a cancer characterized by having the population of cancer cells. In some embodiments of any of the methods described herein, the volume of at least one (e.g., 1, 2, 3, 4, or 5) tumor (e.g., solid tumor) or tumor location (e.g., a site of metastasis) is reduced (e.g., a detectable reduction) by at least 1%, at least 2%, at least 3%, at least 4%, at least 5%, at least 6%, at least 8%, at least 10%, at least 12%, at least 14%, at least 16%, at least 18%, at least 20%, at least 22%, at least 24%, at least 26%, at least 28%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) reduced as compared to the size of the at least one tumor (e.g., solid tumor) before administration of the ABPC.

Also provided herein are methods of inducing cell death in a cancer cell in a subject, wherein the cancer cell has FOLR1 or an epitope of FOLR1 presented on its surface, that include: administering a therapeutically effective amount of any of the pharmaceutical compositions of described herein or any of the ABPCs described herein to a subject identified as having a cancer characterized as having the population of cancer cells. In some embodiments, the cell death that is induced is necrosis. In some embodiments, the cell death that is induced is apoptosis.

In some embodiments of any of the methods described herein, the cancer is a primary tumor.

In some embodiments of any of the methods described herein, the cancer is a metastasis.

In some embodiments of any of the methods described herein, the cancer is a non-T-cell-infiltrating tumor. In some embodiments of any of the methods described herein, the cancer is a T-cell-infiltrating tumor.

Provided herein are methods of decreasing the risk of developing a metastasis or decreasing the risk of developing an additional metastasis in a subject having a cancer, wherein the cancer is characterized by having a population of cancer cells that have FOLR1 or an epitope of FOLR1 presented on their surface, that include: administering a therapeutically effective amount of any of the pharmaceutical compositions of described herein or any of the ABPCs described herein to a subject identified as having a cancer characterized as having the population of cancer cells. In some embodiments, the risk of developing a metastasis or the risk of developing an additional metastasis is decreased (e.g., a detectable decrease) by at least 1%, by at least 2%, at least 3%, at least 4%, at least 5%, at least 6%, at least 8%, at least 10%, at least 12%, at least 14%, at least 16%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% in the subject as compared to the risk of a subject having a similar cancer, but administered no treatment or a treatment that does not include the administration of any of the ABPCs described herein.

In some embodiments of any of the methods described herein, the cancer is a non-T-cell-infiltrating tumor. In some embodiments of any of the methods described herein, the cancer is a T-cell-infiltrating tumor. In some embodiments of any of the methods described herein, the cellular compartment is part of the endosomal/lysosomal pathway. In some embodiments of any of the methods described herein, the cellular compartment is an endosome.

The term "subject" refers to any mammal. In some embodiments, the subject or "subject suitable for treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject suitable for treatment" may be a non-human mammal, especially mammals that are conventionally used as models for demonstrating therapeutic efficacy in humans (e.g., murine, lapine, porcine, canine or primate animals) may be employed.

As used herein, treating includes reducing the number, frequency, or severity of one or more (e.g., two, three, four, or five) signs or symptoms of a cancer in a patient having a cancer (e.g., any of the cancers described herein). For example, treatment can reducing cancer progression, reduce the severity of a cancer, or reduce the risk of re-occurrence of a cancer in a subject having the cancer.

Provided herein are methods of inhibiting the growth of a solid tumor in a subject (e.g., any of the subjects described herein) that include administering to the subject a therapeutically effective amount of any of the ABPCs described herein or any of the pharmaceutical compositions described herein (e.g., as compared to the growth of the solid tumor in the subject prior to treatment or the growth of a similar solid tumor in a different subject receiving a different treatment or receiving no treatment).

In some embodiments of any of the methods described herein, the growth of a solid tumor is primary growth of a solid tumor. In some embodiments of any of the methods described herein, the growth of a solid tumor is recurrent growth of a solid tumor. In some embodiments of any of the methods described herein, the growth of a solid tumor is metastatic growth of a solid tumor. In some embodiments, treatment results in about a 1% decrease to about 99% decrease (or any of the subranges of this range described herein) in the growth of a solid tumor in the subject (e.g., as compared to the growth of the solid tumor in the subject prior to treatment or the growth of a similar solid tumor in a different subject receiving a different treatment or receiving no treatment). The growth of a solid tumor in a subject can be assessed by a variety of different imaging methods, e.g., positron emission tomograph, X-ray computed tomography, computed axial tomography, and magnetic resonance imaging.

Also provided herein are methods of decreasing the risk of developing a metastasis or developing an additional metastasis over a period of time in a subject identified as having a cancer (e.g., any of the exemplary cancers described herein) that include administering to the subject a therapeutically effective amount of any of the proteins described herein or any of the pharmaceutical compositions described herein (e.g., as compared to a subject having a similar cancer and receiving a different treatment or receiving no treatment). In some embodiments of any of the methods described herein, the metastasis or additional metastasis is one or more to a bone, lymph nodes, brain, lung, liver, skin, chest wall including bone, cartilage and soft tissue, abdominal cavity, contralateral breast, soft tissue, muscle, bone marrow, ovaries, adrenal glands, and pancreas.

In some embodiments of any of the methods described herein, the period of time is about 1 month to about 3 years (e.g., about 1 month to about 2.5 years, about 1 month to about 2 years, about 2 months to about 1.5 years, about 1 month to about 1 year, about 1 month to about 10 months, about 1 month to about 8 months, about 1 month to about 6 months, about 1 month to about 5 months, about 1 month to about 4 months, about 1 month to about 3 months, about 1 month to about 2 months, about 2 months to about 3 years, about 2 months to about 2.5 years, about 2 months to about 2 years, about 2 months to about 1.5 years, about 2 months to about 1 year, about 2 months to about 10 months, about 2 months to about 8 months, about 2 months to about 6 months, about 2 months to about 5 months, about 2 months to about 4 months, about 2 months to about 3 months, about 3 months to about 3 years, about 3 months to about 2.5 years, about 3 months to about 2 years, about 3 months to about 1.5 years, about 3 months to about 1 year, about 3 months to about 10 months, about 3 months to about 8 months, about 3 months to about 6 months, about 3 months to about 5 months, about 3 months to about 4 months, about 4 months to about 3 years, about 4 months to about 2.5 years, about 4 months to about 2 years, about 4 months to about 1.5 years, about 4 months to about 1 year, about 4 months to about 10 months, about 4 months to about 8 months, about 4 months to about 6 months, about 4 months to about 5 months, about 5 months to about 3 years, about 5 months to about 2.5 years, about 5 months to about 2 years, about 5 months to about 1.5 years, about 5 months to about 1 year, about 5 months to about 10 months, about 5 months to about 8 months, about 5 months to about 6 months, about 6 months to about 3 years, about 6 months to about 2.5 years, about 6 months to about 2 years, about 6 months to about 1.5 years, about 6 months to about 1 year, about 6 months to about 10 months, about 6 months to about 8 months, about 8 months to about 3 years, about 8 months to about 2.5 years, about 8 months to about 2 years, about 8 months to about 1.5 years, about 8 months to about 1 year, about 8 months to about 10 months, about 10 months to about 3 years, about 10 months to about 2.5 years, about 10 months to about 2 years, about 10 months to about 1.5 years, about 10 months to about 1 year, about 1 year to about 3 years, about 1 year to about 2.5 years, about 1 year to about 2 years, about 1 year to about 1.5 years, about 1.5 years to about 3 years, about 1.5 years to about 2.5 years, about 1.5 years to about 2 years, about 2 years to about 3 years, about 2 years to about 2.5 years, or about 2.5 years to about 3 years).

In some embodiments, the risk of developing a metastasis or developing an additional metastasis over a period of time in a subject identified as having a cancer is decreased by about 1% to about 99% (e.g., or any of the subranges of this range described herein), e.g., as compared to the risk in a subject having a similar cancer receiving a different treatment or receiving no treatment.

Non-limiting examples of cancer include: acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, gliona, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and para-nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms' tumor. Additional examples of cancer are known in the art.

In some embodiments, the patient is further administered one or more additional therapeutic agents (e.g., one or more of a chemotherapeutic agent, a recombinant cytokine or interleukin protein, a kinase inhibitor, and a checkpoint inhibitor). In some embodiments, the one or more additional therapeutic agents is administered to the patient at approximately the same time as any of the ABPCs described herein are administered to the patient. In some embodiments, the one or more additional therapeutic agents are administered to the patient after the administration of any of the ABPCs described herein to the patient. In some embodiments, the one or more additional therapeutic agents are administered to the patient before the administration of any of the ABPCs described herein to the patient. In some embodiments of any of the methods described herein, the cancer is a solid cancer (e.g., breast cancer, prostate cancer, or non-small cell lung cancer).

Compositions

Also provided herein are compositions (e.g., pharmaceutical compositions) that include at least one of any of the ABPCs described herein. In some embodiments, the compositions (e.g., pharmaceutical compositions) can be disposed in a sterile vial or a pre-loaded syringe.

In some embodiments, the compositions (e.g., pharmaceutical compositions) are formulated for different routes of administration (e.g., intravenous, subcutaneous, intramuscular, or intratumoral). In some embodiments, the compositions (e.g., pharmaceutical compositions) can include a pharmaceutically acceptable carrier (e.g., phosphate buffered saline). Single or multiple administrations of any of the pharmaceutical compositions described herein can be given to a subject depending on, for example: the dosage and frequency as required and tolerated by the patient. A dosage of the pharmaceutical composition should provide a sufficient quantity of the ABPC to effectively treat or ameliorate conditions, diseases, or symptoms.

Also provided herein are methods of treating a subject having a cancer (e.g., any of the cancers described herein) that include administering a therapeutically effective amount of at least one of any of the compositions or pharmaceutical compositions provided herein.

Kits

Also provided herein are kits that include any of the ABPCs described herein, any of the compositions described herein, or any of the pharmaceutical compositions described herein. In some embodiments, the kits can include instructions for performing any of the methods described herein. In some embodiments, the kits can include at least one dose of any of the compositions (e.g., pharmaceutical compositions) described herein. In some embodiments, the kits can provide a syringe for administering any of the pharmaceutical compositions described herein.

Protein Constructs

Also provided are protein constructs (PCs) that include: a first antigen-binding domain that is capable of specifically binding FOLR1 or an epitope of FOLR1 presented on the surface of a target mammalian cell, where: (a) the dissociation rate of the first antigen-binding domain at a pH of about 7.0 to about 8.0 (or any of the subranges of this range described herein) is faster than the dissociation rate at a pH of about 4.0 to about 6.5 (or any of the subranges of this range described herein); and/or (b) the dissociation constant (KD) of the first antigen-binding domain at a pH of about 7.0 to about 8.0 (or any of the subranges of this range) is greater than the KD at a pH of about 4.0 to about 6.5.

Also provided herein are pharmaceutical compositions including any of the PCs described herein. Also provided herein are methods of treating a subject in need thereof that include administering a therapeutically effective amount of any of the PCs described herein to the subject.

Methods of Improving pH Dependence of an Antigen-Binding Protein Construct

Also provided herein are methods of improving pH dependence of an antigen-binding protein construct, the method comprises providing a starting antigen-binding protein construct comprising an antigen-binding domain and introducing one or more histidine amino acid substitutions into one or more CDRs of the antigen-binding domain in the starting antigen-binding protein construct, wherein the method results in the generation of an antigen-binding protein construct having one or both of: (a) an increased (e.g., at least a 0.1-fold increase to about a 100-fold increase, or any of the subranges of this range described herein) ratio of the dissociation rate of the antigen-binding domain at a pH of about 4.0 to about 6.5 to the dissociation rate at a pH of about 7.0 to about 8.0, as compared to the starting antigen-binding protein construct, and (b) an increased (e.g., at least a 0.1-fold increase to about a 100-fold increase, or any of the subranges of this range described herein) ratio the dissociation constant (KD) of the antigen-binding domain at a pH of about 4.0 to about 6.5 to the KD at a pH of about 7.0 to about 8.0, as compared to the starting antigen-binding protein construct.

The invention is further described in the following examples, which do not limit the scope of the invention described in the claims.

EXAMPLES

Example 1. Generation of FOLR1 Binders and Engineering of pH Binding Dependence pH-engineered ABPCs specific for FOLR1 are generated using two methods. In the first approach, published monoclonal antibodies against FOLR1 are used as a starting template for introduction of additional mutations that allow engineering of pH-dependent binding to FOLR1 and i) enhanced endolysosomal accumulation of a conjugated toxin, as well as ii) enhanced FOLR1 recycling to the cell surface. The second approach involves discovery of de novo ABPCs specific for FOLR1 via antibody display methods from naive libraries or libraries with defined CDR compositions and screening under conditions designed for selection of pH-engineered ABPCs specific for FOLR1. In either case, histidine residues play an important role in engineering pH-dependent binding proteins. Histidine residues are at least partially protonated at a pH below 6.5 owing to its pKa of 6.0. Therefore, if a histidine side chain in an antigen-binding domain participates in an electrostatic binding interaction with its antigen it will start to turn positively charged at a pH at or below 6.5. This could either weaken or enhance the binding affinity of the interaction at a pH below 6.5, based on the corresponding charge of and interactions with the antigen epitope. Thus, systematic introduction of histidines into antibody complementarity determining regions (CDRs) in an antibody or other binder library (e.g., an scFv library) can be used to identify substitutions that will affect an antigen-binding domain's interaction with an antigen at lower pH values. The first approach therefore involves histidine-scanning of variable region sequences of published monoclonal antibodies to identify pH-dependent variants.

Multiple FOLR1-binding monoclonal antibodies have been described in the literature and can be used as a template for engineering pH-dependent binding [Altwerger G et al (2018) "In Vitro and In Vivo Activity of IMGN853, an Antibody-Drug Conjugate Targeting Folate Receptor Alpha Linked to DM4, in Biologically Aggressive Endometrial Cancers" Molecular Cancer Therapeutics 7(5): 1003-1011]. Briefly, for a subset of the antibody sequences, CDRs in each chain are identified using the methods described by Kabat et al (Kabat et al. (1992) Sequences of Proteins of Immunological Interest (DIANE publishing) and IMGT (Lefranc MP(1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To engineer pH-dependent sequence variants, individual amino acid residues within the heavy chain and/or light chain CDRs are systematically substituted with a histidine, one at a time. In cases where the starting CDR residue is a histidine, it is mutated to an alanine. Antibody variants with only one histidine or alanine mutation in a heavy/light chain CDR are generated by co-transfection of Expi293 cells with a) one heavy chain or light chain sequence variant, and b) the corresponding starting ABPC (e.g., the starting FOLR1-binding monoclonal antibody) light chain or heavy chain, respectively, using methods known to the art. After allowing for a period of protein expression, cell culture supernatants are collected, quantified, and the pH dependence of the variant is evaluated using biolayer interferometry (BLI) or other methods known to the art. Briefly, cell culture supernatants are normalized to an antibody expression level of 50 µg/mL, and captured on an anti-human Fc sensor (FORTEBIO® (biolayer interferometry systems)). A baseline is established using 1× kinetics buffer (FORTEBIO® (biolayer interferometry systems)), and the sensor is associated with 100 nM of FOLR1 in 1×PBS at pH 7.4 for 300 sec to generate an association curve. In the dissociation phase, the antibody-antigen complex on the sensor is exposed to 1×PBS at either pH 5.5 or pH 7.4 for 300-500 sec. Association and dissociation phase curves are examined for the starting ABPC antibody and each corresponding antibody variant at pH 5.5 and pH 7.4 to inform on two criteria: a) enhanced dissociation (i.e., higher $k_{off}$ values) at pH 5.5 due to histidine or alanine substitution compared to the starting ABPC, and b) reduced dissociation at pH 7.4 (i.e., lower $k_{off}$ values) compared to pH 5.5 in the antibody variant itself and with the starting ABPC. Variants that show either enhanced dissociation at pH 5.5 or reduced dissociation at pH 7.4 or both are selected for further analysis. It is also noted that while some histidine and alanine mutations obliterate FOLR1 binding, others are tolerated with little (e.g., less than 1-fold change in KD or dissociation rate) or no change in FOLR1 binding kinetics. Especially because histidine is a large, positively charged amino acid, these histidine variants and alanine variants with no change are noted as positions that may tolerate a wide range of mutations and lead to antibodies with different sequence but similar binding properties, a designation that is not otherwise apparent. The variants selected for further analysis are expressed at a larger scale and purified using protein A affinity chromatography. Binding kinetics ($k_{on}$ and $k_{off}$) of the purified starting ABPC and variant antibodies are measured at pH 5.5 and pH 7.4 using BIACORE® (surface plasmon responance systems) (GE Healthcare). The ratio of the antibody's rate of dissociation ($k_{off}$ at pH 7.4 divided by $k_{off}$ at pH 5.5) is also used as a quantitative assessment of pH-dependent binding; similarly, the dissociation constant $K_D$ is calculated at both pH 5.5 and pH 7.4 as $k_{off}$ divided by $k_{on}$ and the ratio of the antibody's dissociation constant ($K_D$ at pH 7.4 divided by KD at pH 5.5) is also used as a quantitative assessment of pH-dependent binding. Antibodies with a rate of dissociation ratio less than that of the starting ABPC and/or a dissociation constant ratio less than that of the starting ABPC are selected for further assessment of combinatorial substitutions. Favorable histidine and/or alanine amino acid positions can also be combined to enhance pH dependence; this can be done by, e.g., combinatorially or rationally combining histidine and/or alanine substitutions on a given heavy or light chain that individually improve pH dependence, by, e.g., combinatorially or rationally combining modified heavy and light chains such that histidine and/or alanine substitutions are present on both chains, or combinations thereof. Such combinatorial variants are generated and tested/analyzed for differential pH dependence using the methods and protocols described herein, or others known to the art. Antibody variants that have the lowest rate of dissociation ratios and/or dissociation constant ratios are selected as candidates for further analysis (hereafter referred to as "pH-engineered ABPCs specific for FOLR1").

The second method for selection of pH-engineered ABPCs specific for FOLR1 involves either screening libraries to identify de novo pH-dependent ABPCs specific for FOLR1 or ABPCs that could serve as templates for engineering pH-dependent binding as described herein. Two types of libraries can be used for these selections: naive phage/yeast display antibody libraries (e.g., Fab, scFv, VHH, VL, or others known to the art) or phage/yeast display libraries where CDRs have been mutated to express a subset of amino acid residues. Libraries are screened against soluble recombinant FOLR1 extracellular domains using methods known to the art with positive selection for variants that bind weakly (e.g., are eluted from beads) at pH 5.0 and bind strongly (e.g., are bound to beads) at pH 7.4. Three rounds of selections are performed. The final round of binders are screened using ELISA for binding to human FOLR1 and cyno FOLR1 and mouse FOLR1 or via mean fluorescence intensity in flow cytometric analysis. If more binders with cyno or murine cross-reactivity are desired, the final selection round can instead be performed on cyno FOLR1 or murine FOLR1. Selected binding proteins are subcloned into mammalian expression vectors and expressed as either full IgG proteins or Fc fusions in Expi293 cells. BLI analysis is performed as described herein for selection of pH-dependent binder variants and confirmed using BIACORE® (surface plasmon responance systems).

Example 2. In Vitro Demonstration of pH-Dependent Binding to FOLR1, pH-Dependent Release of FOLR1, Enhanced Endolysosomal Delivery in FOLR1+ Cells, and Increased FOLR1 Antigen Density in FOLR1+ Cells after Exposure to pH-Engineered ABPCs Specific for FOLR1 as Compared to Control ABPCs Specific for FOLR1

As discussed herein, pH-engineered ABPCs specific for FOLR1 exhibit the desirable property of decreased FOLR1 binding at acidic pH (e.g., pH 5.0, pH 5.5), but enhanced binding at higher pH (e.g., pH 7.4), which enhances their accumulation in endolysosomes under physiological conditions.

pH-Dependent Binding to FOLR1 on Cells

To demonstrate that pH-engineered ABPCs specific for FOLR1 binds cell surface FOLR1 at neutral pH, a cell surface binding assay is performed. A panel of human cells that are FOLR1+ is assembled (e.g., KB, Igrov, Ovcar-3). Methods of identifying and quantifying gene expression (e.g., FOLR1) for a given cell line are known to the art, and include, e.g., consulting the Cancer Cell Line Encyclopedia (CCLE) to ascertain the expression level and/or mutation status of a given gene in a tumor cell line), rtPCR, microarray, or RNA-Seq analysis, or cell staining with antibodies known in the art (e.g. R&D Systems FOLR1 Antibody, Cat #MAB5646 or Invitrogen FOLR1 Antibody, Cat #548908 for FOLR1). Cells are seeded at approximately 5-10,000 per well in 150 µL of pH 7.4 culture medium and incubated at 37° C. for 5 minutes at several doses (e.g., a two-fold dilution series) from 1 pM to 1 µM with one of the following antibodies: a known, control ABPC specific for FOLR1 (e.g., an antibody, mirvetuximab, or STRO-002, or Farletuzumab), the pH-engineered ABPC specific for FOLR1, and an appropriate negative isotype control mAb (e.g., Biolegend Purified Human IgG1 Isotype Control Recombinant Antibody, Cat #403501). Prior to the onset of the experiment, the binding properties of all antibodies are validated using methods known to the art. Following the 5 minute incubation, cells are fixed with 4% formaldehyde (20 min at room temperature) and incubated with an appropriate fluorophore-labeled secondary antibody (e.g., ThermoFisher Mouse anti-Human IgG1 Fc Secondary Antibody, Alexa Fluor 488, Cat #A-10631) for 60 minutes. Unbound reagents are washed with a series of PBS washes, and the cell panels are imaged using confocal microscopy. Upon analysis of the images, significant fluorescence can be observed on the surface of cells bound with the known, control ABPC specific for FOLR1 as well as the pH-engineered ABPC specific for FOLR1, but little surface binding can be observed for the isotype negative control. To isolate the effect of pH on surface binding, the same experiment is repeated twice, with the primary antibody incubation taking place at sequentially lower pH (e.g., pH 6.5 and 5.5 and 5.0). Analysis of the resulting confocal microscopy images can show significant fluorescence on the surface of cells bound with all mAbs tested, excepting the isotype negative control, and that this fluorescence decreases for the pH-engineered ABPC specific for FOLR1 as the pH decreases. Alternatively, cells are analyzed for mean fluorescent intensity by flow cytometry using methods known in the art. A dissociation constant KD on cells at neutral pH of the antibodies analyzed is determined by nonlinear regression methods known in the art (e.g., a Scatchard plot). Taken together, the results can show that the pH engineering process results in the creation of a pH-engineered ABPC specific for FOLR1 that is pH-dependent in its binding properties and that it more effectively binds at neutral pH as compared to more acidic pH. Other methods of assessing the pH dependence of the pH-engineered ABPCs specific for FOLR1 are known in the art and include, e.g., using flow cytometry to measure ABPC surface binding.

pH-Dependent Release of FOLR1 on Cells

To demonstrate that pH-engineered ABPCs specific for FOLR1 are capable of releasing FOLR1 at low pH after binding at a neutral pH, a variant of the cell surface binding assay described above is performed using methods known to the art (e.g., as generally described in Gera N. (2012) PLoS ONE 7(11): e48928). Briefly, an appropriate FOLR1+ cell line (passage number less than 25) is harvested and 50,000 cells per well are plated in a U-Bottomed 96-well microplate. Three conditions are tested; binding and secondary staining at pH 7.4, binding and secondary staining at pH 5.0, and binding at pH 7.4 followed by release at pH 5.0 for 30 minutes and secondary staining at pH 7.4. Both pH-engineered ABPCs specific for FOLR1 as well as a control ABPC specific for FOLR1 are tested. The cells are washed two times with 200 μL of FACS buffer (1×PBS containing 3% Fetal Bovine Serum) at either pH 7.4 or 5.0 depending on the condition being tested. The purified protein samples are diluted into FACS buffer of the appropriate pH and added to the cells and allowed to bind for one hour on ice. After incubation with the primary antibodies the pH 7.4 and pH 5.0 conditions are washed twice as before, and then 100 μl of secondary rat anti-human Fc AF488 (BioLegend 410706) or other appropriate antibody, diluted 1:50, or anti Myc-Tag mouse mAb-AF488 (Cell Signaling Technologies 2279S) diluted 1:50 is added in FACS buffer of the appropriate pH, and incubated for 30 minutes on ice. The pH 5.0 release condition is washed twice with FACS buffer pH 7.4 and then resuspended in 100 μl of FACS buffer pH 5.0 and incubated on ice for 30 minutes, followed by secondary staining in FACS buffer pH 7.4 as described for the other conditions. The plates are washed twice as before and resuspended in 1% paraformaldehyde in the appropriate FACS buffer to fix them for flow cytometry analysis. All conditions are read on a flow cytometer (Accuri C6, BD Biosciences). Binding is observed as a shift in the FL1 signal (as a mean fluorescence intensity) versus secondary alone. Upon analysis of the data, it can be determined that both the pH-engineered ABPC specific for FOLR1 as well as the control ABPC specific for FOLR1 effectively bind the surface of FOLR1+ cells at neutral pH, but the pH-engineered ABPC specific for FOLR1 binds poorly at pH 5.0; similarly, it can be determined that the pH-engineered ABPC specific for FOLR1 binds effectively at pH 7.4, but then releases/unbinds FOLR1 at pH 5.0.

Enhanced Endolysosomal Delivery in FOLR1+ Cells of pH-Engineered ABPCs Specific for FOLR1 as Compared to Control ABPCs Specific for FOLR1 (pHrodo)

To verify and demonstrate that ABPCs specific for FOLR1 achieve endolysosomal localization following cellular uptake, an internalization assay is performed using methods known to the art (e.g., Mahmutefendic et al., Int. J. Biochem. Cell Bio., 2011). Briefly, as described herein, a panel of human cells that express FOLR1 highly is assembled using methods known to the art. Cells are plated, washed three times with PBS, and incubated at 37 degrees C. for 60 minutes in media at neutral pH, with added concentrations of 2 micrograms per milliliter of a known, control ABPC specific for FOLR1 (e.g., as described herein), the pH-engineered ABPC specific for FOLR1, and an appropriate negative isotype control mAb (e.g., as described herein). In a subset of cells, validation of antibody internalization and endosomal localization is performed using methods known to the art; e.g., cells are fixed in 4% formaldehyde as described herein, permeabilized using TWEEN® (polysorbate surfactants) 20 or other methods known to the art (Jamur M C et al (2010) Penneabilization of cell membranes, Methods Mol Biol. 588:63-6), additionally stained with an endosomal marker, e.g., a fluorescent RAB11 antibody (RAB11 Antibody, Alexa Fluor 488, 3H18L5, ABfinity™ Rabbit Monoclonal), stained with an appropriate fluorescently labeled anti-human secondary antibody (e.g., as described herein), and imaged using confocal fluorescence microscopy, as described herein. Analysis of the confocal images can be used to show that both the pH-engineered ABPC specific for FOLR1 as well as the control ABPC specific for FOLR1 are internalized and accumulate in the endolysosomes.

To demonstrate that pH-engineered ABPCs specific for FOLR1 achieve enhanced endolysosomal accumulation relative to a control ABPC specific for FOLR1, a pHrodo-based internalization assay is performed using both a known, control ABPC specific for FOLR1 (e.g., as described herein) as well as the pH-engineered ABPC specific for FOLR1. The assay makes use of pHrodo™ iFL (P36014, ThermoFisher), a dye whose fluorescence increases with decreasing pH, such that its level of fluorescence outside the cell at neutral pH is lower than its level of fluorescence inside the acidic pH environment of endolysosomes. Briefly, an appropriate FOLR1+ cell line (less than passage 25) is suspended in its recommended media (e.g., by cell banks or cell bank databases ATCC, DSMZ, or ExPASy Cellosaurus) and plated in a 24-well plate at a density of 2,000,000 cells/mL, 1 mL per well. While keeping the cells on ice, 1 mL of 2×pHrodo iFL-labeled antibody (prepared in accordance with the manufacturer's instructions) is added to each well, the well is pipetted/mixed five times, and the plate is incubated in a light-protected environment for 45 minutes, on ice. An identical but separate plate is also incubated on ice that is meant as a no-internalization negative control. Following this incubation, the experimental plate is moved to a 37 degree c. incubator, the negative control plate is kept on ice to slow or block internalization, and samples are taken at designated time points to create an internalization time course. Samples are placed into a U-bottom 96-well plate, and internalization is quenched via addition of 200 μL/well of ice-cold FACS buffer. The plates are spun down at 2000×g for 2 minutes, resuspended in 200 μL ice-cold FACS buffer, spun down again, and resuspended in FACS buffer a second time. Finally, the samples are loaded into a flow cytometer for read-out of cellular pHrodo fluorescence using excitation and emission wavelengths consistent with the excitation and emission maxima of the pHrodo iFL Red dye (566 nm and 590 nm, respectively). Upon completion of the flow cytometry experiment and analysis of the data, it can be observed that cells treated with the pH-engineered ABPC specific for FOLR1 have a higher pHrodo iFL signal relative to a known, control ABPC specific for FOLR1, indicating that pH-engineered ABPCs specific for FOLR1 achieve enhanced endolysosomal accumulation relative to a control ABPC specific for FOLR1.

Alternatively, to demonstrate that pH-engineered ABPCs specific for FOLR1 achieve enhanced endolysosomal accumulation relative to a control ABPC specific for FOLR1, a variation of the above-described experiment is performed. FOLR1+ cells are plated, washed three times with PBS, and incubated at 37 degrees C. for 60 minutes in media at neutral pH with added concentrations of 2 μg/mL of either pH-engineered ABPC specific for FOLR1 or control ABPC specific for FOLR1. Following incubation, cells are washed three times with PBS, fixed and permeabilized, and stained with a panel of appropriately selected antibodies that bind late endosomal markers as well as lysosomes (e.g., RAB7, and LAMP1; Cell Signaling Technology, Endosomal Marker Antibody Sampler Kit #12666; AbCam, Anti-LAMP2 antibody [GL2A7], ab13524). After primary antibody staining, cells are stained with an appropriate mixture of fluorescently labeled secondary antibodies (e.g., Goat Anti-Human IgG (H&L) Secondary Antibody (Alexa Fluor 647) Cat #A-21445, and Abcam Goat Anti-Rabbit IgG H&L (Alexa Fluor 488), Cat #ab150077), imaged using confocal fluorescence microscopy, and regions of co-localization of signal from FOLR1-specific antibodies and endosomal markers are visualized and quantified. Upon analysis of the data, it can be revealed that there is increased co-localization of endolysosmal and FOLR1-specific antibody signal in wells treated with the pH-engineered ABPCs specific for FOLR1 as compared to wells treated with control ABPC specific for FOLR1, and can thereby demonstrate that pH-engineered ABPCs specific for FOLR1 achieve enhanced endolysosomal accumulation relative to control ABPC specific for FOLR1.

Increased FOLR1 Antigen Density in FOLR1+ Cells after Exposure to pH-Engineered ABPCs Specific for FOLR1 as Compared to Control ABPCs Specific for FOLR1

To demonstrate that treatment of cells with the pH-engineered ABPCs specific for FOLR1 does not result in a detectable reduction of the level of FOLR1 on the surface of cells exposed to the pH-engineered ABPCs specific for FOLR1, or that said treatment results in less of a reduction of the level of FOLR1 on the surface of cells exposed to the pH-engineered ABPC specific for FOLR1 versus a control ABPC specific for FOLR1, an antigen density study is performed using flow cytometry. Briefly, 4.0×10^5 cells that express FOLR1 are plated per well in a 96-well plate in 100 μL media. Cells are treated with a titration from 1 pM to 1 μM of i) pH-engineered ABPCs specific for FOLR1, ii) a first control ABPC specific for FOLR1, iii) an appropriate isotype control, and iv) an untreated control. Cells are incubated for 2 hours at 37° C., at which point all cells are incubated with 200 nM of a fluorophore-labeled second control ABPC specific for FOLR1 (e.g., as described herein) which has a different epitope (as determined by, e.g., competitive binding studies on cells) than either the first control ABPC specific for FOLR1 or the pH-engineered ABPCs specific for FOLR1 for 30 minutes at 4° C. Following this 30-minute incubation, the mean fluorescence intensity (MFI) of all cells is read out using, e.g., flow cytometry, using methods known to one of ordinary skill in the art. In parallel, a quantitative standard curve that can be used to quantify the presence of FOLR1 on the surface of treated cells as a function of MFI is generated using a commercially available quantification kit (e.g., BD Biosciences PE Phycoerythrin Fluorescence Quantitation Kit, catalog #340495); the quantitative standard curve is created by following the manufacturer's instructions. Other methods of determining the absolute number of FOLR1 on the cell surface are known in the art and include, e.g., use of radioisotopically labeled reagents. Upon analysis of the data, it can be revealed that at least one antibody concentration, cells treated with a control ABPC specific for FOLR1 experience a reduction of the level of FOLR1 on their surface, whereas cells treated with pH-engineered ABPCs specific for FOLR1 experience a significantly smaller reduction or no reduction at all, both relative to the isotype and untreated controls.

Example 3. Conjugation of pH-Engineered and Control ABPCs Specific for FOLR1 to Cytotoxic Drugs An antigen-binding protein construct conjugate (ADC) is made comprising the FOLR1-binding IgG (hereafter, FOLR1-IgG) described herein linked to monomethyl auristatin E (MMAE) via a valine-citrulline (vc) linker (hereafter, FOLR1-IgG-DC). Conjugation of the antigen-binding protein construct with vcMMAE begins with a partial reduction of the FOLR1-IgG followed by reaction with maleimidocaproyl-Val-Cit-PABC-MMAE (vcMMAE). The FOLR1-IgG (20 mg/mL) is partially reduced by addition of TCEP (molar equivalents of TCEP:mAb is 2:1) followed by incubation at 0° C. overnight. The reduction reaction is then warmed to 20° C. To conjugate all of the thiols, vcMMAE is added to a final vcMMAE:reduced Cys molar ratio of 1:15. The conjugation reaction is carried out in the presence of 10% v/v of DMSO and allowed to proceed at 20° C. for 60 minutes.

After the conjugation reaction, excess free N(acetyl)-Cysteine (2 equivalents vs. vcMMAE charge) is added to quench unreacted vcMMAE to produce the Cys-Val-Cit-MMAE adduct. The Cys quenching reaction is allowed to proceed at 20° C. for approximately 30 minutes. The Cys-quenched reaction mixture is purified as per below. The above conjugation method can also be used to conjugate maleimidocaproyl monomethyllauristatin F (mcMMAF) to an antigen-binding protein construct.

The FOLR1-IgG-DC is purified using a batch purification method. The reaction mixture is treated with the appropriate amount of water washed Bu-HIC resin (ToyoPearl; Tosoh Biosciences), i.e., seven weights of resin is added to the mixture. The resin/reaction mixture is stirred for the appropriate time, and monitored by analytical hydrophobic interaction chromatography for removal of drug conjugate products, filtered through a coarse polypropylene filter, and washed by two bed volumes of a buffer (0.28 M sodium chloride, 7 mM potassium phosphate, pH 7). The combined filtrate and rinses are combined and analyzed for product profile by HIC HPLC. The combined filtrate and rinses are buffer exchanged by ultrafiltration/diafiltration (UF/DF) to 15 mM histidine, pH 6 with 10 diavolumes 15 nM histidine buffer.

A similar protocol can be used to conjugate DNA toxins such as SG3249 and SGD-1910 to FOLR1-IgG (see Tiberghien A C et al (2016) Design and Synthesis of Tesirine, a Clinical Antibody-Drug Conjugate Pyrrolobenzodiazepine Dimer Payload, ACS Med Chem Lett 7:983-987). Briefly, for SG3249, FOLR1-IgG (15 mg, 100 nanomoles) is diluted into 13.5 mL of a reduction buffer containing 10 mM sodium borate pH 8.4, 2.5 mM EDTA and a final antibody concentration of 1.11 mg/mL. A 10 mM solution of TCEP is added (1.5 molar equivalent/antibody, 150 nanomoles, 15 microliters) and the reduction mixture is heated at +37° C. for 1.5 hours in an incubator. After cooling down to room temperature, SG3249 is added as a DMSO solution (5 molar equivalent/antibody, 500 nanomoles, in 1.5 mL DMSO). The solution is mixed for 1.25 hours at room temperature, then the conjugation is quenched by addition of N-acetyl cysteine (1 micromole, 100 microliters at 10 mM), and injected into an AKTA™ Pure FPLC using a GE Healthcare HiLoad™ 26/600 column packed with Superdex 200 PG, and eluted with 2.6 mL/min of sterile-filtered phosphate-buffered saline (PBS). Fractions corresponding to the FOLR1-IgG-DC monomer peak are pooled, concentrated using a 15 mL Amicon Ultracell 50 KDa MWCO spin filter, analysed and sterile-filtered. UHPLC analysis on a Shimadzu Prominence system using a Phenomenex Aeris 3.6u XB-C18 150×2.1 mm column eluting with a gradient of water and acetonitrile on a reduced sample of FOLR1-IgG-DC at 280 nm and 330 nm (SG3249 specific) can show a mixture of light and heavy chains attached to several molecules of SG3249, consistent with a drug-per-antibody ratio (DAR) of 1 to 4 molecules of SG3249 per antibody. UHPLC analysis on a Shimadzu Prominence system using a Phenomenex Yarra 3u SEC-3000 300 mm×4.60 mm column eluting with sterile-filtered SEC buffer containing 200 mM potassium phosphate pH 6.95, 250 mM potassium chloride and 10% isopropanol (v/v) on a sample of FOLR1-IgG-DC at 280 nm can show a monomer purity of over 90% with no impurity detected. UHPLC SEC analysis allows determination of final FOLR1-IgG-DC yield of greater than 30%.

Alternatively, methods to conjugate toxins to antibodies via lysine residues are known in the art (e.g., see Catcott K C et al (2016) Microscale screening of antibody libraries as maytansinoid antibody-drug conjugates, MAbs 8:513-23). In addition, similar methods to the above can be used to conjugate drugs and toxins to non-IgG formats with disulfide bonds, such as Vh-Fcs.

Example 4. Demonstration of Enhanced Cytotoxicity of pH-Engineered ABPC ADCs Specific for FOLR1 in FOLR1+ Cells as Compared to a Control ABPC ADC Specific for FOLR1

The cytotoxic activity of both pH-engineered ADCs specific for FOLR1 (e.g., a pH-engineered FOLR1-IgG-DC) and control ABPC ADCs specific for FOLR1 (e.g., a control ABPC FOLR1-IgG-DC) are separately evaluated on a panel of FOLR1+ cell lines expressing a variety of antigen densities (e.g., as described herein) and a FOLR1− cell line (e.g., A431), selected using the methods described herein, and, optionally, cells expressing transgenic FOLR1, e.g., HEK293 cells transfected with FOLR1 using methods known in the art (e.g., Expi293™ Expression System Kit ThermoFisher Catalog number: A14635). For purposes of validation, prior to use, all cell lines are tested for expression of FOLR1 using methods known to the art, e.g., qPCR, flow cytometry, mRNA RPKM, and antibody staining using anti-FOLR1 antibodies known to the art (e.g., as described herein) followed by visualization of the stain using fluorescence microscopy, immunohistochemistry, flow cytometry, ELISA, or other methods known to the art. To evaluate the cytotoxicity of compounds, cells are seeded at approximately 10-40,000 per well in 150 microliters of culture medium, then treated with graded doses of compounds from 1 pM to 1 µM in quadruplicates at the initiation of the assay. Cytotoxicity assays are carried out for 96 hours after addition of test compounds. Fifty microliters of resazurin dye are added to each well during the last 4 to 6 hours of the incubation to assess viable cells at the end of culture. Dye reduction is determined by fluorescence spectrometry using the excitation and emission wavelengths of 535 nm and 590 nm, respectively. For analysis, the extent of resazurin reduction by the treated cells is compared to that of untreated control cells, and percent cytotoxicity is determined. Alternatively, a WST-8 kit is used to measure cytotoxicity per the manufacturer's instructions (e.g., Dojindo Molecular Technologies Catalog #CCK-8). IC50, the concentration at which half-maximal killing is observed, is calculated using curve-fitting methods known in the art. Upon analysis of the data, it can be determined that pH-engineered and control ABPC ADCs specific for FOLR1 are substantially cytotoxic to one or more FOLR1+ cell line, but less toxic to FOLR1− cells. It also can be determined that pH-engineered ADCs specific for FOLR1 are more cytotoxic to one or more FOLR1+ cell lines than control ABPC ADCs specific for FOLR1 because: a) they show greater depth of killing at one or more concentrations or, b) they show lower IC50 or, c) they show a greater ratio of their dissociation constant KD on cells at neutral pH (as described herein) divided by their IC50 on those same cells.

Additionally, the cytotoxic activity of ABPCs specific for FOLR1 can be measured in a secondary ADC assay. Secondary ADC assays are known in the art (e.g., Moradec Cat #αHFc-NC-MMAF and Cat #αHFc-CL-MMAE, and associated manufacturer's instructions). Briefly, the assay is carried out as in the previous paragraph, except the ABPC specific for FOLR1 is substituted for the ADC specific for FOLR1, and to evaluate the cytotoxicity of compounds, cells are seeded at approximately 10-40,000 per well in 150 microliters of culture medium, then treated with graded doses of ABPC specific for FOLR1 from 1 pM to 1 µM (final concentration in culture medium, having been pre-mixed with 100 nM, final concentration in culture medium, of Moradec Cat #αHFc-NC-MMAF secondary ADC reagent and pre-incubated at 37° C. for 30 min before addition of the mixture to the culture medium) in quadruplicates at the initiation of the assay.

The cytotoxic activity of pH-engineered ADCs specific for FOLR1 and control ABPC ADCs specific for FOLR1 conjugates, as well as ABPCs specific for FOLR1 in a secondary ADC assay, are additionally measured by a cell proliferation assay employing the following protocol (Promega Corp. Technical Bulletin TB288; Mendoza et al., Cancer Res. 62:5485-5488, 2002):

1. An aliquot of 100 microliters of cell culture containing about 104 cells (e.g., FOLR1+ cells as described herein) in medium is deposited in each well of a 96-well, opaque-walled plate.

2. Control wells are prepared containing medium and without cells.

3. ADC specific for FOLR1 is added to the experimental wells at a range of concentrations from 1 pM-1 uM and incubated for 1-5 days. Alternatively, in a secondary ADC assay, 100 nM secondary ADC reagent (final concentration in culture medium, Moradec Cat #αHFc-NC-MMAF) and ABPC specific for FOLR1 at a range of concentrations from 1 pM-1 uM (final concentration in culture medium) are pre-mixed and pre-incubated at 37° C. for 30 min before addition of the mixture to the culture medium, and incubated for 1-5 days.

4. The plates are equilibrated to room temperature for approximately 30 minutes.

5. A volume of CellTiter-Glo Reagent equal to the volume of cell culture medium present in each well is added.

6. The contents are mixed for 2 minutes on an orbital shaker to induce cell lysis.

7. The plate is incubated at room temperature for 10 minutes to stabilize the luminescence signal.

8. Luminescence is recorded and reported in graphs as RLU=relative luminescence units.

Example 5. Demonstration of Enhanced Toxin Liberation of pH-Engineered ABPC ADCs Specific for FOLR1 in FOLR1+ Cells as Compared to a Control ABPC ADC Specific for FOLR1

The pH-engineered ADCs specific for FOLR1 (e.g., a pH-engineered FOLR1-IgG-DC) can also demonstrate increased toxin liberation in FOLR1+ cells as compared to a control ABPC ADC specific for FOLR1 (e.g., a control ABPC FOLR1-IgG-DC). After treatment of FOLR1+ cells with pH-engineered and control ABPC ADCs specific for FOLR1 as described herein, an LC-MS/MS method is used to quantify unconjugated (i.e., liberated) MMAE in treated FOLR1+ cells (Singh, A. P. and Shah, D. K. Drug Metabolism and Disposition 45.11 (2017): 1120-1132.) An LC-MS/MS system with electrospray interphase and triple quadrupole mass spectrometer is used. For the detection of MMAE, a XBridge BEH Amide column (Waters, Milford, MA) is used with mobile phase A as water (with 5 mM ammonium formate and 0.1% formic acid) and mobile phase B as 95:5 acetonitrile/water (with 0.1% formic acid and 1 mM ammonium formate), using a gradient at a flow rate of 0.25 mL/min at 40° C. The total duration of the chromatographic run is 12 minutes, where two MRM scans (718.5/686.5 and 718.5/152.1 amu) are monitored. Deuterated (d8) MMAE (MCE MedChem Express, Monmouth Junction, NJ) is used as an internal standard. First, an equation for quantifying unconjugated MMAE in a biological sample is derived by dividing the peak area for each drug standard by the peak area obtained for the internal standard. The resultant peak area ratios are then plotted as a function of the standard concentrations, and data points are fitted to the curve using linear regression. Three QC samples are included in the low, middle, and upper ranges of the standard curve to assess the predictive capability of the developed standard curve. The standard curves obtained are then used to deduce the observed concentrations of MMAE in a biologic sample. For measurement of MMAE concentration, treated cell samples are pelleted and reconstituted in fresh media to a final concentration of 0.25 million cells/100 μL. Samples are spiked with d8-MMAE (1 ng/mL) before performing cell lysis by the addition of a 2-fold volume of ice-cold methanol followed by freeze-thaw cycle of 45 minutes at –20° C. The final cell lysate is obtained by centrifuging the samples at 13,000 rpm for 15 minutes at 4° C. followed by collection of supernatant. For the preparation of standards and QC samples, a fresh cell suspension (0.25 million/100 μl) is spiked with known concentrations of MMAE and internal standard (d8-MMAE) before a procedure similar to the cell lysis mentioned above. The resulting cell lysates are then evaporated and reconstituted in mobile phase B before injection into LC-MS/MS. The concentration of unconjugated MMAE in lysates of FOLR1+ cells treated with pH-engineered ADCs specific for FOLR1 is observed to be greater than that in FOLR1+ cells treated with control ABPC ADC specific for FOLR1.

For tubulin-inhibiting toxins, toxin liberation is also assessed by monitoring of cell viability and cell cycle phase. ~2.0×10^5 FOLR1+ cells are plated in a 96-well flat bottom plate and treated with pH-engineered and control ABPC ADCs specific for FOLR1 as described herein. After treatment, cells are transferred to a 96-round bottom plate, and the plate is centrifuged at 400 ref for 2 min to decant supernatant. Decanted cells are stained with Live/Dead eFluor 660. Cells are then centrifuged and washed with FACS buffer (PBS with 2% FBS), after which cell cycle distribution is analyzed with a BD Cycletest™ Plus DNA Kit (cat #340242).

Briefly, cells are re-suspended in 76 ul Solution A and incubated for 10 min at room temperature. 61 μL Solution B is then added, and cells are incubated for another 10 min at room temperature. Finally, 61 μL of cold Solution C is added, and cells are again incubated for 10 min at room temp. Immediately after the last incubation step, cells are analyzed by flow cytometry (without washing) at a flow rate of 10 Lt/sec. Increased G2/M-phase arrest can be observed with exposure to pH-engineered ADCs specific for FOLR1 as compared to control ABPC ADC specific for FOLR1.

For DNA-damaging toxins (e.g., pyrrolobenzodiazepine or "PBD"), DNA damage is assessed by measuring the phosphorylated histone H2AX (γH2AX). H2AX is normally phosphorylated in response to double-strand breaks in DNA; however, increased levels γH2AX may also be observed as a result of treatment with DNA-cross-linking toxins such as PBD or cisplatin (Huang, X. et al. 2004, Cytometry Part A 58A, 99-110). FOLR1+ cells are treated with pH-engineered and control ABPC ADCs specific for FOLR1 as described herein. After treatment, cells are rinsed with PBS, and then fixed in suspension in 1% methanol-free formaldehyde (Polysciences, Warrington, PA) in PBS at 0° C. for 15 min. Cells are resuspended in 70% ethanol for at least 2 h at –20° C. Cells are then washed twice in PBS and suspended in 0.2% Triton X-100 (Sigma) in a 1% (w/v) solution of BSA (Sigma) in PBS for 30 min to suppress nonspecific Ab binding. Cells are centrifuged again (200 g, 5 min) and the cell pellet is suspended in 100 μL of 1% BSA containing 1:800 diluted anti-histone γH2AX polyclonal Ab (Trevigen, Gaithersburg, MD). The cells are then incubated overnight at 4° C., washed twice with PBS, and resuspended in 100 μL of 1:30 diluted FITC-conjugated F(ab')2 fragment of swine anti-rabbit immunoglobulin (DAKO, Carpinteria, CA) for 30 min at room temperature in the dark. The cells are then counterstained with 5 μg/mL of PI (Molecular Probes, Eugene, OR) dissolved in PBS containing 100 μg/mL of DNase-free RNase A (Sigma), for 20 min at room temperature. Cellular fluorescence of the FITC 7H2AX signal and the PI counterstain are measured using flow cytometry using methods known in the art. When comparing cells within the same stage of the cell cycle (based on total DNA content), treated FOLR1+ cells can be observed to have an increased FITC γH2AX signal relative to untreated FOLR1+ cells (which serve as a baseline). Furthermore, FOLR1+ cells treated with pH-engineered ADCs specific for FOLR1 can be observed to have a greater increase in levels of γH2AX over baseline than cells treated with a control ABPC ADC specific for FOLR1. In addition to the γH2AX assay, DNA cross-linking can be more directly assessed with a Comet assay (Chandna, S. (2004) Cytometry 61A, 127-133).

In addition, as disclosed herein, pH-engineered and control ABPCs can be assayed using the methods in this example without direct conjugation by performing a secondary ADC assay instead of using primary conjugated ADCs.

Example 6. Demonstration of Decreased Half-Life of pH-Engineered ABPCs Specific for FOLR1 as Compared to a Control ABPC Specific for FOLR1

One of the surprising aspects of the pH-engineered ABPCs specific for FOLR1 described by the invention can be their ability to facilitate increased dissociation of ABPCs from the FOLR1 within the endosome or lysosome resulting in a decreased serum half-life relative to control ABPCs specific for FOLR1 or ABPCs that are not specific for FOLR1. This decreased serum half-life is due to the enhanced frequency with which pH-engineered ABPCs specific for FOLR1 are cleared from circulation due to their enhanced cellular internalization once bound to FOLR1, which over time can be observed through a decrease in serum concentration of unbound pH-engineered ABPC specific for FOLR1. To demonstrate these properties, a series of animal studies in mice and/or monkeys is performed using pH-engineered ABPC specific for FOLR1 and control ABPC specific for FOLR1 using methods known to the art (e.g., Gupta, P., et al. (2016), mAbs, 8:5, 991-997). Briefly, to conduct mouse studies, a single intravenous bolus (e.g., 5 mg/kg) of either pH-engineered ABPC specific for FOLR1 or control ABPC specific for FOLR1 is administered via tail vein to two groups of NOD SCID mice (e.g. Jackson Labs NOD.CB17-Prkdcscid/J Stock No: 001303) xenografted with a FOLR1+ cell line (e.g., as described herein). Xenografted mice are prepared by growing 1-5 million FOLR1+ cells in vitro and inoculating subcutaneously into the right flank of the mouse. Tumors are size matched at 300 mm3. Measurements of the length (L) and width (W) of the tumors are taken via electronic caliper and the volume is calculated according to the following equation: $V=L\times W^2/2$. Blood samples are collected via retro-orbital bleeds from each group at each of the following time points: 15 m, 30 m, 1 h, 8 h, 24 h, and 3 d, 7 d, 10 d, 14 d, 17 d, 21 d, and 28 d. Samples are processed to collect serum, and antibody concentrations are quantified using ELISA or other methods known to the art (e.g., PAC assay or MAC assay; Fischer, S. K. et al. (2012), mAbs, 4:5, 623-631, utilizing, e.g., anti-human Fc antibody Jackson ImmunoResearch Labs, Cat #109-006-006). Antibody concentrations of pH-engineered ABPC specific for FOLR1 and control ABPC specific for FOLR1 are plotted as a function of time. Upon analysis of the data, it can be observed that the pH-engineered ABPC specific for FOLR1 has a significantly shorter serum half-life relative to control ABPC specific for FOLR1, thereby demonstrating the ability of the pH-engineered ABPC specific for FOLR1's pH dependence to facilitate an enhanced dissociation within the endosome or lysosome relative to other, similar binders (e.g., control ABPC specific for FOLR1) that bind the same antigen but that differ in their pH dependence. If the pH-engineered and control ABPCs specific for FOLR1 are cross-reactive with the mouse homolog of FOLR1, a similar experiment can be repeated with non-xenografted mice.

Optionally, if the pH-engineered and control ABPCs specific for FOLR1 are cross-reactive with the cynomolgus monkey homolog of FOLR1, a similar experiment can be performed on monkeys (e.g., cynomolgus monkeys). An equal number of male and female monkeys (e.g., n=1-2 each) are administered a bolus of either pH-engineered ABPC specific for FOLR1 or control ABPC specific for FOLR1 at a dose of, e.g., 1 mg/kg via saphenous vein injection. Alternatively, several different doses of FOLR1-binding protein are administered across a group of several monkeys. Blood samples are collected via the peripheral vein or femoral vein at intervals similar to those described above, and analyzed for the presence of either pH-engineered ABPC specific for FOLR1 or control ABPC specific for FOLR1 using methods known to the art (e.g., ELISA). Upon analysis of the data, it can be observed that pH-engineered ABPC specific for FOLR1 has a significantly shorter serum half-life relative to control ABPC specific for FOLR1, thereby demonstrating the ability of pH-engineered ABPC specific for FOLR1 to facilitate an enhanced dissociation within the endosome or lysosome relative to other, similar binders (e.g., control ABPC specific for FOLR1) that bind the same antigen but that differ in their pH dependence. In some cases, this effect is observed only in certain doses, whereas in others it is observed across doses.

In addition, the half life of pH-engineered and control ABPC ADCs specific for FOLR1 can be assessed using the above methods by substituting pH-engineered and control ABPC ADCs specific for FOLR1 for the pH-engineered and control ABPCs specific for FOLR1 (i.e., studying the ABPCs after conjugation to a drug or toxin, as described herein).

Example 7. Increased Potency of pH-Engineered ADCs Specific for FOLR1 Vs. A Control ABPC ADC Specific for FOLR1 in Mouse Xenograft Models The enhanced anti-tumor activity of the pH-engineered ADCs specific for FOLR1 against FOLR1+ tumors can be demonstrated in a subcutaneous xenograft model of FOLR1+ cells. For the experiments, 1-5 million FOLR1+ cells are grown in vitro and inoculated subcutaneously per mouse into the right flank of female immunodeficient (e.g., SCID-Beige or NOD scid) mice.

Tumors are size matched at 100-200 mm3, and dosed intraperitoneally (IP) (1 dose given every ~4-7 days for a total of ~2-6 doses). Measurements of the length (L) and width (W) of the tumors are taken via electronic caliper and the volume is calculated according to the following equation: $V=L\times W^2/2$. A bolus (e.g., 5 mg/kg) of either pH-engineered ADC specific for FOLR1 or control ABPC ADC specific for FOLR1 is administered via tail vein. Tumor growth inhibition (TGI) and tumor growth delay (TGD) and survival are significantly improved with administration of pH-engineered ADC specific for FOLR1 compared to administration of control ABPC ADC specific for FOLR1 at the same regimen.

Optionally, spread of tumor cells into the various tissues is determined in sacrificed animals. Metastasis is measured according to Schneider, T., et al., Clin. Exp. Metas. 19 (2002) 571-582. Briefly, tissues are harvested and human Alu sequences are quantified by real-time PCR. Higher human DNA levels, quantified by real-time PCR, correspond to higher levels of metastasis. Levels of human Alu sequences (correlating to invasion of tumor cells into secondary tissue) are significantly lower in animals treated with pH-engineered ADC specific for FOLR1, corresponding to reduced metastasis, compared to mice treated with control ABPC ADC specific for FOLR1 at the same regimen. Alternatively, the enhanced anti-tumor activity of the pH-engineered ADC specific for FOLR1 can be shown in FOLR1+ patient-derived xenograft models (e.g., available from Oncotest GmbH).

Example 8. Creation of a pH-Engineered Bispecific FOLR1 Bispecific ABPC and Demonstration of Exemplary Properties as Compared to a Control Bispecific ABPC To create a pH-engineered ABPC specific for FOLR1 with modified toxicity and internalization properties, a bispecific antibody that binds two different epitopes on FOLR1 is constructed. It is known in the art that biparatopic antibodies can show increased antigen-dependent internalization, and are therefore useful for applications such as antibody-drug conjugates (e.g., see Li et al (2016) A Biparatopic HER2-Targeting Antibody-Drug Conjugate Induces Tumor Regression in Primary Models Refractory to or Ineligible for HER2-Targeted Therapy, Cancer Cell 29:117-29). Briefly, a pH-engineered FOLR1×FOLR1 bispecific, biparatopic ABPC specific for FOLR1 is assembled using light chain/heavy chain pairs from two different pH-engineered ABPCs specific for FOLR1, each of which binds a distinct epitope on FOLR1 that does not overlap with the other epitope. A set of pH-engineered ABPCs specific for FOLR1 that bind non-overlapping epitopes are discovered, e.g., using the methods described herein, or others known to one of ordinary skill in the art. Briefly, two binders are selected on the basis that they bind substantially different epitopes on FOLR1, as determined by, e.g., a binding competition assay as in Abdiche Y N et al (2009) Exploring blocking assays using Octet, PROTEON™ (protein interaction array systems), and BIACORE® (surface plasmon responance systems) biosensors, Anal Biochem 386:172-80. Alternatively, briefly, as described herein, cell culture supernatants of cells transfected with a first ABPC specific for FOLR1 are normalized to an antibody expression level of 50 μg/mL, and captured on an anti-human Fc sensor (FORTEBIO® (biolayer interferometry systems)). A baseline is established using 1× kinetics buffer (FORTEBIO® (biolayer interferometry systems)), and the sensor is associated with 50 nM of FOLR1 in 1×PBS (that has been mixed and pre-incubated for 30 min at 37 degrees C. with a second ABPC specific for FOLR1 transfection supernatant or the first ABPC specific for FOLR1 transfection supernatant, both normalized to 50 ug/mL) at pH 7.4 for 300 see to generate an association curve. If the association rate in the presence of the second ABPC specific for FOLR1 is significantly faster (as calculated by the instrument software, or as seen by an elevated level of association over time) than the association rate in the presence of the first ABPC specific for FOLR1, then the second ABPC specific for FOLR1 is deemed to bind a non-overlapping epitope of FOLR1. Optionally, each antibody is screened for its internazation properties when bound to its epitope on a cell expressing FOLR1, and well-internalizing antibodies are selected. Assays for determining the internalization rate of a molecule present on the surface of a cell are known to the art. See, e.g., Wiley et al. (1991) J. Biol. Chem. 266: 11083-11094; and Sorkin and Duex (2010) Curr. Protoc. Cell Biol. Chapter, Unit-15.14; Vainshtein et al. (2015) Pharm Res. 32: 286-299. Once selected, heavy and light chain constructs with engineered mutations for heavy and light chain pairing (Spiess et al., "Alternative molecular formats and therapeutic applications of bispecific antibodies," 2015) are synthesized for both arms. Bispecific ABPCs specific for FOLR1 are produced by co-expression of corresponding heavy and light chain plasmids in, e.g., Expi293 cells. Cell culture supernatants are harvested and subjected to Protein A purification. Heterodimeric ABPCs specific for FOLR1 are separated from homodimeric species via additional purification steps such as ion exchange chromatography, hydrophobic interaction chromatography, and mixed mode chromatography.

The purified pH-engineered FOLR1×FOLR1 bispecific, biparatopic ABPCs specific for FOLR1 are characterized via mass spectrometry to confirm the purity and absence of homodimeric species and size exclusion chromatography to confirm the presence of monomeric antigen-binding protein construct species. For the product antibody, binding to the FOLR1 is confirmed via BIACORE® (surface plasmon responance systems) analysis. Other methods of bispecific antibody production are known to the art and could also be used to create a bispecific antibody, e.g., the FOLR1× FOLR1 bispecific, biparatopic ABPCs specific for FOLR1 described herein (e.g., Labrijn et al (2014) "Controlled Fab-arm exchange for the generation of stable bispecific IgG" Nature Protcols 9:2450-2463), as would be apparent to one of ordinary skill in the art. Alternatively, instead of a FOLR1×FOLR1 ABPC specific for FOLR1, a pH-engineered FOLR1×BINDER ABPC specific for FOLR1 can be constructed using similar methods apparent to one skilled in the art, where BINDER is any antibody that has been published in the art or discovered using methods like those herein or those known in the art (e.g., display-based or immunization-based methods).

Next, exemplary properties of pH-engineered FOLR1× FOLR1 ABPCs specific for FOLR1 can be demonstrated using the methods described herein, with the appropriate control being a control ABPC monospecific or bispecific ABPC specific for FOLR1. Briefly, it can be shown that, as compared to a control, the pH-engineered FOLR1×FOLR1 ABPCs specific for FOLR1: a) bind in a pH-dependent manner to cells, e.g., bind at a neutral pH but not an acidic pH and b) release from cells in a pH-dependent manner, e.g. bind at a neutral pH and release at an acidic pH and c) show enhanced endolysosomal accumulation in FOLR1+ cells and d) show increased FOLR1 antigen density after exposure to FOLR1+ cells and e) when conjugated to a toxin, show increased cytotoxicity to FOLR1+ cells and f) when conjugated to a toxin, show increased toxin liberation when incubated with FOLR1+ cells and g) show decreased half life when exposed to FOLR1 antigen in a relevant animal model and h) when conjugated to a toxin, show increased efficacy in a mouse xenograft model of FOLR1+ cells. Similarly, the exemplary properties of pH-engineered FOLR1×BINDER ABPCs specific for FOLR1 can be demonstrated using the methods described herein, with the appropriate control being a control ABPC FOLR1×BINDER bispecific ABPC specific for FOLR1.

Example 9. Construction and Screening of pH-Engineered FOLR1 ABPCs

Figure 1:
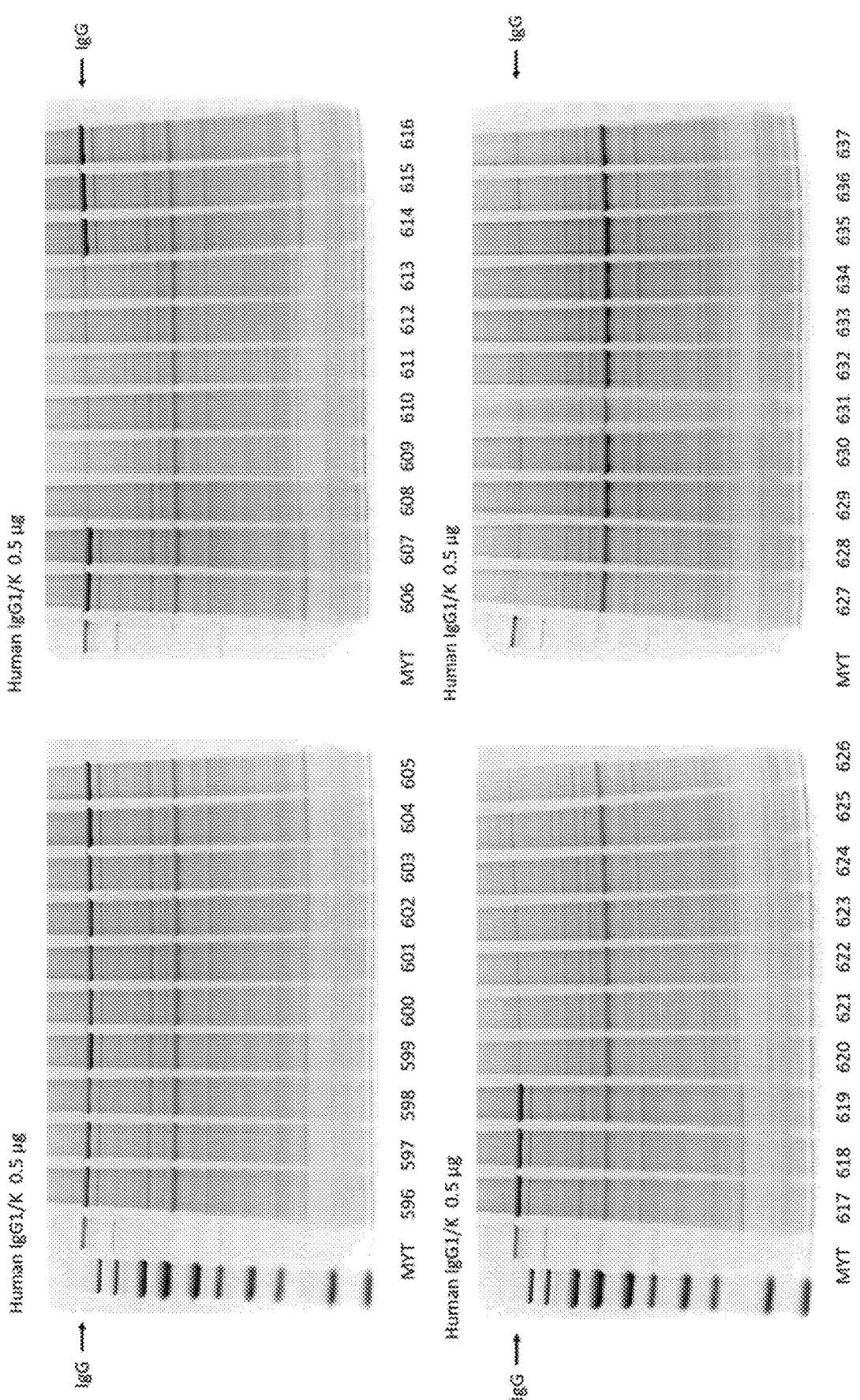
FIG. 1: SDS PAGE for MIRVETUXIMAB histidine scanning and alanine scanning. Expi293 cell culture supernatants post-harvest were loaded on non-reduced SDS PAGE gels to confirm expression of MIRVETUXIMAB and histidine scanning and alanine scanning variants. Arrows show the corresponding size for an IgG on a non-reduced SDS PAGE gel. MYT0596 is MIRVETUXIMAB and the rest of the lanes (MYT0597-MYT0637) are MIRVETUXIMAB heavy chain histidine scanning and alanine scanning variants.
Figure 2A:
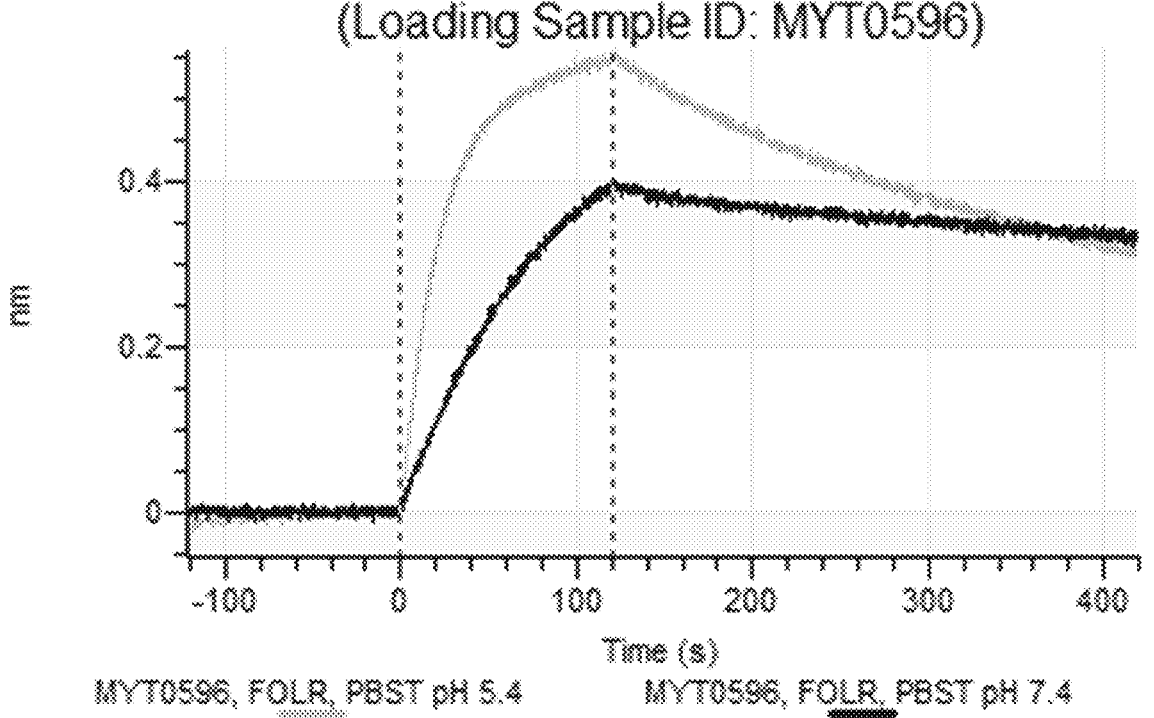
FIGS. 2a to 2ap: Binding of MIRVETUXIMAB starting ABPC and histidine scanning and alanine scanning variants to FOLR1 by biolayer interferometry. MYT0596 (MIR-VETUXIMAB) and MYT0597-MYT0637, heavy chain histidine scanning and alanine scanning variants, were captured on anti-human Fc biosensors and associated with FOLR1 at low pH or high pH, as specified in the figures.
Figure 2B:
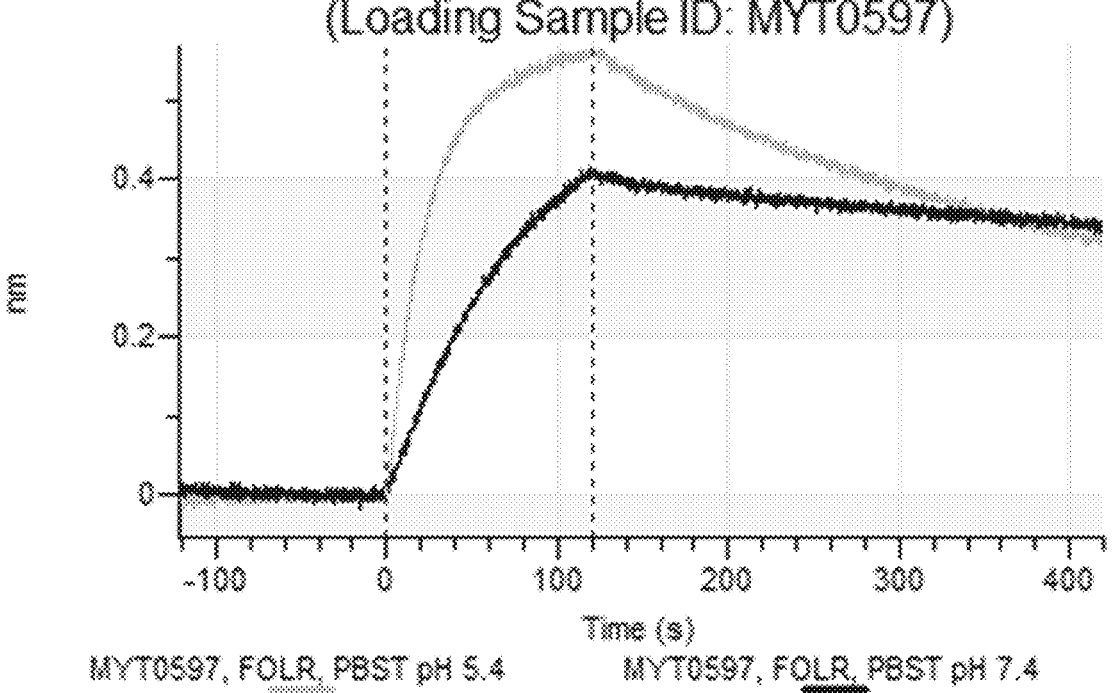
Figure 2C:
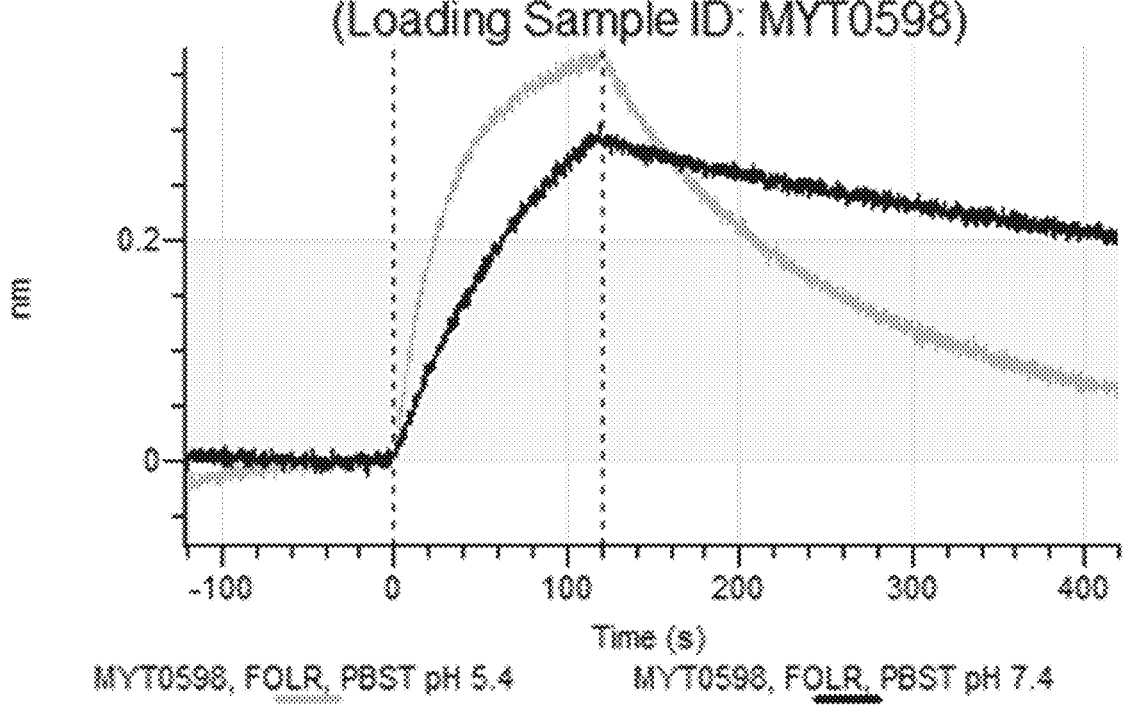
Figure 2D:
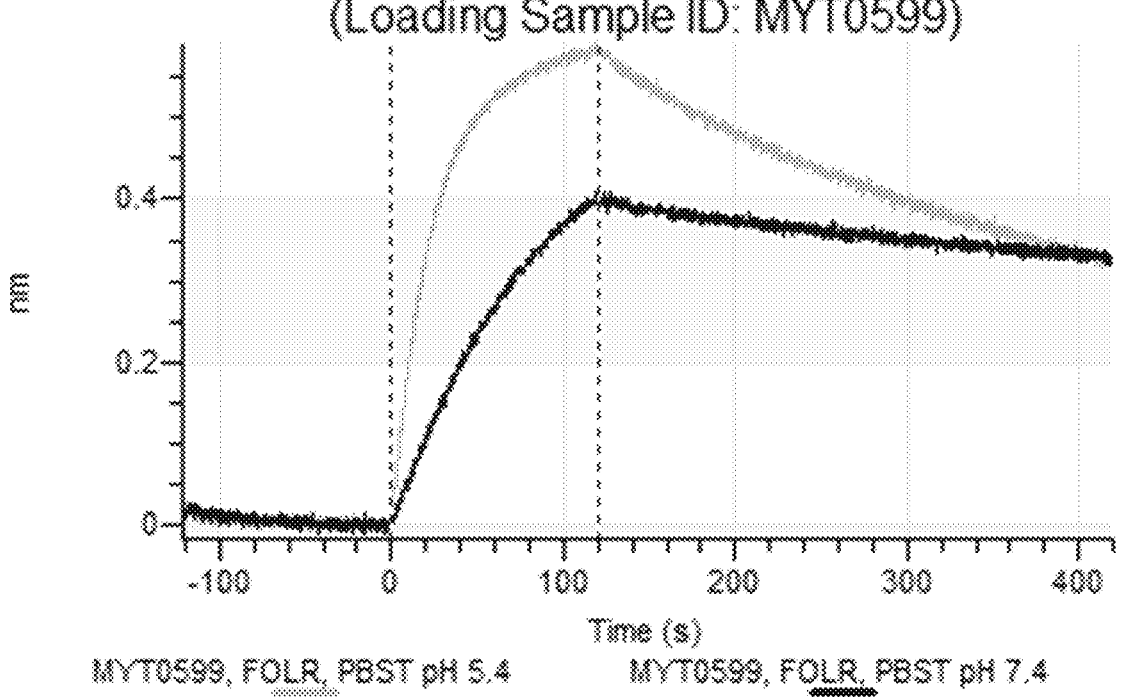
Figure 2E:
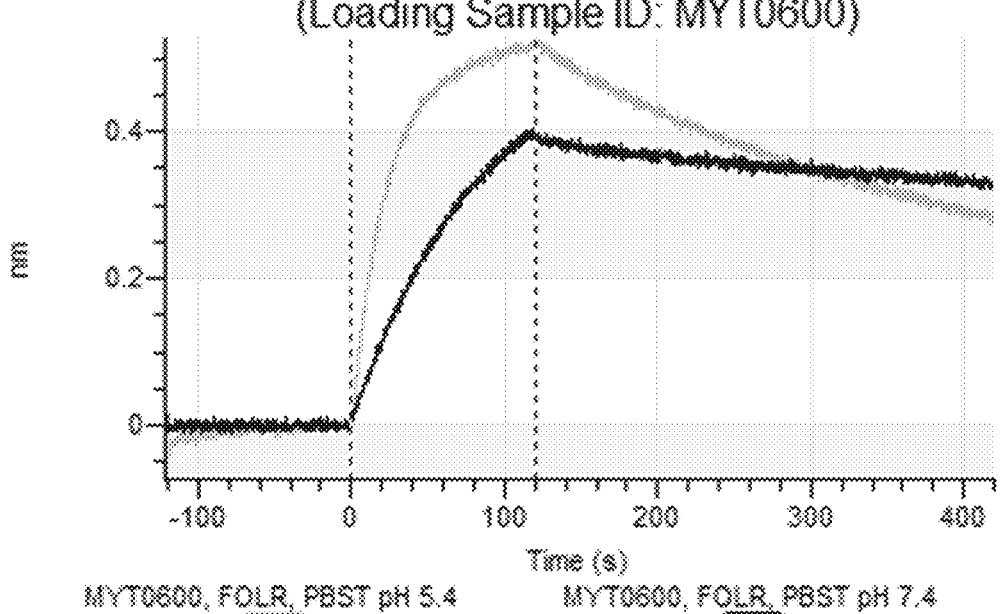
Figure 2F:
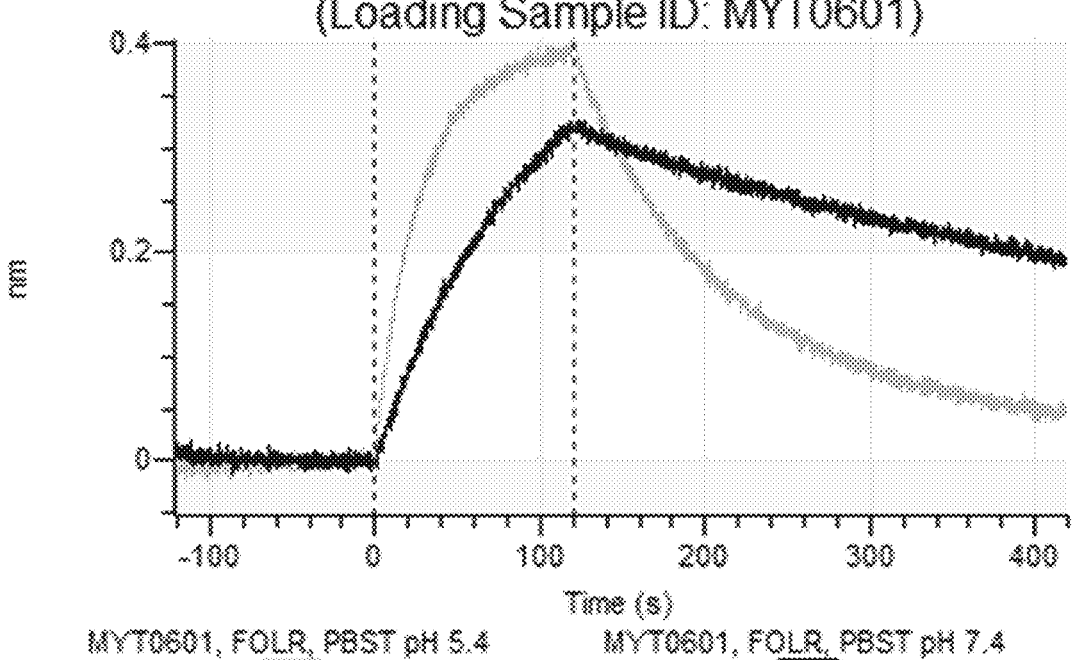
Figure 2G:
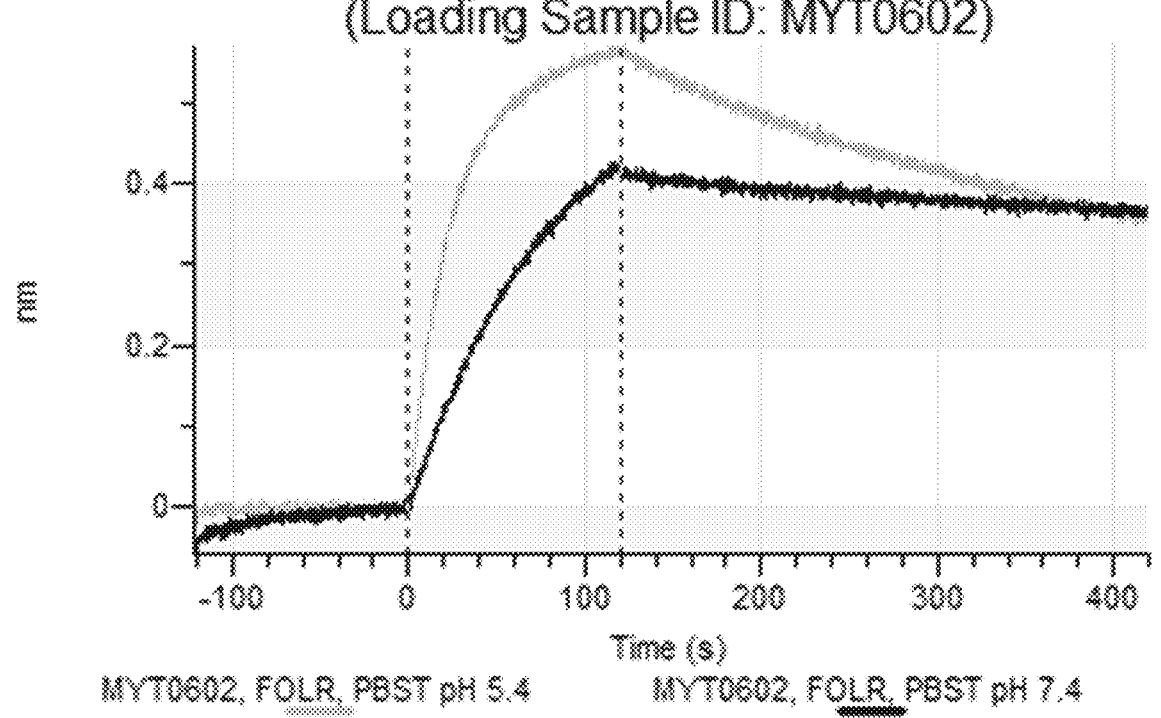
Figure 2H:
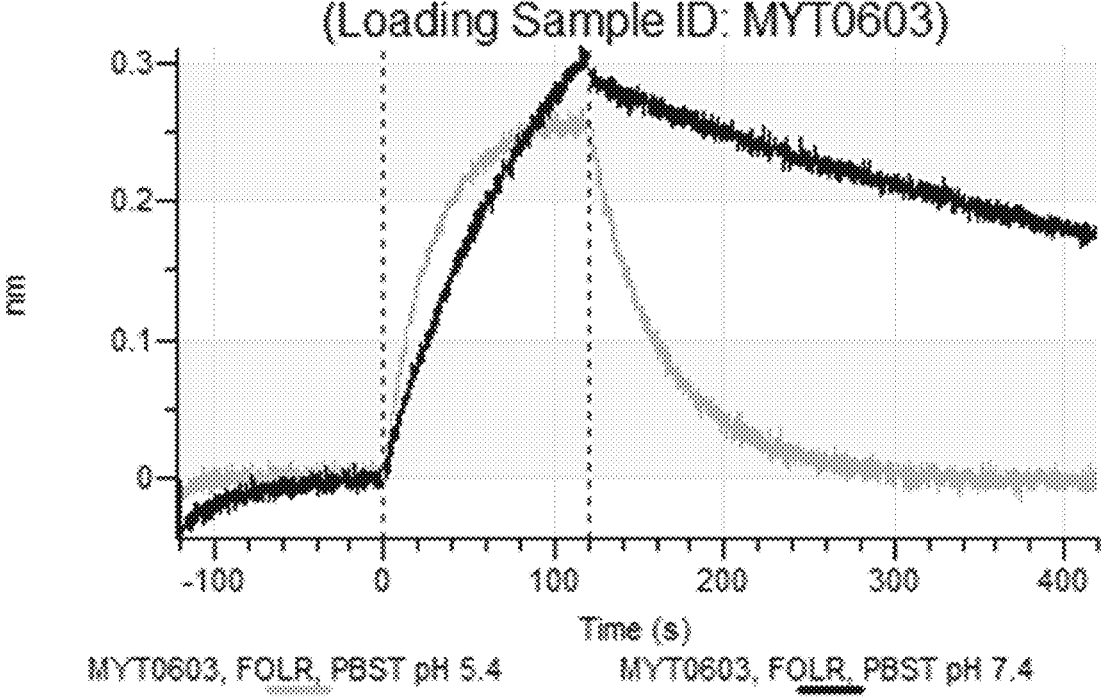
Figure 2I:
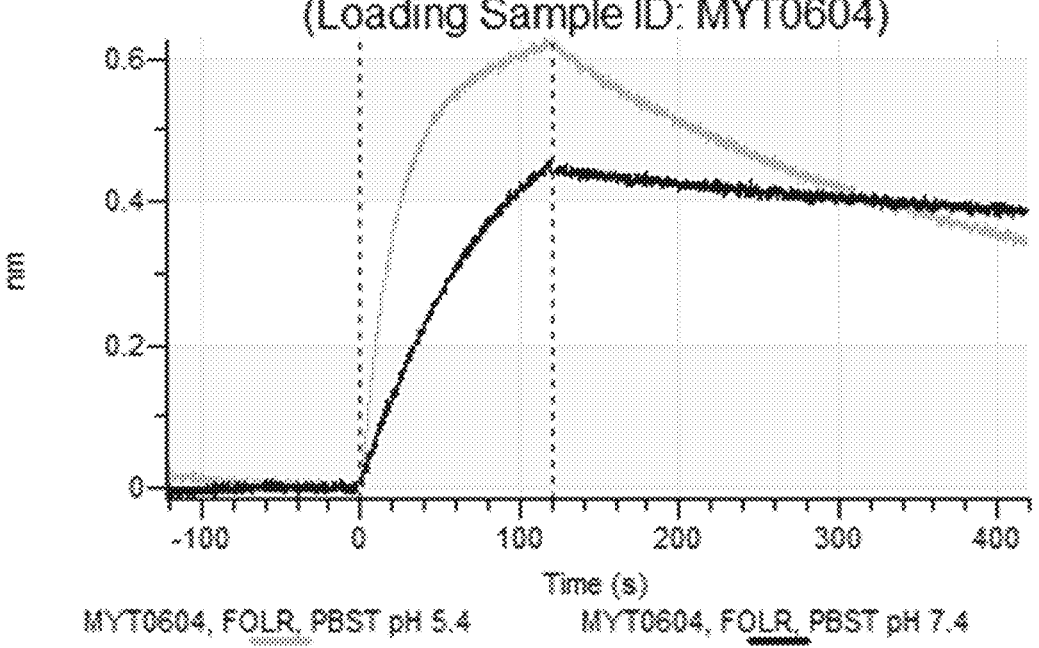
Figure 2J:
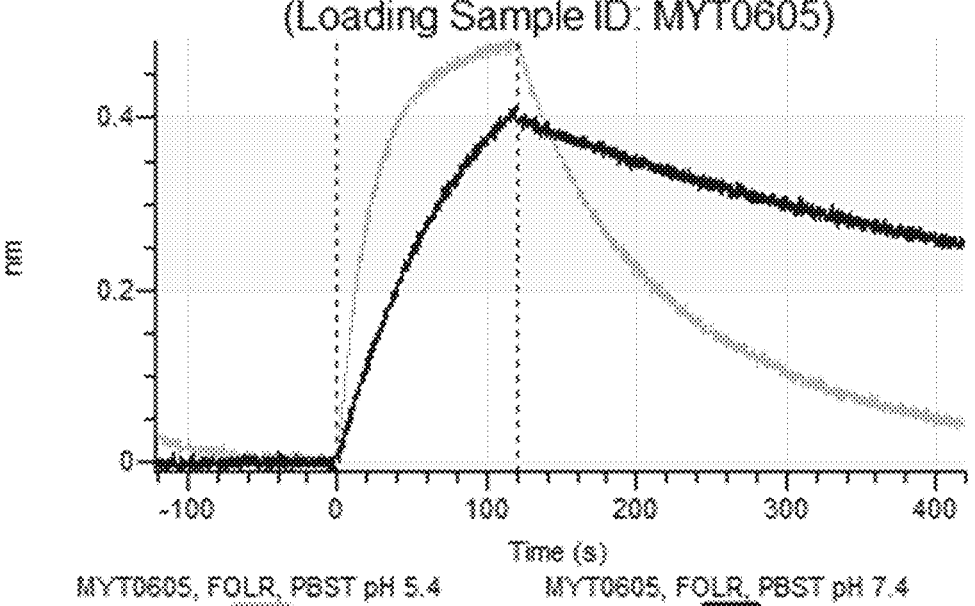
Figure 2K:
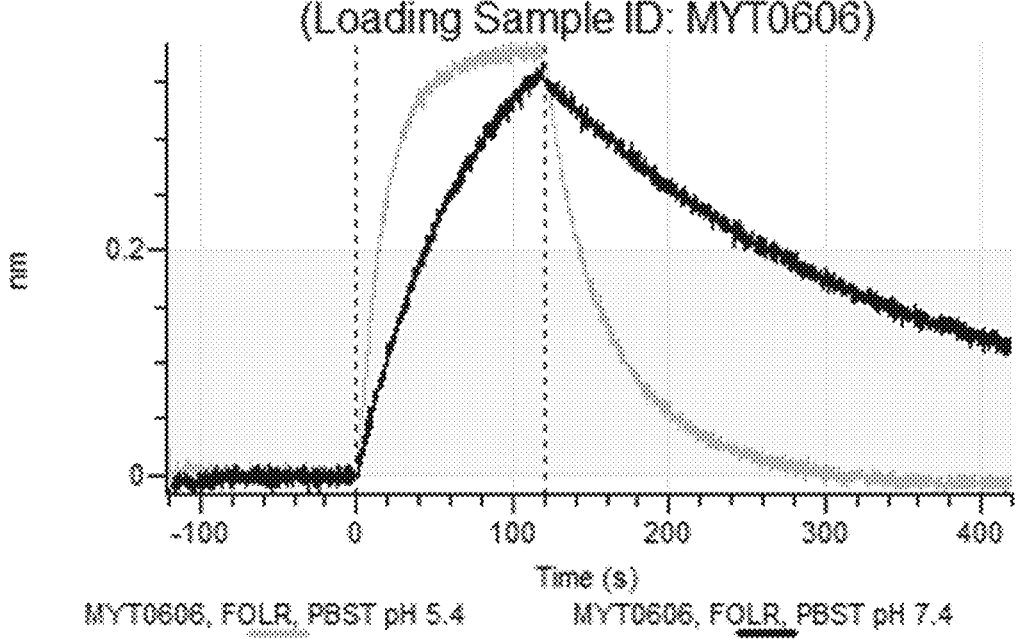
Figure 2I:
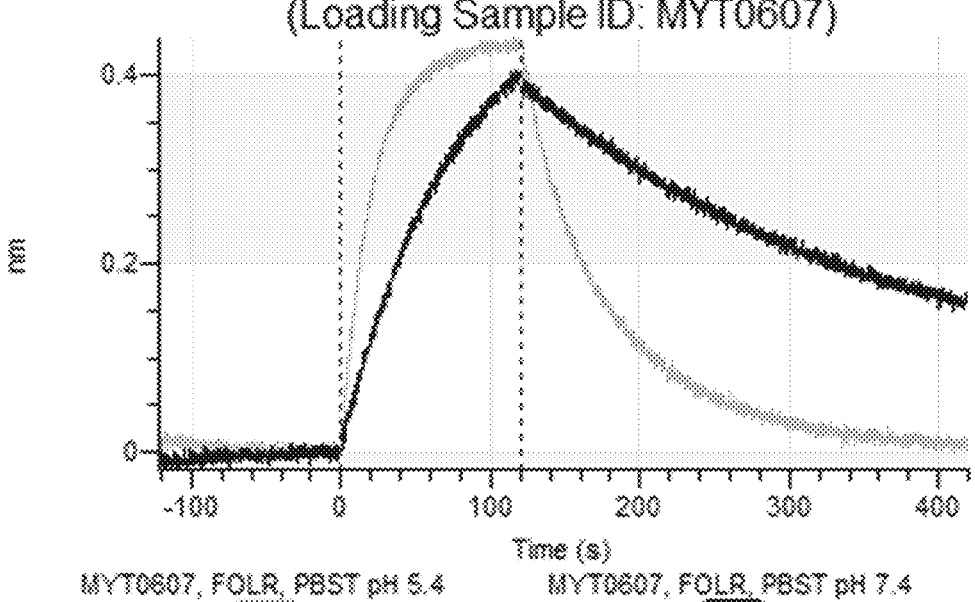
Figure 2M:
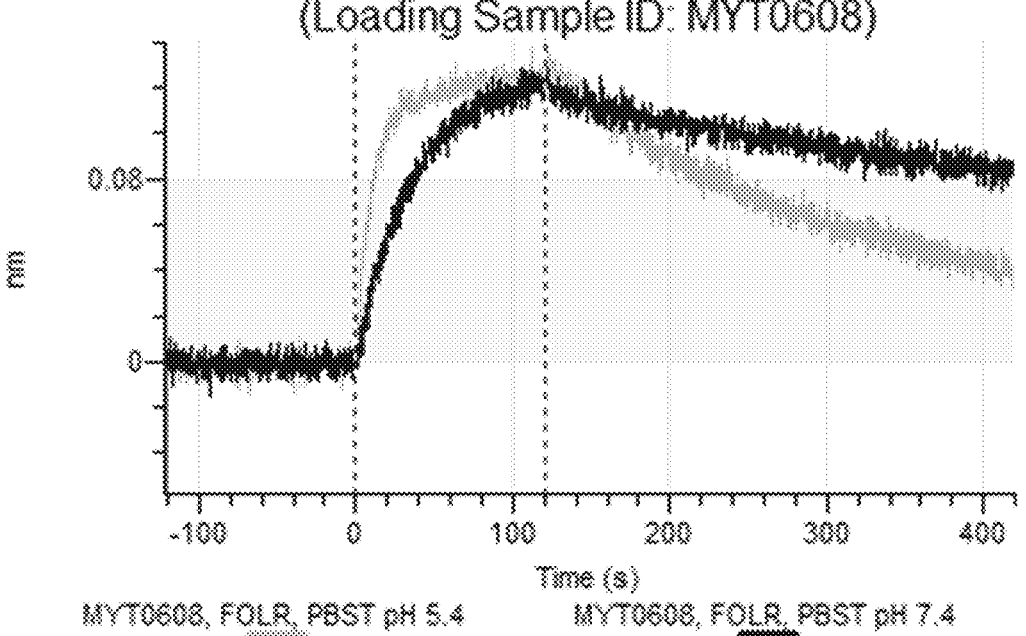
Figure 2N:
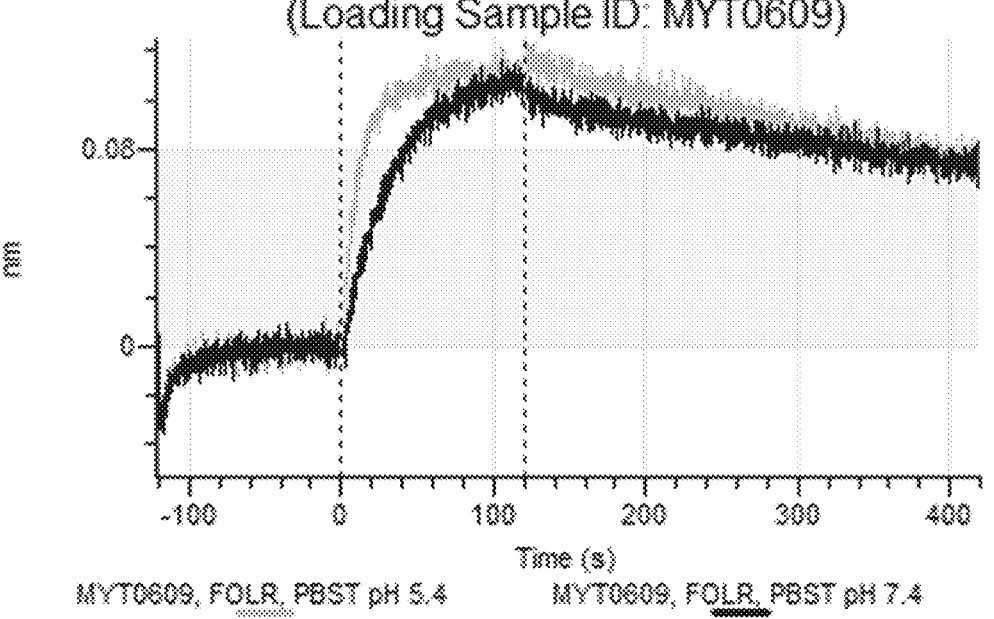
Figure 2O:
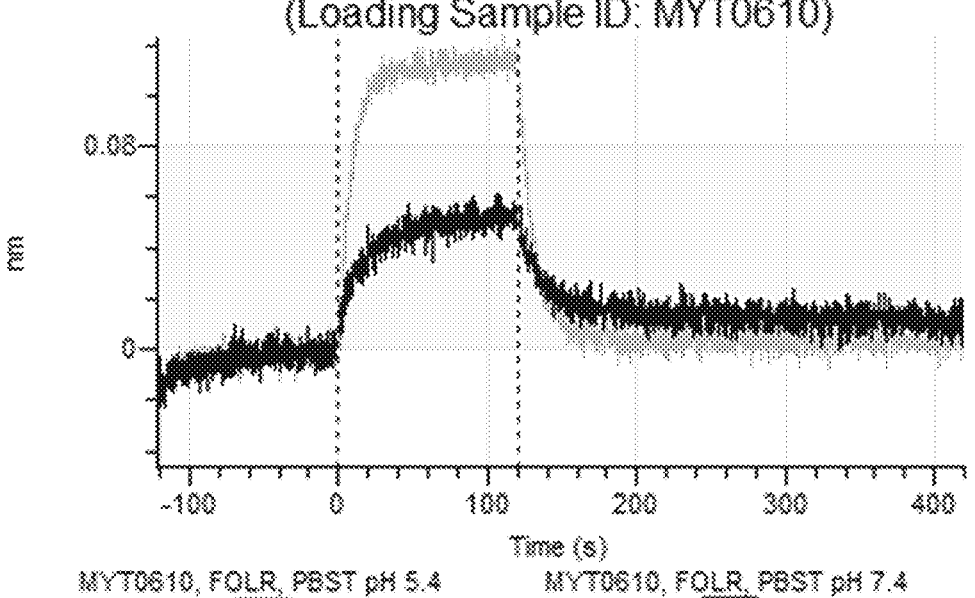
Figure 2P:
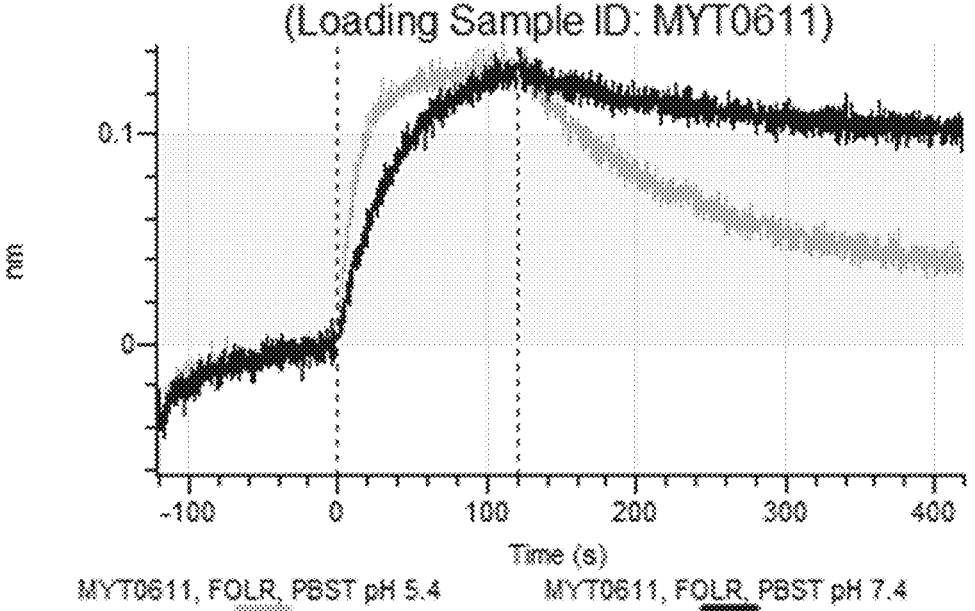
Figure 2Q:
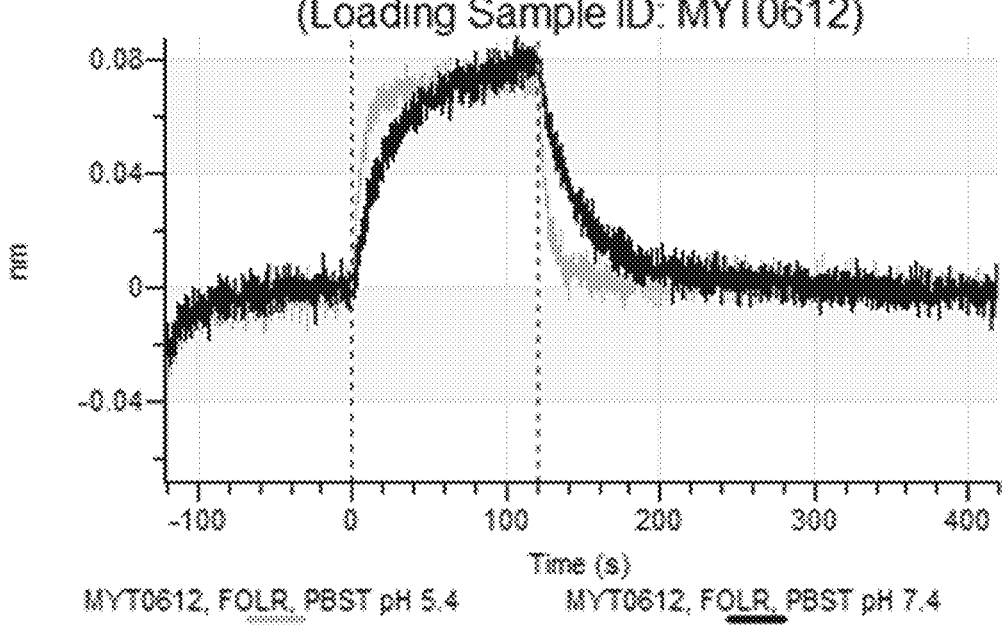
Figure 2R:
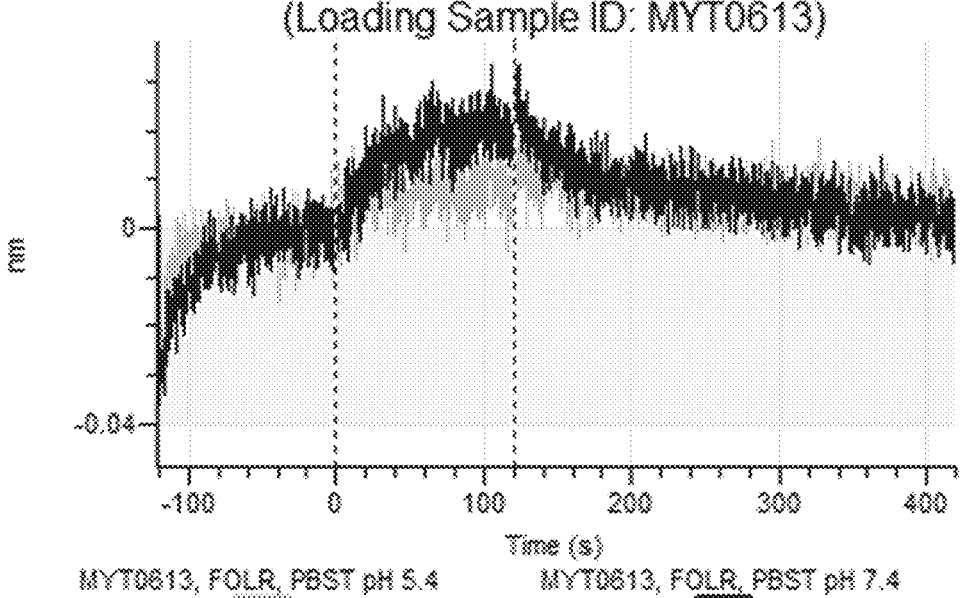
Figure 2S:
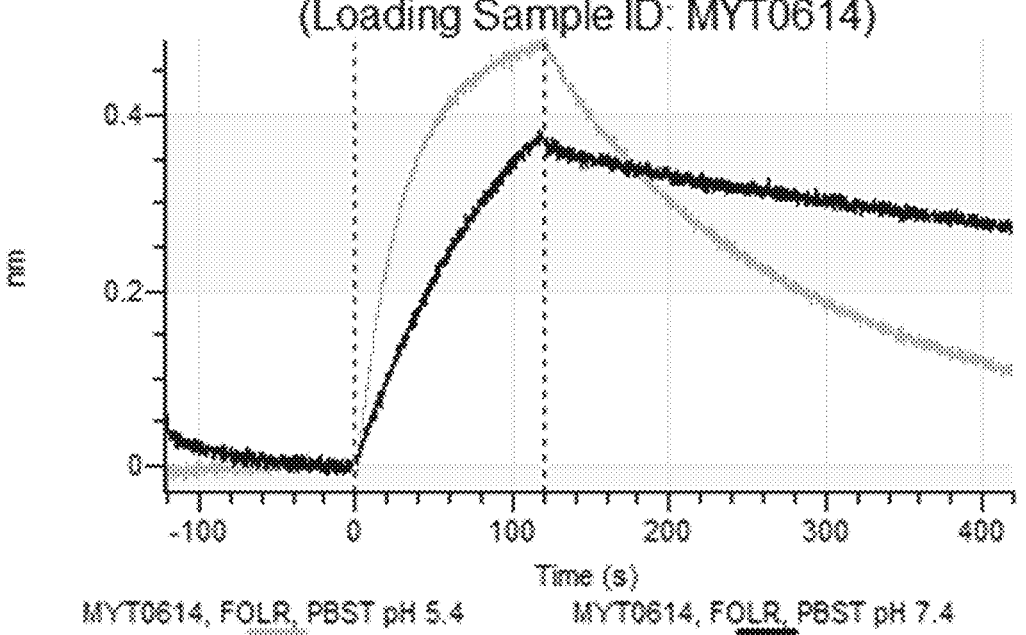
Figure 2T:
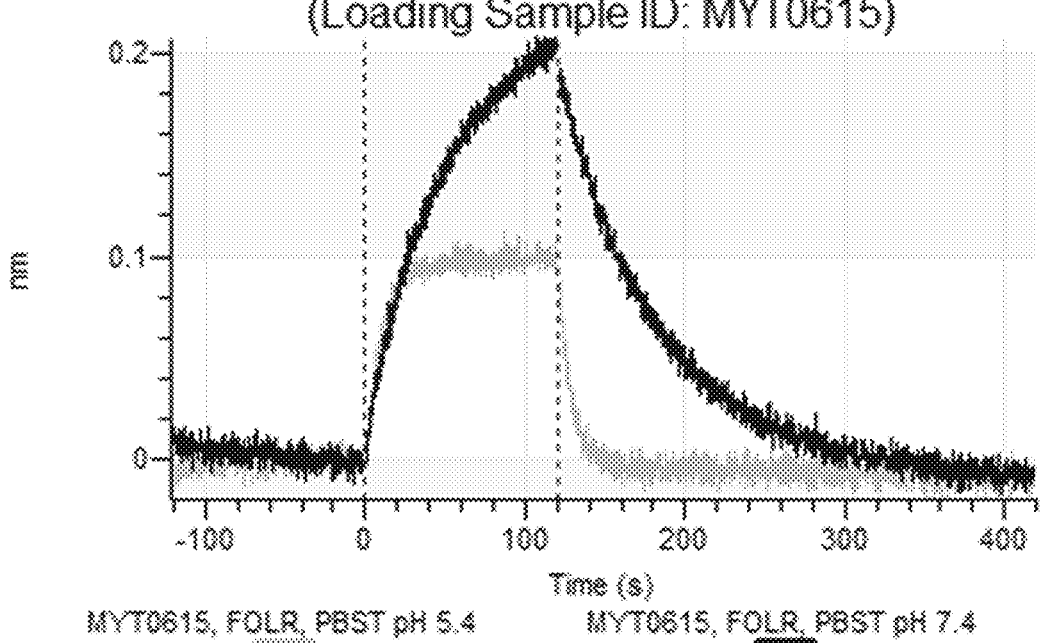
Figure 2U:
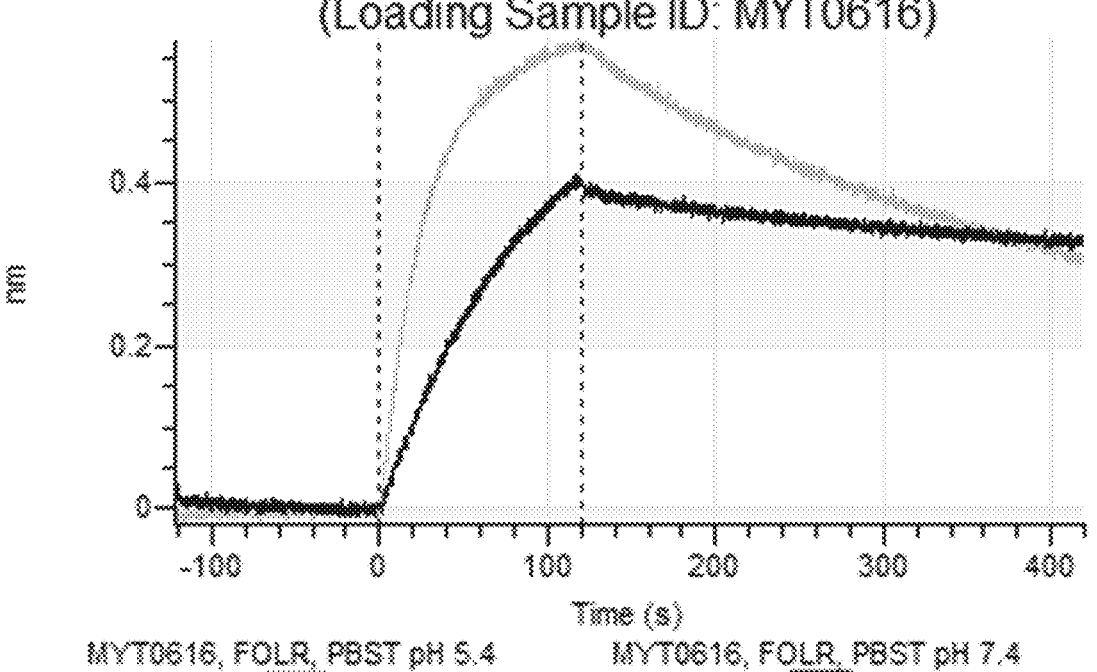
Figure 2V:
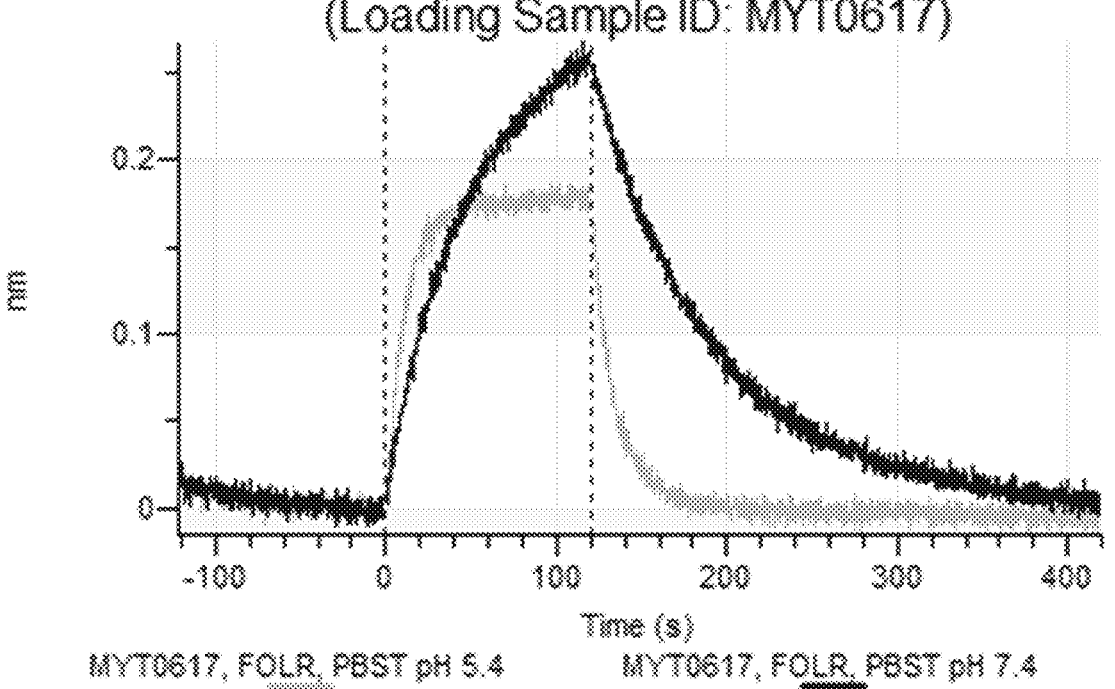
Figure 2W:
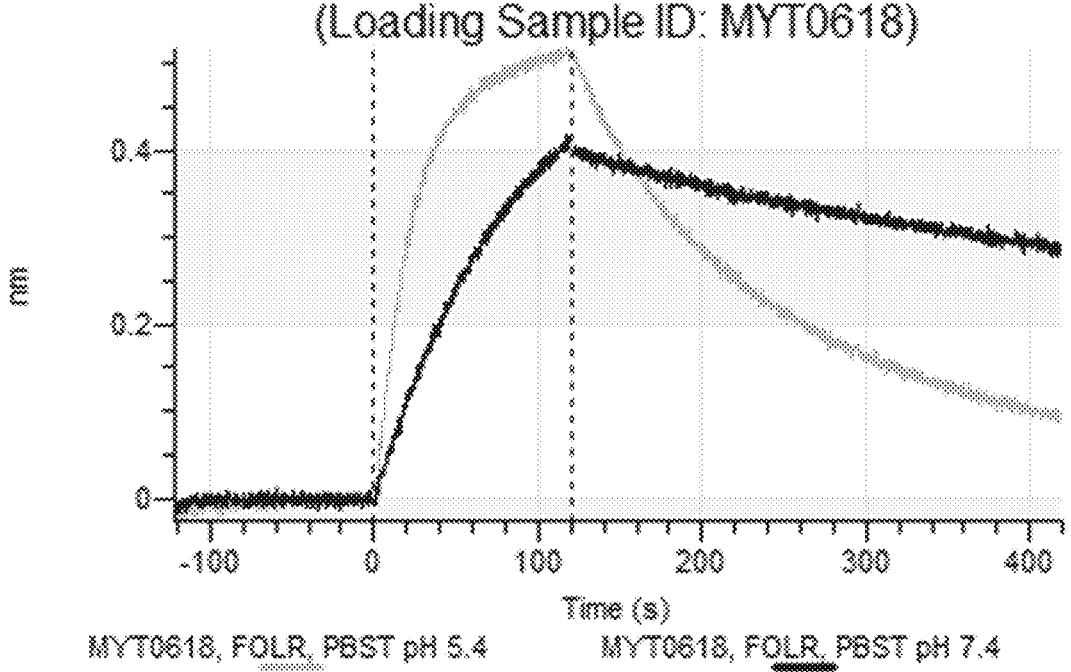
Figure 2X:
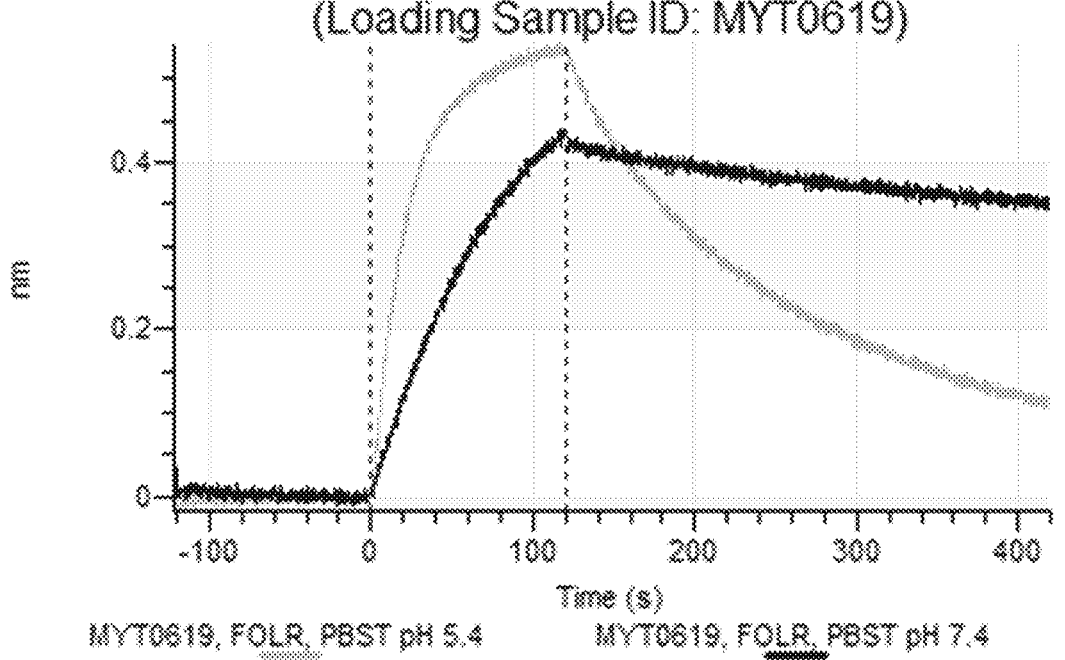
Figure 2Y:
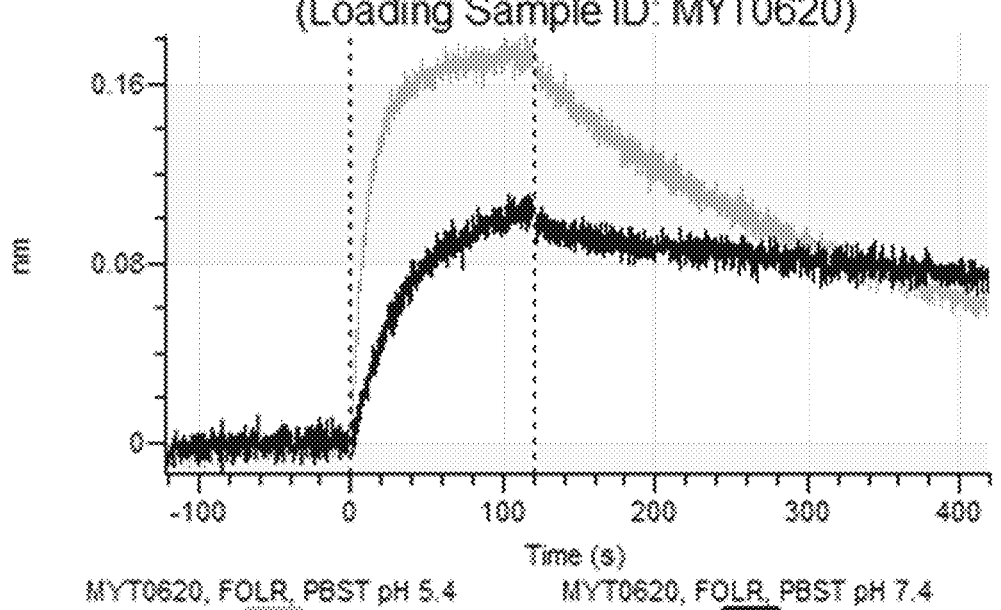
Figure 2Z:
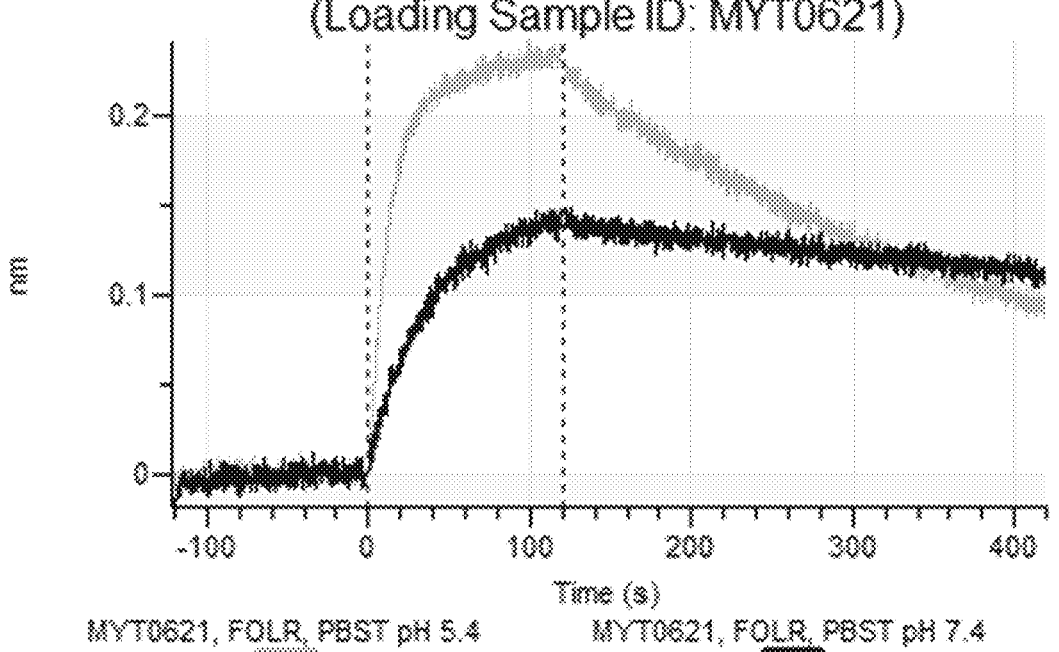
Figure 2A:
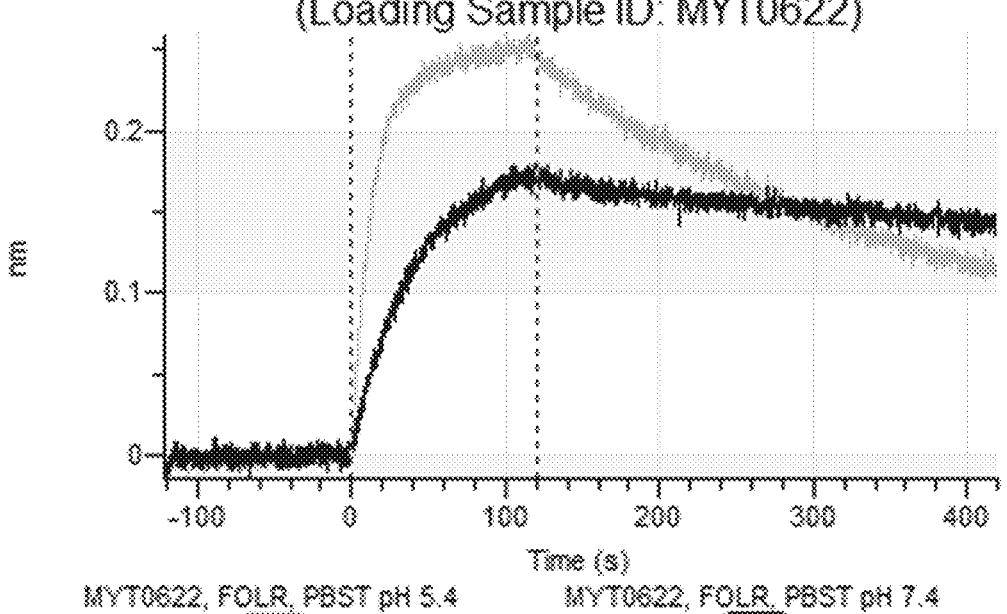
Figure 2A:
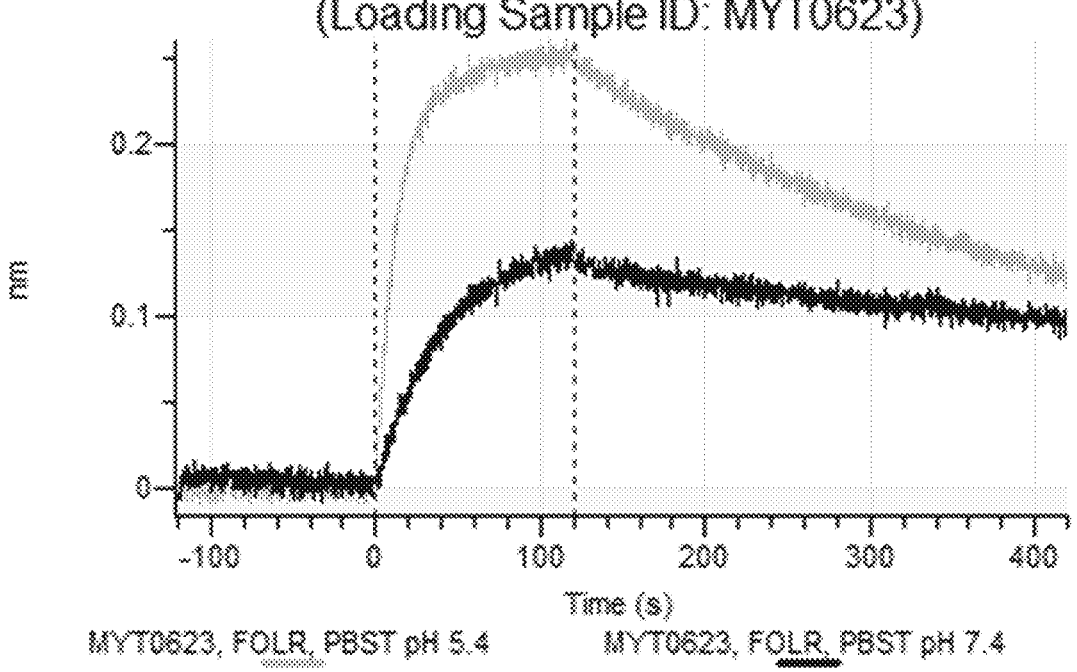
Figure 2A:
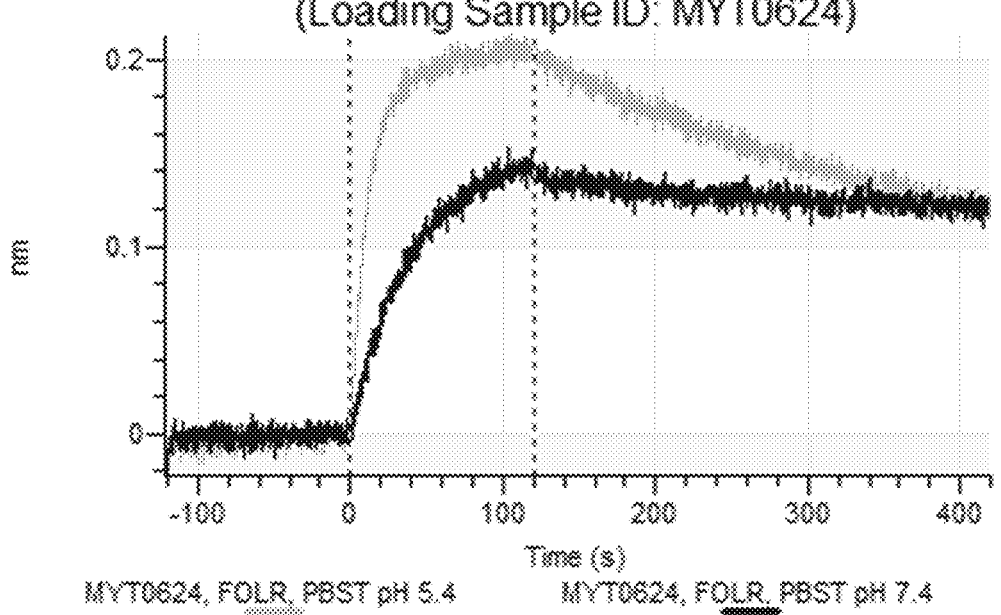
Figure 2A:
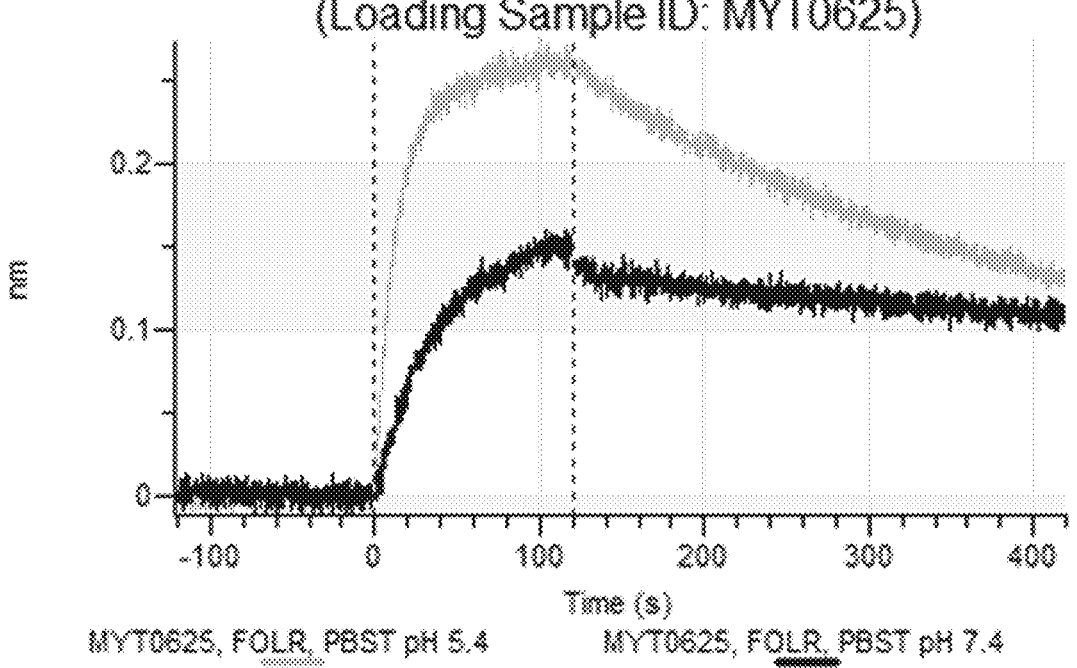
Figure 2A:
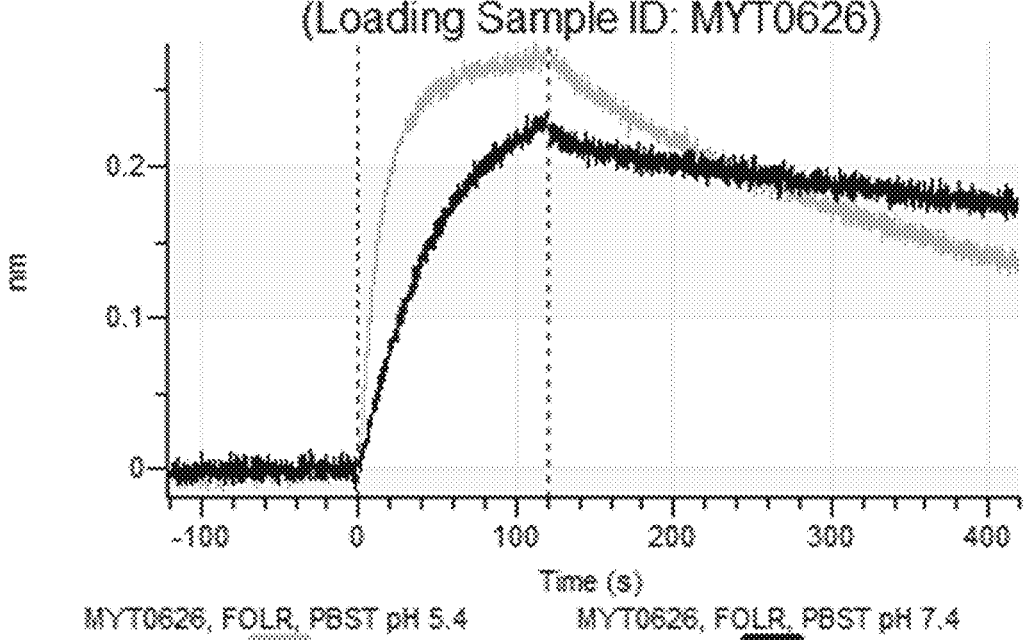
Figure 2A:
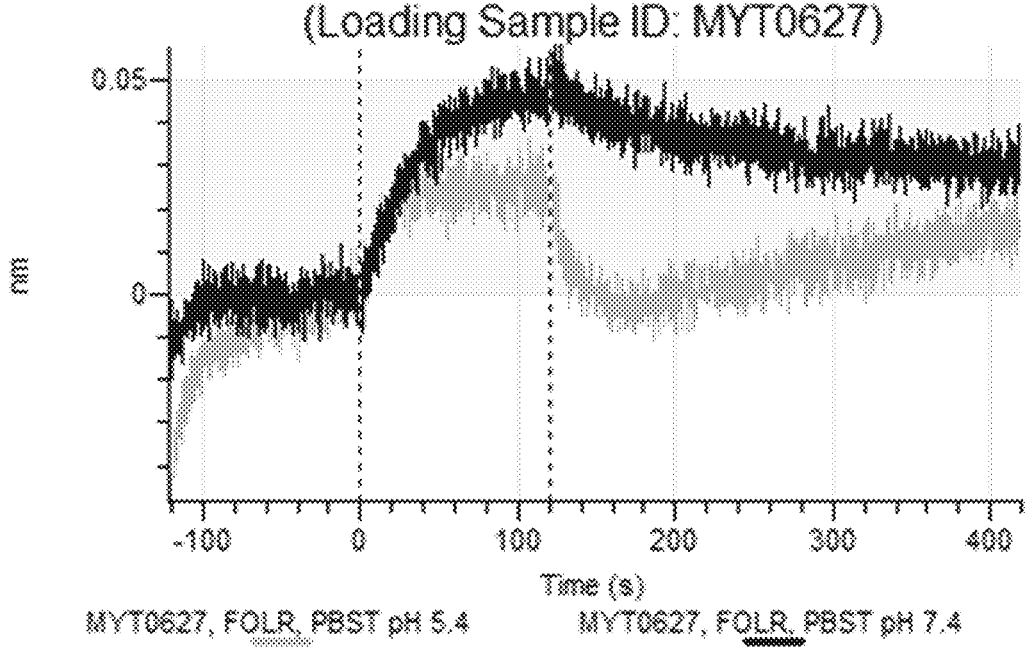
Figure 2A:
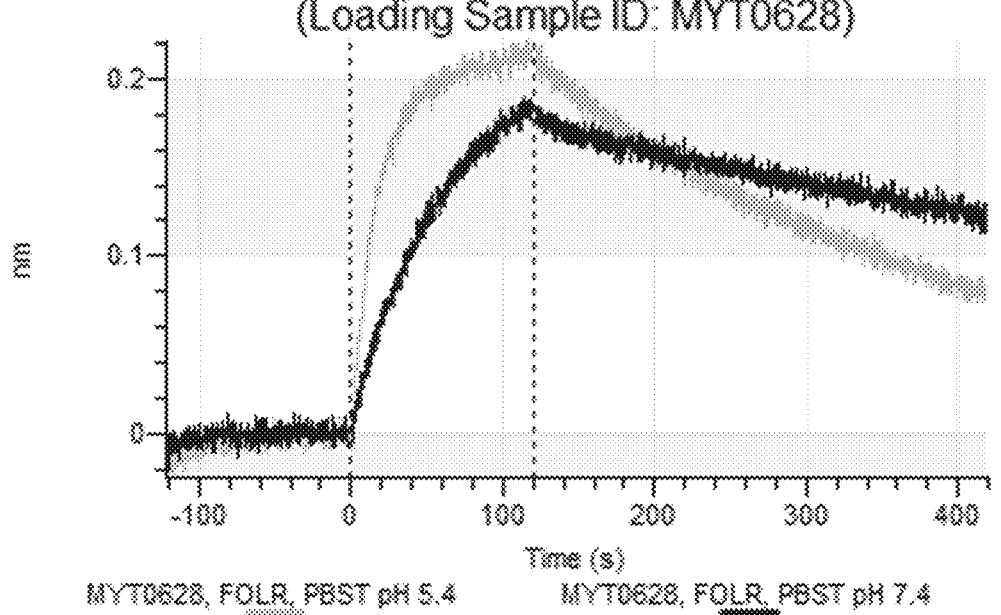
Figure 2A:
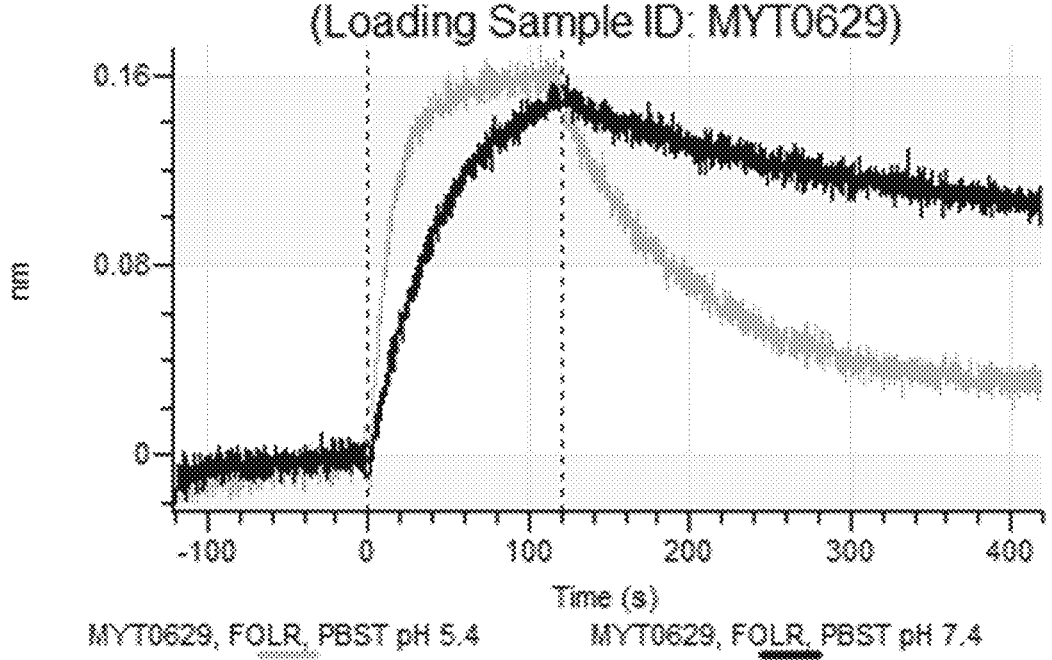
Figure 2A:
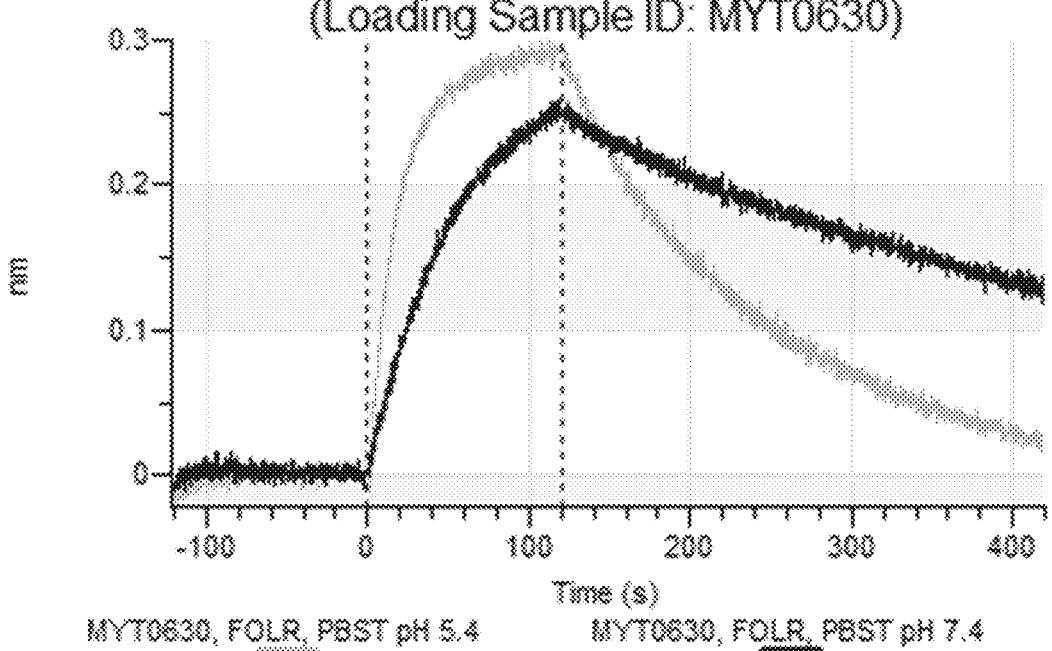
Figure 2A:
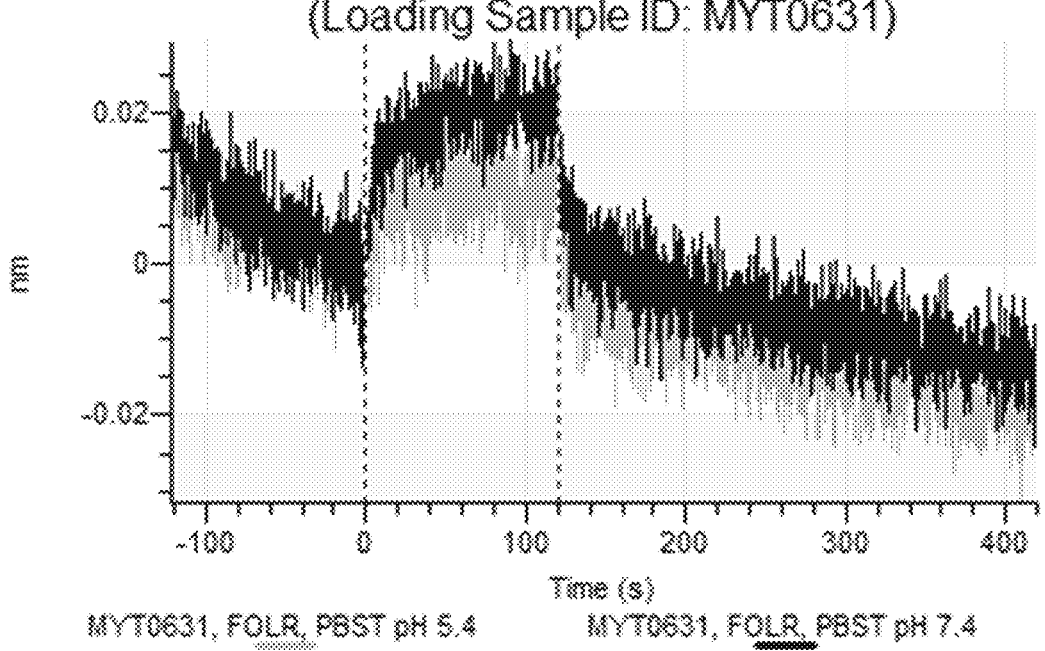
Figure 2A:
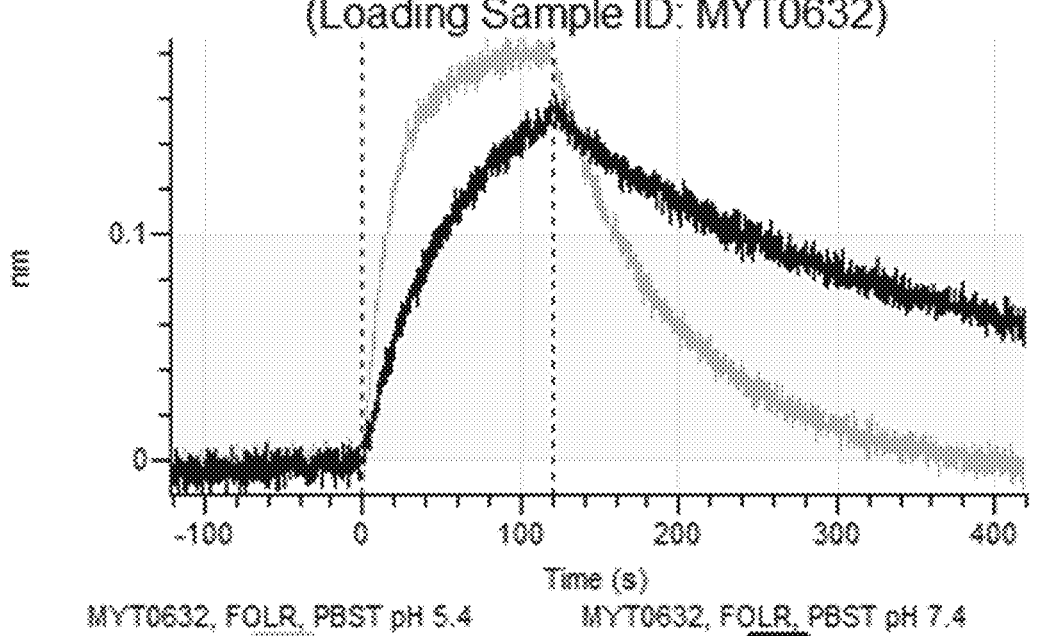
Figure 2A:
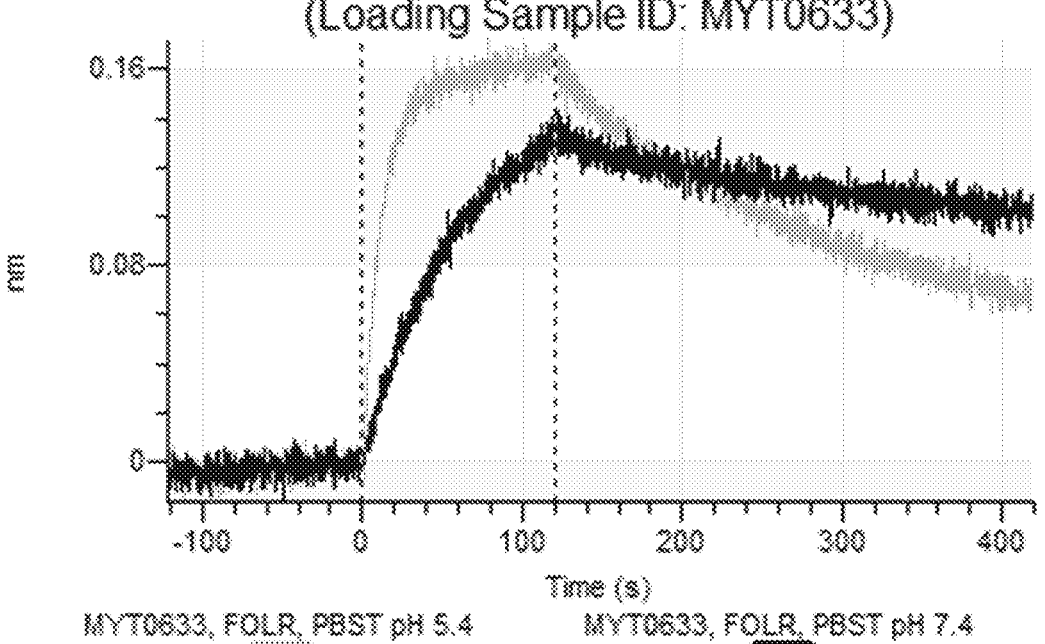
Figure 2A:
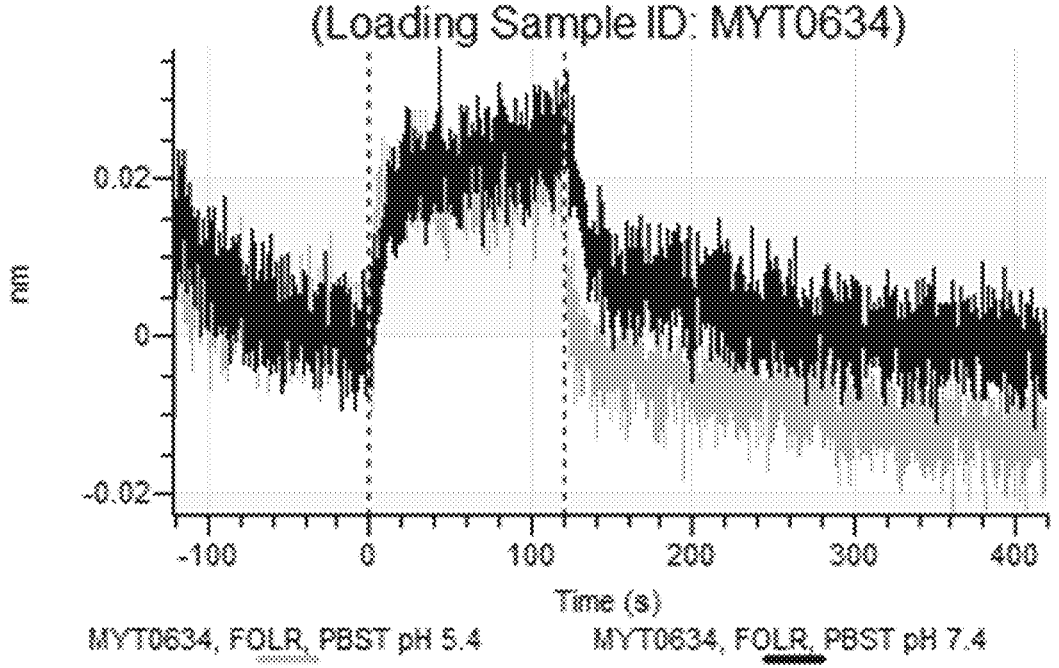
Figure 2A:
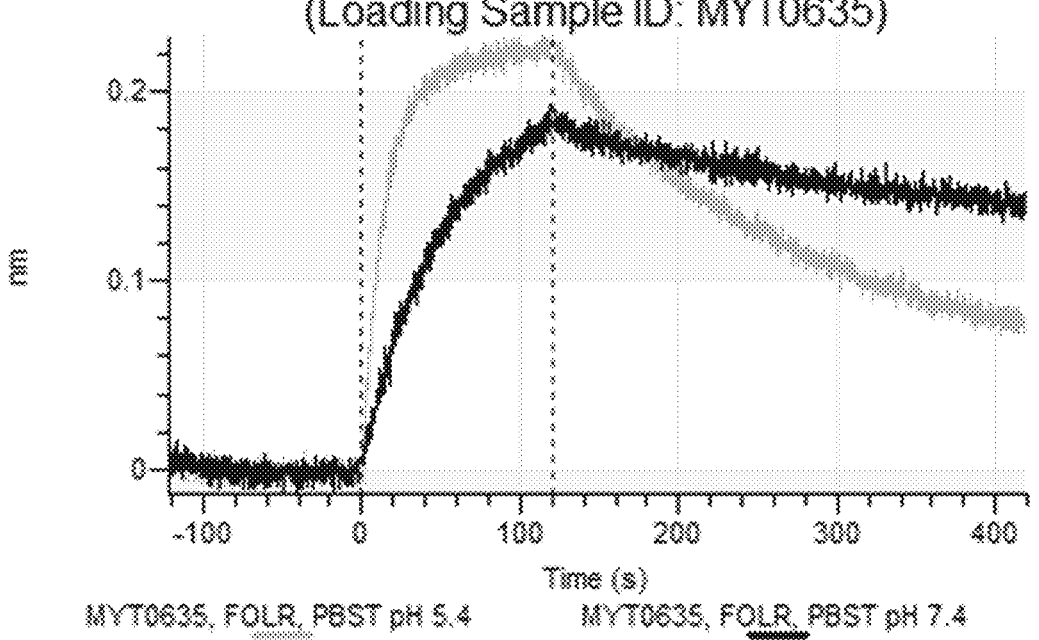
Figure 2A:
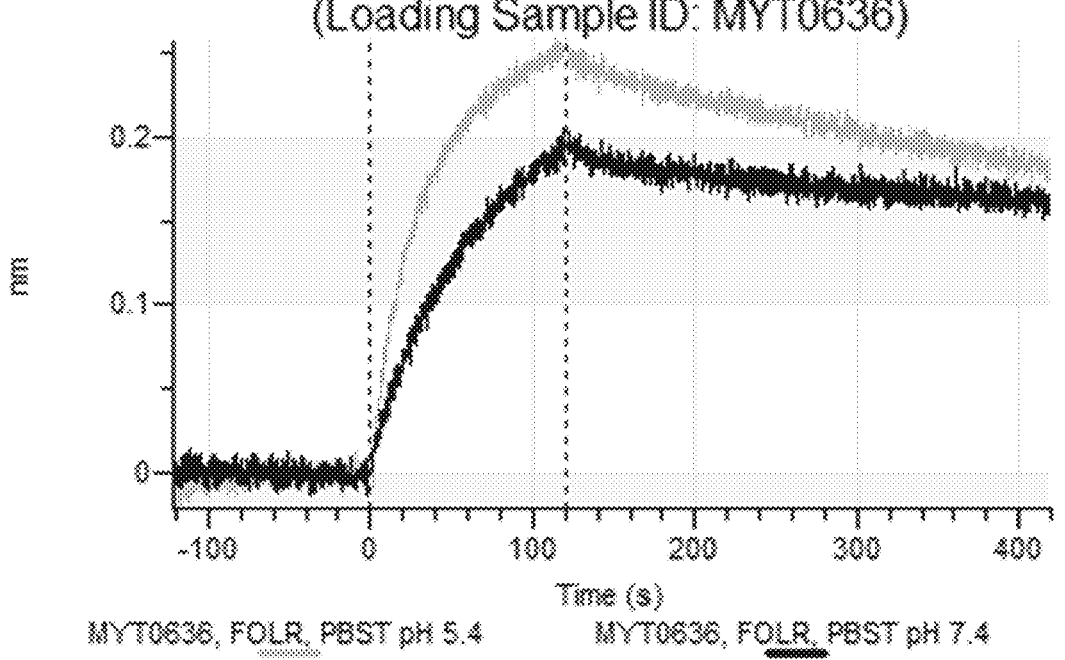
Figure 2A:
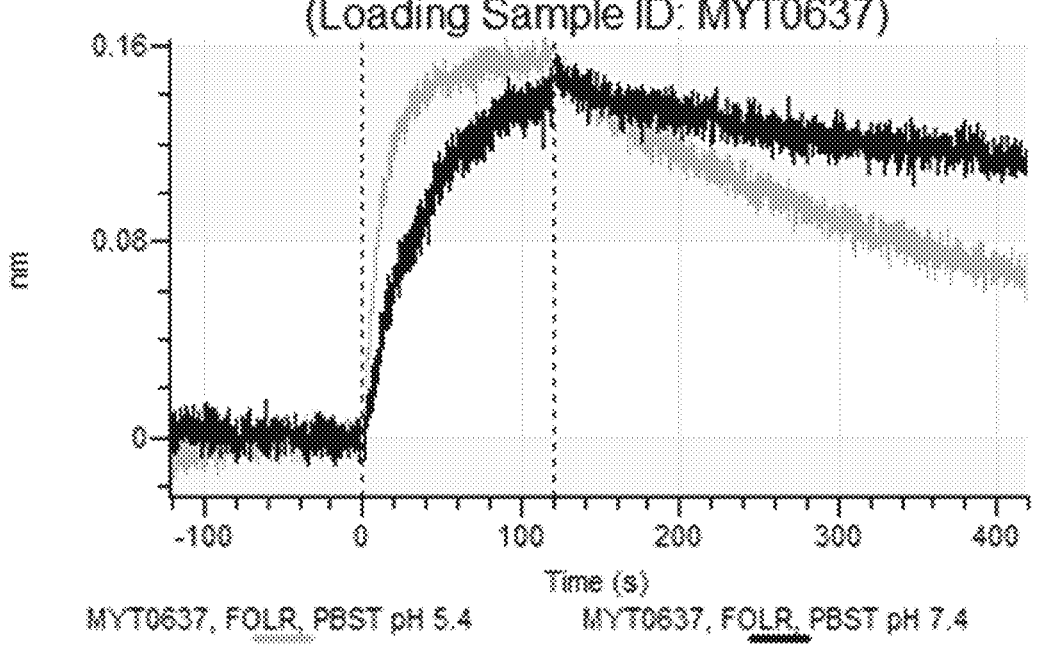

Multiple FOLR1-binding monoclonal antibodies have been described in the literature and can be used as a template for engineering pH-dependent binding (Altwerger G et al (2018) "In Vitro and In Vivo Activity of IMGN853, an Antibody-Drug Conjugate Targeting Folate Receptor Alpha Linked to DM4, in Biologically Aggressive Endometrial Cancers" Molecular Cancer Therapeutics 17(5): 1003-1011). We selected mirvetuximab (Heavy chain SEQ ID NO: 1, Light chain SEQ ID NO: 2) as a FOLR1-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time (MYT0597-MYT0637). In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting ABPC light chain using methods known to the art. After allowing for four days of protein expression, cell culture supernatants were collected, quantified by SDS-PAGE analysis, (FIG. 1), and the pH dependence of the variant was evaluated using biolayer interferometry (BLI) on an Octet RED 384 instrument. Briefly, 100 μL of cell culture supernatant was diluted into 100 μL of 1×PBST pH 7.4 for loading onto the sensor tips. Diluted supernatants were then captured on an anti-human Fe sensor (FORTEBIO® (biolayer interferometry systems)). A baseline was established using 1×PBST (50 mM Potassium Phosphate Buffer+150 mM NaCl+0.05% TWEEN® (polysorbate surfactants) 20) pH 7.4, and the sensor was associated with 50 nM of FOLR1 (R&D Systems, Cat #5646-FR) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (e.g., higher $k_{off}$ values) at pH 5.4 due to histidine or alanine substitution compared to the starting ABPC (with no substitutions), and b) reduced dissociation at pH 7.4 (e.g., lower $k_{off}$ values) compared to pH 5.4 in the antibody variant itself and with the starting ABPC (with no substitutions). Heavy chain variants that showed either enhanced dissociation at pH 5.4 or reduced dissociation at pH 7.4 or both (as compared to the starting ABPC), as shown in FIG. 2 were selected for further analysis (e.g., MYT0598, MYT0601, MYT0603, MYT0605-MYT0608, MYT0610, MYT0612, MYT0614, MYT0615, MYT0617-MYT0620, MYT0627-MYT0630, MYT0632, MYT0633, MYT0635, and MYT0637). It was also noted that while some histidine and alanine mutations obliterated FOLR1 binding (e.g., MYT0613, MYT0631, and MYT0634), others were tolerated with little (e.g., less than 1-fold change in dissociation constant KD or dissociation rate) or no change in FOLR1 binding kinetics (e.g., MYT0597, MYT0599, MYT0600, MYT0602, MYT0604, MYT0611, MYT0616, MYT0621-MYT0626, and MYT0636). Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 10. Construction and Screening of pH-Engineered FOLR1 ABPCs

Figure 4:
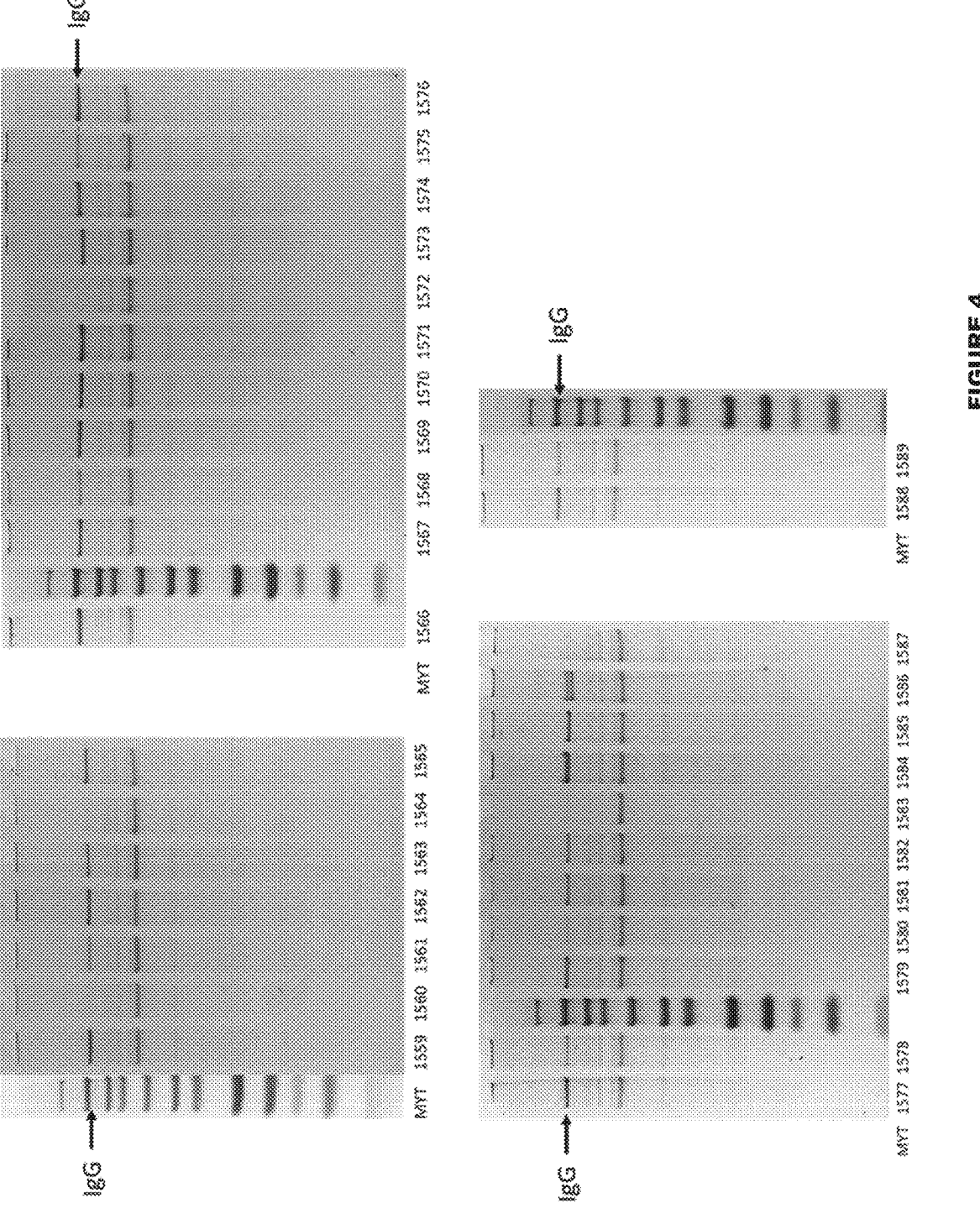
FIG. 4: SDS PAGE for MIRVETUXIMAB histidine scanning and alanine scanning. Expi293 cell culture supernatants post-harvest were loaded on non-reduced SDS PAGE gels to confirm expression of MIRVETUXIMAB histidine scanning and alanine scanning variants. Arrows show the corresponding size for an IgG on a non-reduced SDS PAGE gel. MYT1559-MYT1589 are MIRVETUXIMAB light chain histidine scanning and alanine scanning variants.
Figure 5A:
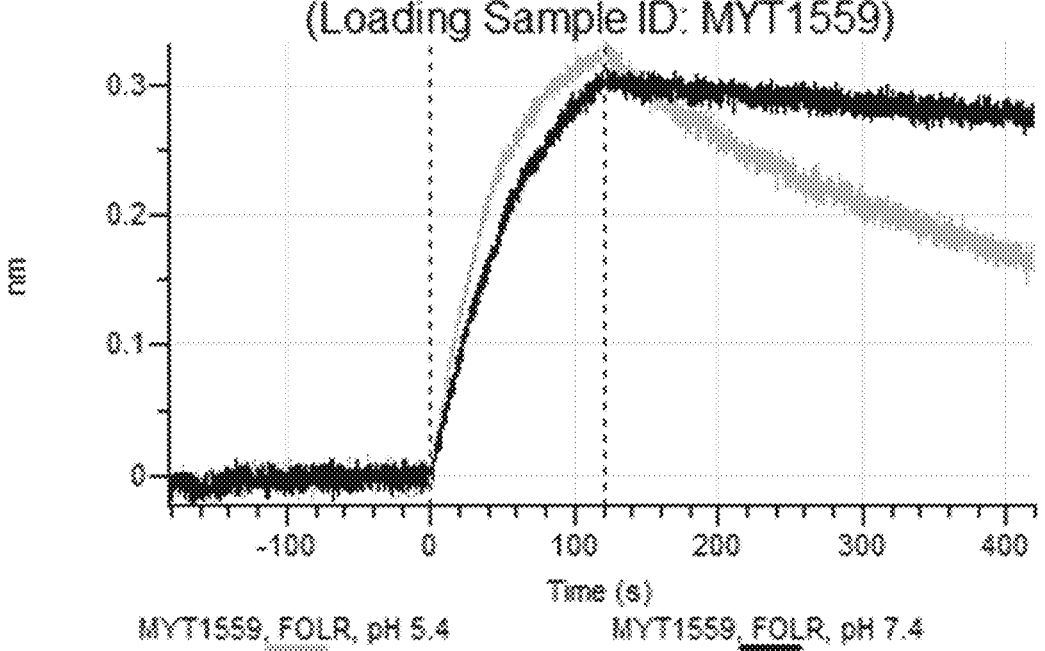
FIGS. 5a to 5ae: Binding of MIRVETUXIMAB histidine scanning and alanine scanning variants to FOLR1 by biolayer interferometry. MYT1559-MYT1589, light chain histidine scanning and alanine scanning variants, were captured on anti-human Fc biosensors and associated with FOLR1 at low pH or high pH, as specified in the figures.
Figure 5B:
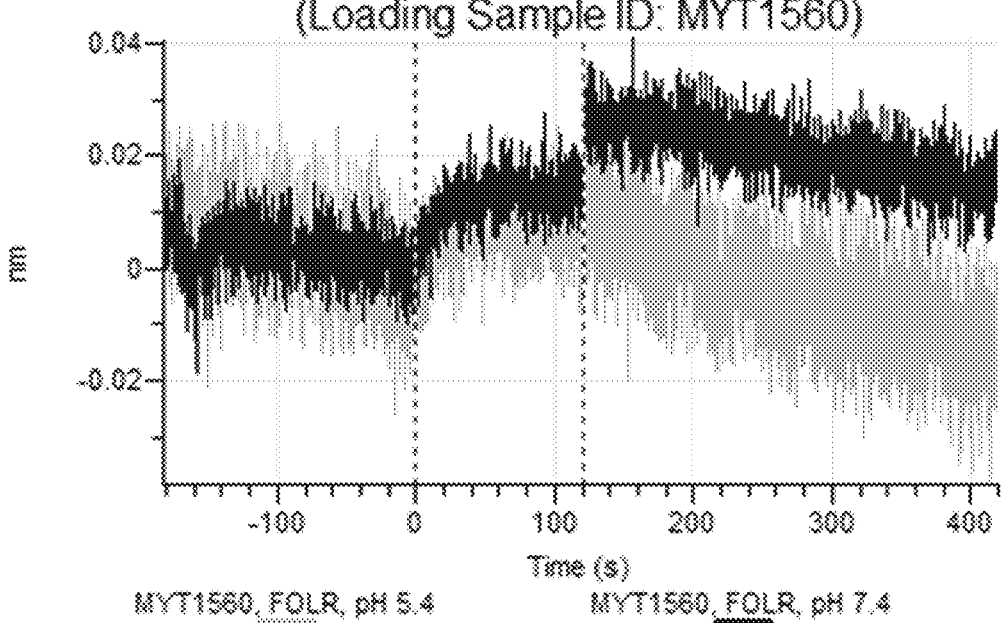
Figure 5C:
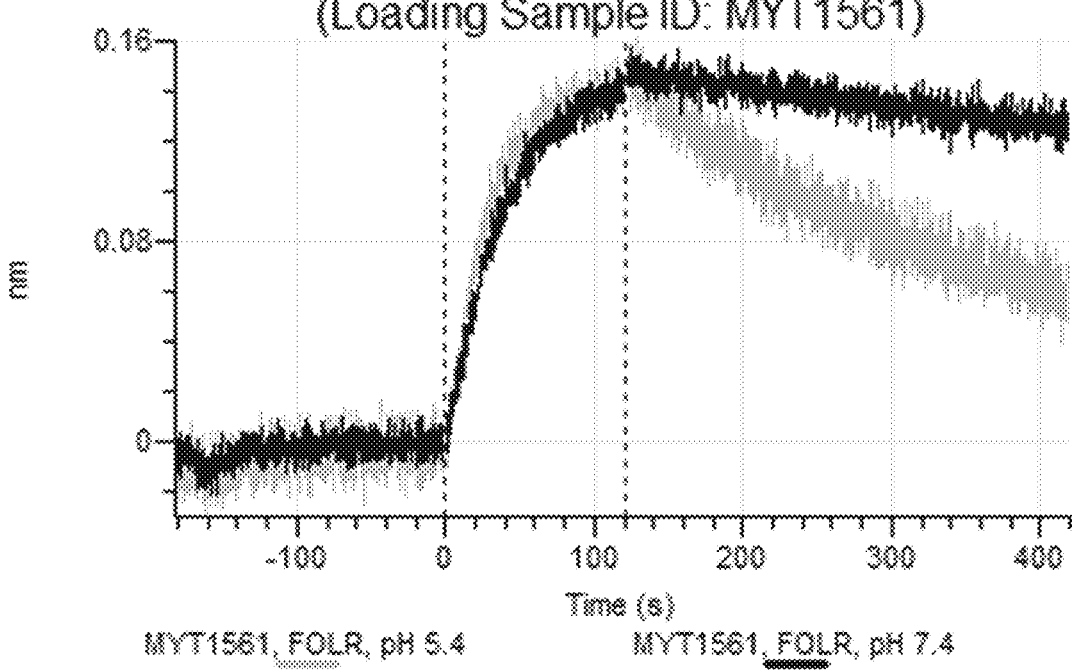
Figure 5D:
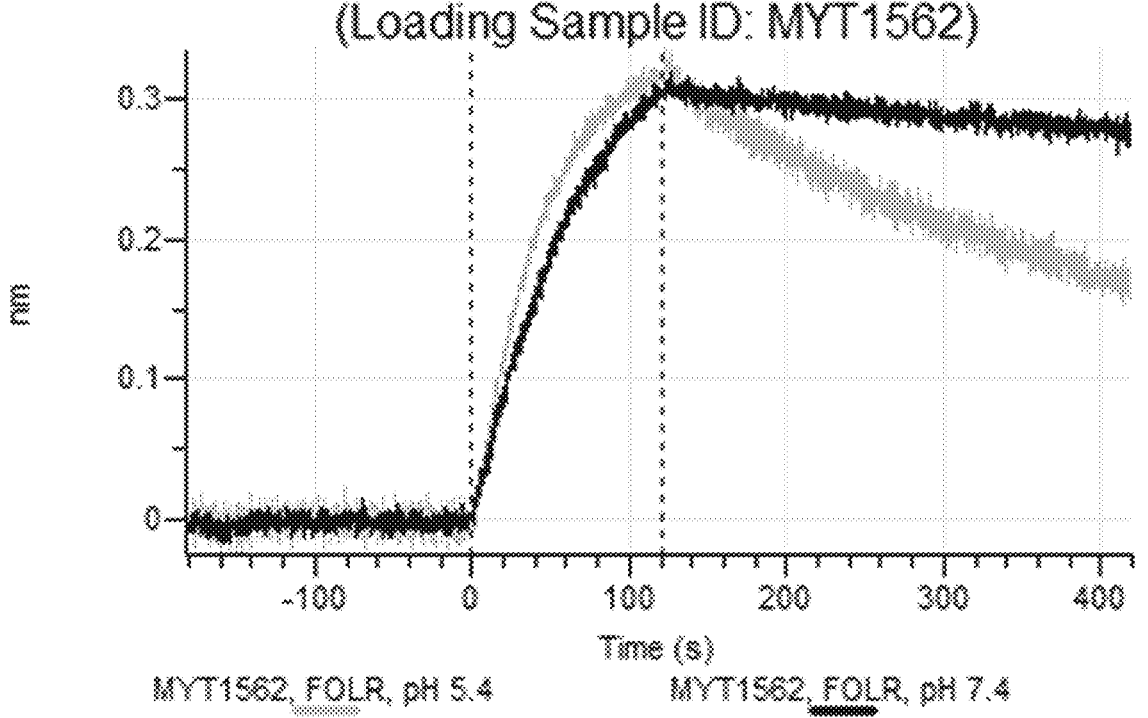
Figure 5E:
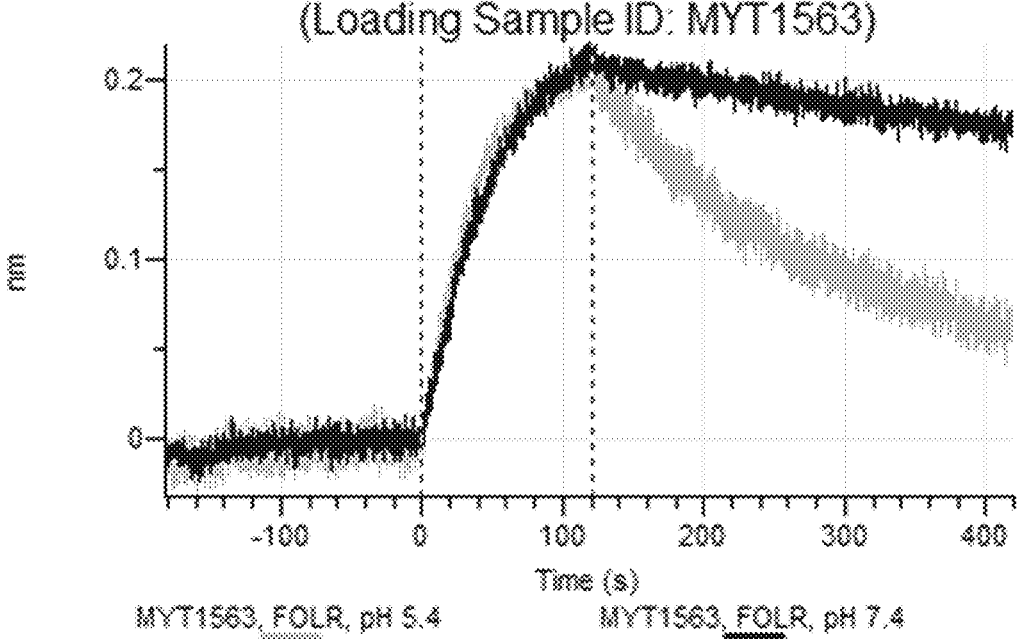
Figure 5F:
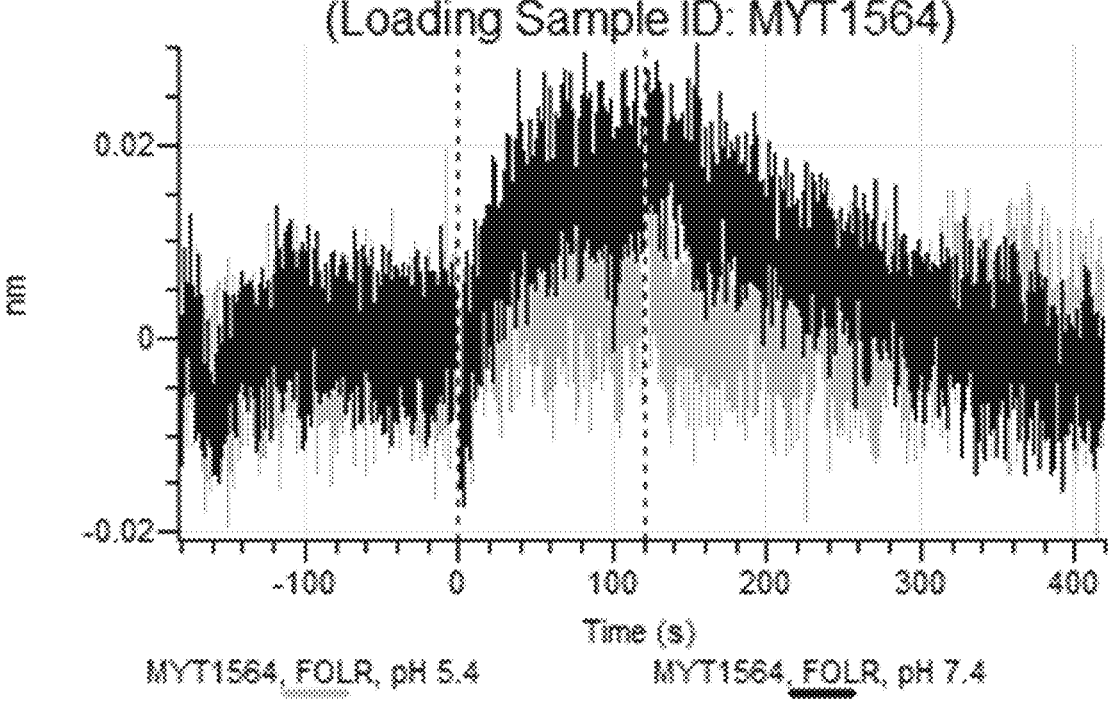
Figure 5G:
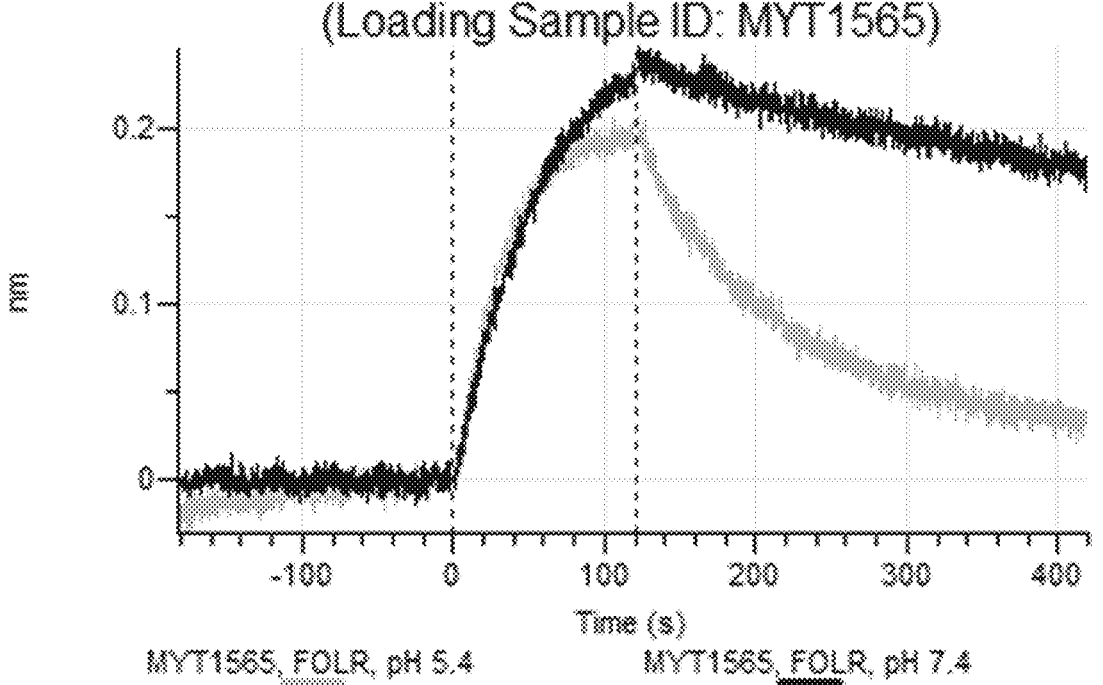
Figure 5H:
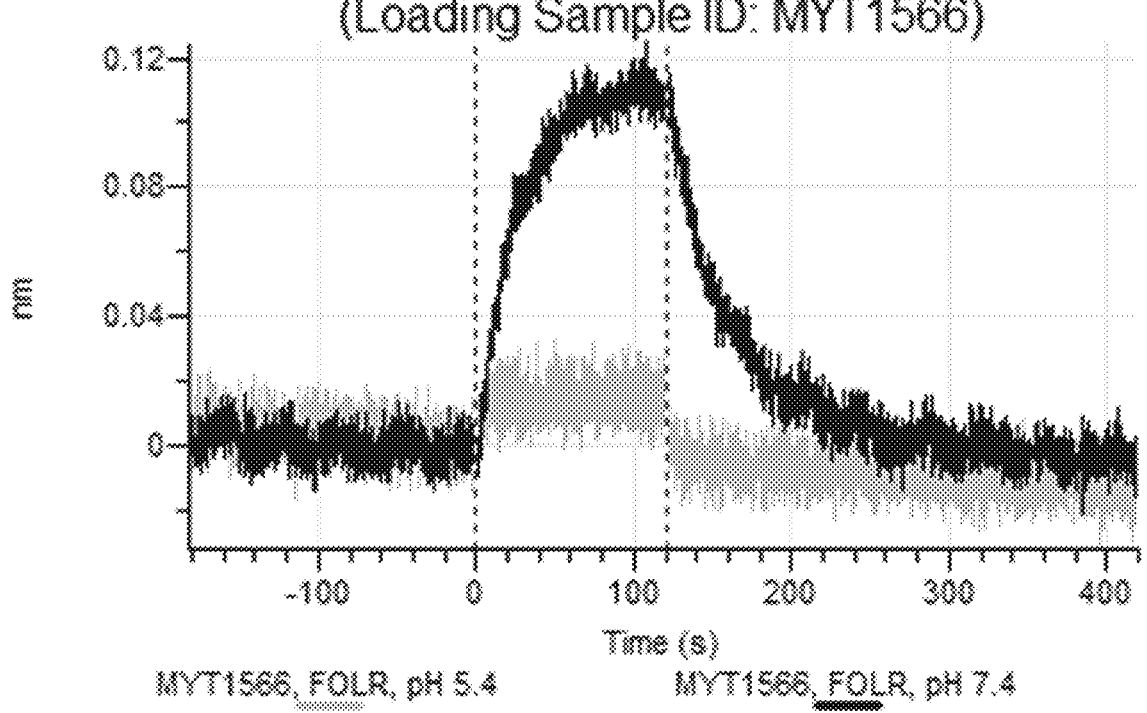
Figure 5I:
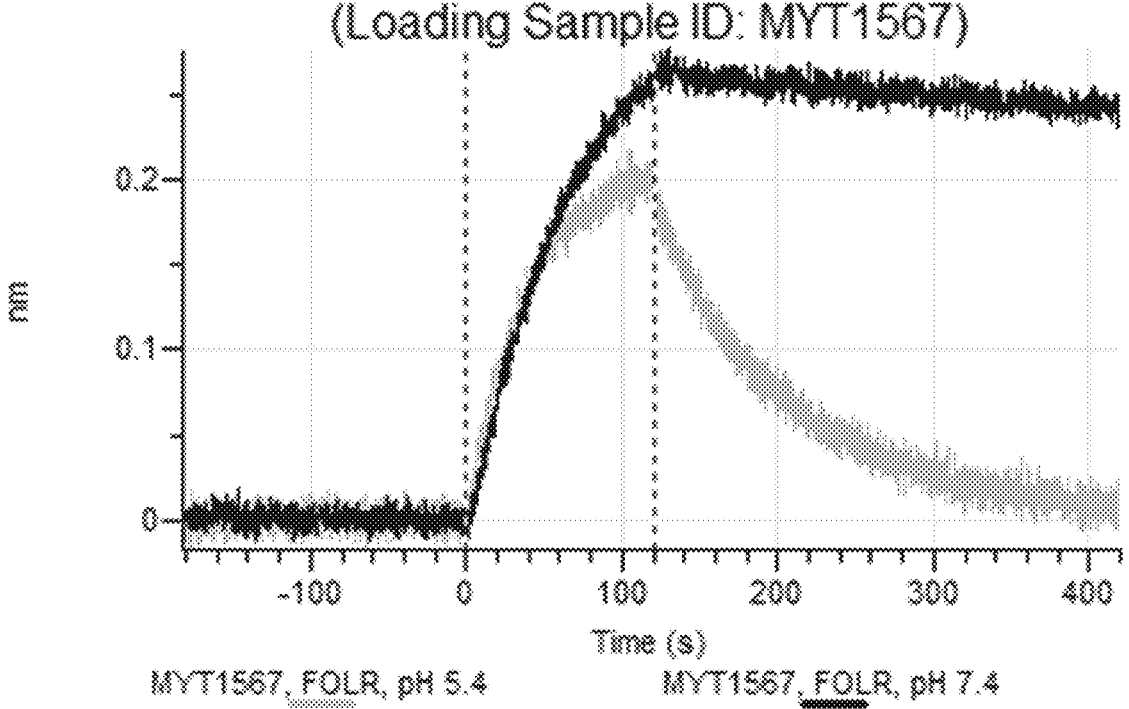
Figure 5J:
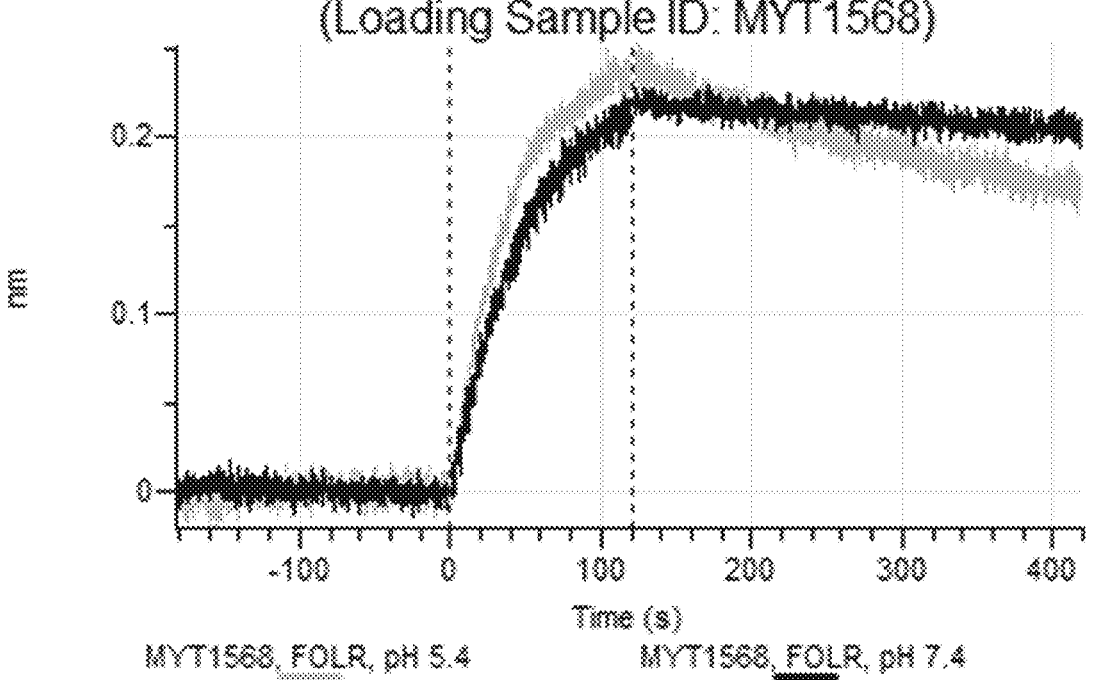
Figure 5K:
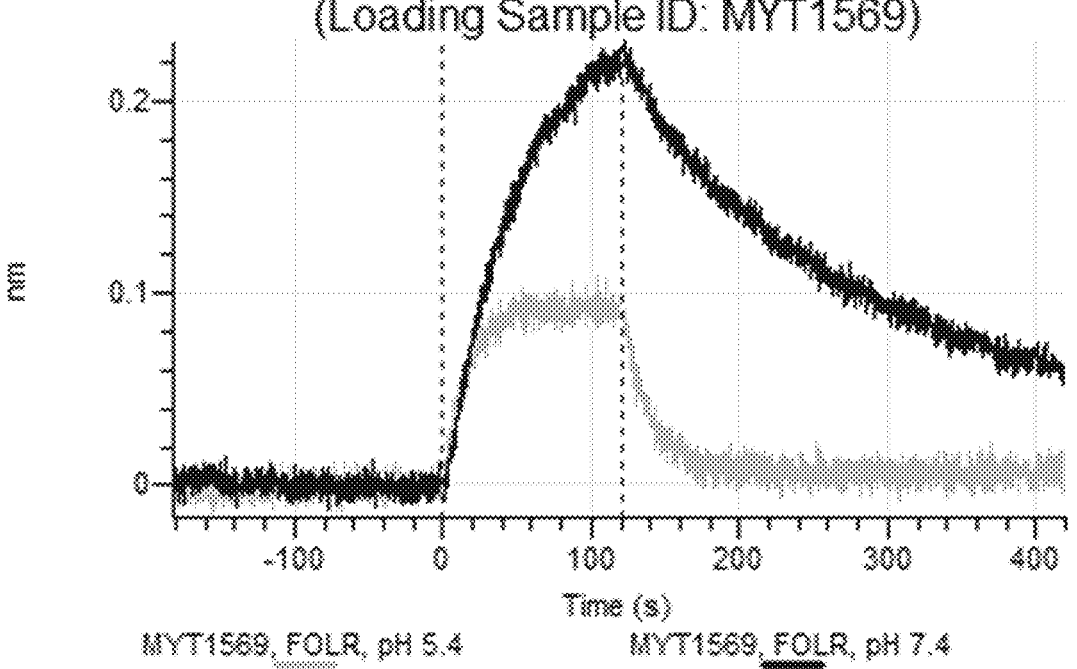
Figure 5I:
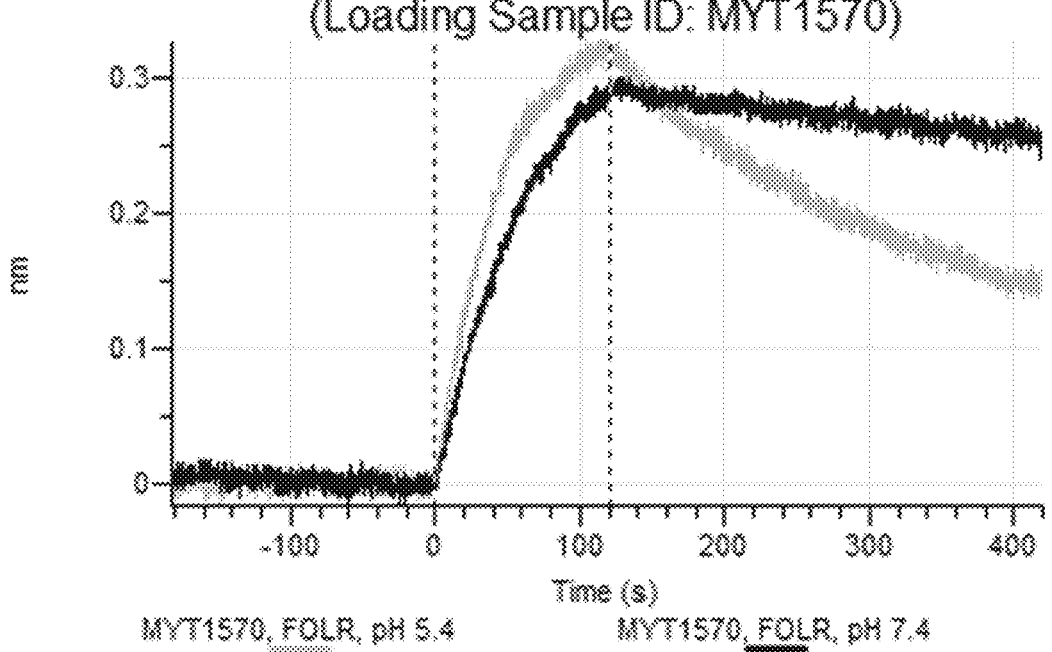
Figure 5M:
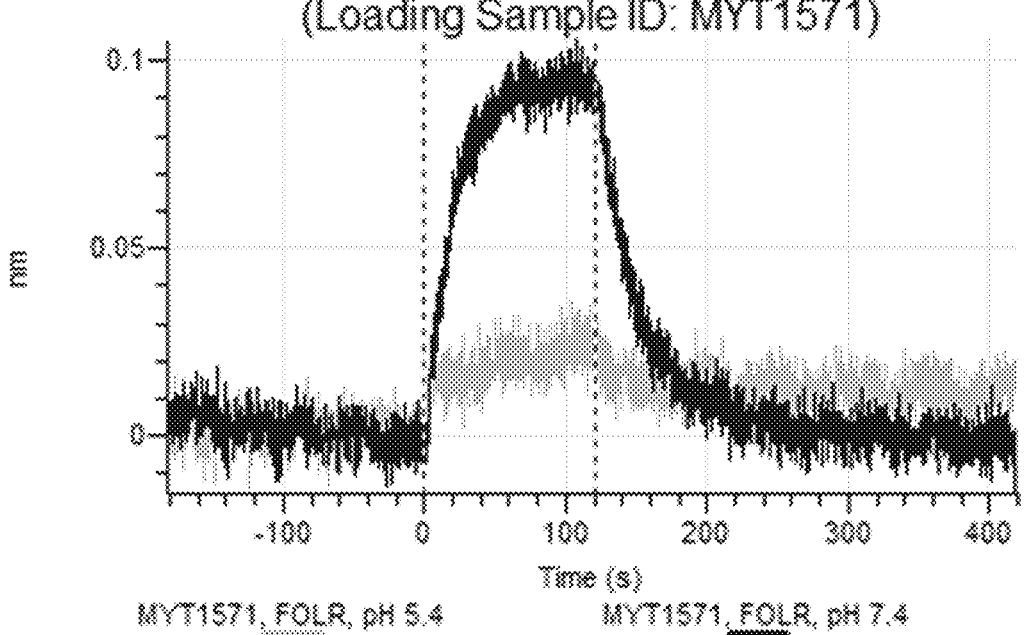
Figure 5N:
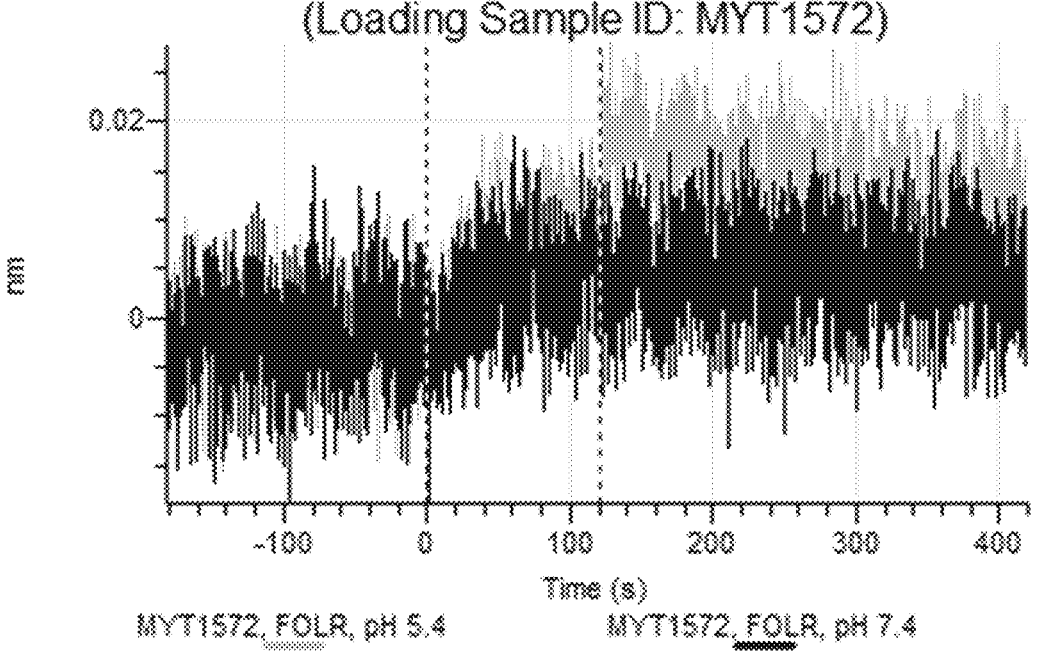
Figure 5O:
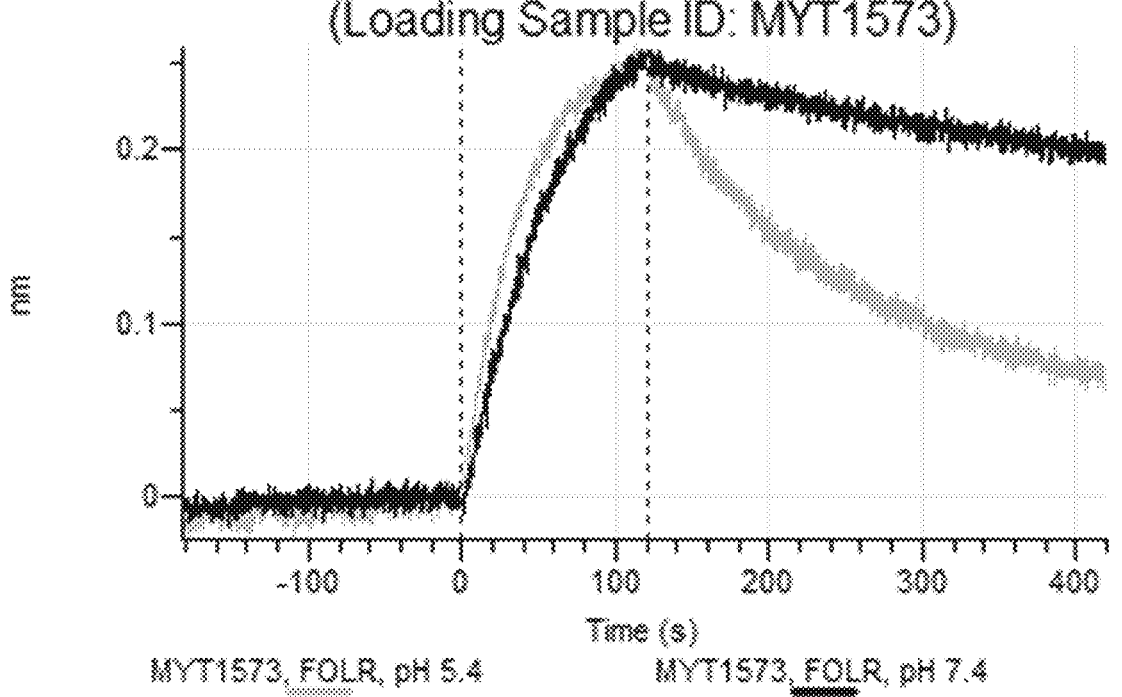
Figure 5P:
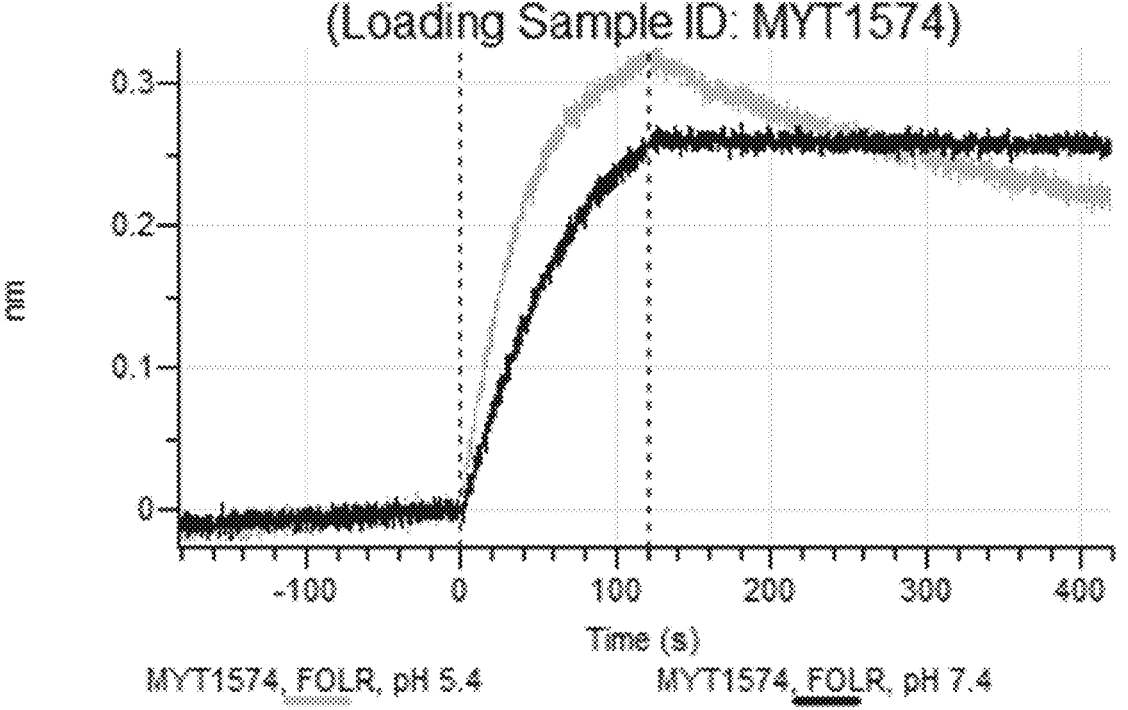
Figure 5Q:
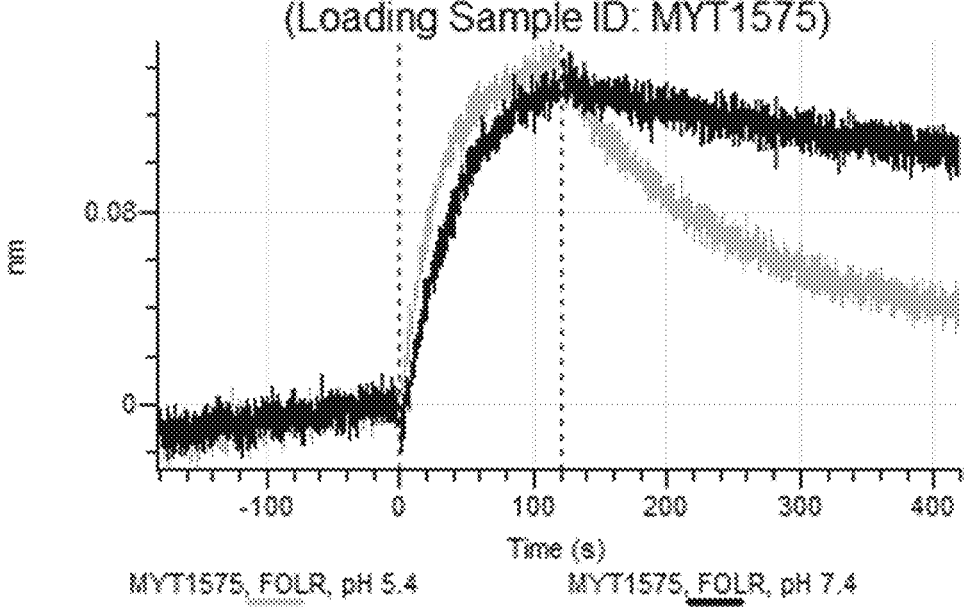
Figure 5R:
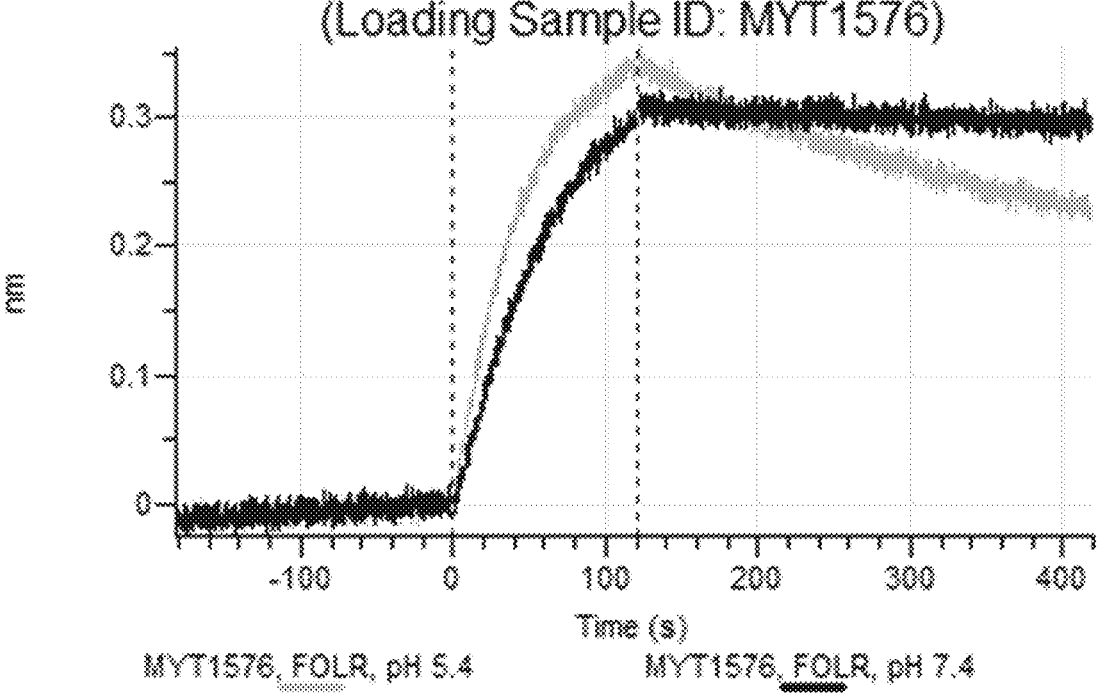
Figure 5S:
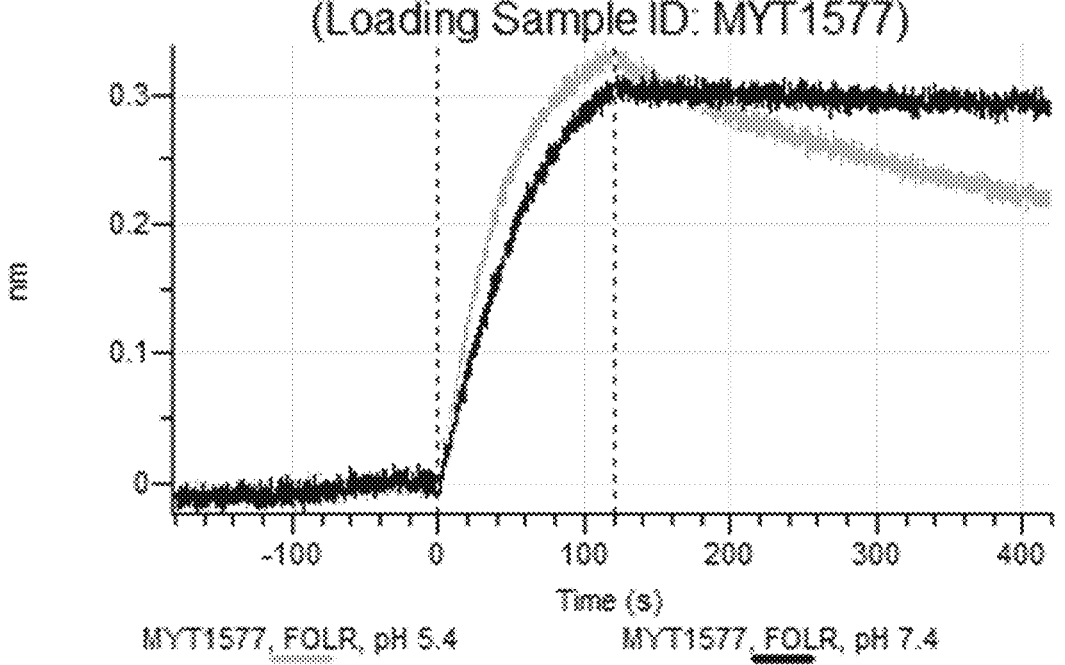
Figure 5T:
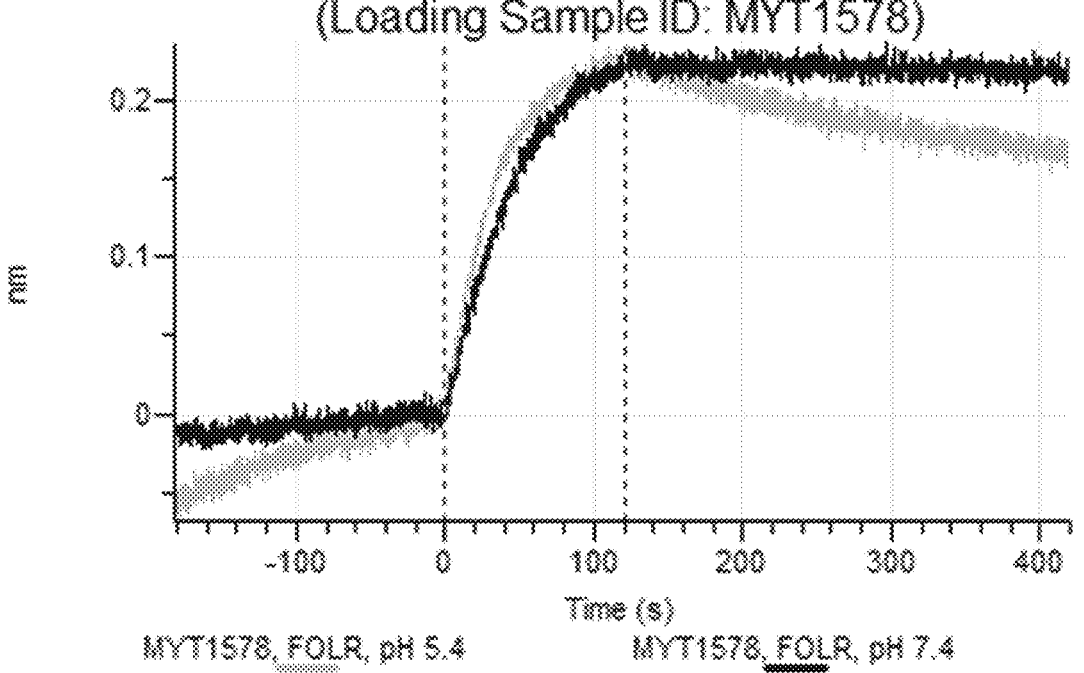
Figure 5U:
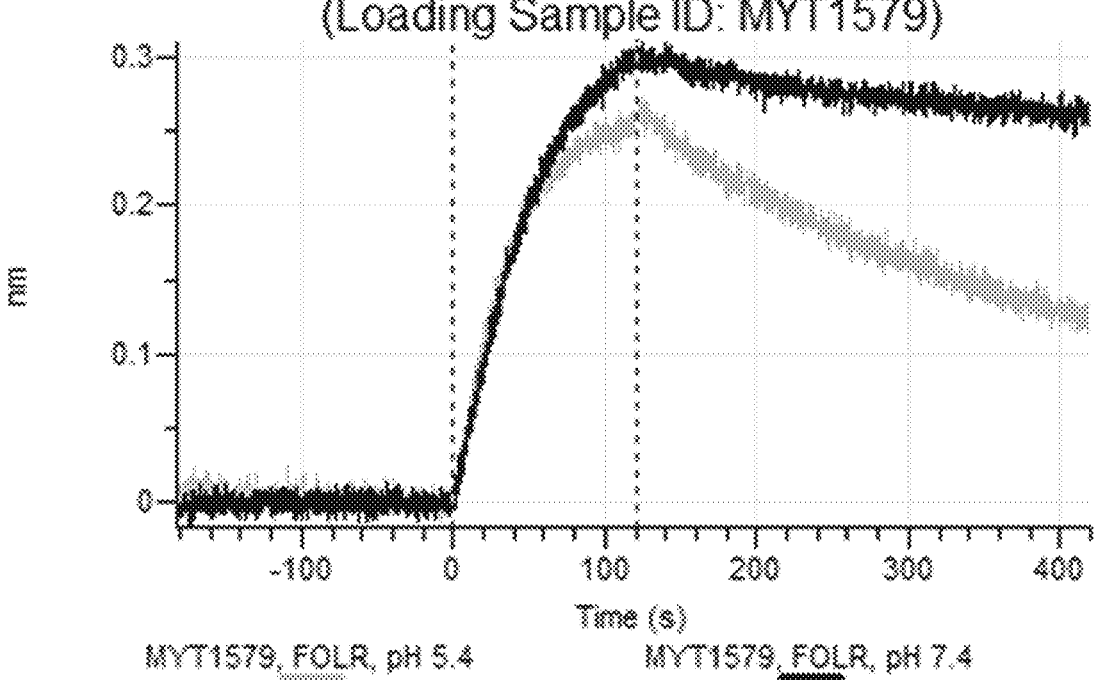
Figure 5V:
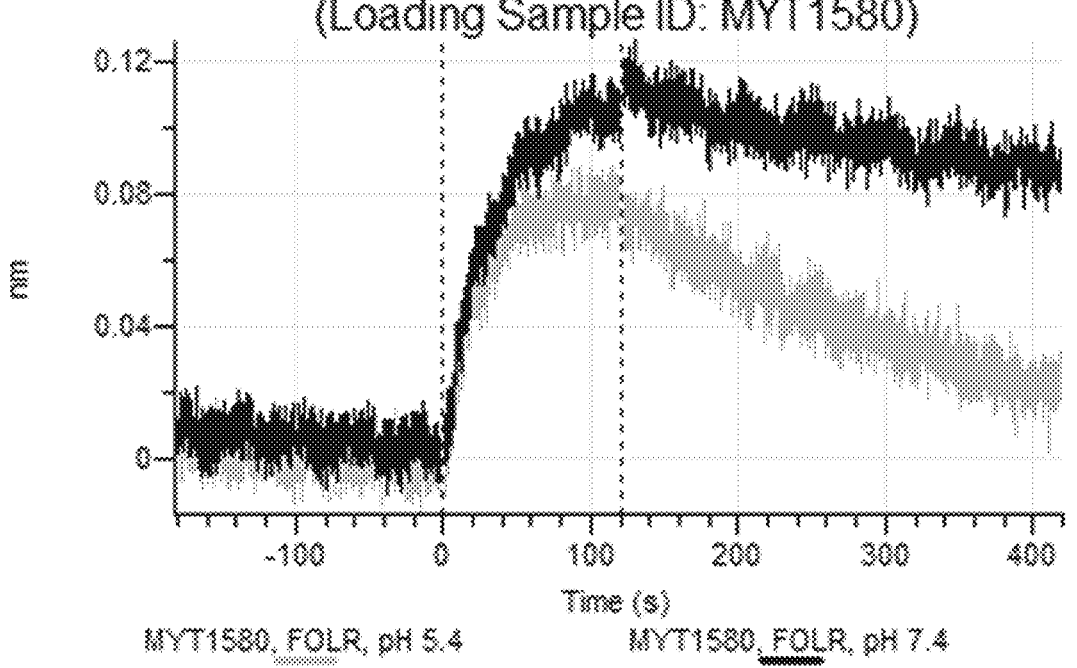
Figure 5W:
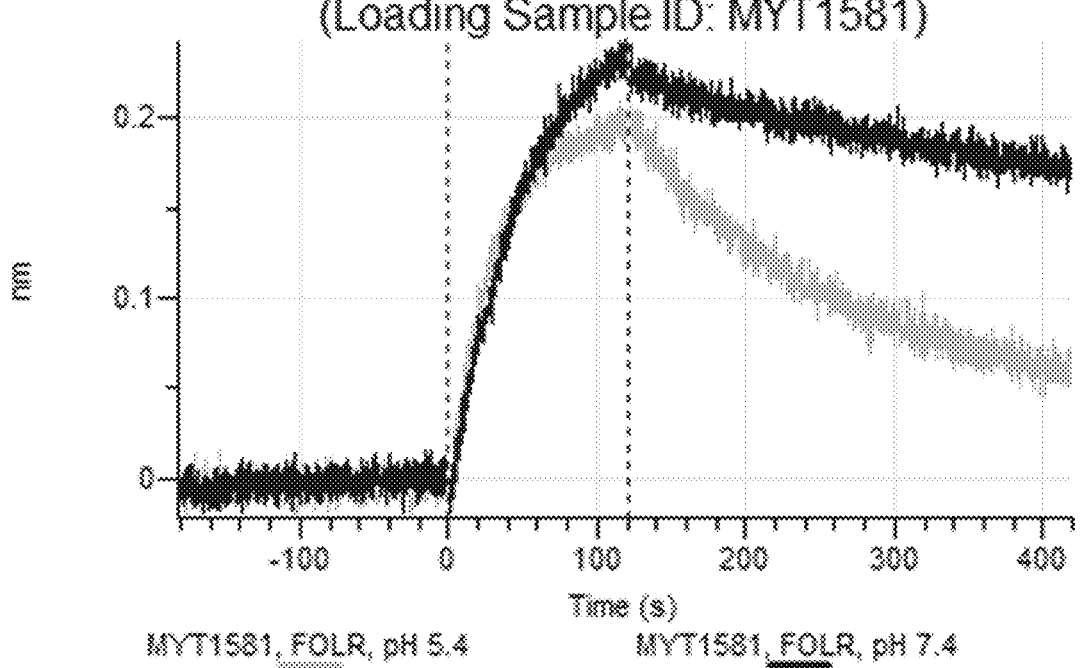
Figure 5X:
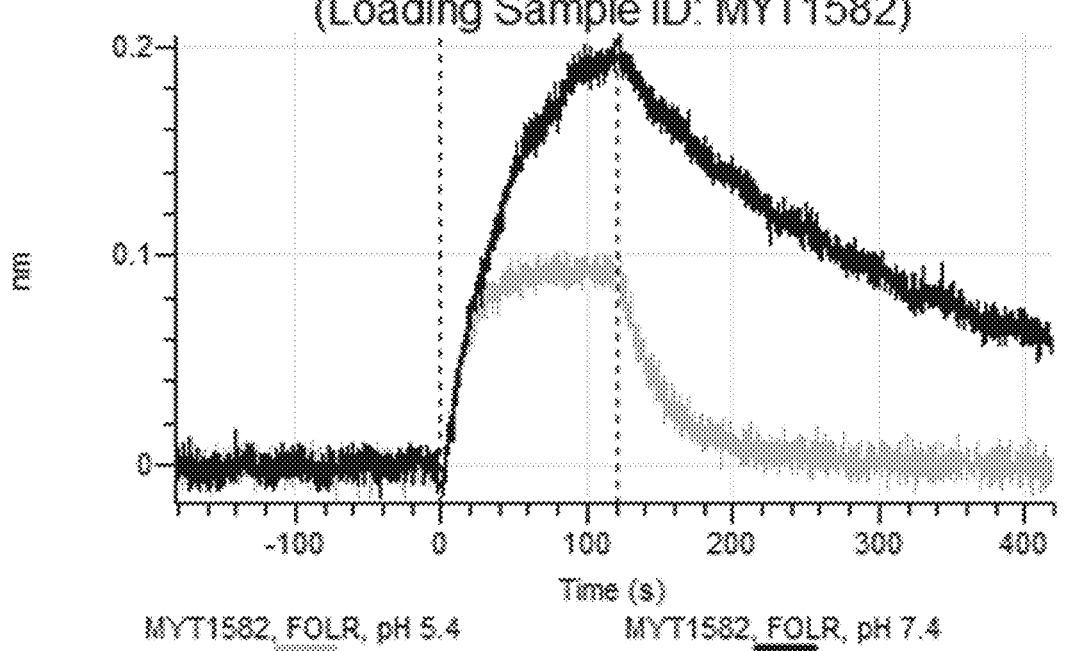
Figure 5Y:
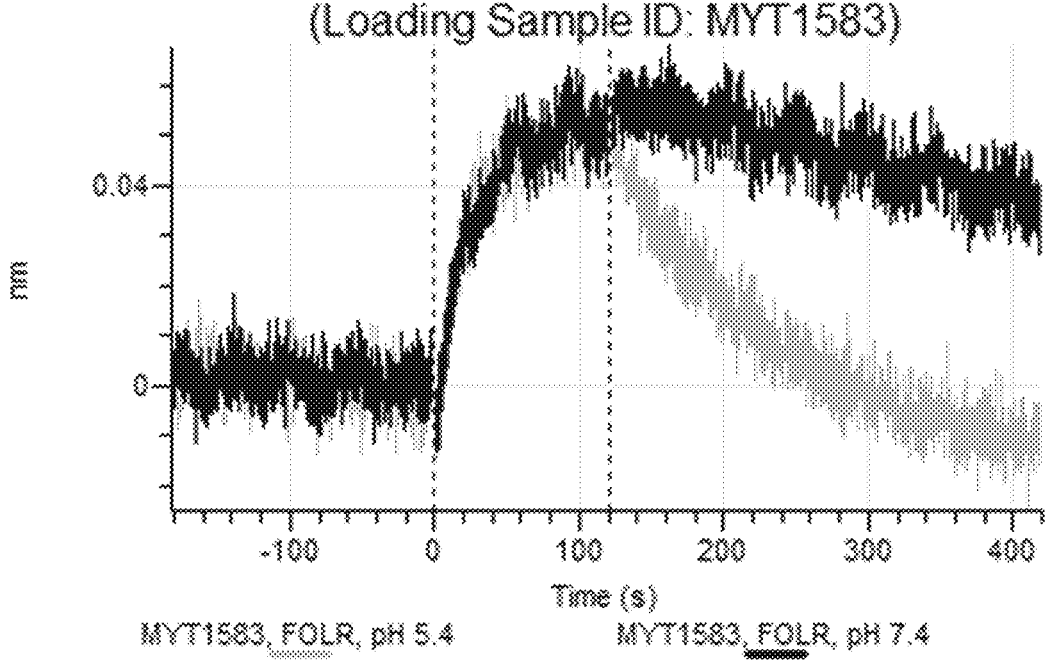
Figure 5Z:
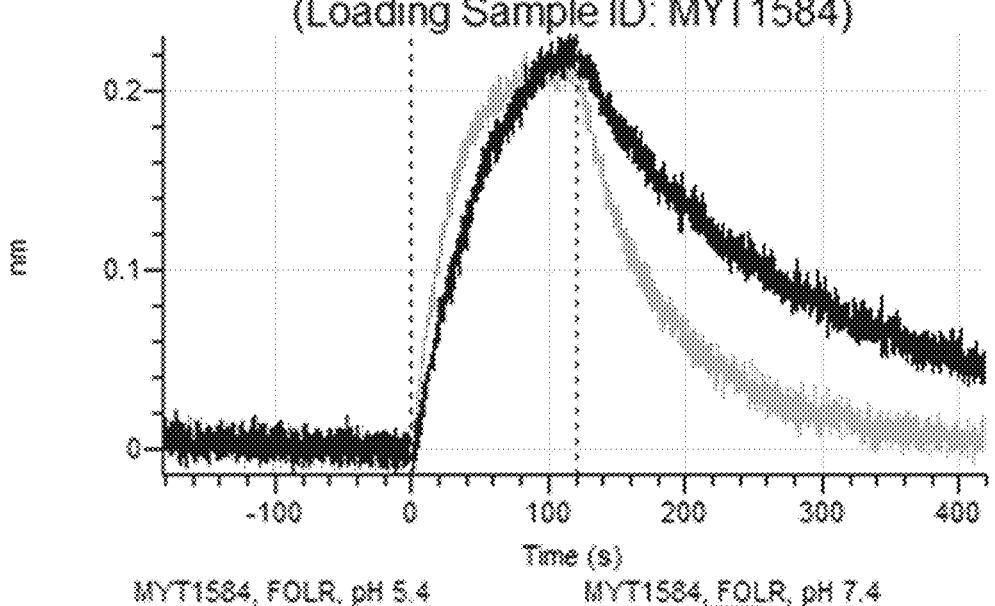
Figure 5A:
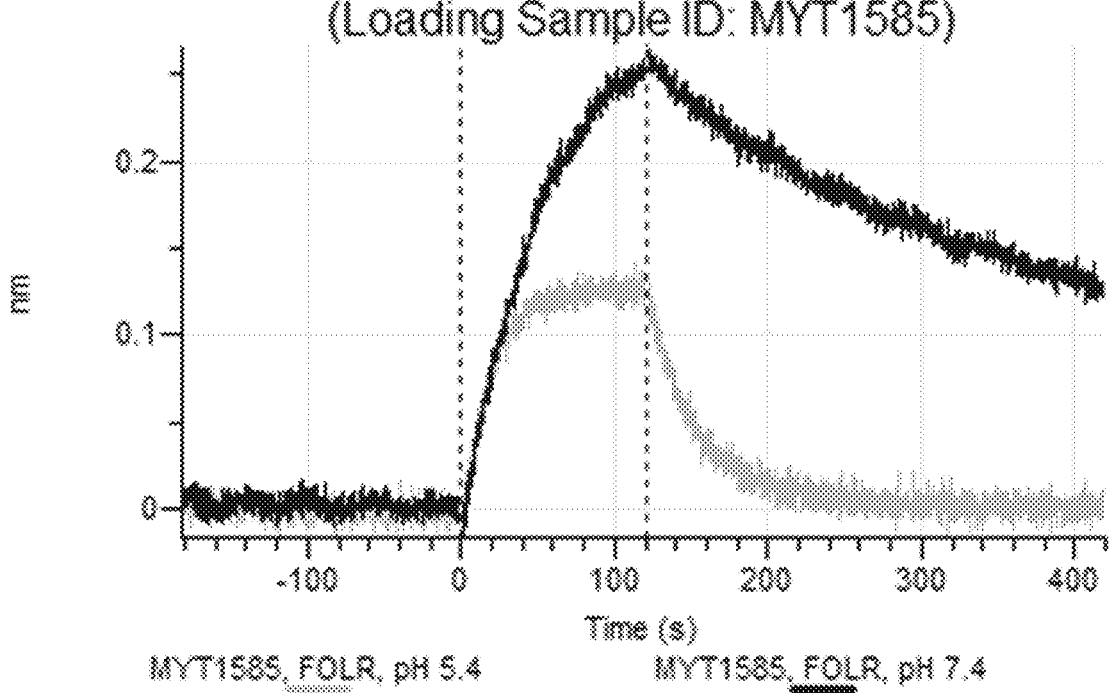
Figure 5A:
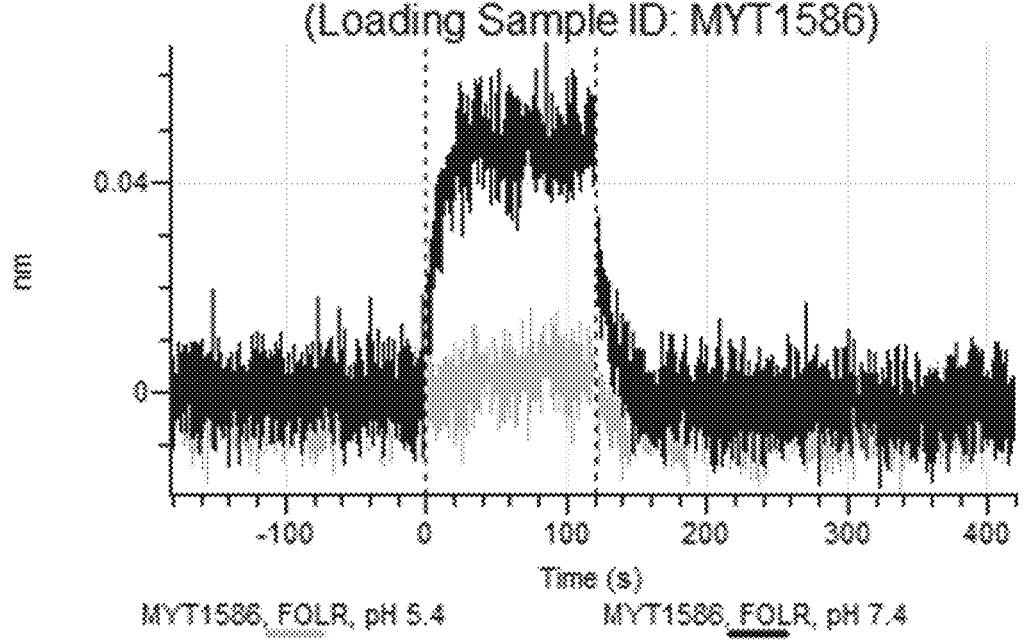
Figure 5A:
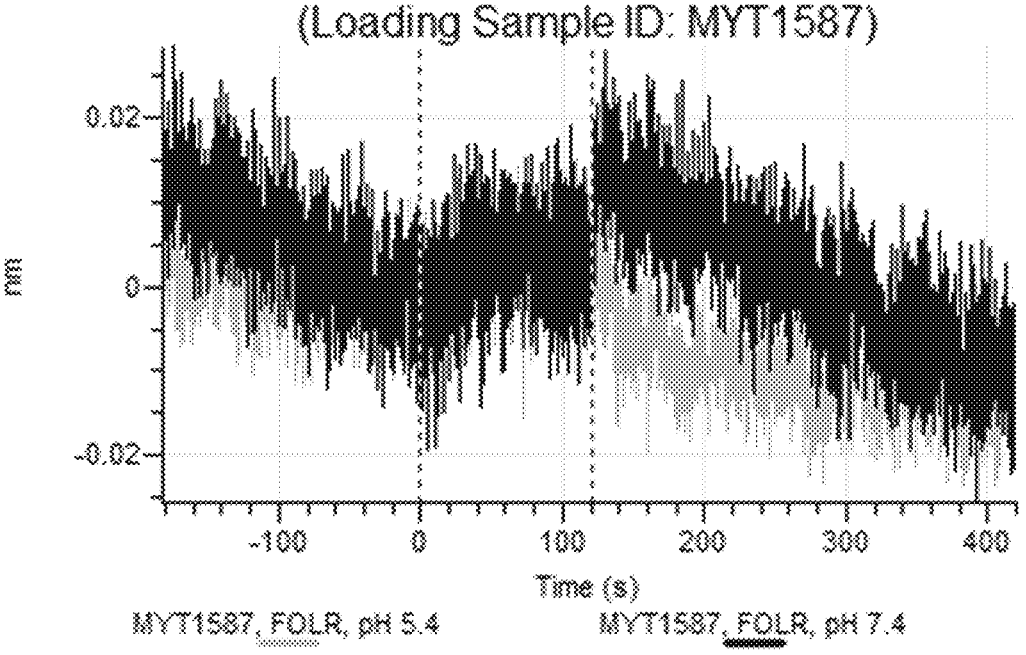
Figure 5A:
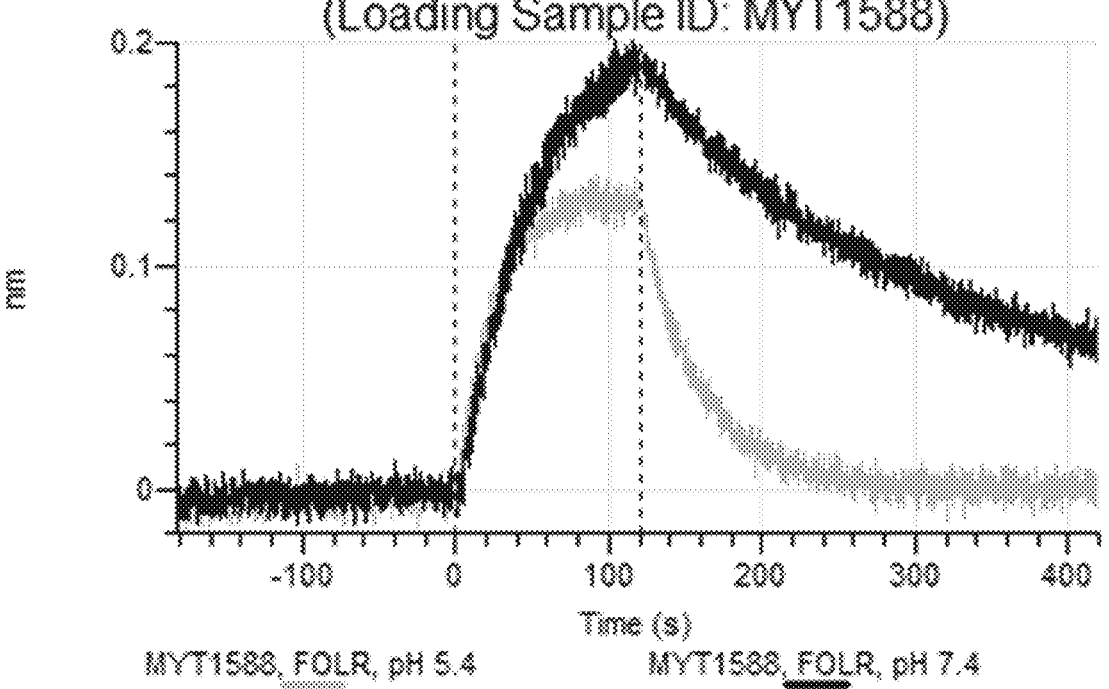
Figure 5A:
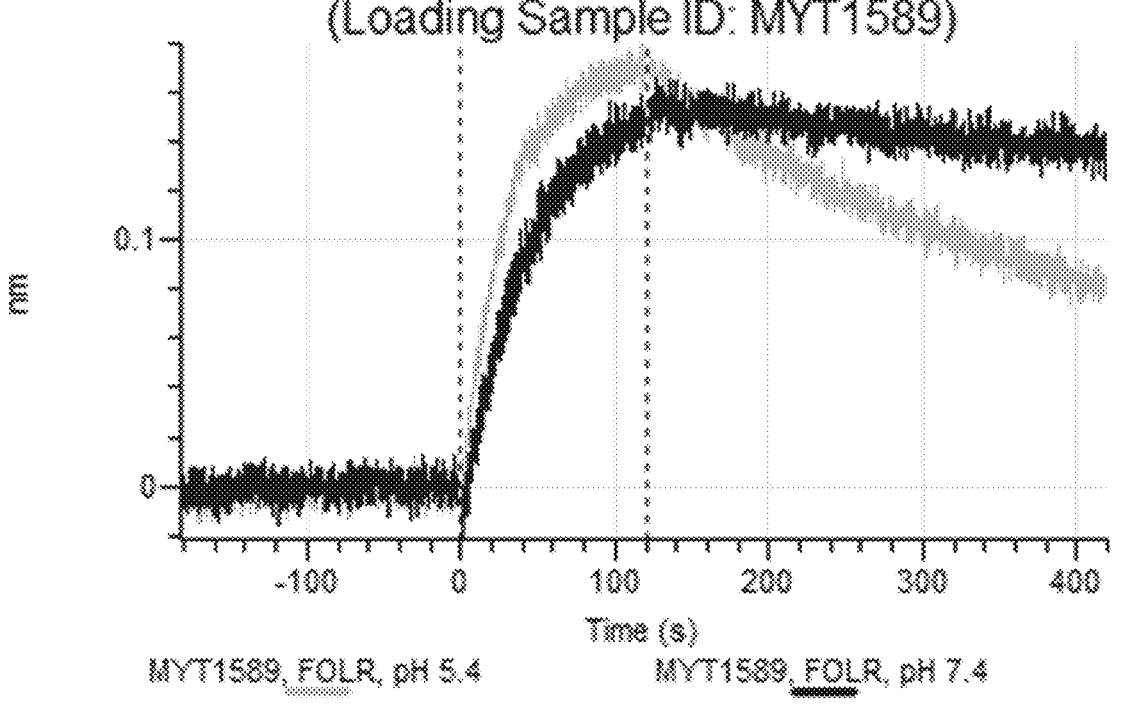

Multiple FOLR1-binding monoclonal antibodies have been described in the literature and can be used as a template for engineering pH-dependent binding [Altwerger G et al (2018) "In Vitro and In Vivo Activity of IMGN853, an Antibody-Drug Conjugate Targeting Folate Receptor Alpha Linked to DM4, in Biologically Aggressive Endometrial Cancers" Molecular Cancer Therapeutics 17(5): 1003-1011]. We selected mirvetuximab (Heavy chain SEQ ID NO: 1, Light chain SEQ ID NO: 2) as a FOLR1-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time (MYT1559-MYT1589). In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting ABPC heavy chain using methods known to the art. After allowing for four days of protein expression, cell culture supernatants were collected, quantified by SDS-PAGE analysis (FIG. 4), and the pH dependence of the variant was evaluated using biolayer interferometry (BLI) on an Octet RED 384 instrument. Briefly, 25 μL of cell culture supernatant was diluted into 175 μL of 1×PBST pH 7.4 for loading onto the sensor tips. Diluted supernatants were then captured on an anti-human Fe sensor (FORTEBIO® (biolayer interferometry systems)). A baseline was established using 1×PBST (50 mM Potassium Phosphate Buffer+150 mM NaCl+0.05% TWEEN® (polysorbate surfactants) 20) pH 7.4, and the sensor was associated with 50 nM of FOLR1 (R&D Systems, Cat #5646-FR, Lot No. RTI0418011) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (e.g., higher $k_{off}$ values) at pH 5.4 due to histidine or alanine substitution compared to the starting ABPC (with no substitutions), and b) reduced dissociation at pH 7.4 (e.g., lower $k_{off}$ values) compared to pH 5.4 in the antibody variant itself and with the starting ABPC (with no substitutions). Light chain variants that showed either enhanced dissociation at pH 5.4 or reduced dissociation at pH 7.4 or both (as compared to the starting ABPC), as shown in FIG. 5 were selected for further analysis (e.g, MYT1563, MYT1565-MYT1567, MYT1569-MYT1571, MYT1573, MYT1575, MYT1579, MYT1581-MYT1586, and MYT1588)). It was also noted that some histidine and alanine mutations were tolerated with little (e.g., less than 1-fold change in dissociation constant KD or dissociation rate) or no change in FOLR1 binding kinetics (e.g., MYT1559, MYT1561, MYT1562, MYT1568, MYT1574, MYT1576-MYT1578, MYT1580, and MYT1589). Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 11. Construction and Screening of pH-Engineered FOLR1 ABPCs

Figure 7:
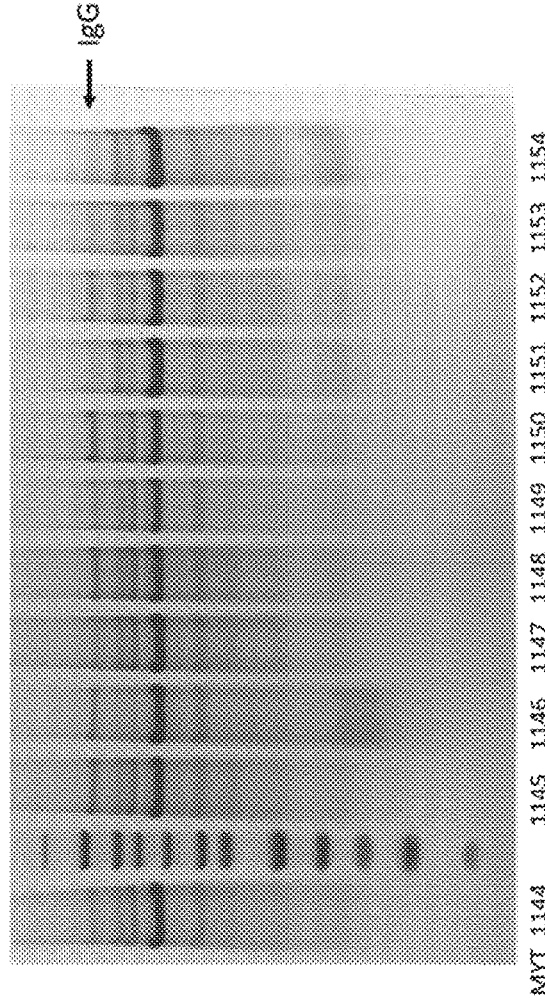
FIG. 7: SDS PAGE for MIRVETUXIMAB histidine scanning and alanine scanning. Expi293 cell culture supernatants post-harvest were loaded on non-reduced SDS PAGE gels to confirm expression of MIRVETUXIMAB histidine scanning and alanine scanning variants.
Figure 7:
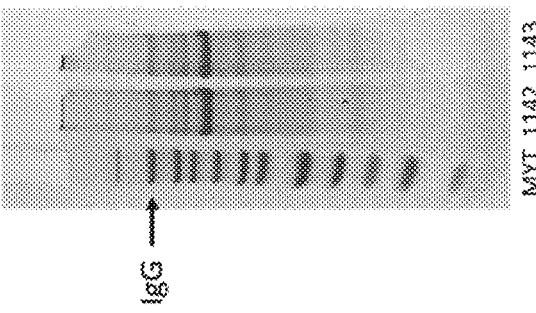
Figure 7:
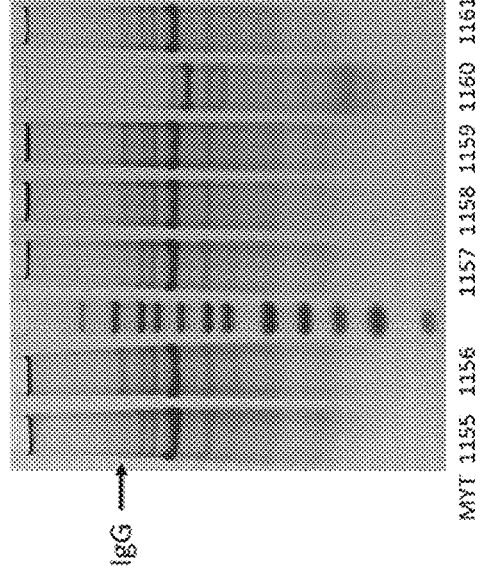

Multiple FOLR1-binding monoclonal antibodies have been described in the literature and can be used as a template for engineering pH-dependent binding [Altwerger G et al (2018) "In Vitro and In Vivo Activity of IMGN853, an Antibody-Drug Conjugate Targeting Folate Receptor Alpha Linked to DM4, in Biologically Aggressive Endometrial Cancers" Molecular Cancer Therapeutics 17(5): 1003-1011]. We selected mirvetuximab (Heavy chain SEQ ID NO: 1, Light chain SEQ ID NO: 2) as a FOLR1-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 9 were systematically combined two or more at a time (MYT1142-MYT1161). In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant, and b) the corresponding starting ABPC light chain using methods known to the art. After allowing for four days of protein expression, cell culture supernatants were collected, quantified by SDS-PAGE analysis (FIG. 7), and the pH dependence of the variant was evaluated using biolayer interferometry (BLI) on an Octet RED 384 instrument. Briefly, 100 µL of cell culture supernatant was diluted into 100 µL of 1×PBST pH 7.4 for loading onto the sensor tips. Diluted supernatants were then captured on an anti-human Fc sensor (FORTEBIO® (biolayer interferometry systems)). A baseline was established using 1×PBST (50 mM Potassium Phosphate Buffer+150 mM NaCl+0.05% TWEEN® (polysorbate surfactants) 20) pH 7.4, and the sensor was associated with 50 nM of FOLR1 (R&D Systems, Cat #5646-FR, Lot No. RTI0418011) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 0.5.4 and pH 7.4 to inform on two criteria: a) enhanced dissociation (e.g., higher $k_{off}$ values) at pH 5.4 due to histidine or alanine substitution compared to the starting ABPC (with no substitutions), and b) reduced dissociation at pH 7.4 (e.g., lower $k_{off}$ values) compared to pH 5.4 in the antibody variant itself and with the starting ABPC (with no substitutions). Heavy chain combinations variants that showed either enhanced dissociation at pH 5.4 or reduced dissociation at pH 7.4 or both (as compared to the starting ABPC), as shown in FIG. 8 were selected for further analysis (e.g, MYT1142-MYT1160).

Example 12. Construction and Screening of pH-Engineered FOLR1 ABPCs

Multiple FOLR1-binding monoclonal antibodies have been described in the literature and can be used as a template for engineering pH-dependent binding (Abrahams, Cristina et al. Preclinical Activity and Safety of STRO-002, a Novel ADC Targeting Folate Receptor Alpha for Ovarian Cancer. Poster session presented at: 12th Biennial Ovarian Cancer Research Symposium; 2018 Sep. 13-15. Seattle, WA). We selected STRO-002 (Heavy chain SEQ ID NO: 105, Light chain SEQ ID NO: 106) as a FOLR1-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time (MYT2225-MYT2268). In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting ABPC light chain using methods known to the art. After allowing for four days of protein expression, cell culture supernatants were collected, quantified by SDS-PAGE analysis, (FIG. 10), and the pH dependence of the variant was evaluated using biolayer interferometry (BLI) on an Octet RED 96e instrument. Briefly, 5 µL of cell culture supernatant was diluted into 195 µL of 1×PBST pH 7.4 for loading onto the sensor tips. Diluted supernatants were then captured on an anti-human Fc sensor (FORTEBIO® (biolayer interferometry systems)). A baseline was established using 1×PBST (50 mM Potassium Phosphate Buffer+150 mM NaCl+0.05% TWEEN® (polysorbate surfactants) 20) pH 7.4, and the sensor was associated with 50 nM of FOLR1 (R&D Systems, Cat #5646-FR, Lot No. RTI0419021) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (e.g., higher $k_{off}$ values) at pH 5.4 due to histidine or alanine substitution compared to the starting ABPC (with no substitutions), and b) reduced dissociation at pH 7.4 (e.g., lower $k_{off}$ values) compared to pH 5.4 in the antibody variant itself and with the starting ABPC (with no substitutions). Heavy chain variants that showed either enhanced dissociation at pH 5.4 or reduced dissociation at pH 7.4 or both (as compared to the starting ABPC), as shown in FIG. 11 were selected for further analysis (e.g, MYT2228, MYT2232-MYT2238, MYT2240-MYT2242, MYT2256-MYT2258, and MYT2263-MYT2268). It was also noted that while some histidine and alanine mutations obliterated FOLR1 binding (e.g., MYT2244, MYT2252, MYT2254, MYT2259, and MYT2261), others were tolerated with little (e.g., less than 1-fold change in dissociation constant KD or dissociation rate) or no change in FOLR1 binding kinetics (e.g., MYT2225-MYT2227, MYT2229-MYT2231, MYT2239, MYT2243, MYT2245-MYT2251, MYT2253, MYT2255, MYT2260, and MYT2262). Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 13. Construction and Screening of pH-Engineered FOLR1 ABPCs

Multiple FOLR1-binding monoclonal antibodies have been described in the literature and can be used as a template for engineering pH-dependent binding (Abrahams, Cristina et al. Preclinical Activity and Safety of STRO-002, a Novel ADC Targeting Folate Receptor Alpha for Ovarian Cancer. Poster session presented at: 12th Biennial Ovarian Cancer Research Symposium; 2018 Sep. 13-15. Seattle, WA). We selected STRO-002 (Heavy chain SEQ ID NO: 105, Light chain SEQ ID NO: 106) as a FOLR1-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time (MYT4493-MYT4519). In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting ABPC heavy chain using methods known to the art. After allowing for four days of protein expression, cell culture supernatants were collected, quantified by SDS-PAGE analysis (FIG. 13), and the pH dependence of the variant was evaluated using biolayer interferometry (BLI) on an Octet RED 384 instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors and 100 μL of cell culture supernatant was diluted into 100 μL of 1×PBST, pH 7.4 for low expressors for loading onto the sensor tips. Diluted supernatants were then captured on an anti-human Fc sensor (FORTEBIO® (biolayer interferometry systems)). A baseline was established using 1×PBST (50 mM Potassium Phosphate Buffer+150 mM NaCl+0.05% TWEEN® (polysorbate surfactants) 20) pH 7.4, and the sensor was associated with 50 nM of FOLR1 (R&D Systems, Cat #5646-FR, Lot No. RTI0419021) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (e.g., higher $k_{off}$ values) at pH 5.4 due to histidine or alanine substitution compared to the starting ABPC (with no substitutions), and b) reduced dissociation at pH 7.4 (e.g., lower $k_{off}$ values) compared to pH 5.4 in the antibody variant itself and with the starting ABPC (with no substitutions). Light chain variants that showed either enhanced dissociation at pH 5.4 or reduced dissociation at pH 7.4 or both (as compared to the starting ABPC), as shown in FIG. 14 were selected for further analysis (e.g, MYT4497-MYT4500, MYT4504, and MYT4513-MYT4518). It was also noted that while some histidine and alanine mutations obliterated FOLR1 binding (e.g., MYT4501 and MYT4503), others were tolerated with little (e.g., less than 1-fold change in dissociation constant KD or dissociation rate) or no change in FOLR1 binding kinetics (e.g., MYT4493-MYT4496, MYT4502, MYT4506-MYT4512, and MYT4519). Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 14. Construction and Screening of pH-Engineered FOLR1 ABPCs

Multiple FOLR1-binding monoclonal antibodies have been described in the literature and can be used as a template for engineering pH-dependent binding (Ebel W, Routhier E L, Foley B, et al. Preclinical evaluation of MORAb-003, a humanized monoclonal antibody antagonizing folate receptor-alpha. Cancer Immun. 2007; 7). We selected Farletuzumab (Heavy chain SEQ ID NO: 184, Light chain SEQ ID NO: 185) as a FOLR1-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time (MYT2185-MYT2223). In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting ABPC light chain using methods known to the art. After allowing for four days of protein-expression, cell culture supernatants were collected, quantified by SDS-PAGE analysis, (FIG. 16), and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fe sensor (FORTEBIO® (biolayer interferometry systems)). A baseline was established using 1×PBST (50 mM Potassium Phosphate Buffer+150 mM NaCl+0.05% TWEEN® (polysorbate surfactants) 20) pH 7.4, and the sensor was associated with 50 nM of FOLR1 (R&D Systems, Cat #5646-FR, Lot No. RTI0419021) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (e.g., higher $k_{off}$ values) at pH 5.4 due to histidine or alanine substitution compared to the starting ABPC (with no substitutions), and b) reduced dissociation at pH 7.4 (e.g., lower $k_{off}$ values) compared to pH 5.4 in the antibody variant itself and with the starting ABPC (with no substitutions). Heavy chain variants that showed either enhanced dissociation at pH 5.4 or reduced dissociation at pH 7.4 or both (as compared to the starting ABPC), as shown in FIG. 17 were selected for further analysis (e.g, MYT2185-MYT2189, MYT2191-MYT2193, MYT2198, MYT2201, MYT2202, MYT2204, MYT2207, MYT2208, MYT2214, MYT2218, and MYT2220). It was also noted that while some histidine and alanine mutations obliterated FOLR1 binding (e.g., MYT2194-MYT2196, MYT2215, MYT2217, MYT2219, and MYT2221), others were tolerated with little (e.g., less than 1-fold change in dissociation constant KD or dissociation rate) or no change in FOLR1 binding kinetics (e.g., MYT2190, MYT2199, MYT2203, MYT2205, MYT2206, MYT2209-MYT2211, MYT2216, MYT2222, and MYT2223). Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 15. Construction and Screening of pH-Engineered FOLR1 ABPCs

Multiple FOLR1-binding monoclonal antibodies have been described in the literature and can be used as a template for engineering pH-dependent binding (Ebel W, Routhier E L, Foley B, et al. Preclinical evaluation of MORAb-003, a humanized monoclonal antibody antagonizing folate receptor-alpha. Cancer Immun. 2007; 7). We selected Farletuzumab (Heavy chain SEQ ID NO: 184, Light chain SEQ ID NO: 185) as a FOLR1-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc MP (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time (MYT4520-MYT4546). In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting ABPC heavy chain using methods known to the art. After allowing for four days of protein expression, cell culture supernatants were collected, quantified by SDS-PAGE analysis (FIG. 19), and the pH dependence of the variant was evaluated using biolayer interferometry (BLI) on an Octet RED 96einstrument. Briefly, cell culture supernatants were diluted based on qualitative expression level of the variant determined by visual examination of SDS-PAGE gels, 5 µL of cell culture supernatant was diluted into 195 µL of 1×PBST, pH 7.4 for high expressors, 25 µL of cell culture supernatant was diluted into 175 µL of 1×PBST, pH 7.4 for medium expressors and 100 µL of cell culture supernatant was diluted into 100 µL of 1×PBST, pH 7.4 for low expressors for loading onto the sensor tips. Diluted supernatants were then captured on an anti-human Fe sensor (FORTEBIO® (biolayer interferometry systems)). A baseline was established using 1×PBST (50 mM Potassium Phosphate Buffer+150 mM NaCl+0.05% TWEEN® (polysorbate surfactants) 20) pH 7.4, and the sensor was associated with 50 nM of FOLR1 (R&D Systems, Cat #5646-FR, Lot No. RTI0419021) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (e.g., higher $k_{off}$ values) at pH 5.4 due to histidine or alanine substitution compared to the starting ABPC (with no substitutions), and b) reduced dissociation at pH 7.4 (e.g., lower $k_{off}$ values) compared to pH 5.4 in the antibody variant itself and with the starting ABPC (with no substitutions). Light chain variants that showed either enhanced dissociation at pH 5.4 or reduced dissociation at pH 7.4 or both (as compared to the starting ABPC), as shown in FIG. 20 were selected for further analysis (e.g, MYT4522, MYT4526-MYT4533, MYT4536, MYT4538, MYT4540, and MYT4542-MYT4546). It was also noted that some histidine and alanine mutations were tolerated with little (e.g., less than 1-fold change in dissociation constant KD or dissociation rate) or no change in FOLR1 binding kinetics (e.g., MYT4520, MYT4521, MYT4523, MYT4524, MYT4534, MYT4535, MYT4537, MYT4539, and MYT4541). Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 16. Characterization of Cellular Internalization and Endolysosomal Delivery of pH Engineered Anti-FOLR1 ABPCs Selected anti-FOLR1 pH engineered antibody variants from Examples 9 and 11 were analyzed for internalization and endolysosomal delivery in NIH:OVCAR-3 (FOLR1+) cells. NIH:OVCAR-3 cells (ATCC; HTB-161) were collected and resuspended in RPMI-1640 medium (ATCC; 30-2001)+20% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 2,000,000 cells/mL and 50p/well was seeded into 96-well flat bottom cell culture plates (Genesee Scientific; 25-109). Anti-FOLR1 pH engineered antibody variants, starting ABPC antibodies, control IgG1 isotype control (BP0297, Bioxcell), and vehicle control were diluted in native culture media to 100 nM and then mixed 1:1 with 300 nM Zenon pHrodo iFL Human IgG Labeling Reagent (ThermoFisher; Z25611). The mixture was incubated for 20 minutes at room temperature, followed by addition of 50 µL to cells. The mixture of cells, anti-FOLR1 antibody variants, and Zenon pHrodo iFL Human IgG Labeling Reagent was incubated at 37° C., 5% C02 for 1-24 hours. Following incubation, 100 µL of ice cold Flow Cytometry (FC) buffer (phosphate buffered saline (PBS), pH 7.4+2 mM ethylenediaminetetraacetic acid (EDTA)+2% (v/v) HI FBS is added to each well. Cells were then spun down at 4° C. for 2 min at 2000 rpm, washed with 200 µL ice cold FC buffer and resuspended in 100 µL ice cold FC buffer. Mean green fluorescence intensity was detected using a BD Accuri C6 flow cytometer. Data was analyzed using Flowjo analysis software. pHrodo green is a pH sensitive dye that fluoresces in the low pH environment of the endosomes and lysosomes and therefore can be used to quantify antibody internalization and endolysosomal delivery. Internalization and endolysosomal delivery of anti-FOLR1 starting ABPC antibody mirvetuximab and variants in NIH:OVCAR-3 (FOLR1+) cells is shown in FIG. 22 as measured by pHrodo green mean fluorescence intensity. Several pH engineered anti-FOLR1 antibody variants showed increased mean fluorescence intensity relative to their corresponding starting ABPC antibodies demonstrating that increased dissociation at lower pH leads to enhanced internalization and endolysosomal delivery inside cells as shown by increased fluorescence or increased fluorescence as compared to IgG1 isotype control. Increased endolysosomal delivery is quantitated for each pH engineered anti-FOLR1 antibody variant on the top of each bar as a ratio of: the variant's mean fluorescence intensity minus the mean fluorescence intensity of the IgG control, then all divided by the variant's corresponding starting ABPC's mean fluorescence intensity minus the mean fluorescence intensity of the IgG control. For example MYT0603, MYT1150, and MYT1154, antibody variants of mirvetuximab, show increased internalization and endolysosomal delivery relative to mirvetuximab (MYT0596). Such pH engineered anti-FOLR1 antibody variants with increased mean fluorescence intensity relative to their starting ABPC antibodies were selected for further analysis (MYT0603, MYT1150, and MYT1154).

Example 17. Characterization of Binding Affinity for Anti-FOLR1 mAbs

Figure 23:
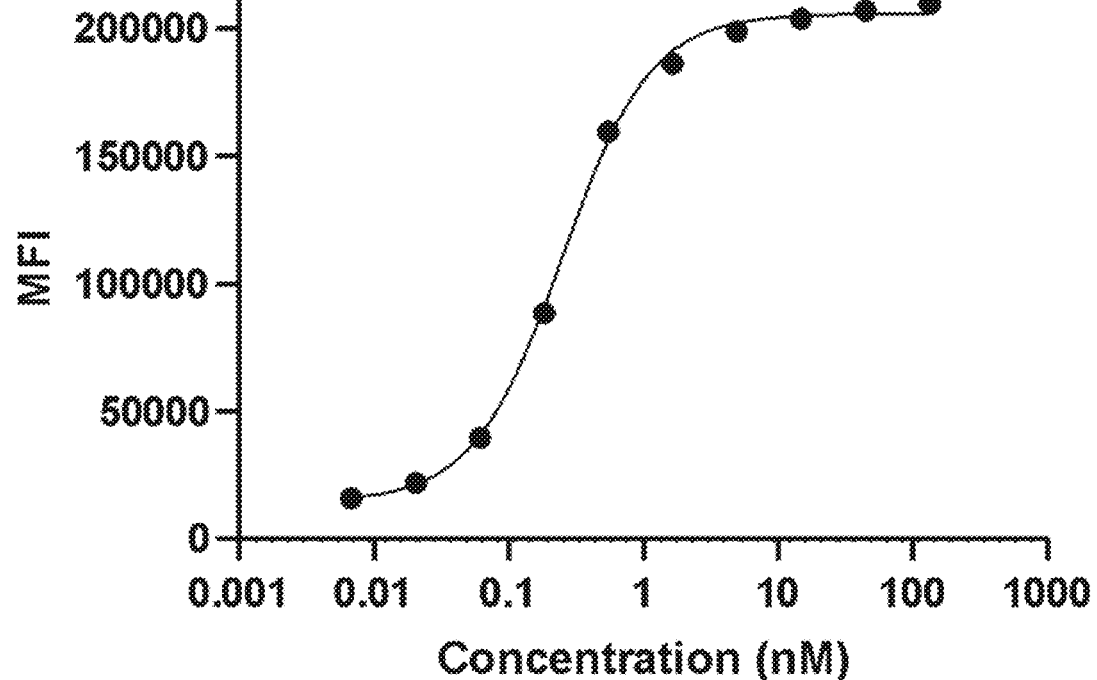
Figure 23:
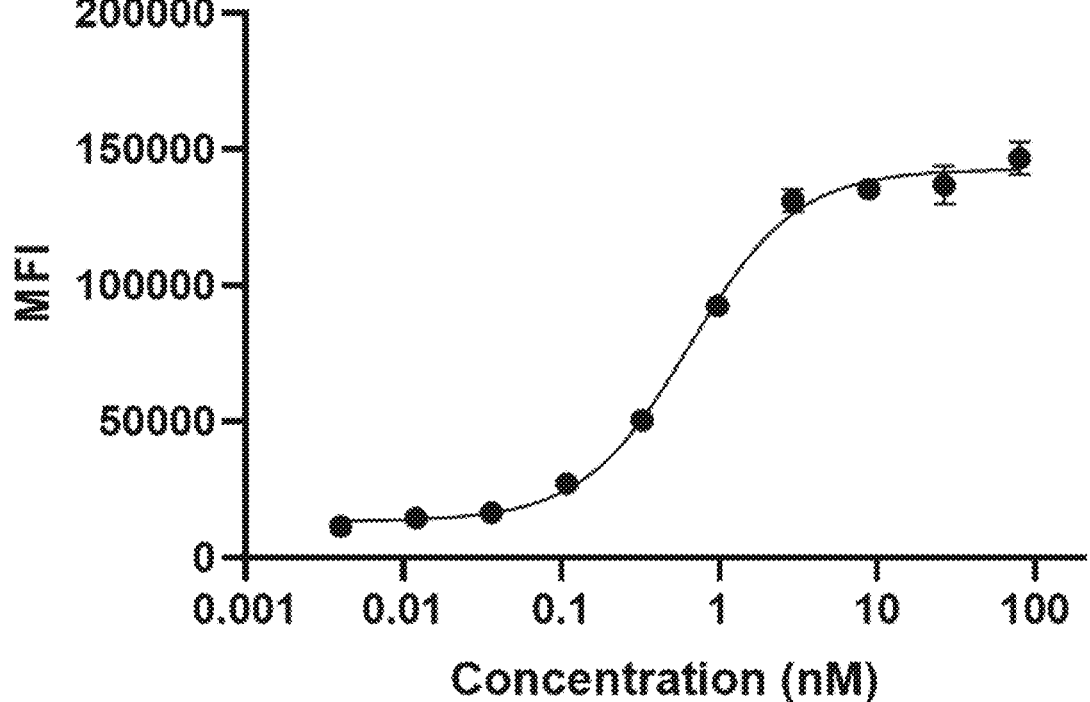
Figure 23:
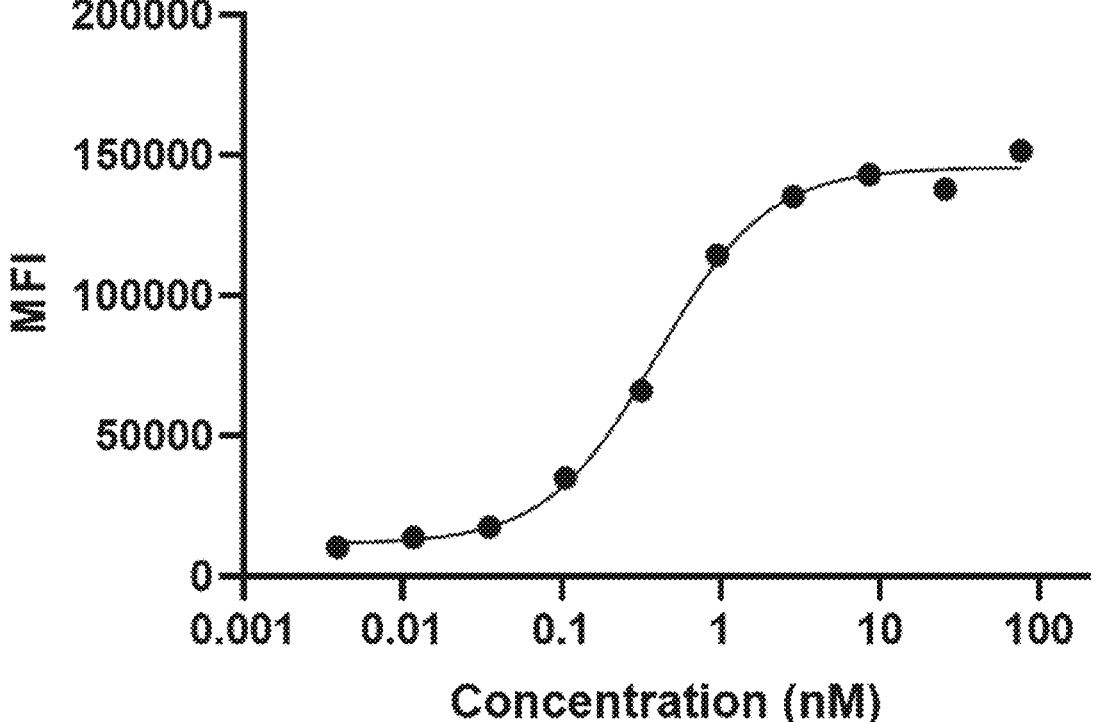

Binding affinity of selected anti-FOLR1 pH engineered antibody variants from Examples 9 and 11 were measured on NIH:OVCAR-3 cells. 100,000 cells per well were resuspended in 900 µL FC buffer in a 96 well deep well plate. Mirvetuximab and pH engineered antibody variants were serially diluted at a 1:3 dilution. 100 µL of diluted antibody was added to each well with final concentration ranging from ~100 nM to 0.024 pM and incubated for 2 hours at 4° C. Post incubation, the cells were spun at 2000 rpm for 2 min and supernatant was discarded. Cells were washed twice with 500 µL of ice-cold FC buffer and resuspended with 100 µL of FC buffer. The cells were then transferred from the deep well plate to 96 well round bottom plate, spun at 2000 rpm for 2 min and incubated with 100 µL of 0 µg/mL Alexa Fluor 488 conjugated goat anti-human IgG secondary antibody (ThermoFisher Scientific, A11013) for 30 min. Post incubation, cells were washed with FC buffer and resuspended in 100 µL of FC buffer to read on a BD Accuri C6 flow cytometer. Mean fluorescence intensity at each concentration per sample was background subtracted and plotted as shown in FIG. 23. Binding affinity was measured as a dissociation constant KD by GraphPad Prism assuming Michaelis-Menten binding kinetics. MYT0603 and MYT1154 show high affinity binding to cell surface FOLR1 on NIH:OVCAR-3 cells in the pM-nM range confirming that variants created through pH engineering can retain functionally appropriate affinities as compared to their corresponding starting ABPCs (e.g., mirvetuximab). Variants with dissociation constants KD less than 100 nM were selected for further analysis.

Example 18. Thermal Stability of Anti-FOLR1 mAbs

Protein melting temperature (Tm) was measured through the use of Differential Scanning Flourimetry (DSF). DSF visualizes protein unfolding by measuring the fluorescent signal from the molecule Sypro Orange (Thermo Scientific cat. no. S6650) as a protein unfolds due to heating. As a protein unfolds it exposes more hydrophilic regions to the Sypro Orange dye, which in turns binds to these hydrophilic regions resulting in increase in signal. The Tm for a protein is calculated as the half-maximal of the unfolding transition and can be visualized by plotting the first derivative of the Sypro Orange signal and finding a local maximum of this derivative plot. 20 µL of protein samples in 1×PBS, pH 7.4, was mixed with 5 µL of 25×Sypro Orange master mix, yielding a final concentration of 5×Sypro Orange. The samples were added to 96-well PCR plates (Thermo Scientific Cat. No. AB-2400/W) and sealed with optical covers (Thermo Scientific Cat. No. 4360954). The PCR plate was inserted into a real-time PCR machine (Thermo Scientific Quant Studio 3) and the plate temperature was stabilized for 3 minutes at 25° C. before ramping to 95° C. by 0.2° C. increments, stabilizing for 1 second before the Sypro Orange signal was measured. The melting temperature (Tm) values for anti-FOLR1 variants are shown in FIG. 24. Several variants (MYT0614, MYT0619 and MYT1150) show similar melting temperature values to mirvetuximab confirming that variants created through pH engineering can retain functionally appropriate thermal stabilities as compared to their corresponding starting ABPCs (e.g., mirvetuximab). Variants (MYT0598, MYT0601, MYT0603, MYT0614, MYT0618, MYT0619, MYT1143, MYT1145, MYT1148, MYT1150, and MYT1154) with melting temperatures greater than or equal to the melting temperature of their corresponding starting ABPC (e.g., mirvetuximab) minus 10° C. were selected for further analysis.

The discoveries herein are in contrast to similar engineering on other antigens such as CLEC12a and two other targets wherein multiple variants per target showed enhanced dissociation at low pH, however, despite the favorable pH-dependent binding properties of these variants (which specifically bound CLEC12a and the two other targets), they had less than 10% increase in cell internalization and endolysosomal delivery as compared to the corresponding starting ABPC (e.g., the starting antibody). These variants (which specifically bound CLEC12a and the two other targets) also had similar biophysical characteristics (e.g., antibody expression, thermal stability, affinity at pH 7.4 etc.) to the corresponding starting ABPC (e.g., the starting antibody) confirming that this was not specific to the biophysical properties of the tested variant (i.e. the biophysical properties unrelated to enhanced dissociation at pH 5.4).

Exemplary Embodiments

Embodiment 1 is a pharmaceutical composition comprising an effective amount of an antigen-binding protein construct (ABPC) comprising: a first antigen-binding domain that is capable of specifically binding FOLR1 or an epitope of FOLR1 presented on the surface of a target mammalian cell, wherein: (a) the dissociation rate of the first antigen-binding domain at a pH of about 4.0 to about 6.5 is faster than the dissociation rate at a pH of about 7.0 to about 8.0; or (b) the dissociation constant (KD) of the first antigen-binding domain at a pH of about 4.0 to about 6.5 is greater than the KD at a pH of about 7.0 to about 8.0.

Embodiment 2 is the pharmaceutical composition of embodiment 1, wherein the first antigen-binding domain comprises a heavy chain variable domain of mirvetuximab with one or more amino acids substituted with a histidine.

Embodiment is the pharmaceutical composition of embodiment 1, wherein the first antigen-binding domain comprises a light chain variable domain of mirvetuximab with one or more amino acids substituted with a histidine.

Embodiment 4 is the pharmaceutical composition of embodiment 1, wherein the first antigen-binding domain comprises: a heavy chain variable domain of mirvetuximab with one or more amino acids substituted with a histidine; and a light chain variable domain of mirvetuximab with one or more amino acids substituted with a histidine.

Embodiment 5 is the pharmaceutical composition of embodiment 2 or 4, wherein the heavy chain variable domain of mirvetuximab comprises SEQ ID NO: 1.

Embodiment 6 is the pharmaceutical composition of embodiment 3 or 4, wherein the light chain variable domain of mirvetuximab comprises SEQ ID NO: 2.

Embodiment 7 is the pharmaceutical composition of embodiment 1, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 8 the pharmaceutical composition of embodiment 1, wherein the first FOLR1-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 9 the pharmaceutical composition of embodiment 1, wherein the first FOLR1-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 10 is the pharmaceutical composition of embodiment 1, 2, or 7, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107.

Embodiment 11 is the pharmaceutical composition of embodiment 1, 3, or 8, wherein the first antigen-binding domain comprises a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 12 is the pharmaceutical composition of embodiment 1, 2, or 7, wherein the first antigen-binding domain comprises a heavy chain variable domain that is at least 90% identical to SEQ ID NO: 1, wherein the heavy chain variable domain includes a histidine at two or more positions in SEQ ID NO: 1 selected from the group consisting of: 24, 27, 54, 58, and 59.

Embodiment 13 is the pharmaceutical composition of embodiment 1, 4, or 9, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107; and a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 14 is the pharmaceutical composition of embodiment 1, wherein the first antigen-binding domain comprises a heavy chain variable domain of SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 43, SEQ ID NO: 45, SEQ ID NO: 46, SEQ ID NO: 48, SEQ ID NO: 49, SEQ ID NO: 50, SEQ ID NO: 51, or SEQ ID NO: 53.

Embodiment 15 is the pharmaceutical composition of embodiment 1 or 14, wherein the first antigen-binding domain comprises a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 16 is the pharmaceutical composition of embodiment 1, wherein the first antigen-binding domain comprises a heavy chain variable domain SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103.

Embodiment 17 is the pharmaceutical composition of embodiment 16, wherein the first antigen-binding domain comprises a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 18 is the pharmaceutical composition of any one of embodiments 1-17, wherein the ABPC is degraded in the target mammalian cell following internalization of the ABPC by the target mammalian cell.

Embodiment 19 is the pharmaceutical composition of any one of embodiments 1-18, wherein the ABPC further comprises a conjugated toxin, radioisotope, drug, or small molecule.

Embodiment 20 is the pharmaceutical composition of embodiment 19, wherein the composition provides for an increase in toxin liberation in the target mammalian cell as compared to a composition comprising the same amount of a control ABPC.

Embodiment 21 is the pharmaceutical composition of embodiment 20, wherein the composition provides for at least a 20% increase in toxin liberation in the target mammalian cell as compared to a composition comprising the same amount of a control ABPC.

Embodiment 22 is the pharmaceutical composition of embodiment 21, wherein the composition provides for at least a 50% increase in toxin liberation in the target mammalian cell as compared to a composition comprising the same amount of a control ABPC.

Embodiment 23 is the pharmaceutical composition of embodiment 20, wherein the composition provides for at least a 2-fold increase in toxin liberation in the target mammalian cell as compared to a composition comprising the same amount of a control ABPC.

Embodiment 24 is the pharmaceutical composition of embodiment 23, wherein the composition provides for at least a 5-fold increase in toxin liberation in the target mammalian cell as compared to a composition comprising the same amount of a control ABPC.

Embodiment 25 the pharmaceutical composition of any one of embodiments 19-24, wherein the composition provides for an increase in target mammalian cell killing as compared to a composition comprising the same amount of a control ABPC.

Embodiment 26 is the pharmaceutical composition of embodiment 25, wherein the composition provides for at least a 20% increase in target mammalian cell killing as compared to a composition comprising the same amount of a control ABPC.

Embodiment 27 is the pharmaceutical composition of embodiment 26, wherein the composition provides for at least a 50% increase in target mammalian cell killing as compared to a composition comprising the same amount of a control ABPC.

Embodiment 28 is the pharmaceutical composition of embodiment 25, wherein the composition provides for at least a 2-fold increase in target mammalian cell killing as compared to a composition comprising the same amount of a control ABPC.

Embodiment 29 is the pharmaceutical composition of embodiment 28, wherein the composition provides for at least a 5-fold increase in target mammalian cell killing as compared to a composition comprising the same amount of a control ABPC.

Embodiment 30 is the pharmaceutical composition of any one of embodiments 1-29, wherein the composition provides for an increase in endolysosomal delivery in the target mammalian cell as compared to a composition comprising the same amount of a control ABPC.

Embodiment 31 is the pharmaceutical composition of embodiment 30, wherein the composition provides for at least a 20% increase in endolysosomal delivery in the target mammalian cell as compared to a composition comprising the same amount of a control ABPC.

Embodiment 32 is the pharmaceutical composition of embodiment 31, wherein the composition provides for at least a 50% increase in endolysosomal delivery in the target mammalian cell as compared to a composition comprising the same amount of a control ABPC.

Embodiment 33 is the pharmaceutical composition of embodiment 30, wherein the composition provides for at least a 2-fold increase in endolysosomal delivery in the target mammalian cell as compared to a composition comprising the same amount of a control ABPC.

Embodiment 34 is the pharmaceutical composition of embodiment 33, wherein the composition provides for at least a 5-fold increase in endolysosomal delivery in the target mammalian cell as compared to a composition comprising the same amount of a control ABPC.

Embodiment 35 is the pharmaceutical composition of any one of embodiments 1-34, wherein the composition results in a less of a reduction in the level of FOLR1 presented on the surface of the target mammalian cell as compared to a composition comprising the same amount of a control ABPC.

Embodiment 36 is the pharmaceutical composition of any one of embodiments 1-34, wherein the composition does not result in a detectable reduction in the level of the FOLR1 presented on the surface of the target mammalian cell.

Embodiment 37 a pharmaceutical composition comprising an effective amount of an antigen-binding protein construct (ABPC) comprising: a first antigen-binding domain that is capable of specifically binding FOLR1 or an epitope of FOLR1 presented on the surface of a target mammalian cell; and a conjugated toxin, radioisotope, drug, or small molecule, wherein: (a) the dissociation rate of the first antigen-binding domain at a pH of about 4.0 to about 6.5 is faster than the dissociation rate at a pH of about 7.0 to about 8.0; or the dissociation constant (KD) of the first antigen-binding domain at a pH of about 4.0 to about 6.5 is greater than the KD at a pH of about 7.0 to about 8.0; and (b) the composition provides for one or more of: an increase in toxin liberation in the target mammalian cell as compared to a composition comprising the same amount of a control ABPC; an increase in target mammalian cell killing as compared to a composition comprising the same amount of a control ABPC; and an increase in endolysosomal delivery in the target mammalian cell as compared to a composition comprising the same amount of a control ABPC.

Embodiment 38 is the pharmaceutical composition of embodiment 37, wherein the first antigen-binding domain comprises a heavy chain variable domain of mirvetuximab with one or more amino acids substituted with a histidine.

Embodiment 39 is the pharmaceutical composition of embodiment 37, wherein the first antigen-binding domain comprises a light chain variable domain of mirvetuximab with one or more amino acids substituted with a histidine.

Embodiment 40 the pharmaceutical composition of embodiment 37, wherein the first antigen-binding domain comprises: a heavy chain variable domain of mirvetuximab with one or more amino acids substituted with a histidine; and a light chain variable domain of mirvetuximab with one or more amino acids substituted with a histidine.

Embodiment 41 is the pharmaceutical composition of embodiment 38 or 40, wherein the heavy chain variable domain of mirvetuximab comprises SEQ ID NO: 1.

Embodiment 42 is the pharmaceutical composition of embodiment 39 or 40, wherein the light chain variable domain of mirvetuximab comprises SEQ ID NO: 2.

Embodiment 43 is the pharmaceutical composition of embodiment 37, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 44 is the pharmaceutical composition of embodiment 37, wherein the first FOLR1-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 45 is the pharmaceutical composition of embodiment 37, wherein the first FOLR1-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 46 is the pharmaceutical composition of embodiment 37, 38, or 43, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107.

Embodiment 47 is the pharmaceutical composition of embodiment 37, 39, or 44, wherein the first antigen-binding domain comprises a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 48 is the pharmaceutical composition of embodiment 37, 38, or 43, wherein the first antigen-binding domain comprises a heavy chain variable domain that is at least 90% identical to SEQ ID NO: 1, wherein the heavy chain variable domain includes a histidine at two or more positions in SEQ ID NO: 1 selected from the group consisting of: 24, 27, 54, 58, and 59.

Embodiment 49 is the pharmaceutical composition of embodiment 37, 40, or 45, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107; and a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 50 is the pharmaceutical composition of embodiment 37, wherein the first antigen-binding domain comprises a heavy chain variable domain of SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 43, SEQ ID NO: 45, SEQ ID NO: 46, SEQ ID NO: 48, SEQ ID NO: 49, SEQ ID NO: 50, SEQ ID NO: 51, or SEQ ID NO: 53.

Embodiment 51 is the pharmaceutical composition of embodiment 37 or 50, wherein the first antigen-binding domain comprises a light chain variable domain of SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 52 is the pharmaceutical composition of embodiment 37, wherein the first antigen-binding domain comprises a heavy chain variable domain of SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103.

Embodiment 53 is the pharmaceutical composition of embodiment 52, wherein the first antigen-binding domain comprises a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 54 is the pharmaceutical composition of any one of embodiments 37-53, wherein the composition provides for an increase in toxin liberation in the target mammalian cell as compared to a composition comprising the same amount of a control ABPC.

Embodiment 55 is the pharmaceutical composition of embodiment 54, wherein the composition provides for at least a 20% increase in toxin liberation in the target mammalian cell as compared to a composition comprising the same amount of a control ABPC.

Embodiment 56 is the pharmaceutical composition of embodiment 55, wherein the composition provides for at least a 50% increase in toxin liberation in the target mammalian cell as compared to a composition comprising the same amount of a control ABPC.

Embodiment 57 is the pharmaceutical composition of embodiment 54, wherein the composition provides for at least a 2-fold increase in toxin liberation in the target mammalian cell as compared to a composition comprising the same amount of a control ABPC.

Embodiment 58 is the pharmaceutical composition of embodiment 57, wherein the composition provides for at least a 5-fold increase in toxin liberation in the target mammalian cell as compared to a composition comprising the same amount of a control ABPC.

Embodiment 59 is the pharmaceutical composition of any one of embodiments 37-58, wherein the composition provides for an increase in target mammalian cell killing as compared to a composition comprising the same amount of a control ABPC.

Embodiment 60 is the pharmaceutical composition of embodiment 59, wherein the composition provides for at least a 20% increase in target mammalian cell killing as compared to a composition comprising the same amount of a control ABPC.

Embodiment 61 is the pharmaceutical composition of embodiment 60, wherein the composition provides for at least a 50% increase in target mammalian cell killing as compared to a composition comprising the same amount of a control ABPC.

Embodiment 62 is the pharmaceutical composition of embodiment 59, wherein the composition provides for at least a 2-fold increase in target mammalian cell killing as compared to a composition comprising the same amount of a control ABPC.

Embodiment 63 is the pharmaceutical composition of embodiment 62, wherein the composition provides for at least a 5-fold increase in target mammalian cell killing as compared to a composition comprising the same amount of a control ABPC.

Embodiment 64 is the pharmaceutical composition of any one of embodiments 37-63, wherein the composition provides for an increase in endolysosomal delivery in the target mammalian cell as compared to a composition comprising the same amount of a control ABPC.

Embodiment 65 is the pharmaceutical composition of embodiment 64, wherein the composition provides for at least a 20% increase in endolysosomal delivery in the target mammalian cell as compared to a composition comprising the same amount of a control ABPC.

Embodiment 66 is the pharmaceutical composition of embodiment 65, wherein the composition provides for at least a 50% increase in endolysosomal delivery in the target mammalian cell as compared to a composition comprising the same amount of a control ABPC.

Embodiment 67 is the pharmaceutical composition of embodiment 64, wherein the composition provides for at least a 2-fold increase in endolysosomal delivery in the target mammalian cell as compared to a composition comprising the same amount of a control ABPC.

Embodiment 68 in the pharmaceutical composition of embodiment 67, wherein the composition provides for at least a 5-fold increase in endolysosomal delivery in the target mammalian cell as compared to a composition comprising the same amount of a control ABPC.

Embodiment 69 the pharmaceutical composition of any one of embodiments 37-68, wherein the composition results in a less of a reduction in the level of FOLR1 presented on the surface of the target mammalian cell as compared to a composition comprising the same amount of a control ABPC.

Embodiment 70 is the pharmaceutical composition of any one of embodiments 37-68, wherein the composition does not result in a detectable reduction in the level of the FOLR1 presented on the surface of the target mammalian cell.

Embodiment 71 is the pharmaceutical composition of any one of embodiments 1-70, wherein the target mammalian cell is a cancer cell.

Embodiment 72 is the pharmaceutical composition of any one of embodiments 1-71, wherein the dissociation rate of the antigen-binding domain at a pH of about 4.0 to about 6.5 is at least 10% faster than the dissociation rate of the antigen-binding domain at a pH of about 7.0 to about 8.0.

Embodiment 73 is the pharmaceutical composition of any one of embodiments 1-71, wherein the dissociation rate of the antigen-binding domain at a pH of about 4.0 to about 6.5 is at least 3-fold faster than the dissociation rate of the antigen-binding domain at a pH of about 7.0 to about 8.0.

Embodiment 74 is the pharmaceutical composition of any one of embodiments 1-71, wherein the dissociation rate of the antigen-binding domain at a pH of about 4.0 to about 6.5 is at least 10-fold faster than the dissociation rate of the antigen-binding domain at a pH of about 7.0 to about 8.0.

Embodiment 75 the pharmaceutical composition of any one of embodiments 1-74, wherein the KD of the antigen-binding domain at a pH of about 4.0 to about 6.5 is at least 10% greater than the KD of the antigen-binding domain at a pH of about 7.0 to about 8.0.

Embodiment 76 is the pharmaceutical composition of any one of embodiments 1-74, wherein the KD of the antigen-binding domain at a pH of about 4.0 to about 6.5 is at least 3-fold greater than the KD of the antigen-binding domain at a pH of about 7.0 to about 8.0.

Embodiment 77 is the pharmaceutical composition of any one of embodiments 1-74, wherein the KD of the antigen-binding domain at a pH of about 4.0 to about 6.5 is at least 10-fold greater than the KD of the antigen-binding domain at a pH of about 7.0 to about 8.0.

Embodiment 78 is he pharmaceutical composition of any one of embodiments 1-77, wherein the ABPC is cytotoxic or cytostatic to the target mammalian cell.

Embodiment 79 is the pharmaceutical composition of any one of embodiments 1-78, wherein the ABPC is cross-reactive with a non-human primate FOLR1 and human FOLR1.

Embodiment 80 is the pharmaceutical composition of any one of embodiments 1-78, wherein the ABPC is cross-reactive with a non-human primate FOLR1, a human FOLR1, and one or both of rat FOLR1 and a mouse FOLR1.

Embodiment 81 is the pharmaceutical composition of embodiment 80, wherein the ABPC is cross-reactive with a non-human primate FOLR1, a human FOLR1, a rat FOLR1, and a mouse FOLR1.

Embodiment 82 is the pharmaceutical composition of any one of embodiments 1-81, wherein the antigen-binding domain binds to an epitope of FOLR1 that is present on the surface of cells from an Old World Monkey.

Embodiment 83 is the pharmaceutical composition of any one of embodiments 1-82, wherein the ABPC comprises a single polypeptide.

Embodiment 84 the pharmaceutical composition of embodiment 83, wherein the antigen-binding domain is selected from the group consisting of: a VH domain, a VHH domain, a VNAR domain, and a scFv.

Embodiment 85 is the pharmaceutical composition of embodiment 83 or 84, wherein the ABPC is a BITE® (bispecific T-cell engagers), a (scFv)2, a NANOBODY® (single-domain antibodies), a NANOBODY® (single-domain antibodies)-HSA, a DART® (proteins comprising two engineered scFv fragments which have their VH and VL domains exchanged), a TANDAB® (tetravalent bispecific molecules comprising antibody variable domains with two binding sites for each antigen), a scDiabody, a scDiabody-CH3, scFv-CH-CL-scFv, a HSAbody, scDiabody-HSA, or a tandem-scFv.

Embodiment 86 is the pharmaceutical composition of any one of embodiments 1-82, wherein the ABPC comprises two or more polypeptides.

Embodiment 87 is the pharmaceutical composition of embodiment 86, wherein the ABPC is selected from the group of an antibody, a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a ick-body, an orthogonal Fab, a DVD-IG™ (dual variable domain immunoglobulins), a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, ZYBODY™ (engineered proteins comprising multiple modular recognition domains), DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fe, a Diabody-Fec, a tandem scFv-Fc, a VHH-Fc, a tandem VHH-Fc, a VHH-Fc KiH, a Fab-VHH-Fc, an Intrabody, a dock and lock, an IMMTAC® (engineered fusion proteins that comprise an engineered T cell receptor based targeting system with a single chain antibody fragment), an IgG-IgG conjugate, a Cov-X-Body, a scFv1-PEG-scFv2, an Adnectin, a DARPIN™ (genetically engineered antibody mimetic proteins), a fibronectin, and a DEP conjugate.

Embodiment 88 is the pharmaceutical composition of any one of embodiments 19-87, wherein at least one polypeptide of the ABPC is conjugated to the toxin, the radioisotope, the drug, or the small molecule via a cleavable linker.

Embodiment 89 is the pharmaceutical composition of any one of embodiments 19-87, wherein at least one polypeptide of the ABPC is conjugated to the toxin, the radioisotope, the drug, or the small molecule via a non-cleavable linker.

Embodiment 90 is the pharmaceutical composition of any of embodiments 1-89, wherein the half-life of the ABPC in vivo is decreased as compared to the half-life of a control ABPC in vivo.

Embodiment 91 is the pharmaceutical composition of embodiment 90, wherein the half-life of the ABPC in vivo is decreased about 5% to about 95% as compared to the half-life of a control ABPC in vivo.

Embodiment 92 is the pharmaceutical composition of embodiment 90, wherein the half-life of the ABPC in vivo is decreased about 10% to about 95% as compared to the half-life of a control ABPC in vivo.

Embodiment 93 is the pharmaceutical composition of embodiment 90, wherein the half-life of the ABPC in vivo is decreased about 30% to about 95% as compared to the half-life of a control ABPC in vivo.

Embodiment 94 is the pharmaceutical composition of embodiment 90, wherein the half-life of the ABPC in vivo is decreased about 50% to about 95% as compared to the half-life of a control ABPC in vivo.

Embodiment 95 is the pharmaceutical composition of embodiment 90, wherein the half-life of the ABPC in vivo is decreased about 70% to about 95% as compared to the half-life of a control ABPC in vivo.

Embodiment 96 is the pharmaceutical composition of any one of embodiments 20-95, wherein the control ABPC is capable of specifically binding to FOLR1 or an epitope of FOLR1 presented on the surface of a target mammalian cell, wherein: (a) the control ABPC comprises a first antigen-binding domain: (b) the dissociation rate of the first antigen-binding domain of the control ABPC at a pH of about 4.0 to about 6.5 is no more than 3-fold faster than the dissociation rate at a pH of about 7.0 to about 8.0; and (c) the dissociation constant (KD) of the first antigen-binding domain of the control ABPC at a pH of about 4.0 to about 6.5 is no more than 3-fold greater than the KD at a pH of about 7.0 to about 8.0.

Embodiment 97 is the pharmaceutical composition of any one of embodiments 20-95, wherein the control ABPC is capable of specifically binding to FOLR1 or an epitope of FOLR1 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 2-fold faster than the dissociation rate at a pH of about 7.0 to about 8.0; and (c) the dissociation constant (KD) of the first antigen-binding domain of the control ABPC at a pH of about 4.0 to about 6.5 is no more than 2-fold greater than the KD at a pH of about 7.0 to about 8.0.

Embodiment 98 is the pharmaceutical composition of any one of embodiments 20-95, wherein the control ABPC is capable of specifically binding to FOLR1 or an epitope of FOLR1 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 1-fold faster than the dissociation rate at a pH of about 7.0 to about 8.0; and (c) the dissociation constant (KD) of the first antigen-binding domain of the control ABPC at a pH of about 4.0 to about 6.5 is no more than 1-fold greater than the KD at a pH of about 7.0 to about 8.0.

Embodiment 99 is the pharmaceutical composition of any one of embodiments 20-95, wherein the control ABPC is mirvetuximab.

Embodiment 100 is the pharmaceutical composition of any one of embodiments 1-99, wherein the ABPC further comprises a second antigen-binding domain.

Embodiment is a kit comprising at least one dose of the pharmaceutical composition of any one of embodiments 1-100.

Embodiment 102 is an antigen-binding protein construct (ABPC) comprising: a first antigen-binding domain that is capable of specifically binding FOLR1 or an epitope of FOLR1 presented on the surface of a target mammalian cell, wherein: (a) the dissociation rate of the first antigen-binding domain at a pH of about 4.0 to about 6.5 is faster than the dissociation rate at a pH of about 7.0 to about 8.0; or (b) the dissociation constant (KD) of the first antigen-binding domain at a pH of about 4.0 to about 6.5 is greater than the KD at a pH of about 7.0 to about 8.0.

Embodiment 103 is the ABPC of embodiment 102, wherein the first antigen-binding domain comprises a heavy chain variable domain of mirvetuximab with one or more amino acids substituted with a histidine.

Embodiment 104 is the ABPC of embodiment 102, wherein the first antigen-binding domain comprises a light chain variable domain of mirvetuximab with one or more amino acids substituted with a histidine.

Embodiment 105 is the ABPC of embodiment 102, wherein the first antigen-binding domain comprises: a heavy chain variable domain of mirvetuximab with one or more amino acids substituted with a histidine; and a light chain variable domain of mirvetuximab with one or more amino acids substituted with a histidine.

Embodiment 106 is the ABPC of embodiment 103 or 105, wherein the heavy chain variable domain of mirvetuximab comprises SEQ ID NO: 1.

Embodiment 107 is the ABPC of embodiment 104 or 105, wherein the light chain variable domain of mirvetuximab comprises SEQ ID NO: 2.

Embodiment 108 is the ABPC of embodiment 102, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 109 is the ABPC of embodiment 102, wherein the first FOLR1-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment is 110 is the ABPC of embodiment 102, wherein the first FOLR1-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 111 is the ABPC of embodiment 102, 103, or 108, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107.

Embodiment 112 is the ABPC of embodiment 102, 104, or 109, wherein the first antigen-binding domain comprises a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 113 is the ABPC of embodiment 102, 103, or 108, wherein the first antigen-binding domain comprises a heavy chain variable domain that is at least 90% identical to SEQ ID NO: 1, wherein the heavy chain variable domain includes a histidine at two or more positions in SEQ ID NO: 1 selected from the group consisting of: 24, 27, 54, 58, and 59.

Embodiment 114 is the ABPC of embodiment 102, 105, or 110, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107; and a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 115 is the ABPC of embodiment 102, wherein the first antigen-binding domain comprises a heavy chain variable domain of SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 43, SEQ ID NO: 45, SEQ ID NO: 46, SEQ ID NO: 48, SEQ ID NO: 49, SEQ ID NO: 50, SEQ ID NO: 51, or SEQ ID NO: 53.

Embodiment 116 is the ABPC of embodiment 102 or 115, wherein the first antigen-binding domain comprises a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 117 is the ABPC of embodiment 102, wherein the first antigen-binding domain comprises a heavy chain variable domain of SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103.

Embodiment 118 is the ABPC of embodiment 117, wherein the first antigen-binding domain comprises a light chain variable domain of SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 119 is the ABPC of any one of embodiments 102-118, wherein the ABPC is degraded in the target mammalian cell following internalization of the ABPC by the target mammalian cell.

Embodiment 120 is the ABPC of any one of embodiments 102-119, wherein the ABPC further comprises a conjugated toxin, radioisotope, drug, or small molecule.

Embodiment 121 is the ABPC of embodiment 120, wherein a composition comprising the ABPC provides for an increase in toxin liberation in the target mammalian cell as compared to a composition comprising the same amount of a control ABPC.

Embodiment 122 is the ABPC of embodiment 121, wherein a composition comprising the ABPC provides for at least a 20% increase in toxin liberation in the target mammalian cell as compared to a composition comprising the same amount of a control ABPC.

Embodiment 123 is the ABPC of embodiment 122, wherein a composition comprising the ABPC provides for at least a 50% increase in toxin liberation in the target mammalian cell as compared to a composition comprising the same amount of a control ABPC.

Embodiment 124 is the ABPC of embodiment 121, wherein a composition comprising the ABPC provides for at least a 2-fold increase in toxin liberation in the target mammalian cell as compared to a composition comprising the same amount of a control ABPC.

Embodiment 125 is the ABPC of embodiment 124, wherein a composition comprising the ABPC provides for at least a 5-fold increase in toxin liberation in the target mammalian cell as compared to a composition comprising the same amount of a control ABPC.

Embodiment 126 is the ABPC of any one of embodiments 120-125, wherein a composition comprising the ABPC provides for an increase in target mammalian cell killing as compared to a composition comprising the same amount of a control ABPC.

Embodiment 127 is the ABPC of embodiment 126, wherein a composition comprising the ABPC provides for at least a 20% increase in target mammalian cell killing as compared to a composition comprising the same amount of a control ABPC.

Embodiment 128 is the ABPC of embodiment 127, wherein a composition comprising the ABPC provides for at least a 50% increase in target mammalian cell killing as compared to a composition comprising the same amount of a control ABPC.

Embodiment 129 is the ABPC of embodiment 126, wherein a composition comprising the ABPC provides for at least a 2-fold increase in target mammalian cell killing as compared to a composition comprising the same amount of a control ABPC.

Embodiment 130 is the ABPC of embodiment 129, wherein a composition comprising the ABPC provides for at least a 5-fold increase in target mammalian cell killing as compared to a composition comprising the same amount of a control ABPC.

Embodiment 131 is the ABPC of any one of embodiments 102-130, wherein a composition comprising the ABPC provides for an increase in endolysosomal delivery in the target mammalian cell as compared to a composition comprising the same amount of a control ABPC.

Embodiment 132 is the ABPC of embodiment 131, wherein a composition comprising the ABPC provides for at least a 20% increase in endolysosomal delivery in the target mammalian cell as compared to a composition comprising the same amount of a control ABPC.

Embodiment 133 is the ABPC of embodiment 132, wherein a composition comprising the ABPC provides for at least a 50% increase in endolysosomal delivery in the target mammalian cell as compared to a composition comprising the same amount of a control ABPC.

Embodiment 134 is the ABPC of embodiment 131, wherein a composition comprising the ABPC provides for at least a 2-fold increase in endolysosomal delivery in the target mammalian cell as compared to a composition comprising the same amount of a control ABPC.

Embodiment 135 is the ABPC of embodiment 134, wherein a composition comprising the ABPC provides for at least a 5-fold increase in endolysosomal delivery in the target mammalian cell as compared to a composition comprising the same amount of a control ABPC.

Embodiment 136 is the ABPC of any one of embodiments 102-135, wherein a composition comprising the ABPC results in a less of a reduction in the level of FOLR1 presented on the surface of the target mammalian cell as compared to a composition comprising the same amount of a control ABPC.

Embodiment 137 is the ABPC of any one of embodiments 102-135, wherein a composition comprising the ABPC does not result in a detectable reduction in the level of the FOLR1 presented on the surface of the target mammalian cell.

Embodiment 138 is an antigen-binding protein construct (ABPC) comprising: a first antigen-binding domain that is capable of specifically binding FOLR1 or an epitope of FOLR1 presented on the surface of a target mammalian cell; and a conjugated toxin, radioisotope, drug, or small molecule, wherein: (a) the dissociation rate of the first antigen-binding domain at a pH of about 4.0 to about 6.5 is faster than the dissociation rate at a pH of about 7.0 to about 8.0; or the dissociation constant (KD) of the first antigen-binding domain at a pH of about 4.0 to about 6.5 is greater than the KD at a pH of about 7.0 to about 8.0; and (b) the composition provides for one or more of: an increase in toxin liberation in the target mammalian cell as compared to a composition comprising the same amount of a control ABPC; an increase in target mammalian cell killing as compared to a composition comprising the same amount of a control BPC; and an increase in endolysosomal delivery in the target mammalian cell as compared to a composition comprising the same amount of a control ABPC.

Embodiment 139 is the ABPC of embodiment 138, wherein the first antigen-binding domain comprises a heavy chain variable domain of mirvetuximab with one or more amino acids substituted with a histidine.

Embodiment 140 is the ABPC of embodiment 138, wherein the first antigen-binding domain comprises a light chain variable domain of mirvetuximab with one or more amino acids substituted with a histidine.

Embodiment 141 is the ABPC of embodiment 138, wherein the first antigen-binding domain comprises: a heavy chain variable domain of mirvetuximab with one or more amino acids substituted with a histidine; and a light chain variable domain of mirvetuximab with one or more amino acids substituted with a histidine.

Embodiment 142 is the ABPC of embodiment 139 or 141, wherein the heavy chain variable domain of mirvetuximab comprises SEQ ID NO: 1.

Embodiment 143 is the ABPC of embodiment 140 or 141, wherein the light chain variable domain of mirvetuximab comprises SEQ ID NO: 2.

Embodiment 144 is the ABPC of embodiment 138, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 145 is the ABPC of embodiment 138, wherein the first FOLR1-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 146 is the ABPC of embodiment 138, wherein the first FOLR1-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 147 is the ABPC of embodiment 138, 139, or 144, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107.

Embodiment 148 is the ABPC of embodiment 138, 140, or 145, wherein the first antigen-binding domain comprises a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 149 is the ABPC of embodiment 138, 139, or 144, wherein the first antigen-binding domain comprises a heavy chain variable domain that is at least 90% identical to SEQ ID NO: 1, wherein the heavy chain variable domain includes a histidine at two more positions in SEQ ID NO: 1 selected from the group consisting of: 24, 27, 54, 58, and 59.

Embodiment 150 is the ABPC of embodiment 138, 141, or 146, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 24, 27, 29, 31, 32, 33, 34, 35, 50, 54, 55, 57, 58, 59, 97, 99, 100, 102, 103, 104, 105, and 107; and a light chain variable domain that is at least 90% identical to SEQ ID NO: 2, wherein the light chain variable domain includes a histidine at one or more positions in SEQ ID NO: 2 selected from the group consisting of: 28, 30, 31, 32, 34, 35, 36, 55, 93, 94, 95, 96, 97, 98, and 100.

Embodiment 151 is the ABPC of embodiment 138, wherein the first antigen-binding domain comprises a heavy chain variable domain of SEQ ID NO: 14, SEQ ID NO: 17, SEQ ID NO: 19, SEQ ID NO: 21, SEQ ID NO: 22, SEQ ID NO: 23, SEQ ID NO: 24, SEQ ID NO: 25, SEQ ID NO: 26, SEQ ID NO: 28, SEQ ID NO: 30, SEQ ID NO: 31, SEQ ID NO: 33, SEQ ID NO: 34, SEQ ID NO: 35, SEQ ID NO: 43, SEQ ID NO: 45, SEQ ID NO: 46, SEQ ID NO: 48, SEQ ID NO: 49, SEQ ID NO: 50, SEQ ID NO: 51, or SEQ ID NO: 53.

Embodiment 152 is the ABPC of embodiment 138 or 151, wherein the first antigen-binding domain comprises a light chain variable domain of SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 153 is the ABPC of embodiment 138, wherein the first antigen-binding domain comprises a heavy chain variable domain of SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, or SEQ ID NO: 103.

Embodiment 154 is the ABPC of embodiment 153, wherein the first antigen-binding domain comprises a light chain variable domain of SEQ ID NO: 2, SEQ ID NO: 58, SEQ ID NO: 60, SEQ ID NO: 61, SEQ ID NO: 62, SEQ ID NO: 64, SEQ ID NO: 65, SEQ ID NO: 66, SEQ ID NO: 68, SEQ ID NO: 70, SEQ ID NO: 76, SEQ ID NO: 77, SEQ ID NO: 78, SEQ ID NO: 79, SEQ ID NO: 80, SEQ ID NO: 81, or SEQ ID NO: 83.

Embodiment 155 is the ABPC of any one of embodiments 138-154, wherein a composition comprising the ABPC provides for an increase in toxin liberation in the target mammalian cell as compared to a composition comprising the same amount of a control ABPC.

Embodiment 156 is the ABPC of embodiment 155, wherein a composition comprising the ABPC provides for at least a 20% increase in toxin liberation in the target mammalian cell as compared to a composition comprising the same amount of a control ABPC.

Embodiment 157 is the ABPC of embodiment 156, wherein a composition comprising the ABPC provides for at least a 50% increase in toxin liberation in the target mammalian cell as compared to a composition comprising the same amount of a control ABPC.

Embodiment 158 is the ABPC of embodiment 155, wherein a composition comprising the ABPC provides for at least a 2-fold increase in toxin liberation in the target mammalian cell as compared to a Embodiment 159 is the ABPC of embodiment 158, wherein a composition comprising the ABPC provides for at least a 5-fold increase in toxin liberation in the target mammalian cell as compared to a composition comprising the same amount of a control ABPC.

Embodiment 160 is the ABPC of any one of embodiments 138-159, wherein a composition comprising the ABPC provides for an increase in target mammalian cell killing as compared to a composition comprising the same amount of a control ABPC.

Embodiment 161 is the ABPC of embodiment 160, wherein a composition comprising the ABPC provides for at least a 20% increase in target mammalian cell killing as compared to a composition comprising the same amount of a control ABPC.

Embodiment 162 is the ABPC of embodiment 161, wherein a composition comprising the ABPC provides for at least a 50% increase in target mammalian cell killing as compared to a composition comprising the same amount of a control ABPC.

Embodiment 163 is the ABPC of embodiment 160, wherein a composition comprising the ABPC provides for at least a 2-fold increase in target mammalian cell killing as compared to a composition comprising the same amount of a control ABPC.

Embodiment 164 is the ABPC of embodiment 163, wherein a composition comprising the ABPC provides for at least a 5-fold increase in target mammalian cell killing as compared to a composition comprising the same amount of a control ABPC.

Embodiment 165 is the ABPC of any one of embodiments 138-164, wherein a composition comprising the ABPC provides for an increase in endolysosomal delivery in the target mammalian cell as compared to a composition comprising the same amount of a control ABPC.

Embodiment 166 is the ABPC of embodiment 165, wherein a composition comprising the ABPC provides for at least a 20% increase in endolysosomal delivery in the target mammalian cell as compared to a composition comprising the same amount of a control ABPC.

Embodiment 167 is the ABPC of embodiment 166, wherein a composition comprising the ABPC provides for at least a 50% increase in endolysosomal delivery in the target mammalian cell as compared to a composition comprising the same amount of a control ABPC.

Embodiment 168 is the ABPC of embodiment 165, wherein a composition comprising the ABPC provides for at least a 2-fold increase in endolysosomal delivery in the target mammalian cell as compared to a composition comprising the same amount of a control ABPC.

Embodiment 169 is the ABPC of embodiment 168, wherein a composition comprising the ABPC provides for at least a 5-fold increase in endolysosomal delivery in the target mammalian cell as compared to a composition comprising the same amount of a control ABPC.

Embodiment 170 is the ABPC of any one of embodiments 138-169, wherein a composition comprising the ABPC results in a less of a reduction in the level of FOLR1 presented on the surface of the target mammalian cell as compared to a composition comprising the same amount of a control ABPC.

Embodiment 171 is the ABPC of any one of embodiments 138-169, wherein a composition comprising the ABPC does not result in a detectable reduction in the level of the FOLR1 presented on the surface of the target mammalian cell.

Embodiment 172 is the ABPC of any one of embodiments 102-171, wherein the target mammalian cell is a cancer cell.

Embodiment 173 is the ABPC of any one of embodiments 102-172, wherein the dissociation rate of the antigen-binding domain at a pH of about 4.0 to about 6.5 is at least 10% faster than the dissociation rate of the antigen-binding domain at a pH of about 7.0 to about 8.0.

Embodiment 174 is the ABPC of any one of embodiments 102-172, wherein the dissociation rate of the antigen-binding domain at a pH of about 4.0 to about 6.5 is at least 3-fold faster than the dissociation rate of the antigen-binding domain at a pH of about 7.0 to about 8.0.

Embodiment 175 is the ABPC of any one of embodiments 102-172, wherein the dissociation rate of the antigen-binding domain at a pH of about 4.0 to about 6.5 is at least 10-fold faster than the dissociation rate of the antigen-binding domain at a pH of about 7.0 to about 8.0.

Embodiment 176 is the ABPC of any one of embodiments 102-175, wherein the KD of the antigen-binding domain at a pH of about 4.0 to about 6.5 is at least 10% greater than the KD of the antigen-binding domain at a pH of about 7.0 to about 8.0.

Embodiment 177 is the ABPC of any one of embodiments 102-175, wherein the KD of the antigen-binding domain at a pH of about 4.0 to about 6.5 is at least 3-fold greater than the KD of the antigen-binding domain at a pH of about 7.0 to about 8.0.

Embodiment 178 is the ABPC of any one of embodiments 102-175, wherein the KD of the antigen-binding domain at a pH of about 4.0 to about 6.5 is at least 10-fold greater than the KD of the antigen-binding domain at a pH of about 7.0 to about 8.0.

Embodiment 179 is the ABPC of any one of embodiments 102-178, wherein the ABPC is cytotoxic or cytostatic to the target mammalian cell.

Embodiment 180 is the ABPC of any one of embodiments 102-179, wherein the ABPC is cross-reactive with a non-human primate FOLR1 and human FOLR1.

Embodiment 181 is the pharmaceutical composition of any one of embodiments 102-179, wherein the ABPC is cross-reactive with a non-human primate FOLR1, a human FOLR1, and one or both of rat FOLR1 and a mouse FOLR1.

Embodiment 182 is the pharmaceutical composition of embodiment 181, wherein the ABPC is cross-reactive with a non-human primate FOLR1, a human FOLR1, a rat FOLR1, and a mouse FOLR1.

Embodiment 183 is the ABPC of any one of embodiments 102-182, wherein the antigen-binding domain binds to an epitope of FOLR1 that is present on the surface of cells from an Old World Monkey.

Embodiment 184 is the ABPC of any one of embodiments 102-183, wherein the ABPC comprises a single polypeptide.

Embodiment 185 is the ABPC of embodiment 184, wherein the antigen-binding domain is selected from the group consisting of: a VH domain, a VHH domain, a VNAR domain, and a scFv.

Embodiment 186 is the ABPC of embodiment 184 or 185, wherein the ABPC is a BITE® (bispecific T-cell engagers), a (scFv)2, a NANOBODY® (single-domain antibodies), a NANOBODY® (single-domain antibodies)-HSA, a DART® (proteins comprising two engineered scFv fragments which have their VH and VL domains exchanged), a TANDAB® (tetravalent bispecific molecules comprising antibody variable domains with two binding sites for each antigen), a scDiabody, a scDiabody-CH3, scFv-CH-CL-scFv, a HSAbody, scDiabody-HSA, or a tandem-scFv.

Embodiment 187 is the ABPC of any one of embodiments 102-183, wherein the ABPC comprises two or more polypeptides.

Embodiment 188 is the ABPC of embodiment 187, wherein the ABPC is selected from the group of an antibody, a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a KX-body, an orthogonal Fab, a DVD-IG™ (dual variable domain immunoglobulins), a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, ZYBODY™ (engineered proteins comprising multiple modular recognition domains), DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, a VHH-Fc, a tandem VHH-Fc, a VHH-Fc KiH, a Fab-VHH-Fc, an Intrabody, a dock and lock, an IMMTAC® (engineered fusion proteins that comprise an engineered T cell receptor based targeting system with a single chain antibody fragment), an IgG-IgG conjugate, a Cov-X-Body, a scFv1-PEG-scFv2, an Adnectin, a DARPIN™ (genetically engineered antibody mimetic proteins), a fibronectin, and a DEP conjugate.

Embodiment 189 is the ABPC of any one of embodiments 120-188, wherein at least one polypeptide of the ABPC is conjugated to the toxin, the radioisotope, the drug, or the small molecule via a cleavable linker.

Embodiment 190 is the ABPC of any one of embodiments 120-188, wherein at least one polypeptide of the ABPC is conjugated to the toxin, the radioisotope, the drug, or the small molecule via a non-cleavable linker.

Embodiment 191 is the ABPC of any of embodiments 102-190, wherein the half-life of the ABPC in vivo is decreased as compared to the half-life of a control ABPC in vivo.

Embodiment 192 is the ABPC of embodiment 191, wherein the half-life of the ABPC in vivo is decreased about 5% to about 95% as compared to the half-life of a control ABPC in vivo.

Embodiment 193 is the ABPC of embodiment 191, wherein the half-life of the ABPC in vivo is decreased about 10% to about 95% as compared to the half-life of a control ABPC in vivo.

Embodiment 194 the ABPC of embodiment 191, wherein the half-life of the ABPC in vivo is decreased about 30% to about 95% as compared to the half-life of a control ABPC in vivo.

Embodiment 195 is the ABPC of embodiment 191, wherein the half-life of the ABPC in vivo is decreased about 50% to about 95% as compared to the half-life of a control ABPC in vivo.

Embodiment 196 is the ABPC of embodiment 191, wherein the half-life of the ABPC in vivo is decreased about 70% to about 95% as compared to the half-life of a control ABPC in vivo.

Embodiment 197 is the ABPC of any one of embodiments 121-196, wherein the control ABPC is capable of specifically binding to FOLR1 or an epitope of FOLR1 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 3-fold faster than the dissociation rate at a pH of about 7.0 to about 8.0; and (c) the dissociation constant (KD) of the first antigen-binding domain of the control ABPC at a pH of about 4.0 to about 6.5 is no more than 3-fold greater than the KD at a pH of about 7.0 to about 8.0.

Embodiment 198 is the ABPC of any one of embodiments 121-196, wherein the control ABPC is capable of specifically binding to FOLR1 or an epitope of FOLR1 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 2-fold faster than the dissociation rate at a pH of about 7.0 to about 8.0; and (c) the dissociation constant (KD) of the first antigen-binding domain of the ABPC at a pH of about 4.0 to about 6.5 is no more than 2-fold greater than the KD at a pH of about 7.0 to about 8.0.

Embodiment 199 is the ABPC of any one of embodiments 121-196, wherein the control ABPC is capable of specifically binding to FOLR1 or an epitope of FOLR1 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 1-fold faster than the dissociation rate at a pH of about 7.0 to about 8.0; and (c) the dissociation constant (KD) of the first antigen-binding domain of the control ABPC at a pH of about 4.0 to about 6.5 is no more than 1-fold greater than the KD at a pH of about 7.0 to about 8.0.

Embodiment 200 is the ABPC of any one of embodiments 121-196, wherein the control ABPC is mirvetuximab.

Embodiment 201 is the ABPC of any one of embodiments 102-200, wherein the ABPC further comprises a second antigen-binding domain.

Embodiment 202 is a kit comprising at least one dose of the ABPC of any one of embodiments 102-201.

Embodiment 203 is a method of treating a cancer characterized by having a population of cancer cells that have FOLR1 or an epitope of FOLR1 presented on their surface, the method comprising: administering a therapeutically effective amount of the pharmaceutical composition of any one of embodiments 1-100 or the ABPC of any one of embodiments 102-201 to a subject identified as having a cancer characterized by having the population of cancer cells.

Embodiment 204 is a method of reducing the volume of a tumor in a subject, wherein the tumor is characterized by having a population of cancer cells that have FOLR1 or an epitope of FOLR1 presented on their surface, the method comprising: administering a therapeutically effective amount of the pharmaceutical composition of any one of embodiments 1-100 or the ABPC of any one of embodiments 102-201 to a subject identified as having a cancer characterized by having the population of cancer cells.

Embodiment 205 is a method of inducing cell death in a cancer cell in a subject, wherein the cancer cell has FOLR1 or an epitope of FOLR1 presented on its surface, wherein the method comprises: administering a therapeutically effective amount of the pharmaceutical composition of any one of embodiments 1-98 or the ABPC of any one of embodiments 102-201 to a subject identified as having a cancer characterized by having a population of the cancer cells.

Embodiment 206 is the method of any one of embodiments 203-205, wherein the cancer is a primary tumor.

Embodiment 207 is the method of any one of embodiments 203-205, wherein the cancer is a metastasis.

Embodiment 208 is the method of any one of embodiments 203-207, wherein the cancer is a non-T-cell-infiltrating tumor.

Embodiment 209 is the method of any one of embodiments 203-207, wherein the cancer is a T-cell infiltrating tumor.

Embodiment 210 is a method of decreasing the risk of developing a metastasis or decreasing the risk of developing an additional metastasis in a subject having a cancer, wherein the cancer is characterized by having a population of cancer cells that have FOLR1 or an epitope of FOLR1 presented on their surface the method comprising: administering a therapeutically effective amount of the pharmaceutical composition of any one of embodiments 1-100 or the ABPC of any one of embodiments 102-201 to a subject identified as having a cancer characterized by having the population of cancer cells.

Embodiment 211 is the method of embodiment 210, wherein the cancer is a non-T-cell-infiltrating tumor.

Embodiment 212 is the method of embodiment 210, wherein the cancer is a T-cell infiltrating tumor.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

```
Sequence Appendix
>Heavy Chain of mirvetuximab IgG
                                        (SEQ ID NO: 1)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Light Chain of mirvetuximab IgG
                                        (SEQ ID NO: 2)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQSREYPYTFGGGTKLEIK

>Heavy Chain CDR1 of mirvetuximab
                                        (SEQ ID NO: 3)
KASGYTFTGYFMN
```

>Heavy Chain CDR2 of mirvetuximab
                                        (SEQ ID NO: 4)
RIHPYDGDTFYNQKFQG >Heavy Chain CDR3 of mirvetuximab
                                        (SEQ ID NO: 5)
TRYDGSRAMDY >Light Chain CDR1 of mirvetuximab
                                        (SEQ ID NO: 6)
KASQSVSFAGTSLMH >Light Chain CDR2 of mirvetuximab
                                        (SEQ ID NO: 7)
RASNLEA >Light Chain CDR3 of mirvetuximab
                                        (SEQ ID NO: 8)
QQSREYPYT >Mature Human FOLR1
                                        (SEQ ID NO: 9)
RIAWARTELLNVCMNAKHHKEKPGPEDKLHEQCRPWRKNACCSTNTSQEAHKDVSY

LYRFNWNHCGEMAPACKRHFIQDTCLYECSPNLGPWIQQVDQSWRKERVLNVPLCKE

DCEQWWEDCRTSYTCKSNWHKGWNWTSGFNKCAVGAACQPFHFYFPTPTVLCNEIW

THSYKVSNYSRGSGRCIQMWFDPAQGNPNEEVARFYAAAM

>cDNA Encoding Mature Human FOLR1
                                        (SEQ ID NO: 10)
ATGGCTCAGCGGATGACAACACAGCTGCTGCTCCTTCTAGTGTGGGTGGCTGTAGT

AGGGGAGGCTCAGACAAGGATTGCATGGGCCAGGACTGAGCTTCTCAATGTCTGCA

TGAACGCCAAGCACCACAAGGAAAAGCCAGGCCCCGAGGACAAGTTGCATGAGCA

GTGTCGACCCTGGAGGAAGAATGCCTGCTGTTCTACCAACACCAGCCAGGAAGCCC

ATAAGGATGTTTCCTACCTATATAGATTCAACTGGAACCACTGTGGAGAGATGGCA

CCTGCCTGCAAACGGCATTTCATCCAGGACACCTGCCTCTACGAGTGCTCCCCCAA

CTTGGGGCCCTGGATCCAGCAGGTGGATCAGAGCTGGCGCAAAGAGCGGGTACTG

AACGTGCCCCTGTGCAAAGAGGACTGTGAGCAATGGTGGGAAGATTGTCGCACCTC

CTACACCTGCAAGAGCAACTGGCACAAGGGCTGGAACTGGACTTCAGGGTTTAACA

AGTGCGCAGTGGGAGCTGCCTGCCAACCTTTCCATTTCTACTTCCCCACACCCACTG

TTCTGTGCAATGAAATCTGGACTCACTCCTACAAGGTCAGCAACTACAGCCGAGGG

AGTGGCCGCTGCATCCAGATGTGGTTCGACCCAGCCCAGGGCAACCCCAATGAGGA

GGTGGCGAGGTTCTATGCTGCAGCCATGAGTGGGGCTGGGCCCTGGGCAGCCTGGC

CTTTCCTGCTTAGCCTGGCCCTAATGCTGCTGTGGCTGCTCAGC

>Extracellular Domain of FOLR1
                                        (SEQ ID NO: 11)
RIAWARTELLNVCMNAKHHKEKPGPEDKLHEQCRPWRKNACCSTNTSQEAHKDVSY

LYRFNWNHCGEMAPACKRHFIQDTCLYECSPNLGPWIQQVDQSWRKERVLNVPLCKE

DCEQWWEDCRTSYTCKSNWHKGWNWTSGFNKCAVGAACQPFHFYFPTPTVLCNEIW

THSYKVSNYSRGSGRCIQMWFDPAQGNPNEEVARFYAAAM

>cDNA Encoding Extracellular Domain of FOLR1
                                        (SEQ ID NO: 12)
ATGGCTCAGCGGATGACAACACAGCTGCTGCTCCTTCTAGTGTGGGTGGCTGTAGT

AGGGGAGGCTCAGACAAGGATTGCATGGGCCAGGACTGAGCTTCTCAATGTCTGCA

TGAACGCCAAGCACCACAAGGAAAAGCCAGGCCCCGAGGACAAGTTGCATGAGCA

GTGTCGACCCTGGAGGAAGAATGCCTGCTGTTCTACCAACACCAGCCAGGAAGCCC

ATAAGGATGTTTCCTACCTATATAGATTCAACTGGAACCACTGTGGAGAGATGGCA

CCTGCCTGCAAACGGCATTTCATCCAGGACACCTGCCTCTACGAGTGCTCCCCCAA

CTTGGGGCCCTGGATCCAGCAGGTGGATCAGAGCTGGCGCAAAGAGCGGGTACTG

AACGTGCCCCTGTGCAAAGAGGACTGTGAGCAATGGTGGGAAGATTGTCGCACCTC

CTACACCTGCAAGAGCAACTGGCACAAGGGCTGGAACTGGACTTCAGGGTTTAACA

AGTGCGCAGTGGGAGCTGCCTGCCAACCTTTCCATTTCTACTTCCCCACACCCACTG

TTCTGTGCAATGAAATCTGGACTCACTCCTACAAGGTCAGCAACTACAGCCGAGGG

AGTGGCCGCTGCATCCAGATGTGGTTCGACCCAGCCCAGGGCAACCCCAATGAGGA

GGTGGCGAGGTTCTATGCTGCAGCCATGAGTGGGGCTGGGCCCTGGGCAGCCTGGC

CTTTCCTGCTTAGCCTGGCCCTAATGCTGCTGTGGCTGCTCAGC

>Heavy Chain of mirvetuximab IgG histidine scanning
variant #1
                                                        (SEQ ID NO: 13)
QVQLVQSGAEVVKPGASVKISCHASGYTFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #2
                                                        (SEQ ID NO: 14)
QVQLVQSGAEVVKPGASVKISCKHSGYTFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #3
                                                        (SEQ ID NO: 15)
QVQLVQSGAEVVKPGASVKISCKAHGYTFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #4
                                                        (SEQ ID NO: 16)
QVQLVQSGAEVVKPGASVKISCKASHYTFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #5
                                                        (SEQ ID NO: 17)
QVQLVQSGAEVVKPGASVKISCKASGHTFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #6
                                                        (SEQ ID NO: 18)
QVQLVQSGAEVVKPGASVKISCKASGYHFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

-continued

>Heavy Chain of mirvetuximab IgG histidine scanning
variant #7
                                                    (SEQ ID NO: 19)
QVQLVQSGAEVVKPGASVKISCKASGYTHTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #8
                                                    (SEQ ID NO: 20)
QVQLVQSGAEVVKPGASVKISCKASGYTFHGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #9
                                                    (SEQ ID NO: 21)
QVQLVQSGAEVVKPGASVKISCKASGYTFTHYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #10
                                                    (SEQ ID NO: 22)
QVQLVQSGAEVVKPGASVKISCKASGYTFTGHFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #11
                                                    (SEQ ID NO: 23)
QVQLVQSGAEVVKPGASVKISCKASGYTFTGYHMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #12
                                                    (SEQ ID NO: 24)
QVQLVQSGAEVVKPGASVKISCKASGYTFTGYFHNWVKQSPGQSLEWIGRIHPYDGDT

FYNQKFQGKATLTVDKSSNTAHMELLSLTSEDFAVYYCTRYDGSRAMDYWGQGTTV

TVSS

>Heavy Chain of mirvetuximab IgG histidine scanning
variant #13
                                                    (SEQ ID NO: 25)
QVQLVQSGAEVVKPGASVKISCKASGYTFTGYFMHWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #14
                                                    (SEQ ID NO: 26)
QVQLVQSGAEVVKPGASVKISCKASGYTFTGYFMNWVKQSPGQSLEWIGHIHPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #15
                                                    (SEQ ID NO: 27)
QVQLVQSGAEVVKPGASVKISCKASGYTFTGYFMNWVKQSPGQSLEWIGRHHPYDGD

TFYNQKFQGKATLTVDKSSNTAHMELLSLTSEDFAVYYCTRYDGSRAMDYWGQGTT

VTVSS

-continued

>Heavy Chain of mirvetuximab IgG histidine scanning
variant #16

(SEQ ID NO: 28)

QVQLVQSGAEVVKPGASVKISCKASGYTFTGYFMNWVKQSPGQSLEWIGRIAPYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #17

(SEQ ID NO: 29)

QVQLVQSGAEVVKPGASVKISCKASGYTFTGYFMNWVKQSPGQSLEWIGRIHHYDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #18

(SEQ ID NO: 30)

QVQLVQSGAEVVKPGASVKISCKASGYTFTGYFMNWVKQSPGQSLEWIGRIHPHDGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #19

(SEQ ID NO: 31)

QVQLVQSGAEVVKPGASVKISCKASGYTFTGYFMNWVKQSPGQSLEWIGRIHPYHGD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #20

(SEQ ID NO: 32)

QVQLVQSGAEVVKPGASVKISCKASGYTFTGYFMNWVKQSPGQSLEWIGRIHPYDHD

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #21

(SEQ ID NO: 33)

QVQLVQSGAEVVKPGASVKISCKASGYTFTGYFMNWVKQSPGQSLEWIGRIHPYDGH

TFYNQKFQGKATLTVDKSSNTAHMELLSLTSEDFAVYYCTRYDGSRAMDYWGQGTT

VTVSS

>Heavy Chain of mirvetuximab IgG histidine scanning
variant #22

(SEQ ID NO: 34)

QVQLVQSGAEVVKPGASVKISCKASGYTFTGYFMNWVKQSPGQSLEWIGRIHPYDGD

HFYNQKFQGKATLTVDKSSNTAHMELLSLTSEDFAVYYCTRYDGSRAMDYWGQGTT

VTVSS

>Heavy Chain of mirvetuximab IgG histidine scanning
variant #23

(SEQ ID NO: 35)

QVQLVQSGAEVVKPGASVKISCKASGYTFTGYFMNWVKQSPGQSLEWIGRIHPYDGD

THYNQKFQGKATLTVDKSSNTAHMELLSLTSEDFAVYYCTRYDGSRAMDYWGQGTT

VTVSS

>Heavy Chain of mirvetuximab IgG histidine scanning
variant #24

(SEQ ID NO: 36)

QVQLVQSGAEVVKPGASVKISCKASGYTFTGYFMNWVKQSPGQSLEWIGRIHPYDGD

TFHNQKFQGKATLTVDKSSNTAHMELLSLTSEDFAVYYCTRYDGSRAMDYWGQGTT

VTVSS

-continued

```
>Heavy Chain of mirvetuximab IgG histidine scanning
variant #25
                                        (SEQ ID NO: 37)
QVQLVQSGAEVVKPGASVKISCKASGYTFTGYFMNWVKQSPGQSLEWIGRIHPYDGD

TFYHQKFQGKATLTVDKSSNTAHMELLSLTSEDFAVYYCTRYDGSRAMDYWGQGTT

VTVSS

>Heavy Chain of mirvetuximab IgG histidine scanning
variant #26
                                        (SEQ ID NO: 38)
QVQLVQSGAEVVKPGASVKISCKASGYTFTGYFMNWVKQSPGQSLEWIGRIHPYDGD

TFYNHKFQGKATLTVDKSSNTAHMELLSLTSEDFAVYYCTRYDGSRAMDYWGQGTT

VTVSS

>Heavy Chain of mirvetuximab IgG histidine scanning
variant #27
                                        (SEQ ID NO: 39)
QVQLVQSGAEVVKPGASVKISCKASGYTFTGYFMNWVKQSPGQSLEWIGRIHPYDGD

TFYNQHFQGKATLTVDKSSNTAHMELLSLTSEDFAVYYCTRYDGSRAMDYWGQGTT

VTVSS

>Heavy Chain of mirvetuximab IgG histidine scanning
variant #28
                                        (SEQ ID NO: 40)
QVQLVQSGAEVVKPGASVKISCKASGYTFTGYFMNWVKQSPGQSLEWIGRIHPYDGD

TFYNQKHQGKATLTVDKSSNTAHMELLSLTSEDFAVYYCTRYDGSRAMDYWGQGTT

VTVSS

>Heavy Chain of mirvetuximab IgG histidine scanning
variant #29
                                        (SEQ ID NO: 41)
QVQLVQSGAEVVKPGASVKISCKASGYTFTGYFMNWVKQSPGQSLEWIGRIHPYDGD

TFYNQKFHGKATLTVDKSSNTAHMELLSLTSEDFAVYYCTRYDGSRAMDYWGQGTT

VTVSS

>Heavy Chain of mirvetuximab IgG histidine scanning
variant #30
                                        (SEQ ID NO: 42)
QVQLVQSGAEVVKPGASVKISCKASGYTFTGYFMNWVKQSPGQSLEWIGRIHPYDGD

TFYNQKFQHKATLTVDKSSNTAHMELLSLTSEDFAVYYCTRYDGSRAMDYWGQGTT

VTVSS

>Heavy Chain of mirvetuximab IgG histidine scanning
variant #31
                                        (SEQ ID NO: 43)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCHRYDGSRAMDYWGQGTT

VTVSS

>Heavy Chain of mirvetuximab IgG histidine scanning
variant #32
                                        (SEQ ID NO: 44)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTHYDGSRAMDYWGQGTT

VTVSS

>Heavy Chain of mirvetuximab IgG histidine scanning
variant #33
                                        (SEQ ID NO: 45)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRHDGSRAMDYWGQGTT

VTVSS
```

-continued

>Heavy Chain of mirvetuximab IgG histidine scanning
variant #34
                                        (SEQ ID NO: 46)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYHGSRAMDYWGQGTT

VTVSS

>Heavy Chain of mirvetuximab IgG histidine scanning
variant #35
                                        (SEQ ID NO: 47)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDHSRAMDYWGQGTT

VTVSS

>Heavy Chain of mirvetuximab IgG histidine scanning
variant #36
                                        (SEQ ID NO: 48)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDGHRAMDYWGQGTT

VTVSS

>Heavy Chain of mirvetuximab IgG histidine scanning
variant #37
                                        (SEQ ID NO: 49)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDGSHAMDYWGQGTT

VTVSS

>Heavy Chain of mirvetuximab IgG histidine scanning
variant #38
                                        (SEQ ID NO: 50)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDGSRHMDYWGQGTT

VTVSS

>Heavy Chain of mirvetuximab IgG histidine scanning
variant #39
                                        (SEQ ID NO: 51)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDGSRAHDYWGQGTTV

TVSS

>Heavy Chain of mirvetuximab IgG histidine scanning
variant #40
                                        (SEQ ID NO: 52)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDGSRAMHYWGQGTT

VTVSS

>Heavy Chain of mirvetuximab IgG histidine scanning
variant #41
                                        (SEQ ID NO: 53)
QVQLVQSGAEVVKPGASVKISCKASGYTFTGYFMNWVKQSPGQSLEWIGRIHPYDGD

TFYNQKFQGKATLTVDKSSNTAHMELLSLTSEDFAVYYCTRYDGSRAMDHWGQGTT

VTVSS

>Light Chain of mirvetuximab IgG histidine scanning
variant #1
                                        (SEQ ID NO: 54)
DIVLTQSPLSLAVSLGQPAIISCHASQSVSFAGTSLMHWYHQKPGQQPRLLIYRASNLEA

GVPDRFSGSGSKTDFTLTISPVEAEDAATYYCQQSREYPYTFGGGTKLEIK

-continued

>Light Chain of mirvetuximab IgG histidine scanning
variant #2

(SEQ ID NO: 55)

DIVLTQSPLSLAVSLGQPAIISCKHSQSVSFAGTSLMHWYHQKPGQQPRLLIYRASNLEA

GVPDRFSGSGSKTDFTLTISPVEAEDAATYYCQQSREYPYTFGGGTKLEIK

>Light Chain of mirvetuximab IgG histidine scanning
variant #3

(SEQ ID NO: 56)

DIVLTQSPLSLAVSLGQPAIISCKAHQSVSFAGTSLMHWYHQKPGQQPRLLIYRASNLE

AGVPDRFSGSGSKTDFTLTISPVEAEDAATYYCQQSREYPYTFGGGTKLEIK

>Light Chain of mirvetuximab IgG histidine scanning
variant #4

(SEQ ID NO: 57)

DIVLTQSPLSLAVSLGQPAIISCKASHSVSFAGTSLMHWYHQKPGQQPRLLIYRASNLEA

GVPDRFSGSGSKTDFTLTISPVEAEDAATYYCQQSREYPYTFGGGTKLEIK

>Light Chain of mirvetuximab IgG histidine scanning
variant #5

(SEQ ID NO: 58)

DIVLTQSPLSLAVSLGQPAIISCKASQHVSFAGTSLMHWYHQKPGQQPRLLIYRASNLE

AGVPDRFSGSGSKTDFTLTISPVEAEDAATYYCQQSREYPYTFGGGTKLEIK

>Light Chain of mirvetuximab IgG histidine scanning
variant #6

(SEQ ID NO: 59)

DIVLTQSPLSLAVSLGQPAIISCKASQSHSFAGTSLMHWYHQKPGQQPRLLIYRASNLEA

GVPDRFSGSGSKTDFTLTISPVEAEDAATYYCQQSREYPYTFGGGTKLEIK

>Light Chain of mirvetuximab IgG histidine scanning
variant #7

(SEQ ID NO: 60)

DIVLTQSPLSLAVSLGQPAIISCKASQSVHFAGTSLMHWYHQKPGQQPRLLIYRASNLE

AGVPDRFSGSGSKTDFTLTISPVEAEDAATYYCQQSREYPYTFGGGTKLEIK

>Light Chain of mirvetuximab IgG histidine scanning
variant #8

(SEQ ID NO: 61)

DIVLTQSPLSLAVSLGQPAIISCKASQSVSHAGTSLMHWYHQKPGQQPRLLIYRASNLE

AGVPDRFSGSGSKTDFTLTISPVEAEDAATYYCQQSREYPYTFGGGTKLEIK

>Light Chain of mirvetuximab IgG histidine scanning
variant #9

(SEQ ID NO: 62)

DIVLTQSPLSLAVSLGQPAIISCKASQSVSFHGTSLMHWYHQKPGQQPRLLIYRASNLEA

GVPDRFSGSGSKTDFTLTISPVEAEDAATYYCQQSREYPYTFGGGTKLEIK

>Light Chain of mirvetuximab IgG histidine scanning
variant #10

(SEQ ID NO: 63)

DIVLTQSPLSLAVSLGQPAIISCKASQSVSFAHTSLMHWYHQKPGQQPRLLIYRASNLEA

GVPDRFSGSGSKTDFTLTISPVEAEDAATYYCQQSREYPYTFGGGTKLEIK

>Light Chain of mirvetuximab IgG histidine scanning
variant #11

(SEQ ID NO: 64)

DIVLTQSPLSLAVSLGQPAIISCKASQSVSFAGHSLMHWYHQKPGQQPRLLIYRASNLEA

GVPDRFSGSGSKTDFTLTISPVEAEDAATYYCQQSREYPYTFGGGTKLEIK

>Light Chain of mirvetuximab IgG histidine scanning
variant #12

(SEQ ID NO: 65)

DIVLTQSPLSLAVSLGQPAIISCKASQSVSFAGTHLMHWYHQKPGQQPRLLIYRASNLE

AGVPDRFSGSGSKTDFTLTISPVEAEDAATYYCQQSREYPYTFGGGTKLEIK

-continued

>Light Chain of mirvetuximab IgG histidine scanning
variant #13
```
                                        (SEQ ID NO: 66)
DIVLTQSPLSLAVSLGQPAIISCKASQSVSFAGTSHMHWYHQKPGQQPRLLIYRASNLEA

GVPDRFSGSGSKTDFTLTISPVEAEDAATYYCQQSREYPYTFGGGTKLEIK
```

>Light Chain of mirvetuximab IgG histidine scanning
variant #14
```
                                        (SEQ ID NO: 67)
DIVLTQSPLSLAVSLGQPAIISCKASQSVSFAGTSLHHWYHQKPGQQPRLLIYRASNLEA

GVPDRFSGSGSKTDFTLTISPVEAEDAATYYCQQSREYPYTFGGGTKLEIK
```

>Light Chain of mirvetuximab IgG histidine scanning
variant #15
```
                                        (SEQ ID NO: 68)
DIVLTQSPLSLAVSLGQPAIISCKASQSVSFAGTSLMAWYHQKPGQQPRLLIYRASNLEA

GVPDRFSGSGSKTDFTLTISPVEAEDAATYYCQQSREYPYTFGGGTKLEIK
```

>Light Chain of mirvetuximab IgG histidine scanning
variant #16
```
                                        (SEQ ID NO: 69)
DIVLTQSPLSLAVSLGQPAIISCKASQSVSFAGTSLMHWYHQKPGQQPRLLIYHASNLEA

GVPDRFSGSGSKTDFTLTISPVEAEDAATYYCQQSREYPYTFGGGTKLEIK
```

>Light Chain of mirvetuximab IgG histidine scanning
variant #17
```
                                        (SEQ ID NO: 70)
DIVLTQSPLSLAVSLGQPAIISCKASQSVSFAGTSLMHWYHQKPGQQPRLLIYRHSNLEA

GVPDRFSGSGSKTDFTLTISPVEAEDAATYYCQQSREYPYTFGGGTKLEIK
```

>Light Chain of mirvetuximab IgG histidine scanning
variant #18
```
                                        (SEQ ID NO: 71)
DIVLTQSPLSLAVSLGQPAIISCKASQSVSFAGTSLMHWYHQKPGQQPRLLIYRAHNLE

AGVPDRFSGSGSKTDFTLTISPVEAEDAATYYCQQSREYPYTFGGGTKLEIK
```

>Light Chain of mirvetuximab IgG histidine scanning
variant #19
```
                                        (SEQ ID NO: 72)
DIVLTQSPLSLAVSLGQPAIISCKASQSVSFAGTSLMHWYHQKPGQQPRLLIYRASHLEA

GVPDRFSGSGSKTDFTLTISPVEAEDAATYYCQQSREYPYTFGGGTKLEIK
```

>Light Chain of mirvetuximab IgG histidine scanning
variant #20
```
                                        (SEQ ID NO: 73)
DIVLTQSPLSLAVSLGQPAIISCKASQSVSFAGTSLMHWYHQKPGQQPRLLIYRASNHEA

GVPDRFSGSGSKTDFTLTISPVEAEDAATYYCQQSREYPYTFGGGTKLEIK
```

>Light Chain of mirvetuximab IgG histidine scanning
variant #21
```
                                        (SEQ ID NO: 74)
DIVLTQSPLSLAVSLGQPAIISCKASQSVSFAGTSLMHWYHQKPGQQPRLLIYRASNLHA

GVPDRFSGSGSKTDFTLTISPVEAEDAATYYCQQSREYPYTFGGGTKLEIK
```

>Light Chain of mirvetuximab IgG histidine scanning
variant #22
```
                                        (SEQ ID NO: 75)
DIVLTQSPLSLAVSLGQPAIISCKASQSVSFAGTSLMHWYHQKPGQQPRLLIYRASNLEH

GVPDRFSGSGSKTDFTLTISPVEAEDAATYYCQQSREYPYTFGGGTKLEIK
```

>Light Chain of mirvetuximab IgG histidine scanning
variant #23
```
                                        (SEQ ID NO: 76)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCHQSREYPYTFGGGTKLEIK
```

-continued

>Light Chain of mirvetuximab IgG histidine scanning
variant #24
(SEQ ID NO: 77)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQHSREYPYTFGGGTKLEIK

>Light Chain of mirvetuximab IgG histidine scanning
variant #25
(SEQ ID NO: 78)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQHREYPYTFGGGTKLEIK

>Light Chain of mirvetuximab IgG histidine scanning
variant #26
(SEQ ID NO: 79)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQSHEYPYTFGGGTKLEIK

>Light Chain of mirvetuximab IgG histidine scanning
variant #27
(SEQ ID NO: 80)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQSRHYPYTFGGGTKLEIK

>Light Chain of mirvetuximab IgG histidine scanning
variant #28
(SEQ ID NO: 81)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQSREHPYTFGGGTKLEIK

>Light Chain of mirvetuximab IgG histidine scanning
variant #29
(SEQ ID NO: 82)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQSREYHYTFGGGTKLEIK

>Light Chain of mirvetuximab IgG histidine scanning
variant #30
(SEQ ID NO: 83)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQSREYPHTFGGGTKLEIK

>Light Chain of mirvetuximab IgG histidine scanning
variant #31
(SEQ ID NO: 84)
DIVLTQSPLSLAVSLGQPAIISCKASQSVSFAGTSLMHWYHQKPGQQPRLLIYRASNLEA

GVPDRFSGSGSKTDFTLTISPVEAEDAATYYCQQSREYPYHFGGGTKLEIK

>Heavy Chain Combinations of mirvetuximab IgG histidine
scanning variant #1
(SEQ ID NO: 85)
QVQLVQSGAEVVKPGASVKISCKHSGHTFTGYFMNWVKQSPGQSLEWIGRIHPYDGD

TFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #2
(SEQ ID NO: 86)
QVQLVQSGAEVVKPGASVKISCKHSGYTFTGYFMNWVKQSPGQSLEWIGRIHPHDGD

TFYNQKFQGKATLTVDKSSNTAHMELLSLTSEDFAVYYCTRYDGSRAMDYWGQGTT

VTVSS

-continued

>Heavy Chain Combinations of mirvetuximab IgG histidine
scanning variant #3

(SEQ ID NO: 87)

QVQLVQSGAEVVKPGASVKISCKHSGYTFTGYFMNWVKQSPGQSLEWIGRIHPYDGD

HFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #4

(SEQ ID NO: 88)

QVQLVQSGAEVVKPGASVKISCKHSGYTFTGYFMNWVKQSPGQSLEWIGRIHPYDGD

THYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #5

(SEQ ID NO: 89)

QVQLVQSGAEVVKPGASVKISCKASGHTFTGYFMNWVKQSPGQSLEWIGRIHPHDGD

TFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #6

(SEQ ID NO: 90)

QVQLVQSGAEVVKPGASVKISCKASGHTFTGYFMNWVKQSPGQSLEWIGRIHPYDGD

HFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #7

(SEQ ID NO: 91)

QVQLVQSGAEVVKPGASVKISCKASGHTFTGYFMNWVKQSPGQSLEWIGRIHPYDGD

THYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #8

(SEQ ID NO: 92)

QVQLVQSGAEVVKPGASVKISCKASGYTFTGYFMNWVKQSPGQSLEWIGRIHPHDGD

HFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #9

(SEQ ID NO: 93)

QVQLVQSGAEVVKPGASVKISCKASGYTFTGYFMNWVKQSPGQSLEWIGRIHPHDGD

THYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #10

(SEQ ID NO: 94)

QVQLVQSGAEVVKPGASVKISCKASGYTFTGYFMNWVKQSPGQSLEWIGRIHPYDGD

HHYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #11

(SEQ ID NO: 95)

QVQLVQSGAEVVKPGASVKISCKHSGHTFTGYFMNWVKQSPGQSLEWIGRIHPHDGD

TFYNQKFQGKATLTVDKSSNTAHMELLSLTSEDFAVYYCTRYDGSRAMDYWGQGTT

VTVSS

-continued

>Heavy Chain Combinations of mirvetuximab IgG histidine
scanning variant #12

(SEQ ID NO: 96)

QVQLVQSGAEVVKPGASVKISCKHSGHTFTGYFMNWVKQSPGQSLEWIGRIHPYDGD

HFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #13

(SEQ ID NO: 97)

QVQLVQSGAEVVKPGASVKISCKHSGHTFTGYFMNWVKQSPGQSLEWIGRIHPYDGD

THYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #14

(SEQ ID NO: 98)

QVQLVQSGAEVVKPGASVKISCKHSGYTFTGYFMNWVKQSPGQSLEWIGRIHPHDGD

HFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #15

(SEQ ID NO: 99)

QVQLVQSGAEVVKPGASVKISCKHSGYTFTGYFMNWVKQSPGQSLEWIGRIHPHDGD

THYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #16

(SEQ ID NO: 100)

QVQLVQSGAEVVKPGASVKISCKHSGYTFTGYFMNWVKQSPGQSLEWIGRIHPYDGD

FIHYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #17

(SEQ ID NO: 101)

QVQLVQSGAEVVKPGASVKISCKASGHTFTGYFMNWVKQSPGQSLEWIGRIHPHDGD

HFYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #18

(SEQ ID NO: 102)

QVQLVQSGAEVVKPGASVKISCKASGHTFTGYFMNWVKQSPGQSLEWIGRIHPHDGD

THYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #19

(SEQ ID NO: 103)

QVQLVQSGAEVVKPGASVKISCKASGHTFTGYFMNWVKQSPGQSLEWIGRIHPYDGD

FIHYNQKFQGKATLTVDKSSNTAHMELLSLTSEDFAVYYCTRYDGSRAMDYWGQGTT

VTVSS

>Heavy Chain Combinations of mirvetuximab IgG histidine
scanning variant #20

(SEQ ID NO: 104)

QVQLVQSGAEVVKPGASVKISCKASGYTFTGYFMNWVKQSPGQSLEWIGRIHPHDGD

FIHYNQKFQGKATLTVDKSSNTAHMELLSLTSEDFAVYYCTRYDGSRAMDYWGQGTT

VTVSS

-continued

>Heavy Chain of STRO-002 IgG (SEQ ID NO: 105)

EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGMDYYLDYWGQ

GTLVTVSS

>Light Chain of STRO-022 IgG (SEQ ID NO: 106)

DIQMTQSPSSLSASVGDRVTITCRASQDVNTAVAWYQQKPGKAPKLLIYSASFLYSGVP

SRFSGSRSGTDFTLTISSLQPEDFATYYCQQHYTTPPTFGQGTKVEIK

>Heavy Chain CDR1 of STRO-002

(SEQ ID NO: 107)

GFNIRTQSIH

>Heavy Chain CDR2 of STRO-002

(SEQ ID NO: 108)

DIFPIDGITDYADSVKG

>Heavy Chain CDR3 of STRO-002

(SEQ ID NO: 109)

ARGSWSWPSGMDYYLDY

>Light Chain CDR1 of STRO-002

(SEQ ID NO: 110)

RASQDVNTAVA

>Light Chain CDR2 of STRO-002

(SEQ ID NO: 111)

SASFLYS

>Light Chain CDR3 of STRO-002

(SEQ ID NO: 112)

QQHYTTPPT

>Heavy Chain of STRO-002 IgG histidine scanning
variant #1

(SEQ ID NO: 113)

EVQLVESGGGLVQPGGSLRLSCAASHFNIRTQSIHWVRQAPGKGLEWIGDIFPIDGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #2

(SEQ ID NO: 114)

EVQLVESGGGLVQPGGSLRLSCAASGHNIRTQSIHWVRQAPGKGLEWIGDIFPIDGITD

YADSVKGRFTISADTSKNTAYLQMNSLRAEDTAVYYCARGSWSWPSGMDYYLDYWG

QGTLVTVSS

>Heavy Chain of STRO-002 IgG histidine scanning
variant #3

(SEQ ID NO: 115)

EVQLVESGGGLVQPGGSLRLSCAASGFHIRTQSIHWVRQAPGKGLEWIGDIFPIDGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #4

(SEQ ID NO: 116)

EVQLVESGGGLVQPGGSLRLSCAASGFNHRTQSIHWVRQAPGKGLEWIGDIFPIDGITD

YADSVKGRFTISADTSKNTAYLQMNSLRAEDTAVYYCARGSWSWPSGMDYYLDYWG

QGTLVTVSS

-continued

```
>Heavy Chain of STRO-002 IgG histidine scanning
variant #5
                              (SEQ ID NO: 117)
EVQLVESGGGLVQPGGSLRLSCAASGFNIHTQSIHWVRQAPGKGLEWIGDIFPIDGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #6
                              (SEQ ID NO: 118)
EVQLVESGGGLVQPGGSLRLSCAASGFNIRHQSIHWVRQAPGKGLEWIGDIFPIDGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #7
                              (SEQ ID NO: 119)
EVQLVESGGGLVQPGGSLRLSCAASGFNIRTHSIHWVRQAPGKGLEWIGDIFPIDGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #8
                              (SEQ ID NO: 120)
EVQLVESGGGLVQPGGSLRLSCAASGFNIRTQHIHWVRQAPGKGLEWIGDIFPIDGITD

YADSVKGRFTISADTSKNTAYLQMNSLRAEDTAVYYCARGSWSWPSGMDYYLDYWG

QGTLVTVSS

>Heavy Chain of STRO-002 IgG histidine scanning
variant #9
                              (SEQ ID NO: 121)
EVQLVESGGGLVQPGGSLRLSCAASGFNIRTQSHHWVRQAPGKGLEWIGDIFPIDGITD

YADSVKGRFTISADTSKNTAYLQMNSLRAEDTAVYYCARGSWSWPSGMDYYLDYWG

QGTLVTVSS

>Heavy Chain of STRO-002 IgG histidine scanning
variant #10
                              (SEQ ID NO: 122)
EVQLVESGGGLVQPGGSLRLSCAASGFNIRTQSIAWVRQAPGKGLEWIGDIFPIDGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #11
                              (SEQ ID NO: 123)
EVQLVESGGGLVQPGGSLRLSCAASGFNIRTQSIHWVRQAPGKGLEWIGHIFPIDGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #12
                              (SEQ ID NO: 124)
EVQLVESGGGLVQPGGSLRLSCAASGFNIRTQSIHWVRQAPGKGLEWIGDHFPIDGITD

YADSVKGRFTISADTSKNTAYLQMNSLRAEDTAVYYCARGSWSWPSGMDYYLDYWG

QGTLVTVSS

>Heavy Chain of STRO-002 IgG histidine scanning
variant #13
                              (SEQ ID NO: 125)
EVQLVESGGGLVQPGGSLRLSCAASGFNIRTQSIHWVRQAPGKGLEWIGDIHPIDGITD

YADSVKGRFTISADTSKNTAYLQMNSLRAEDTAVYYCARGSWSWPSGMDYYLDYWG

QGTLVTVSS
```

-continued

>Heavy Chain of STRO-002 IgG histidine scanning
variant #14
                                        (SEQ ID NO: 126)
EVQLVESGGGLVQPGGSLRLSCAASGFNIRTQSIHWVRQAPGKGLEWIGDIFHIDGITD

YADSVKGRFTISADTSKNTAYLQMNSLRAEDTAVYYCARGSWSWPSGMDYYLDYWG

QGTLVTVSS

>Heavy Chain of STRO-002 IgG histidine scanning
variant #15
                                        (SEQ ID NO: 127)
EVQLVESGGGLVQPGGSLRLSCAASGFNIRTQSIHWVRQAPGKGLEWIGDIFPHDGITD

YADSVKGRFTISADTSKNTAYLQMNSLRAEDTAVYYCARGSWSWPSGMDYYLDYWG

QGTLVTVSS

>Heavy Chain of STRO-002 IgG histidine scanning
variant #16
                                        (SEQ ID NO: 128)
EVQLVESGGGLVQPGGSLRLSCAASGFNIRTQSIHWVRQAPGKGLEWIGDIFPIHGITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #17
                                        (SEQ ID NO: 129)
EVQLVESGGGLVQPGGSLRLSCAASGFNIRTQSIHWVRQAPGKGLEWIGDIFPIDHITDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #18
                                        (SEQ ID NO: 130)
EVQLVESGGGLVQPGGSLRLSCAASGFNIRTQSIHWVRQAPGKGLEWIGDIFPIDGHTD

YADSVKGRFTISADTSKNTAYLQMNSLRAEDTAVYYCARGSWSWPSGMDYYLDYWG

QGTLVTVSS

>Heavy Chain of STRO-002 IgG histidine scanning
variant #19
                                        (SEQ ID NO: 131)
EVQLVESGGGLVQPGGSLRLSCAASGFNIRTQSIHWVRQAPGKGLEWIGDIFPIDGIHDY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #20
                                        (SEQ ID NO: 132)
EVQLVESGGGLVQPGGSLRLSCAASGFNIRTQSIHWVRQAPGKGLEWIGDIFPIDGITHY

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #21
                                        (SEQ ID NO: 133)
EVQLVESGGGLVQPGGSLRLSCAASGFNIRTQSIHWVRQAPGKGLEWIGDIFPIDGITDH

ADSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #22
                                        (SEQ ID NO: 134)
EVQLVESGGGLVQPGGSLRLSCAASGFNIRTQSIHWVRQAPGKGLEWIGDIFPIDGITDY

HDSVKGRFTISADTSKNTAYLQMNSLRAEDTAVYYCARGSWSWPSGMDYYLDYWGQ

GTLVTVSS

-continued

>Heavy Chain of STRO-002 IgG histidine scanning
variant #23
                                        (SEQ ID NO: 135)
EVQLVESGGGLVQPGGSLRLSCAASGFNIRTQSIHWVRQAPGKGLEWIGDIFPIDGITDY

AHSVKGRFTISADTSKNTAYLQMNSLRAEDTAVYYCARGSWSWPSGMDYYLDYWGQ

GTLVTVSS

>Heavy Chain of STRO-002 IgG histidine scanning
variant #24
                                        (SEQ ID NO: 136)
EVQLVESGGGLVQPGGSLRLSCAASGFNIRTQSIHWVRQAPGKGLEWIGDIFPIDGITDY

ADHVKGRFTISADTSKNTAYLQMNSLRAEDTAVYYCARGSWSWPSGMDYYLDYWG

QGTLVTVSS

>Heavy Chain of STRO-002 IgG histidine scanning
variant #25
                                        (SEQ ID NO: 137)
EVQLVESGGGLVQPGGSLRLSCAASGFNIRTQSIHWVRQAPGKGLEWIGDIFPIDGITDY

ADSHKGRFTISADTSKNTAYLQMNSLRAEDTAVYYCARGSWSWPSGMDYYLDYWGQ

GTLVTVSS

>Heavy Chain of STRO-002 IgG histidine scanning
variant #26
                                        (SEQ ID NO: 138)
EVQLVESGGGLVQPGGSLRLSCAASGFNIRTQSIHWVRQAPGKGLEWIGDIFPIDGITDY

ADSVHGRFTISADTSKNTAYLQMNSLRAEDTAVYYCARGSWSWPSGMDYYLDYWGQ

GTLVTVSS

>Heavy Chain of STRO-002 IgG histidine scanning
variant #27
                                        (SEQ ID NO: 139)
EVQLVESGGGLVQPGGSLRLSCAASGFNIRTQSIHWVRQAPGKGLEWIGDIFPIDGITDY

ADSVKHRFTISADTSKNTAYLQMNSLRAEDTAVYYCARGSWSWPSGMDYYLDYWGQ

GTLVTVSS

>Heavy Chain of STRO-002 IgG histidine scanning
variant #28
                                        (SEQ ID NO: 140)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCHRGSWSWPSGMDYYLDYWGQ

GTLVTVSS

>Heavy Chain of STRO-002 IgG histidine scanning
variant #29
                                        (SEQ ID NO: 141)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCAHGSWSWPSGMDYYLDYWGQ

GTLVTVSS

>Heavy Chain of STRO-002 IgG histidine scanning
variant #30
                                        (SEQ ID NO: 142)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARHSWSWPSGMDYYLDYWGQ

GTLVTVSS

>Heavy Chain of STRO-002 IgG histidine scanning
variant #31
                                        (SEQ ID NO: 143)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGHWSWPSGMDYYLDYWG

QGTLVTVSS

-continued

```
>Heavy Chain of STRO-002 IgG histidine scanning
variant #32
                                       (SEQ ID NO: 144)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSHSWPSGMDYYLDYWGQ

GTLVTVSS

>Heavy Chain of STRO-002 IgG histidine scanning
variant #33
                                       (SEQ ID NO: 145)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWHWPSGMDYYLDYWG

QGTLVTVSS

>Heavy Chain of STRO-002 IgG histidine scanning
variant #34
                                       (SEQ ID NO: 146)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSHPSGMDYYLDYWGQ

GTLVTVSS

>Heavy Chain of STRO-002 IgG histidine scanning
variant #35
                                       (SEQ ID NO: 147)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWHSGMDYYLDYWG

QGTLVTVSS

>Heavy Chain of STRO-002 IgG histidine scanning
variant #36
                                       (SEQ ID NO: 148)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPHGMDYYLDYWG

QGTLVTVSS

>Heavy Chain of STRO-002 IgG histidine scanning
variant #37
                                       (SEQ ID NO: 149)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSHMDYYLDYWGQ

GTLVTVSS

>Heavy Chain of STRO-002 IgG histidine scanning
variant #38
                                       (SEQ ID NO: 150)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGHDYYLDYWGQ

GTLVTVSS

>Heavy Chain of STRO-002 IgG histidine scanning
variant #39
                                       (SEQ ID NO: 151)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGMHYYLDYWGQ

GTLVTVSS

>Heavy Chain of STRO-002 IgG histidine scanning
variant #40
                                       (SEQ ID NO: 152)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGMDHYLDYWGQ

GTLVTVSS
```

-continued

>Heavy Chain of STRO-002 IgG histidine scanning
variant #41
                                    (SEQ ID NO: 153)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGMDYHLDYWGQ

GTLVTVSS

>Heavy Chain of STRO-002 IgG histidine scanning
variant #42
                                    (SEQ ID NO: 154)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGMDYYHDYWGQ

GTLVTVSS

>Heavy Chain of STRO-002 IgG histidine scanning
variant #43
                                    (SEQ ID NO: 155)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGMDYYLHYWGQ

GTLVTVSS

>Heavy Chain of STRO-002 IgG histidine scanning
variant #44
                                    (SEQ ID NO: 156)
EVQLVESGGGLVQPGGSLRLSCAASGFNIRTQSIHWVRQAPGKGLEWIGDIFPIDGITDY

ADSVKGRFTISADTSKNTAYLQMNSLRAEDTAVYYCARGSWSWPSGMDYYLDHWGQ

GTLVTVSS

>Light Chain of STRO-002 IgG histidine scanning
variant #1
                                    (SEQ ID NO: 157)
DIQMTQSPSSLSASVGDRVTITCHASQDVNTAVAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #2
                                    (SEQ ID NO: 158)
DIQMTQSPSSLSASVGDRVTITCRHSQDVNTAVAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #3
                                    (SEQ ID NO: 159)
DIQMTQSPSSLSASVGDRVTITCRAHQDVNTAVAWYQQKPGKAPKWYSASFLYSGV

PSRFSGSRSGTDFTLTISSLQPEDFATYYCQQHYTTPPTFGQGTKVEIK

>Light Chain of STRO-002 IgG histidine scanning
variant #4
                                    (SEQ ID NO: 160)
DIQMTQSPSSLSASVGDRVTITCRASHDVNTAVAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #5
                                    (SEQ ID NO: 161)
DIQMTQSPSSLSASVGDRVTITCRASQHVNTAVAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #6
                                    (SEQ ID NO: 162)
DIQMTQSPSSLSASVGDRVTITCRASQDHNTAVAWYQQKPGKAPKLLIYSASFLYSGVP

SRFSGSRSGTDFTLTISSLQPEDFATYYCQQHYTTPPTFGQGTKVEIK

-continued

>Light Chain of STRO-002 IgG histidine scanning
variant #7
                                    (SEQ ID NO: 163)
DIQMTQSPSSLSASVGDRVTITCRASQDVHTAVAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #8
                                    (SEQ ID NO: 164)
DIQMTQSPSSLSASVGDRVTITCRASQDVNHAVAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #9
                                    (SEQ ID NO: 165)
DIQMTQSPSSLSASVGDRVTITCRASQDVNTHVAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #10
                                    (SEQ ID NO: 166)
DIQMTQSPSSLSASVGDRVTITCRASQDVNTAHAWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #11
                                    (SEQ ID NO: 167)
DIQMTQSPSSLSASVGDRVTITCRASQDVNTAVHWYQQKPGKAPKLLIYSASFLYSGVP

SRFSGSRSGTDFTLTISSLQPEDFATYYCQQHYTTPPTFGQGTKVEIK

>Light Chain of STRO-002 IgG histidine scanning
variant #12
                                    (SEQ ID NO: 168)
DIQMTQSPSSLSASVGDRVTITCRASQDVNTAVAWYQQKPGKAPKLLIYHASFLYSGV

PSRFSGSRSGTDFTLTISSLQPEDFATYYCQQHYTTPPTFGQGTKVEIK

>Light Chain of STRO-002 IgG histidine scanning
variant #13
                                    (SEQ ID NO: 169)
DIQMTQSPSSLSASVGDRVTITCRASQDVNTAVAWYQQKPGKAPKLLIYSHSFLYSGVP

SRFSGSRSGTDFTLTISSLQPEDFATYYCQQHYTTPPTFGQGTKVEIK

>Light Chain of STRO-002 IgG histidine scanning
variant #14
                                    (SEQ ID NO: 170)
DIQMTQSPSSLSASVGDRVTITCRASQDVNTAVAWYQQKPGKAPKLLIYSAHFLYSGV

PSRFSGSRSGTDFTLTISSLQPEDFATYYCQQHYTTPPTFGQGTKVEIK

>Light Chain of STRO-002 IgG histidine scanning
variant #15
                                    (SEQ ID NO: 171)
DIQMTQSPSSLSASVGDRVTITCRASQDVNTAVAWYQQKPGKAPKLLIYSASHLYSGV

PSRFSGSRSGTDFTLTISSLQPEDFATYYCQQHYTTPPTFGQGTKVEIK

>Light Chain of STRO-002 IgG histidine scanning
variant #16
                                    (SEQ ID NO: 172)
DIQMTQSPSSLSASVGDRVTITCRASQDVNTAVAWYQQKPGKAPKLLIYSASFHYSGVP

SRFSGSRSGTDFTLTISSLQPEDFATYYCQQHYTTPPTFGQGTKVEIK

>Light Chain of STRO-002 IgG histidine scanning
variant #17
                                    (SEQ ID NO: 173)
DIQMTQSPSSLSASVGDRVTITCRASQDVNTAVAWYQQKPGKAPKLLIYSASFLHSGVP

SRFSGSRSGTDFTLTISSLQPEDFATYYCQQHYTTPPTFGQGTKVEIK

-continued

>Light Chain of STRO-002 IgG histidine scanning
variant #18
                                        (SEQ ID NO: 174)
DIQMTQSPSSLSASVGDRVTITCRASQDVNTAVAWYQQKPGKAPKLLIYSASFLYHGV

PSRFSGSRSGTDFTLTISSLQPEDFATYYCQQHYTTPPTFGQGTKVEIK

>Light Chain of STRO-002 IgG histidine scanning
variant #19
                                        (SEQ ID NO: 175)
DIQMTQSPSSLSASVGDRVTITCRASQDVNTAVAWYQQKPGKAPKLLIYSASFLYSGVP

SRFSGSRSGTDFTLTISSLQPEDFATYYCHQHYTTPPTFGQGTKVEIK

>Light Chain of STRO-002 IgG histidine scanning
variant #20
                                        (SEQ ID NO: 176)
DIQMTQSPSSLSASVGDRVTITCRASQDVNTAVAWYQQKPGKAPKLLIYSASFLYSGVP

SRFSGSRSGTDFTLTISSLQPEDFATYYCQHHYTTPPTFGQGTKVEIK

>Light Chain of STRO-002 IgG histidine scanning
variant #21
                                        (SEQ ID NO: 177)
DIQMTQSPSSLSASVGDRVTITCRASQDVNTAVAWYQQKPGKAPKLLIYSASFLYSGVP

SRFSGSRSGTDFTLTISSLQPEDFATYYCQQAYTTPPTFGQGTKVEIK

>Light Chain of STRO-002 IgG histidine scanning
variant #22
                                        (SEQ ID NO: 178)
DIQMTQSPSSLSASVGDRVTITCRASQDVNTAVAWYQQKPGKAPKLLIYSASFLYSGVP

SRFSGSRSGTDFTLTISSLQPEDFATYYCQQHHTTPPTFGQGTKVEIK

>Light Chain of STRO-002 IgG histidine scanning
variant #23
                                        (SEQ ID NO: 179)
DIQMTQSPSSLSASVGDRVTITCRASQDVNTAVAWYQQKPGKAPKLLIYSASFLYSGVP

SRFSGSRSGTDFTLTISSLQPEDFATYYCQQHYHTPPTFGQGTKVEIK

>Light Chain of STRO-002 IgG histidine scanning
variant #24
                                        (SEQ ID NO: 180)
DIQMTQSPSSLSASVGDRVTITCRASQDVNTAVAWYQQKPGKAPKLLIYSASFLYSGVP

SRFSGSRSGTDFTLTISSLQPEDFATYYCQQHYTHPPTFGQGTKVEIK

>Light Chain of STRO-002 IgG histidine scanning
variant #25
                                        (SEQ ID NO: 181)
DIQMTQSPSSLSASVGDRVTITCRASQDVNTAVAWYQQKPGKAPKLLIYSASFLYSGVP

SRFSGSRSGTDFTLTISSLQPEDFATYYCQQHYTTHPTFGQGTKVEIK

>Light Chain of STRO-002 IgG histidine scanning
variant #26
                                        (SEQ ID NO: 182)
DIQMTQSPSSLSASVGDRVTITCRASQDVNTAVAWYQQKPGKAPKLLIYSASFLYSGVP

SRFSGSRSGTDFTLTISSLQPEDFATYYCQQHYTTPHTFGQGTKVEIK

>Light Chain of STRO-002 IgG histidine scanning
variant #27
                                        (SEQ ID NO: 183)
DIQMTQSPSSLSASVGDRVTITCRASQDVNTAVAWYQQKPGKAPKLLIYSASFLYSGVP

SRFSGSRSGTDFTLTISSLQPEDFATYYCQQHYTTPPHFGQGTKVEIK

>Heavy Chain of farletuzumab IgG
                                        (SEQ ID NO: 184)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDDPAWFAYWGQGTP

VTVSS

-continued

>Light Chain of farletuzumab IgG (SEQ ID NO: 185)

DIQLTQSPSSLSASVGDRVTITCSVSSSISSNNLHWYQQKPGKAPKPWIYGTSNLASGVP

SRFSGSGSGTDYTFTISSLQPEDIATYYCQQWSSYPYMYTFGQGTKVEIK

>Heavy Chain CDR1 of farletuzumab (SEQ ID NO: 186)

GFTFSGYGLS

>Heavy Chain CDR2 of farletuzumab (SEQ ID NO: 187)

MISSGGSYTYYADSVKG

>Heavy Chain CDR3 of farletuzumab (SEQ ID NO: 188)

ARHGDDPAWFAY

>Light Chain CDR1 of farletuzumab (SEQ ID NO: 189)

SSISSNNLH

>Light Chain CDR2 of farletuzumab (SEQ ID NO: 190)

GTSNLAS

>Light Chain CDR3 of farletuzumab (SEQ ID NO: 191)

QQWSSYPYMYT

>Heavy Chain of farletuzumab IgG histidine scanning
variant #1

(SEQ ID NO: 192)

EVQLVESGGGVVQPGRSLRLSCSASHFTFSGYGLSWVRQAPGKGLEWVAMISSGGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #2

(SEQ ID NO: 193)

EVQLVESGGGVVQPGRSLRLSCSASGHTFSGYGLSWVRQAPGKGLEWVAMISSGGSY

TYYADSVKGRFAISRDNAKNTLFLQMDSLRPEDTGVYFCARHGDDPAWFAYWGQGTP

VTVSS

>Heavy Chain of farletuzumab IgG histidine scanning
variant #3

(SEQ ID NO: 194)

EVQLVESGGGVVQPGRSLRLSCSASGFHFSGYGLSWVRQAPGKGLEWVAMISSGGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #4

(SEQ ID NO: 195)

EVQLVESGGGVVQPGRSLRLSCSASGFTHSGYGLSWVRQAPGKGLEWVAMISSGGSY

TYYADSVKGRFAISRDNAKNTLFLQMDSLRPEDTGVYFCARHGDDPAWFAYWGQGTP

VTVSS

>Heavy Chain of farletuzumab IgG histidine scanning
variant #5

(SEQ ID NO: 196)

EVQLVESGGGVVQPGRSLRLSCSASGFTFHGYGLSWVRQAPGKGLEWVAMISSGGSY

TYYADSVKGRFAISRDNAKNTLFLQMDSLRPEDTGVYFCARHGDDPAWFAYWGQGTP

VTVSS

-continued

>Heavy Chain of farletuzumab IgG histidine scanning
variant #6
                                        (SEQ ID NO: 197)
EVQLVESGGGVVQPGRSLRLSCSASGFTFSHYGLSWVRQAPGKGLEWVAMISSGGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #7
                                        (SEQ ID NO: 198)
EVQLVESGGGVVQPGRSLRLSCSASGFTFSGHGLSWVRQAPGKGLEWVAMISSGGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #8
                                        (SEQ ID NO: 199)
EVQLVESGGGVVQPGRSLRLSCSASGFTFSGYHLSWVRQAPGKGLEWVAMISSGGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #9
                                        (SEQ ID NO: 200)
EVQLVESGGGVVQPGRSLRLSCSASGFTFSGYGHSWVRQAPGKGLEWVAMISSGGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #10
                                        (SEQ ID NO: 201)
EVQLVESGGGVVQPGRSLRLSCSASGFTFSGYGLHWVRQAPGKGLEWVAMISSGGSY

TYYADSVKGRFAISRDNAKNTLFLQMDSLRPEDTGVYFCARHGDDPAWFAYWGQGTP

VTVSS

>Heavy Chain of farletuzumab IgG histidine scanning
variant #11
                                        (SEQ ID NO: 202)
EVQLVESGGGVVQPGRSLRLSCSASGFTFSGYGLSWVRQAPGKGLEWVAHISSGGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #12
                                        (SEQ ID NO: 203)
EVQLVESGGGVVQPGRSLRLSCSASGFTFSGYGLSWVRQAPGKGLEWVAMHSSGGSY

TYYADSVKGRFAISRDNAKNTLFLQMDSLRPEDTGVYFCARHGDDPAWFAYWGQGTP

VTVSS

>Heavy Chain of farletuzumab IgG histidine scanning
variant #13
                                        (SEQ ID NO: 204)
EVQLVESGGGVVQPGRSLRLSCSASGFTFSGYGLSWVRQAPGKGLEWVAMIHSGGSY

TYYADSVKGRFAISRDNAKNTLFLQMDSLRPEDTGVYFCARHGDDPAWFAYWGQGTP

VTVSS

>Heavy Chain of farletuzumab IgG histidine scanning
variant #14
                                        (SEQ ID NO: 205)
EVQLVESGGGVVQPGRSLRLSCSASGFTFSGYGLSWVRQAPGKGLEWVAMISHGGSY

TYYADSVKGRFAISRDNAKNTLFLQMDSLRPEDTGVYFCARHGDDPAWFAYWGQGTP

VTVSS

-continued

>Heavy Chain of farletuzumab IgG histidine scanning
variant #15

(SEQ ID NO: 206)

EVQLVESGGGVVQPGRSLRLSCSASGFTFSGYGLSWVRQAPGKGLEWVAMISSHGSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #16

(SEQ ID NO: 207)

EVQLVESGGGVVQPGRSLRLSCSASGFTFSGYGLSWVRQAPGKGLEWVAMISSGHSYT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #17

(SEQ ID NO: 208)

EVQLVESGGGVVQPGRSLRLSCSASGFTFSGYGLSWVRQAPGKGLEWVAMISSGGHY

TYYADSVKGRFAISRDNAKNTLFLQMDSLRPEDTGVYFCARHGDDPAWFAYWGQGTP

VTVSS

>Heavy Chain of farletuzumab IgG histidine scanning
variant #18

(SEQ ID NO: 209)

EVQLVESGGGVVQPGRSLRLSCSASGFTFSGYGLSWVRQAPGKGLEWVAMISSGGSHT

YYADSVKGRFAISRDNAKNTLFLQMDSLRPEDTGVYFCARHGDDPAWFAYWGQGTP

VTVSS

>Heavy Chain of farletuzumab IgG histidine scanning
variant #19

(SEQ ID NO: 210)

EVQLVESGGGVVQPGRSLRLSCSASGFTFSGYGLSWVRQAPGKGLEWVAMISSGGSYH

YYADSVKGRFAISRDNAKNTLFLQMDSLRPEDTGVYFCARHGDDPAWFAYWGQGTP

VTVSS

>Heavy Chain of farletuzumab IgG histidine scanning
variant #20

(SEQ ID NO: 211)

EVQLVESGGGVVQPGRSLRLSCSASGFTFSGYGLSWVRQAPGKGLEWVAMISSGGSYT

HYADSVKGRFAISRDNAKNTLFLQMDSLRPEDTGVYFCARHGDDPAWFAYWGQGTP

VTVSS

>Heavy Chain of farletuzumab IgG histidine scanning
variant #21

(SEQ ID NO: 212)

EVQLVESGGGVVQPGRSLRLSCSASGFTFSGYGLSWVRQAPGKGLEWVAMISSGGSYT

YHADSVKGRFAISRDNAKNTLFLQMDSLRPEDTGVYFCARHGDDPAWFAYWGQGTP

VTVSS

>Heavy Chain of farletuzumab IgG histidine scanning
variant #22

(SEQ ID NO: 213)

EVQLVESGGGVVQPGRSLRLSCSASGFTFSGYGLSWVRQAPGKGLEWVAMISSGGSYT

YYHDSVKGRFAISRDNAKNTLFLQMDSLRPEDTGVYFCARHGDDPAWFAYWGQGTP

VTVSS

>Heavy Chain of farletuzumab IgG histidine scanning
variant #23

(SEQ ID NO: 214)

EVQLVESGGGVVQPGRSLRLSCSASGFTFSGYGLSWVRQAPGKGLEWVAMISSGGSYT

YYAHSVKGRFAISRDNAKNTLFLQMDSLRPEDTGVYFCARHGDDPAWFAYWGQGTP

VTVSS

```
-continued
```

```
>Heavy Chain of farletuzumab IgG histidine scanning
variant #24
                                    (SEQ ID NO: 215)
EVQLVESGGGVVQPGRSLRLSCSASGFTFSGYGLSWVRQAPGKGLEWVAMISSGGSYT

YYADHVKGRFAISRDNAKNTLFLQMDSLRPEDTGVYFCARHGDDPAWFAYWGQGTP

VTVSS

>Heavy Chain of farletuzumab IgG histidine scanning
variant #25
                                    (SEQ ID NO: 216)
EVQLVESGGGVVQPGRSLRLSCSASGFTFSGYGLSWVRQAPGKGLEWVAMISSGGSYT

YYADSHKGRFAISRDNAKNTLFLQMDSLRPEDTGVYFCARHGDDPAWFAYWGQGTP

VTVSS

>Heavy Chain of farletuzumab IgG histidine scanning
variant #26
                                    (SEQ ID NO: 217)
EVQLVESGGGVVQPGRSLRLSCSASGFTFSGYGLSWVRQAPGKGLEWVAMISSGGSYT

YYADSVHGRFAISRDNAKNTLFLQMDSLRPEDTGVYFCARHGDDPAWFAYWGQGTP

VTVSS

>Heavy Chain of farletuzumab IgG histidine scanning
variant #27
                                    (SEQ ID NO: 218)
EVQLVESGGGVVQPGRSLRLSCSASGFTFSGYGLSWVRQAPGKGLEWVAMISSGGSYT

YYADSVKHRFAISRDNAKNTLFLQMDSLRPEDTGVYFCARHGDDPAWFAYWGQGTP

VTVSS

>Heavy Chain of farletuzumab IgG histidine scanning
variant #28
                                    (SEQ ID NO: 219)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCHRHGDDPAWFAYWGQGTP

VTVSS

>Heavy Chain of farletuzumab IgG histidine scanning
variant #29
                                    (SEQ ID NO: 220)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCAHHGDDPAWFAYWGQGTP

VTVSS

>Heavy Chain of farletuzumab IgG histidine scanning
variant #30
                                    (SEQ ID NO: 221)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARAGDDPAWFAYWGQGTP

VTVSS

>Heavy Chain of farletuzumab IgG histidine scanning
variant #31
                                    (SEQ ID NO: 222)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHHDDPAWFAYWGQGTP

VTVSS

>Heavy Chain of farletuzumab IgG histidine scanning
variant #32
                                    (SEQ ID NO: 223)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGHDPAWFAYWGQGTP

VTVSS
```

-continued

```
>Heavy Chain of farletuzumab IgG histidine scanning
variant #33
                                        (SEQ ID NO: 224)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDHPAWFAYWGQGTP

VTVSS

>Heavy Chain of farletuzumab IgG histidine scanning
variant #34
                                        (SEQ ID NO: 225)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDDHAWFAYWGQGTP

VTVSS

>Heavy Chain of farletuzumab IgG histidine scanning
variant #35
                                        (SEQ ID NO: 226)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDDPHWFAYWGQGTP

VTVSS

>Heavy Chain of farletuzumab IgG histidine scanning
variant #36
                                        (SEQ ID NO: 227)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDDPAHFAYWGQGTPV

TVSS

>Heavy Chain of farletuzumab IgG histidine scanning
variant #37
                                        (SEQ ID NO: 228)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDDPAWHAYWGQGTP

VTVSS

>Heavy Chain of farletuzumab IgG histidine scanning
variant #38
                                        (SEQ ID NO: 229)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDDPAWFHYWGQGTP

VTVSS

>Heavy Chain of farletuzumab IgG histidine scanning
variant #39
                                        (SEQ ID NO: 230)
EVQLVESGGGVVQPGRSLRLSCSASGFTFSGYGLSWVRQAPGKGLEWVAMISSGGSYT

YYADSVKGRFAISRDNAKNTLFLQMDSLRPEDTGVYFCARHGDDPAWFAHWGQGTP

VTVSS

>Light Chain of farletuzumab IgG histidine scanning
variant #1
                                        (SEQ ID NO: 231)
DIQLTQSPSSLSASVGDRVTITCSVSHSISSNNLHWYQQKPGKAPKPWIYGTSNLASGVP

SRFSGSGSGTDYTFTISSLQPEDIATYYCQQWSSYPYMYTFGQGTKVEIK

>Light Chain of farletuzumab IgG histidine scanning
variant #2
                                        (SEQ ID NO: 232)
DIQLTQSPSSLSASVGDRVTITCSVSSHISSNNLHWYQQKPGKAPKPWIYGTSNLASGVP

SRFSGSGSGTDYTFTISSLQPEDIATYYCQQWSSYPYMYTFGQGTKVEIK
```

-continued

>Light Chain of farletuzumab IgG histidine scanning
variant #3

```
                                               (SEQ ID NO: 233)
DIQLTQSPSSLSASVGDRVTITCSVSSSHSSNNLHWYQQKPGKAPKPWIYGTSNLASGV

PSRFSGSGSGTDYTFTISSLQPEDIATYYCQQWSSYPYMYTFGQGTKVEIK
```

>Light Chain of farletuzumab IgG histidine scanning
variant #4

```
                                               (SEQ ID NO: 234)
DIQLTQSPSSLSASVGDRVTITCSVSSSIHSNNLHWYQQKPGKAPKPWIYGTSNLASGVP

SRFSGSGSGTDYTFTISSLQPEDIATYYCQQWSSYPYMYTFGQGTKVEIK
```

>Light Chain of farletuzumab IgG histidine scanning
variant #5

```
                                               (SEQ ID NO: 235)
DIQLTQSPSSLSASVGDRVTITCSVSSSISHNNLHWYQQKPGKAPKPWIYGTSNLASGVP

SRFSGSGSGTDYTFTISSLQPEDIATYYCQQWSSYPYMYTFGQGTKVEIK
```

>Light Chain of farletuzumab IgG histidine scanning
variant #6

```
                                               (SEQ ID NO: 236)
DIQLTQSPSSLSASVGDRVTITCSVSSSISSHNLHWYQQKPGKAPKPWIYGTSNLASGVP

SRFSGSGSGTDYTFTISSLQPEDIATYYCQQWSSYPYMYTFGQGTKVEIK
```

>Light Chain of farletuzumab IgG histidine scanning
variant #7

```
                                               (SEQ ID NO: 237)
DIQLTQSPSSLSASVGDRVTITCSVSSSISSNHLHWYQQKPGKAPKPWIYGTSNLASGVP

SRFSGSGSGTDYTFTISSLQPEDIATYYCQQWSSYPYMYTFGQGTKVEIK
```

>Light Chain of farletuzumab IgG histidine scanning
variant #8

```
                                               (SEQ ID NO: 238)
DIQLTQSPSSLSASVGDRVTITCSVSSSISSNNHHWYQQKPGKAPKPWIYGTSNLASGVP

SRFSGSGSGTDYTFTISSLQPEDIATYYCQQWSSYPYMYTFGQGTKVEIK
```

>Light Chain of farletuzumab IgG histidine scanning
variant #9

```
                                               (SEQ ID NO: 239)
DIQLTQSPSSLSASVGDRVTITCSVSSSISSNNLAWYQQKPGKAPKPWIYGTSNLASGVP

SRFSGSGSGTDYTFTISSLQPEDIATYYCQQWSSYPYMYTFGQGTKVEIK
```

>Light Chain of farletuzumab IgG histidine scanning
variant #10

```
                                               (SEQ ID NO: 240)
DIQLTQSPSSLSASVGDRVTITCSVSSSISSNNLHWYQQKPGKAPKPWIYHTSNLASGVP

SRFSGSGSGTDYTFTISSLQPEDIATYYCQQWSSYPYMYTFGQGTKVEIK
```

>Light Chain of farletuzumab IgG histidine scanning
variant #11

```
                                               (SEQ ID NO: 241)
DIQLTQSPSSLSASVGDRVTITCSVSSSISSNNLHWYQQKPGKAPKPWIYGHSNLASGVP

SRFSGSGSGTDYTFTISSLQPEDIATYYCQQWSSYPYMYTFGQGTKVEIK
```

>Light Chain of farletuzumab IgG histidine scanning
variant #12

```
                                               (SEQ ID NO: 242)
DIQLTQSPSSLSASVGDRVTITCSVSSSISSNNLHWYQQKPGKAPKPWIYGTHNLASGVP

SRFSGSGSGTDYTFTISSLQPEDIATYYCQQWSSYPYMYTFGQGTKVEIK
```

>Light Chain of farletuzumab IgG histidine scanning
variant #13

```
                                               (SEQ ID NO: 243)
DIQLTQSPSSLSASVGDRVTITCSVSSSISSNNLHWYQQKPGKAPKPWIYGTSHLASGVP

SRFSGSGSGTDYTFTISSLQPEDIATYYCQQWSSYPYMYTFGQGTKVEIK
```

-continued

>Light Chain of farletuzumab IgG histidine scanning
variant #14

(SEQ ID NO: 244)
DIQLTQSPSSLSASVGDRVTITCSVSSSISSNNLHWYQQKPGKAPKPWIYGTSNHASGVP

SRFSGSGSGTDYTFTISSLQPEDIATYYCQQWSSYPYMYTFGQGTKVEIK

>Light Chain of farletuzumab IgG histidine scanning
variant #15

(SEQ ID NO: 245)
DIQLTQSPSSLSASVGDRVTITCSVSSSISSNNLHWYQQKPGKAPKPWIYGTSNLHSGVP

SRFSGSGSGTDYTFTISSLQPEDIATYYCQQWSSYPYMYTFGQGTKVEIK

>Light Chain of farletuzumab IgG histidine scanning
variant #16

(SEQ ID NO: 246)
DIQLTQSPSSLSASVGDRVTITCSVSSSISSNNLHWYQQKPGKAPKPWIYGTSNLAHGVP

SRFSGSGSGTDYTFTISSLQPEDIATYYCQQWSSYPYMYTFGQGTKVEIK

>Light Chain of farletuzumab IgG histidine scanning
variant #17

(SEQ ID NO: 247)
DIQLTQSPSSLSASVGDRVTITCSVSSSISSNNLHWYQQKPGKAPKPWIYGTSNLASGVP

SRFSGSGSGTDYTFTISSLQPEDIATYYCHQWSSYPYMYTFGQGTKVEIK

>Light Chain of farletuzumab IgG histidine scanning
variant #18

(SEQ ID NO: 248)
DIQLTQSPSSLSASVGDRVTITCSVSSSISSNNLHWYQQKPGKAPKPWIYGTSNLASGVP

SRFSGSGSGTDYTFTISSLQPEDIATYYCQHWSSYPYMYTFGQGTKVEIK

>Light Chain of farletuzumab IgG histidine scanning
variant #19

(SEQ ID NO: 249)
DIQLTQSPSSLSASVGDRVTITCSVSSSISSNNLHWYQQKPGKAPKPWIYGTSNLASGVP

SRFSGSGSGTDYTFTISSLQPEDIATYYCQQHSSYPYMYTFGQGTKVEIK

>Light Chain of farletuzumab IgG histidine scanning
variant #20

(SEQ ID NO: 250)
DIQLTQSPSSLSASVGDRVTITCSVSSSISSNNLHWYQQKPGKAPKPWIYGTSNLASGVP

SRFSGSGSGTDYTFTISSLQPEDIATYYCQQWHSYPYMYTFGQGTKVEIK

>Light Chain of farletuzumab IgG histidine scanning
variant #21

(SEQ ID NO: 251)
DIQLTQSPSSLSASVGDRVTITCSVSSSISSNNLHWYQQKPGKAPKPWIYGTSNLASGVP

SRFSGSGSGTDYTFTISSLQPEDIATYYCQQWSHPYMYTFGQGTKVEIK

>Light Chain of farletuzumab IgG histidine scanning
variant #22

(SEQ ID NO: 252)
DIQLTQSPSSLSASVGDRVTITCSVSSSISSNNLHWYQQKPGKAPKPWIYGTSNLASGVP

SRFSGSGSGTDYTFTISSLQPEDIATYYCQQWSSHPYMYTFGQGTKVEIK

>Light Chain of farletuzumab IgG histidine scanning
variant #23

(SEQ ID NO: 253)
DIQLTQSPSSLSASVGDRVTITCSVSSSISSNNLHWYQQKPGKAPKPWIYGTSNLASGVP

SRFSGSGSGTDYTFTISSLQPEDIATYYCQQWSSYHMYTFGQGTKVEIK

>Light Chain of farletuzumab IgG histidine scanning
variant #24

(SEQ ID NO: 254)
DIQLTQSPSSLSASVGDRVTITCSVSSSISSNNLHWYQQKPGKAPKPWIYGTSNLASGVP

SRFSGSGSGTDYTFTISSLQPEDIATYYCQQWSSYPHMYTFGQGTKVEIK

-continued

>Light Chain of farletuzumab IgG histidine scanning
variant #25
                                                    (SEQ ID NO: 255)
DIQLTQSPSSLSASVGDRVTITCSVSSSISSNNLHWYQQKPGKAPKPWIYGTSNLASGVP

SRFSGSGSGTDYTFTISSLQPEDIATYYCQQWSSYPYHYTFGQGTKVEIK

>Light Chain of farletuzumab IgG histidine scanning
variant #26
                                                    (SEQ ID NO: 256)
DIQLTQSPSSLSASVGDRVTITCSVSSSISSNNLHWYQQKPGKAPKPWIYGTSNLASGVP

SRFSGSGSGTDYTFTISSLQPEDIATYYCQQWSSYPYMHTFGQGTKVEIK

>Light Chain of farletuzumab IgG histidine scanning
variant #27
                                                    (SEQ ID NO: 257)
DIQLTQSPSSLSASVGDRVTITCSVSSSISSNNLHWYQQKPGKAPKPWIYGTSNLASGVP

SRFSGSGSGTDYTFTISSLQPEDIATYYCQQWSSYPYMYHFGQGTKVEIK

What is claimed is:

1. A pharmaceutical composition comprising an effective amount of an antigen-binding protein construct (ABPC) comprising:

a first antigen-binding domain that is capable of specifically binding FOLR1 or an epitope of FOLR1 presented on the surface of a target cancer cell, wherein the first antigen-binding domain comprises:

(a) a heavy chain variable domain comprising any one of SEQ ID NOs: 14, 17, 19, 21-24, 26, 30, 31, 33-36, 43-46, 48, 49, 51, 53, and 85-103 and a light chain variable domain comprising SEQ ID NO: 2; or (b) a heavy chain variable domain comprising SEQ ID NO: 1 and a light chain variable domain comprising any one of SEQ ID NOs: 58, 60-62, 64-66, 70, 74, 76-81, and 83; and wherein:

(i) the dissociation rate of the first antigen-binding domain at a pH of about 4.0 to about 6.5 is faster than the dissociation rate at a pH of about 7.0 to about 8.0; or (ii) the dissociation constant (KD) of the first antigen-binding domain at a pH of about 4.0 to about 6.5 is greater than the KD at a pH of about 7.0 to about 8.0.

2. The pharmaceutical composition of claim 1, wherein the ABPC further comprises a conjugated toxin, radioisotope, drug, or small molecule.

3. The pharmaceutical composition of claim 1, wherein the ABPC comprises a single polypeptide.

4. The pharmaceutical composition of claim 3, wherein the antigen-binding domain is a scFv.

5. The pharmaceutical composition of claim 1, wherein the ABPC comprises two or more polypeptides.

6. The pharmaceutical composition of claim 5, wherein the ABPC is an antibody.

7. The pharmaceutical composition of claim 1, wherein the ABPC further comprises a second antigen-binding domain.

8. A kit comprising at least one dose of the pharmaceutical composition of claim 1.

9. A method of treating a cancer having a population of cancer cells that have FOLR1 or an epitope of FOLR1 presented on their surface, the method comprising:

administering a therapeutically effective amount of the pharmaceutical composition of claim 1 to a subject previously identified as having a cancer having the population of cancer cells.

10. A method of reducing the volume of a tumor in a subject, wherein the tumor has a population of cancer cells that have FOLR1 or an epitope of FOLR1 presented on their surface, the method comprising:

administering a therapeutically effective amount of the pharmaceutical composition of claim 1 to a subject previously identified as having a cancer having the population of cancer cells.

11. A method of inducing cell death in a cancer cell in a subject, wherein the cancer cell has FOLR1 or an epitope of FOLR1 presented on its surface, wherein the method comprises:

administering a therapeutically effective amount of the pharmaceutical composition of claim 1 to a subject previously identified as having a cancer having the cancer cell.

12. A method of decreasing the risk of developing a metastasis or decreasing the risk of developing an additional metastasis in a subject having a cancer, wherein the cancer has a population of cancer cells that have FOLR1 or an epitope of FOLR1 presented on their surface the method comprising:

administering a therapeutically effective amount of the pharmaceutical composition of claim 1 to a subject previously identified as having a cancer having the population of cancer cells.

13. A pharmaceutical composition comprising an effective amount of an antigen-binding protein construct (ABPC) comprising:

a first antigen-binding domain that is capable of specifically binding FOLR1 or an epitope of FOLR1 presented on the surface of a target cancer cell; and a conjugated toxin, radioisotope, drug, or small molecule,
wherein the first antigen-binding domain comprises:

(a) a heavy chain variable domain comprising any one of SEQ ID NOs: NO: 14, 17, 19, 21-24, 26, 30, 31, 33-36, 43-46, 48, 49, 51, 53, and 85-103 and a light chain variable domain comprising SEQ ID NO: 2; or (b) a heavy chain variable domain comprising SEQ ID NO: 1 and a light chain variable domain comprising any one of SEQ ID NOs: 58, 60-62, 64-66, 70, 74, 76-81, and 83; and wherein:

(i) the dissociation rate of the first antigen-binding domain at a pH of about 4.0 to about 6.5 is faster than the dissociation rate at a pH of about 7.0 to about 8.0; or the dissociation constant (KD) of the first antigen-binding domain at a pH of about 4.0 to about 6.5 is greater than the KD at a pH of about 7.0 to about 8.0; and (ii) the composition provides for one or more of:

an increase in toxin liberation in the target cancer cell as compared to a composition comprising the same amount of a control ABPC;

an increase in target cancer cell killing as compared to a composition comprising the same amount of a control ABPC; and an increase in endolysosomal delivery in the target cancer cell as compared to a composition comprising the same amount of a control ABPC.

14. The pharmaceutical composition of claim 13, wherein the ABPC comprises two or more polypeptides.

15. The pharmaceutical composition of claim 14, wherein the ABPC is an antibody.

16. An antigen-binding protein construct (ABPC) comprising:

a first antigen-binding domain that is capable of specifically binding FOLR1 or an epitope of FOLR1 presented on the surface of a target cancer cell, wherein the first antigen-binding domain comprises:

(a) a heavy chain variable domain comprising any one of SEQ ID NOs: NO: 14, 17, 19, 21-24, 26, 30, 31, 33-36, 43-46, 48, 49, 51, 53, and 85-103 and a light chain variable domain comprising SEQ ID NO: 2; or (b) a heavy chain variable domain comprising SEQ ID NO: 1 and a light chain variable domain comprising any one of SEQ ID NOs: 58, 60-62, 64-66, 70, 74, 76-81, and 83; and wherein:

(i) the dissociation rate of the first antigen-binding domain at a pH of about 4.0 to about 6.5 is faster than the dissociation rate at a pH of about 7.0 to about 8.0; or (ii) the dissociation constant (KD) of the first antigen-binding domain at a pH of about 4.0 to about 6.5 is greater than the KD at a pH of about 7.0 to about 8.0.

17. The ABPC of claim 16, wherein the ABPC comprises two or more polypeptides.

18. The ABPC of claim 16, wherein the ABPC is an antibody.

19. An antigen-binding protein construct (ABPC) comprising:

a first antigen-binding domain that is capable of specifically binding FOLR1 or an epitope of FOLR1 presented on the surface of a target cancer cell; and a conjugated toxin, radioisotope, drug, or small molecule,
wherein the first antigen-binding domain comprises:

(a) a heavy chain variable domain comprising any one of SEQ ID NOs: NO: 14, 17, 19, 21-24, 26, 30, 31, 33-36, 43-46, 48, 49, 51, 53, and 85-103 and a light chain variable domain comprising SEQ ID NO: 2; or (b) a heavy chain variable domain comprising SEQ ID NO: 1 and a light chain variable domain comprising any one of SEQ ID NOs: 58, 60-62, 64-66, 70, 74, 76-81, and 83; and wherein:

(i) the dissociation rate of the first antigen-binding domain at a pH of about 4.0 to about 6.5 is faster than the dissociation rate at a pH of about 7.0 to about 8.0; or the dissociation constant (KD) of the first antigen-binding domain at a pH of about 4.0 to about 6.5 is greater than the KD at a pH of about 7.0 to about 8.0; and (ii) the composition provides for one or more of:

an increase in toxin liberation in the target cancer cell as compared to a composition comprising the same amount of a control ABPC;

an increase in target cancer cell killing as compared to a composition comprising the same amount of a control ABPC; and an increase in endolysosomal delivery in the target cancer cell as compared to a composition comprising the same amount of a control ABPC.

20. The ABPC of claim 19, wherein the ABPC comprises two or more polypeptides.

21. The ABPC of claim 20, wherein the ABPC is an antibody.

* * * * *

SEQUENCE LISTING

<160> NUMBER OF SEQ ID NOS: 257

<210> SEQ ID NO 1
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG"

<400> SEQUENCE: 1

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 2
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG"

-continued

```
<400> SEQUENCE: 2

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR1 of mirvetuximab"

<400> SEQUENCE: 3

Lys Ala Ser Gly Tyr Thr Phe Thr Gly Tyr Phe Met Asn
1               5                   10

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR2 of mirvetuximab"

<400> SEQUENCE: 4

Arg Ile His Pro Tyr Asp Gly Asp Thr Phe Tyr Asn Gln Lys Phe Gln
1               5                   10                  15

Gly

<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR3 of mirvetuximab"

<400> SEQUENCE: 5

Thr Arg Tyr Asp Gly Ser Arg Ala Met Asp Tyr
1               5                   10
```

-continued

```
<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR1 of mirvetuximab"

<400> SEQUENCE: 6

Lys Ala Ser Gln Ser Val Ser Phe Ala Gly Thr Ser Leu Met His
1               5                   10                  15

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR2 of mirvetuximab"

<400> SEQUENCE: 7

Arg Ala Ser Asn Leu Glu Ala
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR3 of mirvetuximab"

<400> SEQUENCE: 8

Gln Gln Ser Arg Glu Tyr Pro Tyr Thr
1               5

<210> SEQ ID NO 9
<211> LENGTH: 209
<212> TYPE: PRT
<213> ORGANISM: Homo sapiens
<220> FEATURE:
<221> NAME/KEY: source
<223> OTHER INFORMATION: /note="Mature Human FOLR1"

<400> SEQUENCE: 9

Arg Ile Ala Trp Ala Arg Thr Glu Leu Leu Asn Val Cys Met Asn Ala
1               5                   10                  15

Lys His His Lys Glu Lys Pro Gly Pro Glu Asp Lys Leu His Glu Gln
                20                  25                  30

Cys Arg Pro Trp Arg Lys Asn Ala Cys Cys Ser Thr Asn Thr Ser Gln
        35                  40                  45

Glu Ala His Lys Asp Val Ser Tyr Leu Tyr Arg Phe Asn Trp Asn His
    50                  55                  60

Cys Gly Glu Met Ala Pro Ala Cys Lys Arg His Phe Ile Gln Asp Thr
65                  70                  75                  80
```

-continued

```
Cys Leu Tyr Glu Cys Ser Pro Asn Leu Gly Pro Trp Ile Gln Gln Val
            85                  90                  95

Asp Gln Ser Trp Arg Lys Glu Arg Val Leu Asn Val Pro Leu Cys Lys
            100                 105                 110

Glu Asp Cys Glu Gln Trp Trp Glu Asp Cys Arg Thr Ser Tyr Thr Cys
            115                 120                 125

Lys Ser Asn Trp His Lys Gly Trp Asn Trp Thr Ser Gly Phe Asn Lys
    130                 135                 140

Cys Ala Val Gly Ala Ala Cys Gln Pro Phe His Phe Tyr Phe Pro Thr
145                 150                 155                 160

Pro Thr Val Leu Cys Asn Glu Ile Trp Thr His Ser Tyr Lys Val Ser
            165                 170                 175

Asn Tyr Ser Arg Gly Ser Gly Arg Cys Ile Gln Met Trp Phe Asp Pro
            180                 185                 190

Ala Gln Gly Asn Pro Asn Glu Glu Val Ala Arg Phe Tyr Ala Ala Ala
        195                 200                 205

Met
```

```
<210> SEQ ID NO 10
<211> LENGTH: 771
<212> TYPE: DNA
<213> ORGANISM: Homo sapiens
<220> FEATURE:
<221> NAME/KEY: source
<223> OTHER INFORMATION: /note="cDNA Encoding Mature Human FOLR1"

<400> SEQUENCE: 10
atggctcagc ggatgacaac acagctgctg ctccttctag tgtgggtggc tgtagtaggg        60
gaggctcaga caaggattgc atgggccagg actgagcttc tcaatgtctg catgaacgcc       120
aagcaccaca aggaaaagcc aggccccgag acaagttgc atgagcagtg tcgaccctgg        180
aggaagaatg cctgctgttc taccaacacc agccaggaag cccataagga tgtttcctac       240
ctatatagat tcaactggaa ccactgtgga gagatggcac ctgcctgcaa acggcatttc       300
atccaggaca cctgcctcta cgagtgctcc cccaacttgg gcccctggat ccagcaggtg       360
gatcagagct ggcgcaaaga gcgggtactg aacgtgcccc tgtgcaaaga ggactgtgag       420
caatggtggg aagattgtcg cacctcctac acctgcaaga gcaactggca caagggctgg       480
aactggactt cagggtttaa caagtgcgca gtgggagctg cctgccaacc tttccatttc       540
tacttcccca cacccactgt tctgtgcaat gaaatctgga ctcactccta caaggtcagc       600
aactacagcc gagggagtgg ccgctgcatc cagatgtggt tcgacccagc ccagggcaac       660
cccaatgagg aggtggcgag gttctatgct gcagccatga gtggggctgg gccctgggca       720
gcctggcctt tcctgcttag cctggcccta atgctgctgt ggctgctcag c                771
```

```
<210> SEQ ID NO 11
<211> LENGTH: 209
<212> TYPE: PRT
<213> ORGANISM: Homo sapiens
<220> FEATURE:
<221> NAME/KEY: source
<223> OTHER INFORMATION: /note="Extracellular Domain of FOLR1"

<400> SEQUENCE: 11

Arg Ile Ala Trp Ala Arg Thr Glu Leu Leu Asn Val Cys Met Asn Ala
1               5                   10                  15

Lys His His Lys Glu Lys Pro Gly Pro Glu Asp Lys Leu His Glu Gln
```

-continued

```
            20              25              30
Cys Arg Pro Trp Arg Lys Asn Ala Cys Cys Ser Thr Asn Thr Ser Gln
        35              40              45
Glu Ala His Lys Asp Val Ser Tyr Leu Tyr Arg Phe Asn Trp Asn His
    50              55              60
Cys Gly Glu Met Ala Pro Ala Cys Lys Arg His Phe Ile Gln Asp Thr
65              70              75              80
Cys Leu Tyr Glu Cys Ser Pro Asn Leu Gly Pro Trp Ile Gln Gln Val
            85              90              95
Asp Gln Ser Trp Arg Lys Glu Arg Val Leu Asn Val Pro Leu Cys Lys
        100             105             110
Glu Asp Cys Glu Gln Trp Trp Glu Asp Cys Arg Thr Ser Tyr Thr Cys
        115             120             125
Lys Ser Asn Trp His Lys Gly Trp Asn Trp Thr Ser Gly Phe Asn Lys
    130             135             140
Cys Ala Val Gly Ala Ala Cys Gln Pro Phe His Phe Tyr Phe Pro Thr
145             150             155             160
Pro Thr Val Leu Cys Asn Glu Ile Trp Thr His Ser Tyr Lys Val Ser
            165             170             175
Asn Tyr Ser Arg Gly Ser Gly Arg Cys Ile Gln Met Trp Phe Asp Pro
            180             185             190
Ala Gln Gly Asn Pro Asn Glu Glu Val Ala Arg Phe Tyr Ala Ala Ala
        195             200             205
Met
```

```
<210> SEQ ID NO 12
<211> LENGTH: 771
<212> TYPE: DNA
<213> ORGANISM: Homo sapiens
<220> FEATURE:
<221> NAME/KEY: source
<223> OTHER INFORMATION: /note="cDNA Encoding Extracellular Domain of
      FOLR1"

<400> SEQUENCE: 12
atggctcagc ggatgacaac acagctgctg ctccttctag tgtgggtggc tgtagtaggg      60
gaggctcaga caaggattgc atgggccagg actgagcttc tcaatgtctg catgaacgcc     120
aagcaccaca aggaaaagcc aggccccgag gacaagttgc atgagcagtg tcgaccctgg     180
aggaagaatg cctgctgttc taccaacacc agccaggaag cccataagga tgtttcctac     240
ctatatagat tcaactggaa ccactgtgga gagatggcac tgcctgcaa acggcatttc     300 atccaggaca cctgcctcta cgagtgctcc cccaacttgg ggccctggat ccagcaggtg     360
gatcagagct ggcgcaaaga gcgggtactg aacgtgcccc tgtgcaaaga ggactgtgag     420
caatggtggg aagattgtcg cacctcctac acctgcaaga gcaactggca caagggctgg     480
aactggactt cagggtttaa caagtgcgca gtgggagctg cctgccaacc tttccatttc     540
tacttcccca cacccactgt tctgtgcaat gaaatctgga ctcactccta caaggtcagc     600
aactacagcc gagggagtgg ccgctgcatc cagatgtggt tcgacccagc ccagggcaac     660
cccaatgagg aggtggcgag gttctatgct gcagccatga gtggggctgg gccctgggca     720
gcctggcctt tcctgcttag cctggcccta atgctgctgt ggctgctcag c              771
```

```
<210> SEQ ID NO 13
<211> LENGTH: 118
<212> TYPE: PRT
```

-continued

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #1"

<400> SEQUENCE: 13

Gln Val Gln Leu Val Gln Ser Gly Ala Glu Val Val Lys Pro Gly Ala
1               5                   10                  15

Ser Val Lys Ile Ser Cys His Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 14
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #2"

<400> SEQUENCE: 14

Gln Val Gln Leu Val Gln Ser Gly Ala Glu Val Val Lys Pro Gly Ala
1               5                   10                  15

Ser Val Lys Ile Ser Cys Lys His Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 15
<211> LENGTH: 118
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #3"

<400> SEQUENCE: 15

Gln Val Gln Leu Val Gln Ser Gly Ala Glu Val Val Lys Pro Gly Ala
1               5                   10                  15

Ser Val Lys Ile Ser Cys Lys Ala His Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 16
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #4"

<400> SEQUENCE: 16

Gln Val Gln Leu Val Gln Ser Gly Ala Glu Val Val Lys Pro Gly Ala
1               5                   10                  15

Ser Val Lys Ile Ser Cys Lys Ala Ser His Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 17

```
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #5"

<400> SEQUENCE: 17

Gln Val Gln Leu Val Gln Ser Gly Ala Glu Val Val Lys Pro Gly Ala
1               5                   10                  15

Ser Val Lys Ile Ser Cys Lys Ala Ser Gly His Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 18
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #6"

<400> SEQUENCE: 18

Gln Val Gln Leu Val Gln Ser Gly Ala Glu Val Val Lys Pro Gly Ala
1               5                   10                  15

Ser Val Lys Ile Ser Cys Lys Ala Ser Gly Tyr His Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

-continued

```
<210> SEQ ID NO 19
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #7"

<400> SEQUENCE: 19

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr His Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 20
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #8"

<400> SEQUENCE: 20

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe His Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

<210> SEQ ID NO 21
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #9"

<400> SEQUENCE: 21

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr His Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 22
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #10"

<400> SEQUENCE: 22

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly His
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

-continued

<210> SEQ ID NO 23
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #11"

<400> SEQUENCE: 23

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

His Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 24
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #12"

<400> SEQUENCE: 24

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe His Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser

-continued

115

<210> SEQ ID NO 25
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #13"

<400> SEQUENCE: 25

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met His Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 26
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #14"

<400> SEQUENCE: 26

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly His Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

-continued

```
Thr Val Thr Val Ser Ser
        115

<210> SEQ ID NO 27
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #15"

<400> SEQUENCE: 27

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg His His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 28
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #16"

<400> SEQUENCE: 28

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile Ala Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110
```

```
Thr Val Thr Val Ser Ser
        115

<210> SEQ ID NO 29
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #17"

<400> SEQUENCE: 29

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His His Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 30
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #18"

<400> SEQUENCE: 30

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro His Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
```

-continued

```
                100               105               110

Thr Val Thr Val Ser Ser
        115

<210> SEQ ID NO 31
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #19"

<400> SEQUENCE: 31

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr His Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100               105               110

Thr Val Thr Val Ser Ser
        115

<210> SEQ ID NO 32
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #20"

<400> SEQUENCE: 32

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp His Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95
```

-continued

```
Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 33
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #21"

<400> SEQUENCE: 33

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly His Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 34
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #22"

<400> SEQUENCE: 34

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp His Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95
```

-continued

```
Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 35
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #23"

<400> SEQUENCE: 35

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr His Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 36
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #24"

<400> SEQUENCE: 36

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe His Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
```

-continued

```
                  85              90              95

Thr Arg Tyr Asp Gly Ser Arg Ala Met Asp Tyr Trp Gly Gln Gly Thr
            100             105             110

Thr Val Thr Val Ser Ser
        115

<210> SEQ ID NO 37
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #25"

<400> SEQUENCE: 37

Gln Val Gln Leu Val Gln Ser Gly Ala Glu Val Val Lys Pro Gly Ala
1               5               10              15

Ser Val Lys Ile Ser Cys Lys Ala Ser Gly Tyr Thr Phe Thr Gly Tyr
            20              25              30

Phe Met Asn Trp Val Lys Gln Ser Pro Gly Gln Ser Leu Glu Trp Ile
        35              40              45

Gly Arg Ile His Pro Tyr Asp Gly Asp Thr Phe Tyr His Gln Lys Phe
    50              55              60

Gln Gly Lys Ala Thr Leu Thr Val Asp Lys Ser Ser Asn Thr Ala His
65              70              75              80

Met Glu Leu Leu Ser Leu Thr Ser Glu Asp Phe Ala Val Tyr Tyr Cys
                85              90              95

Thr Arg Tyr Asp Gly Ser Arg Ala Met Asp Tyr Trp Gly Gln Gly Thr
            100             105             110

Thr Val Thr Val Ser Ser
        115

<210> SEQ ID NO 38
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #26"

<400> SEQUENCE: 38

Gln Val Gln Leu Val Gln Ser Gly Ala Glu Val Val Lys Pro Gly Ala
1               5               10              15

Ser Val Lys Ile Ser Cys Lys Ala Ser Gly Tyr Thr Phe Thr Gly Tyr
            20              25              30

Phe Met Asn Trp Val Lys Gln Ser Pro Gly Gln Ser Leu Glu Trp Ile
        35              40              45

Gly Arg Ile His Pro Tyr Asp Gly Asp Thr Phe Tyr Asn His Lys Phe
    50              55              60

Gln Gly Lys Ala Thr Leu Thr Val Asp Lys Ser Ser Asn Thr Ala His
65              70              75              80
```

-continued

```
Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 39
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #27"

<400> SEQUENCE: 39

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln His Phe
    50                  55                  60

Gln Gly Lys Ala Thr Leu Thr Val Asp Lys Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 40
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #28"

<400> SEQUENCE: 40

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys His
    50                  55                  60

Gln Gly Lys Ala Thr Leu Thr Val Asp Lys Ser Ser Asn Thr Ala His
65                  70                  75                  80
```

-continued

```
Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 41
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #29"

<400> SEQUENCE: 41

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

His Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 42
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #30"

<400> SEQUENCE: 42

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln His Lys Ala Thr Leu Thr Val Asp Lys Ser Ser Asn Thr Ala His
```

-continued

```
65                  70                  75                  80
Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 43
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #31"

<400> SEQUENCE: 43

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

His Arg Tyr Asp Gly Ser Arg Ala Met Asp Tyr Trp Gly Gln Gly Thr
            100                 105                 110

Thr Val Thr Val Ser Ser
        115

<210> SEQ ID NO 44
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #32"

<400> SEQUENCE: 44

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60
```

```
Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr His Tyr Asp Gly Ser Arg Ala Met Asp Tyr Trp Gly Gln Gly Thr
            100                 105                 110

Thr Val Thr Val Ser Ser
        115

<210> SEQ ID NO 45
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #33"

<400> SEQUENCE: 45

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg His Asp Gly Ser Arg Ala Met Asp Tyr Trp Gly Gln Gly Thr
            100                 105                 110

Thr Val Thr Val Ser Ser
        115

<210> SEQ ID NO 46
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #34"

<400> SEQUENCE: 46

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60
```

```
Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr His Gly Ser Arg Ala Met Asp Tyr Trp Gly Gln Gly Thr
            100                 105                 110

Thr Val Thr Val Ser Ser
        115
```

```
<210> SEQ ID NO 47
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #35"

<400> SEQUENCE: 47
```

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp His Ser Arg Ala Met Asp Tyr Trp Gly Gln Gly Thr
            100                 105                 110

Thr Val Thr Val Ser Ser
        115
```

```
<210> SEQ ID NO 48
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #36"

<400> SEQUENCE: 48
```

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
```

-continued

```
         50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly His Arg Ala Met Asp Tyr Trp Gly Gln Gly Thr
            100                 105                 110

Thr Val Thr Val Ser Ser
        115

<210> SEQ ID NO 49
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #37"

<400> SEQUENCE: 49

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser His Ala Met Asp Tyr Trp Gly Gln Gly Thr
            100                 105                 110

Thr Val Thr Val Ser Ser
        115

<210> SEQ ID NO 50
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #38"

<400> SEQUENCE: 50

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45
```

Gly Arg Ile His Pro Tyr Asp Gly Asp Thr Phe Tyr Asn Gln Lys Phe
    50                  55              60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg His Met Asp Tyr Trp Gly Gln Gly Thr
            100                 105                 110

Thr Val Thr Val Ser Ser
        115

<210> SEQ ID NO 51
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #39"

<400> SEQUENCE: 51

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55              60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala His Asp Tyr Trp Gly Gln Gly Thr
            100                 105                 110

Thr Val Thr Val Ser Ser
        115

<210> SEQ ID NO 52
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #40"

<400> SEQUENCE: 52

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

-continued

```
Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met His Tyr Trp Gly Gln Gly Thr
            100                 105                 110

Thr Val Thr Val Ser Ser
        115
```

<210> SEQ ID NO 53
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of mirvetuximab IgG
      histidine scanning variant #41"

<400> SEQUENCE: 53

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp His Trp Gly Gln Gly Thr
            100                 105                 110

Thr Val Thr Val Ser Ser
        115
```

<210> SEQ ID NO 54
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #1"

<400> SEQUENCE: 54

```
Asp Ile Val Leu Thr Gln Ser Pro Leu Ser Leu Ala Val Ser Leu Gly
1               5                   10                  15

Gln Pro Ala Ile Ile Ser Cys His Ala Ser Gln Ser Val Ser Phe Ala
            20                  25                  30

Gly Thr Ser Leu Met His Trp Tyr His Gln Lys Pro Gly Gln Gln Pro
```

-continued

```
         35              40              45
Arg Leu Leu Ile Tyr Arg Ala Ser Asn Leu Glu Ala Gly Val Pro Asp
    50              55              60

Arg Phe Ser Gly Ser Gly Ser Lys Thr Asp Phe Thr Leu Thr Ile Ser
65              70              75              80

Pro Val Glu Ala Glu Asp Ala Ala Thr Tyr Tyr Cys Gln Gln Ser Arg
                85              90              95

Glu Tyr Pro Tyr Thr Phe Gly Gly Gly Thr Lys Leu Glu Ile Lys
            100             105             110
```

```
<210> SEQ ID NO 55
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #2"

<400> SEQUENCE: 55
```

```
Asp Ile Val Leu Thr Gln Ser Pro Leu Ser Leu Ala Val Ser Leu Gly
1               5               10              15

Gln Pro Ala Ile Ile Ser Cys Lys His Ser Gln Ser Val Ser Phe Ala
                20              25              30

Gly Thr Ser Leu Met His Trp Tyr His Gln Lys Pro Gly Gln Gln Pro
            35              40              45

Arg Leu Leu Ile Tyr Arg Ala Ser Asn Leu Glu Ala Gly Val Pro Asp
    50              55              60

Arg Phe Ser Gly Ser Gly Ser Lys Thr Asp Phe Thr Leu Thr Ile Ser
65              70              75              80

Pro Val Glu Ala Glu Asp Ala Ala Thr Tyr Tyr Cys Gln Gln Ser Arg
                85              90              95

Glu Tyr Pro Tyr Thr Phe Gly Gly Gly Thr Lys Leu Glu Ile Lys
            100             105             110
```

```
<210> SEQ ID NO 56
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #3"

<400> SEQUENCE: 56
```

```
Asp Ile Val Leu Thr Gln Ser Pro Leu Ser Leu Ala Val Ser Leu Gly
1               5               10              15

Gln Pro Ala Ile Ile Ser Cys Lys Ala His Gln Ser Val Ser Phe Ala
                20              25              30

Gly Thr Ser Leu Met His Trp Tyr His Gln Lys Pro Gly Gln Gln Pro
            35              40              45

Arg Leu Leu Ile Tyr Arg Ala Ser Asn Leu Glu Ala Gly Val Pro Asp
    50              55              60
```

```
Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

```
<210> SEQ ID NO 57
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #4"

<400> SEQUENCE: 57
```

```
Asp Ile Val Leu Thr Gln Ser Pro Leu Ser Leu Ala Val Ser Leu Gly
1                   5                   10                  15

Gln Pro Ala Ile Ile Ser Cys Lys Ala Ser His Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

```
<210> SEQ ID NO 58
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #5"

<400> SEQUENCE: 58
```

```
Asp Ile Val Leu Thr Gln Ser Pro Leu Ser Leu Ala Val Ser Leu Gly
1                   5                   10                  15

Gln Pro Ala Ile Ile Ser Cys Lys Ala Ser Gln His Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95
```

```
Glu Tyr Pro Tyr Thr Phe Gly Gly Gly Thr Lys Leu Glu Ile Lys
            100                 105                 110
```

<210> SEQ ID NO 59
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #6"

<400> SEQUENCE: 59

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser His Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

<210> SEQ ID NO 60
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #7"

<400> SEQUENCE: 60

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val His Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

```
<210> SEQ ID NO 61
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #8"

<400> SEQUENCE: 61

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser His Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 62
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #9"

<400> SEQUENCE: 62

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe His
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 63
<211> LENGTH: 111
<212> TYPE: PRT
<213> ORGANISM: Artificial Sequence
<220> FEATURE:
```

<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Light Chain of mirvetuximab IgG
     histidine scanning variant #10"

<400> SEQUENCE: 63

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

His Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

<210> SEQ ID NO 64
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Light Chain of mirvetuximab IgG
     histidine scanning variant #11"

<400> SEQUENCE: 64

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly His Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

<210> SEQ ID NO 65
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source -continued
<223> OTHER INFORMATION: /note="Light Chain of mirvetuximab IgG
      histidine scanning variant #12"

<400> SEQUENCE: 65

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr His Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 66
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #13"

<400> SEQUENCE: 66

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser His Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 67
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #14"

<400> SEQUENCE: 67

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu His His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

```
<210> SEQ ID NO 68
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #15"

<400> SEQUENCE: 68
```

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met Ala Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110
```

```
<210> SEQ ID NO 69
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #16"

<400> SEQUENCE: 69
```

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30
```

-continued

```
Gly Thr Ser Leu Met His Trp Tyr His Gln Lys Pro Gly Gln Gln Pro
        35                  40                  45

Arg Leu Leu Ile Tyr His Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 70
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #17"

<400> SEQUENCE: 70

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
        35                  40                  45

Arg Leu Leu Ile Tyr Arg His Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 71
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #18"

<400> SEQUENCE: 71

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
        35                  40                  45

Arg Leu Leu Ile Tyr Arg Ala His Asn Leu Glu Ala Gly Val Pro Asp
```

```
             50              55              60

Arg Phe Ser Gly Ser Gly Ser Lys Thr Asp Phe Thr Leu Thr Ile Ser
65              70              75              80

Pro Val Glu Ala Glu Asp Ala Ala Thr Tyr Tyr Cys Gln Gln Ser Arg
                85              90              95

Glu Tyr Pro Tyr Thr Phe Gly Gly Gly Thr Lys Leu Glu Ile Lys
            100             105             110
```

```
<210> SEQ ID NO 72
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #19"
```

```
<400> SEQUENCE: 72

Asp Ile Val Leu Thr Gln Ser Pro Leu Ser Leu Ala Val Ser Leu Gly
1               5               10              15

Gln Pro Ala Ile Ile Ser Cys Lys Ala Ser Gln Ser Val Ser Phe Ala
                20              25              30

Gly Thr Ser Leu Met His Trp Tyr His Gln Lys Pro Gly Gln Gln Pro
            35              40              45

Arg Leu Leu Ile Tyr Arg Ala Ser His Leu Glu Ala Gly Val Pro Asp
    50              55              60

Arg Phe Ser Gly Ser Gly Ser Lys Thr Asp Phe Thr Leu Thr Ile Ser
65              70              75              80

Pro Val Glu Ala Glu Asp Ala Ala Thr Tyr Tyr Cys Gln Gln Ser Arg
                85              90              95

Glu Tyr Pro Tyr Thr Phe Gly Gly Gly Thr Lys Leu Glu Ile Lys
            100             105             110
```

```
<210> SEQ ID NO 73
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #20"
```

```
<400> SEQUENCE: 73

Asp Ile Val Leu Thr Gln Ser Pro Leu Ser Leu Ala Val Ser Leu Gly
1               5               10              15

Gln Pro Ala Ile Ile Ser Cys Lys Ala Ser Gln Ser Val Ser Phe Ala
                20              25              30

Gly Thr Ser Leu Met His Trp Tyr His Gln Lys Pro Gly Gln Gln Pro
            35              40              45

Arg Leu Leu Ile Tyr Arg Ala Ser Asn His Glu Ala Gly Val Pro Asp
    50              55              60

Arg Phe Ser Gly Ser Gly Ser Lys Thr Asp Phe Thr Leu Thr Ile Ser
65              70              75              80
```

Pro Val Glu Ala Glu Asp Ala Ala Thr Tyr Tyr Cys Gln Gln Ser Arg
            85                  90                  95

Glu Tyr Pro Tyr Thr Phe Gly Gly Gly Thr Lys Leu Glu Ile Lys
            100                 105                 110

<210> SEQ ID NO 74
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #21"

<400> SEQUENCE: 74

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu His Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
            85                  90                  95

Glu Tyr Pro Tyr Thr Phe Gly Gly Gly Thr Lys Leu Glu Ile Lys
            100                 105                 110

<210> SEQ ID NO 75
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #22"

<400> SEQUENCE: 75

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu His Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
            85                  90                  95

Glu Tyr Pro Tyr Thr Phe Gly Gly Gly Thr Lys Leu Glu Ile Lys
            100                 105                 110

-continued

```
<210> SEQ ID NO 76
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #23"

<400> SEQUENCE: 76

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys His Gln Ser Arg
                85                  90                  95

Glu Tyr Pro Tyr Thr Phe Gly Gly Gly Thr Lys Leu Glu Ile Lys
            100                 105                 110

<210> SEQ ID NO 77
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #24"

<400> SEQUENCE: 77

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln His Ser Arg
                85                  90                  95

Glu Tyr Pro Tyr Thr Phe Gly Gly Gly Thr Lys Leu Glu Ile Lys
            100                 105                 110

<210> SEQ ID NO 78
<211> LENGTH: 111
<212> TYPE: PRT
```

-continued

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #25"

<400> SEQUENCE: 78

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln His Arg
                85                  90                  95

Glu Tyr Pro Tyr Thr Phe Gly Gly Gly Thr Lys Leu Glu Ile Lys
            100                 105                 110

<210> SEQ ID NO 79
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #26"

<400> SEQUENCE: 79

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser His
                85                  90                  95

Glu Tyr Pro Tyr Thr Phe Gly Gly Gly Thr Lys Leu Glu Ile Lys
            100                 105                 110

<210> SEQ ID NO 80
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<220> FEATURE:
<221> NAME/KEY: source
<223> OTHER INFORMATION: /note="Light Chain of mirvetuximab IgG
      histidine scanning variant #27"

<400> SEQUENCE: 80

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

His Tyr Pro Tyr Thr Phe Gly Gly Gly Thr Lys Leu Glu Ile Lys
            100                 105                 110

<210> SEQ ID NO 81
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #28"

<400> SEQUENCE: 81

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu His Pro Tyr Thr Phe Gly Gly Gly Thr Lys Leu Glu Ile Lys
            100                 105                 110

<210> SEQ ID NO 82
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #29"
```

<400> SEQUENCE: 82

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr His Tyr Thr Phe Gly Gly Gly Thr Lys Leu Glu Ile Lys
            100                 105                 110
```

<210> SEQ ID NO 83
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #30"

<400> SEQUENCE: 83

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro His Thr Phe Gly Gly Gly Thr Lys Leu Glu Ile Lys
            100                 105                 110
```

<210> SEQ ID NO 84
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of mirvetuximab IgG
      histidine scanning variant #31"

<400> SEQUENCE: 84

```
Asp Ile Val Leu Thr Gln Ser Pro Leu Ser Leu Ala Val Ser Leu Gly
1               5                   10                  15
```

-continued

```
Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr His Phe Gly Gly Gly Thr Lys Leu Glu Ile Lys
            100                 105                 110
```

```
<210> SEQ ID NO 85
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #1"

<400> SEQUENCE: 85
```

```
Gln Val Gln Leu Val Gln Ser Gly Ala Glu Val Val Lys Pro Gly Ala
1               5                   10                  15

Ser Val Lys Ile Ser Cys Lys His Ser Gly His Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

```
<210> SEQ ID NO 86
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #2"

<400> SEQUENCE: 86
```

```
Gln Val Gln Leu Val Gln Ser Gly Ala Glu Val Val Lys Pro Gly Ala
1               5                   10                  15

Ser Val Lys Ile Ser Cys Lys His Ser Gly Tyr Thr Phe Thr Gly Tyr
            20                  25                  30
```

-continued

```
Phe Met Asn Trp Val Lys Gln Ser Pro Gly Gln Ser Leu Glu Trp Ile
        35                  40                  45

Gly Arg Ile His Pro His Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

```
<210> SEQ ID NO 87
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #3"

<400> SEQUENCE: 87

Gln Val Gln Leu Val Gln Ser Gly Ala Glu Val Val Lys Pro Gly Ala
1               5                   10                  15

Ser Val Lys Ile Ser Cys Lys His Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp His Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

```
<210> SEQ ID NO 88
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #4"

<400> SEQUENCE: 88

Gln Val Gln Leu Val Gln Ser Gly Ala Glu Val Val Lys Pro Gly Ala
1               5                   10                  15

Ser Val Lys Ile Ser Cys Lys His Ser Gly Tyr Thr Phe Thr Gly Tyr
```

-continued

```
                20              25              30

Phe Met Asn Trp Val Lys Gln Ser Pro Gly Gln Ser Leu Glu Trp Ile
        35              40              45

Gly Arg Ile His Pro Tyr Asp Gly Asp Thr His Tyr Asn Gln Lys Phe
    50              55              60

Gln Gly Lys Ala Thr Leu Thr Val Asp Lys Ser Ser Asn Thr Ala His
65              70              75              80

Met Glu Leu Leu Ser Leu Thr Ser Glu Asp Phe Ala Val Tyr Tyr Cys
                85              90              95

Thr Arg Tyr Asp Gly Ser Arg Ala Met Asp Tyr Trp Gly Gln Gly Thr
            100             105             110

Thr Val Thr Val Ser Ser
        115
```

<210> SEQ ID NO 89
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #5"

<400> SEQUENCE: 89

```
Gln Val Gln Leu Val Gln Ser Gly Ala Glu Val Val Lys Pro Gly Ala
1               5               10              15

Ser Val Lys Ile Ser Cys Lys Ala Ser Gly His Thr Phe Thr Gly Tyr
            20              25              30

Phe Met Asn Trp Val Lys Gln Ser Pro Gly Gln Ser Leu Glu Trp Ile
        35              40              45

Gly Arg Ile His Pro His Asp Gly Asp Thr Phe Tyr Asn Gln Lys Phe
    50              55              60

Gln Gly Lys Ala Thr Leu Thr Val Asp Lys Ser Ser Asn Thr Ala His
65              70              75              80

Met Glu Leu Leu Ser Leu Thr Ser Glu Asp Phe Ala Val Tyr Tyr Cys
                85              90              95

Thr Arg Tyr Asp Gly Ser Arg Ala Met Asp Tyr Trp Gly Gln Gly Thr
            100             105             110

Thr Val Thr Val Ser Ser
        115
```

<210> SEQ ID NO 90
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #6"

<400> SEQUENCE: 90

```
Gln Val Gln Leu Val Gln Ser Gly Ala Glu Val Val Lys Pro Gly Ala
1               5               10              15
```

Ser Val Lys Ile Ser Cys Lys Ala Ser Gly His Thr Phe Thr Gly Tyr
                20                    25                    30

Phe Met Asn Trp Val Lys Gln Ser Pro Gly Gln Ser Leu Glu Trp Ile
            35                    40                    45

Gly Arg Ile His Pro Tyr Asp Gly Asp His Phe Tyr Asn Gln Lys Phe
        50                    55                    60

Gln Gly Lys Ala Thr Leu Thr Val Asp Lys Ser Ser Asn Thr Ala His
65                    70                    75                    80

Met Glu Leu Leu Ser Leu Thr Ser Glu Asp Phe Ala Val Tyr Tyr Cys
                85                    90                    95

Thr Arg Tyr Asp Gly Ser Arg Ala Met Asp Tyr Trp Gly Gln Gly Thr
                100                   105                   110

Thr Val Thr Val Ser Ser
        115

<210> SEQ ID NO 91
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #7"

<400> SEQUENCE: 91

Gln Val Gln Leu Val Gln Ser Gly Ala Glu Val Val Lys Pro Gly Ala
1                   5                     10                    15

Ser Val Lys Ile Ser Cys Lys Ala Ser Gly His Thr Phe Thr Gly Tyr
                20                    25                    30

Phe Met Asn Trp Val Lys Gln Ser Pro Gly Gln Ser Leu Glu Trp Ile
            35                    40                    45

Gly Arg Ile His Pro Tyr Asp Gly Asp Thr His Tyr Asn Gln Lys Phe
        50                    55                    60

Gln Gly Lys Ala Thr Leu Thr Val Asp Lys Ser Ser Asn Thr Ala His
65                    70                    75                    80

Met Glu Leu Leu Ser Leu Thr Ser Glu Asp Phe Ala Val Tyr Tyr Cys
                85                    90                    95

Thr Arg Tyr Asp Gly Ser Arg Ala Met Asp Tyr Trp Gly Gln Gly Thr
                100                   105                   110

Thr Val Thr Val Ser Ser
        115

<210> SEQ ID NO 92
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #8"

<400> SEQUENCE: 92

Gln Val Gln Leu Val Gln Ser Gly Ala Glu Val Val Lys Pro Gly Ala
1                   5                     10                    15

-continued

```
Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
            35                  40                  45

Gly Arg Ile His Pro His Asp Gly Asp His Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

```
<210> SEQ ID NO 93
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #9"

<400> SEQUENCE: 93

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
            35                  40                  45

Gly Arg Ile His Pro His Asp Gly Asp Thr His Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

```
<210> SEQ ID NO 94
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #10"

<400> SEQUENCE: 94

Gln Val Gln Leu Val Gln Ser Gly Ala Glu Val Val Lys Pro Gly Ala
```

-continued

```
1                   5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp His His Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
                100                 105                 110

Thr Val Thr Val Ser Ser
        115
```

```
<210> SEQ ID NO 95
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #11"

<400> SEQUENCE: 95

Gln Val Gln Leu Val Gln Ser Gly Ala Glu Val Val Lys Pro Gly Ala
1                   5                   10                  15

Ser Val Lys Ile Ser Cys Lys His Ser Gly His Thr Phe Thr Gly Tyr
                20                  25                  30

Phe Met Asn Trp Val Lys Gln Ser Pro Gly Gln Ser Leu Glu Trp Ile
        35                  40                  45

Gly Arg Ile His Pro His Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
                100                 105                 110

Thr Val Thr Val Ser Ser
        115
```

```
<210> SEQ ID NO 96
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #12"

<400> SEQUENCE: 96
```

-continued

```
Gln Val Gln Leu Val Gln Ser Gly Ala Glu Val Val Lys Pro Gly Ala
1               5                   10                  15

Ser Val Lys Ile Ser Cys Lys His Ser Gly His Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp His Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

```
<210> SEQ ID NO 97
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #13"

<400> SEQUENCE: 97
```

```
Gln Val Gln Leu Val Gln Ser Gly Ala Glu Val Val Lys Pro Gly Ala
1               5                   10                  15

Ser Val Lys Ile Ser Cys Lys His Ser Gly His Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr His Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

```
<210> SEQ ID NO 98
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #14"

<400> SEQUENCE: 98
```

Gln Val Gln Leu Val Gln Ser Gly Ala Glu Val Val Lys Pro Gly Ala
1               5                   10                  15

Ser Val Lys Ile Ser Cys Lys His Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro His Asp Gly Asp His Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 99
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #15"

<400> SEQUENCE: 99

Gln Val Gln Leu Val Gln Ser Gly Ala Glu Val Val Lys Pro Gly Ala
1               5                   10                  15

Ser Val Lys Ile Ser Cys Lys His Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro His Asp Gly Asp Thr His Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 100
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #16"

<400> SEQUENCE: 100

Gln Val Gln Leu Val Gln Ser Gly Ala Glu Val Val Lys Pro Gly Ala
1               5                   10                  15

Ser Val Lys Ile Ser Cys Lys His Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp His His Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 101
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #17"

<400> SEQUENCE: 101

Gln Val Gln Leu Val Gln Ser Gly Ala Glu Val Val Lys Pro Gly Ala
1               5                   10                  15

Ser Val Lys Ile Ser Cys Lys Ala Ser Gly His Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro His Asp Gly Asp His Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 102
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #18"

<400> SEQUENCE: 102

Gln Val Gln Leu Val Gln Ser Gly Ala Glu Val Val Lys Pro Gly Ala
1               5                   10                  15

Ser Val Lys Ile Ser Cys Lys Ala Ser Gly His Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro His Asp Gly Asp Thr His Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 103
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab
      IgG histidine scanning variant #19"

<400> SEQUENCE: 103

Gln Val Gln Leu Val Gln Ser Gly Ala Glu Val Val Lys Pro Gly Ala
1               5                   10                  15

Ser Val Lys Ile Ser Cys Lys Ala Ser Gly His Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp His His Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 104
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of mirvetuximab -continued IgG histidine scanning variant #20"

<400> SEQUENCE: 104

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro His Asp Gly Asp His His Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

<210> SEQ ID NO 105
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG"

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

<210> SEQ ID NO 106
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-022 IgG"

-continued

<400> SEQUENCE: 106

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 107
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR1 of STRO-002"

<400> SEQUENCE: 107

```
Gly Phe Asn Ile Arg Thr Gln Ser Ile His
1               5                   10
```

<210> SEQ ID NO 108
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR2 of STRO-002"

<400> SEQUENCE: 108

```
Asp Ile Phe Pro Ile Asp Gly Ile Thr Asp Tyr Ala Asp Ser Val Lys
1               5                   10                  15

Gly
```

<210> SEQ ID NO 109
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR3 of STRO-002"

<400> SEQUENCE: 109

```
Ala Arg Gly Ser Trp Ser Trp Pro Ser Gly Met Asp Tyr Tyr Leu Asp
1               5                   10                  15
```

-continued

Tyr

<210> SEQ ID NO 110
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR1 of STRO-002"

<400> SEQUENCE: 110

Arg Ala Ser Gln Asp Val Asn Thr Ala Val Ala
1               5                   10

<210> SEQ ID NO 111
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR2 of STRO-002"

<400> SEQUENCE: 111

Ser Ala Ser Phe Leu Tyr Ser
1               5

<210> SEQ ID NO 112
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR3 of STRO-002"

<400> SEQUENCE: 112

Gln Gln His Tyr Thr Thr Pro Pro Thr
1               5

<210> SEQ ID NO 113
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #1"

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser His Phe Asn Ile Arg Thr Gln
            20                  25                  30

-continued

```
Ser Ile His Trp Val Arg Gln Ala Pro Gly Lys Gly Leu Glu Trp Ile
    35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

```
<210> SEQ ID NO 114
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #2"

<400> SEQUENCE: 114
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly His Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

```
<210> SEQ ID NO 115
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #3"

<400> SEQUENCE: 115
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe His Ile Arg Thr Gln
            20                  25                  30
```

-continued

```
Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

```
<210> SEQ ID NO 116
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #4"

<400> SEQUENCE: 116
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn His Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

```
<210> SEQ ID NO 117
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #5"

<400> SEQUENCE: 117
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile His Thr Gln
```

-continued

```
        20              25              30

Ser Ile His Trp Val Arg Gln Ala Pro Gly Lys Gly Leu Glu Trp Ile
        35              40              45

Gly Asp Ile Phe Pro Ile Asp Gly Ile Thr Asp Tyr Ala Asp Ser Val
    50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
                85              90              95

Ala Arg Gly Ser Trp Ser Trp Pro Ser Gly Met Asp Tyr Tyr Leu Asp
            100             105             110

Tyr Trp Gly Gln Gly Thr Leu Val Thr Val Ser Ser
        115             120
```

```
<210> SEQ ID NO 118
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #6"

<400> SEQUENCE: 118

Glu Val Gln Leu Val Glu Ser Gly Gly Gly Leu Val Gln Pro Gly Gly
1               5               10              15

Ser Leu Arg Leu Ser Cys Ala Ala Ser Gly Phe Asn Ile Arg His Gln
            20              25              30

Ser Ile His Trp Val Arg Gln Ala Pro Gly Lys Gly Leu Glu Trp Ile
        35              40              45

Gly Asp Ile Phe Pro Ile Asp Gly Ile Thr Asp Tyr Ala Asp Ser Val
    50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
                85              90              95

Ala Arg Gly Ser Trp Ser Trp Pro Ser Gly Met Asp Tyr Tyr Leu Asp
            100             105             110

Tyr Trp Gly Gln Gly Thr Leu Val Thr Val Ser Ser
        115             120
```

```
<210> SEQ ID NO 119
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #7"

<400> SEQUENCE: 119

Glu Val Gln Leu Val Glu Ser Gly Gly Gly Leu Val Gln Pro Gly Gly
1               5               10              15
```

```
Ser Leu Arg Leu Ser Cys Ala Ala Ser Gly Phe Asn Ile Arg Thr His
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

<210> SEQ ID NO 120
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Heavy Chain of STRO-002 IgG histidine
     scanning variant #8"

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

His Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

<210> SEQ ID NO 121
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Heavy Chain of STRO-002 IgG histidine
     scanning variant #9"

<400> SEQUENCE: 121

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Arg Thr Gln
          20                  25                  30

Ser His His Trp Val Arg Gln Ala Pro Gly Lys Gly Leu Glu Trp Ile
          35                  40                  45

Gly Asp Ile Phe Pro Ile Asp Gly Ile Thr Asp Tyr Ala Asp Ser Val
      50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
              85                  90                  95

Ala Arg Gly Ser Trp Ser Trp Pro Ser Gly Met Asp Tyr Tyr Leu Asp
          100                 105                 110

Tyr Trp Gly Gln Gly Thr Leu Val Thr Val Ser Ser
          115                 120

<210> SEQ ID NO 122
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #10"

<400> SEQUENCE: 122

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Asn Ile Arg Thr Gln
          20                  25                  30

Ser Ile Ala Trp Val Arg Gln Ala Pro Gly Lys Gly Leu Glu Trp Ile
          35                  40                  45

Gly Asp Ile Phe Pro Ile Asp Gly Ile Thr Asp Tyr Ala Asp Ser Val
      50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
              85                  90                  95

Ala Arg Gly Ser Trp Ser Trp Pro Ser Gly Met Asp Tyr Tyr Leu Asp
          100                 105                 110

Tyr Trp Gly Gln Gly Thr Leu Val Thr Val Ser Ser
          115                 120

<210> SEQ ID NO 123
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #11"

<400> SEQUENCE: 123

Glu Val Gln Leu Val Glu Ser Gly Gly Gly Leu Val Gln Pro Gly Gly

-continued

```
1                   5                       10                      15

Ser Leu Arg Leu Ser Cys Ala Ala Ser Gly Phe Asn Ile Arg Thr Gln
                20                      25                      30

Ser Ile His Trp Val Arg Gln Ala Pro Gly Lys Gly Leu Glu Trp Ile
        35                      40                      45

Gly His Ile Phe Pro Ile Asp Gly Ile Thr Asp Tyr Ala Asp Ser Val
    50                      55                      60

Lys Gly Arg Phe Thr Ile Ser Ala Asp Thr Ser Lys Asn Thr Ala Tyr
65                      70                      75                      80

Leu Gln Met Asn Ser Leu Arg Ala Glu Asp Thr Ala Val Tyr Tyr Cys
                85                      90                      95

Ala Arg Gly Ser Trp Ser Trp Pro Ser Gly Met Asp Tyr Tyr Leu Asp
            100                     105                     110

Tyr Trp Gly Gln Gly Thr Leu Val Thr Val Ser Ser
        115                     120
```

```
<210> SEQ ID NO 124
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #12"

<400> SEQUENCE: 124
```

```
Glu Val Gln Leu Val Glu Ser Gly Gly Gly Leu Val Gln Pro Gly Gly
1                   5                       10                      15

Ser Leu Arg Leu Ser Cys Ala Ala Ser Gly Phe Asn Ile Arg Thr Gln
                20                      25                      30

Ser Ile His Trp Val Arg Gln Ala Pro Gly Lys Gly Leu Glu Trp Ile
        35                      40                      45

Gly Asp His Phe Pro Ile Asp Gly Ile Thr Asp Tyr Ala Asp Ser Val
    50                      55                      60

Lys Gly Arg Phe Thr Ile Ser Ala Asp Thr Ser Lys Asn Thr Ala Tyr
65                      70                      75                      80

Leu Gln Met Asn Ser Leu Arg Ala Glu Asp Thr Ala Val Tyr Tyr Cys
                85                      90                      95

Ala Arg Gly Ser Trp Ser Trp Pro Ser Gly Met Asp Tyr Tyr Leu Asp
            100                     105                     110

Tyr Trp Gly Gln Gly Thr Leu Val Thr Val Ser Ser
        115                     120
```

```
<210> SEQ ID NO 125
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #13"

<400> SEQUENCE: 125
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile His Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
            115                 120
```

<210> SEQ ID NO 126
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #14"

<400> SEQUENCE: 126

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe His Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
            115                 120
```

<210> SEQ ID NO 127
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #15"

<400> SEQUENCE: 127

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro His Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

```
<210> SEQ ID NO 128
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #16"

<400> SEQUENCE: 128
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile His Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

```
<210> SEQ ID NO 129
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #17"
```

<400> SEQUENCE: 129

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp His Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

<210> SEQ ID NO 130
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #18"

<400> SEQUENCE: 130

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly His Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120
```

<210> SEQ ID NO 131
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #19"

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile His Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 132
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #20"

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 133
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine scanning variant #21"

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp His Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 134
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #22"

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr His Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 135
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source

```
<223> OTHER INFORMATION: /note="Heavy Chain of STRO-002 IgG histidine
      scanning variant #23"

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala His Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 136
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #24"

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp His Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 137
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
```

-continued

<221> NAME/KEY: source
<223> OTHER INFORMATION: /note="Heavy Chain of STRO-002 IgG histidine
      scanning variant #25"

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser His
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 138
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #26"

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

His Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 139
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<220> FEATURE:
<221> NAME/KEY: source
<223> OTHER INFORMATION: /note="Heavy Chain of STRO-002 IgG histidine
     scanning variant #27"

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys His Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 140
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Heavy Chain of STRO-002 IgG histidine
     scanning variant #28"

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

His Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 141
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"
<220> FEATURE:
<221> NAME/KEY: source
<223> OTHER INFORMATION: /note="Heavy Chain of STRO-002 IgG histidine
      scanning variant #29"

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala His Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 142
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #30"

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 143
<211> LENGTH: 124
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #31"

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly His Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 144
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #32"

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser His Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 145
<211> LENGTH: 124
<212> TYPE: PRT
<213> ORGANISM: Artificial Sequence
<220> FEATURE:
```

-continued

<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #33"

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp His Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 146
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #34"

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser His Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 147
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #35"

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp His Ser Gly Met Asp Tyr Tyr Leu Asp
            100                 105                 110

Tyr Trp Gly Gln Gly Thr Leu Val Thr Val Ser Ser
        115                 120

<210> SEQ ID NO 148
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #36"

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro His Gly Met Asp Tyr Tyr Leu Asp
            100                 105                 110

Tyr Trp Gly Gln Gly Thr Leu Val Thr Val Ser Ser
        115                 120

<210> SEQ ID NO 149
<211> LENGTH: 124
<212> TYPE: PRT

-continued

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #37"

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser His Met Asp Tyr Tyr Leu Asp
            100                 105                 110

Tyr Trp Gly Gln Gly Thr Leu Val Thr Val Ser Ser
        115                 120

<210> SEQ ID NO 150
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #38"

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly His Asp Tyr Tyr Leu Asp
            100                 105                 110

Tyr Trp Gly Gln Gly Thr Leu Val Thr Val Ser Ser
        115                 120

<210> SEQ ID NO 151
<211> LENGTH: 124
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #39"

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met His Tyr Tyr Leu Asp
            100                 105                 110

Tyr Trp Gly Gln Gly Thr Leu Val Thr Val Ser Ser
        115                 120

<210> SEQ ID NO 152
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #40"

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp His Tyr Leu Asp
            100                 105                 110

Tyr Trp Gly Gln Gly Thr Leu Val Thr Val Ser Ser
        115                 120

<210> SEQ ID NO 153
```

-continued

```
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Heavy Chain of STRO-002 IgG histidine
     scanning variant #41"

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr His Leu Asp
            100                 105                 110

Tyr Trp Gly Gln Gly Thr Leu Val Thr Val Ser Ser
        115                 120

<210> SEQ ID NO 154
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Heavy Chain of STRO-002 IgG histidine
     scanning variant #42"

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr His Asp
            100                 105                 110

Tyr Trp Gly Gln Gly Thr Leu Val Thr Val Ser Ser
        115                 120
```

-continued

```
<210> SEQ ID NO 155
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #43"

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu His
            100                 105                 110

Tyr Trp Gly Gln Gly Thr Leu Val Thr Val Ser Ser
        115                 120

<210> SEQ ID NO 156
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of STRO-002 IgG histidine
      scanning variant #44"

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

His Trp Gly Gln Gly Thr Leu Val Thr Val Ser Ser
        115                 120
```

-continued

<210> SEQ ID NO 157
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #1"

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 158
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #2"

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg His Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 159
<211> LENGTH: 107
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #3"

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala His Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 160
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #4"

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser His Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 161
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
```

<221> NAME/KEY: source
<223> OTHER INFORMATION: /note="Light Chain of STRO-002 IgG histidine
      scanning variant #5"

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 162
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #6"

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp His Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 163
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #7"

<400> SEQUENCE: 163

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

```
<210> SEQ ID NO 164
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #8"

<400> SEQUENCE: 164
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn His Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

```
<210> SEQ ID NO 165
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #9"

<400> SEQUENCE: 165
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr His
```

-continued

```
                20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 166
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #10"

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

His Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 167
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #11"

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val His Trp Tyr Gln Gln Lys Pro Gly Lys Ala Pro Lys Leu Leu Ile
        35                  40                  45
```

-continued

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 168
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #12"

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr His Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 169
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #13"

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser His Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

-continued

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 170
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #14"

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala His Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 171
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #15"

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser His Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys

-continued

```
                100              105

<210> SEQ ID NO 172
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #16"

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe His Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 173
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #17"

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu His Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 174
<211> LENGTH: 107
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #18"

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr His Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 175
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #19"

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys His Gln His Tyr Thr Thr Pro Pro
                85                  90                  95

Thr Phe Gly Gln Gly Thr Lys Val Glu Ile Lys
            100                 105

<210> SEQ ID NO 176
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"
<220> FEATURE:
<221> NAME/KEY: source
<223> OTHER INFORMATION: /note="Light Chain of STRO-002 IgG histidine
      scanning variant #20"

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Thr Thr Pro Pro
                85                  90                  95

Thr Phe Gly Gln Gly Thr Lys Val Glu Ile Lys
            100                 105

<210> SEQ ID NO 177
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #21"

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Thr Thr Pro Pro
                85                  90                  95

Thr Phe Gly Gln Gly Thr Lys Val Glu Ile Lys
            100                 105

<210> SEQ ID NO 178
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #22"

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His His Thr Thr Pro Pro
                85                  90                  95

Thr Phe Gly Gln Gly Thr Lys Val Glu Ile Lys
            100                 105
```

<210> SEQ ID NO 179
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #23"

<400> SEQUENCE: 179

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr His Thr Pro Pro
                85                  90                  95

Thr Phe Gly Gln Gly Thr Lys Val Glu Ile Lys
            100                 105
```

<210> SEQ ID NO 180
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #24"

<400> SEQUENCE: 180

```
Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr His Pro Pro
            85                  90                  95

Thr Phe Gly Gln Gly Thr Lys Val Glu Ile Lys
            100                 105
```

```
<210> SEQ ID NO 181
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #25"

<400> SEQUENCE: 181
```

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr His Pro
            85                  90                  95

Thr Phe Gly Gln Gly Thr Lys Val Glu Ile Lys
            100                 105
```

```
<210> SEQ ID NO 182
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #26"

<400> SEQUENCE: 182
```

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
```

-continued

```
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro His
                85                  90                  95

Thr Phe Gly Gln Gly Thr Lys Val Glu Ile Lys
            100                 105

<210> SEQ ID NO 183
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of STRO-002 IgG histidine
      scanning variant #27"

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

His Phe Gly Gln Gly Thr Lys Val Glu Ile Lys
            100                 105

<210> SEQ ID NO 184
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG"

<400> SEQUENCE: 184

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
                20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
```

-continued

```
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
                100                 105                 110

Thr Pro Val Thr Val Ser Ser
            115

<210> SEQ ID NO 185
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG"

<400> SEQUENCE: 185

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
                20                  25                  30

Asn Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
                100                 105                 110

<210> SEQ ID NO 186
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR1 of farletuzumab"

<400> SEQUENCE: 186

Gly Phe Thr Phe Ser Gly Tyr Gly Leu Ser
1               5                   10

<210> SEQ ID NO 187
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR2 of farletuzumab"

<400> SEQUENCE: 187
```

```
Met Ile Ser Ser Gly Gly Ser Tyr Thr Tyr Tyr Ala Asp Ser Val Lys
1               5                   10                  15

Gly

<210> SEQ ID NO 188
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR3 of farletuzumab"

<400> SEQUENCE: 188

Ala Arg His Gly Asp Asp Pro Ala Trp Phe Ala Tyr
1               5                   10

<210> SEQ ID NO 189
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR1 of farletuzumab"

<400> SEQUENCE: 189

Ser Ser Ile Ser Ser Asn Asn Leu His
1               5

<210> SEQ ID NO 190
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR2 of farletuzumab"

<400> SEQUENCE: 190

Gly Thr Ser Asn Leu Ala Ser
1               5

<210> SEQ ID NO 191
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR3 of farletuzumab"

<400> SEQUENCE: 191

Gln Gln Trp Ser Ser Tyr Pro Tyr Met Tyr Thr
1               5                   10
```

```
<210> SEQ ID NO 192
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #1"

<400> SEQUENCE: 192

Glu Val Gln Leu Val Glu Ser Gly Gly Gly Val Val Gln Pro Gly Arg
1               5                   10                  15

Ser Leu Arg Leu Ser Cys Ser Ala Ser His Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 193
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #2"

<400> SEQUENCE: 193

Glu Val Gln Leu Val Glu Ser Gly Gly Gly Val Val Gln Pro Gly Arg
1               5                   10                  15

Ser Leu Arg Leu Ser Cys Ser Ala Ser Gly His Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115
```

<210> SEQ ID NO 194
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #3"

<400> SEQUENCE: 194

Glu Val Gln Leu Val Glu Ser Gly Gly Gly Val Val Gln Pro Gly Arg
1               5                   10                  15

Ser Leu Arg Leu Ser Cys Ser Ala Ser Gly Phe His Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 195
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #4"

<400> SEQUENCE: 195

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr His Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

```
<210> SEQ ID NO 196
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #5"

<400> SEQUENCE: 196

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe His Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 197
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #6"

<400> SEQUENCE: 197

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser His Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
```

-continued

115

<210> SEQ ID NO 198
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #7"

<400> SEQUENCE: 198

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly His
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 199
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #8"

<400> SEQUENCE: 199

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

His Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

```
Thr Pro Val Thr Val Ser Ser
        115

<210> SEQ ID NO 200
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #9"

<400> SEQUENCE: 200

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly His Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 201
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #10"

<400> SEQUENCE: 201

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu His Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110
```

-continued

Thr Pro Val Thr Val Ser Ser
        115

<210> SEQ ID NO 202
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #11"

<400> SEQUENCE: 202

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala His Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 203
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #12"

<400> SEQUENCE: 203

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met His Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly

-continued

```
                100             105             110

Thr Pro Val Thr Val Ser Ser
        115

<210> SEQ ID NO 204
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #13"

<400> SEQUENCE: 204

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile His Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 205
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #14"

<400> SEQUENCE: 205

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser His Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95
```

```
Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 206
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #15"

<400> SEQUENCE: 206

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser His Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 207
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #16"

<400> SEQUENCE: 207

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly His Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95
```

-continued

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 208
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #17"

<400> SEQUENCE: 208

Glu Val Gln Leu Val Glu Ser Gly Gly Gly Val Val Gln Pro Gly Arg
1                 5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
            35                  40                  45

Ala Met Ile Ser Ser Gly Gly His Tyr Thr Tyr Tyr Ala Asp Ser Val
        50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 209
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #18"

<400> SEQUENCE: 209

Glu Val Gln Leu Val Glu Ser Gly Gly Gly Val Val Gln Pro Gly Arg
1                 5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
            35                  40                  45

Ala Met Ile Ser Ser Gly Gly Ser His Thr Tyr Tyr Ala Asp Ser Val
        50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys

-continued

```
                85              90              95

Ala Arg His Gly Asp Asp Pro Ala Trp Phe Ala Tyr Trp Gly Gln Gly
            100             105             110

Thr Pro Val Thr Val Ser Ser
        115

<210> SEQ ID NO 210
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #19"

<400> SEQUENCE: 210

Glu Val Gln Leu Val Glu Ser Gly Gly Gly Val Val Gln Pro Gly Arg
1               5               10              15

Ser Leu Arg Leu Ser Cys Ser Ala Ser Gly Phe Thr Phe Ser Gly Tyr
            20              25              30

Gly Leu Ser Trp Val Arg Gln Ala Pro Gly Lys Gly Leu Glu Trp Val
        35              40              45

Ala Met Ile Ser Ser Gly Gly Ser Tyr His Tyr Tyr Ala Asp Ser Val
    50              55              60

Lys Gly Arg Phe Ala Ile Ser Arg Asp Asn Ala Lys Asn Thr Leu Phe
65              70              75              80

Leu Gln Met Asp Ser Leu Arg Pro Glu Asp Thr Gly Val Tyr Phe Cys
                85              90              95

Ala Arg His Gly Asp Asp Pro Ala Trp Phe Ala Tyr Trp Gly Gln Gly
            100             105             110

Thr Pro Val Thr Val Ser Ser
        115

<210> SEQ ID NO 211
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #20"

<400> SEQUENCE: 211

Glu Val Gln Leu Val Glu Ser Gly Gly Gly Val Val Gln Pro Gly Arg
1               5               10              15

Ser Leu Arg Leu Ser Cys Ser Ala Ser Gly Phe Thr Phe Ser Gly Tyr
            20              25              30

Gly Leu Ser Trp Val Arg Gln Ala Pro Gly Lys Gly Leu Glu Trp Val
        35              40              45

Ala Met Ile Ser Ser Gly Gly Ser Tyr Thr His Tyr Ala Asp Ser Val
    50              55              60

Lys Gly Arg Phe Ala Ile Ser Arg Asp Asn Ala Lys Asn Thr Leu Phe
65              70              75              80
```

```
Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115
```

```
<210> SEQ ID NO 212
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #21"

<400> SEQUENCE: 212
```

```
Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr His Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115
```

```
<210> SEQ ID NO 213
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #22"

<400> SEQUENCE: 213
```

```
Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr His Asp Ser Val
    50                  55                  60

Lys Gly Arg Phe Ala Ile Ser Arg Asp Asn Ala Lys Asn Thr Leu Phe
65                  70                  75                  80
```

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 214
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #23"

<400> SEQUENCE: 214

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala His Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 215
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #24"

<400> SEQUENCE: 215

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp His Val
    50                  55                  60

Lys Gly Arg Phe Ala Ile Ser Arg Asp Asn Ala Lys Asn Thr Leu Phe

-continued

```
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 216
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #25"

<400> SEQUENCE: 216

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser His
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 217
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #26"

<400> SEQUENCE: 217

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60
```

-continued

```
His Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 218
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #27"

<400> SEQUENCE: 218

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys His Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 219
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #28"

<400> SEQUENCE: 219

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60
```

```
Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

His Arg His Gly Asp Asp Pro Ala Trp Phe Ala Tyr Trp Gly Gln Gly
            100                 105                 110

Thr Pro Val Thr Val Ser Ser
        115

<210> SEQ ID NO 220
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #29"

<400> SEQUENCE: 220

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
                20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala His His Gly Asp Asp Pro Ala Trp Phe Ala Tyr Trp Gly Gln Gly
            100                 105                 110

Thr Pro Val Thr Val Ser Ser
        115

<210> SEQ ID NO 221
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #30"

<400> SEQUENCE: 221

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
                20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
```

```
        50                 55                 60
Lys Gly Arg Phe Ala Ile Ser Arg Asp Asn Ala Lys Asn Thr Leu Phe
65                 70                 75                 80

Leu Gln Met Asp Ser Leu Arg Pro Glu Asp Thr Gly Val Tyr Phe Cys
                85                 90                 95

Ala Arg Ala Gly Asp Asp Pro Ala Trp Phe Ala Tyr Trp Gly Gln Gly
            100                105                110

Thr Pro Val Thr Val Ser Ser
        115
```

<210> SEQ ID NO 222
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #31"

<400> SEQUENCE: 222

```
Glu Val Gln Leu Val Glu Ser Gly Gly Gly Val Val Gln Pro Gly Arg
1                 5                 10                 15

Ser Leu Arg Leu Ser Cys Ser Ala Ser Gly Phe Thr Phe Ser Gly Tyr
                20                 25                 30

Gly Leu Ser Trp Val Arg Gln Ala Pro Gly Lys Gly Leu Glu Trp Val
            35                 40                 45

Ala Met Ile Ser Ser Gly Gly Ser Tyr Thr Tyr Tyr Ala Asp Ser Val
        50                 55                 60

Lys Gly Arg Phe Ala Ile Ser Arg Asp Asn Ala Lys Asn Thr Leu Phe
65                 70                 75                 80

Leu Gln Met Asp Ser Leu Arg Pro Glu Asp Thr Gly Val Tyr Phe Cys
                85                 90                 95

Ala Arg His His Asp Asp Pro Ala Trp Phe Ala Tyr Trp Gly Gln Gly
            100                105                110

Thr Pro Val Thr Val Ser Ser
        115
```

<210> SEQ ID NO 223
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #32"

<400> SEQUENCE: 223

```
Glu Val Gln Leu Val Glu Ser Gly Gly Gly Val Val Gln Pro Gly Arg
1                 5                 10                 15

Ser Leu Arg Leu Ser Cys Ser Ala Ser Gly Phe Thr Phe Ser Gly Tyr
                20                 25                 30

Gly Leu Ser Trp Val Arg Gln Ala Pro Gly Lys Gly Leu Glu Trp Val
            35                 40                 45
```

-continued

Ala Met Ile Ser Ser Gly Gly Ser Tyr Thr Tyr Tyr Ala Asp Ser Val
    50              55                  60

Lys Gly Arg Phe Ala Ile Ser Arg Asp Asn Ala Lys Asn Thr Leu Phe
65              70                  75                  80

Leu Gln Met Asp Ser Leu Arg Pro Glu Asp Thr Gly Val Tyr Phe Cys
                85                  90                  95

Ala Arg His Gly His Asp Pro Ala Trp Phe Ala Tyr Trp Gly Gln Gly
            100                 105                 110

Thr Pro Val Thr Val Ser Ser
        115

<210> SEQ ID NO 224
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #33"

<400> SEQUENCE: 224

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
                20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
    50              55                  60

Lys Gly Arg Phe Ala Ile Ser Arg Asp Asn Ala Lys Asn Thr Leu Phe
65              70                  75                  80

Leu Gln Met Asp Ser Leu Arg Pro Glu Asp Thr Gly Val Tyr Phe Cys
                85                  90                  95

Ala Arg His Gly Asp His Pro Ala Trp Phe Ala Tyr Trp Gly Gln Gly
            100                 105                 110

Thr Pro Val Thr Val Ser Ser
        115

<210> SEQ ID NO 225
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #34"

<400> SEQUENCE: 225

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
                20                  25                  30

Gly Leu Ser Trp Val Arg Gln Ala Pro Gly Lys Gly Leu Glu Trp Val
            35                  40                  45

-continued

```
Ala Met Ile Ser Ser Gly Gly Ser Tyr Thr Tyr Tyr Ala Asp Ser Val
    50              55              60

Lys Gly Arg Phe Ala Ile Ser Arg Asp Asn Ala Lys Asn Thr Leu Phe
65              70              75              80

Leu Gln Met Asp Ser Leu Arg Pro Glu Asp Thr Gly Val Tyr Phe Cys
                85              90              95

Ala Arg His Gly Asp Asp His Ala Trp Phe Ala Tyr Trp Gly Gln Gly
            100             105             110

Thr Pro Val Thr Val Ser Ser
        115

<210> SEQ ID NO 226
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #35"

<400> SEQUENCE: 226

Glu Val Gln Leu Val Glu Ser Gly Gly Gly Val Val Gln Pro Gly Arg
1               5               10              15

Ser Leu Arg Leu Ser Cys Ser Ala Ser Gly Phe Thr Phe Ser Gly Tyr
            20              25              30

Gly Leu Ser Trp Val Arg Gln Ala Pro Gly Lys Gly Leu Glu Trp Val
        35              40              45

Ala Met Ile Ser Ser Gly Gly Ser Tyr Thr Tyr Tyr Ala Asp Ser Val
    50              55              60

Lys Gly Arg Phe Ala Ile Ser Arg Asp Asn Ala Lys Asn Thr Leu Phe
65              70              75              80

Leu Gln Met Asp Ser Leu Arg Pro Glu Asp Thr Gly Val Tyr Phe Cys
                85              90              95

Ala Arg His Gly Asp Asp Pro His Trp Phe Ala Tyr Trp Gly Gln Gly
            100             105             110

Thr Pro Val Thr Val Ser Ser
        115

<210> SEQ ID NO 227
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #36"

<400> SEQUENCE: 227

Glu Val Gln Leu Val Glu Ser Gly Gly Gly Val Val Gln Pro Gly Arg
1               5               10              15

Ser Leu Arg Leu Ser Cys Ser Ala Ser Gly Phe Thr Phe Ser Gly Tyr
            20              25              30

Gly Leu Ser Trp Val Arg Gln Ala Pro Gly Lys Gly Leu Glu Trp Val
```

```
                35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala His Phe Ala Tyr Trp Gly Gln Gly
            100                 105                 110

Thr Pro Val Thr Val Ser Ser
        115

<210> SEQ ID NO 228
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #37"

<400> SEQUENCE: 228

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp His Ala Tyr Trp Gly Gln Gly
            100                 105                 110

Thr Pro Val Thr Val Ser Ser
        115

<210> SEQ ID NO 229
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #38"

<400> SEQUENCE: 229

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30
```

-continued

```
Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe His Tyr Trp Gly Gln Gly
            100                 105                 110

Thr Pro Val Thr Val Ser Ser
        115
```

```
<210> SEQ ID NO 230
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of farletuzumab IgG
      histidine scanning variant #39"

<400> SEQUENCE: 230

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala His Trp Gly Gln Gly
            100                 105                 110

Thr Pro Val Thr Val Ser Ser
        115
```

```
<210> SEQ ID NO 231
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #1"

<400> SEQUENCE: 231

Asp Ile Gln Leu Thr Gln Ser Pro Ser Ser Leu Ser Ala Ser Val Gly
1               5                   10                  15

Asp Arg Val Thr Ile Thr Cys Ser Val Ser His Ser Ile Ser Ser Asn
            20                  25                  30
```

-continued

```
Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
                100                 105                 110

<210> SEQ ID NO 232
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #2"

<400> SEQUENCE: 232

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser His Ile Ser Ser Asn
                20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
                100                 105                 110

<210> SEQ ID NO 233
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #3"

<400> SEQUENCE: 233

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser His Ser Ser Asn
                20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
```

-continued

```
         50             55             60

Gly Ser Gly Ser Gly Thr Asp Tyr Thr Phe Thr Ile Ser Ser Leu Gln
65                  70             75                  80

Pro Glu Asp Ile Ala Thr Tyr Tyr Cys Gln Gln Trp Ser Ser Tyr Pro
                 85             90                  95

Tyr Met Tyr Thr Phe Gly Gln Gly Thr Lys Val Glu Ile Lys
                100             105                110

<210> SEQ ID NO 234
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #4"

<400> SEQUENCE: 234

Asp Ile Gln Leu Thr Gln Ser Pro Ser Ser Leu Ser Ala Ser Val Gly
1                5             10                  15

Asp Arg Val Thr Ile Thr Cys Ser Val Ser Ser Ser Ile His Ser Asn
                20             25                  30

Asn Leu His Trp Tyr Gln Gln Lys Pro Gly Lys Ala Pro Lys Pro Trp
             35             40                  45

Ile Tyr Gly Thr Ser Asn Leu Ala Ser Gly Val Pro Ser Arg Phe Ser
    50             55                  60

Gly Ser Gly Ser Gly Thr Asp Tyr Thr Phe Thr Ile Ser Ser Leu Gln
65                  70             75                  80

Pro Glu Asp Ile Ala Thr Tyr Tyr Cys Gln Gln Trp Ser Ser Tyr Pro
                 85             90                  95

Tyr Met Tyr Thr Phe Gly Gln Gly Thr Lys Val Glu Ile Lys
                100             105                110

<210> SEQ ID NO 235
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #5"

<400> SEQUENCE: 235

Asp Ile Gln Leu Thr Gln Ser Pro Ser Ser Leu Ser Ala Ser Val Gly
1                5             10                  15

Asp Arg Val Thr Ile Thr Cys Ser Val Ser Ser Ser Ile Ser His Asn
                20             25                  30

Asn Leu His Trp Tyr Gln Gln Lys Pro Gly Lys Ala Pro Lys Pro Trp
             35             40                  45

Ile Tyr Gly Thr Ser Asn Leu Ala Ser Gly Val Pro Ser Arg Phe Ser
    50             55                  60

Gly Ser Gly Ser Gly Thr Asp Tyr Thr Phe Thr Ile Ser Ser Leu Gln
65                  70             75                  80
```

```
Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 236
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #6"

<400> SEQUENCE: 236

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser His
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 237
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #7"

<400> SEQUENCE: 237

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

His Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110
```

<210> SEQ ID NO 238
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #8"

<400> SEQUENCE: 238

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn His His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 239
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #9"

<400> SEQUENCE: 239

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu Ala Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 240
<211> LENGTH: 110
<212> TYPE: PRT

-continued

<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #10"

<400> SEQUENCE: 240

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr His Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 241
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #11"

<400> SEQUENCE: 241

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly His Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 242
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

```
<220> FEATURE:
<221> NAME/KEY: source
<223> OTHER INFORMATION: /note="Light Chain of farletuzumab IgG
      histidine scanning variant #12"

<400> SEQUENCE: 242

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr His Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
                100                 105                 110

<210> SEQ ID NO 243
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #13"

<400> SEQUENCE: 243

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser His Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
                100                 105                 110

<210> SEQ ID NO 244
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #14"
```

-continued

<400> SEQUENCE: 244

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn His Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110
```

<210> SEQ ID NO 245
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #15"

<400> SEQUENCE: 245

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu His Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110
```

<210> SEQ ID NO 246
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #16"

<400> SEQUENCE: 246

```
Asp Ile Gln Leu Thr Gln Ser Pro Ser Ser Leu Ser Ala Ser Val Gly
1               5                   10                  15
```

-continued

```
Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala His Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110
```

<210> SEQ ID NO 247
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Light Chain of farletuzumab IgG
     histidine scanning variant #17"

<400> SEQUENCE: 247

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys His Gln Trp Ser Ser Tyr Pro
                85                  90                  95

Tyr Met Tyr Thr Phe Gly Gln Gly Thr Lys Val Glu Ile Lys
            100                 105                 110
```

<210> SEQ ID NO 248
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: source
<223> OTHER INFORMATION: /note="Light Chain of farletuzumab IgG
     histidine scanning variant #18"

<400> SEQUENCE: 248

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45
```

```
Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln His Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 249
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #19"

<400> SEQUENCE: 249

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
                20                  25                  30

Asn Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln His Ser Ser Tyr Pro
                85                  90                  95

Tyr Met Tyr Thr Phe Gly Gln Gly Thr Lys Val Glu Ile Lys
            100                 105                 110

<210> SEQ ID NO 250
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #20"

<400> SEQUENCE: 250

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
                20                  25                  30

Asn Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
```

-continued

```
65                  70                  75                  80

Pro Glu Asp Ile Ala Thr Tyr Tyr Cys Gln Gln Trp His Ser Tyr Pro
                85                  90                  95

Tyr Met Tyr Thr Phe Gly Gln Gly Thr Lys Val Glu Ile Lys
            100                 105                 110
```

```
<210> SEQ ID NO 251
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #21"

<400> SEQUENCE: 251

Asp Ile Gln Leu Thr Gln Ser Pro Ser Ser Leu Ser Ala Ser Val Gly
1                   5                   10                  15

Asp Arg Val Thr Ile Thr Cys Ser Val Ser Ser Ser Ile Ser Ser Asn
                20                  25                  30

Asn Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
        50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser His Tyr Pro
                85                  90                  95

Tyr Met Tyr Thr Phe Gly Gln Gly Thr Lys Val Glu Ile Lys
            100                 105                 110
```

```
<210> SEQ ID NO 252
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #22"

<400> SEQUENCE: 252

Asp Ile Gln Leu Thr Gln Ser Pro Ser Ser Leu Ser Ala Ser Val Gly
1                   5                   10                  15

Asp Arg Val Thr Ile Thr Cys Ser Val Ser Ser Ser Ile Ser Ser Asn
                20                  25                  30

Asn Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
        50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser His Pro
                85                  90                  95
```

-continued

```
Tyr Met Tyr Thr Phe Gly Gln Gly Thr Lys Val Glu Ile Lys
            100                 105                 110
```

<210> SEQ ID NO 253
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #23"

<400> SEQUENCE: 253

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr His
            85                  90                  95

Tyr Met Tyr Thr Phe Gly Gln Gly Thr Lys Val Glu Ile Lys
            100                 105                 110
```

<210> SEQ ID NO 254
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #24"

<400> SEQUENCE: 254

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
            85                  90                  95

His Met Tyr Thr Phe Gly Gln Gly Thr Lys Val Glu Ile Lys
            100                 105                 110
```

<210> SEQ ID NO 255

```
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #25"

<400> SEQUENCE: 255

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr His Tyr Thr Phe Gly Gln Gly Thr Lys Val Glu Ile Lys
                100                 105                 110

<210> SEQ ID NO 256
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #26"

<400> SEQUENCE: 256

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met His Thr Phe Gly Gln Gly Thr Lys Val Glu Ile Lys
                100                 105                 110

<210> SEQ ID NO 257
<211> LENGTH: 110
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of farletuzumab IgG
      histidine scanning variant #27"

<400> SEQUENCE: 257

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr His Phe Gly Gln Gly Thr Lys Val Glu Ile Lys
                100                 105                 110
```